United States Patent
Burns et al.

(10) Patent No.: US 10,464,952 B2
(45) Date of Patent: *Nov. 5, 2019

(54) BETA-LACTAMASE INHIBITORS

(71) Applicant: VenatoRx Pharmaceuticals, Inc., Malvern, PA (US)

(72) Inventors: Christopher J. Burns, Malvern, PA (US); Daniel C. Pevear, Downingtown, PA (US); Robert E. Lee Trout, Collegeville, PA (US); Randy W. Jackson, Livingston, MT (US); Jodie Hamrick, New Holland, PA (US); Allison L. Zulli, Chesterbrook, PA (US); Eugen F. Mesaros, Wallingford, PA (US); Steven A. Boyd, Chester Springs, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/002,363

(22) Filed: Jun. 7, 2018

(65) Prior Publication Data

US 2018/0291039 A1 Oct. 11, 2018

Related U.S. Application Data

(63) Continuation of application No. PCT/US2016/065771, filed on Dec. 9, 2016.

(60) Provisional application No. 62/265,843, filed on Dec. 10, 2015.

(51) Int. Cl.

| C07F 5/02 | (2006.01) |
| A61K 31/69 | (2006.01) |
| A61P 31/04 | (2006.01) |
| A61K 45/06 | (2006.01) |
| A61K 31/427 | (2006.01) |
| A61K 31/43 | (2006.01) |
| A61K 31/545 | (2006.01) |
| A61K 31/546 | (2006.01) |

(52) U.S. Cl.
CPC ............ *C07F 5/025* (2013.01); *A61K 31/427* (2013.01); *A61K 31/43* (2013.01); *A61K 31/545* (2013.01); *A61K 31/546* (2013.01); *A61K 31/69* (2013.01); *A61K 45/06* (2013.01); *A61P 31/04* (2018.01); *A61K 2300/00* (2013.01)

(58) Field of Classification Search
None
See application file for complete search history.

(56) References Cited

U.S. PATENT DOCUMENTS

| 4,427,690 | A | 1/1984 | Cole et al. | |
|---|---|---|---|---|
| 7,271,186 | B1 | 9/2007 | Shoichet et al. | |
| 8,680,136 | B2 | 3/2014 | Hirst et al. | |
| 8,912,169 | B2 | 12/2014 | Burns et al. | |
| 9,040,504 | B2* | 5/2015 | Burns | C07F 5/025 514/64 |
| 9,101,638 | B2 | 8/2015 | Reddy et al. | |
| 9,376,454 | B2* | 6/2016 | Burns | C07F 5/025 |
| 9,403,850 | B2* | 8/2016 | Burns | C07F 5/025 |
| 9,422,314 | B2 | 8/2016 | Burns et al. | |
| 9,511,142 | B2 | 12/2016 | Burns et al. | |
| 9,637,504 | B2* | 5/2017 | Burns | C07F 5/025 |
| 9,771,382 | B2* | 9/2017 | Burns | C07F 5/025 |
| 9,783,555 | B2* | 10/2017 | Burns | C07F 5/025 |
| 9,802,996 | B2 | 10/2017 | Burns et al. | |
| 9,828,391 | B2 | 11/2017 | Burns et al. | |
| 9,926,336 | B2* | 3/2018 | Burns | C07F 5/025 |
| 9,944,658 | B2* | 4/2018 | Burns | C07F 5/025 |
| 9,963,467 | B2* | 5/2018 | Reddy | C07F 5/025 |
| 10,125,152 | B2* | 11/2018 | Burns | C07F 5/025 |
| 2010/0056478 | A1 | 3/2010 | Desarbre et al. | |
| 2010/0120715 | A1 | 5/2010 | Burns et al. | |
| 2010/0286092 | A1 | 11/2010 | Burns et al. | |
| 2010/0292185 | A1 | 11/2010 | Burns et al. | |
| 2010/0317621 | A1 | 12/2010 | Burns et al. | |
| 2011/0294777 | A1 | 12/2011 | Blizzard et al. | |
| 2014/0194385 | A1 | 7/2014 | Reddy et al. | |
| 2015/0094472 | A1 | 4/2015 | Hecker et al. | |
| 2015/0361107 | A1 | 12/2015 | Trout | |
| 2015/0361108 | A1 | 12/2015 | Burns et al. | |
| 2017/0073360 | A1 | 3/2017 | Burns et al. | |
| 2017/0145037 | A1 | 5/2017 | Burns et al. | |
| 2017/0342093 | A1 | 11/2017 | Burns et al. | |
| 2018/0079760 | A1 | 3/2018 | Burns et al. | |
| 2018/0194783 | A1 | 7/2018 | Burns et al. | |

(Continued)

FOREIGN PATENT DOCUMENTS

| CN | 1965838 A | 5/2007 |
| CN | 105801610 A | 7/2016 |
| RU | 2012107163 A | 9/2013 |

(Continued)

OTHER PUBLICATIONS

Ness et al. Biochemistry (2000) 39, 5312-5321. (Year: 2000).*
Bacterial Infection 101. Available at http://www.onhealth.com/content/l/bacterial_infections (34 pgs) (2017).
Bodner Research Web. The Chemistry of the Halogens. Available from http://web.archive.org/web/20090414155348/http://chemechem/topicreview/bp/ch10/group3.php (11 pgs.) (2009).

(Continued)

*Primary Examiner* — Kristin A Vajda
(74) *Attorney, Agent, or Firm* — Wilson Sonsini Goodrich & Rosati

(57) ABSTRACT

Described herein are compounds and compositions that modulate the activity of beta-lactamases. In some embodiments, the compounds described herein inhibit beta-lactamase. In certain embodiments, the compounds described herein are useful in the treatment of bacterial infections.

13 Claims, No Drawings

(56) References Cited

U.S. PATENT DOCUMENTS

2018/0273552 A1  9/2018  Burns et al.

FOREIGN PATENT DOCUMENTS

| WO | WO-2005004799 A2 | 1/2005 |
| --- | --- | --- |
| WO | WO-2009064413 A1 | 5/2009 |
| WO | WO-2009064414 A1 | 5/2009 |
| WO | WO-2010056827 A1 | 5/2010 |
| WO | WO-2010130708 A1 | 11/2010 |
| WO | WO-2012021455 A1 | 2/2012 |
| WO | WO-2013014497 A1 | 1/2013 |
| WO | WO-2013053372 A1 | 4/2013 |
| WO | WO-2013092979 A1 | 6/2013 |
| WO | WO-2013122888 A2 | 8/2013 |
| WO | WO-2014086664 A1 | 6/2014 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |
| WO | WO-2014151959 A1 | 9/2014 |
| WO | WO-2015157618 A1 | 10/2015 |
| WO | WO-2015171398 A1 | 11/2015 |
| WO | WO-2015171430 A1 | 11/2015 |
| WO | WO-2015179308 A1 | 11/2015 |
| WO | WO-2015191907 A1 | 12/2015 |
| WO | WO-2016003929 A1 | 1/2016 |
| WO | WO-2017100537 A1 | 6/2017 |
| WO | WO-2018027062 A1 | 2/2018 |
| WO | WO-2018165048 A1 | 9/2018 |
| WO | WO-2018218154 A1 | 11/2018 |
| WO | WO-2018218190 A1 | 11/2018 |

OTHER PUBLICATIONS

Bundgaard. Design of Prodrugs. Elsevier. Chapter 1. pp. 1-3 (1985).
Co-pending U.S. Appl. No. 15/886,490, filed Feb. 1, 2018.
Definition of Quinoxaline from PubChem. http://pubchem.ncbi.nlm.nih.gov/compund/quinoxaline#section=information-sources. (24 pgs) (2005).
Definition of Quinoxaline from Wikipedia. http://en.wikipedia.org/wiki/Quinoxaline (3 pgs.) (2016).
Eidam et al. Design, synthesis, crystal structures, and antimicrobial activity of sulfonamide boronic acids as ß-lactamase inhibitors. J. Med. Chem. 53(21):7852-7863 (2010).
Ettmayer et al. Lessons Learned from Marketed and Investigational Prodrugs. J Medicinal Chem 47(10):2393-2404 (2004).
Evans et al. Prevention of Clostridium difficile Infection With Probiotics. © Apr. 28, 2015. Accessed Jul. 7, 2018. (8 pgs) (2015).
Han. Targeted Prodrug Design to Optimize Drug Delivery. AAPS Pharmsci. 2(1)Article 6:1-11 (2000).
Ishikawa et al. Synthesis and antimicrobial activity of 2,3-bis(bromomethyl)quinoxaline derivatives. Bioorg Chem 41-42:1-5 (2012).
Isomer. https://en.wikipedia.org/wiki/Isomer (5 pgs.) (2015).
Isomer. https://en.wikipedia.org/wiki/Isomer (5 pgs) (2017).
Lima et al. Bioisosterism: A Useful Strategy for Molecular Modification and Drug Design. Current Medicinal Chemistry 12:23-49 (2005).
Morandi et al. Structure-based optimization of cephalothin-analogue boronic acids as ß-lactamase inhibitors. Bioorg. Med. Chem. 16(3):1195-1205 (2008) (Epub: Nov. 7, 2007).
Ness et al. Structure-based design guides the improved efficacy of deacylation transition state analogue inhibitors of TEM-1 β-lactamase. Biochemistry 39(18):5312-5321 (2000).
Patani et al. Bioisosterism: A Rational Approach in Drug Design. Chemical Reviews 96:3147-3176 (1996).
PCT/US2015/035407 International Search Report and Written Opinion dated Oct. 20, 2015.
PCT/US2016/065771 International Search Report and Written Opinion dated Apr. 21, 2017.
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry 40(31):9207-9214 (2001).
Pub Chem Substance Record for SID 197433672. https://pubchem.ncbi.nim.nih/substance/197433672. Created Aug. 18, 2014. Retrieved Jan. 10, 2017 ( 5 pgs).
Teitelman. Can Anything Prevent Recurrent Bacterial Vaginosis? Medscape. © Jan. 4, 2010. Accessed Jul. 7, 2018. (3 pgs) (2010).
Testa. Prodrug research: futile or fertile? Biochem. Pharm. 68:2097-2106 (2004).
U.S. Appl. No. 15/162,395 Office Action dated Oct. 5, 2016.
U.S. Appl. No. 15/675,253 Office Action dated Oct. 4, 2017.
Watkins et al. Novel β-lactamase inhibitors: a therapeutic hope against the scourge of multi-drug resistance. © Dec. 24, 2013. Accessed Jul. 7, 2018. (18 pgs) (2013).
Weston et al. Structure-based enhancement of boronic acid-based inhibitors of AmpC β-lactamase. J. Med. Chem. 41(23):4577-4586 (1998).
Co-pending U.S. Appl. No. 16/103,445, filed Aug. 14, 2018.
Co-pending U.S. Appl. No. 16/148,941, filed Oct. 1, 2018.
Winkler et al. Design and exploration of novel boronic acid inhibitors reveals important interactions with a clavulanic acid-resistant sulfhydryl-variable (SHV) β-lactamase. J Med Chem 56:1084-1097 (2013) (Publication Date (Web): Dec. 19, 2012).

* cited by examiner

BETA-LACTAMASE INHIBITORS

CROSS REFERENCE

This application is a continuation of International Application No. PCT/US16/65771, which claims the benefit of U.S. Provisional Application No. 62/265,843 filed Dec. 10, 2015, the content of which are incorporated by reference in their entirety.

STATEMENT AS TO FEDERALLY SPONSORED RESEARCH

This invention was made with government support under Grant No. R01AI111539 and Grant No. R43AI109879 awarded by the National Institutes of Health. The government has certain rights in the invention.

FIELD OF INVENTION

The present invention relates to boron-containing compounds, compositions, preparations and their use as inhibitors of beta-lactamase enzymes and as antibacterial agents. The present invention also relates to orally bioavailable boron-containing compounds, compositions, preparations and their use as inhibitors of beta-lactamase enzymes and as antibacterial agents.

BACKGROUND OF THE INVENTION

Antibiotics are the most effective drugs for curing bacteria-infectious diseases clinically. They have a wide market due to their advantages of good antibacterial effect with limited side effects. Among them, the beta-lactam class of antibiotics (for example, penicillins, cephalosporins, and carbapenems) is widely used because they have a strong bactericidal effect and low toxicity.

To counter the efficacy of the various beta-lactams, bacteria have evolved to produce variants of beta-lactam deactivating enzymes called beta-lactamases, and in the ability to share this tool inter- and intra-species. These beta-lactamases are categorized as "serine" or "metallo" based, respectively, on presence of a key serine or zinc in the enzyme active site. The rapid spread of this mechanism of bacterial resistance can severely limit beta-lactam treatment options in the hospital and in the community.

SUMMARY OF THE INVENTION

Described herein are compounds that modulate the activity of beta-lactamases. In some embodiments, the compounds described herein inhibit beta-lactamases. In certain embodiments, the compounds described herein are useful in the treatment of bacterial infections. In other embodiments, the compounds described herein are esters designed to deliver the corresponding carboxylic acid compounds.

In one aspect, provided herein are compounds of Formula (Ia) or (Ib) or pharmaceutically acceptable salts, isomers, stereoisomers, dimers, trimers, tautomers, or N-oxides thereof:

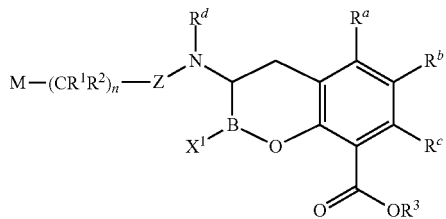

Formula (Ia)

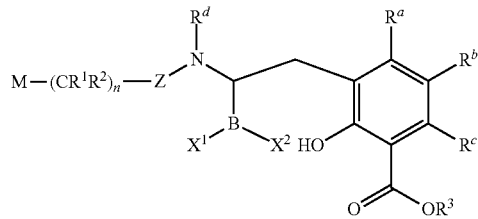

Formula (Ib)

wherein:

M is hydrogen, fluoro, chloro, bromo, —$CF_3$, —CN, —$OR^4$, —$SR^4$, —S(=O)$R^4$, —S(=O)$_2R^4$, —S(=O)$_2$N($R^4R^5$), —N($R^4R^5$), —N($R^4$)C(=O)$R^4$, —N($R^4$)C(=O)N($R^4R^5$), —N($R^4$)S(=O)$_2R^4$, —N($R^4$)Heteroaryl, —C(=O)$R^4$, —C(=O)N($R^4R^5$), —C(=O)($C_1$-$C_3$alkylene)C(=O)$R^4$, optionally substituted oxyimino, optionally substituted alkenyl, optionally substituted alkynyl, optionally substituted heteroaryl, or optionally substituted heterocycloalkyl;

each $R^1$ and $R^2$ are independently hydrogen, fluoro, chloro, bromo, optionally substituted $C_1$-$C_6$ alkyl, optionally substituted aryl, —$OR^4$, —$SR^4$, or —N($R^4R^5$); or $R^1$ and $R^2$ are taken together with the carbon to which they are attached to form an optionally substituted cycloalkyl; or when n is at least 2, two $R^1$ on adjacent carbons are taken together to form a double bond; or two $R^1$ and two $R^2$ on adjacent carbons are taken together to form a triple bond;

provided that M is —$CF_3$ or at least one of $R^1$ or $R^2$ is fluoro;

n is 0, 1, 2, 3, 4, 5, or 6;

$X^1$ and $X^2$ are independently —$OR^4$, or F; when present;

Z is >C(=O), >C(=S), or >S(=O)$_2$;

$R^3$ is $R^{31}$, —($R^{30}$)$_q$$OR^{31}$, —($R^{30}$)$_q$O($R^{30}$)$_q$$OR^{31}$, —$R^{30}$OC(=O)$R^{31}$, —$R^{30}$OC(=O)$OR^{31}$, —$R^{30}$OC(=O)NH$R^{31}$, —$R^{30}$OC(=O)N($R^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 1, 2, 3, 4, 5, or 6;

each $R^{30}$ is independently —$CH_2$—, —CH($R^{32}$)—, or —C($R^{32}$)$_2$—;

each $R^{31}$ is independently optionally substituted $C_1$-$C_{12}$ alkyl, optionally substituted alkoxyalkyl, optionally substituted $C_1$-$C_{12}$ alkenyl, optionally substituted $C_1$-$C_{12}$ alkynyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; or two $R^{31}$ are taken together with the nitrogen to which they are attached to form a heterocycloalkyl;

each $R^{32}$ is independently optionally substituted $C_1$-$C_6$ alkyl;

or two $R^{32}$ are taken together with the carbon to which they are attached to form a cycloalkyl;

$R^a$, $R^b$, and $R^c$ are independently hydrogen, fluoro, chloro, bromo, optionally substituted $C_1$-$C_6$ alkyl, optionally substituted cycloalkyl, optionally substituted heterocycloalkyl, optionally substituted aryl, optionally substituted heteroaryl, —$OR^4$, —$N(R^4R^5)$, or —$SR^4$;

$R^d$, $R^4$ and $R^5$ are independently hydrogen, —OH, —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ are taken together with the nitrogen to which they are attached to form a heterocycloalkyl.

In some embodiments of a compound of Formula (Ia) or (Ib), M is —$CF_3$.

In some embodiments of a compound of Formula (Ia) or (Ib), M is hydrogen, —CN, —$OR^4$, —$SR^4$, —$C(=O)R^4$, or alkynyl.

In some embodiments of a compound of Formula (Ia) or (Ib), each $R^1$ and $R^2$ are independently hydrogen, fluoro, chloro, $C_1$-$C_6$ alkyl, or —$CF_3$. In some embodiments of a compound of Formula (Ia) or (Ib), each $R^1$ and $R^2$ are independently hydrogen or fluoro. In some embodiments of a compound of Formula (Ia) or (Ib), each $R^1$ and $R^2$ are hydrogen.

In some embodiments of a compound of Formula (Ia) or (Ib), at least one of $R^1$ or $R^2$ is fluoro. In some embodiments of a compound of Formula (Ia) or (Ib), at least two of $R^1$ or $R^2$ are fluoro. In some embodiments of a compound of Formula (Ia) or (Ib), at least three of $R^1$ or $R^2$ are fluoro.

In some embodiments of a compound of Formula (Ia) or (Ib),

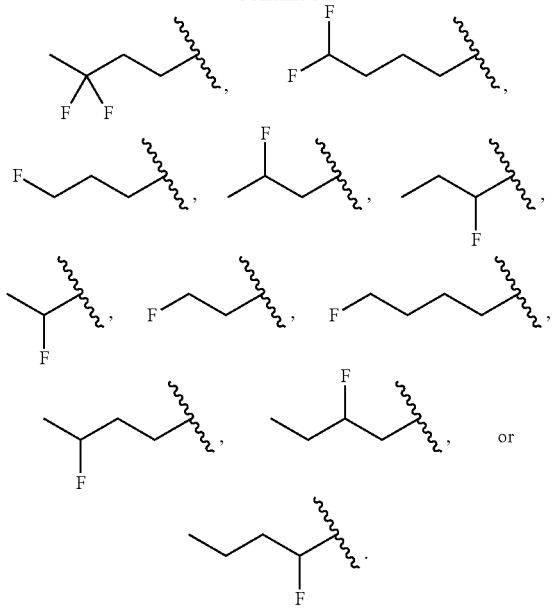

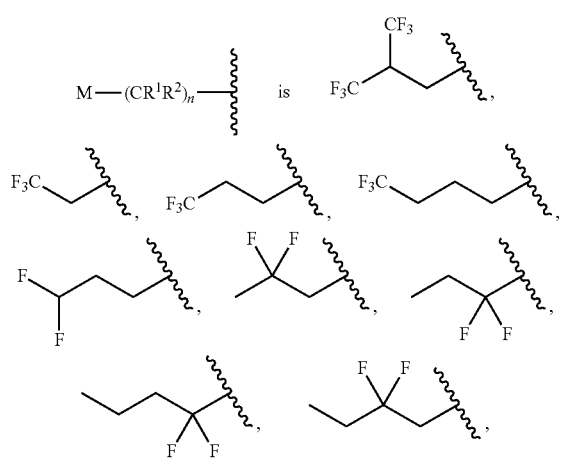

In some embodiments of a compound of Formula (Ia) or (Ib),

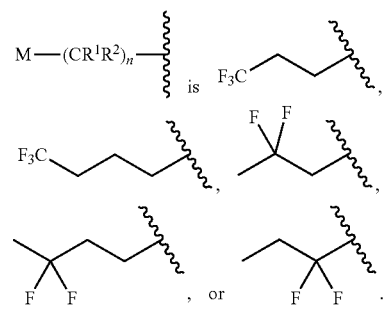

In some embodiments of a compound of Formula (Ia) or (Ib), $R^3$ is $R^{31}$, —$R^{30}OC(=O)R^{31}$, or —$R^{30}OC(=O)OR^{31}$.

In some embodiments of a compound of Formula (Ia) or (Ib), $R^3$ is $R^{31}$; and $R^{31}$ is optionally substituted $C_1$-$C_{12}$ alkyl, optionally substituted alkylaryl, optionally substituted heterocycloalkyl, optionally substituted alkylcycloalkyl, or optionally substituted alkylheterocycloalkyl.

In some embodiments of a compound of Formula (Ia) or (Ib), $R^3$ is $R^{31}$; and $R^{31}$ is $C_1$-$C_{12}$ alkyl, alkylaryl, heterocycloalkyl, alkylcycloalkyl, or alkylheterocycloalkyl.

In some embodiments of a compound of Formula (Ia) or (Ib), $R^3$ is $R^{31}$; and $R^{31}$ is $C_1$-$C_{12}$ alkyl, alkylaryl, heterocycloalkyl, alkylcycloalkyl, or alkylheterocycloalkyl; each optionally substituted with halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$.

In some embodiments of a compound of Formula (Ia) or (Ib), $R^3$ is $R^{31}$; and $R^{31}$ is $C_1$-$C_{12}$ alkyl, —$(C_1$-$C_6$ alkylene)$S(=O)_2R^4$ or —$(C_1$-$C_6$ alkylene)$C(=O)N(R^4R^5)$.

In some embodiments of a compound of Formula (Ia) or (Ib), $R^3$ is $R^{31}$; and $R^{31}$ is:

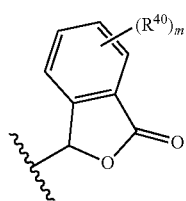

wherein:
each $R^{40}$ is independently hydrogen, halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$; and m is 0, 1, 2, 3, or 4.

In some embodiments of a compound of Formula (Ia) or (Ib), $R^{40}$ is hydrogen.

In some embodiments of a compound of Formula (Ia) or (Ib), $R^3$ is $R^{31}$; and $R^{31}$ is:

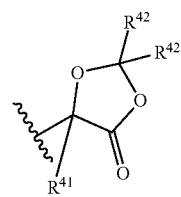

wherein:
each $R^{41}$ and $R^{42}$ are independently hydrogen, halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$.

In some embodiments of a compound of Formula (Ia) or (Ib), each $R^{41}$ and $R^{42}$ are independently $C_1$-$C_6$ alkyl.

In some embodiments of a compound of Formula (Ia) or (Ib), wherein $R^3$ is $R^{31}$; and $R^{31}$ is:

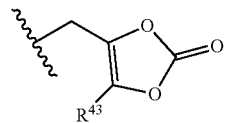

wherein:
$R^{43}$ is hydrogen, halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$.

In some embodiments of a compound of Formula (Ia) or (Ib), $R^{43}$ is $C_1$-$C_6$ alkyl.

In some embodiments of a compound of Formula (Ia) or (Ib), $R^3$ is $R^{31}$; and $R^{31}$ is:

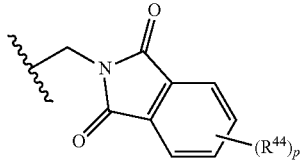

wherein:
$R^{44}$ is hydrogen, halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$; and p is 0, 1, 2, 3, or 4.

In some embodiments of a compound of Formula (Ia) or (Ib), $R^{44}$ is hydrogen.

In some embodiments of a compound of Formula (Ia) or (Ib), $R^3$ is $R^{31}$; and $R^{31}$ is

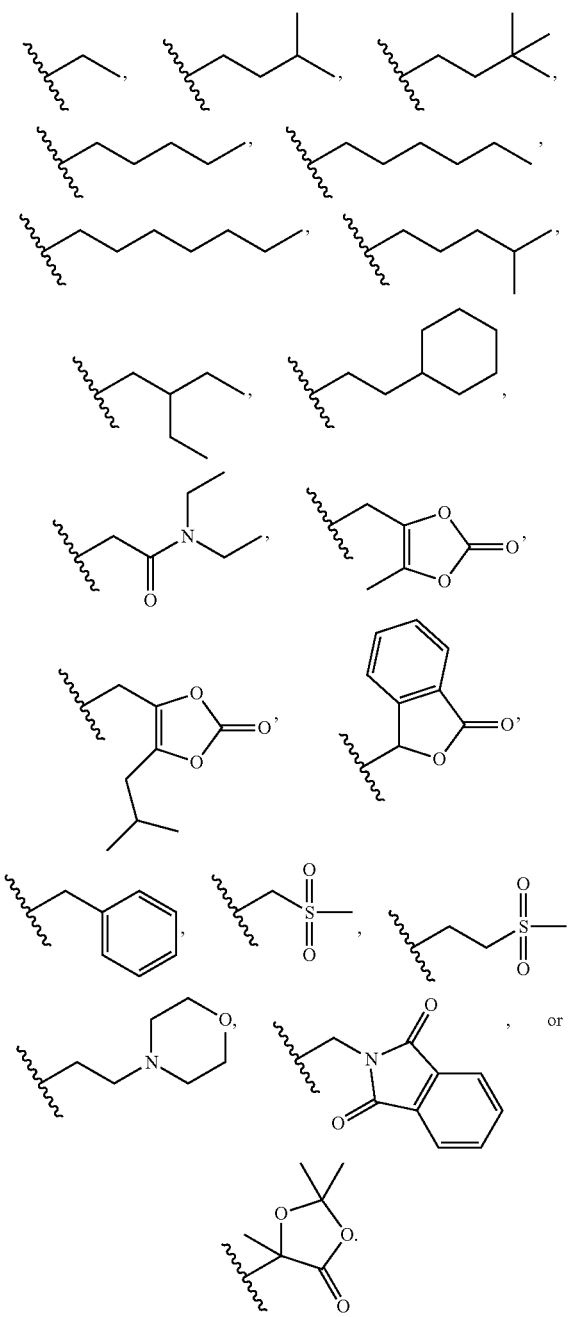

In some embodiments of a compound of Formula (Ia) or (Ib), $R^3$ is $R^{31}$; and $R^{31}$ is

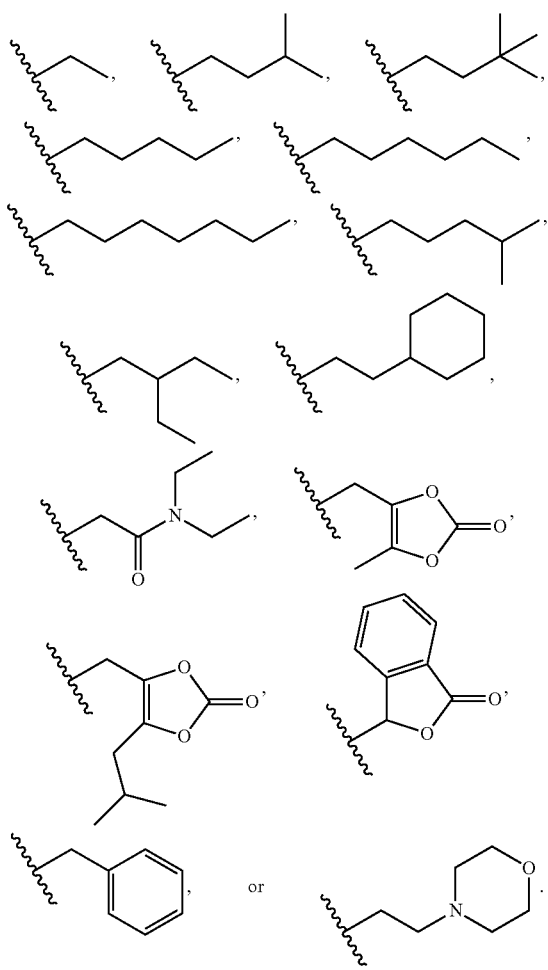

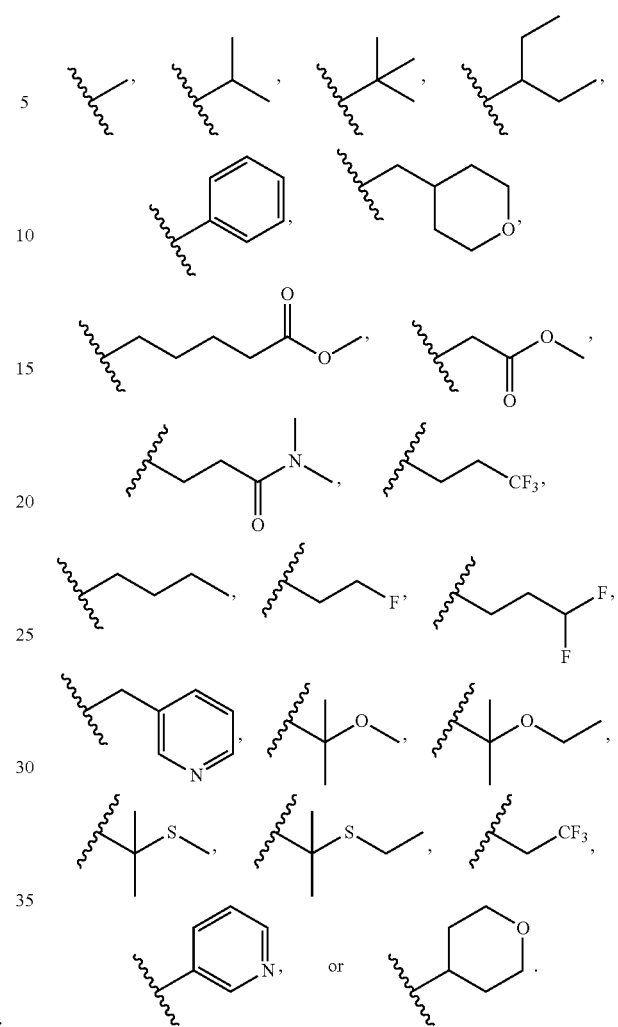

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is optionally substituted $C_1$-$C_{12}$ alkyl, optionally substituted aryl, optionally substituted alkylheterocycloalkyl, optionally substituted alkylheteroaryl, optionally substituted heteroaryl, or optionally substituted heterocycloalkyl.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ alkyl, aryl, alkylheterocycloalkyl, alkylheteroaryl, heteroaryl, or heterocycloalkyl.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ alkyl, aryl, alkylheterocycloalkyl, alkylheteroaryl, heteroaryl, or heterocycloalkyl; each optionally substituted with halogen, $-CN$, $C_1$-$C_6$ alkyl, $-CF_3$, cycloalkyl, heterocycloalkyl, $-OR^4$, $-N(R^4R^5)$, $-SR^4$, $-(S=O)_2R^4$, $-C(=O)OR^4$, or $-C(=O)N(R^4R^5)$.

In some embodiments of a compound of Formula (Ia) or (Ib), $R^3$ is $-R^{30}OC(=O)R^{31}$; $R^{30}$ is $-CH_2-$ or $-CH(CH_3)-$; and $R^{31}$ is $C_i$-$C_{12}$ alkyl, $C_i$-$C_{12}$ fluoroalkyl, $-(C_1$-$C_6$ alkylene)$OR^4$, $-(C_1$-$C_6$ alkylene)$SR^4$, $-(C_1$-$C_6$ alkylene)$C(=O)OR^4$, or $-(C_1$-$C_6$ alkylene)$C(=O)N(R^4R^5)$.

In some embodiments of a compound of Formula (Ia) or (Ib), $R^3$ is $-R^{30}OC(=O)R^{31}$; $R^{30}$ is $-CH_2-$ or $-CH(CH_3)-$; and $R^{31}$ is In some embodiments of a compound of Formula (Ia) or (Ib), $R^3$ is $-R^{30}OC(=O)R^{31}$; $R^{30}$ is $-CH_2-$ or $-CH(CH_3)-$; and $R^{31}$ is

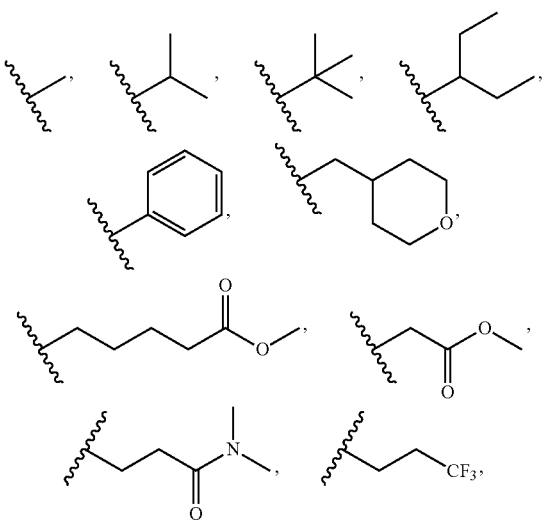

-continued

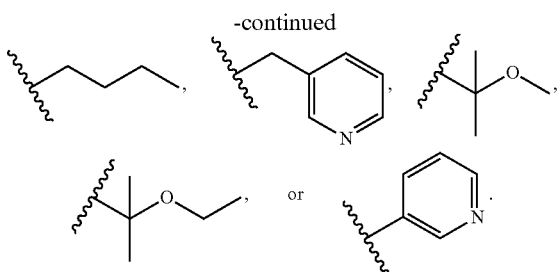

In some embodiments of a compound of Formula (Ia) or (Ib), $R^3$ is $-R^{30}OC(=O)OR^{31}$; $R^{30}$ is $-CH_2-$ or $-CH(R^{32})-$; $R^{32}$ is $C_1-C_6$ alkyl; and $R^{31}$ is optionally substituted $C_1-C_{12}$ alkyl or optionally substituted cycloalkyl.

In some embodiments of a compound of Formula (Ia) or (Ib), $R^3$ is $-R^{30}OC(=O)OR^{31}$; $R^{30}$ is $-CH_2-$ or $-CH(CH_3)-$; and $R^{31}$ is $C_1-C_{12}$ alkyl or cycloalkyl.

In some embodiments of a compound of Formula (Ia) or (Ib), $R^3$ is $-R^{30}OC(=O)OR^{31}$; $R^{30}$ is $-CH_2-$ or $-CH(CH_3)-$; and $R^{31}$ is $C_1-C_{12}$ alkyl or cycloalkyl; each optionally substituted with halogen, $-CN$, $C_1-C_6$ alkyl, $-CF_3$, cycloalkyl, heterocycloalkyl, $-OR^4$, $-N(R^4R^5)$, $-SR^4$, $-S(=O)_2R^4$, $-C(=O)OR^4$, or $-C(=O)N(R^4R^5)$.

In some embodiments of a compound of Formula (Ia) or (Ib), $R^3$ is $-R^{30}OC(=O)OR^{31}$; $R^{30}$ is $-CH_2-$ or $-CH(CH_3)-$; and $R^{31}$ is

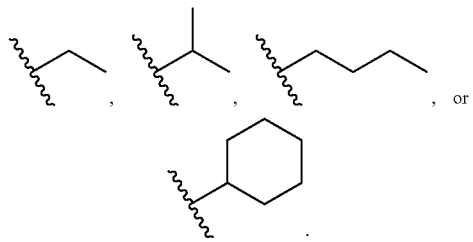

In another aspect, provided herein are compounds of Formula (IIa) or (IIb) or pharmaceutically acceptable salts, isomers, stereoisomers, dimers, trimers, tautomers, or N-oxides thereof:

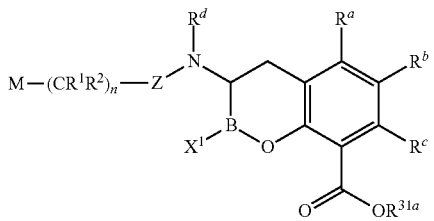

Formula (IIa)

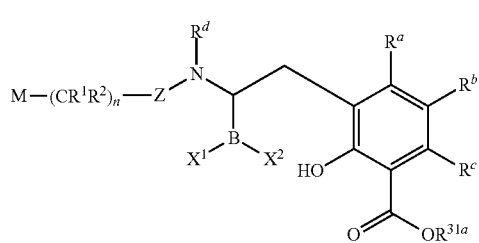

Formula (IIb)

wherein:
M is hydrogen, fluoro, chloro, bromo, $-CF_3$, $-CN$, $-OR^4$, $-SR^4$, $-S(=O)R^4$, $-S(=O)_2R^4$, $-S(=O)_2N(R^4R^5)$, $-N(R^4R^5)$, $-N(R^4)C(=O)R^4$, $-N(R^4)C(=O)N(R^4R^5)$, $-N(R^4)S(=O)_2R^4$, $-N(R^4)$Heteroaryl, $-C(=O)R^4$, $-C(=O)N(R^4R^5)$, $-C(=O)(C_1-C_3\text{alkylene})C(=O)R^4$, optionally substituted oxyimino, optionally substituted alkenyl, optionally substituted alkynyl, heteroaryl, or heterocycloalkyl;

each $R^1$ and $R^2$ are independently hydrogen, fluoro, chloro, bromo, optionally substituted $C_1-C_6$ alkyl, optionally substituted aryl, $-OR^4$, $-SR^4$, or $-N(R^4R^5)$; or $R^1$ and $R^2$ are taken together with the carbon to which they are attached to form an optionally substituted cycloalkyl; or when n is at least 2, two $R^1$ on adjacent carbons are taken together to form a double bond; or two $R^1$ and two $R^2$ on adjacent carbons are taken together to form a triple bond;

n is 0, 1, 2, 3, 4, 5, or 6;

$X^1$ and $X^2$ are independently $-OR^4$, or F; when present;

Z is $>C(=O)$, $>C(=S)$, or $>S(=O)_2$;

$R^{31a}$ is optionally substituted $C_5-C_{12}$ alkyl, $-(C_1-C_6$ alkylene$)C(=O)N(R^4R^5)$, $-(C_1-C_6$ alkylene$)S(=O)_2R^4$, optionally substituted heterocycloalkyl, optionally substituted alkylcycloalkyl, optionally substituted alkylheterocycloalkyl, optionally substituted aryl, optionally substituted heteroaryl, optionally substituted alkylaryl, or optionally substituted alkylheteroaryl;

$R^a$, $R^b$, and $R^c$ are independently hydrogen, fluoro, chloro, bromo, optionally substituted $C_1-C_6$ alkyl, optionally substituted cycloalkyl, optionally substituted heterocycloalkyl, optionally substituted aryl, optionally substituted heteroaryl, $-OR^4$, $-N(R^4R^5)$, or $-SR^4$;

$R^d$, $R^4$ and $R^5$ are independently hydrogen, $-OH$, $-CN$, $-CF_3$, optionally substituted $C_1-C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ are taken together with the nitrogen to which they are attached to form a heterocycloalkyl; provided that the compound is not (5-methyl-2-oxo-1,3-dioxol-4-yl)methyl 3-(3-cyanopropanamido)-2-hydroxy-3,4-dihydro-2H-benzo[e][1,2]oxaborinine-8-carboxylate
or 3-oxo -1,3-dihydroisobenzofuran-1-yl 3-acetamido-2-hydroxy-3,4-dihydro-2H-benzo[e][1,2]oxaborinine-8-carboxylate.

In some embodiments of a compound of Formula (IIa) or (IIb), M is hydrogen, $-CF_3$, $-CN$, $-OR^4$, $-SR^4$, $-C(=O)R^4$, or alkynyl. In some embodiments of a compound of Formula (IIa) or (IIb), M is hydrogen.

In some embodiments of a compound of Formula (IIa) or (IIb), each $R^1$ and $R^2$ are independently hydrogen, fluoro, chloro, $C_1-C_6$ alkyl, or $-CF_3$. In some embodiments of a compound of Formula (IIa) or (IIb), each $R^1$ and $R^2$ are independently hydrogen or fluoro. In some embodiments of a compound of Formula (IIa) or (IIb), each $R^1$ and $R^2$ are hydrogen.

In some embodiments of a compound of Formula (IIa) or (IIb), $R^{31a}$ is optionally substituted $C_5-C_{12}$ alkyl, $-(C_1-C_6$ alkylene)C(=O)N(R⁴R⁵), —(C₁-C₆ alkylene)S(=O)₂R⁴, optionally substituted heterocycloalkyl, optionally substituted alkylcycloalkyl, optionally substituted alkylheterocycloalkyl, or optionally substituted alkylaryl.

In some embodiments of a compound of Formula (IIa) or (IIb), R³¹ᵃ is C₅-C₁₂ alkyl, —(C₁-C₆ alkylene)C(=O)N(R⁴R⁵), —(C₁-C₆ alkylene)S(=O)₂R⁴, heterocycloalkyl, alkylcycloalkyl, alkylheterocycloalkyl, or aralkyl.

In some embodiments of a compound of Formula (IIa) or (IIb), R³¹ᵃ is C₅-C₁₂ alkyl, heterocycloalkyl, alkylcycloalkyl, alkylheterocycloalkyl, or aralkyl; each optionally substituted with halogen, —CN, C₁-C₆ alkyl, —CF₃, cycloalkyl, heterocycloalkyl, —OR⁴, —N(R⁴R⁵), —SR⁴, —(S=O)₂R⁴, —C(=O)OR⁴, or —C(=O)N(R⁴R⁵).

In some embodiments of a compound of Formula (IIa) or (IIb), R³¹ᵃ is:

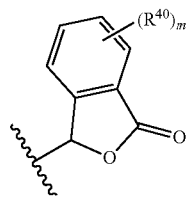

wherein:
each R⁴⁰ is independently hydrogen, halogen, —CN, C₁-C₆ alkyl, —CF₃, cycloalkyl, heterocycloalkyl, —OR⁴, —N(R⁴R⁵), —SR⁴, —(S=O)₂R⁴, —C(=O)OR⁴, or —C(=O)N(R⁴R⁵); and
m is 0, 1, 2, 3, or 4.

In some embodiments of a compound of Formula (IIa) or (IIb), R⁴⁰ is hydrogen.

In some embodiments of a compound of Formula (IIa) or (IIb), R³¹ᵃ is:

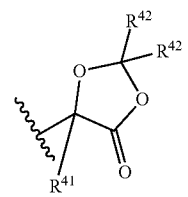

wherein:
each R⁴¹ and R⁴² are independently hydrogen, halogen, —CN, C₁-C₆ alkyl, —CF₃, cycloalkyl, heterocycloalkyl, —OR⁴, —N(R⁴R⁵), —SR⁴, —(S=O)₂R⁴, —C(=O)OR⁴, or —C(=O)N(R⁴R⁵).

In some embodiments of a compound of Formula (IIa) or (IIb), each R⁴¹ and R⁴² are independently C₁-C₆ alkyl.

In some embodiments of a compound of Formula (IIa) or (IIb), R³¹ᵃ is:

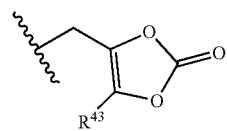

wherein:
R⁴³ is hydrogen, halogen, —CN, C₁-C₆ alkyl, —CF₃, cycloalkyl, heterocycloalkyl, —OR⁴, —N(R⁴R⁵), —SR⁴, —(S=O)₂R⁴, —C(=O)OR⁴, or —C(=O)N(R⁴R⁵).

In some embodiments of a compound of Formula (IIa) or (IIb), R⁴³ is C₁-C₆ alkyl.

In some embodiments of a compound of Formula (IIa) or (IIb), R³¹ᵃ is:

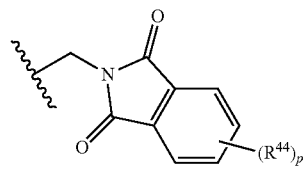

wherein:
R⁴⁴ is hydrogen, halogen, —CN, C₁-C₆ alkyl, —CF₃, cycloalkyl, heterocycloalkyl, —OR⁴, —N(R⁴R⁵), —SR⁴, —(S=O)₂R⁴, —C(=O)OR⁴, or —C(=O)N(R⁴R⁵); and
p is 0, 1, 2, 3, or 4.

In some embodiments of a compound of Formula (IIa) or (IIb), R⁴⁴ is hydrogen.

In some embodiments of a compound of Formula (IIa) or (IIb), R³¹ᵃ is

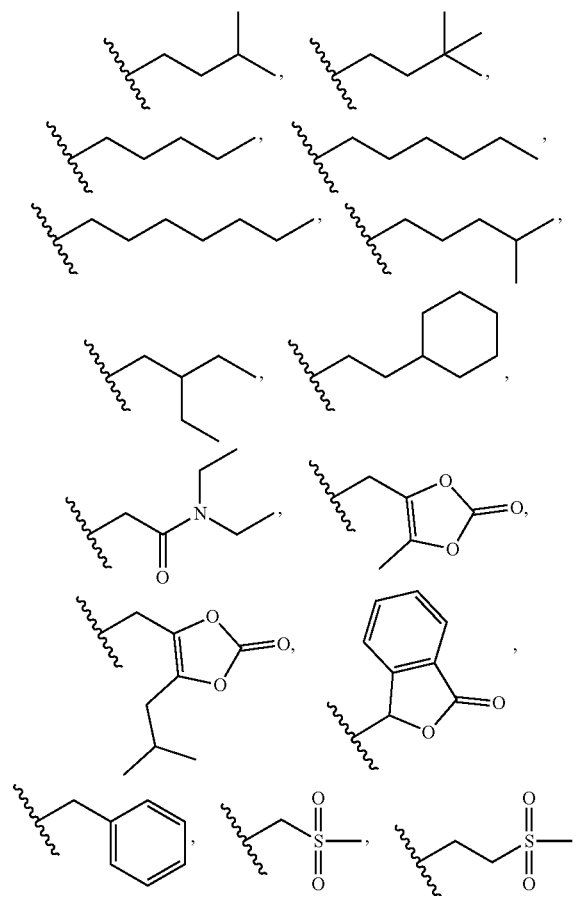

-continued

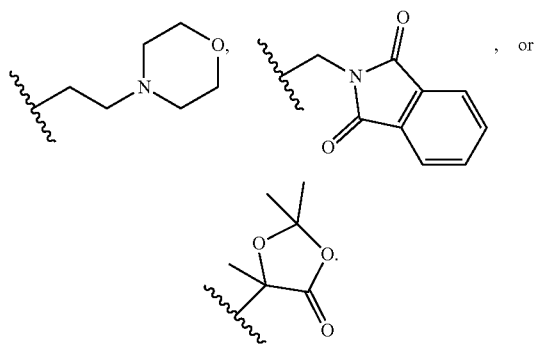

In some embodiments of a compound of Formula (IIa) or (IIb), $R^{31a}$ is

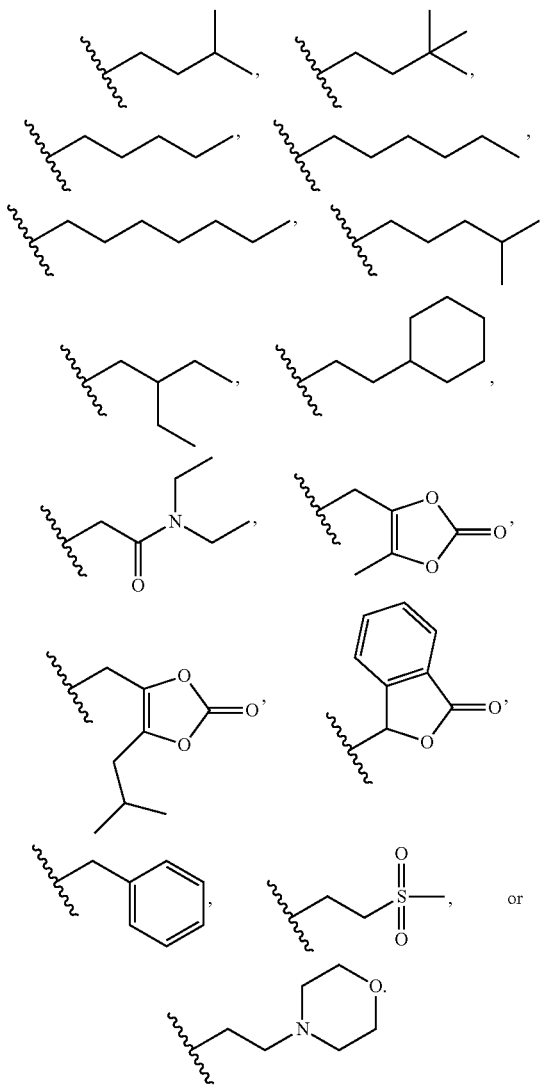

In another aspect, provided herein are compounds of Formula (IIIa) or (IIIb) or pharmaceutically acceptable salts, isomers, stereoisomers, dimers, trimers, tautomers, or N-oxides thereof:

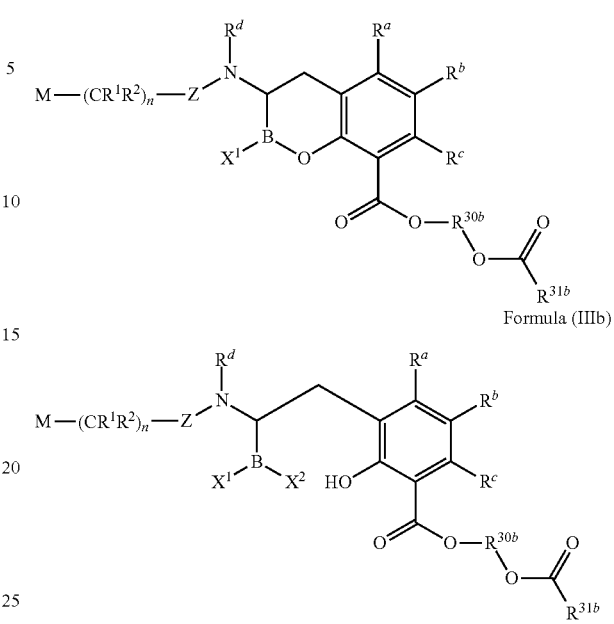

wherein:
M is hydrogen, fluoro, chloro, bromo, —CF$_3$, —CN, —OR$^4$, —SR$^4$, —S(=O)R$^4$, —S(=O)$_2$R$^4$, —S(=O)$_2$N(R$^4$R$^5$), —N(R$^4$R$^5$), —N(R$^4$)C(=O)R$^4$, —N(R$^4$)C(=O)N(R$^4$R$^5$), —N(R$^4$)S(=O)$_2$R$^4$, —N(R$^4$)Heteroaryl, —C(=O)R$^4$, —C(=O)N(R$^4$R$^5$), —C(=O)(C$_1$-C$_3$alkylene)C(=O)R$^4$, optionally substituted oxyimino, optionally substituted alkenyl, optionally substituted alkynyl, heteroaryl, or heterocycloalkyl;
each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$); or
R$^1$ and R$^2$ are taken together with the carbon to which they are attached to form an optionally substituted cycloalkyl; or
when n is at least 2, two R$^1$ on adjacent carbons are taken together to form a double bond; or two R$^1$ and two R$^2$ on adjacent carbons are taken together to form a triple bond;
n is 0, 1, 2, 3, 4, 5, or 6;
X$^1$ and X$^2$ are independently —OR$^4$, or F; when present;
Z is >C(=O), >C(=S), or >S(=O)$_2$;
R$^{30b}$ is —CH$_2$—, —CH(R$^{32b}$)—, or —C(R$^{32b}$)$_2$—;
R$^{31b}$ is linear C$_4$-C$_{12}$ alkyl, —(C$_1$-C$_6$ alkylene)OR$^4$, —(C$_1$-C$_6$ alkylene)SR$^4$, —(C$_1$-C$_6$ alkylene)C(=O) OR$^4$, —(C$_1$-C$_6$ alkylene)C(=O)N(R$^4$R$^5$), optionally substituted C$_1$-C$_{12}$ fluoroalkyl, optionally substituted C$_3$-C$_5$ cycloalkyl, optionally substituted heteroaryl, optionally substituted alkylheterocycloalkyl, optionally substituted alkylaryl, or optionally substituted alkylheteroaryl;
each R$^{32b}$ is independently optionally substituted C$_1$-C$_6$ alkyl;
or two R$^{32b}$ are taken together with the carbon to which they are attached to form a cycloalkyl.
R$^a$, R$^b$, and R$^c$ are independently hydrogen, fluoro, chloro, bromo, optionally substituted C$_1$-C$_6$ alkyl, optionally substituted cycloalkyl, optionally substituted heterocycloalkyl, optionally substituted aryl, optionally substituted heteroaryl, —OR⁴, —N(R⁴R⁵), or —SR⁴;

R$^d$, R⁴ and R⁵ are independently hydrogen, —OH, —CN, —CF₃, optionally substituted C₁-C₆ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or R⁴ and R⁵ are taken together with the nitrogen to which they are attached to form a heterocycloalkyl.

In some embodiments of a compound of Formula (IIIa) or (IIIb), M is hydrogen, —CF₃, —CN, —OR⁴, —SR⁴, —C(=O)R⁴, or alkynyl. In some embodiments of a compound of Formula (IIIa) or (IIIb), M is hydrogen.

In some embodiments of a compound of Formula (IIIa) or (IIIb), each R¹ and R² are independently hydrogen, fluoro, chloro, C₁-C₆ alkyl, or —CF₃. In some embodiments of a compound of Formula (IIIa) or (IIIb), each R¹ and R² are independently hydrogen or fluoro. In some embodiments of a compound of Formula (IIIa) or (IIIb), each R¹ and R² are hydrogen.

In some embodiments of a compound of Formula (IIIa) or (IIIb), R$^{30b}$ is —CH₂—, —CH(CH₃)—, or —CH(isopropyl). In some embodiments of a compound of Formula (IIIa) or (IIIb), R$^{30b}$ is —CH₂— or —CH(CH₃)—.

In some embodiments of a compound of Formula (IIIa) or (IIIb), R$^{31b}$ is linear C₄—C₁₂ alkyl, —(C₁-C₆ alkylene)OR⁴, —(C₁-C₆ alkylene)C(=O)OR⁴, —(C₁-C₆ alkylene)SR⁴, —(C₁-C₆ alkylene)C(=O)N(R⁴R⁵), optionally substituted C₁-C₁₂ fluoroalkyl, optionally substituted C₃-C₅ cycloalkyl, optionally substituted alkylheterocycloalkyl, optionally substituted heteroaryl, or optionally substituted alkylheteroaryl.

In some embodiments of a compound of Formula (IIIa) or (IIIb), R$^{31b}$ is alkylheterocycloalkyl, heteroaryl, or alkylheteroaryl; each optionally substituted with halogen, —CN, C₁-C₆ alkyl, —CF₃, cycloalkyl, heterocycloalkyl, —OR⁴, —N(R⁴R⁵), —SR⁴, —(S=O)₂R⁴, —C(=O)OR⁴, or —C(=O)N(R⁴R⁵).

In some embodiments of a compound of Formula (IIIa) or (IIIb), R$^{31b}$ is linear C₄-C₁₂ alkyl, —(C₁-C₆ alkylene)OR⁴, —(C₁-C₆ alkylene)C(=O)OR⁴, —(C₁-C₆ alkylene)SR⁴, —(C₁-C₆ alkylene)C(=O)N(R⁴R⁵), C₁-C₁₂ fluoroalkyl, optionally substituted C₃-C₅ cycloalkyl, alkylheterocycloalkyl, heteroaryl, or alkylheteroaryl.

In some embodiments of a compound of Formula (IIIa) or (IIIb), R$^{31b}$ is

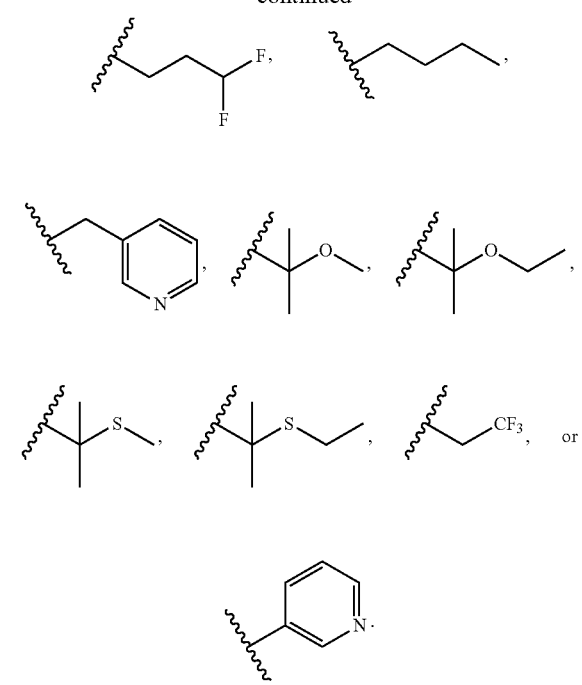

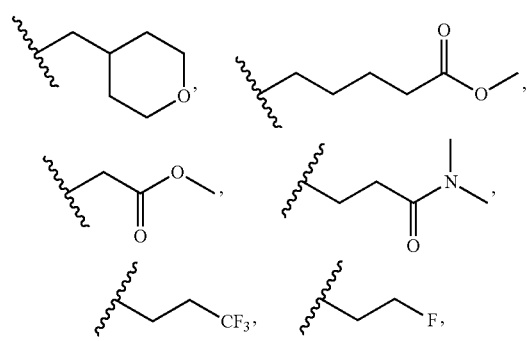

In some embodiments of a compound of Formula (IIIa) or (IIIb), R$^{31b}$ is

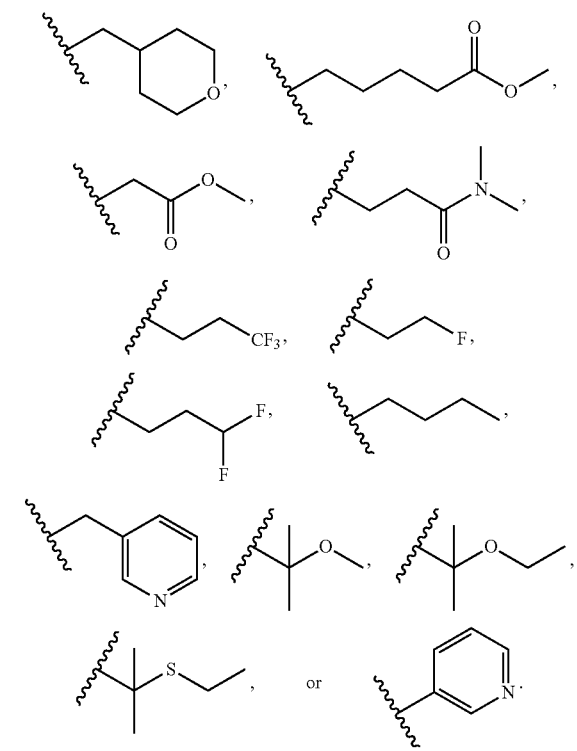

In another aspect, provided herein are compounds of Formula (IVa) or (IVb) or pharmaceutically acceptable salts, isomers, stereoisomers, dimers, trimers, tautomers, or N-oxides thereof:

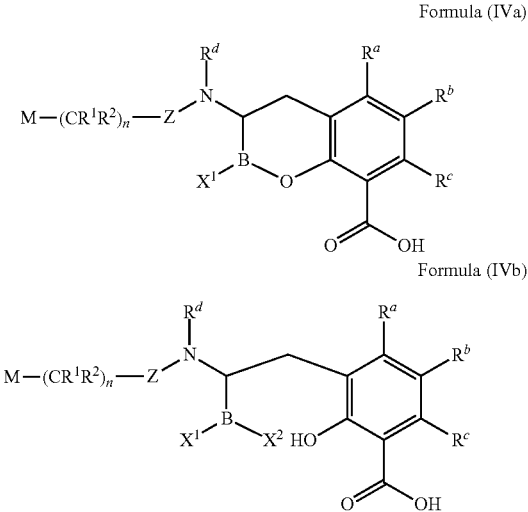

Formula (IVa)

Formula (IVb)

wherein:
M is hydrogen, fluoro, chloro, bromo, —CF$_3$, —CN, —OR$^4$, —SR$^4$, —S(=O)R$^4$, —S(=O)$_2$R$^4$, —S(=O)$_2$N(R$^4$R$^5$), —N(R$^4$R$^5$), —N(R$^4$)C(=O)R$^4$, —N(R$^4$)C(=O)N(R$^4$R$^5$), —N(R$^4$)S(=O)$_2$R$^4$, —N(R$^4$)Heteroaryl, —C(=O)R$^4$, —C(=O)N(R$^4$R$^5$), —C(=O)(C$_1$-C$_3$alkylene)C(=O)R$^4$, optionally substituted oxyimino, optionally substituted alkenyl, optionally substituted alkynyl, heteroaryl, or heterocycloalkyl;
each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$); or
R$^1$ and R$^2$ are taken together with the carbon to which they are attached to form an optionally substituted cycloalkyl; or
two R$^1$ on adjacent carbons are taken together to form a double bond; or two R$^1$ and two R$^2$ on adjacent carbons are taken together to form a triple bond;
provided that M is —CF$_3$ or at least one of R$^1$ or R$^2$ is fluoro;
n is 0, 1, 2, 3, 4, 5, or 6;
X$^1$ and X$^2$ are independently —OR$^4$, or F; when present;
Z is >C(=O), >C(=S), or >S(=O)$_2$;
R$^a$, R$^b$, and R$^c$ are independently hydrogen, fluoro, chloro, bromo, optionally substituted C$_1$-C$_6$ alkyl, optionally substituted cycloalkyl, optionally substituted heterocycloalkyl, optionally substituted aryl, optionally substituted heteroaryl, —OR$^4$, —N(R$^4$R$^5$), or —SR$^4$;
R$^d$, R$^4$ and R$^5$ are independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;
or R$^4$ and R$^5$ are taken together with the nitrogen to which they are attached to form a heterocycloalkyl; provided that the compound is not 3 —(2-chloro-4,4-difluorobutanamido)-2-hydroxy-3,4-dihydro-2H -benzo[e] [1,2] oxaborinine-8-carboxylic acid, 2-hydroxy-3-(3,3,3-trifluoropropanamido)-3,4-dihydro-2H -benzo[e][1,2] oxaborinine-8-carboxylic acid, 2-hydroxy-3-(4,4,4-trifluorobutanamido)-3,4-dihydro-2H -benzo[e][1,2] oxaborinine-8-carboxylic acid, or 2-hydroxy-3-(4,4,4-trifluoro-3-(trifluoromethyl)butanamido)-3,4-dihydro-2H-benzo[e][1,2]oxaborinine-8-carboxylic acid.

In some embodiments of a compound of Formula (IVa) or (IVb), M is hydrogen. In some embodiments of a compound of Formula (IVa) or (IVb), M is —CF$_3$. In some embodiments of a compound of Formula (IVa) or (IVb), M is hydrogen, —CN, —OR$^4$, —SR$^4$, —C(=O)R$^4$, or alkynyl.

In some embodiments of a compound of Formula (IVa) or (IVb), at least one of R$^1$ or R$^2$ is fluoro. In some embodiments of a compound of Formula (IVa) or (IVb), at least two of R$^1$ or R$^2$ are fluoro. In some embodiments of a compound of Formula (IVa) or (IVb), at least three of R$^1$ or R$^2$ are fluoro.

In some embodiments of a compound of Formula (IVa) or (IVb), M—(CR$^1$R$^2$)$_n$—| is

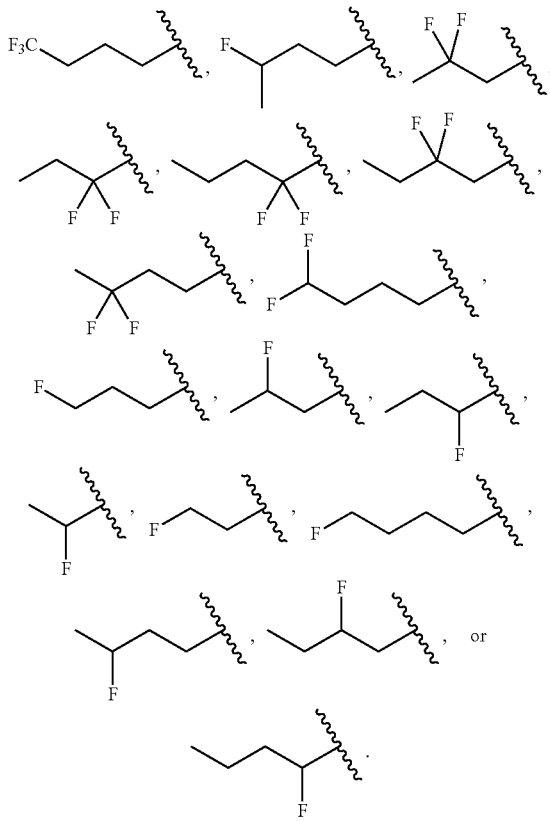

In some embodiments of a compound of Formula (IVa) or (IVb),

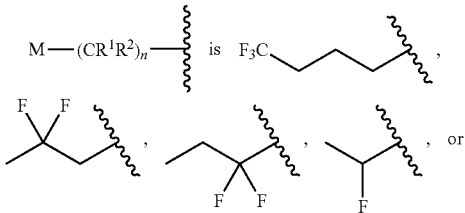

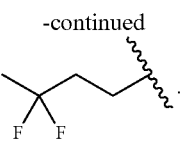

In another aspect, provided herein are compounds of Formula (Va) or (Vb) or pharmaceutically acceptable salts, isomers, stereoisomers, dimers, trimers, tautomers, or N-oxides thereof:

Formula (Va)

Formula (Vb)

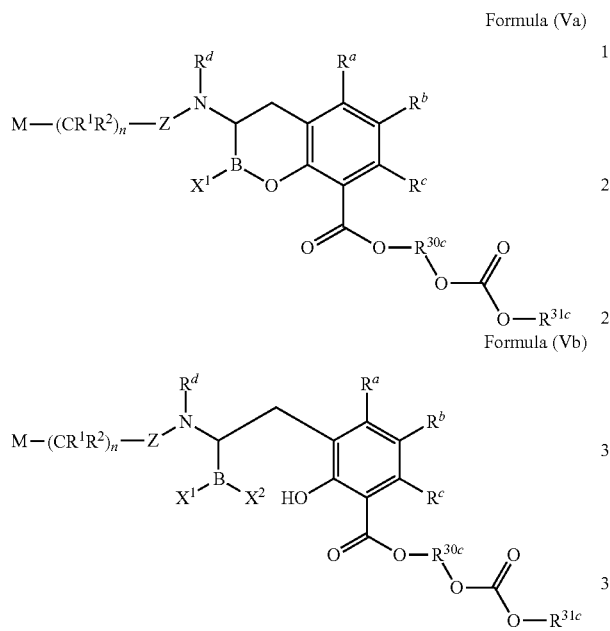

wherein:
M is hydrogen, fluoro, chloro, bromo, —$CF_3$, —CN, —$OR^4$, —$SR^4$, —S(=O)$R^4$, —S(=O)$_2R^4$, —S(=O)$_2$N($R^4R^5$), —N($R^4R^5$), —N($R^4$)C(=O)$R^4$, —N($R^4$)C(=O)N($R^4R^5$), —N($R^4$)S(=O)$_2R^4$, —N($R^4$)Heteroaryl, —C(=O)$R^4$, —C(=O)N($R^4R^5$), —C(=O)($C_1$-$C_3$alkylene)C(=O)$R^4$, optionally substituted oxyimino, optionally substituted alkenyl, optionally substituted alkynyl, heteroaryl, or heterocycloalkyl;
  each $R^1$ and $R^2$ are independently hydrogen, fluoro, chloro, bromo, optionally substituted $C_1$-$C_6$ alkyl, optionally substituted aryl, —$OR^4$, —$SR^4$, or —N($R^4R^5$); or
  $R^1$ and $R^2$ are taken together with the carbon to which they are attached to form an optionally substituted cycloalkyl; or
  when n is at least 2, two $R^1$ on adjacent carbons are taken together to form a double bond; or two $R^1$ and two $R^2$ on adjacent carbons are taken together to form a triple bond;
n is 0, 1, 2, 3, 4, 5, or 6;
$X^1$ and $X^2$ are independently —$OR^4$, or F; when present;
Z is >C(=O), >C(=S), or >S(=O)$_2$;
$R^{30c}$ is —$CH_2$—, —CH($R^{32c}$)—, or —C($R^{32c}$)$_2$—;
$R^{31}c$ is optionally substituted $C_5$-$C_{12}$ alkyl, —($C_1$-$C_6$ alkylene)$OR^4$, —($C_1$-$C_6$ alkylene)$SR^4$, —($C_1$-$C_6$ alkylene)C(=O)$OR^4$, —($C_1$-$C_6$ alkylene)C(=O)N($R^4R^5$), optionally substituted $C_3$-$C_5$ cycloalkyl, optionally substituted —($C_1$-$C_6$ alkylene)($C_3$-$C_5$ cycloalkyl), optionally substituted heterocycloalkyl, optionally substituted alkylheterocycloalkyl, optionally substituted aryl, optionally substituted alkylaryl, optionally substituted heteroaryl, or optionally substituted alkylheteroaryl;
  each $R^{32c}$ are independently optionally substituted $C_1$-$C_6$ alkyl;
  or two $R^{32c}$ are taken together with the carbon to which they are attached to form a cycloalkyl.
$R^a$, $R^b$, and $R^c$ are independently hydrogen, fluoro, chloro, bromo, optionally substituted $C_1$-$C_6$ alkyl, optionally substituted cycloalkyl, optionally substituted heterocycloalkyl, optionally substituted aryl, optionally substituted heteroaryl, —$OR^4$, —N($R^4R^5$), or —$SR^4$;
$R^d$, $R^4$ and $R^5$ are independently hydrogen, —OH, —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;
  or $R^4$ and $R^5$ are taken together with the nitrogen to which they are attached to form a heterocycloalkyl; provided that the compound is not ((((tetrahydro-2H-pyran-4-yl)oxy)carbonyl)oxy)methyl 2-hydroxy-3-(4-oxopentanamido)-3,4-dihydro-2H-benzo[e][1,2]oxaborinine-8-carboxylate.

In some embodiments of a compound of Formula (Va) or (Vb), M is hydrogen, —$CF_3$, —CN, —$OR^4$, —$SR^4$, —C(=O)$R^4$, or alkynyl. In some embodiments of a compound of Formula (Va) or (Vb), M is hydrogen.

In some embodiments of a compound of Formula (Va) or (Vb), each $R^1$ and $R^2$ are independently hydrogen, fluoro, chloro, $C_1$-$C_6$ alkyl, or —$CF_3$.

In some embodiments of a compound of Formula (Va) or (Vb), each $R^1$ and $R^2$ are independently hydrogen or fluoro. In some embodiments of a compound of Formula (Va) or (Vb), each $R^1$ and $R^2$ are hydrogen.

In some embodiments of a compound of Formula (Va) or (Vb), $R^{30c}$ is —$CH_2$—, —CH($CH_3$)—, or —CH(isopropyl). In some embodiments of a compound of Formula (Va) or (Vb), $R^{30c}$ is —$CH_2$— or —CH($CH_3$)—.

In some embodiments of a compound of Formula (Va) or (Vb), $R^{31c}$ is optionally substituted $C_5$-$C_{12}$ alkyl, or optionally substituted $C_3$-$C_5$ cycloalkyl.

In some embodiments of a compound of Formula (Va) or (Vb), $R^{31c}$ is $C_5$-$C_{12}$ alkyl or $C_3$-$C_5$ cycloalkyl; each optionally substituted with halogen, —CN, $C_1$-$C_6$ alkyl, —$CF_3$, cycloalkyl, heterocycloalkyl, —$OR^4$, —N($R^4R^5$), —$SR^4$, —(S=O)$_2R^4$, —C(=O)$OR^4$, or —C(=O)N($R^4R^5$).

In some embodiments of a compound of Formula (Va) or (Vb), $R^{31c}$ is

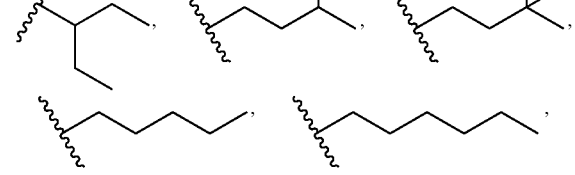

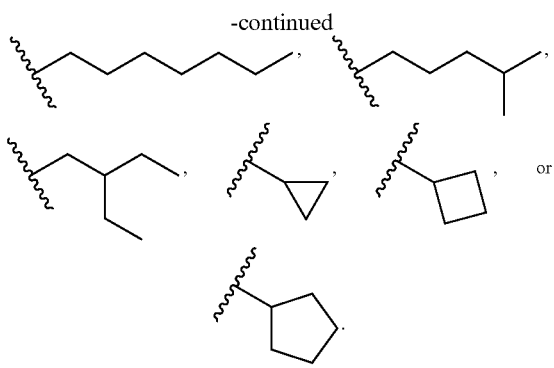

In some embodiments of a compound of Formula (Va) or (Vb), $R^{31c}$ is

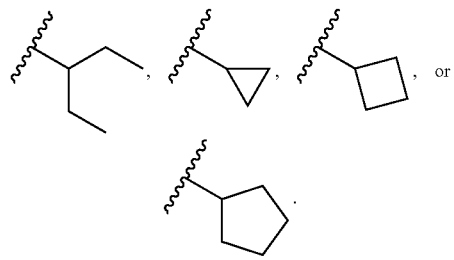

In some embodiments of a compound of Formula (Ia), (Ib), (IIa), (IIb), (IIIa), (IIIb), (IVa), (IVb), (Va), or (Vb), n is 0, 1, 2, or 3. In some embodiments of a compound of Formula (Ia), (Ib), (IIa), (IIb), (IIIa), (IIIb), (IVa), (IVb), (Va), or (Vb), n is 2, 3, or 4. In some embodiments of a compound of Formula (Ia), (Ib), (IIa), (IIb), (IIIa), (IIIb), (IVa), (IVb), (Va), or (Vb), n is 2, 3. In some embodiments of a compound of Formula (Ia), (Ib), (IIa), (IIb), (IIIa), (IIIb), (IVa), (IVb), (Va), or (Vb), n is 1. In some embodiments of a compound of Formula (Ia), (Ib), (IIa), (IIb), (IIIa), (IIIb), (IVa), (IVb), (Va), or (Vb), n is 2. In some embodiments of a compound Formula (Ia), (Ib), (IIa), (IIb), (IIIa), (IIIb), (IVa), (IVb), (Va), or (Vb), n is 3.

In some embodiments of a compound of Formula (Ia), (Ib), (IIa), (IIb), (IIIa), (IIIb), (IVa), (IVb), (Va), or (Vb), $R^a$, $R^b$, and $R^c$ are independently hydrogen, fluoro, optionally substituted $C_1$-$C_6$ alkyl, —$OR^4$, —$N(R^4R^5)$, or —$SR^4$. In some embodiments of a compound of Formula (Ia), (Ib), (IIa), (IIb), (IIIa), (IIIb), (IVa), (IVb), (Va), or (Vb), $R^a$, $R^b$, and $R^c$ are independently hydrogen, fluoro, chloro, —OH, or —$OCH_3$. In some embodiments of a compound of Formula (Ia), (Ib), (IIa), (IIb), (IIIa), (IIIb), (IVa), (IVb), (Va), or (Vb), $R^a$, $R^b$, and $R^c$ are hydrogen.

In some embodiments of a compound of Formula (Ia), (Ib), (IIa), (IIb), (IIIa), (IIIb), (IVa), (IVb), (Va), or (Vb), $X^1$ and $X^2$ are —OH; when present.

In some embodiments of a compound of Formula (Ia), (Ib), (IIa), (IIb), (IIIa), (IIIb), (IVa), (IVb), (Va), or (Vb), $R^d$ is hydrogen or $C_1$-$C_4$ alkyl. In some embodiments of a compound of Formula (Ia), (Ib), (IIa), (IIb), (IIIa), (IIIb), (IVa), (IVb), (Va), or (Vb), $R^d$ is hydrogen.

In some embodiments of a compound of Formula (Ia), (Ib), (IIa), (IIb), (IIIa), (IIIb), (IVa), (IVb), (Va), or (Vb), Z is >C(=O).

In some embodiments of a compound of Formula (Ia), (Ib), (IIa), (IIb), (IIIa), (IIIb), (IVa), (IVb), (Va), or (Vb), $R^4$ and $R^5$ are independently hydrogen or $C_1$-$C_6$ alkyl.

In another aspect, provided herein are pharmaceutical compositions comprising at least one compound of Formula (Ia), (Ib), (IIa), (IIb), (IIIa), (IIIb), (IVa), (IVb), (Va), or (Vb), or pharmaceutically acceptable salts, isomers, stereoisomers, dimers, trimers, tautomers, or N-oxides thereof, and a pharmaceutically acceptable excipient.

In some embodiments, the pharmaceutical composition comprising at least one compound of Formula (Ia), (Ib), (IIa), (IIb), (IIIa), (IIIb), (IVa), (IVb), (Va), or (Vb), or pharmaceutically acceptable salts, isomers, stereoisomers, dimers, trimers, tautomers, or N-oxides thereof, and a pharmaceutically acceptable excipient further comprises a beta-lactam antibiotic. In some embodiments, the beta-lactam antibiotic is a penicillin, cephalosporin, carbapenem, monobactam, bridged monobactam, or a combination thereof In some embodiments, the beta-lactam antibiotic is ertapenem or ceftriaxone.

In a further aspect, provided herein are methods of treating a bacterial infection in a subject, comprising administering to the subject a compound of Formula (Ia), (Ib), (IIa), (IIb), (IIIa), (IIIb), (IVa), (IVb), (Va), or (Vb), or pharmaceutically acceptable salts, isomers, stereoisomers, dimers, trimers, tautomers, or N-oxides thereof In a further aspect, provided herein are methods of treating a bacterial infection in a subject, comprising administering to the subject a compound of Formula (Ia), (Ib), (IIa), (IIb), (IIIa), (Mb), (IVa), (IVb), (Va), or (Vb), or pharmaceutically acceptable salts, isomers, stereoisomers, dimers, trimers, tautomers, or N-oxides thereof, in combination with a therapeutically effective amount of a beta-lactam antibiotic.

In a further aspect, provided herein are methods of treating a bacterial infection in a subject, comprising administering to the subject a pharmaceutical composition comprising at least one compound of Formula (Ia), (Ib), (IIa), (IIb), (IIIa), (Mb), (IVa), (IVb), (Va), or (Vb), or pharmaceutically acceptable salts, isomers, stereoisomers, dimers, trimers, tautomers, or N-oxides thereof, and a pharmaceutically acceptable excipient.

In a further aspect, provided herein are methods of treating a bacterial infection in a subject, comprising administering to the subject a pharmaceutical composition comprising at least one compound of Formula (Ia), (Ib), (IIa), (IIb), (IIIa), (Mb), (IVa), (IVb), (Va), or (Vb), or pharmaceutically acceptable salts, isomers, stereoisomers, dimers, trimers, tautomers, or N-oxides thereof, and a pharmaceutically acceptable excipient in combination with a therapeutically effective amount of a beta-lactam antibiotic.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Beta-lactamases are typically grouped into 4 classes: Ambler classes A, B, C, and D, based on their amino acid sequences. Enzymes in classes A, C, and D are active-site serine beta-lactamases, while class B enzymes are Zn-dependent. Newer generation cephalosporins and carbapenems were developed partly based on their ability to evade the deactivating effect of the early serine-based beta-lactamase variants. However, a recent surge in new versions of serine-based beta-lactamases—for example Class A Extended-Spectrum Beta-Lactamase (ESBL) enzymes, Class A carbapenemases (e.g. KPC-2), chromosomal and plasmid mediated Class C cephalosporinases (AmpC, CMY, etc.), and Class D oxacillinases—as well as Class B metallo-beta-lactamases (e.g. VIM, NDM) has begun to diminish the utility of the beta-lactam antibiotic family, including the more recent generation beta-lactam drugs, leading to a serious medical problem. Indeed, the number of catalogued serine-based beta-lactamases has exploded from less than ten in the 1970s to over 750 variants (see, e.g., Jacoby & Bush, "Amino Acid Sequences for TEM, SHV and OXA Extended-Spectrum and Inhibitor Resistant β-Lactamases", on the Lahey Clinic website).

The commercially available beta-lactamase inhibitors (clavulanic acid, sulbactam, tazobactam) were developed to address the beta-lactamases that were clinically relevant in the 1970s and 1980s (e.g. penicillinases). These enzyme inhibitors are available only as fixed combinations with penicillin derivatives. No combinations with cephalosporins (or carbapenems) are clinically available. This fact, combined with the increased use of newer generation cephalosporins and carbapenems, is driving the selection and spread of the new beta-lactamase variants (ESBLs, carbapenemases, chromosomal and plasmid-mediated Class C, Class D oxacillinases, etc.). While maintaining good inhibitory activity against ESBLs, the legacy beta -lactamase inhibitors are largely ineffective against the new Class A and Class B carbapenemases, against the chromosomal and plasmid-mediated Class C cephalosporinases and against many of the Class D oxacillinases. To address this growing therapeutic vulnerability, a new generation of beta-lactamase inhibitors must be developed with broad spectrum functionality.

Use of a boronic acid compound to inhibit a beta-lactamase enzyme has been limited. For example, U.S. Pat. No. 7,271,186 discloses beta-lactamase inhibitors that target AmpC (from class C). Ness et al. (Biochemistry (2000) 39:5312-21) discloses beta-lactamase inhibitors that target TEM-1 (a non-ESBL TEM variant from class A; one of approximately 140 known TEM-type beta-lactamase variants). Because there are four major molecular classes of serine-based beta-lactamases, and each of these classes contains significant numbers of beta-lactamase variants, inhibition of one or a small number of beta-lactamases is unlikely to be of therapeutic value. Therefore, there is an imperative need to develop novel beta-lactamase inhibitors with broad spectrum functionality. In particular, there is a need for compounds that are active against both serine- and metallo-based beta-lactamase enzymes.

Moreover, these beta-lactamase inhibitor boronic acid compounds are typically not highly absorbed when orally administered. Thus, higher drug dosages may be required for oral administration in order to obtain a therapeutically effective plasma level of the beta-lactamase inhibitors. Since these beta-lactamase inhibitors are usually administered in combination with an oral antibiotic, there is a need to develop novel beta-lactamase inhibitors with oral bioavailability and activity. The novel boronic acid based inhibitors described herein address this medical need.

The present invention is directed to certain boron-based compounds (boronic acids and cyclic boronic acid esters) which are beta-lactamase inhibitors and antibacterial compounds. The present invention is also directed to certain orally bioavailable boron-based compounds (boronic acids and cyclic boronic acid esters) which are beta-lactamase inhibitors and antibacterial compounds. The compounds and their pharmaceutically acceptable salts are useful alone and in combination with beta-lactam antibiotics for the treatment of bacterial infections, particularly antibiotic resistant bacterial infections. Some embodiments include compounds, compositions, pharmaceutical compositions, use and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" means that a particular feature, structure or characteristic described in connection with the embodiment is included in at least one embodiment. Thus, the appearances of the phrases "in one embodiment" or "in an embodiment" or "some embodiments" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a (β-lactam functionality. Non-limiting examples of 0-lactam antibiotics useful with respect to the invention include penicillins, cephalosporins, penems, carbapenems, and monobactams.

The term "β-lactamase" denotes a protein capable of inactivating a β-lactam antibiotic. The (β-lactamase can be an enzyme which catalyzes the hydrolysis of the β-lactam ring of a β-lactam antibiotic. Of particular interest herein are microbial β-lactamases. The β-lactamase may be, for example, a serine (β-lactamase or a metallo-β-lactamase. β-Lactamases of interest include those disclosed in an ongoing website that monitors beta-lactamase nomenclature and in Bush, K. and G. A. Jacoby. 2010. An updated functional classification of β-lactamases. Antimicrob.

Agents Chemother. 54:969-976. β-Lactamases of particular interest herein include β-lactamases found in bacteria such as class A β-lactamases including the SHV, CTX-M and KPC subclasses, class B β-lactamases such as VIM, class C β-lactamases (both chromosomal and plasmid-mediated), and class D β-lactamases. The term "β-lactamase inhibitor" refers to a compound which is capable of inhibiting β-lactamase activity. Inhibiting β-lactamase activity means inhibiting the activity of a class A, B, C, or D (β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" (β-lactamases are understood by those skilled in the art and are described in Bush, K. and G. A. Jacoby. 2010. An updated functional classification of β-lactamases. Antimicrob. Agents Chemother. 54:969-976.

The term "oral bioavailability" (F %) denotes the fraction of an oral administered drug that reaches systemic circulation. After intravenous administration, a drug is directly and fully available in the bloodstream and can be distributed via systemic circulation to the point where a pharmacological effect takes place. If a drug is administered orally, it has to cross further barriers to reach the systemic circulation, which can significantly reduce the final extent of a drug in the bloodstream. Oral bioavailability is one of the most important properties in drug design and development. A high oral bioavailability reduces the amount of an administered drug necessary to achieve a desired pharmacological effect and therefore could reduce the risk of side-effects and toxicity. A poor oral bioavailability can result in low efficacy and higher inter -individual variability and therefore can lead to unpredictable response to a drug. In some embodiments the F % is greater than about 5%, greater than about 10%, greater than about 15%, greater than about 20%, greater than about 25%, greater than about 30%, greater than about 35%, greater than about 40%, greater than about 50%, greater than about 55%, greater than about 60%, greater than about 65%, greater than about 70%, greater than about 75%, greater than about 80%, greater than about 85%, greater than about 90%, or greater than about 95%.

A compound of Formula (I), as described herein, includes a compound of Formula (Ia), (Ib), or pharmaceutically acceptable salts, isomers, stereoisomers, dimers, trimers, tautomers, or N-oxides thereof A compound of Formula (II), as described herein, includes a compound of Formula (IIa), (IIb), or pharmaceutically acceptable salts, isomers, stereoisomers, dimers, trimers, tautomers, or N-oxides thereof A compound of Formula (III), as described herein, includes a compound of Formula (IIIa), (IIIb), or pharmaceutically acceptable salts, isomers, stereoisomers, dimers, trimers, tautomers, or N-oxides thereof A compound of Formula (IV), as described herein, includes a compound of Formula (IVa), (IVb), or pharmaceutically acceptable salts, isomers, stereoisomers, dimers, trimers, tautomers, or N-oxides thereof A compound of Formula (V), as described herein, includes a compound of Formula (Va), (Vb), or pharmaceutically acceptable salts, isomers, stereoisomers, dimers, trimers, tautomers, or N-oxides thereof The terms below, as used herein, have the following meanings, unless indicated otherwise:

"Amino" refers to the —$NH_2$ radical.

"Cyano" or "nitrile" refers to the —CN radical.

"Hydroxy" or "hydroxyl" refers to the —OH radical.

"Nitro" refers to the —$NO_2$ radical.

"Oxo" refers to the =O substituent.

"Oxime" refers to the =N—OH substituent.

"Thioxo" refers to the =S substituent.

"Alkyl" refers to a linear or branched hydrocarbon chain radical which is fully saturated, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl, $C_4$-$C_8$ alkyl, and $C_5$-$C_{12}$ alkyl. Representative alkyl groups include, but are not limited to, methyl, ethyl, n-propyl, 1-methylethyl (isopropyl), n-butyl, i-butyl, s-butyl, n-pentyl, 1,1-dimethylethyl (t-butyl), 2-ethylpropyl, 3-pentyl, 3-methylhexyl, 2-methylhexyl, and the like. Representative linear alkyl groups include, but are not limited to, methyl, ethyl, n-propyl, n-butyl, n-pentyl and the like. Unless stated otherwise specifically in the specification, an alkyl group may be optionally substituted. In some embodiments, an alkyl is optionally substituted with halogen, —CN, —$CF_3$, cycloalkyl, heterocycloalkyl, —$OR^4$, —$N(R^4R^5)$, —$SR^4$, -(S=O)$_2R^4$, —C(=O)$OR^4$, or —C(=O)$N(R^4R^5)$ and $R^4$ and $R^5$ as defined in the detailed description. In some embodiments, an alkyl is optionally substituted with halogen, —CN, —$CF_3$, —OH, —OMe, —$NH_2$, —C(=O)OH, —C(=O)OMe, or —C(=O)$NH_2$.

"Alkenyl" refers to a straight or branched hydrocarbon chain radical, containing at least one carbon- carbon double bond. Alkenyls comprising any number of carbon atoms from 2 to 30 are included. An alkenyl comprising up to 30 carbon atoms is referred to as a $C_2$-$C_{30}$ alkenyl, likewise, for example, an alkenyl comprising up to 12 carbon atoms is a $C_2$-$C_{12}$ alkenyl. Alkenyl groups include, but are not limited to, $C_2$-$C_{30}$ alkenyl, $C_2$-$C_{20}$ alkenyl, $C_2$-$C_{15}$ alkenyl, $C_2$-$C_{10}$ alkenyl, $C_2$-$C_8$ alkenyl, $C_2$-$C_6$ alkenyl, $C_2$-$C_4$ alkenyl, $C_2$-$C_3$ alkenyl, $C_3$-$C_8$ alkenyl, $C_4$-$C_8$ alkenyl, and $C_5$-$C_{12}$ alkenyl. The alkenyl may be attached to the rest of the molecule by a single bond, for example, ethenyl (i.e., vinyl), prop-1-enyl (i.e., allyl), but-1-enyl, pent-1-enyl, penta-1,4-dienyl, and the like. Alkenyl may be attached to the rest of the molecule by a double bond, e.g., =$CH_2$, =$CH(CH_2)_3CH_3$. Unless stated otherwise specifically in the specification, an alkenyl group may be optionally substituted as described below. In some embodiments, an alkenyl is optionally substituted with halogen, —CN, —$CF_3$, cycloalkyl, heterocycloalkyl, —$OR^4$, —$N(R^4R^5)$, —$SR^4$, —(S=O)$_2R^4$, —C(=O)$OR^4$, or —C(=O)$N(R^4R^5)$ and $R^4$ and $R^5$ as defined in the detailed description. In some embodiments, an alkenyl is optionally substituted with halogen, —CN, —$CF_3$, —OH, —OMe, —$NH_2$, —C(=O)OH, —C(=O)OMe, or —C(=O)$NH_2$.

"Alkynyl" refers to a straight or branched hydrocarbon chain radical, containing at least one carbon- carbon triple bond. Alkynyls comprising any number of carbon atoms from 2 to 30 are included. An alkynyl comprising up to 30 carbon atoms is referred to as a $C_2$-$C_{30}$ alkynyl, likewise, for example, an alkynyl comprising up to 12 carbon atoms is a $C_2$-$C_{12}$ alkynyl. Alkynyl groups include, but are not limited to, $C_2$-$C_{30}$ alkynyl, $C_2$-$C_{20}$ alkynyl, $C_2$-$C_{15}$ alkynyl, $C_2$-$C_{10}$ alkynyl, $C_2$-$C_8$ alkynyl, $C_2$-$C_6$ alkynyl, $C_2$-$C_4$ alkynyl, $C_2$-$C_3$ alkynyl, $C_3$-$C_8$ alkynyl, $C_4$-$C_8$ alkynyl, and $C_5$-$C_{12}$ alkynyl. The alkynyl may be attached to the rest of the molecule by a single bond, for example, ethynyl, propynyl, butynyl, pentynyl, hexynyl, and the like. Unless stated otherwise specifically in the specification, an alkynyl group may be optionally substituted. In some embodiments, an alkynyl is optionally substituted with halogen, —CN, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$) and R$^4$ and R$^5$ as defined in the detailed description. In some embodiments, an alkynyl is optionally substituted with halogen, —CN, —CF$_3$, —OH, —OMe, —NH$_2$, —C(=O)OH, —C(=O)OMe, or —C(=O)NH$_2$.

"Alkylene" or "alkylene chain" refers to a linear or branched divalent hydrocarbon chain, as described for alkyl above. Alkylenes comprising any number of carbon atoms from 1 to 30 are included. An alkylene comprising up to 30 carbon atoms is referred to as a C$_1$-C$_{30}$ alkylene, likewise, for example, an alkylene comprising up to 12 carbon atoms is a C$_1$-C$_{12}$ alkylene. Alkylenes (and other moieties defined herein) comprising other numbers of carbon atoms are represented similarly. Alkylene groups include, but are not limited to, C$_1$-C$_{30}$ alkylene, C$_1$-C$_{20}$ alkylene, C$_1$-C$_{15}$ alkylene, C$_1$-C$_{10}$ alkylene, C$_1$-C$_8$ alkylene, C$_1$-C$_6$ alkylene, C$_1$-C$_4$ alkylene, C$_1$-C$_3$ alkylene, and C$_1$-C$_2$ alkylene. Representative alkylene groups include, but are not limited to, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH(CH$_3$)—, —CH(CH$_3$)$_2$—, and the like. Alkyl comprising unsaturations include alkenylene and alkynylene groups. Unless stated otherwise specifically in the specification, an alkylene group may be optionally substituted. In some embodiments, an alkylene is optionally substituted with halogen, —CN, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$) and R$^4$ and R$^5$ as defined in the detailed description. In some embodiments, an alkylene is optionally substituted with halogen, —CN, —CF$_3$, —OH, —OMe, —NH$_2$, —C(=O)OH, —C(=O)OMe, or —C(=O)NH$_2$.

"Alkoxy" refers to a radical of the formula —ORa where Ra is an alkyl radical as defined. Unless stated otherwise specifically in the specification, an alkoxy group may be optionally substituted. In some embodiments, an alkoxy is optionally substituted with halogen, —CN, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$) and R$^4$ and R$^5$ as defined in the detailed description. In some embodiments, an alkoxy is optionally substituted with halogen, -CN, —CF$_3$, —OH, —OMe, —NH$_2$, —C(=O)OH, —C(=O)OMe, or —C(=O)NH$_2$.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted. In some embodiments, an aryl is optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$) and R$^4$ and R$^5$ as defined in the detailed description. In some embodiments, an aryl is optionally substituted with halogen, —CN, methyl, ethyl, propyl, —CF$_3$, —OH, —OMe, —NH$_2$, —C(=O)OH, —C(=O)OMe, or —C(=O)NH$_2$.

"Cycloalkyl" or "carbocycle" refers to a stable, non-aromatic, monocyclic or polycyclic carbocyclic ring, which may include fused (when fused with an aryl or a heteroaryl ring, the cycloalkyl is bonded through a non-aromatic ring atom) or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo [3.3.0] octane, bicyclo [4.3.0]nonane, cis-decalin, trans-decalin, bicyclo [2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. In some embodiments, a cycloalkyl is optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$) and R$^4$ and R$^5$ as defined in the detailed description. In some embodiments, a cycloalkyl is optionally substituted with halogen, —CN, methyl, ethyl, propyl, —CF$_3$, —OH, —OMe, —NH$_2$, —C(=O)OH, —C(=O)OMe, or —C(=O)NH$_2$.

"Fused" refers to any ring structure described herein which is fused to an existing ring structure. When the fused ring is a heretocycloalkyl ring or a heteroaryl ring, any carbon atom on the existing ring structure which becomes part of the fused heretocycloalkyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —ORa where Ra is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized; and the heterocycloalkyl radical may be partially or fully saturated. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted. In some embodiments, a heterocycloalkyl is optionally substituted with halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$ and $R^4$ and $R^5$ as defined in the detailed description. In some embodiments, a heterocycloalkyl is optionally substituted with halogen, —CN, methyl, ethyl, propyl, —$CF_3$, —OH, —OMe, —$NH_2$, —$C(=O)OH$, —$C(=O)OMe$, or —$C(=O)NH_2$.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted. In some embodiments, a heteroaryl is optionally substituted with halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$ and $R^4$ and $R^5$ as defined in the detailed description. In some embodiments, an heteroaryl is optionally substituted with halogen, —CN, methyl, ethyl, propyl, —$CF_3$, —OH, —OMe, —$NH_2$, —$C(=O)OH$, —$C(=O)OMe$, or —$C(=O)NH_2$.

All the above groups may be either substituted or unsubstituted. The term "substituted" as used herein means any of the above groups (e.g., alkyl, alkenyl, alkynyl, alkylene, alkoxy, aryl, cycloalkyl, haloalkyl, heterocycloalkyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —$CO_2H$, nitrile, nitro, hydroxyl, thiooxy, alkyl, alkylene, alkoxy, aryl, cycloalkyl, heterocycloalkyl, heteroaryl, dialkylamines, arylamines, alkylarylamines, diarylamines, trialkylammonium (—$N^+R_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NH_2$, —$NRgC(=O)$ $NRgRh$, —$NRgC(=O)ORh$, —$NRgSO_2Rh$, —$OC(=O)$ $NRgRh$, —$ORg$, —$SRg$, —$SORg$, —$SO_2Rg$, —$OSO_2Rg$, —$SO_2ORg$, =$NSO_2Rg$, and —$SO_2NRgRh$. In the foregoing, Rg and Rh are the same or different and independently hydrogen, alkyl, alkoxy, alkylamino, thioalkyl, aryl, aralkyl, cycloalkyl, cycloalkylalkyl, haloalkyl, heterocycloalkyl, N-heterocycloalkyl, heterocycloalkylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_2$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). It will be understood by those skilled in the art with respect to any group containing one or more substituents that such groups are not intended to introduce any substitution or substitution patterns that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

Compounds

Described herein are compounds that modulate the activity of beta-lactamase. In some embodiments, the compounds described herein inhibit beta-lactamase. In certain embodiments, the compounds described herein are orally bioavailable. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula (Ia) or (Ib) or pharmaceutically acceptable salts, isomers, stereoisomers, dimers, trimers, tautomers, or N-oxides thereof:

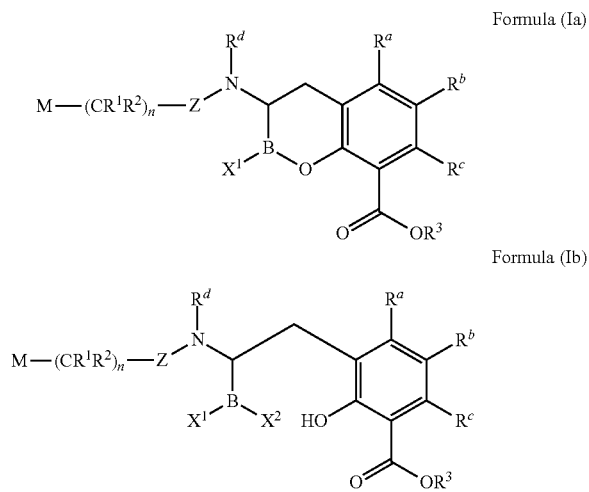

Formula (Ia)

Formula (Ib)

wherein:

M is hydrogen, fluoro, chloro, bromo, —$CF_3$, —CN, —$OR^4$, —$SR^4$, —S(=O)$R^4$, —S(=O)$_2R^4$, —S(=O)$_2$N($R^4R^5$), —N($R^4R^5$), —N($R^4$)C(=O)$R^4$, —N($R^4$)C(=O)N($R^4R^5$), —N($R^4$)S(=O)$_2R^4$, —N($R^4$)Heteroaryl, —C(=O)$R^4$, —C(=O)N($R^4R^5$), —C(=O)($C_1$-$C_3$alkylene)C(=O)$R^4$, optionally substituted oxyimino, optionally substituted alkenyl, optionally substituted alkynyl, optionally substituted heteroaryl, or optionally substituted heterocycloalkyl;

each $R^1$ and $R^2$ are independently hydrogen, fluoro, chloro, bromo, optionally substituted $C_1$-$C_6$ alkyl, optionally substituted aryl, —$OR^4$, —$SR^4$, or —N($R^4R^5$); or $R^1$ and $R^2$ are taken together with the carbon to which they are attached to form an optionally substituted cycloalkyl; or when n is at least 2, two $R^1$ on adjacent carbons are taken together to form a double bond; or two $R^1$ and two $R^2$ on adjacent carbons are taken together to form a triple bond;

provided that M is —$CF_3$ or at least one of $R^1$ or $R^2$ is fluoro;

n is 0, 1, 2, 3, 4, 5, or 6;

$X^1$ and $X^2$ are independently —$OR^4$, or F; when present;

Z is >C(=O), >C(=S), or >S(=O)$_2$;

$R^3$ is $R^{31}$, —($R^{30}$)$_q$O$R^{31}$, —($R^{30}$)$_q$O($R^{30}$)$_q$O$R^{31}$, —$R^{30}$OC(=O)$R^{31}$, —$R^{30}$OC(=O)O$R^{31}$, —$R^{30}$OC(=O)NHR$^{31}$, —$R^{30}$OC(=O)N($R^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each q is independently 1, 2, 3, 4, 5, or 6;

each $R^{30}$ is independently —$CH_2$—, —CH($R^{32}$)—, or —C($R^{32}$)$_2$—;

each $R^{31}$ is independently optionally substituted $C_1$-$C_{12}$ alkyl, optionally substituted alkoxyalkyl, optionally substituted $C_1$-$C_{12}$ alkenyl, optionally substituted $C_1$-$C_{12}$ alkynyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; or two $R^{31}$ are taken together with the nitrogen to which they are attached to form a heterocycloalkyl;

each $R^{32}$ is independently optionally substituted $C_1$-$C_6$ alkyl;

or two $R^{32}$ are taken together with the carbon to which they are attached to form a cycloalkyl;

$R^a$, $R^b$, and $R^c$ are independently hydrogen, fluoro, chloro, bromo, optionally substituted $C_1$-$C_6$ alkyl, optionally substituted cycloalkyl, optionally substituted heterocycloalkyl, optionally substituted aryl, optionally substituted heteroaryl, —$OR^4$, —N($R^4R^5$), or —$SR^4$;

$R^d$, $R^4$ and $R^5$ are independently hydrogen, —OH, —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ are taken together with the nitrogen to which they are attached to form a heterocycloalkyl.

In some embodiments of a compound of Formula (Ia) or (Ib), M is —$CF_3$. In some embodiments of a compound of Formula (Ia) or (Ib), M is not —$CF_3$.

In some embodiments of a compound of Formula (Ia) or (Ib), M is hydrogen, —$CF_3$, —CN, —$OR^4$, —$SR^4$, —C(=O)$R^4$, or alkynyl. In some embodiments of a compound of Formula (Ia) or (Ib), M is hydrogen, —CN, —$OR^4$, —$SR^4$, —C(=O)$R^4$, or alkynyl. In some embodiments of a compound of Formula (Ia) or (Ib), M is hydrogen or —$CF_3$.

In some embodiments of a compound of Formula (Ia) or (Ib), M is —CN. In some embodiments of a compound of Formula (Ia) or (Ib), M is $SR^4$. In some embodiments of a compound of Formula (Ia) or (Ib), M is $SR^4$ and $R^4$ is $C_1$-$C_4$ alkyl. In some embodiments of a compound of Formula (Ia) or (Ib), M is $SR^4$ and $R^4$ is methyl. In some embodiments of a compound of Formula (Ia) or (Ib), M is —C(=O)$R^4$. In some embodiments of a compound of Formula (Ia) or (Ib), M is —C(=O)$R^4$ and $R^4$ is $C_1$-$C_4$ alkyl. In some embodiments of a compound of Formula (Ia) or (Ib), M is —C(=O)$R^4$ and $R^4$ is methyl. In some embodiments of a compound of Formula (Ia) or (Ib), M is alkynyl. In some embodiments of a compound of Formula (Ia) or (Ib), M is hydrogen.

In some embodiments of a compound of Formula (Ia) or (Ib), each $R^1$ and $R^2$ are independently hydrogen, fluoro, chloro, bromo, optionally substituted $C_1$-$C_6$ alkyl, optionally substituted aryl, —$OR^4$, —$SR^4$, or —$N(R^4R^5)$. In some embodiments of a compound of Formula (Ia) or (Ib), each $R^1$ and $R^2$ are independently hydrogen, fluoro, chloro, $C_1$-$C_6$ alkyl, or —$CF_3$. In some embodiments of a compound of Formula (Ia) or (Ib), each $R^1$ and $R^2$ are independently hydrogen or fluoro. In some embodiments of a compound of Formula (Ia) or (Ib), $R^1$ and $R^2$ are taken together with the carbon to which they are attached to form a cycloalkyl. In some embodiments of a compound of Formula (Ia) or (Ib), when n is at least 2, two $R^1$ on adjacent carbons are taken together to form a double bond; or two $R^1$ and two $R^2$ on adjacent carbons are taken together to form a triple bond.

In some embodiments of a compound of Formula (Ia) or (Ib), at least one of $R^1$ or $R^2$ is fluoro. In some embodiments of a compound of Formula (Ia) or (Ib), at least two of $R^1$ or $R^2$ are fluoro. In some embodiments of a compound of Formula (Ia) or (Ib), at least three of $R^1$ or $R^2$ are fluoro. In some embodiments of a compound of Formula (Ia) or (Ib), two of $R^1$ or $R^2$ are fluoro on the same carbon. In some embodiments of a compound of Formula (Ia) or (Ib), two of $R^1$ or $R^2$ are fluoro on adjacent carbon.

In some embodiments of a compound of Formula (Ia) or (Ib), M is hydrogen, —CN, —$OR^4$, —$SR^4$, —C(=O)$R^4$, or alkynyl; and at least one of $R^1$ or $R^2$ is fluoro. In some embodiments of a compound of Formula (Ia) or (Ib), M is hydrogen, —CN, —$OR^4$, —$SR^4$, —C(=O)$R^4$, or alkynyl; and at least two of $R^1$ or $R^2$ is fluoro. In some embodiments of a compound of Formula (Ia) or (Ib), M is hydrogen, —CN, —$OR^4$, —$SR^4$, —C(=O)$R^4$, or alkynyl; and at least three of $R^1$ or $R^2$ is fluoro.

In some embodiments of a compound of Formula (Ia) or (Ib), M is —$CF_3$; and at least one of $R^1$ or $R^2$ is fluoro. In some embodiments of a compound of Formula (Ia) or (Ib), M is —$CF_3$; and at least two of $R^1$ or $R^2$ is fluoro. In some embodiments of a compound of Formula (Ia) or (Ib), M is —$CF_3$; and at least three of $R^1$ or $R^2$ is fluoro. In some embodiments of a compound of Formula (Ia) or (Ib), M is —$CF_3$; and each $R^1$ and each $R^2$ are hydrogen.

In some embodiments of a compound of Formula (Ia) or (Ib),

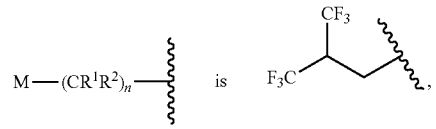

In some embodiments of a compound of Formula (Ia) or (Ib),

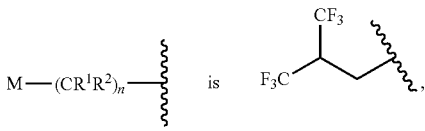

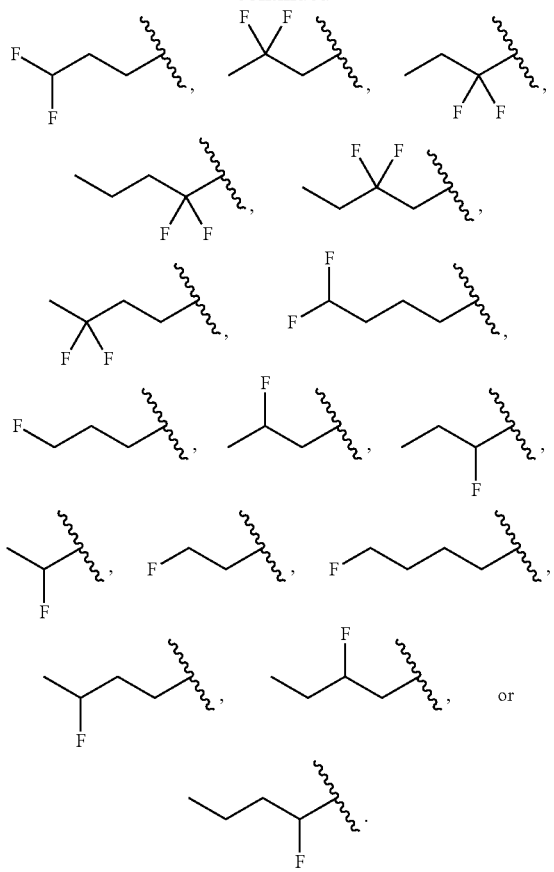

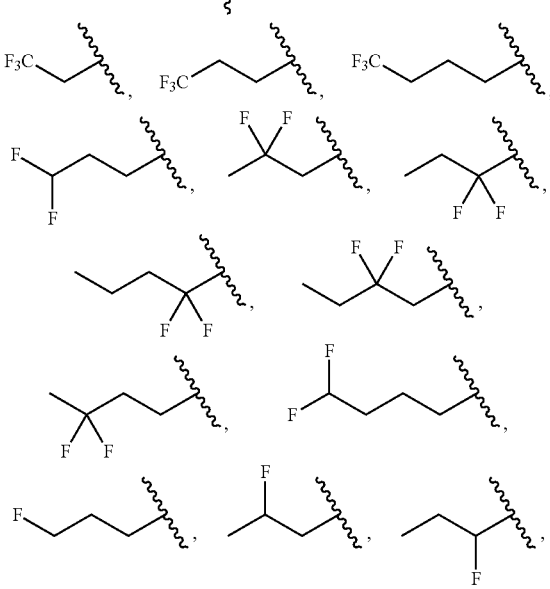

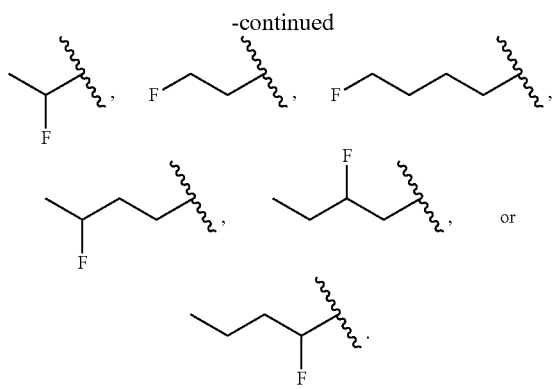

In some embodiments of a compound of Formula (Ia) or (Ib),

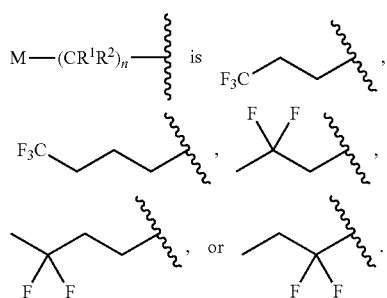

In some embodiments of a compound of Formula (Ia) or (Ib),

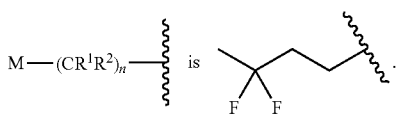

In some embodiments of a compound of Formula (Ia) or (Ib), $R^3$ is $R^{31}$, —$R^{30}OC(=O)R^{31}$, or —$R^{30}OC(=O)OR^{31}$.

In some embodiments of a compound of Formula (Ia) or (Ib), $R^3$ is $R^{31}$; and $R^{31}$ is optionally substituted $C_1$-$C_{12}$ alkyl, optionally substituted alkylaryl, optionally substituted heterocycloalkyl, optionally substituted alkylcycloalkyl, or optionally substituted alkylheterocycloalkyl.

In some embodiments of a compound of Formula (Ia) or (Ib), $R^3$ is $R^{31}$; and $R^{31}$ is $C_1$-$C_{12}$ alkyl, alkylaryl, heterocycloalkyl, alkylcycloalkyl, or alkylheterocycloalkyl; each optionally substituted with halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$.

In some embodiments of a compound of Formula (Ia) or (Ib), $R^3$ is $R^{31}$; and $R^{31}$ is $C_1$-$C_{12}$ alkyl, —$(C_1$-$C_6$ alkylene)$S(=O)_2R^4$, or —$(C_1$-$C_6$ alkylene)$C(=O)N(R^4R^5)$.

In some embodiments of a compound of Formula (Ia) or (Ib), $R^3$ is $R^{31}$; and $R^{31}$ is $C_1$-$C_{12}$ alkyl, alkylaryl, heterocycloalkyl, or alkylheterocycloalkyl.

In some embodiments of a compound of Formula (Ia) or (Ib), $R^3$ is $R^{31}$; and $R^{31}$ is $C_1$-$C_{12}$ alkyl. In some embodiments of a compound of Formula (Ia) or (Ib), $R^3$ is $R^{31}$; and $R^{31}$ is methyl, ethyl, propyl, isopropyl, butyl, isobutyl, tert-butyl, pentyl, isopentyl, hexyl, 5-methylhexyl, 3,3-dimethylbutyl, 2-ethylbutyl, or heptyl. In some embodiments of a compound of Formula (Ia) or (Ib), $R^3$ is $R^{31}$; and $R^{31}$ is isobutyl, pentyl, isopentyl, hexyl, 5-methylhexyl, 3,3-dimethylbutyl, 2-ethylpropyl, 3-pentyl, 2-ethylbutyl, or heptyl.

In some embodiments of a compound of Formula (Ia) or (Ib), $R^3$ is $R^{31}$; and $R^{31}$ is $C_1$-$C_{12}$ alkyl. In some embodiments of a compound of Formula (Ia) or (Ib), $R^3$ is $R^{31}$; and $R^{31}$ is methyl, ethyl, propyl, isopropyl, butyl, isobutyl, tert-butyl, pentyl, isopentyl, hexyl, 5-methylhexyl, 3,3-dimethylbutyl, 2-ethylbutyl, or heptyl. In some embodiments of a compound of Formula (Ia) or (Ib), $R^3$ is $R^{31}$; and $R^{31}$ is isobutyl, pentyl, isopentyl, hexyl, 5-methylhexyl, 3,3-dimethylbutyl, 2-ethylbutyl, or heptyl.

In some embodiments of a compound of Formula (Ia) or (Ib), $R^3$ is $R^{31}$; and $R^{31}$ is —$(C_1$-$C_6$ alkylene)$S(=O)_2R^4$. In some embodiments of a compound of Formula (Ia) or (Ib), $R^3$ is $R^{31}$; $R^{31}$ is —$(C_1$-$C_6$ alkylene)$S(=O)_2R^4$; and $R_4$ is $C_1$-$C_6$ alkyl. In some embodiments of a compound of Formula (Ia) or (Ib), $R^3$ is $R^{31}$; $R^{31}$ is —$(C_1$ alkylene)$S(=O)_2R^4$; and $R_4$ is $C_1$-$C_6$ alkyl. In some embodiments of a compound of Formula (Ia) or (Ib), $R^3$ is $R^{31}$; $R^{31}$ is —$(C_2$ alkylene)$S(=O)_2R^4$; and $R_4$ is $C_1$-$C_6$ alkyl.

In some embodiments of a compound of Formula (Ia) or (Ib), $R^3$ is $R^{31}$; and $R^{31}$ is —$(C_1$-$C_6$ alkylene)$C(=O)N(R^4R^5)$. In some embodiments of a compound of Formula (Ia) or (Ib), $R^3$ is $R^{31}$; $R^{31}$ is —$(C_1$-$C_6$ alkylene)$C(=O)N(R^4R^5)$; and $R^4$ and $R^5$ are independently hydrogen or $C_1$-$C_6$ alkyl. In some embodiments of a compound of Formula (Ia) or (Ib), $R^3$ is $R^{31}$; $R^{31}$ is —$(C_1$-$C_6$ alkylene)$C(=O)N(R^4R^5)$; and $R^4$ and $R^5$ are independently $C_1$-$C_6$ alkyl. In some embodiments of a compound of Formula (Ia) or (Ib), $R^3$ is $R^{31}$; $R^{31}$ is —$(C_1$ alkylene)$C(=O)N(R^4R^5)$; and $R^4$ and $R^5$ are independently hydrogen or $C_1$-$C_6$ alkyl. In some embodiments of a compound of Formula (Ia) or (Ib), $R^3$ is $R^{31}$; $R^{31}$ is —$(C_2$ alkylene)$C(=O)N(R^4R^5)$; and $R^4$ and $R^5$ are independently hydrogen or $C_1$-$C_6$ alkyl.

In some embodiments of a compound of Formula (Ia) or (Ib), $R^3$ is $R^{31}$; and $R^{31}$ is:

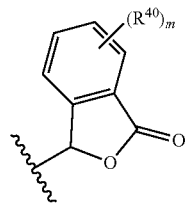

wherein:
each $R^{4o}$ is independently hydrogen, halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$; and
m is 0, 1, 2, 3, or 4.

In some embodiments of a compound of Formula (Ia) or (Ib), m is 0. In some embodiments of a compound of Formula (Ia) or (Ib), m is 1. In some embodiments of a compound of Formula (Ia) or (Ib), m is 2. In some embodiments of a compound of Formula (Ia) or (Ib), m is 1; and $R^{4o}$ is halogen, —CN, $C_1$-$C_6$ alkyl, —$CF_3$, —$OR^4$, or —$N(R^4R^5)$. In some embodiments of a compound of Formula (Ia) or (Ib), m is 2; and each $R^{40}$ are independently halogen, —CN, $C_1$-$C_6$ alkyl, —$CF_3$, —$OR^4$, or —$N(R^4R^5)$. In some embodiments of a compound of Formula (Ia) or (Ib), $R^{40}$ is hydrogen.

In some embodiments of a compound of Formula (Ia) or (Ib), $R^3$ is $R^{31}$; and $R^{31}$ is:

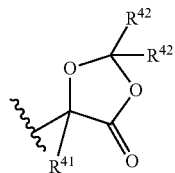

wherein:
each $R^{41}$ and $R^{42}$ are independently hydrogen, halogen, —CN, $C_1$-$C_6$ alkyl, —$CF_3$, cycloalkyl, heterocycloalkyl, —$OR^4$, —$N(_R4_R5)$, —$SR^4$, —$(S=O)_2R^4$, —$C(=O)OR^4$, or —$C(=O)N(R^4R^5)$.

In some embodiments of a compound of Formula (Ia) or (Ib), each $R^{41}$ and $R^{42}$ are independently $C_1$-$C_6$ alkyl. In some embodiments of a compound of Formula (Ia) or (Ib), each $R^{41}$ and $R^{42}$ are independently methyl or ethyl. In some embodiments of a compound of Formula (Ia) or (Ib), $R^{41}$ and each $R^{42}$ are methyl.

In some embodiments of a compound of Formula (Ia) or (Ib), wherein $R^3$ is $R^{31}$; and $R^{31}$ is:

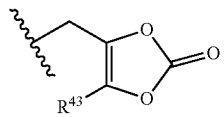

wherein:
$R^{43}$ is hydrogen, halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$.

In some embodiments of a compound of Formula (Ia) or (Ib), $R^{43}$ is hydrogen, $C_1$-$C_6$ alkyl, cycloalkyl, or heterocycloalkyl. In some embodiments of a compound of Formula (Ia) or (Ib), $R^{43}$ is hydrogen or $C_1$-$C_6$ alkyl. In some embodiments of a compound of Formula (Ia) or (Ib), $R^{43}$ is $C_1$-$C_6$ alkyl. In some embodiments of a compound of Formula (Ia) or (Ib), $R^{43}$ is methyl, ethyl, propyl, isopropyl, butyl or isobutyl. In some embodiments of a compound of Formula (Ia) or (Ib), $R^{43}$ is methyl. In some embodiments of a compound of Formula (Ia) or (Ib), $R^{43}$ is isobutyl.

In some embodiments of a compound of Formula (Ia) or (Ib), $R^3$ is $R^{31}$; and $R^{31}$ is:

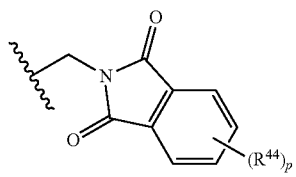

wherein:
$R^{44}$ is hydrogen, halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$; and
p is 0, 1, 2, 3, or 4.

In some embodiments of a compound of Formula (Ia) or (Ib), p is 0. In some embodiments of a compound of Formula (Ia) or (Ib), p is 1. In some embodiments of a compound of Formula (Ia) or (Ib), p is 2. In some embodiments of a compound of Formula (Ia) or (Ib), p is 1; and $R^{44}$ is halogen, —CN, $C_1$-$C_6$ alkyl, —$CF_3$, —$OR^4$, or —$N(R^4R^5)$. In some embodiments of a compound of Formula (Ia) or (Ib), p is 2; and each $R^{44}$ is independently halogen, —CN, $C_1$-$C_6$ alkyl, —$CF_3$, —$OR^4$, or —$N(R^4R^5)$. In some embodiments of a compound of Formula (Ia) or (Ib), $R^{44}$ is hydrogen.

In some embodiments of a compound of Formula (Ia) or (Ib), $R^3$ is $R^{31}$; and $R^{31}$ is alkylaryl. In some embodiments of a compound of Formula (Ia) or (Ib), $R^3$ is $R^{31}$; and $R^{31}$ is —($C_1$-$C_6$ alkylene)aryl. In some embodiments of a compound of Formula (Ia) or (Ib), $R^3$ is $R^{31}$; $R^{31}$ is —($C_1$-$C_2$ alkylene)aryl; and aryl is phenyl. In some embodiments of a compound of Formula (Ia) or (Ib), $R^3$ is $R^{31}$; and $R^{31}$ is benzyl optionally substituted with halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$.

In some embodiments of a compound of Formula (Ia) or (Ib), $R^3$ is $R^{31}$; and $R^{31}$ is heterocycloalkyl. In some embodiments of a compound of Formula (Ia) or (Ib), $R^3$ is $R^{31}$; and $R^{31}$ is aziridinyl, azetidinyl, pyrrolidinyl, piperidinyl, piperazinyl, morpholinyl, tetrahydropyranyl, isobenzofuranone, and 2,2,5-trimethyl-1,3-dioxolan-4-one.

In some embodiments of a compound of Formula (Ia) or (Ib), $R^3$ is $R^{31}$; and $R^{31}$ is alkylcycloalkyl. In some embodiments of a compound of Formula (Ia) or (Ib), $R^3$ is $R^{31}$; and $R^{31}$ is —($C_1$-$C_6$ alkylene)cycloalkyl. In some embodiments of a compound of Formula (Ia) or (Ib), $R^3$ is $R^{31}$; $R^{31}$ is —($C_1$-$C_2$ alkylene)cycloalkyl and the cycloalkyl is cyclopropyl, cyclobutyl, cyclopentyl, cyclohexyl, or cycloheptyl.

In some embodiments of a compound of Formula (Ia) or (Ib), $R^3$ is $R^{31}$; and $R^{31}$ is alkylheterocycloalkyl. In some embodiments of a compound of Formula (Ia) or (Ib), $R^3$ is $R^{31}$; and $R^{31}$ is —($C_1$-$C_6$ alkylene)heterocycloalkyl. In some embodiments of a compound of Formula (Ia) or (Ib), $R^3$ is $R^{31}$; $R^{31}$ is —($C_1$-$C_6$ alkylene)heterocycloalkyl; and the heterocycloalkyl is aziridinyl, azetidinyl, pyrrolidinyl, piperidinyl, piperazinyl, morpholinyl, tetrahydropyranyl, 4-methyl-1,3-dioxo1-2-one, or isoindoline-1,3-dione.

In some embodiments of a compound of Formula (Ia) or (Ib), $R^3$ is $R^{31}$; and $R^{31}$ is

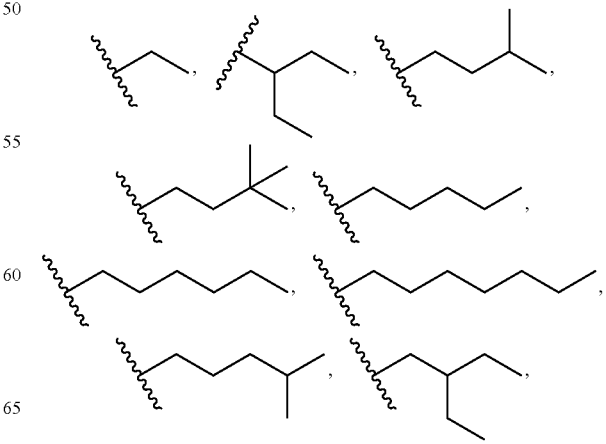

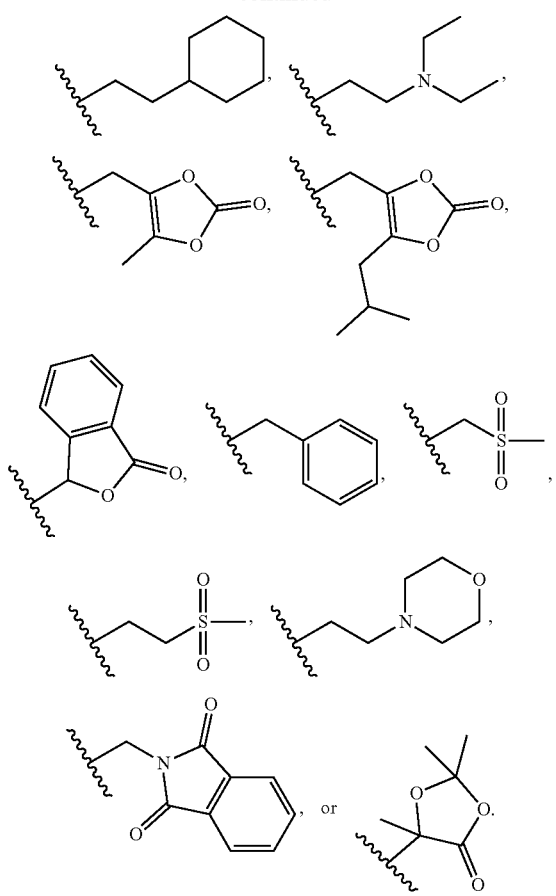
In some embodiments of a compound of Formula (Ia) or (Ib), $R^3$ is $R^{31}$; and $R^{31}$ is
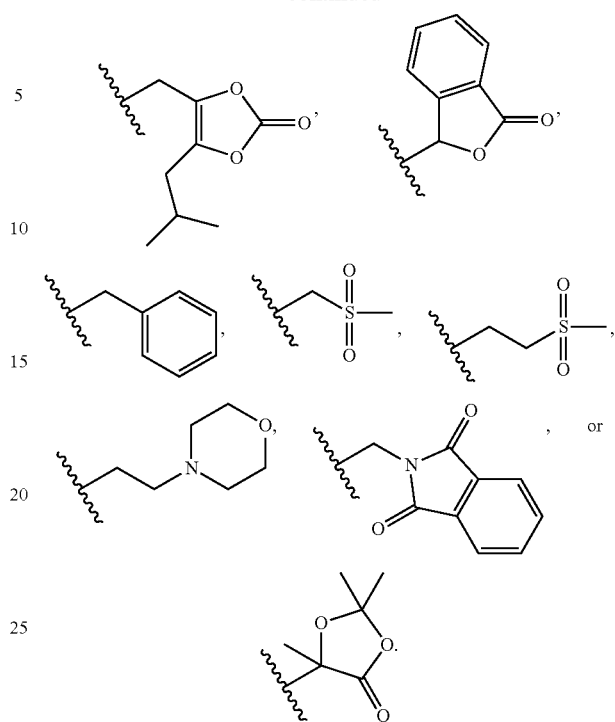
In some embodiments of a compound of Formula (Ia) or (Ib), $R^3$ is $R^{31}$; and $R^{31}$ is
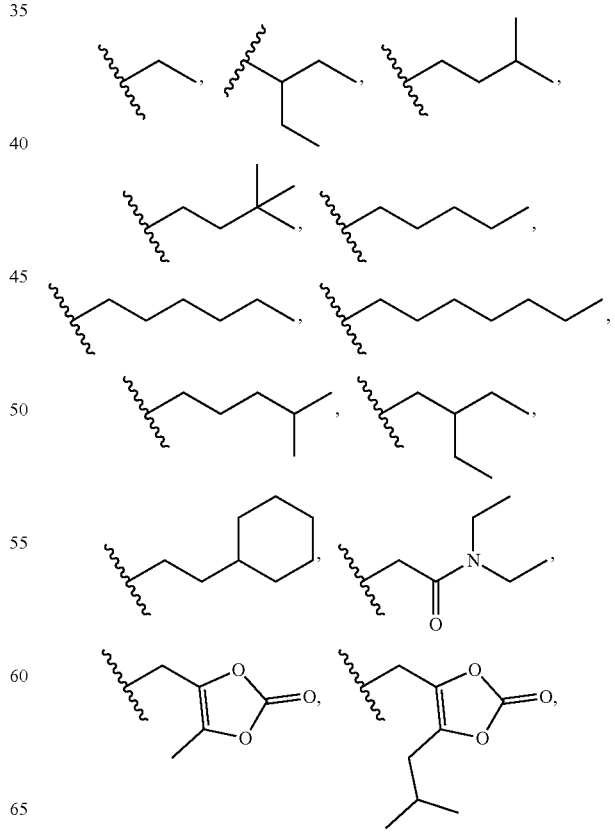

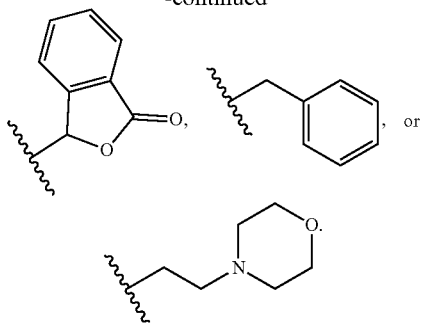

In some embodiments of a commund of Formula (Ia.) or (Ib), $R^3$ is $R^{31}$; and $R^{31}$ is

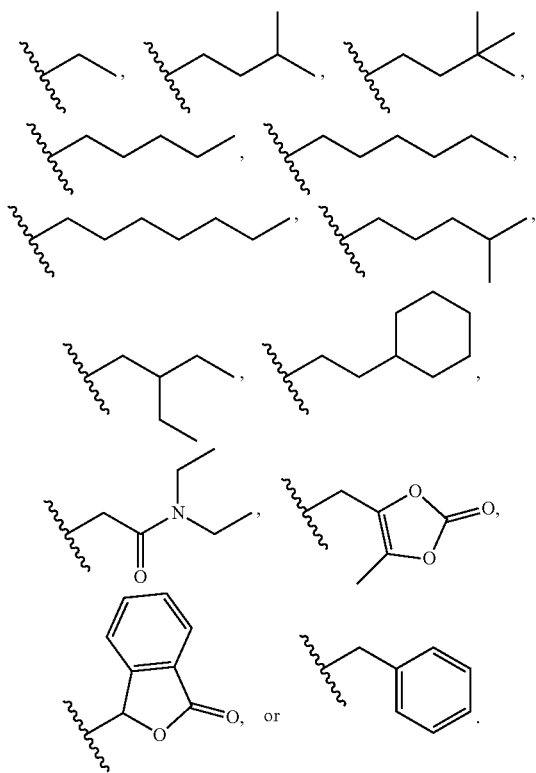

In some embodiments of a compound of Formula (Ia) or (Ib), $R^3$ is $-R^{30}OC(=O)R^{31}$. In some embodiments of a compound of Formula (Ia) or (Ib), $R^3$ is $-R^{30}OC(=O)R^{31}$; and $R^{30}$ is $-CH_2-$. In some embodiments of a compound of Formula (Ia) or (Ib), $R^3$ is $-R^{30}OC(=O)R^{31}$; and $R^{30}$ is $-CH(R^{32})-$. In some embodiments of a compound of Formula (Ia) or (Ib), $R^3$ is $-R^{30}OC(=O)R^{31}$; $R^{30}$ is $-CH(R^{32})-$; and $R^{32}$ is $C_1$-$C_6$ alkyl. In some embodiments of a compound of Formula (Ia) or (Ib), $R^3$ is $-R^{30}OC(=O)R^{31}$; $R^{30}$ is $-CH(R^{32})-$; and $R^{32}$ is methyl, ethyl, propyl, isopropyl, butyl, or isobutyl. In some embodiments of a compound of Formula (Ia) or (Ib), $R^3$ is $-R^{30}OC(=O)R^{31}$; $R^{30}$ is $-CH(R^{32})-$; and $R^{32}$ is methyl or isopropyl.

In some embodiments of a compound of Formula (Ia) or (Ib), $R^3$ is $-R^{30}OC(=O)R^{31}$; and $R^{30}$ is $-C(R^{32})_2-$. In some embodiments of a compound of Formula (Ia) or (Ib), $R^3$ is $-R^{30}OC(=O)R^{31}$; $R^{30}$ is $-C(R^{32})_2-$; and each $R^{32}$ is independently methyl, ethyl, propyl, isopropyl, butyl, or isobutyl. In some embodiments of a compound of Formula (Ia) or (Ib), $R^3$ is $-R^{30}OC(=O)R^{31}$; $R^{30}$ is $-C(R^{32})_2-$; and each $R^{32}$ is methyl. In some embodiments of a compound of Formula (Ia) or (Ib), $R^3$ is $-R^{30}OC(=O)R^{31}$; $R^{30}$ is $-C(R^{32})_2-$; and two $R^{32}$ are taken together with the carbon to which they are attached to form a cycloalkyl. In some embodiments of a compound of Formula (Ia) or (Ib), $R^3$ is $-R^{30}OC(=O)R^{31}$; $R^{30}$ is $-C(R^{32})_2-$; and two $R^{32}$ are taken together with the carbon to which they are attached to form a cyclopropyl, cyclobutyl, cyclopentyl, cyclohexyl, or cycloheptyl. In some embodiments of a compound of Formula (Ia) or (Ib), $R^3$ is $-R^{30}OC(=O)R^{31}$; $R^{30}$ is $-C(R^{32})_2-$; and two $R^{32}$ are taken together with the carbon to which they are attached to form a cyclopropyl.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is optionally substituted $C_1$-$C_{12}$ alkyl, optionally substituted aryl, optionally substituted alkylheterocycloalkyl, optionally substituted alkylheteroaryl, optionally substituted heteroaryl, or optionally substituted heterocycloalkyl.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ alkyl, aryl, alkylheterocycloalkyl, alkylheteroaryl, heteroaryl, or heterocycloalkyl.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ alkyl, aryl, alkylheterocycloalkyl, alkylheteroaryl, heteroaryl, or heterocycloalkyl; each optionally substituted with halogen, $-CN$, $C_1$-$C_6$ alkyl, $-CF_3$, cycloalkyl, heterocycloalkyl, $-OR^4$, $-N(R^4R^5)$, $-SR^4$, $-(S=O)_2R^4$, $-C(=O)OR^4$, or $-C(=O)N(R^4R^5)$.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ alkyl, $C_1$-$C_{12}$ fluoroalkyl, $-(C_1$-$C_6$ alkylene)$OR^4$, $-(C_1$-$C_6$ alkylene)$SR^4$, $-(C_1$-$C_6$ alkylene)$C(=O)OR^4$, $-(C_1$-$C_6$ alkylene)$C(=O)N(R^4R^5)$.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ alkyl, $C_1$-$C_{12}$ fluoroalkyl, $-(C_1$-$C_6$ alkylene)$OR^4$, $-(C_1$-$C_6$ alkylene)$C(=O)OR^4$, $-(C_1$-$C_6$ alkylene)$C(=O)N(R^4R^5)$.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ alkyl. In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is methyl, ethyl, propyl, isopropyl, butyl, isobutyl, tert-butyl, pentyl, isopentyl, hexyl, 5-methylhexyl, 3,3-dimethylbutyl, 2-ethylpropyl, 3-pentyl, 2-ethylbutyl, or heptyl.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ alkyl. In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is methyl, ethyl, propyl, isopropyl, butyl, isobutyl, tert-butyl, pentyl, isopentyl, hexyl, 5-methylhexyl, 3,3-dimethylbutyl, 2-ethylbutyl, or heptyl.

In some embodiments of a compound of Formula (Ia) or (Ib), $R^3$ is $-R^{30}OC(=O)R^{31}$; $R^{30}$ is $-CH_2-$ or $-CH(R^{32})-$; $R^{32}$ is $C_1$-$C_6$ alkyl; and $R^{31}$ is $C_1$-$C_{12}$ fluoroalkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is C$_1$-C$_6$ fluoroalkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is C$_1$-C$_4$ fluoroalkyl.

In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$-C$_6$ alkylene)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$ alkylene)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_2$ alkylene)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_3$ alkylene)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(—C(CH$_3$)$_2$—)O$R^4$; and $R^4$ is C$_1$-C$_6$ alkyl.

In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$-C$_6$ alkylene)S$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$ alkylene)S$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH$_{(R32)}$—; $R^{32}$ is C$_1$-C$_6$ alkyl; $R^{31}$ is —(C$_2$ alkylene)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_3$ alkylene)S$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(—C(CH$_3$)$_2$—)S$R^4$; and $R^4$ is C$_1$-C$_6$ alkyl.

In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$-C$_6$ alkylene)C(=O)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$ alkylene)C(=O)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_2$ alkylene)C(=O)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_3$ alkylene)C(=O)O$R^4$; and $R^4$ is C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_4$ alkylene)C(=O)O$R^4$; and $R^4$ is C$_1$-C$_6$ alkyl.

In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$-C$_6$ alkylene)C(=O)N($R^4R^5$); and $R^4$ and $R^5$ are independently hydrogen or C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$-C$_6$ alkylene)C(=O)N($R^4R^5$); and $R^4$ and $R^5$ are independently hydrogen or C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$ alkylene)C(=O)N($R^4R^5$); and $R^4$ and $R^5$ are independently hydrogen or C$_1$-C$_6$ alkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{31}$ is —(C$_2$ alkylene)C(=O)N($R^4R^5$); and $R^4$ and $R^5$ are independently hydrogen or C$_1$-C$_6$ alkyl.

In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is aryl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is phenyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is phenyl optionally substituted with halogen, —CN, C$_1$-C$_6$ alkyl, —CF$_3$, cycloalkyl, heterocycloalkyl, —O$R^4$, —N($R^4R^5$), —S$R^4$, —(S=O)$_2R^4$, —C(=O)O$R^4$, or —C(=O)N($R^4R^5$).

In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is alkylheterocycloalkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is —(C$_1$-C$_6$ alkylene)heterocycloalkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$-C$_2$ alkylene)heterocycloalkyl; and the heterocycloalkyl is aziridinyl, azetidinyl, pyrrolidinyl, piperidinyl, piperazinyl, morpholinyl, or tetrahydropyranyl.

In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is alkylheteroaryl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is —(C$_1$-C$_6$ alkylene)heteroaryl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; $R^{31}$ is —(C$_1$-C$_2$ alkylene)heteroaryl; and the heteroaryl is pyridyl, pyrimidyl, pyrazinyl, or pyperazinyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is heteroaryl. In some embodiments of a compound of Formula (Ia) or (Ib), $R^3$ is —$R^{30}$OC(=O)$R^{31}$; $R^{30}$ is —CH$_2$— or —CH—; $R^{32}$ is C$_1$-C$_6$ alkyl; and $R^{31}$ is pyridyl, pyrimidyl, pyrazinyl, or pyperazinyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is pyridyl optionally substituted with halogen, —CN, C$_1$-C$_6$ alkyl, —CF$_3$, cycloalkyl, heterocycloalkyl, —O$R^4$, —N($R^4R^5$), —S$R^4$, -(S=O)$_2R^4$, —C(=O)O$R^4$, or —C(=O)N($R^4R^5$).

In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is heterocycloalkyl. In some embodiments of a compound of Formula (Ia) or (Ib), $R^3$ is —$R^{30}$OC(=O)$R^{31}$; $R^{30}$ is —CH$_2$— or —CH($R^{32}$)—; $R^{32}$ is C$_1$-C$_6$ alkyl; and $R^{31}$ is aziridinyl, azetidinyl, pyrrolidinyl, piperidinyl, piperazinyl, morpholinyl, or tetrahydropyranyl.

In some embodiments of a compound of Formula (Ia) or (Ib), $R^3$ is —$R^{30}$OC(=O)$R^{31}$; $R^{30}$ is —CH$_2$— or —CH(CH$_3$)—; and $R^{31}$ is

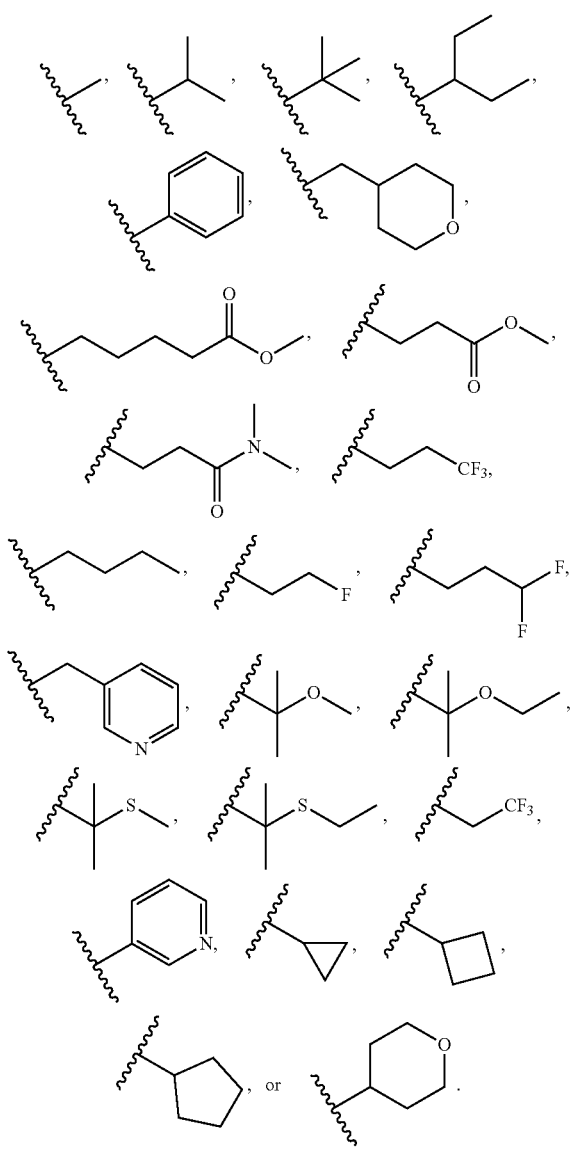
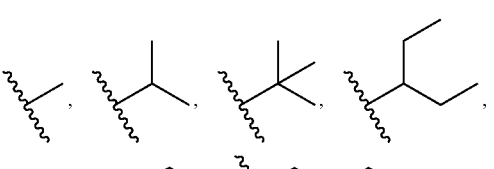
In some embodiments of a compound of Formula (Ia) or (Ib), $R^3$ is $-R^{30}OC(=O)R^{31}$; $R^{30}$ is $-CH_2-$ or $-CH(CH_3)-$; and $R^{31}$ is
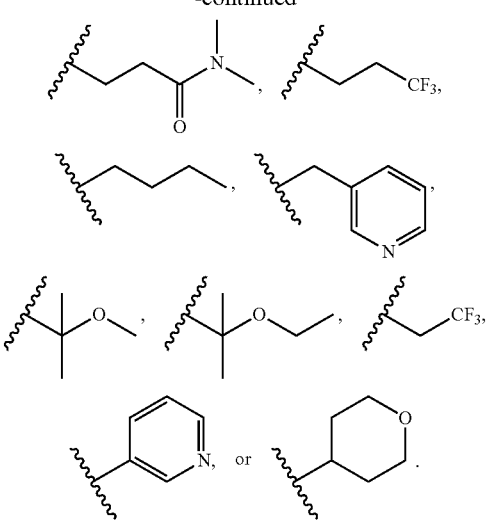
In some embodiments of a compound of Formula (Ia) or (Ib), $R^3$ is $-R^{30}OC(=O)R^{31}$; $R^{30}$ is $-CH_2-$ or $-CH(CH_3)-$; and $R^{31}$ is
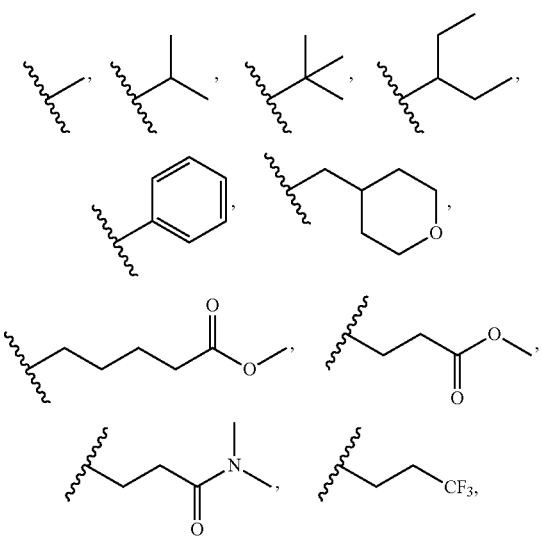
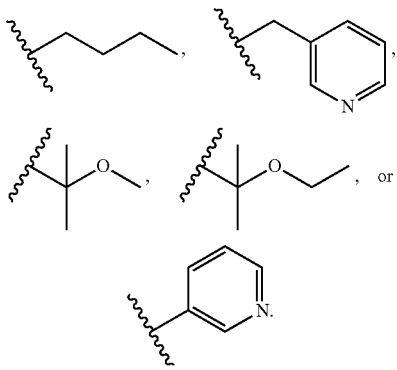
In some embodiments of a compound of Formula (Ia) or (Ib), $R^3$ is $-R^{30}OC(=O)R^{31}$; $R^{30}$ is $-CH_2-$ or $-CH(CH_3)-$; and $R^{31}$ is

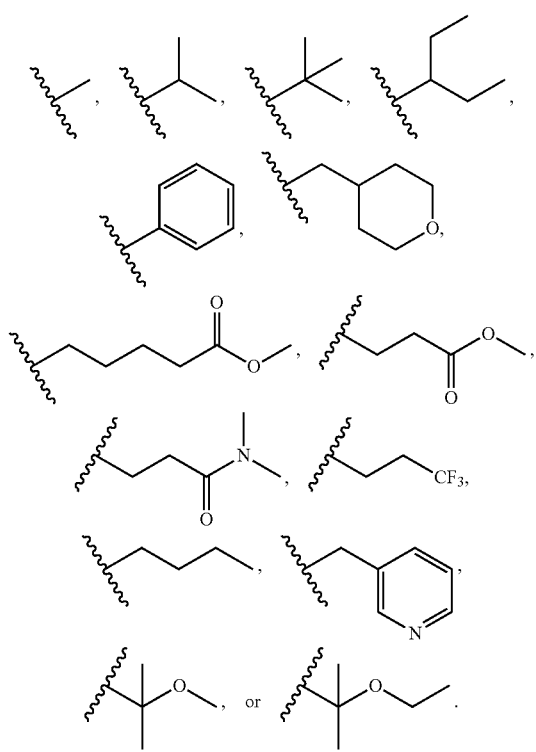

In some embodiments of a compound of Formula (Ia) or (Ib), $R^3$ is —$R^{30}$OC(=O)O$R^{31}$.

In some embodiments of a compound of Formula (Ia) or (Ib), $R^3$ is —$R^{30}$OC(=O)O$R^{31}$; $R^{30}$ is —CH$_2$— or —CH($R^{32}$)—; $R^{32}$ is $C_1$-$C_6$ alkyl. In some embodiments of a compound of Formula (Ia) or (Ib), $R^3$ is —$R^{30}$OC(=O)OR$^{31}$; and $R^{30}$ is —CH($R^{32}$)—. In some embodiments of a compound of Formula (Ia) or (Ib), $R^3$ is —$R^{30}$OC(=O)OR$^{31}$; and $R^{30}$ is —CH($R^{32}$)— and $R^{32}$ is $C_1$-$C_6$ alkyl. In some embodiments of a compound of Formula (Ia) or (Ib), $R^3$ is —$R^{30}$OC(=O)OR$^{31}$; and $R^{30}$ is —CH($R^{32}$)— and $R^{32}$ is methyl, ethyl, propyl, isopropyl, butyl, or isobutyl. In some embodiments of a compound of Formula (Ia) or (Ib), $R^3$ is —$R^{30}$OC(=O)OR$^{31}$; and $R^{30}$ is —CH($R^{32}$)— and $R^{32}$ is methyl or isopropyl.

In some embodiments of a compound of Formula (Ia) or (Ib), $R^3$ is —$R^{30}$OC(=O)OR$^{31}$; and $R^{30}$ is —C($R^{32}$)$_2$—. In some embodiments of a compound of Formula (Ia) or (Ib), $R^3$ is —$R^{30}$OC(=O)OR$^{31}$; and $R^{30}$ is —C($R^{32}$)$_2$— and each $R^{32}$ is independently methyl, ethyl, propyl, isopropyl, butyl, or isobutyl. In some embodiments of a compound of Formula (Ia) or (Ib), $R^3$ is —$R^{30}$OC(=O)OR$^{31}$; $R^{30}$ is —C($R^{32}$)$_2$—; and each $R^{32}$ is independently methyl. In some embodiments of a compound of Formula (Ia) or (Ib), $R^3$ is —$R^{30}$OC(=O)OR$^{31}$; $R^{30}$ is —C($R^{32}$)$_2$—; and two $R^{32}$ are taken together with the carbon to which they are attached to form a cycloalkyl. In some embodiments of a compound of Formula (Ia) or (Ib), $R^3$ is —$R^{30}$OC(=O)OR$^{31}$; $R^{30}$ is —C($R^{32}$)$_2$—; and two $R^{32}$ are taken together with the carbon to which they are attached to form a cyclopropyl, cyclobutyl, cyclopentyl, cyclohexyl, or cycloheptyl. In some embodiments of a compound of Formula (Ia) or (Ib), $R^3$ is —$R^{30}$OC(=O)OR$^{31}$; $R^{30}$ is —C($R^{32}$)$_2$—; and two $R^{32}$ are taken together with the carbon to which they are attached to form a cyclopropyl.

In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is optionally substituted $C_1$-$C_{12}$ alkyl or optionally substituted cycloalkyl. In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is $C_1$-$C_{12}$ alkyl or cycloalkyl.

In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is $C_1$-$C_{12}$ alkyl or cycloalkyl; each optionally substituted with halogen, —CN, $C_1$-$C_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$).

In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is $C_1$-$C_{12}$ alkyl. In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is methyl, ethyl, propyl, isopropyl, butyl, isobutyl, tert-butyl, pentyl, isopentyl, hexyl, 5-methylhexyl, 3,3-dimethylbutyl, 2-ethylpropyl, 3-pentyl, 2-ethylbutyl, or heptyl.

In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is $C_1$-$C_{12}$ alkyl. In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is methyl, ethyl, propyl, isopropyl, butyl, isobutyl, tert-butyl, pentyl, isopentyl, hexyl, 5-methylhexyl, 3,3-dimethylbutyl, 2-ethylbutyl, or heptyl.

In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is cycloalkyl. In some embodiments of a compound of Formula (Ia) or (Ib), $R^3$ is —$R^{30}$OC(=O)OR$^{31}$; $R^{30}$ is —CH$_2$— or —CH($R^{32}$)—; $R^{32}$ is $C_1$-$C_6$ alkyl; and $R^{31}$ is cyclopropyl, cyclobutyl, cyclopentyl, cyclohexyl, or cycloheptyl.

In some embodiments of a compound of Formula (Ia) or (Ib), $R^3$ is —$R^{30}$OC(=O)OR$^{31}$; $R^{30}$ is —CH$_2$— or —CH(CH$_3$)—; and $R^{31}$ is

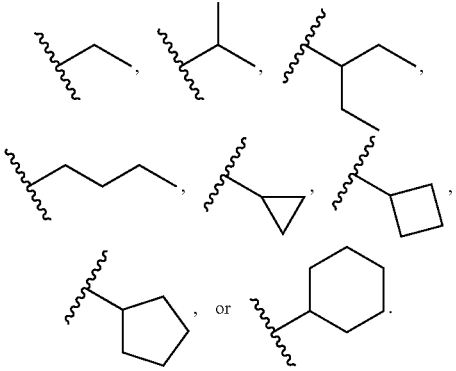

In some embodiments of a compound of Formula (Ia) or (Ib), $R^3$ is —$R^{30}$OC(=O)OR$^{31}$; $R^{30}$ is —CH$_2$— or —CH(CH$_3$)—; and $R^{31}$ is

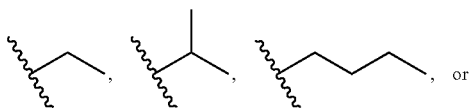

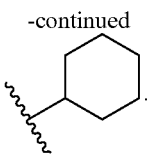

In some embodiments of a compound of Formula (Ia) or (Ib), n is 0, 1, 2, 3, or 4. In some embodiments of a compound of Formula (Ia) or (Ib), n is 0, 1, 2, or 3. In some embodiments of a compound of Formula (Ia) or (Ib), n is 1, 2, 3, or 4. In some embodiments of a compound of Formula (Ia) or (Ib), n is 2, 3, or 4. In some embodiments of a compound of Formula (Ia) or (Ib), n is 2, 3. In some embodiments of a compound of Formula (Ia) or (Ib), n is 1. In some embodiments of a compound of Formula (Ia) or (Ib), n is 2. In some embodiments of a compound of Formula (Ia) or (Ib), n is 3. In some embodiments of a compound of Formula (Ia) or (Ib), n is 4. In some embodiments of a compound of Formula (Ia) or (Ib), n is 5. In some embodiments of a compound of Formula (Ia) or (Ib), n is 6.

In some embodiments of a compound of Formula (Ia) or (Ib), $R^a$, $R^b$, and $R^c$ are independently hydrogen, fluoro, optionally substituted $C_1$-$C_6$ alkyl, —$OR^4$, —$N(R^4R^5)$, or —$SR^4$. In some embodiments of a compound of Formula (Ia) or (Ib), $R^a$, $R^b$, and $R^c$ are independently hydrogen, fluoro, chloro, —OH, or —$OCH_3$. In some embodiments of a compound of Formula (Ia) or (Ib), $R^a$, $R^b$, and $R^c$ are hydrogen. In some embodiments of a compound of Formula (Ia) or (Ib), at least one of $R^a$, $R^b$, or $R^c$ is not hydrogen.

In some embodiments of a compound of Formula (Ia) or (Ib), $X^1$ and $X^2$ are —OH; when present.

In some embodiments of a compound of Formula (Ia) or (Ib), $R^d$ is hydrogen or $C_1$-$C_4$ alkyl. In some embodiments of a compound of Formula (Ia) or (Ib), $R^d$ is hydrogen.

In some embodiments of a compound of Formula (Ia) or (Ib), Z is >C(=O). In some embodiments of a compound of Formula (Ia) or (Ib), Z is >S(=O)$_2$. In some embodiments of a compound of Formula (Ia) or (Ib), Z is >C(=S).

In some embodiments of a compound of Formula (Ia) or (Ib),
M is hydrogen, —$CF_3$, —CN, —$OR^4$, —$SR^4$, —C(=O)$R^4$, or alkynyl;
each $R^1$ and $R^2$ are independently hydrogen, fluoro, chloro, $C_1$-$C_6$ alkyl, or —$CF_3$;
provided that M is —$CF_3$ or at least one of $R^1$ or $R^2$ is fluoro;
n is 1, 2, 3, or 4;
$X^1$ and $X^2$ are —OH; when present;
Z is >C(=O);
$R^3$ is $R^{31}$, —$R^{30}OC(=O)R^{31}$, or —$R^{30}OC(=O)OR^{31}$;
 $R^{30}$ is independently —$CH_2$— or —$CH(R^{32})$—;
 $R^{31}$ is independently optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;
 $R^{32}$ is optionally substituted $C_1$-$C_6$ alkyl;
$R^a$, $R^b$, and $R^c$ are independently hydrogen, fluoro, optionally substituted $C_1$-$C_6$ alkyl, —$OR^4$, —$N(R^4R^5)$, or —$SR^4$;
$R^d$, $R^4$ and $R^5$ are independently hydrogen or $C_1$-$C_6$ alkyl; or $R^4$ and $R^5$ are taken together with the nitrogen to which they are attached to form a heterocycloalkyl.

In some embodiments of a compound of Formula (Ia) or (Ib),
M is hydrogen, —$CF_3$, —CN, —$OR^4$, —$SR^4$, —C(=O)$R^4$, or alkynyl;
each $R^1$ and $R^2$ are independently hydrogen, fluoro, chloro, $C_1$-$C_6$ alkyl, or —$CF_3$;
provided that M is —$CF_3$ or at least one of $R^1$ or $R^2$ is fluoro;
n is 1, 2, 3, or 4;
$X^1$ and $X^2$ are —OH; when present;
Z is >C(=O);
$R^3$ is $R^{31}$;
 $R^{31}$ is optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;
$R^a$, $R^b$, and $R^c$ are independently hydrogen, fluoro, optionally substituted $C_1$-$C_6$ alkyl, —$OR^4$, —$N(R^4R^5)$, or —$SR^4$;
$R^d$, $R^4$ and $R^5$ are independently hydrogen or $C_1$-$C_6$ alkyl; or $R^4$ and $R^5$ are taken together with the nitrogen to which they are attached to form a heterocycloalkyl.

In some embodiments of a compound of Formula (Ia) or (Ib),
M is hydrogen, —$CF_3$, —CN, —$OR^4$, —$SR^4$, —C(=O)$R^4$, or alkynyl;
each $R^1$ and $R^2$ are independently hydrogen, fluoro, chloro, $C_1$-$C_6$ alkyl, or —$CF_3$;
provided that M is —$CF_3$ or at least one of $R^1$ or $R^2$ is fluoro;
n is 1, 2, 3, or 4;
$X^1$ and $X^2$ are —OH; when present;
Z is >C(=O);
$R^3$ is —$R^{30}OC(=O)R^{31}$;
 $R^{30}$ is —$CH_2$— or —$CH(R^{32})$—;
 $R^{31}$ is optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;
 $R^{32}$ is optionally substituted $C_1$-$C_6$ alkyl;
$R^a$, $R^b$, and $R^c$ are independently hydrogen, fluoro, optionally substituted $C_1$-$C_6$ alkyl, —$OR^4$, —$N(R^4R^5)$, or —$SR^4$;
$R^d$, $R^4$ and $R^5$ are independently hydrogen or $C_1$-$C_6$ alkyl; or $R^4$ and $R^5$ are taken together with the nitrogen to which they are attached to form a heterocycloalkyl.

In some embodiments of a compound of Formula (Ia) or (Ib),
M is hydrogen, —$CF_3$, —CN, —$OR^4$, —$SR^4$, —C(=O)$R^4$, or alkynyl;
each $R^1$ and $R^2$ are independently hydrogen, fluoro, chloro, $C_1$-$C_6$ alkyl, or —$CF_3$;
provided that M is —$CF_3$ or at least one of $R^1$ or $R^2$ is fluoro;
n is 1, 2, 3, or 4;
$X^1$ and $X^2$ are —OH; when present;
Z is >C(=O);
$R^3$ is —$R^{30}OC(=O)OR^{31}$;
 $R^{30}$ is —$CH_2$— or —$CH(R^{32})$—;
 $R^{31}$ is optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;

$R^{32}$ is optionally substituted $C_1$-$C_6$ alkyl;

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl;

or $R^4$ and $R^5$ are taken together with the nitrogen to which they are attached to form a heterocycloalkyl.

In some embodiments of a compound of Formula (Ia) or (Ib),

M is hydrogen or —$CF_3$;

each $R^1$ and $R^2$ are independently hydrogen, fluoro, chloro, $C_1$-$C_6$ alkyl, or —$CF_3$;

provided that M is —$CF_3$ or at least one of $R^1$ or $R^2$ is fluoro;

n is 1, 2, 3, or 4;

$X^1$ and $X^2$ are —OH; when present;

Z is >C(=O);

$R^3$ is $R^{31}$, —$R^{30}OC(=O)R^{31}$, or —$R^{30}OC(=O)OR^{31}$;

$R^{30}$ is independently —$CH_2$— or —$CH(R^{32})$—;

$R^{31}$ is independently optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;

$R^{32}$ is optionally substituted $C_1$-$C_6$ alkyl;

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl;

or $R^4$ and $R^5$ are taken together with the nitrogen to which they are attached to form a heterocycloalkyl.

In some embodiments of a compound of Formula (Ia) or (Ib),

M is hydrogen or —$CF_3$;

each $R^1$ and $R^2$ are independently hydrogen, fluoro, chloro, $C_1$-$C_6$ alkyl, or —$CF_3$;

provided that M is —$CF_3$ or at least one of $R^1$ or $R^2$ is fluoro;

n is 1, 2, 3, or 4;

$X^1$ and $X^2$ are —OH; when present;

Z is >C(=O);

$R^3$ is $R^{31}$;

$R^{31}$ is optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl;

or $R^4$ and $R^5$ are taken together with the nitrogen to which they are attached to form a heterocycloalkyl.

In some embodiments of a compound of Formula (Ia) or (Ib),

M is hydrogen or —$CF_3$;

each $R^1$ and $R^2$ are independently hydrogen, fluoro, chloro, $C_1$-$C_6$ alkyl, or —$CF_3$;

provided that M is —$CF_3$ or at least one of $R^1$ or $R^2$ is fluoro;

n is 1, 2, 3, or 4;

$X^1$ and $X^2$ are —OH; when present;

Z is >C(=O);

$R^3$ is —$R^{30}OC(=O)R^{31}$;

$R^{30}$ is —$CH_2$— or —$CH(R^{32})$—;

$R^{31}$ is optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;

$R^{32}$ is optionally substituted $C_1$-$C_6$ alkyl;

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl;

or $R^4$ and $R^5$ are taken together with the nitrogen to which they are attached to form a heterocycloalkyl.

In some embodiments of a compound of Formula (Ia) or (Ib),

M is hydrogen or —$CF_3$;

each $R^1$ and $R^2$ are independently hydrogen, fluoro, chloro, $C_1$-$C_6$ alkyl, or —$CF_3$;

provided that M is —$CF_3$ or at least one of $R^1$ or $R^2$ is fluoro;

n is 1, 2, 3, or 4;

$X^1$ and $X^2$ are —OH; when present;

Z is >C(=O);

$R^3$ is —$R^{30}OC(=O)OR^{31}$;

$R^{30}$ is —$CH_2$— or —$CH(R^{32})$—;

$R^{31}$ is optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl;

$R^{32}$ is optionally substituted $C_1$-$C_6$ alkyl;

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl;

or $R^4$ and $R^5$ are taken together with the nitrogen to which they are attached to form a heterocycloalkyl.

In some embodiments, the compound of Formula (Ia) or (Ib) is of Formula (Ia-1) or (Ib-1) or pharmaceutically acceptable salts, isomers, stereoisomers, dimers, trimers, tautomers, or N-oxides thereof:

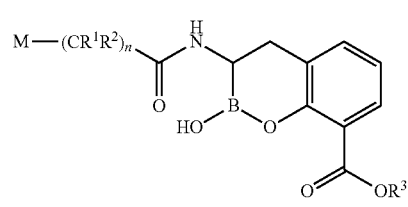

Formula (Ia-1)

Formula (Ib-1)

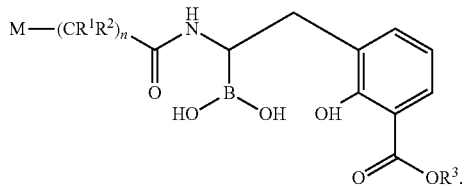

In some embodiments of a compound of Formula (Ia-1) or (Ib-1), M is —CF$_3$, n is 1, 2, 3, or 4; each R$^1$ and R$^2$ are independently hydrogen, fluoro, or C$_1$-C$_6$ alkyl; R$^3$ is R$^{31}$, —R$^{30}$OC(=O)R$^{31}$, or —R$^{30}$OC(=O)OR$^{31}$; each R$^{30}$ is independently —CH$_2$—, —CH(R$^{32}$)—, or —C(R$^{32}$)$_2$—; each R$^{31}$ is independently optionally substituted C$_1$-C$_{12}$ alkyl, optionally substituted alkoxyalkyl, optionally substituted C$_1$-C$_{12}$ alkenyl, optionally substituted C$_1$-C$_{12}$ alkynyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; and each R$^{32}$ is independently optionally substituted C$_1$-C$_6$ alkyl; or two R$^{32}$ are taken together with the carbon to which they are attached to form a cycloalkyl.

In some embodiments of a compound of Formula (Ia-1) or (Ib-1), M is —CF$_3$; n is 1, 2, 3, or 4; each R$^1$ and R$^2$ are independently hydrogen, fluoro, or C$_1$-C$_6$ alkyl; R$^3$ is R$^{31}$, —R$^{30}$OC(=O)R$^{31}$, or —R$^{30}$OC(=O)OR$^{31}$; each R$^{30}$ is independently —CH$_2$— or —CH(R$^{32}$)—; each R$^{31}$ is independently optionally substituted C$_1$-C$_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; and R$^{32}$ is optionally substituted C$_1$-C$_6$ alkyl.

In some embodiments of a compound of Formula (Ia-1) or (Ib-1), M is —CF$_3$; n is 1, 2, 3, or 4; each R$^1$ and R$^2$ are independently hydrogen, fluoro, or C$_1$-C$_6$ alkyl; R$^3$ is R$^{31}$, —R$^{30}$OC(=O)R$^{31}$, or —R$^{30}$OC(=O)OR$^{31}$; each R$^{30}$ is independently —CH$_2$— or —CH(R$^{32}$)—; each R$^{31}$ is independently C$_1$-C$_{12}$ alkyl, cycloalkyl, heterocycloalkyl, aryl, heteroaryl, alkylcycloalkyl, alkylheterocycloalkyl, alkylaryl, or alkylheteroaryl; each optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); and R$^{32}$ is C$_1$-C$_6$ alkyl.

In some embodiments of a compound of Formula (Ia-1) or (Ib-1), M is hydrogen; n is 1, 2, 3, or 4; each R$^1$ and R$^2$ are independently hydrogen, fluoro, or C$_1$-C$_6$ alkyl; provided that at least one of R$^1$ or R$^2$ is fluoro; R$^3$ is R$^{31}$, —R$^{30}$OC(=O)R$^{31}$, or —R$^{30}$OC(=O)OR$^{31}$; each R$^{30}$ is independently —CH$_2$—, —CH(R$^{32}$)—, or —C(R$^{32}$)$_2$—; each R$^{31}$ is independently optionally substituted C$_1$-C$_{12}$ alkyl, optionally substituted alkoxyalkyl, optionally substituted C$_1$-C$_{12}$ alkenyl, optionally substituted C$_1$-C$_{12}$ alkynyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; and each R$^{32}$ is independently optionally substituted C$_1$-C$_6$ alkyl; or two R$^{32}$ are taken together with the carbon to which they are attached to form a cycloalkyl.

In some embodiments of a compound of Formula (Ia-1) or (Ib-1), M is hydrogen; n is 1, 2, 3, or 4; each R$^1$ and R$^2$ are independently hydrogen, fluoro, or C$_1$-C$_6$ alkyl; provided that at least one of R$^1$ or R$^2$ is fluoro; R$^3$ is R$^{31}$, —R$^{30}$OC(=O)R$^{31}$, or —R$^{30}$OC(=O)OR$^{31}$; each R$^{30}$ is independently —CH$_2$— or —CH(R$^{32}$)—; each R$^{31}$ is independently optionally substituted C$_1$-C$_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; and R$^{32}$ is optionally substituted C$_1$-C$_6$ alkyl.

In some embodiments of a compound of Formula (Ia-1) or (Ib-1), M is hydrogen; n is 1, 2, 3, or 4; each R$^1$ and R$^2$ are independently hydrogen, fluoro, or C$_1$-C$_6$ alkyl; provided that at least one of R$^1$ or R$^2$ is fluoro; R$^3$ is R$^{31}$, —R$^{30}$OC(=O)R$^{31}$, or —R$^{30}$OC(=O)OR$^{31}$; each R$^{30}$ is independently —CH$_2$— or —CH(R$^{32}$)—; each R$^{31}$ is independently C$_1$-C$_{12}$ alkyl, cycloalkyl, heterocycloalkyl, aryl, heteroaryl, alkylcycloalkyl, alkylheterocycloalkyl, alkylaryl, or alkylheteroaryl; each optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); and R$^{32}$ is C$_1$-C$_6$ alkyl.

In some embodiments of a compound of Formula (Ia-1) or (Ib-1), M is —CN, -OR$^4$, —SR$^4$, —C(=O)R$^4$, or alkynyl; n is 1, 2, 3, or 4; each R$^1$ and R$^2$ are independently hydrogen, fluoro, or C$_1$-C$_6$ alkyl; provided that at least one of R$^1$ or R$^2$ is fluoro; R$^3$ is R$^{31}$, —R$^{30}$OC(=O)R$^{31}$, or —R$^{30}$OC(=O)OR$^{31}$; each R$^{30}$ is independently —CH$_2$-, —CH(R$^{32}$)-, or —C(R$^{32}$)$_2$—; each R$^{31}$ is independently optionally substituted C$_1$-C$_{12}$ alkyl, optionally substituted alkoxyalkyl, optionally substituted C$_1$-C$_u$ alkenyl, optionally substituted C$_1$-C$_{12}$ alkynyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; and each R$^{32}$ is independently optionally substituted C$_1$-C$_6$ alkyl; or two R$^{32}$ are taken together with the carbon to which they are attached to form a cycloalkyl.

In some embodiments of a compound of Formula (Ia-1) or (Ib-1), M is —CN, —OR$^4$, —SR$^4$, —C(=O)R$^4$, or alkynyl; n is 1, 2, 3, or 4; each R$^1$ and R$^2$ are independently hydrogen, fluoro, or C$_1$-C$_6$ alkyl; provided that at least one of R$^1$ or R$^2$ is fluoro; R$^3$ is R$^{31}$, —R$^{30}$OC(=O)R$^{31}$, or —R$^{30}$OC(=O)OR$^{31}$; each R$^{30}$ is independently —CH$_2$— or —CH(R$^{32}$)—; each R$^{31}$ is independently optionally substituted C$_1$-C$_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; and R$^{32}$ is optionally substituted C$_1$-C$_6$ alkyl.

In some embodiments of a compound of Formula (Ia-1) or (Ib-1), M is —CN, —OR$^4$, —SR$^4$, —C(=O)R$^4$, or alkynyl; n is 1, 2, 3, or 4; each R$^1$ and R$^2$ are independently hydrogen, fluoro, or C$_1$-C$_6$ alkyl; provided that at least one of R$^1$ or R$^2$ is fluoro; R$^3$ is R$^{31}$, —R$^{30}$OC(=O)R$^{31}$, or —R$^{30}$OC(=O)OR$^{31}$; each R$^{30}$ is independently —CH$_2$— or —CH(R$^{32}$)—; each R$^{31}$ is independently C$_1$-C$_{12}$ alkyl, cycloalkyl, heterocycloalkyl, aryl, heteroaryl, alkylcycloalkyl, alkylheterocycloalkyl, alkylaryl, or alkylheteroaryl; each optionally substituted with halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$; and $R^{32}$ is $C_1$-$C_6$ alkyl.

In some embodiments of a compound of Formula (Ia-1) or (Ib-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; provided that at least one of $R^1$ or $R^2$ is fluoro; $R^3$ is $R^{31}$, —$R^{30}OC(=O)R^{31}$, or —$R^{30}OC(=O)OR^{31}$; each $R^{30}$ is independently —$CH_2$—, —CH—, or —$C(R^{32})_2$—; each $R^{31}$ is independently optionally substituted $C_1$-$C_{12}$ alkyl, optionally substituted alkoxyalkyl, optionally substituted $C_1$-$C_{12}$ alkenyl, optionally substituted $C_1$-$C_{12}$ alkynyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; and each $R^{32}$ is independently optionally substituted $C_1$-$C_6$ alkyl; or two $R^{32}$ are taken together with the carbon to which they are attached to form a cycloalkyl.

In some embodiments of a compound of Formula (Ia-1) or (Ib-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; provided that at least one of $R^1$ or $R^2$ is fluoro; $R^3$ is $R^{31}$, —$R^{30}OC(=O)R^{31}$, or —$R^{30}OC(=O)OR^{31}$; each $R^{30}$ is independently —$CH_2$— or —$CH(R^{32})$—; each $R^{31}$ is independently optionally substituted $C_1$-$C_{12}$ alkyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; and $R^{32}$ is optionally substituted $C_1$-$C_6$ alkyl.

In some embodiments of a compound of Formula (Ia-1) or (Ib-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; provided that at least one of $R^1$ or $R^2$ is fluoro; $R^3$ is $R^{31}$, —$R^{30}OC(=O)R^{31}$, or —$R^{30}OC(=O)OR^{31}$; each $R^{30}$ is independently —$CH_2$— or —$CH(R^{32})$—; each $R^{31}$ is independently $C_1$-$C_{12}$ alkyl, cycloalkyl, heterocycloalkyl, aryl, heteroaryl, alkylcycloalkyl, alkylheterocycloalkyl, alkylaryl, or alkylheteroaryl; each optionally substituted with halogen, —CN, $C_1$-$C_6$ alkyl, —$CF_3$, cycloalkyl, heterocycloalkyl, —$OR^4$, —$N(R^4R^5)$, —$SR^4$, —$(S=O)_2R^4$, —$C(=O)OR^4$, or —$C(=O)N(R^4R^5)$; and $R^{32}$ is $C_1$-$C_6$ alkyl.

In another aspect, provided herein are compounds Formula (IIa) or (IIb) or pharmaceutically acceptable salts, isomers, stereoisomers, dimers, trimers, tautomers, or N-oxides thereof:

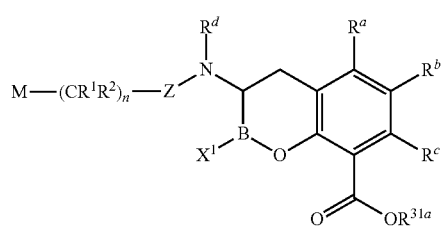

Formula (IIa)

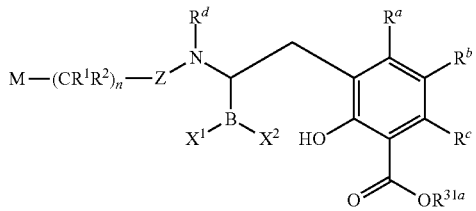

Formula (IIb)

wherein:

M is hydrogen, fluoro, chloro, bromo, —$CF_3$, —CN, —$OR^4$, —$SR^4$, —$S(=O)R^4$, —$S(=O)_2R^4$, —$S(=O)_2N(R^4R^5)$, —$N(R^4R^5)$, —$N(R^4)C(=O)R^4$, —$N(R^4)C(=O)N(R^4R^5)$, —$N(R^4)S(=O)_2R^4$, —$N(R^4)$Heteroaryl, —$C(=O)R^4$, —$C(=O)N(R^4R^5)$, —$C(=O)(C_1$-$C_3$alkylene)$C(=O)R^4$, optionally substituted oxyimino, optionally substituted alkenyl, optionally substituted alkynyl, heteroaryl, or heterocycloalkyl;

each $R^1$ and $R^2$ are independently hydrogen, fluoro, chloro, bromo, optionally substituted $C_1$-$C_6$ alkyl, optionally substituted aryl, —$OR^4$, —$SR^4$, or —$N(R^4R^5)$; or $R^1$ and $R^2$ are taken together with the carbon to which they are attached to form an optionally substituted cycloalkyl; or when n is at least 2, two $R^1$ on adjacent carbons are taken together to form a double bond; or two $R^1$ and two $R^2$ on adjacent carbons are taken together to form a triple bond;

n is 0, 1, 2, 3, 4, 5, or 6;

$X^1$ and $X^2$ are independently —$OR^4$, or F; when present;

Z is >C(=O), >C(=S), or >$S(=O)_2$;

$R^{31a}$ is optionally substituted $C_5$-$C_{12}$ alkyl, —$(C_1$-$C_6$ alkylene)$C(=O)N(R^4R^5)$, —$(C_1$-$C_6$ alkylene)$S(=O)_2R^4$, optionally substituted heterocycloalkyl, optionally substituted alkylcycloalkyl, optionally substituted alkylheterocycloalkyl, optionally substituted aryl, optionally substituted heteroaryl, optionally substituted alkylaryl, or optionally substituted alkylheteroaryl;

$R^a$, $R^b$, and $R^c$ are independently hydrogen, fluoro, chloro, bromo, optionally substituted $C_1$-$C_6$ alkyl, optionally substituted cycloalkyl, optionally substituted heterocycloalkyl, optionally substituted aryl, optionally substituted heteroaryl, —$OR^4$, —$N(R^4R^5)$, or —$SR^4$;

$R^d$, $R^4$ and $R^5$ are independently hydrogen, —OH, —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ are taken together with the nitrogen to which they are attached to form a heterocycloalkyl;

provided that the compound is not (5-methyl-2-oxo-1,3-dioxol-4-yl)methyl 3-(3-cyanopropanamido)-2-hydroxy-3,4-dihydro-2H-benzo[e][1,2]oxaborinine-8- carboxylate or 3-oxo-1,3-dihydroisobenzofuran-1-yl 3-acetamido-2-hydroxy-3,4-dihydro-2H-benzo[e][1,2]oxaborinine-8-carboxylate.

In some embodiments of a compound of Formula (IIa) or (IIb), when $R^{31a}$ is

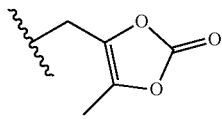 [SMILES: *Cc1oc(=O)oc1C]

and n is 2; then M is not —CN.

In some embodiments of a compound of Formula (IIa) or (IIb), when $R^{31a}$ is

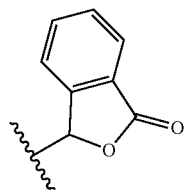 [SMILES: *C1OC(=O)c2ccccc21]

and n is 1; then M, $R^1$, and $R^2$ are not hydrogen.

In some embodiments of a compound of Formula (IIa) or (IIb), M is hydrogen, —CF$_3$, —CN, —OR$^4$, —SR$^4$, —C(═O)R$^4$, or alkynyl. In some embodiments of a compound of Formula (IIa) or (IIb), M is hydrogen or —CF$_3$. In some embodiments of a compound of Formula (IIa) or (IIb), M is —CF$_3$. In some embodiments of a compound of Formula (IIa) or (IIb), M is —CN. In some embodiments of a compound of Formula (IIa) or (IIb), M is SR$^4$. In some embodiments of a compound of Formula (IIa) or (IIb), M is SR$^4$ and R$^4$ is C$_1$-C$_4$ alkyl. In some embodiments of a compound of Formula (IIa) or (IIb), M is SR$^4$ and R$^4$ is methyl. In some embodiments of a compound of Formula (IIa) or (IIb), M is —C(═O)R$^4$. In some embodiments of a compound of Formula (IIa) or (IIb), M is —C(═O)R$^4$ and R$^4$ is C$_1$-C$_4$ alkyl. In some embodiments of a compound of Formula (IIa) or (IIb), M is —C(═O)R$^4$ and R$^4$ is methyl. In some embodiments of a compound of Formula (IIa) or (IIb), M is alkynyl. In some embodiments of a compound of Formula (IIa) or (IIb), M is hydrogen.

In some embodiments of a compound of Formula (IIa) or (IIb), each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$). In some embodiments of a compound of Formula (IIa) or (IIb), R$^1$ and R$^2$ are taken together with the carbon to which they are attached to form a cycloalkyl. In some embodiments of a compound of Formula (IIa) or (IIb), when n is at least 2, two R$^1$ on adjacent carbons are taken together to form a double bond; or two R$^1$ and two R$^2$ on adjacent carbons are taken together to form a triple bond. In some embodiments of a compound of Formula (IIa) or (IIb), each R$^1$ and R$^2$ are independently hydrogen, fluoro, chloro, C$_1$-C$_6$ alkyl, or —CF$_3$. In some embodiments of a compound of Formula (IIa) or (IIb), each R$^1$ and R$^2$ are independently hydrogen or fluoro. In some embodiments of a compound of Formula (IIa) or (IIb), each R$^1$ and R$^2$ are hydrogen. In some embodiments of a compound of Formula (IIa) or (IIb), at least one of R$^1$ or R$^2$ is fluoro. In some embodiments of a compound of Formula (IIa) or (IIb), at least two of R$^1$ or R$^2$ are fluoro.

In some embodiments of a compound of Formula (IIa) or (IIb), at least three of R$^1$ or R$^2$ are fluoro.

In some embodiments of a compound of Formula (IIa) or (IIb), R$^{31}$a is optionally substituted C$_5$-C$_{12}$ alkyl, —(C$_1$-C$_6$ alkylene)C(═O)N(R$^4$R$^5$), —(C$_1$-C$_6$ alkylene)S(═O)$_2$R$^4$, optionally substituted heterocycloalkyl, optionally substituted alkylcycloalkyl, optionally substituted alkylheterocycloalkyl, or optionally substituted alkylaryl.

In some embodiments of a compound of Formula (IIa) or (IIb), R$^{31a}$ is C$_5$-C$_{12}$ alkyl, —(C$_1$-C$_6$ alkylene)C(═O)N(R$^4$R$^5$), —(C$_1$-C$_6$ alkylene)S(═O)$_2$R$^4$, heterocycloalkyl, alkylcycloalkyl, alkylheterocycloalkyl, or aralkyl.

In some embodiments of a compound of Formula (IIa) or (IIb), R$^{31a}$ is C$_5$-C$_{12}$ alkyl, heterocycloalkyl, alkylcycloalkyl, alkylheterocycloalkyl, or aralkyl; each optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S═O)$_2$R$^4$, —C(═O)OR$^4$, or —C(═O)N(R$^4$R$^5$).

In some embodiments of a compound of Formula (IIa) or (IIb), R$^{31a}$ is C$_5$-C$_{12}$ alkyl. In some embodiments of a compound of Formula (IIa) or (IIb), R$^{31a}$ is pentyl, isopentyl, hexyl, 5-methylhexyl, 3,3-dimethylbutyl, 2-ethylpropyl, 3-pentyl, 2-ethylbutyl, or heptyl.

In some embodiments of a compound of Formula (IIa) or (IIb), R$^{31a}$ is C$_5$-C$_{12}$ alkyl. In some embodiments of a compound of Formula (IIa) or (IIb), R$^{31a}$ is pentyl, isopentyl, hexyl, 5-methylhexyl, 3,3-dimethylbutyl, 2-ethylbutyl, or heptyl.

In some embodiments of a compound of Formula (IIa) or (IIb), R$^{31a}$ is —(C$_1$-C$_6$ alkylene)S(═O)$_2$R$^4$. In some embodiments of a compound of Formula (IIa) or (IIb), R$^{31a}$ is —(C$_1$-C$_6$ alkylene)S(═O)$_2$R$^4$; and R$_4$ is C$_1$-C$_6$ alkyl. In some embodiments of a compound of Formula (IIa) or (IIb), R$^{31a}$ is —(C$_1$ alkylene)S(═O)$_2$R$^4$; and R$_4$ is C$_1$-C$_6$ alkyl. In some embodiments of a compound of Formula (IIa) or (IIb), R$^{31a}$ is —(C$_2$ alkylene)S(═O)$_2$R$^4$; and R$_4$ is C$_1$-C$_6$ alkyl.

In some embodiments of a compound of Formula (IIa) or (IIb), R$^{31a}$ is —(C$_1$-C$_6$ alkylene)C(═O)N(R$^4$R$^5$). In some embodiments of a compound of Formula (IIa) or (IIb), R$^{31a}$ is —(C$_1$-C$_6$ alkylene)C(═O)N(R$^4$R$^5$); and R$^4$ and R$^5$ are independently hydrogen or C$_1$-C$_6$ alkyl. In some embodiments of a compound of Formula (IIa) or (IIb), R$^{31a}$ is —(C$_1$-C$_6$ alkylene)C(═O)N(R$^4$R$^5$); and R$^4$ and R$^5$ are independently C$_1$-C$_6$ alkyl. In some embodiments of a compound of Formula (IIa) or (IIb), R$^{31a}$ is —(C$_1$ alkylene)C(═O)N(R$^4$R$^5$); and R$^4$ and R$^5$ are independently hydrogen or C$_1$-C$_6$ alkyl. In some embodiments of a compound of Formula (IIa) or (IIb), R$^{31a}$ is —(C$_2$ alkylene)C(═O)N(R$^4$R$^5$); and R$^4$ and R$^5$ are independently hydrogen or C$_1$-C$_6$ alkyl.

In some embodiments of a compound of Formula (IIa) or (IIb), R$^{31a}$ is:

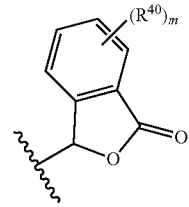

wherein:
each R$^{40}$ is independently hydrogen, halogen, —CN, C$_1$-C$_6$ alkyl, —CF$_3$, cycloalkyl, heterocycloalkyl, —OR⁴, —N(R⁴R⁵), —SR⁴, —(S═O)₂R⁴, —C(═O) OR⁴, or —C(═O)N(R⁴R⁵); and m is 0, 1, 2, 3, or 4.

In some embodiments of a compound of Formula (IIa) or (IIb), m is 0. In some embodiments of a compound of Formula (IIa) or (IIb), m is 1. In some embodiments of a compound of Formula (IIa) or (IIb), m is 2. In some embodiments of a compound of Formula (IIa) or (IIb), m is 1; and $R^{40}$ is halogen, —CN, $C_1$-$C_6$ alkyl, —CF₃, —OR⁴, or —N(R⁴R⁵). In some embodiments of a compound of Formula (IIa) or (IIb), m is 2; and each $R^{40}$ are independently halogen, —CN, $C_1$-$C_6$ alkyl, —CF₃, —OR⁴, or —N(R⁴R⁵). In some embodiments of a compound of Formula (IIa) or (IIb), $R^{40}$ is hydrogen.

In some embodiments of a compound of Formula (IIa) or (IIb), $R^{31a}$ is:

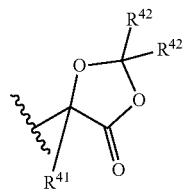

wherein:
each $R^{41}$ and $R^{42}$ are independently hydrogen, halogen, —CN, $C_1$-$C_6$ alkyl, —CF₃, cycloalkyl, heterocycloalkyl, —OR⁴, —N(R⁴R⁵), —SR⁴, —(S═O)₂R⁴, —C(═O)OR⁴, or —C(═O)N(R⁴R⁵).

In some embodiments of a compound of Formula (IIa) or (IIb), each $R^{41}$ and $R^{42}$ are independently $C_1$-$C_6$ alkyl. In some embodiments of a compound of Formula (IIa) or (IIb), each $R^{41}$ and $R^{42}$ are independently methyl or ethyl. In some embodiments of a compound of Formula (IIa) or (IIb), $R^{41}$ and each $R^{42}$ are methyl.

In some embodiments of a compound of Formula (IIa) or (IIb), wherein $R^{31a}$ is:

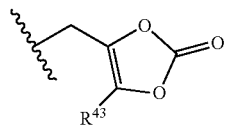

wherein:
$R^{43}$ is hydrogen, halogen, —CN, $C_1$-$C_6$ alkyl, —CF₃, cycloalkyl, heterocycloalkyl, —OR⁴, —N(R⁴R⁵), —SR⁴, —(S═O)₂R⁴, —C(═O)OR⁴, or —C(═O)N(R⁴R⁵).

In some embodiments of a compound of Formula (Ia) or (Ib), $R^{43}$ is hydrogen, $C_1$-$C_6$ alkyl, cycloalkyl, or heterocycloalkyl. In some embodiments of a compound of Formula (Ia) or (Ib), $R^{43}$ is hydrogen or $C_1$-$C_6$ alkyl. In some embodiments of a compound of Formula (IIa) or (IIb), $R^{43}$ is $C_1$-$C_6$ alkyl. In some embodiments of a compound of Formula (IIa) or (IIb), $R^{43}$ is methyl, ethyl, propyl, isopropyl, butyl or isobutyl. In some embodiments of a compound of Formula (IIa) or (IIb), $R^{43}$ is methyl. In some embodiments of a compound of Formula (IIa) or (IIb), $R^{43}$ is isobutyl.

In some embodiments of a compound of Formula (IIa) or (IIb), $R^{31a}$ is:

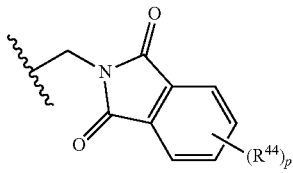

wherein:
$R^{44}$ is hydrogen, halogen, —CN, $C_1$-$C_6$ alkyl, —CF₃, cycloalkyl, heterocycloalkyl, —OR⁴, —N(R⁴R⁵), —SR⁴, —(S═O)₂R⁴, —C(═O)OR⁴, or —C(═O)N(R⁴R⁵); and p is 0, 1, 2, 3, or 4.

In some embodiments of a compound of Formula (IIa) or (IIb), p is 0. In some embodiments of a compound of Formula (IIa) or (IIb), p is 1. In some embodiments of a compound of Formula (IIa) or (IIb), p is 2. In some embodiments of a compound of Formula (IIa) or (IIb), p is 1; and $R^{44}$ is halogen, —CN, $C_1$-$C_6$ alkyl, —CF₃, —OR⁴, or —N(R⁴R⁵). In some embodiments of a compound of Formula (IIa) or (IIb), p is 2; and each $R^{44}$ is independently halogen, —CN, $C_1$-$C_6$ alkyl, —CF₃, —OR⁴, or —N(R⁴R⁵). In some embodiments of a compound of Formula (IIa) or (IIb), $R^{44}$ is hydrogen.

In some embodiments of a compound of Formula (IIa) or (IIb), $R^{31a}$ is alkylaryl. In some embodiments of a compound of Formula (IIa) or (IIb), $R^{31a}$ is —($C_1$-$C_6$ alkylene)aryl. In some embodiments of a compound of Formula (Ia) or (Ib), $R^{31a}$ is —($C_1$-$C_2$ alkylene)aryl; and aryl is phenyl. In some embodiments of a compound of Formula (IIa) or (IIb), $R^{31a}$ is benzyl optionally substituted with halogen, —CN, $C_1$-$C_6$ alkyl, —CF₃, cycloalkyl, heterocycloalkyl, —OR⁴, —N(R⁴R⁵), —SR⁴, —(S═O)₂R⁴, —C(═O)OR⁴, or —C(═O)N(R⁴R⁵).

In some embodiments of a compound of Formula (IIa) or (IIb), $R^{31a}$ is heterocycloalkyl. In some embodiments of a compound of Formula (IIa) or (IIb), $R^{31a}$ is aziridinyl, azetidinyl, pyrrolidinyl, piperidinyl, piperazinyl, morpholinyl, tetrahydropyranyl, isobenzofuranonyl, or 2,2,5-trimethyl-1,3-dioxolan-4-onyl.

In some embodiments of a compound of Formula (IIa) or (IIb), $R^{31a}$ is alkylcycloalkyl. In some embodiments of a compound of Formula (IIa) or (IIb), $R^{31a}$ is —($C_1$-$C_6$ alkylene)cycloalkyl. In some embodiments of a compound of Formula (IIa) or (IIb), $R^{31a}$ is —($C_1$-$C_2$ alkylene)cycloalkyl; and cycloalkyl is cyclopropyl, cyclobutyl, cyclopentyl, cyclohexyl, or cycloheptyl.

In some embodiments of a compound of Formula (IIa) or (IIb), $R^{31a}$ is alkylheterocycloalkyl. In some embodiments of a compound of Formula (IIa) or (IIb), $R^{31a}$ is —($C_1$-$C_6$ alkylene)heterocycloalkyl. In some embodiments of a compound of Formula (IIa) or (IIb), $R^{31a}$ is —($C_1$-$C_2$ alkylene)heterocycloalkyl; and the heterocycloalkyl is aziridinyl, azetidinyl, pyrrolidinyl, piperidinyl, piperazinyl, morpholinyl, tetrahydropyranyl, 4-methyl-1,3-dioxol-2-one, or isoindoline-1,3-dione.

In some embodiments of a compound of Formula (IIa) or (IIb), $R^{31a}$ is

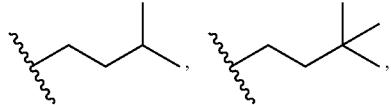

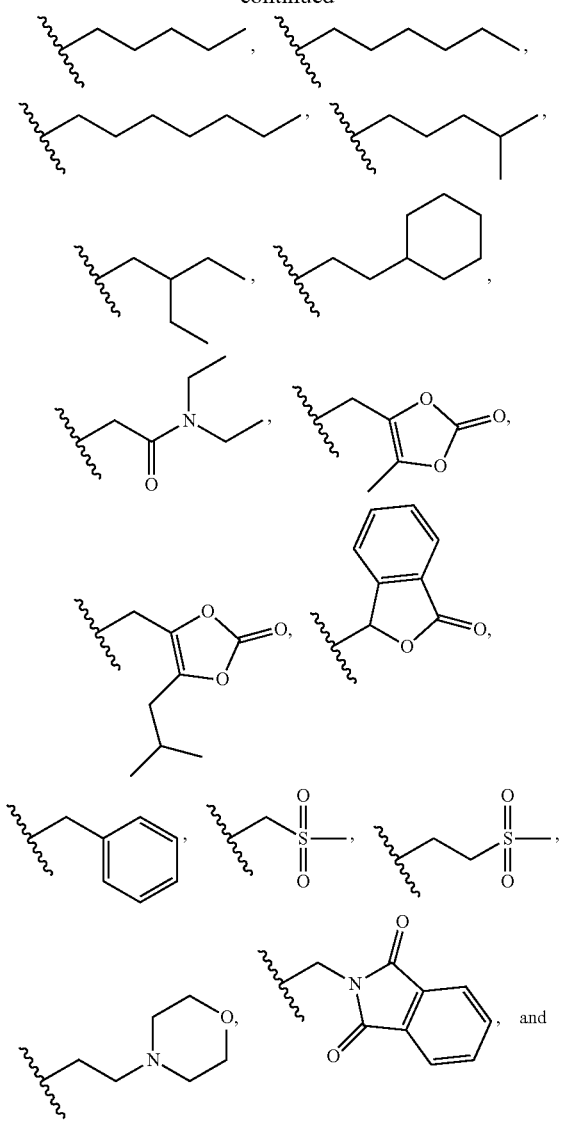
In some embodiments of a compound of Formula (IIa) or (IIb), $R^{31a}$ is
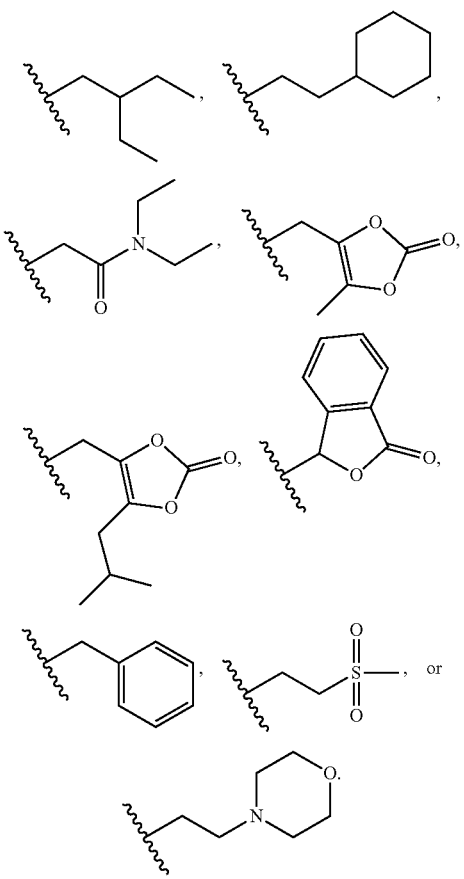
In some embodiments of a compound of Formula (IIa) or (IIb), $R^{31a}$ is
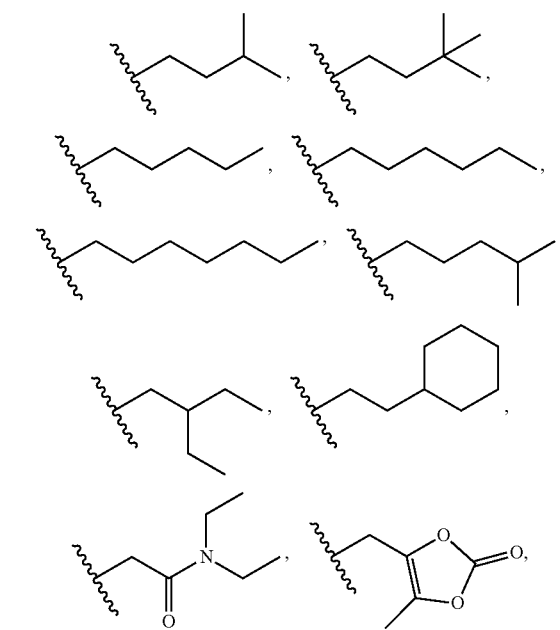

-continued

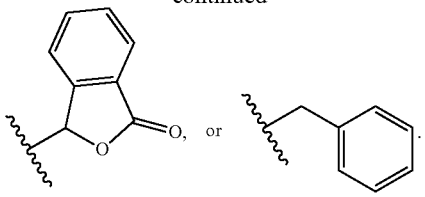

In some embodiments of a compound of Formula (IIa) or (IIb), n is 0, 1, 2, 3, or 4. In some embodiments of a compound of Formula (IIa) or (IIb), n is 0, 1, 2, or 3. In some embodiments of a compound of Formula (IIa) or (IIb), n is 1, 2, 3, or 4. In some embodiments of a compound of Formula (IIa) or (IIb), n is 2, 3, or 4. In some embodiments of a compound of Formula (IIa) or (IIb), n is 2, 3. In some embodiments of a compound of Formula (IIa) or (IIb), n is 1. In some embodiments of a compound of Formula (IIa) or (IIb), n is 2. In some embodiments of a compound of Formula (IIa) or (IIb), n is 3. In some embodiments of a compound of Formula (IIa) or (IIb), n is 4. In some embodiments of a compound of Formula (IIa) or (IIb), n is 5. In some embodiments of a compound of Formula (IIa) or (IIb), n is 6.

In some embodiments of a compound of Formula (IIa) or (IIb), $R^a$, $R^b$, and $R^c$ are independently hydrogen, fluoro, optionally substituted $C_1$-$C_6$ alkyl, —$OR^4$, —$N(R^4R^5)$, or —$SR^4$. In some embodiments of a compound of Formula (IIa) or (IIb), $R^a$, $R^b$, and $R^c$ are independently hydrogen, fluoro, chloro, —OH, or —$OCH_3$. In some embodiments of a compound of Formula (IIa) or (IIb), $R^a$, $R^b$, and $R^c$ are hydrogen. In some embodiments of a compound of Formula (IIa) or (IIb), at least one of $R^a$, $R^b$, or $R^c$ is not hydrogen.

In some embodiments of a compound of Formula (IIa) or (IIb), $X^1$ and $X^2$ are —OH; when present.

In some embodiments of a compound of Formula (IIa) or (IIb), $R^d$ is hydrogen or $C_1$-$C_4$ alkyl. In some embodiments of a compound of Formula (IIa) or (IIb), $R^d$ is hydrogen.

In some embodiments of a compound of Formula (IIa) or (IIb), Z is >C(=O). In some embodiments of a compound of Formula (IIa) or (IIb), Z is >S(=O)$_2$. In some embodiments of a compound of Formula (IIa) or (IIb), Z is >C(=S).

In some embodiments of a compound of Formula (IIa) or (IIb),
M is hydrogen, —$CF_3$, —CN, —$OR^4$, —$SR^4$, —C(=O)$R^4$, or alkynyl;
each $R^1$ and $R^2$ are independently hydrogen, fluoro, chloro, $C_1$-$C_6$ alkyl, or —$CF_3$;
n is 1, 2, 3, or 4;
$X^1$ and $X^2$ are —OH; when present;
Z is >C(=O);
$R^{31a}$ is optionally substituted $C_5$-$C_{12}$ alkyl, —($C_1$-$C_6$ alkylene)C(=O)N($R^4R^5$), —($C_1$-$C_6$ alkylene)S(=O)$_2R^4$, optionally substituted heterocycloalkyl, optionally substituted alkylcycloalkyl, optionally substituted alkylheterocycloalkyl, or optionally substituted alkylaryl;
$R^a$, $R^b$, and $R^c$ are independently hydrogen, fluoro, optionally substituted $C_1$-$C_6$ alkyl, —$OR^4$, —$N(R^4R^5)$, or —$SR^4$;
$R^d$, $R^4$ and $R^5$ are independently hydrogen or $C_1$-$C_6$ alkyl;
or $R^4$ and $R^5$ are taken together with the nitrogen to which they are attached to form a heterocycloalkyl;
provided that the compound is not (5-methyl-2-oxo-1,3-dioxol-4-yl)methyl 3-(3-cyanopropanamido)-2-hydroxy-3,4-dihydro-2H-benzo[e][1,2]oxaborinine-8-carboxylate or 3-oxo-1,3-dihydroisobenzofuran-1-yl 3-acetamido-2-hydroxy-3,4-dihydro-2H-benzo[e][1,2]oxaborinine-8-carboxylate.

In some embodiments of a compound of Formula (IIa) or (IIb),
M is hydrogen or —$CF_3$;
each $R^1$ and $R^2$ are independently hydrogen, fluoro, chloro, $C_1$-$C_6$ alkyl, or —$CF_3$;
n is 1, 2, 3, or 4;
$X^1$ and $X^2$ are —OH; when present;
Z is >C(=O);
$R^{31a}$ is optionally substituted $C_5$-$C_{12}$ alkyl, —($C_1$-$C_6$ alkylene)C(=O)N($R^4R^5$), —($C_1$-$C_6$ alkylene)S(=O)$_2R^4$, optionally substituted heterocycloalkyl, optionally substituted alkylcycloalkyl, optionally substituted alkylheterocycloalkyl, or optionally substituted alkylaryl;
$R^a$, $R^b$, and $R^c$ are independently hydrogen, fluoro, optionally substituted $C_1$-$C_6$ alkyl, —$OR^4$, —$N(R^4R^5)$, or —$SR^4$;
$R^d$, $R^4$ and $R^5$ are independently hydrogen or $C_1$-$C_6$ alkyl;
or $R^4$ and $R^5$ are taken together with the nitrogen to which they are attached to form a heterocycloalkyl;
provided that the compound is not (5-methyl-2-oxo-1,3-dioxol-4-yl)methyl 3-(3-cyanopropanamido)-2-hydroxy-3,4-dihydro-2H-benzo[e][1,2]oxaborinine-8-carboxylate or 3-oxo-1,3-dihydroisobenzofuran-1-yl 3-acetamido-2-hydroxy-3,4-dihydro-2H-benzo[e][1,2]oxaborinine-8-carboxylate.

In some embodiments, the compound of Formula (IIa) or (IIb) is of Formula (IIa-1) or (IIb-1) or pharmaceutically acceptable salts, isomers, stereoisomers, dimers, trimers, tautomers, or N-oxides thereof:

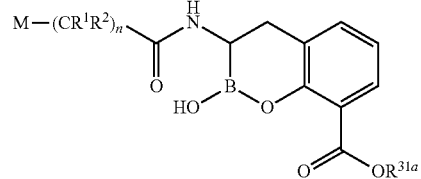

Formula (IIa-1)

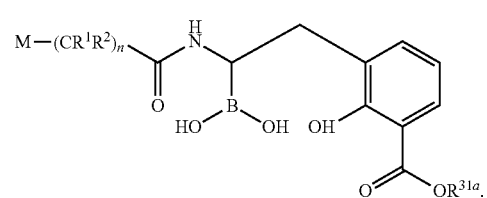

Formula (IIb-1)

In some embodiments of a compound of Formula (IIa-1) or (IIb-1), M is —$CF_3$; n is 1, 2, 3, or 4; each $R^1$ and $R^2$ are independently hydrogen, fluoro, or $C_1$-$C_6$ alkyl; and $R^{31a}$ is optionally substituted $C_5$-$C_{12}$ alkyl, —($C_1$-$C_6$ alkylene)C(=O)N($R^4R^5$), —($C_1$-$C_6$ alkylene)S(=O)$_2R^4$, optionally substituted heterocycloalkyl, optionally substituted alkylcycloalkyl, optionally substituted alkylheterocycloalkyl, optionally substituted aryl, optionally substituted heteroaryl, optionally substituted alkylaryl, or optionally substituted alkylheteroaryl.

In some embodiments of a compound of Formula (IIa-1) or (IIb-1), M is —$CF_3$; n is 1, 2, 3, or 4; each $R^1$ and $R^2$ are independently hydrogen, fluoro, or $C_1$-$C_6$ alkyl; and $R^{31a}$ is optionally substituted $C_5$-$C_{12}$ alkyl, —($C_1$-$C_6$ alkylene)C(=O)N($R^4R^5$), —($C_1$-$C_6$ alkylene)S(=O)$_2R^4$, optionally substituted heterocycloalkyl, optionally substituted alkylcycloalkyl, optionally substituted alkylheterocycloalkyl, or optionally substituted alkylaryl.

In some embodiments of a compound of Formula (IIa-1) or (IIb-1), M is —CF$_3$; n is 1, 2, 3, or 4; each R$^1$ and R$^2$ are independently hydrogen, fluoro, or C$_1$-C$_6$ alkyl; and R$^{31a}$ is C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, heterocycloalkyl, alkylcycloalkyl, alkylheterocycloalkyl, or alkylaryl; each optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$).

In some embodiments of a compound of Formula (IIa-1) or (IIb-1), M is hydrogen; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, optionally substituted heterocycloalkyl, optionally substituted alkylcycloalkyl, optionally substituted alkylheterocycloalkyl, optionally substituted aryl, optionally substituted heteroaryl, optionally substituted alkylaryl, or optionally substituted alkylheteroaryl; provided that the compound is not 3-oxo-1,3-dihydroisobenzofuran-1-yl 3-acetamido-2-hydroxy-3,4-dihydro-2H-benzo[e][1,2]oxaborinine-8-carboxylate.

In some embodiments of a compound of Formula (IIa-1) or (IIb-1), M is hydrogen; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, optionally substituted heterocycloalkyl, optionally substituted alkylcycloalkyl, optionally substituted alkylheterocycloalkyl, optionally substituted alkylaryl, or optionally substituted alkylheteroaryl; provided that the compound is not 3-oxo-1,3-dihydroisobenzofuran-1-yl 3-acetamido-2-hydroxy-3,4-dihydro-2H-benzo[e][1,2]oxaborinine-8-carboxylate.

In some embodiments of a compound of Formula (IIa-1) or (IIb-1), M is hydrogen; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, heterocycloalkyl, alkylcycloalkyl, alkylheterocycloalkyl, alkylaryl, or alkylheteroaryl; each optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); provided that the compound is not 3-oxo-1,3-dihydroisobenzofuran-1-yl 3-acetamido-2-hydroxy-3,4-dihydro-2H-benzo[e][1,2]oxaborinine-8-carboxylate.

In some embodiments of a compound of Formula (IIa-1) or (IIb-1), M is —CN, —OR$^4$, —SR$^4$, —C(=O)R$^4$, or alkynyl; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, optionally substituted heterocycloalkyl, optionally substituted alkylcycloalkyl, optionally substituted alkylheterocycloalkyl, optionally substituted aryl, optionally substituted heteroaryl, optionally substituted alkylaryl, or optionally substituted alkylheteroaryl; provided that the compound is not (5-methyl-2-oxo-1,3-dioxol-4-yl)methyl 3-(3-cyanopropanamido)-2-hydroxy-3,4-dihydro-2H-benzo[e][1,2]oxaborinine-8-carboxylate.

In some embodiments of a compound of Formula (IIa-1) or (IIb-1), M is —CN, —OR$^4$, —SR$^4$, —C(=O)R$^4$, or alkynyl; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, optionally substituted heterocycloalkyl, optionally substituted alkylcycloalkyl, optionally substituted alkylheterocycloalkyl, optionally substituted alkylaryl, or optionally substituted alkylheteroaryl; provided that the compound is not (5-methyl-2-oxo-1,3-dioxol-4-yl)methyl 3-(3-cyanopropanamido)-2-hydroxy-3,4—dihydro-2H-benzo[e] [1,2]oxaborinine-8-carboxylate.

In some embodiments of a compound of Formula (IIa-1) or (IIb-1), M is —CN, —OR$^4$, —SR$^4$, —C(=O)R$^4$, or alkynyl; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, heterocycloalkyl, alkylcycloalkyl, alkylheterocycloalkyl, alkylaryl, or alkylheteroaryl; each optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); provided that the compound is not (5-methyl-2-oxo-1,3-dioxol-4-yl)methyl 3-(3-cyanopropanamido)-2-hydroxy-3,4-dihydro-2H-benzo[e][1,2]oxaborinine-8-carboxylate.

In some embodiments of a compound of Formula (IIa-1) or (IIb-1), M is optionally substituted heteroaryl or optionally substituted heterocycloalkyl; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, optionally substituted heterocycloalkyl, optionally substituted alkylcycloalkyl, optionally substituted alkylheterocycloalkyl, optionally substituted aryl, optionally substituted heteroaryl, optionally substituted alkylaryl, or optionally substituted alkylheteroaryl.

In some embodiments of a compound of Formula (IIa-1) or (IIb-1), M is optionally substituted heteroaryl or optionally substituted heterocycloalkyl; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, optionally substituted heterocycloalkyl, optionally substituted alkylcycloalkyl, optionally substituted alkylheterocycloalkyl, optionally substituted alkylaryl, or optionally substituted alkylheteroaryl.

In some embodiments of a compound of Formula (IIa-1) or (IIb-1), M is optionally substituted heteroaryl or optionally substituted heterocycloalkyl; n is 1, 2, 3, or 4; each R$^1$ and R$^2$ are independently hydrogen, fluoro, or C$_1$-C$_6$ alkyl; and R$^{31a}$ is optionally substituted C$_5$-C$_{12}$ alkyl, —(C$_1$-C$_6$ alkylene)C(=O)N(R$^4$R$^5$), —(C$_1$-C$_6$ alkylene)S(=O)$_2$R$^4$, heterocycloalkyl, alkylcycloalkyl, alkylheterocycloalkyl, alkylaryl, or alkylheteroaryl; each optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$).

In another aspect, provided herein are compounds of Formula (IIIa) or (IIIb) or pharmaceutically acceptable salts, isomers, stereoisomers, dimers, trimers, tautomers, or N-oxides thereof:

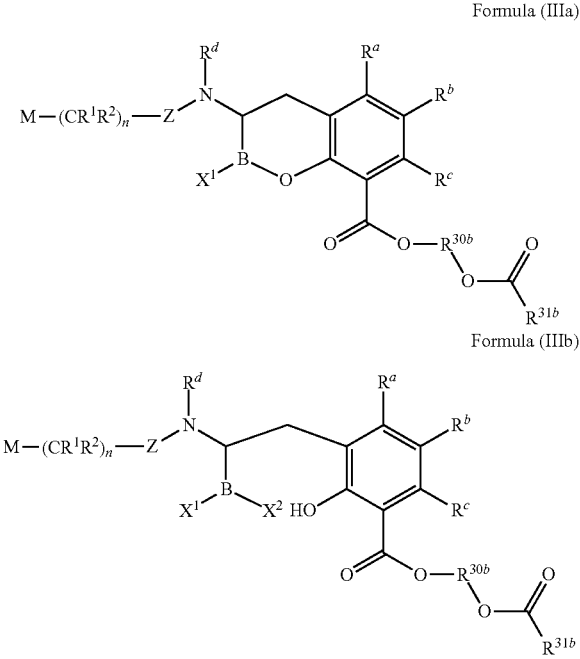

Formula (IIIa)

Formula (IIIb)

wherein:
M is hydrogen, fluoro, chloro, bromo, —CF$_3$, —CN, —OR$^4$, —SR$^4$, —S(=O)R$^4$, —S(=O)$_2$R$^4$, —S(=O)$_2$N(R$^4$R$^5$), —N(R$^4$R$^5$), —N(R$^4$)C(=O)R$^4$, —N(R$^4$)C(=O)N(R$^4$R$^5$), —N(R$^4$)S(=O)$_2$R$^4$, —N(R$^4$)Heteroaryl, —C(=O)R$^4$, —C(=O)N(R$^4$R$^5$), —C(=O)(C$_1$-C$_3$alkylene)C(=O)R$^4$, optionally substituted oxyimino, optionally substituted alkenyl, optionally substituted alkynyl, heteroaryl, or heterocycloalkyl;

each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$); or R$^1$ and R$^2$ are taken together with the carbon to which they are attached to form an optionally substituted cycloalkyl; or when n is at least 2, two R$^1$ on adjacent carbons are taken together to form a double bond; or two R$^1$ and two R$^2$ on adjacent carbons are taken together to form a triple bond;

n is 0, 1, 2, 3, 4, 5, or 6;

X$^1$ and X$^2$ are independently —OR$^4$, or F; when present;

Z is >C(=O), >C(=S), or >S(=O)$_2$;

R$^{30b}$ is —CH$_2$—, —CH(R$^{32b}$)—, or —C(R$^{32b}$)$_2$—;

R$^{31b}$ is linear C$_4$–C$_{12}$ alkyl, —(C$_1$-C$_6$ alkylene)OR$^4$, —(C$_1$-C$_6$ alkylene)SR$^4$, —(C$_1$-C$_6$ alkylene)C(=O)OR$^4$, —(C$_1$-C$_6$ alkylene)C(=O)N(R$^4$R$^5$), optionally substituted C$_1$-C$_{12}$ fluoroalkyl, optionally substituted C$_3$-C$_5$ cycloalkyl, optionally substituted heteroaryl, optionally substituted alkylheterocycloalkyl, optionally substituted alkylaryl, or optionally substituted alkylheteroaryl;

each R$^{32b}$ are independently optionally substituted C$_1$-C$_6$ alkyl;

or two R$^{32b}$ are taken together with the carbon to which they are attached to form a cycloalkyl.

R$^a$, R$^b$, and R$^c$ are independently hydrogen, fluoro, chloro, bromo, optionally substituted C$_1$-C$_6$ alkyl, optionally substituted cycloalkyl, optionally substituted heterocloalkyl, optionally substituted aryl, optionally substituted heteroaryl, —OR$^4$, —N(R$^4$R$^5$), or —SR$^4$;

R$^d$, R$^4$ and R$^5$ are independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or R$^4$ and R$^5$ are taken together with the nitrogen to which they are attached to form a heterocycloalkyl.

In some embodiments of a compound of Formula (IIIa) or (IIb),

M is hydrogen, fluoro, chloro, bromo, —CF$_3$, —CN, —OR$^4$, —SR$^4$, —S(=O)R$^4$, —S(=O)$_2$R$^4$, —S(=O)$_2$N(R$^4$R$^5$), —N(R$^4$R$^5$), —N(R$^4$)C(=O)R$^4$, —N(R$^4$)C(=O)N(R$^4$R$^5$), —N(R$^4$)S(=O)$_2$R$^4$, —N(R$^4$)Heteroaryl, —C(=O)R$^4$, —C(=O)N(R$^4$R$^5$), —C(=O)(C$_1$-C$_3$alkylene)C(=O)R$^4$, optionally substituted oxyimino, optionally substituted alkenyl, optionally substituted alkynyl, heteroaryl, or heterocycloalkyl;

each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$); or R$^1$ and R$^2$ are taken together with the carbon to which they are attached to form an optionally substituted cycloalkyl; or when n is at least 2, two R$^1$ on adjacent carbons are taken together to form a double bond; or two R$^1$ and two R$^2$ on adjacent carbons are taken together to form a triple bond;

n is 0, 1, 2, 3, 4, 5, or 6;

X$^1$ and X$^2$ are independently —OR$^4$, or F; when present;

Z is >C(=O), >C(=S), or >S(=O)$_2$;

R$^{30b}$ is —CH$_2$—, —CH(R$^{32b}$)—, or —C(R$^{32b}$)$_2$—;

R$^{31b}$ is linear C$_4$–C$_{12}$ alkyl, —(C$_1$-C$_6$ alkylene)OR$^4$, —(C$_1$-C$_6$ alkylene)C(=O)OR$^4$, —(C$_1$-C$_6$ alkylene)C(=O)N(R$^4$R$^5$), optionally substituted C$_1$-C$_{12}$ fluoroalkyl, optionally substituted heteroaryl, optionally substituted alkylheterocycloalkyl, optionally substituted alkylaryl, or optionally substituted alkylheteroaryl;

each R$^{32b}$ are independently optionally substituted C$_1$-C$_6$ alkyl;

or two R$^{32b}$ are taken together with the carbon to which they are attached to form a cycloalkyl.

R$^a$, R$^b$, and R$^c$ are independently hydrogen, fluoro, chloro, bromo, optionally substituted C$_1$-C$_6$ alkyl, optionally substituted cycloalkyl, optionally substituted heterocloalkyl, optionally substituted aryl, optionally substituted heteroaryl, —OR$^4$, —N(R$^4$R$^5$), or —SR$^4$;

R$^d$, R$^4$ and R$^5$ are independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ are taken together with the nitrogen to which they are attached to form a heterocycloalkyl.

In some embodiments of a compound of Formula (IIIa) or (IIIb), M is hydrogen, $-CF_3$, $-CN$, $-OR^4$, $-SR^4$, $-C(=O)R^4$, or alkynyl. In some embodiments of a compound of Formula (IIIa) or (IIIb), M is hydrogen or $-CF_3$. In some embodiments of a compound of Formula (IIIa) or (IIIb), M is $-CF_3$. In some embodiments of a compound of Formula (IIIa) or (IIIb), M is $-CN$. In some embodiments of a compound of Formula (IIIa) or (IIIb), M is $SR^4$. In some embodiments of a compound of Formula (IIIa) or (IIIb), M is $SR^4$ and $R^4$ is $C_1$-$C_4$ alkyl. In some embodiments of a compound of Formula (IIIa) or (IIIb), M is $SR^4$ and $R^4$ is methyl. In some embodiments of a compound of Formula (IIIa) or (IIIb), M is $-C(=O)R^4$. In some embodiments of a compound of Formula (IIIa) or (IIIb), M is $-C(=O)R^4$ and $R^4$ is $C_1$-$C_4$ alkyl. In some embodiments of a compound of Formula (IIIa) or (IIIb), M is $-C(=O)R^4$ and $R^4$ is methyl. In some embodiments of a compound of Formula (IIIa) or (IIIb), M is alkynyl. In some embodiments of a compound of Formula (IIIa) or (IIIb), M is hydrogen. In some embodiments of a compound of Formula (IIIa) or (IIIb), M is not $-CF_3$.

In some embodiments of a compound of Formula (IIIa) or (IIIb), each $R^1$ and $R^2$ are independently hydrogen, fluoro, chloro, bromo, optionally substituted $C_1$-$C_6$ alkyl, optionally substituted aryl, $-OR^4$, $-SR^4$, or $-N(R^4R^5)$. In some embodiments of a compound of Formula (IIIa) or (IIIb), $R^1$ and $R^2$ are taken together with the carbon to which they are attached to form a cycloalkyl. In some embodiments of a compound of Formula (IIIa) or (IIIb), when n is at least 2, two $R^1$ on adjacent carbons are taken together to form a double bond; or two $R^1$ and two $R^2$ on adjacent carbons are taken together to form a triple bond. In some embodiments of a compound of Formula (IIIa) or (IIIb), each $R^1$ and $R^2$ are independently hydrogen, fluoro, chloro, $C_1$-$C_6$ alkyl, or $-CF_3$. In some embodiments of a compound of Formula (IIIa) or (IIIb), each $R^1$ and $R^2$ are independently hydrogen or fluoro. In some embodiments of a compound of Formula (IIIa) or (IIIb), each $R^1$ and $R^2$ are hydrogen. In some embodiments of a compound of Formula (IIIa) or (IIIb), at least one of $R^1$ or $R^2$ is fluoro. In some embodiments of a compound of Formula (IIIa) or (IIIb), at least two of $R^1$ or $R^2$ are fluoro. In some embodiments of a compound of Formula (IIIa) or (Mb), at least three of $R^1$ or $R^2$ are fluoro.

In some embodiments of a compound of Formula (IIIa) or (IIIb), $R^{30b}$ is $-CH_2-$. In some embodiments of a compound of Formula (IIIa) or (IIIb), $R^{30b}$ is $-CH(R^{32b})-$. In some embodiments of a compound of Formula (IIIa) or (IIIb), $R^{30b}$ is $-CH(R^{32b})-$ and $R^{32b}$ is $C_1$-$C_6$ alkyl. In some embodiments of a compound of Formula (IIIa) or (IIIb), $R^{30b}$ is $-CH(R^{32b})-$; and $R^{32b}$ is methyl, ethyl, propyl, isopropyl, butyl, or isobutyl. In some embodiments of a compound of Formula (IIIa) or (IIIb), $R^{30b}$ is $-CH(R^{32b})-$; and $R^{32b}$ is methyl or isopropyl.

In some embodiments of a compound of Formula (IIIa) or (IIIb), $R^{30b}$ is $-C(R^{32b})_2-$. In some embodiments of a compound of Formula (IIIa) or (IIIb), $R^{30b}$ is $-C(R^{32b})_2-$; and each $R^{32b}$ is independently methyl, ethyl, propyl, isopropyl, butyl, or isobutyl. In some embodiments of a compound of Formula (IIIa) or (IIIb), $R^{30b}$ is $-C(R^{32b})_2-$; and each $R^{32b}$ is independently methyl. In some embodiments of a compound of Formula (IIIa) or (IIIb), $R^{30b}$ is $-C(R^{32b})_2-$; and two $R^{32b}$ are taken together with the carbon to which they are attached to form a cycloalkyl. In some embodiments of a compound of Formula (IIIa) or (IIIb), $R^{30b}$ is $-C(R^{32b})_2-$; and two $R^{32b}$ are taken together with the carbon to which they are attached to form a cyclopropyl, cyclobutyl, cyclopentyl, cyclohexyl, or cycloheptyl. In some embodiments of a compound of Formula (IIIa) or (IIIb), $R^{30b}$ is $-C(R^{32b})_2-$; and two $R^{32b}$ are taken together with the carbon to which they are attached to form a cyclopropyl.

In some embodiments of a compound of Formula (IIIa) or (IIIb), $R^{30b}$ is $-CH_2-$, $-CH(CH_3)-$, or $-CH(isopropyl)-$. In some embodiments of a compound of Formula (IIIa) or (IIIb), $R^{30b}$ is $-CH_2-$ or $-CH(CH_3)-$.

In some embodiments of a compound of Formula (IIIa) or (IIIb), $R^{30b}$ is $-CH_2-$ or $-CH(R^{32b})-$; and $R^{31b}$ is linear $C_4$-$C_{12}$ alkyl, $-(C_1$-$C_6$ alkylene)$OR^4$, $-(C_1$-$C_6$ alkylene)$SR^4$, $-(C_1$-$C_6$ alkylene)$C(=O)OR^4$, $-(C_1$-$C_6$ alkylene)$C(=O)N(R^4R^5)$, optionally substituted $C_1$-$C_{12}$ fluoroalkyl, optionally substituted $C_3$-$C_5$ cycloalkyl, optionally substituted alkylheterocycloalkyl, optionally substituted heteroaryl, or optionally substituted alkylheteroaryl.

In some embodiments of a compound of Formula (IIIa) or (IIIb), $R^{30b}$ is $-CH_2-$ or $-CH(R^{32b})-$; and $R^{31b}$ is linear $C_4$-$C_{12}$ alkyl, $-(C_1$-$C_6$ alkylene)$OR^4$, $-(C_1$-$C_6$ alkylene)$C(=O)OR^4$, $-(C_1$-$C_6$ alkylene)$C(=O)N(R^4R^5)$, optionally substituted $C_1$-$C_{12}$ fluoroalkyl, optionally substituted alkylheterocycloalkyl, optionally substituted heteroaryl, or optionally substituted alkylheteroaryl.

In some embodiments of a compound of Formula (IIIa) or (IIIb), $R^{30b}$ is $-CH_2-$ or $-CH(R^{32b})-$; and $R^{31b}$ is alkylheterocycloalkyl, heteroaryl, or alkylheteroaryl; each optionally substituted with halogen, $-CN$, $C_1$-$C_6$ alkyl, $-CF_3$, cycloalkyl, heterocycloalkyl, $-OR^4$, $-N(R^4R^5)$, $-SR^4$, $-(S=O)_2R^4$, $-C(=O)OR^4$, or $-C(=O)N(R^4R^5)$.

In some embodiments of a compound of Formula (IIIa) or (IIIb), $R^{30b}$ is $-CH_2-$ or $-CH(R^{32b})-$; and $R^{31b}$ is linear $C_4$-$C_{12}$ alkyl, $-(C_1$-$C_6$ alkylene)$OR^4$, $-(C_1$-$C_6$ alkylene)$SR^4$, $-(C_1$-$C_6$ alkylene)$C(=O)OR^4$, $-(C_1$-$C_6$ alkylene)$C(=O)N(R^4R^5)$, $C_1$-$C_{12}$ fluoroalkyl, $C_3$-$C_5$ cycloalkyl, alkylheterocycloalkyl, heteroaryl, or alkylheteroaryl.

In some embodiments of a compound of Formula (IIIa) or (IIIb), $R^{30b}$ is $-CH_2-$ or $-CH(R^{32b})-$; and $R^{31b}$ is linear $C_4$-$C_{12}$ alkyl, $-(C_1$-$C_6$ alkylene)$OR^4$, $-(C_1$-$C_6$ alkylene)$C(=O)OR^4$, $-(C_1$-$C_6$ alkylene)$C(=O)N(R^4R^5)$, $C_1$-$C_{12}$ fluoroalkyl, alkylheterocycloalkyl, heteroaryl, or alkylheteroaryl.

In some embodiments of a compound of Formula (IIIa) or (IIIb), $R^{30b}$ is $-CH_2-$ or $-CH(R^{32b})-$; $R^{32b}$ is $C_1$-$C_6$ alkyl; and $R^{31b}$ is linear $C_4$-$C_{12}$ alkyl. In some embodiments of a compound of Formula (IIIa) or (IIIb), $R_{30b}$ is $-CH_2-$ or $-CH(R^{32b})-$; $R^{32b}$ is $C_1$-$C_6$ alkyl; and $R^{31b}$ is butyl, pentyl, hexyl, heptyl.

In some embodiments of a compound of Formula (IIIa) or (IIIb), $R^{30b}$ is $-CH_2-$ or $-CH(R^{32b})-$; $R^{32b}$ is $C_1$-$C_6$ alkyl; and $R^{31b}$ is $C_1$-$C_{12}$ fluoroalkyl. In some embodiments of a compound of Formula (IIIa) or (IIIb), $R^{30b}$ is $-CH_2-$ or $-CH(R^{32b})-$; $R^{32b}$ is $C_1$-$C_6$ alkyl; and $R^{31b}$ is $C_1$-$C_6$ fluoroalkyl. In some embodiments of a compound of Formula (IIIa) or (IIIb), $R^{30b}$ is $-CH_2-$ or $-CH(R^{32b})-$; $R^{32b}$ is $C_1$-$C_6$ alkyl; and $R^{31b}$ is $C_1$-$C_4$ fluoroalkyl.

In some embodiments of a compound of Formula (IIIa) or (IIIb), $R^{30b}$ is $-CH_2-$ or $-CH(R^{32b})-$; $R^{32b}$ is $C_1$-$C_6$ alkyl; and $R^{31b}$ is $C_3$-$C_5$ cycloalkyl. In some embodiments of a compound of Formula (IIIa) or (IIIb), $R^{30b}$ is $-CH_2-$ or $-CH(R^{32b})-$; $R^{32b}$ is $C_1$-$C_6$ alkyl; and $R^{31b}$ is $C_3$ cycloalkyl. In some embodiments of a compound of Formula (IIIa) or (IIIb), $R^{30b}$ is $-CH_2-$ or $-CH(R^{32b})-$; $R^{32b}$ is $C_1$-$C_6$ alkyl; and $R^{31b}$ is $C_4$ cycloalkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; and $R^{31b}$ is C$_5$ cycloalkyl.

In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_6$ alkylene)OR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_6$ alkylene)OR$^4$; and R$^4$ is methyl or ethyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$ alkylene)OR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_2$ alkylene)OR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_3$ alkylene)OR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(—C(CH$_3$)$_2$—)OR$^4$; and R$^4$ is C$_1$-C$_6$ alkyl.

In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_6$ alkylene)SR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_6$ alkylene)SR$^4$; and R$^4$ is methyl or ethyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$ alkylene)SR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_2$ alkylene)SR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_3$ alkylene)SR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(—C(CH$_3$)$_2$—)SR$^4$; and R$^4$ is C$_1$-C$_6$ alkyl.

In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_6$ alkylene)C(=O)OR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_6$ alkylene)C(=O)OR$^4$; and R$^4$ is methyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$ alkylene)C(=O)OR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_2$ alkylene)C(=O)OR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_3$ alkylene)C(=O)OR$^4$; and R$^4$ is C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_4$ alkylene)C(=O)OR$^4$; and R$^4$ is C$_1$-C$_6$ alkyl.

In some embodiments of a compound of Formula (IIIa) or (IIIb), $R^{30b}$ is —CH$_2$— or —CH(R32b)—; $R^{32b}$ is C$_1$-C$_6$ alkyl; $R^{31b}$ is —(C$_1$-C$_6$ alkylene)C(=O)N(R$^4$R$^5$); and R$^4$ and R$^5$ are independently hydrogen or C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_6$ alkylene)C(=O)N(R$^4$R$^5$); and R$^4$ and R$^5$ are independently C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_6$ alkylene)C(=O)N(R$^4$R$^5$); and R$^4$ and R$^5$ are each methyl or ethyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$ alkylene)C(=O)N(R$^4$R$^5$); and R$^4$ and R$^5$ are independently hydrogen or C$_1$-C$_6$ alkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_2$ alkylene)C(=O)N(R$^4$R$^5$); and R$^4$ and R$^5$ are independently hydrogen or C$_1$-C$_6$ alkyl.

In some embodiments of a compound of Formula (IIIa) or (IIIb), $R^{30b}$ is —CH$_2$— or —CH(R$^{32b}$)—; $R^{32b}$ is C$_1$-C$_6$ alkyl; and $R^{31b}$ is alkylheterocycloalkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; and $R^{31b}$ is —(C$_1$-C$_6$ alkylene)heterocycloalkyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_2$ alkylene)heterocycloalkyl; and the heterocycloalkyl is aziridinyl, azetidinyl, pyrrolidinyl, piperidinyl, piperazinyl, morpholinyl, or tetrahydropyranyl.

In some embodiments of a compound of Formula (IIIa) or (IIIb), $R^{30b}$ is —CH$_2$— or —CH(R$^{32b}$)—; $R^{32b}$ is C$_1$-C$_6$ alkyl; and $R^{31b}$ is alkylheteroaryl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; $R^{31b}$ is —(C$_1$-C$_2$ alkylene)heteroaryl; and the heteroaryl is pyridyl, pyrimidyl, pyrazinyl, or pyperazinyl.

In some embodiments of a compound of Formula (IIIa) or (IIIb), $R^{30b}$ is —CH$_2$— or —CH(R$^{32b}$)—; $R^{32b}$ is C$_1$-C$_6$ alkyl; and $R^{31b}$ is heteroaryl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; and $R^{31b}$ is pyridyl, pyrimidyl, pyrazinyl, or pyperazinyl. In some embodiments of a compound of Formula (IIIa) or (IIIb), $R^{30b}$ is —CH$_2$— or —CH(R$^{32b}$)—; $R^{32b}$ is C$_1$-C$_6$ alkyl; and $R^{31b}$ is pyridyl optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$).

In some embodiments of a compound of Formula (IIIa) or (IIIb), $R^{31b}$ is

-continued

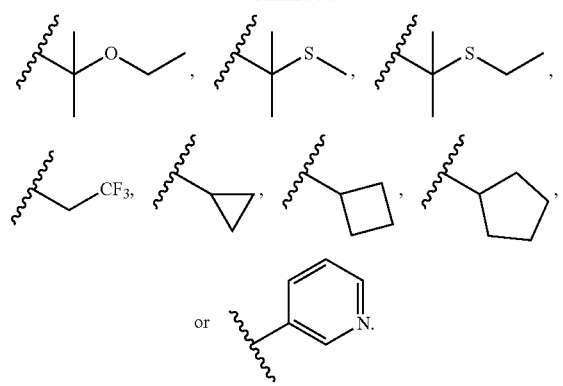

In some embodiments of a compound of Formula (IIIa) or (IIIb), $R^{31b}$ is

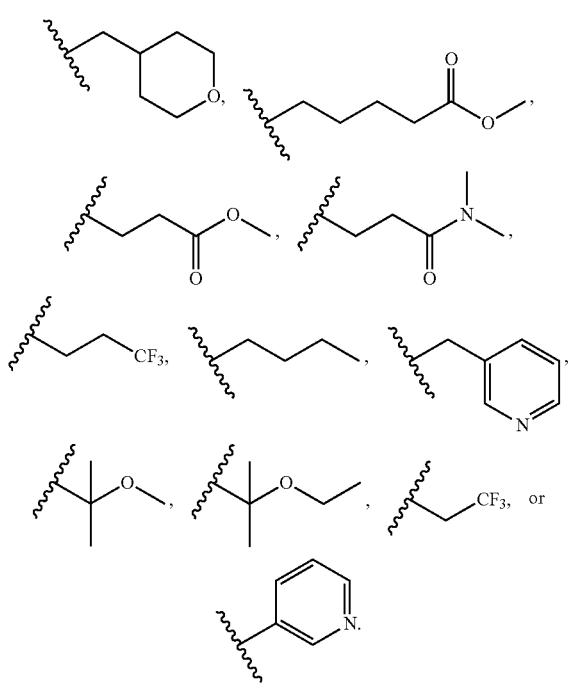

In some embodiments of a compound of Formula (IIIa) or (IIIb), $R^{31b}$ is

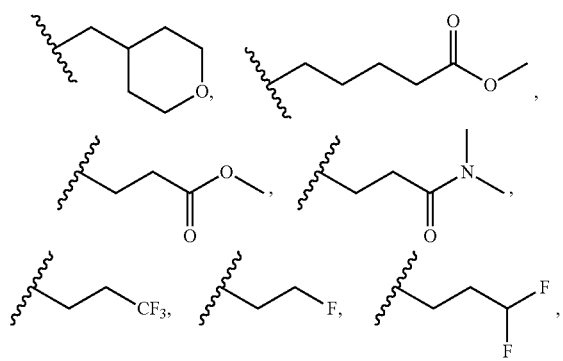

-continued

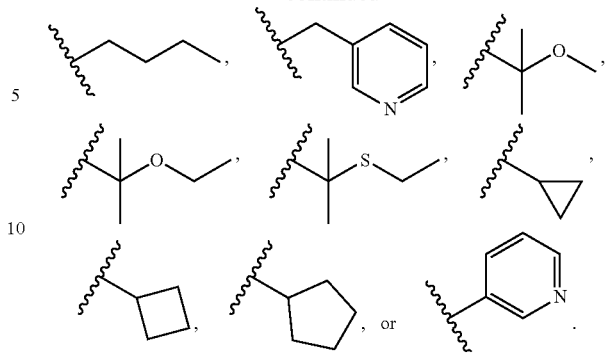

In some embodiments of a compound of Formula (IIIa) or (IIIb), $R^{31b}$ is

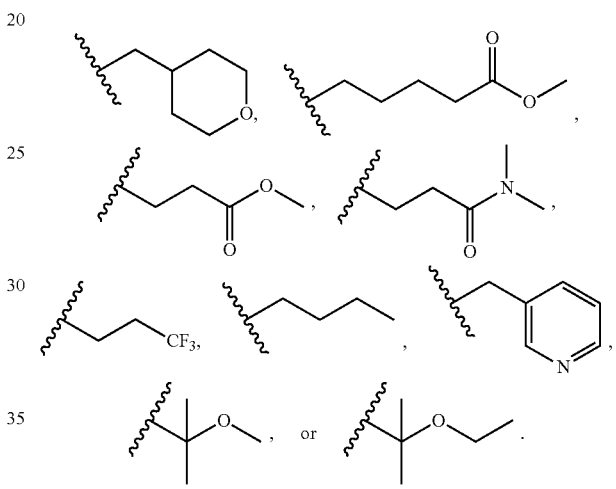

In some embodiments of a compound of Formula (IIIa) or (IIIb), n is 0, 1, 2, 3, or 4. In some embodiments of a compound of Formula (IIIa) or (IIIb), n is 0, 1, 2, or 3. In some embodiments of a compound of Formula (IIIa) or (IIIb), n is 1, 2, 3, or 4. In some embodiments of a compound of Formula (IIIa) or (IIIb), n is 2, 3, or 4. In some embodiments of a compound of Formula (IIIa) or (IIIb), n is 2, 3. In some embodiments of a compound of Formula (IIIa) or (IIIb), n is 1. In some embodiments of a compound of Formula (IIIa) or (IIIb), n is 2. In some embodiments of a compound of Formula (IIIa) or (IIIb), n is 3. In some embodiments of a compound of Formula (IIIa) or (IIIb), n is 4. In some embodiments of a compound of Formula (IIIa) or (IIIb), n is 5. In some embodiments of a compound of Formula (IIIa) or (IIIb), n is 6.

In some embodiments of a compound of Formula (IIIa) or (IIIb), $R^a$, $R^b$, and are independently hydrogen, fluoro, optionally substituted $C_1$-$C_6$ alkyl, —$OR^4$, —$N(R^4R^5)$, or —$SR^4$. In some embodiments of a compound of Formula (IIIa) or (IIIb), $R^a$, $R^b$, and $R^c$ are independently hydrogen, fluoro, chloro, —OH, or —$OCH_3$. In some embodiments of a compound of Formula (IIIa) or (IIIb), $R^a$, $R^b$, and $R^c$ are hydrogen. In some embodiments of a compound of Formula (IIIa) or (IIIb), at least one of $R^a$, $R^b$, or $R^c$ is not hydrogen.

In some embodiments of a compound of Formula (IIIa) or (IIIb), $X^1$ and $X^2$ are —OH; when present.

In some embodiments of a compound of Formula (IIIa) or (IIIb), $R^d$ is hydrogen or $C_1$-$C_4$ alkyl. In some embodiments of a compound of Formula (IIIa) or (IIIb), $R^d$ is hydrogen.

In some embodiments of a compound of Formula (IIIa) or (IIIb), Z is >C(=O). In some embodiments of a compound of Formula (IIIa) or (IIIb), Z is >S(=O)$_2$. In some embodiments of a compound of Formula (IIIa) or (IIIb), Z is >C(=S).

In some embodiments of a compound of Formula (IIIa) or (IIIb),
- M is hydrogen, —CF$_3$, —CN, —OR$^4$, —SR$^4$, —C(=O)R$^4$, or alkynyl;
- each R$^1$ and R$^2$ are independently hydrogen, fluoro, chloro, C$_1$-C$_6$ alkyl, or —CF$_3$;
- n is 1, 2, 3, or 4;
- X$^1$ and X$^2$ are —OH; when present;
- Z is >C(=O);
- R$^{30b}$ is —CH$_2$—, or —CH(R$^{32b}$)—;
- R$^{31b}$ is linear C$_4$–C$_{12}$ alkyl, —(C$_1$-C$_6$ alkylene)OR$^4$, —(C$_1$-C$_6$ alkylene)SR$^4$, —(C$_1$-C$_6$ alkylene)C(=O)OR$^4$, —(C$_1$-C$_6$ alkylene)C(=O)N(R$^4$R$^5$), optionally substituted C$_1$-C$_{12}$ fluoroalkyl, optionally substituted C$_3$-C$_5$ cycloalkyl, optionally substituted heteroaryl, optionally substituted alkylheterocycloalkyl, or optionally substituted alkylheteroaryl;
- R$^{32b}$ is optionally substituted C$_1$-C$_6$ alkyl;
- R$^a$, R$^b$, and R$^c$ are independently hydrogen, fluoro, optionally substituted C$_1$-C$_6$ alkyl, —OR$^4$, —N(R$^4$R$^5$), or —SR$^4$;
- R$^d$, R$^4$ and R$^5$ are independently hydrogen or C$_1$-C$_6$ alkyl;
- or R$^4$ and R$^5$ are taken together with the nitrogen to which they are attached to form a heterocycloalkyl.

In some embodiments of a compound of Formula (IIIa) or (IIIb),
- M is hydrogen, —CF$_3$, —CN, —OR$^4$, —SR$^4$, —C(=O)R$^4$, or alkynyl;
- each R$^1$ and R$^2$ are independently hydrogen, fluoro, chloro, C$_1$-C$_6$ alkyl, or —CF$_3$;
- n is 1, 2, 3, or 4;
- X$^1$ and X$^2$ are —OH; when present;
- Z is >C(=O);
- R$^{30b}$ is —CH$_2$—, or —CH(R$^{32b}$)—;
- R$^{31b}$ is linear C$_4$-C$_{12}$ alkyl, —(C$_1$-C$_6$ alkylene)OR$^4$, —(C$_1$-C$_6$ alkylene)C(=O)OR$^4$, —(C$_1$-C$_6$ alkylene)C(=O)N(R$^4$R$^5$), optionally substituted C$_1$-C$_{12}$ fluoroalkyl, optionally substituted heteroaryl, optionally substituted alkylheterocycloalkyl, or optionally substituted alkylheteroaryl;
- R$^{32b}$ is optionally substituted C$_1$-C$_6$ alkyl;
- R$^a$, R$^b$, and R$^c$ are independently hydrogen, fluoro, optionally substituted C$_1$-C$_6$ alkyl, —OR$^4$, —N(R$^4$R$^5$), or —SR$^4$;
- R$^d$, R$^4$ and R$^5$ are independently hydrogen or C$_1$-C$_6$ alkyl;
- or R$^4$ and R$^5$ are taken together with the nitrogen to which they are attached to form a heterocycloalkyl.

In some embodiments of a compound of Formula (IIIa) or (IIIb),
- M is hydrogen or —CF$_3$;
- each R$^1$ and R$^2$ are independently hydrogen, fluoro, chloro, C$_1$-C$_6$ alkyl, or —CF$_3$;
- n is 1, 2, 3, or 4;
- X$^1$ and X$^2$ are —OH; when present;
- Z is >C(=O);
- R$^{30b}$ is —CH$_2$—, or —CH(R$^{32b}$)—;
- R$^{31b}$ is linear C$_4$-C$_{12}$ alkyl, —(C$_1$-C$_6$ alkylene)OR$^4$, —(C$_1$-C$_6$ alkylene)SR$^4$, —(C$_1$-C$_6$ alkylene)C(=O)OR$^4$, —(C$_1$-C$_6$ alkylene)C(=O)N(R$^4$R$^5$), optionally substituted C$_1$-C$_{12}$ fluoroalkyl, optionally substituted C$_3$-C$_5$ cycloalkyl, optionally substituted heteroaryl, optionally substituted alkylheterocycloalkyl, or optionally substituted alkylheteroaryl;
- R$^{32b}$ is optionally substituted C$_1$-C$_6$ alkyl;
- R$^a$, R$^b$, and R$^c$ are independently hydrogen, fluoro, optionally substituted C$_1$-C$_6$ alkyl, —OR$^4$, —N(R$^4$R$^5$), or —SR$^4$;
- R$^d$, R$^4$ and R$^5$ are independently hydrogen or C$_1$-C$_6$ alkyl;
- or R$^4$ and R$^5$ are taken together with the nitrogen to which they are attached to form a heterocycloalkyl.

In some embodiments, the compound of Formula (IIIa) or (IIIb) is of Formula (IIIa-1) or (IIIb-1) or pharmaceutically acceptable salts, isomers, stereoisomers, dimers, trimers, tautomers, or N-oxides thereof:

Formula (IIIa-1)

Formula (IIIb-1)

In some embodiments of a compound of Formula (IIIa-1) or (IIIb-1), M is —CF$_3$; n is 1, 2, 3, or 4; each R$^1$ and R$^2$ are independently hydrogen, fluoro, or C$_1$-C$_6$ alkyl; R$^{30b}$ is —CH$_2$—, —CH(R$^{32b}$)—, or —C(R$^{32b}$)$_2$—; R$^{31b}$ is linear C$_4$-C$_{12}$ alkyl, —(C$_1$-C$_6$ alkylene)OR$^4$, —(C$_1$-C$_6$ alkylene)SR$^4$, —(C$_1$-C$_6$ alkylene)C(=O)OR$^4$, —(C$_1$-C$_6$ alkylene)C(=O)N(R$^4$R$^5$), optionally substituted C$_1$-C$_{12}$ fluoroalkyl, optionally substituted C$_3$-C$_5$ cycloalkyl, optionally substituted heteroaryl, optionally substituted alkylheterocycloalkyl, optionally substituted alkylaryl, or optionally substituted alkylheteroaryl; each R$^{32b}$ are independently optionally substituted C$_1$-C$_6$ alkyl; or two R$^{32b}$ are taken together with the carbon to which they are attached to form a cycloalkyl.

In some embodiments of a compound of Formula (IIIa-1) or (IIIb-1), M is —CF$_3$; n is 1, 2, 3, or 4; each R$^1$ and R$^2$ are independently hydrogen, fluoro, or C$_1$-C$_6$ alkyl; R$^{30b}$ is —CH$_2$—, —CH(R$^{32b}$)—, or —C(R$^{32b}$)$_2$—; R$^{31b}$ is linear C$_4$-C$_{12}$ alkyl, —(C$_1$-C$_6$ alkylene)OR$^4$, —(C$_1$-C$_6$ alkylene)C(=O)OR$^4$, —(C$_1$-C$_6$ alkylene)C(=O)N(R$^4$R$^5$), optionally substituted C$_1$-C$_{12}$ fluoroalkyl, optionally substituted heteroaryl, optionally substituted alkylheterocycloalkyl, optionally substituted alkylaryl, or optionally substituted alkylheteroaryl; each R$^{32b}$ are independently optionally substituted C$_1$-C$_6$ alkyl; or two R$^{32b}$ are taken together with the carbon to which they are attached to form a cycloalkyl.

In some embodiments of a compound of Formula (IIIa-1) or (IIIb-1), M is —CF$_3$; n is 1, 2, 3, or 4; each R$^1$ and R$^2$ are independently hydrogen, fluoro, or $C_1$-$C_6$ alkyl; $R^{30b}$ is —$CH_2$— or —$CH(R^{32b})$; $R^{31b}$ is linear $C_4$-$C_{12}$ alkyl, —($C_1$-$C_6$ alkylene)$OR^4$, —($C_1$-$C_6$ alkylene)$SR^4$, —($C_1$-$C_6$ alkylene)C(=O)$OR^4$, —($C_1$-$C_6$ alkylene)C(=O)N($R^4R^5$), optionally substituted $C_1$-$C_{12}$ fluoroalkyl, optionally substituted $C_3$-$C_5$ cycloalkyl, optionally substituted heteroaryl, optionally substituted alkylheterocycloalkyl, or optionally substituted alkylheteroaryl; and $R^{32b}$ is optionally substituted $C_1$-$C_6$ alkyl.

In some embodiments of a compound of Formula (IIIa-1) or (IIIb-1), M is —$CF_3$; n is 1, 2, 3, or 4; each $R^1$ and $R^2$ are independently hydrogen, fluoro, or $C_1$-$C_6$ alkyl; $R^{30b}$ is —$CH_2$— or —$CH(R^{32b})$; $R^{31b}$ is linear $C_4$-$C_{12}$ alkyl, —($C_1$-$C_6$ alkylene)$OR^4$, —($C_1$-$C_6$ alkylene)C(=O)$OR^4$, —($C_1$-$C_6$ alkylene)C(=O)N($R^4R^5$), optionally substituted $C_1$-$C_{12}$ fluoroalkyl, optionally substituted heteroaryl, optionally substituted alkylheterocycloalkyl, or optionally substituted alkylheteroaryl; and $R^{32b}$ is optionally substituted $C_1$-$C_6$ alkyl.

In some embodiments of a compound of Formula (IIIa-1) or (IIIb-1), M is —$CF_3$; n is 1, 2, 3, or 4; each $R^1$ and $R^2$ are independently hydrogen, fluoro, or $C_1$-$C_6$ alkyl; $R^{30b}$ is —$CH_2$— or —$CH(R^{32b})$; $R^{31b}$ is —($C_1$-$C_6$ alkylene)$OR^4$, —($C_1$-$C_6$ alkylene)$SR^4$, —($C_1$-$C_6$ alkylene)C(=O)$OR^4$, —($C_1$-$C_6$ alkylene)C(=O)N($R^4R^5$), $C_1$-$C_{12}$ fluoroalkyl, $C_3$-$C_5$ cycloalkyl, heteroaryl, alkylheterocycloalkyl, or alkylheteroaryl; each optionally substituted with halogen, —CN, $C_1$-$C_6$ alkyl, —$CF_3$, cycloalkyl, heterocycloalkyl, —$OR^4$, —N($R^4R^5$), —$SR^4$, —(S=O)$_2R^4$, —C(=O)$OR^4$, or —C(=O)N($R^4R^5$); and $R^{32b}$ is $C_1$-$C_6$ alkyl.

In some embodiments of a compound of Formula (IIIa-1) or (IIIb-1), M is —$CF_3$; n is 1, 2, 3, or 4; each $R^1$ and $R^2$ are independently hydrogen, fluoro, or $C_1$-$C_6$ alkyl; $R^{30b}$ is —$CH_2$— or —$CH(R^{32b})$; $R^{31b}$ is —($C_1$-$C_6$ alkylene)$OR^4$, —($C_1$-$C_6$ alkylene)C(=O)$OR^4$, —($C_1$-$C_6$ alkylene)C(=O)N($R^4R^5$), $C_1$-$C_{12}$ fluoroalkyl, heteroaryl, alkylheterocycloalkyl, or alkylheteroaryl; each optionally substituted with halogen, —CN, $C_1$-$C_6$ alkyl, —$CF_3$, cycloalkyl, heterocycloalkyl, —$OR^4$, —N($R^4R^5$), —$SR^4$, —(S=O)$_2R^4$, —C(=O)$OR^4$, or —C(=O)N($R^4R^5$); and $R^{32b}$ is $C_1$-$C_6$ alkyl.

In some embodiments of a compound of Formula (IIIa-1) or (IIIb-1), M is hydrogen; n is 1, 2, 3, or 4; each $R^1$ and $R^2$ are independently hydrogen, fluoro, or $C_1$-$C_6$ alkyl; $R^{30b}$ is —$CH_2$—, —$CH(R^{32b})$—, or —$C(R^{32b})_2$—; $R^{31b}$ is linear $C_4$-$C_{12}$ alkyl, —($C_1$-$C_6$ alkylene)$OR^4$, —($C_1$-$C_6$ alkylene)$SR^4$, —($C_1$-$C_6$ alkylene)C(=O)$OR^4$, —($C_1$-$C_6$ alkylene)C(=O)N($R^4R^5$), optionally substituted $C_1$-$C_{12}$ fluoroalkyl, optionally substituted $C_3$-$C_5$ cycloalkyl, optionally substituted heteroaryl, optionally substituted alkylheterocycloalkyl, optionally substituted alkylaryl, or optionally substituted alkylheteroaryl; each $R^{32b}$ are independently optionally substituted $C_1$-$C_6$ alkyl; or two $R^{32b}$ are taken together with the carbon to which they are attached to form a cycloalkyl.

In some embodiments of a compound of Formula (IIIa-1) or (IIIb-1), M is hydrogen; n is 1, 2, 3, or 4; each $R^1$ and $R^2$ are independently hydrogen, fluoro, or $C_1$-$C_6$ alkyl; $R^{30b}$ is —$CH_2$—, —$CH(R^{32b})$—, or —$C(R^{32b})_2$—; $R^{31b}$ is linear $C_4$-$C_{12}$ alkyl, —($C_1$-$C_6$ alkylene)$OR^4$, —($C_1$-$C_6$ alkylene)C(=O)$OR^4$, —($C_1$-$C_6$ alkylene)C(=O)N($R^4R^5$), optionally substituted $C_1$-$C_{12}$ fluoroalkyl, optionally substituted heteroaryl, optionally substituted alkylheterocycloalkyl, optionally substituted alkylaryl, or optionally substituted alkylheteroaryl; each $R^{32b}$ are independently optionally substituted $C_1$-$C_6$ alkyl; or two $R^{32b}$ are taken together with the carbon to which they are attached to form a cycloalkyl.

In some embodiments of a compound of Formula (IIIa-1) or (IIIb-1), M is hydrogen; n is 1, 2, 3, or 4; each $R^1$ and $R^2$ are independently hydrogen, fluoro, or $C_1$-$C_6$ alkyl; $R^{30b}$ is —$CH_2$— or —$CH(R^{32b})$—; $R^{31b}$ is linear $C_4$-$C_{12}$ alkyl, —($C_1$-$C_6$ alkylene)$OR^4$, —($C_1$-$C_6$ alkylene)$SR^4$, —($C_1$-$C_6$ alkylene)C(=O)$OR^4$, —($C_1$-$C_6$ alkylene)C(=O)N($R^4R^5$), optionally substituted $C_1$-$C_{12}$ fluoroalkyl, optionally substituted $C_3$-$C_5$ cycloalkyl, optionally substituted heteroaryl, optionally substituted alkylheterocycloalkyl, or optionally substituted alkylheteroaryl; and $R^{32b}$ is optionally substituted $C_1$-$C_6$ alkyl.

In some embodiments of a compound of Formula (IIIa-1) or (IIIb-1), M is hydrogen; n is 1, 2, 3, or 4; each $R^1$ and $R^2$ are independently hydrogen, fluoro, or $C_1$-$C_6$ alkyl; $R^{30b}$ is —$CH_2$— or —$CH(R^{32b})$—; $R^{31b}$ is linear $C_4$-$C_{12}$ alkyl, —($C_1$-$C_6$ alkylene)$OR^4$, —($C_1$-$C_6$ alkylene)C(=O)$OR^4$, —($C_1$-$C_6$ alkylene)C(=O)N($R^4R^5$), optionally substituted $C_1$-$C_{12}$ fluoroalkyl, optionally substituted heteroaryl, optionally substituted alkylheterocycloalkyl, or optionally substituted alkylheteroaryl; and $R^{32b}$ is optionally substituted $C_1$-$C_6$ alkyl.

In some embodiments of a compound of Formula (IIIa-1) or (IIIb-1), M is hydrogen; n is 1, 2, 3, or 4; each $R^1$ and $R^2$ are independently hydrogen, fluoro, or $C_1$-$C_6$ alkyl; $R^{30b}$ is —$CH_2$— or —$CH(R^{32b})$—; $R^{31b}$ is is —($C_1$-$C_6$ alkylene)$OR^4$, —($C_1$-$C_6$ alkylene)$SR^4$, —($C_1$-$C_6$ alkylene)C(=O)$OR^4$, —($C_1$-$C_6$ alkylene)C(=O)N($R^4R^5$), $C_1$-$C_{12}$ fluoroalkyl, $C_3$-$C_5$ cycloalkyl, heteroaryl, alkylheterocycloalkyl, or alkylheteroaryl; each optionally substituted with halogen, —CN, $C_1$-$C_6$ alkyl, —$CF_3$, cycloalkyl, heterocycloalkyl, —$OR^4$, —N($R^4R^5$), —$SR^4$, —(S=O)$_2R^4$, —C(=O)$OR^4$, or —C(=O)N($R^4R^5$); and $R^{32b}$ is $C_1$-$C_6$ alkyl.

In some embodiments of a compound of Formula (IIIa-1) or (IIIb-1), M is hydrogen; n is 1, 2, 3, or 4; each $R^1$ and $R^2$ are independently hydrogen, fluoro, or $C_1$-$C_6$ alkyl; $R^{30b}$ is —$CH_2$— or —$CH(R^{32b})$—; $R^{31b}$ is —($C_1$-$C_6$ alkylene)$OR^4$, —($C_1$-$C_6$ alkylene)C(=O)$OR^4$, —($C_1$-$C_6$ alkylene)C(=O)N($R^4R^5$), $C_1$-$C_{12}$ fluoroalkyl, heteroaryl, alkylheterocycloalkyl, or alkylheteroaryl; each optionally substituted with halogen, —CN, $C_1$-$C_6$ alkyl, —$CF_3$, cycloalkyl, heterocycloalkyl, —$OR^4$, —N($R^4R^5$), —$SR^4$, —(S=O)$_2R^4$, —C(=O)$OR^4$, or —C(=O)N($R^4R^5$); and $R^{31b}$ is $C_1$-$C_6$ alkyl.

In some embodiments of a compound of Formula (IIIa-1) or (IIIb-1), M is —CN, —$OR^4$, —$SR^4$, —C(=O)$R^4$, or alkynyl; n is 1, 2, 3, or 4; each $R^1$ and $R^2$ are independently hydrogen, fluoro, or $C_1$-$C_6$ alkyl; $R^{30b}$ is —$CH_2$—, —$CH(R^{32b})$—, or —$C(R^{32b})_2$—; $R^{31b}$ is linear $C_4$-$C_{12}$ alkyl, —($C_1$-$C_6$ alkylene)$OR^4$, —($C_1$-$C_6$ alkylene)$SR^4$, —($C_1$-$C_6$ alkylene)C(=O)$OR^4$, —($C_1$-$C_6$ alkylene)C(=O)N($R^4R^5$), optionally substituted $C_1$-$C_{12}$ fluoroalkyl, optionally substituted $C_3$-$C_5$ cycloalkyl, optionally substituted heteroaryl, optionally substituted alkylheterocycloalkyl, optionally substituted alkylaryl, or optionally substituted alkylheteroaryl; each $R^{32b}$ are independently optionally substituted $C_1$-$C_6$ alkyl; or two $R^{32b}$ are taken together with the carbon to which they are attached to form a cycloalkyl.

In some embodiments of a compound of Formula (IIIa-1) or (IIIb-1), M is —CN, —$OR^4$, —$SR^4$, —C(=O)$R^4$, or alkynyl; n is 1, 2, 3, or 4; each $R^1$ and $R^2$ are independently hydrogen, fluoro, or $C_1$-$C_6$ alkyl; $R^{30b}$ is —$CH_2$—, —$CH(R^{32b})$—, or —$C(R^{32b})_2$—; $R^{31b}$ is linear $C_4$-$C_{12}$ alkyl, —($C_1$-$C_6$ alkylene)$OR^4$, —($C_1$-$C_6$ alkylene)C(=O)$OR^4$, —($C_1$-$C_6$ alkylene)C(=O)N($R^4R^5$), optionally substituted $C_1$-$C_{12}$ fluoroalkyl, optionally substituted heteroaryl, optionally substituted alkylheterocycloalkyl, optionally substituted alkylaryl, or optionally substituted alkylheteroaryl;

each $R^{32b}$ are independently optionally substituted $C_1$-$C_6$ alkyl; or two $R^{32b}$ are taken together with the carbon to which they are attached to form a cycloalkyl.

In some embodiments of a compound of Formula (IIIa-1) or (IIIb-1), M is —CN, —OR$^4$, —SR$^4$, —C(=O)R$^4$, or alkynyl; n is 1, 2, 3, or 4; each $R^1$ and $R^2$ are independently hydrogen, fluoro, or $C_1$-$C_6$ alkyl; $R^{30b}$ is —CH$_2$— or —CH(R$^{32b}$)—; $R^{31b}$ is linear $C_4$-$C_{12}$ alkyl, —($C_1$-$C_6$ alkylene)OR$^4$, —($C_1$-$C_6$ alkylene)SR$^4$, —($C_1$-$C_6$ alkylene)C(=O)OR$^4$, —($C_1$-$C_6$ alkylene)C(=O)N(R$^4$R$^5$), optionally substituted $C_1$-$C_{12}$ fluoroalkyl, optionally substituted $C_3$-$C_5$ cycloalkyl, optionally substituted heteroaryl, optionally substituted alkylheterocycloalkyl, or optionally substituted alkylheteroaryl; and $R^{32b}$ is optionally substituted $C_1$-$C_6$ alkyl.

In some embodiments of a compound of Formula (IIIa-1) or (IIIb-1), M is —CN, —OR$^4$, —SR$^4$, —C(=O)R$^4$, or alkynyl; n is 1, 2, 3, or 4; each $R^1$ and $R^2$ are independently hydrogen, fluoro, or $C_1$-$C_6$ alkyl; $R^{30b}$ is —CH$_2$— or —CH(R$^{32b}$)—; $R^{31b}$ is linear $C_4$-$C_{12}$ alkyl, —($C_1$-$C_6$ alkylene)OR$^4$, —($C_1$-$C_6$ alkylene)C(=O)OR$^4$, —($C_1$-$C_6$ alkylene)C(=O)N(R$^4$R$^5$), optionally substituted $C_1$-$C_{12}$ fluoroalkyl, optionally substituted heteroaryl, optionally substituted alkylheterocycloalkyl, or optionally substituted alkylheteroaryl; and $R^{32b}$ is optionally substituted $C_1$-$C_6$ alkyl.

In some embodiments of a compound of Formula (IIIa-1) or (IIIb-1), M is —CN, —OR$^4$, —SR$^4$, —C(=O)R$^4$, or alkynyl; n is 1, 2, 3, or 4; each $R^1$ and $R^2$ are independently hydrogen, fluoro, or $C_1$-$C_6$ alkyl; $R^{30b}$ is —CH$_2$— or —CH(R$^{32b}$)—; R31b is ($C_1$-$C_6$ alkylene)OR$^4$, —($C_1$-$C_6$ alkylene)SR$^4$, —($C_1$-$C_6$ alkylene)C(=O)OR$^4$, —($C_1$-$C_6$ alkylene)C(=O)N(R$^4$R$^5$), $C_1$-$C_{12}$ fluoroalkyl, $C_3$-$C_5$ cycloalkyl, heteroaryl, alkylheterocycloalkyl, or alkylheteroaryl; each optionally substituted with halogen, —CN, $C_1$-$C_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); and $R^{32b}$ is $C_1$-$C_6$ alkyl.

In some embodiments of a compound of Formula (IIIa-1) or (IIIb-1), M is —CN, —OR$^4$, —SR$^4$, —C(=O)R$^4$, or alkynyl; n is 1, 2, 3, or 4; each $R^1$ and $R^2$ are independently hydrogen, fluoro, or $C_1$-$C_6$ alkyl; $R^{30b}$ is —CH$_2$— or —CH(R$^{32}$)—; $R^{31b}$ is ($C_1$-$C_6$ alkylene)OR$^4$, —($C_1$-$C_6$ alkylene)C(=O)OR$^4$, —($C_1$-$C_6$ alkylene)C(=O)N(R$^4$R$^5$), $C_1$-$C_{12}$ fluoroalkyl, heteroaryl, alkylheterocycloalkyl, or alkylheteroaryl; each optionally substituted with halogen, —CN, $C_1$-$C_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); and $R^{32b}$ is $C_1$-$C_6$ alkyl.

In some embodiments of a compound of Formula (IIIa-1) or (IIIb-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; $R^{30b}$ is —CH$_2$—, —CH(R$^{32b}$)—, or —C(R$^{32b}$)$_2$—; $R^{31b}$ is linear $C_4$-$C_{12}$ alkyl, —($C_1$-$C_6$ alkylene)OR$^4$, —($C_1$-$C_6$ alkylene)SR$^4$, —($C_1$-$C_6$ alkylene)C(=O)OR$^4$, —($C_1$-$C_6$ alkylene)C(=O)N(R$^4$R$^5$), optionally substituted $C_1$-$C_{12}$ fluoroalkyl, optionally substituted $C_3$-$C_5$ cycloalkyl, optionally substituted heteroaryl, optionally substituted alkylheterocycloalkyl, optionally substituted alkylaryl, or optionally substituted alkylheteroaryl; each $R^{32b}$ are independently optionally substituted $C_1$-$C_6$ alkyl; or two $R^{32b}$ are taken together with the carbon to which they are attached to form a cycloalkyl.

In some embodiments of a compound of Formula (IIIa-1) or (IIIb-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; $R^{30b}$ is —CH$_2$—, —CH(R$^{32b}$)—, or —C(R$^{32b}$)$_2$—; $R^{31b}$ is linear $C_4$-$C_{12}$ alkyl, —($C_1$-$C_6$ alkylene)OR$^4$, —($C_1$-$C_6$ alkylene)C(=O)OR$^4$, —($C_1$-$C_6$ alkylene)C(=O)N(R$^4$R$^5$), optionally substituted $C_1$-$C_{12}$ fluoroalkyl, optionally substituted heteroaryl, optionally substituted alkylheterocycloalkyl, optionally substituted alkylaryl, or optionally substituted alkylheteroaryl; each $R^{32b}$ are independently optionally substituted $C_1$-$C_6$ alkyl; or two $R^{32b}$ are taken together with the carbon to which they are attached to form a cycloalkyl.

In some embodiments of a compound of Formula (IIIa-1) or (IIIb-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; $R^{30b}$ is —CH$_2$— or —CH(R$^{32b}$)—; $R^{31b}$ is linear $C_4$-$C_{12}$ alkyl, —($C_1$-$C_6$ alkylene)OR$^4$, —($C_1$-$C_6$ alkylene)SR$^4$, —($C_1$-$C_6$ alkylene)C(=O)OR$^4$, —($C_1$-$C_6$ alkylene)C(=O)N(R$^4$R$^5$), optionally substituted $C_1$-$C_{12}$ fluoroalkyl, optionally substituted $C_3$-$C_5$ cycloalkyl, optionally substituted heteroaryl, optionally substituted alkylheterocycloalkyl, or optionally substituted alkylheteroaryl; and $R^{32b}$ is optionally substituted $C_1$-$C_6$ alkyl.

In some embodiments of a compound of Formula (IIIa-1) or (IIIb-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; $R^{30b}$ is —CH$_2$— or —CH(R$^{32b}$)—; $R^{31b}$ is linear $C_4$-$C_{12}$ alkyl, —($C_1$-$C_6$ alkylene)OR$^4$, —($C_1$-$C_6$ alkylene)C(=O)OR$^4$, —($C_1$-$C_6$ alkylene)C(=O)N(R$^4$R$^5$), optionally substituted $C_1$-$C_{12}$ fluoroalkyl, optionally substituted heteroaryl, optionally substituted alkylheterocycloalkyl, or optionally substituted alkylheteroaryl; and $R^{32b}$ is optionally substituted $C_1$-$C_6$ alkyl.

In some embodiments of a compound of Formula (IIIa-1) or (IIIb-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; $R^{30b}$ is —CH$_2$— or —CH(R$^{32b}$)—; $R^{31b}$ is —($C_1$-$C_6$ alkylene)OR$^4$ —($C_1$-$C_6$ alkylene)SR$^4$, —($C_1$-$C_6$ alkylene)C(=O)OR$^4$, —($C_1$-$C_6$ alkylene)C(=O)N(R$^4$R$^5$), $C_1$-$C_{12}$ fluoroalkyl, $C_3$-$C_5$ cycloalkyl, heteroaryl, alkylheterocycloalkyl, or alkylheteroaryl; each optionally substituted with halogen, —CN, $C_1$-$C_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); and $R^{32b}$ is $C_1$-$C_6$ alkyl.

In some embodiments of a compound of Formula (IIIa-1) or (IIIb-1), M is optionally substituted heteroaryl or optionally substituted heterocycloalkyl; n is 1, 2, 3, or 4; each $R^1$ and $R^2$ are independently hydrogen, fluoro, or $C_1$-$C_6$ alkyl; $R^{30b}$ is —CH$_2$— or —CH(R$^{32b}$)—; $R^{31b}$ is —($C_1$-$C_6$ alkylene)OR$^4$, —($C_1$-$C_6$ alkylene)C(=O)OR$^4$, —($C_1$-$C_6$ alkylene)C(=O)N(R$^4$R$^5$), $C_1$-$C_{12}$ fluoroalkyl, heteroaryl, alkylheterocycloalkyl, or alkylheteroaryl; each optionally substituted with halogen, —CN, $C_1$-$C_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); and $R^{32b}$ is $C_1$-$C_6$ alkyl.

In another aspect, provided herein are compounds of Formula (IVa) or (IVb) or pharmaceutically acceptable salts, isomers, stereoisomers, dimers, trimers, tautomers, or N-oxides thereof:

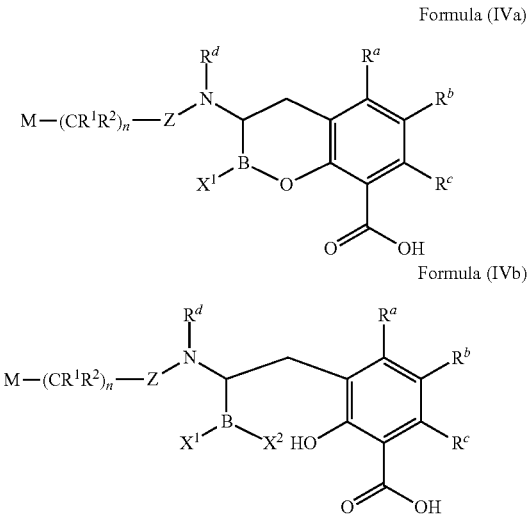

Formula (IVa)

Formula (IVb)

wherein:
M is hydrogen, fluoro, chloro, bromo, —CF$_3$, —CN, —OR$^4$, —SR$^4$, —S(=O)R$^4$, —S(=O)$_2$R$^4$, —S(=O)$_2$N(R$^4$R$^5$), —N(R$^4$R$^5$), —N(R$^4$)C(=O)R$^4$, —N(R$^4$)C(=O)N(R$^4$R$^5$), —N(R$^4$)S(=O)$_2$R$^4$, —N(R$^4$)Heteroaryl, —C(=O)R$^4$, —C(=O)N(R$^4$R$^5$), —C(=O)(C$_1$-C$_3$alkylene)C(=O)R$^4$, optionally substituted oxyimino, optionally substituted alkenyl, optionally substituted alkynyl, heteroaryl, or heterocycloalkyl;

each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$); or R$^1$ and R$^2$ are taken together with the carbon to which they are attached to form an optionally substituted cycloalkyl; or two R$^1$ on adjacent carbons are taken together to form a double bond; or two R$^1$ and two R$^2$ on adjacent carbons are taken together to form a triple bond;

provided that M is —CF$_3$ or at least one of R$^1$ or R$^2$ is fluoro;

n is 0, 1, 2, 3, 4, 5, or 6;

X$^1$ and X$^2$ are independently —OR$^4$, or F; when present;

Z is >C(=O), >C(=S), or >S(=O)$_2$;

R$^a$, R$^b$, and R$^c$ are independently hydrogen, fluoro, chloro, bromo, optionally substituted C$_1$-C$_6$ alkyl, optionally substituted cycloalkyl, optionally substituted heterocycloalkyl, optionally substituted aryl, optionally substituted heteroaryl, —OR$^4$, —N(R$^4$R$^5$), or —SR$^4$;

R$^d$, R$^4$ and R$^5$ are independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or R$^4$ and R$^5$ are taken together with the nitrogen to which they are attached to form a heterocycloalkyl;

provided that the compound is not 3-(2-chloro-4,4-difluorobutanamido)-2-hydroxy-3,4-dihydro-2H-benzo[e][1,2]oxaborinine-8-carboxylic acid, 2-hydroxy-3-(3,3,3-trifluoropropanamido)-3,4-dihydro-2H-benzo[e][1,2]oxaborinine-8-carboxylic acid, 2-hydroxy-3-(4,4,4-trifluorobutanamido)-3,4-dihydro-2H-benzo[e][1,2]oxaborinine-8-carboxylic acid, or 2-hydroxy-3-(4,4,4-trifluoro-3-(trifluoromethyl)butanamido)-3,4-dihydro-2H-benzo[e][1,2]oxaborinine-8-carboxylic acid.

In some embodiments of a compound of Formula (IVa) or (IVb), M is —CF$_3$. In some embodiments of a compound of Formula (IVa) or (IVb), M is not —CF$_3$.

In some embodiments of a compound of Formula (IVa) or (IVb), M is hydrogen, —CF$_3$, —CN, —OR$^4$, —SR$^4$, —C(=O)R$^4$, or alkynyl. In some embodiments of a compound of Formula (IVa) or (IVb), M is hydrogen, —CN, —OR$^4$, —SR$^4$, —C(=O)R$^4$, or alkynyl. In some embodiments of a compound of Formula (IVa) or (IVb), M is hydrogen or —CF$_3$. In some embodiments of a compound of Formula (IVa) or (IVb), M is —CN. In some embodiments of a compound of Formula (IVa) or (IVb), M is SR$^4$. In some embodiments of a compound of Formula (IVa) or (IVb), M is SR$^4$ and R$^4$ is C$_1$-C$_4$ alkyl. In some embodiments of a compound of Formula (IVa) or (IVb), M is SR$^4$ and R$^4$ is methyl. In some embodiments of a compound of Formula (IVa) or (IVb), M is —C(=O)R$^4$. In some embodiments of a compound of Formula (IVa) or (IVb), M is —C(=O)R$^4$ and R$^4$ is C$_1$-C$_4$ alkyl. In some embodiments of a compound of Formula (IVa) or (IVb), M is —C(=O)R$^4$ and R$^4$ is methyl. In some embodiments of a compound of Formula (IVa) or (IVb), M is alkynyl. In some embodiments of a compound of Formula (IVa) or (IVb), M is hydrogen.

In some embodiments of a compound of Formula (IVa) or (IVb), at least one of R$^1$ or R$^2$ is fluoro. In some embodiments of a compound of Formula (IVa) or (IVb), at least two of R$^1$ or R$^2$ are fluoro. In some embodiments of a compound of Formula (IVa) or (IVb), at least three of R$^1$ or R$^2$ are fluoro. In some embodiments of a compound of Formula (IVa) or (IVb), two of R$^1$ or R$^2$ are fluoro on the same carbon. In some embodiments of a compound of Formula (IVa) or (IVb), two of R$^1$ or R$^2$ are fluoro on adjacent carbon.

In some embodiments of a compound of Formula (IVa) or (IVb), M is hydrogen, —CN, —OR$^4$, —SR$^4$, —C(=O)R$^4$, or alkynyl; and at least one of R$^1$ or R$^2$ is fluoro. In some embodiments of a compound of Formula (IVa) or (IVb), M is hydrogen, —CN, —OR$^4$, —SR$^4$, —C(=O)R$^4$, or alkynyl; and at least two of R$^1$ or R$^2$ is fluoro. In some embodiments of a compound of Formula (IVa) or (IVb), M is hydrogen, —CN, —OR$^4$, —SR$^4$, —C(=O)R$^4$, or alkynyl; and at least three of R$^1$ or R$^2$ is fluoro.

In some embodiments of a compound of Formula (IVa) or (IVb), each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$). In some embodiments of a compound of Formula (IVa) or (IVb), each R$^1$ and R$^2$ are independently hydrogen, fluoro, chloro, C$_1$-C$_6$ alkyl, or —CF$_3$. In some embodiments of a compound of Formula (IVa) or (IVb), each R$^1$ and R$^2$ are independently hydrogen or fluoro. In some embodiments of a compound of Formula (IVa) or (IVb), R$^1$ and R$^2$ are taken together with the carbon to which they are attached to form a cycloalkyl. In some embodiments of a compound of Formula (IVa) or (IVb), when n is at least 2, two R$^1$ on adjacent carbons are taken together to form a double bond; or two R$^1$ and two R$^2$ on adjacent carbons are taken together to form a triple bond.

In some embodiments of a compound of Formula (IVa) or (IVb), M is —CF$_3$; and at least one of R$^1$ or R$^2$ is fluoro. In some embodiments of a compound of Formula (IVa) or (IVb), M is —CF$_3$; and at least two of R$^1$ or R$^2$ is fluoro. In some embodiments of a compound of Formula (IVa) or (IVb), M is —CF$_3$; and at least three of R$^1$ or R$^2$ is fluoro. In some embodiments of a compound of Formula (IVa) or (IVb), M is —CF$_3$; and R$^1$ and R$^2$ are hydrogen. In some embodiments of a compound of Formula (IVa) or (IVb), R$^1$ or R$^2$ are not chloro. In some embodiments of a compound of Formula (IVa) or (IVb), M is not —CF$_3$; and R$^1$ or R$^2$ are not —CF$_3$.

In some embodiments of a compound of Formula (IVa) or (IVb),

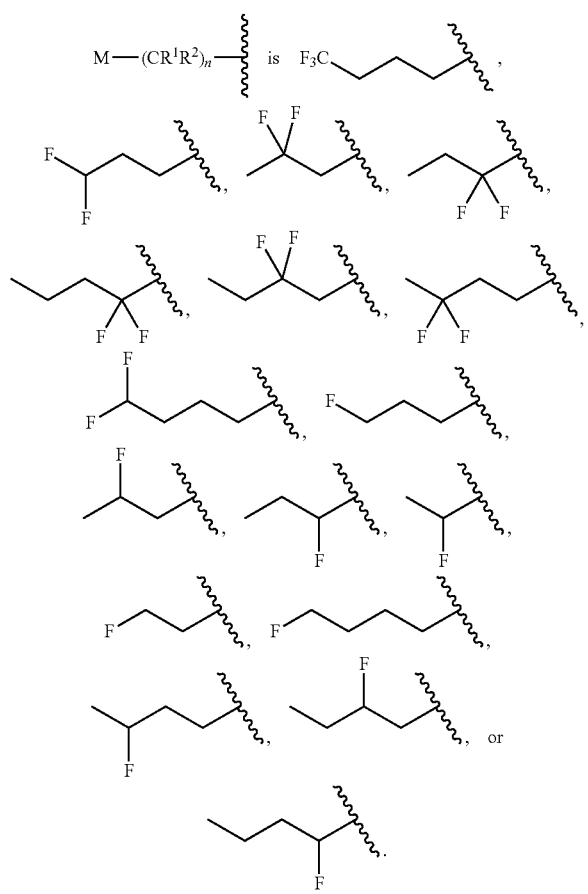

In some embodiments of a compound of Formula (IVa) or (IVb),

In some embodiments of a compound of Formula (IVa) or (IVb),

In some embodiments of a compound of Formula (IVa) or (IVb),

In some embodiments of a compound of Formula (IVa) or (IVb),

In some embodiments of a compound of Formula (IVa) or (IVb), n is 0, 1, 2, 3, or 4. In some embodiments of a compound of Formula (IVa) or (IVb), n is 0, 1, 2, or 3. In some embodiments of a compound of Formula (IVa) or (IVb), n is 1, 2, 3, or 4. In some embodiments of a compound of Formula (IVa) or (IVb), n is 2, 3, or 4. In some embodiments of a compound of Formula (IVa) or (IVb), n is 2, 3. In some embodiments of a compound of Formula (IVa) or (IVb), n is 1. In some embodiments of a compound of Formula (IVa) or (IVb), n is 2. In some embodiments of a compound of Formula (IVa) or (IVb), n is 3. In some embodiments of a compound of Formula (IVa) or (IVb), n is 4. In some embodiments of a compound of Formula (IVa) or (IVb), n is 5. In some embodiments of a compound of Formula (IVa) or (IVb), n is 6.

In some embodiments of a compound of Formula (IVa) or (IVb), $R^a$, $R^b$, and are independently hydrogen, fluoro, optionally substituted $C_1$-$C_6$ alkyl, —$OR^4$, —$N(R^4R^5)$, or —$SR^4$. In some embodiments of a compound of Formula (IVa) or (IVb), $R^a$, $R^b$, and are independently hydrogen, fluoro, chloro, —OH, or —$OCH_3$. In some embodiments of a compound of Formula (IVa) or (IVb), $R^a$, $R^b$, and $R^c$ are hydrogen. In some embodiments of a compound of Formula (IVa) or (IVb), at least one of $R^a$, $R^b$, or is not hydrogen.

In some embodiments of a compound of Formula (IVa) or (IVb), $X^1$ and $X^2$ are —OH; when present.

In some embodiments of a compound of Formula (IVa) or (IVb), $R^d$ is hydrogen or $C_1$-$C_4$ alkyl. In some embodiments of a compound of Formula (IVa) or (IVb), $R^d$ is hydrogen.

In some embodiments of a compound of Formula (IVa) or (IVb), Z is >C(=O). In some embodiments of a compound of Formula (IVa) or (IVb), Z is >S(=O)$_2$. In some embodiments of a compound of Formula (IVa) or (IVb), Z is >C(=S).

In some embodiments of a compound of Formula (IVa) or (IVb),
- M is hydrogen, —$CF_3$, —CN, —$OR^4$, —$SR^4$, —C(=O)$R^4$, or alkynyl;
- each $R^1$ and $R^2$ are independently hydrogen, fluoro, chloro, $C_1$-$C_6$ alkyl, or —$CF_3$;
- provided that M is —$CF_3$ or at least one of $R^1$ or $R^2$ is fluoro;
- n is 1, 2, 3, or 4;
- $X^1$ and $X^2$ are —OH; when present;
- Z is >C(=O);
- $R^a$, $R^b$, and $R^c$ are independently hydrogen, fluoro, optionally substituted $C_1$-$C_6$ alkyl, —$OR^4$, —$N(R^4R^5)$, or —$SR^4$;
- $R^d$, $R^4$ and $R^5$ are independently hydrogen or $C_1$-$C_6$ alkyl;
- or $R^4$ and $R^5$ are taken together with the nitrogen to which they are attached to form a heterocycloalkyl;
- provided that the compound is not 3-(2-chloro-4,4-difluorobutanamido)-2-hydroxy-3,4-dihydro-2H -benzo[e][1,2]oxaborinine-8-carboxylic acid, 2-hydroxy-3-(3,3,3-trifluoropropanamido)-3,4-dihydro -2H-benzo[e][1,2]oxaborinine-8-carboxylic acid, 2-hydroxy-3-(4,4,4-trifluorobutanamido)-3,4-dihydro-2H-benzo[e][1,2]oxaborinine-8-carboxylic acid, or 2-hydroxy-3-(4,4,4-trifluoro-3-(trifluoromethyl)butanamido)-3,4-dihydro-2H-benzo[e][1,2]oxaborinine-8-carboxylic acid.

In some embodiments of a compound of Formula (IVa) or (IVb),
- M is hydrogen, —$CF_3$, —CN, —$OR^4$, —$SR^4$, —C(=O)$R^4$, or alkynyl;
- each $R^1$ and $R^2$ are independently hydrogen, fluoro, chloro, $C_1$-$C_6$ alkyl, or —$CF_3$;
- provided that M is —$CF_3$ or at least one of $R^1$ or $R^2$ is fluoro;
- n is 2, 3, or 4;
- $X^1$ and $X^2$ are —OH; when present;
- Z is >C(=O);
- $R^a$, $R^b$, and $R^c$ are independently hydrogen, fluoro, optionally substituted $C_1$-$C_6$ alkyl, —$OR^4$, —$N(R^4R^5)$, or —$SR^4$;
- $R^d$, $R^4$ and $R^5$ are independently hydrogen or $C_1$-$C_6$ alkyl;
- or $R^4$ and $R^5$ are taken together with the nitrogen to which they are attached to form a heterocycloalkyl;
- provided that the compound is not 3-(2-chloro-4,4-difluorobutanamido)-2-hydroxy-3,4-dihydro-2H -benzo[e][1,2]oxaborinine-8-carboxylic acid, 2-hydroxy-3-(3,3,3-trifluoropropanamido)-3,4-dihydro -2H-benzo[e][1,2]oxaborinine-8-carboxylic acid, 2-hydroxy-3-(4,4,4-trifluorobutanamido)-3,4-dihydro-2H-benzo[e][1,2]oxaborinine-8-carboxylic acid, or 2-hydroxy-3-(4,4,4-trifluoro-3-(trifluoromethyl)butanamido)-3,4-dihydro-2H-benzo[e][1,2]oxaborinine-8-carboxylic acid.

In some embodiments of a compound of Formula (IVa) or (IVb),
- M is hydrogen, —$CF_3$, —CN, —$OR^4$, —$SR^4$, —C(=O)$R^4$, or alkynyl;
- each $R^1$ and $R^2$ are independently hydrogen, fluoro, chloro, $C_1$-$C_6$ alkyl, or —$CF_3$;
- provided that M is —$CF_3$ or at least one of $R^1$ or $R^2$ is fluoro;
- n is 3 or 4;
- $X^1$ and $X^2$ are —OH; when present;
- Z is >C(=O);
- $R^a$, $R^b$, and $R^c$ are independently hydrogen, fluoro, optionally substituted $C_1$-$C_6$ alkyl, —$OR^4$, —$N(R^4R^5)$, or —$SR^4$;
- $R^d$, $R^4$ and $R^5$ are independently hydrogen or $C_1$-$C_6$ alkyl;
- or $R^4$ and $R^5$ are taken together with the nitrogen to which they are attached to form a heterocycloalkyl;
- provided that the compound is not 3-(2-chloro-4,4-difluorobutanamido)-2-hydroxy-3,4-dihydro-2H -benzo[e][1,2]oxaborinine-8-carboxylic acid, 2-hydroxy-3-(3,3,3-trifluoropropanamido)-3,4-dihydro -2H-benzo[e][1,2]oxaborinine-8-carboxylic acid, 2-hydroxy-3-(4,4,4-trifluorobutanamido)-3,4-dihydro-2H-benzo[e][1,2]oxaborinine-8-carboxylic acid, or 2-hydroxy-3-(4,4,4-trifluoro-3-(trifluoromethyl)butanamido)-3,4-dihydro-2H-benzo[e][1,2]oxaborinine-8-carboxylic acid.

In some embodiments of a compound of Formula (IVa) or (IVb),
- M is hydrogen or —$CF_3$;
- each $R^1$ and $R^2$ are independently hydrogen, fluoro, chloro, $C_1$-$C_6$ alkyl, or —$CF_3$;
- provided that M is —$CF_3$ or at least one of $R^1$ or $R^2$ is fluoro;
- n is 1, 2, 3, or 4;
- $X^1$ and $X^2$ are —OH; when present;
- Z is >C(=O);
- $R^a$, $R^b$, and $R^c$ are independently hydrogen, fluoro, optionally substituted $C_1$-$C_6$ alkyl, —$OR^4$, —$N(R^4R^5)$, or —$SR^4$;
- $R^d$, $R^4$ and $R^5$ are independently hydrogen or $C_1$-$C_6$ alkyl;
- or $R^4$ and $R^5$ are taken together with the nitrogen to which they are attached to form a heterocycloalkyl;
- provided that the compound is not 3-(2-chloro-4,4-difluorobutanamido)-2-hydroxy-3,4-dihydro-2H -benzo[e][1,2]oxaborinine-8-carboxylic acid, 2-hydroxy-3-(3,3,3-trifluoropropanamido)-3,4-dihydro -2H-benzo[e][1,2]oxaborinine-8-carboxylic acid, 2-hydroxy-3-(4,4,4-trifluorobutanamido)-3,4-dihydro-2H-benzo[e][1,2]oxaborinine-8-carboxylic acid, or 2-hydroxy-3-(4,4,4-trifluoro-3-(trifluoromethyl)butanamido)-3,4-dihydro-2H-benzo[e][1,2]oxaborinine-8-carboxylic acid.

In some embodiments of a compound of Formula (IVa) or (IVb),
- M is hydrogen or —$CF_3$;
- each $R^1$ and $R^2$ are independently hydrogen, fluoro, chloro, $C_1$-$C_6$ alkyl, or —$CF_3$;

provided that M is —$CF_3$ or at least one of $R^1$ or $R^2$ is fluoro;

n is 2, 3, or 4;

$X^1$ and $X^2$ are —OH; when present;

Z is >C(=O);

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl;

or $R^4$ and $R^5$ are taken together with the nitrogen to which they are attached to form a heterocycloalkyl;

provided that the compound is not 3-(2-chloro-4,4-difluorobutanamido)-2-hydroxy-3,4-dihydro-2H-benzo[e][1,2]oxaborinine-8-carboxylic acid, 2-hydroxy-3-(3,3,3-trifluoropropanamido)-3,4-dihydro-2H-benzo[e][1,2]oxaborinine-8-carboxylic acid, 2-hydroxy-3-(4,4,4-trifluorobutanamido)-3,4-dihydro-2H-benzo[e][1,2]oxaborinine-8-carboxylic acid, or 2-hydroxy-3-(4,4,4-trifluoro-3-(trifluoromethyl)butanamido)-3,4-dihydro-2H-benzo[e][1,2]oxaborinine-8-carboxylic acid.

In some embodiments of a compound of Formula (IVa) or (IVb),

M is hydrogen or —$CF_3$;

each $R^1$ and $R^2$ are independently hydrogen, fluoro, chloro, $C_1$-$C_6$ alkyl, or —$CF_3$;

provided that M is —$CF_3$ or at least one of $R^1$ or $R^2$ is fluoro;

n is 3 or 4;

$X^1$ and $X^2$ are —OH; when present;

Z is >C(=O);

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl;

or $R^4$ and $R^5$ are taken together with the nitrogen to which they are attached to form a heterocycloalkyl;

provided that the compound is not 3-(2-chloro-4,4-difluorobutanamido)-2-hydroxy-3,4-dihydro-2H-benzo[e][1,2]oxaborinine-8-carboxylic acid, 2-hydroxy-3-(3,3,3-trifluoropropanamido)-3,4-dihydro-2H-benzo[e][1,2]oxaborinine-8-carboxylic acid, 2-hydroxy-3-(4,4,4-trifluorobutanamido)-3,4-dihydro-2H-benzo[e][1,2]oxaborinine-8-carboxylic acid, or 2-hydroxy-3-(4,4,4-trifluoro-3-(trifluoromethyl)butanamido)-3,4-dihydro-2H-benzo[e][1,2]oxaborinine-8-carboxylic acid.

In some embodiments, the compound of Formula (IVa) or (IVb) is of Formula (IVa-1) or (IVb-1) or pharmaceutically acceptable salts, isomers, stereoisomers, dimers, trimers, tautomers, or N-oxides thereof:

Formula (IVa-1)

Formula (IVb-1)

In some embodiments of a compound of Formula (IVa-1) or (IVb-1), M is —$CF_3$; n is 1, 2, 3, or 4;

and each $R^1$ and $R^2$ are independently hydrogen, fluoro, or $C_1$-$C_6$ alkyl;

provided that the compound is not 2-hydroxy-3(3,3,3-trifluoropropanamido)-3,4-dihydro-2H-benzo[e][1,2]oxaborinine-8-carboxylic acid, 2-hydroxy-3(4,4,4-trifluorobutanamido)-3,4-dihydro-2H-benzo[e][1,2]oxaborinine-8-carboxylic acid, or 2-hydroxy-3(4,4,4-trifluoro-3-(trifluoromethyl)butanamido)-3,4-dihydro-2H-benzo[e][1,2]oxaborinine-8-carboxylic acid.

In some embodiments of a compound of Formula (IVa-1) or (IVb-1), M is hydrogen; n is 1, 2, 3, or 4; and each $R^1$ and $R^2$ are independently hydrogen, fluoro, or $C_1$-$C_6$ alkyl; provided that at least one of $R^1$ and $R^2$ is fluoro;

provided that the compound is not 3-(2-chloro-4,4-difluorobutanamido)-2-hydroxy-3,4-dihydro-2H-benzo[e][1,2]oxaborinine-8-carboxylic acid.

In some embodiments of a compound of Formula (IVa-1) or (IVb-1), M is —CN, —$OR^4$, —$SR^4$, —C(=O)$R^4$, or alkynyl; n is 1, 2, 3, or 4; and each $R^1$ and $R^2$ are independently hydrogen, fluoro, or $C_1$-$C_6$ alkyl; provided that at least one of $R^1$ and $R^2$ is fluoro.

In some embodiments of a compound of Formula (IVa-1) or (IVb-1), M is optionally substituted heteroaryl or optionally substituted heterocycloalkyl; n is 1, 2, 3, or 4; and each $R^1$ and $R^2$ are independently hydrogen, fluoro, or $C_1$-$C_6$ alkyl; provided that at least one of $R^1$ and $R^2$ is fluoro.

In another aspect, provided herein are compounds of Formula (Va) or (Vb) or pharmaceutically acceptable salts, isomers, stereoisomers, dimers, trimers, tautomers, or N-oxides thereof:

Formula (Va)

-continued

Formula (Vb)

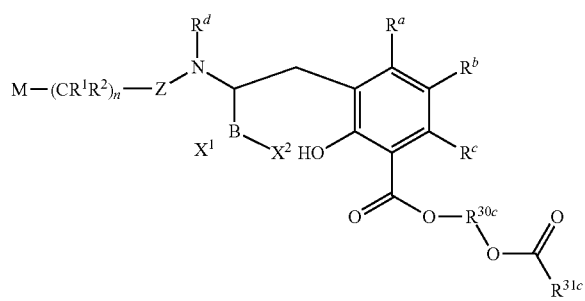

wherein:
M is hydrogen, fluoro, chloro, bromo, —CF$_3$, —CN, —OR$^4$, —SR$^4$, —S(=O)R$^4$, —S(=O)$_2$R$^4$, —S(=O)$_2$N(R$^4$R$^5$), —N(R$^4$R$^5$), —N(R$^4$)C(=O)R$^4$, —N(R$^4$)C(=O)N(R$^4$R$^5$), —N(R$^4$)S(=O)$_2$R$^4$, —N(R$^4$)Heteroaryl, —C(=O)R$^4$, —C(=O)N(R$^4$R$^5$), —C(=O)(C$_1$-C$_3$alkylene)C(=O)R$^4$, optionally substituted oxyimino, optionally substituted alkenyl, optionally substituted alkynyl, heteroaryl, or heterocycloalkyl;

each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$); or R$^1$ and R$^2$ are taken together with the carbon to which they are attached to form an optionally substituted cycloalkyl; or when n is at least 2, two R$^1$ on adjacent carbons are taken together to form a double bond; or two R$^1$ and two R$^2$ on adjacent carbons are taken together to form a triple bond;

n is 0, 1, 2, 3, 4, 5, or 6;

X$^1$ and X$^2$ are independently —OR$^4$, or F; when present;

Z is >C(=O), >C(=S), or >S(=O)$_2$;

R$^{30c}$ is —CH$_2$—, —CH(R$^{32c}$)—, or —C(R$^{32c}$)$_2$—;

R$^{31c}$ is optionally substituted C$_5$-C$_{12}$ alkyl, —(C$_1$-C$_6$ alkylene)OR$^4$, —(C$_1$-C$_6$ alkylene)SR$^4$, —(C$_1$-C$_6$ alkylene)C(=O)OR$^4$, —(C$_1$-C$_6$ alkylene)C(=O)N(R$^4$R$^5$), optionally substituted C$_3$-C$_5$ cycloalkyl, optionally substituted —(C$_1$-C$_6$ alkylene)(C$_3$-C$_5$ cycloalkyl), optionally substituted heterocycloalkyl, optionally substituted alkylheterocycloalkyl, optionally substituted aryl, optionally substituted alkylaryl, optionally substituted heteroaryl, or optionally substituted alkylheteroaryl;

each R$^{32c}$ are independently optionally substituted C$_1$-C$_6$ alkyl;

or two R$^{32c}$ are taken together with the carbon to which they are attached to form a cycloalkyl.

R$^a$, R$^b$, and R$^c$ are independently hydrogen, fluoro, chloro, bromo, optionally substituted C$_1$-C$_6$ alkyl, optionally substituted cycloalkyl, optionally substituted heterocycloalkyl, optionally substituted aryl, optionally substituted heteroaryl, —OR$^4$, —N(R$^4$R$^5$), or —SR$^4$;

R$^d$, R$^4$ and R$^5$ are independently hydrogen, —OH, —CN, —CF$_3$, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or R$^4$ and R$^5$ are taken together with the nitrogen to which they are attached to form a heterocycloalkyl;

provided that the compound is not ((((tetrahydro-2H-pyran-4-yl)oxy)carbonyl)oxy)methyl 2-hydroxy-3-(4-oxopentanamido)-3,4-dihydro-2H-benzo[e][1,2]oxaborinine-8-carboxylate.

In some embodiments of a compound of Formula (Va) or (Vb), M is hydrogen, —CF$_3$, —CN, —OR$^4$, —SR$^4$, —C(=O)R$^4$, or alkynyl. In some embodiments of a compound of Formula (Va) or (Vb), M is hydrogen or —CF$_3$. In some embodiments of a compound of Formula (Va) or (Vb), M is —CF$_3$. In some embodiments of a compound of Formula (Va) or (Vb), M is —CN. In some embodiments of a compound of Formula (Va) or (Vb), M is SR$^4$. In some embodiments of a compound of Formula (Va) or (Vb), M is SR$^4$ and R$^4$ is C$_1$-C$_4$ alkyl. In some embodiments of a compound of Formula (Va) or (Vb), M is SR$^4$ and R$^4$ is methyl. In some embodiments of a compound of Formula (Va) or (Vb), M is —C(=O)R$^4$. In some embodiments of a compound of Formula (Va) or (Vb), M is —C(=O)R$^4$ and R$^4$ is C$_1$-C$_4$ alkyl. In some embodiments of a compound of Formula (Va) or (Vb), M is —C(=O)R$^4$ and R$^4$ is methyl. In some embodiments of a compound of Formula (Va) or (Vb), M is alkynyl. In some embodiments of a compound of Formula (Va) or (Vb), M is hydrogen. In some embodiments of a compound of Formula (Va) or (Vb), M is not —CF$_3$. In some embodiments of a compound of Formula (Va) or (Vb), M is not —C(=O)R$^4$. In some embodiments of a compound of Formula (Va) or (Vb), M is not —C(=O)Me when R$^{31c}$ is tetrahydro-2H-pyran-4-yl.

In some embodiments of a compound of Formula (Va) or (Vb), each R$^1$ and R$^2$ are independently hydrogen, fluoro, chloro, bromo, optionally substituted C$_1$-C$_6$ alkyl, optionally substituted aryl, —OR$^4$, —SR$^4$, or —N(R$^4$R$^5$). In some embodiments of a compound of Formula (Va) or (Vb), R$^1$ and R$^2$ are taken together with the carbon to which they are attached to form a cycloalkyl. In some embodiments of a compound of Formula (Va) or (Vb), when n is at least 2, two R$^1$ on adjacent carbons are taken together to form a double bond; or two R$^1$ and two R$^2$ on adjacent carbons are taken together to form a triple bond. In some embodiments of a compound of Formula (Va) or (Vb), each R$^1$ and R$^2$ are independently hydrogen, fluoro, chloro, C$_1$-C$_6$ alkyl, or —CF$_3$. In some embodiments of a compound of Formula (Va) or (Vb), each R$^1$ and R$^2$ are independently hydrogen or fluoro. In some embodiments of a compound of Formula (Va) or (Vb), each R$^1$ and R$^2$ are hydrogen. In some embodiments of a compound of Formula (Va) or (Vb), at least one of R$^1$ or R$^2$ is fluoro. In some embodiments of a compound of Formula (Va) or (Vb), at least two of R$^1$ or R$^2$ are fluoro. In some embodiments of a compound of Formula (Va) or (Vb), at least three of R$^1$ or R$^2$ are fluoro.

In some embodiments of a compound of Formula (Va) or (Vb), R$^{30c}$ is —CH$_2$—. In some embodiments of a compound of Formula (Va) or (Vb), R$^{30c}$ is —CH(R$^{32c}$)—. In some embodiments of a compound of Formula (Va) or (Vb), R$^{30c}$ is —CH(R$^{32c}$)— and R$^{32c}$ is C$_1$-C$_6$ alkyl. In some embodiments of a compound of Formula (Va) or (Vb), R$^{30c}$ is —CH(R$^{32c}$)—; and R$^{32c}$ is methyl, ethyl, propyl, isopropyl, butyl, or isobutyl. In some embodiments of a compound of Formula (Va) or (Vb), R$^{30c}$ is —CH(R$^{32c}$)—; and R$^{32c}$ is methyl or isopropyl.

In some embodiments of a compound of Formula (Va) or (Vb), R$^{30c}$ is —C(R$^{32c}$)$_2$—. In some embodiments of a compound of Formula (Va) or (Vb), R$^{30c}$ is —C(R$^{32c}$)$_2$—;

and each $R^{32c}$ is independently methyl, ethyl, propyl, isopropyl, butyl, or isobutyl. In some embodiments of a compound of Formula (Va) or (Vb), $R^{30c}$ is $-C(R^{32c})_2-$; and each $R^{32c}$ is independently methyl. In some embodiments of a compound of Formula (Va) or (Vb), $R^{30c}$ is $-C(R^{32c})_2-$; and two $R^{32c}$ are taken together with the carbon to which they are attached to form a cycloalkyl. In some embodiments of a compound of Formula (Va) or (Vb), $R^{30c}$ is $-C(R^{32c})_2-$; and two $R^{32c}$ are taken together with the carbon to which they are attached to form a cyclopropyl, cyclobutyl, cyclopentyl, cyclohexyl, or cycloheptyl. In some embodiments of a compound of Formula (Va) or (Vb), $R^{30c}$ is $-C(R^{32c})_2-$; and two $R^{32c}$ are taken together with the carbon to which they are attached to form a cyclopropyl.

In some embodiments of a compound of Formula (Va) or (Vb), $R^{30c}$ is $-CH_2-$, $-CH(CH_3)-$, or $-CH(isopropyl)$. In some embodiments of a compound of Formula (Va) or (Vb), $R^{30c}$ is $-CH_2-$ or $-CH(CH_3)-$.

In some embodiments of a compound of Formula (Va) or (Vb), $R^{30c}$ is $-CH_2-$ or $-CH(R^{32c})-$; and $R^{31c}$ is optionally substituted $C_5-C_{12}$ alkyl, $-(C_1-C_6$ alkylene)$OR^4$, $-(C_1-C_6$ alkylene)$SR^4$, $-(C_1-C_6$ alkylene)$C(=O)OR^4$, $-(C_1-C_6$ alkylene)$C(=O)N(R^4R^5)$, optionally substituted $C_3-C_5$ cycloalkyl, optionally substituted $-(C_1-C_6$ alkylene)($C_3-C_5$ cycloalkyl), optionally substituted heterocycloalkyl, optionally substituted alkylheterocycloalkyl, optionally substituted aryl, optionally substituted alkylaryl, optionally substituted heteroaryl, or optionally substituted alkylheteroaryl.

In some embodiments of a compound of Formula (Va) or (Vb), $R^{30c}$ is $-CH_2-$ or $-CH(R^{32c})-$; and $R^{31c}$ is $C_5-C_{12}$ alkyl, $C_3-C_5$ cycloalkyl, $-(C_1-C_6$ alkylene)($C_3-C_5$ cycloalkyl), heterocycloalkyl, alkylheterocycloalkyl, aryl, alkylaryl, heteroaryl, or alkylheteroaryl; each optionally substituted with halogen, $-CN$, $C_1-C_6$ alkyl, $-CF_3$, cycloalkyl, heterocycloalkyl, $-OR^4$, $-N(R^4R^5)$, $-SR^4$, $-(S=O)_2R^4$, $-C(=O)OR^4$, or $-C(=O)N(R^4R^5)$.

In some embodiments of a compound of Formula (Va) or (Vb), $R^{30c}$ is $-CH_2-$ or $-CH(R^{32c})-$; and $R^{31c}$ is optionally substituted $C_5-C_{12}$ alkyl or optionally substituted $C_3-C_5$ cycloalkyl.

In some embodiments of a compound of Formula (Va) or (Vb), $R^{30c}$ is $-CH_2-$ or $-CH(R^{32c})-$; and $R^{31c}$ is $C_5-C_{12}$ alkyl or $C_3-C_5$ cycloalkyl; each optionally substituted with halogen, $-CN$, $C_1-C_6$ alkyl, $-CF_3$, cycloalkyl, heterocycloalkyl, $-OR^4$, $-N(R^4R^5)$, $-SR^4$, $-(S=O)_2R^4$, $-C(=O)OR^4$, or $-C(=O)N(R^4R^5)$.

In some embodiments of a compound of Formula (Va) or (Vb), $R^{30c}$ is $-CH_2-$ or $-CH(R^{32c})-$; and $R^{31c}$ is $C_5-C_{12}$ alkyl or $C_3-C_5$ cycloalkyl.

In some embodiments of a compound of Formula (Va) or (Vb), $R^{30}c$ is $-CH_2-$ or $-CH(R^{32}c)-$; $R^{32c}$ is $C_1-C_6$ alkyl; and $R^{31c}$ is $C_5-C_{12}$ alkyl. In some embodiments of a compound of Formula (Va) or (Vb), $R^{30c}$ is $-CH_2-$ or $-CH(R^{32c})-$; $R^{32c}$ is $C_5-C_{12}$ alkyl; and $R^{31c}$ is pentyl, isopentyl, hexyl, 5-methylhexyl, 3,3-dimethylbutyl, 2-ethylpropyl, 3-pentyl, 2-ethylbutyl, or heptyl.

In some embodiments of a compound of Formula (Va) or (Vb), $R^{30}c$ is $-CH_2-$ or $-CH(R^{32c})-$; $R^{32c}$ is $C_1-C_6$ alkyl; and $R^{31c}$ is $C_3-C_5$ cycloalkyl. In some embodiments of a compound of Formula (Va) or (Vb), $R^{30c}$ is $-CH_2-$ or $-CH(R^{32c})-$; $R^{32c}$ is $C_1-C_6$ alkyl; and $R^{31c}$ is $C_3$ cycloalkyl. In some embodiments of a compound of Formula (Va) or (Vb), $R^{30c}$ is $-CH_2-$ or $-CH(R^{32c})-$; $R^{32c}$ is $C_1-C_6$ alkyl; and $R^{31c}$ is $C_4$ cycloalkyl. In some embodiments of a compound of Formula (Va) or (Vb), $R^{30c}$ is $-CH_2-$ or $-CH(R^{32c})-$; $R^{32c}$ is $C_1-C_6$ alkyl; and $R^{31c}$ is $C_5$ cycloalkyl.

In some embodiments of a compound of Formula (Va) or (Vb), $R^{30c}$ is $-CH_2-$ or $-CH(R^{32c})-$; $R^{32c}$ is $C_1-C_6$ alkyl; $R^{31c}$ is $-(C_1-C_6$ alkylene)$OR^4$; and $R^4$ is $C_1-C_6$ alkyl. In some embodiments of a compound of Formula (Va) or (Vb), $R^{30c}$ is $-CH_2-$ or $-CH(R^{32c})-$; $R^{32c}$ is $C_1-C_6$ alkyl; $R^{31c}$ is $-(C_1-C_6$ alkylene)$OR^4$; and $R^4$ is methyl or ethyl.

In some embodiments of a compound of Formula (Va) or (Vb), $R^{30c}$ is $-CH_2-$ or $-CH(R^{32c})-$; $R^{32c}$ is $C_1-C_6$ alkyl; $R^{31c}$ is $-(C_1-C_6$ alkylene)$C(=O)OR^4$; and $R^4$ is $C_1-C_6$ alkyl. In some embodiments of a compound of Formula (Va) or (Vb), $R^{30c}$ is $-CH_2-$ or $-CH(R^{32c})-$; $R^{32c}$ is $C_1-C_6$ alkyl; $R^{31c}$ c is $-(C_1-C_6$ alkylene)$C(=O)OR^4$; and $R^4$ is methyl.

In some embodiments of a compound of Formula (Va) or (Vb), $R^{30c}$ is $-CH_2-$ or $-CH(R^{32c})-$; $R^{32c}$ is $C_1-C_6$ alkyl; $R^{31c}$ is $-(C_1-C_6$ alkylene)$C(=O)N(R^4R^5)$; and $R^4$ and $R^5$ are independently hydrogen or $C_1-C_6$ alkyl. In some embodiments of a compound of Formula (Va) or (Vb), $R^{30c}$ is $-CH_2-$ or $-CH(R^{32c})-$; $R^{32c}$ is $C_1-C_6$ alkyl; $R^{31c}$ is $-(C_1-C_6$ alkylene)$C(=O)N(R^4R^5)$; and $R^4$ and $R^5$ are independently $C_1-C_6$ alkyl.

In some embodiments of a compound of Formula (Va) or (Vb), $R^{31c}$ is

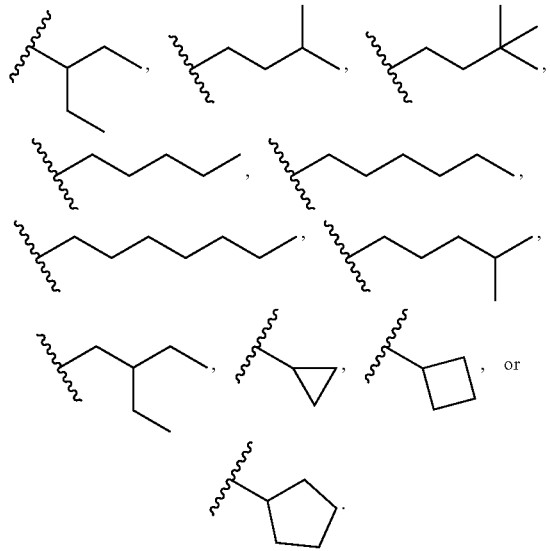

In some embodiments of a compound of Formula (Va) or (Vb), $R^{31c}$ is

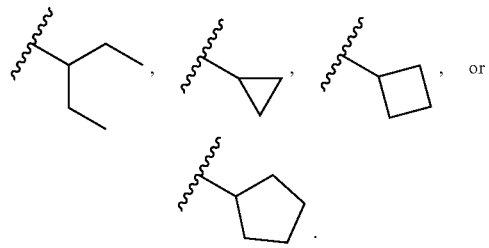

In some embodiments of a compound of Formula (Va) or (Vb), n is 0, 1, 2, 3, or 4. In some embodiments of a compound of Formula (Va) or (Vb), n is 0, 1, 2, or 3. In some embodiments of a compound of Formula (Va) or (Vb), n is 1, 2, 3, or 4. In some embodiments of a compound of Formula (Va) or (Vb), n is 2, 3, or 4. In some embodiments of a compound of Formula (Va) or (Vb), n is 2, 3. In some embodiments of a compound of Formula (Va) or (Vb), n is 1. In some embodiments of a compound of Formula (Va) or (Vb), n is 2. In some embodiments of a compound of Formula (Va) or (Vb), n is 3. In some embodiments of a compound of Formula (Va) or (Vb), n is 4. In some embodiments of a compound of Formula (Va) or (Vb), n is 5. In some embodiments of a compound of Formula (Va) or (Vb), n is 6.

In some embodiments of a compound of Formula (Va) or (Vb), $R^a$, $R^b$, and $R^c$ are independently hydrogen, fluoro, optionally substituted $C_1$-$C_6$ alkyl, —$OR^4$, —$N(R^4R^5)$, or —$SR^4$. In some embodiments of a compound of Formula (Va) or (Vb), $R^a$, $R^b$, and $R^c$ are independently hydrogen, fluoro, chloro, —OH, or —$OCH_3$. In some embodiments of a compound of Formula (Va) or (Vb), $R^a$, $R^b$, and $R^c$ are hydrogen. In some embodiments of a compound of Formula (Va) or (Vb), at least one of $R^a$, $R^b$, or $R^c$ is not hydrogen.

In some embodiments of a compound of Formula (Va) or (Vb), $X^1$ and $X^2$ are —OH; when present.

In some embodiments of a compound of Formula (Va) or (Vb), $R^d$ is hydrogen or $C_1$-$C_4$ alkyl. In some embodiments of a compound of Formula (Va) or (Vb), $R^d$ is hydrogen.

In some embodiments of a compound of Formula (Va) or (Vb), Z is >C(═O). In some embodiments of a compound of Formula (Va) or (Vb), Z is >S(═O)$_2$. In some embodiments of a compound of Formula (Va) or (Vb), Z is >C(═S).

In some embodiments of a compound of Formula (Va) or (Vb),

M is hydrogen, —$CF_3$, —CN, —$OR^4$, —$SR^4$, —C(═O)$R^4$, or alkynyl;

each $R^1$ and $R^2$ are independently hydrogen, fluoro, chloro, $C_1$-$C_6$ alkyl, or —$CF_3$;

n is 1, 2, 3, or 4;

$X^1$ and $X^2$ are —OH; when present;

Z is >C(═O);

$R^{30c}$ is —$CH_2$—, or —$CH(R^{32c})$—;

$R^{31c}$ is optionally substituted $C_5$-$C_{12}$ alkyl or optionally substituted $C_3$-$C_5$ cycloalkyl;

$R^{32c}$ is optionally substituted $C_1$-$C_6$ alkyl;

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl; or $R^4$ and $R^5$ are taken together with the nitrogen to which they are attached to form a heterocycloalkyl;

provided that the compound is not (((((tetrahydro-2H-pyran-4-yl)oxy)carbonyl)oxy)methyl 2-hydroxy-3-(4-oxopentanamido)-3,4-dihydro-2H-benzo[e][1,2]oxaborinine-8-carboxylate.

In some embodiments of a compound of Formula (Va) or (Vb),

M is hydrogen or —$CF_3$;

each $R^1$ and $R^2$ are independently hydrogen, fluoro, chloro, $C_1$-$C_6$ alkyl, or —$CF_3$;

n is 1, 2, 3, or 4;

$X^1$ and $X^2$ are —OH; when present;

Z is >C(═O);

$R^{30c}$ is —$CH_2$—, or —$CH(R^{32c})$—;

$R^{31c}$ is optionally substituted $C_5$-$C_{12}$ alkyl or optionally substituted $C_3$-$C_5$ cycloalkyl;

$R^{32c}$ is optionally substituted $C_1$-$C_6$ alkyl;

$R^a$, $R^b$, and $R^c$ are independently hydrogen, fluoro, optionally substituted $C_1$-$C_6$ alkyl, —$OR^4$, —$N(R^4R^5)$, or —$SR^4$;

$R^d$, $R^4$ and $R^5$ are independently hydrogen or $C_1$-$C_6$ alkyl; or $R^4$ and $R^5$ are taken together with the nitrogen to which they are attached to form a heterocycloalkyl;

provided that the compound is not (((((tetrahydro-2H-pyran-4-yl)oxy)carbonyl)oxy)methyl 2-hydroxy-3-(4-oxopentanamido)-3,4-dihydro-2H-benzo[e][1,2]oxaborinine-8-carboxylate.

In some embodiments, the compound of Formula (Va) or (Vb) is of Formula (Va-1) or (Vb-1) or pharmaceutically acceptable salts, isomers, stereoisomers, dimers, trimers, tautomers, or N-oxides thereof:

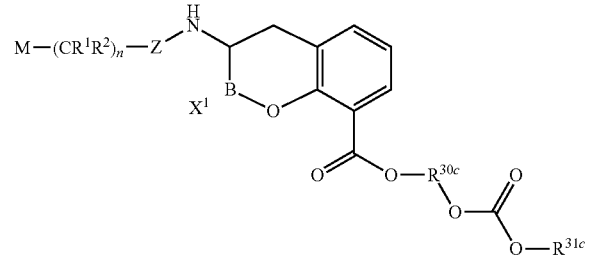

Formula (Va-1)

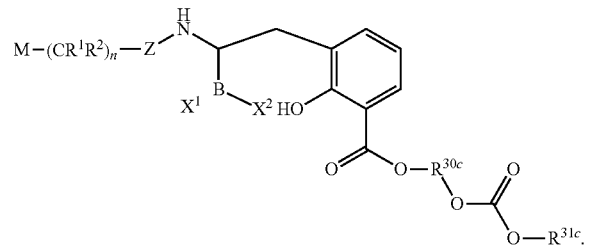

Formula (Vb-1)

In some embodiments of a compound of Formula (Va-1) or (Vb-1), M is —$CF_3$; n is 1, 2, 3, or 4; each $R^1$ and $R^2$ are independently hydrogen, fluoro, or $C_1$-$C_6$ alkyl; $R^{30c}$ is —$CH_2$—, —$CH(R^{32c})$—, or —$C(R^{32c})_2$—; $R^{31c}$ is optionally substituted $C_5$-$C_{12}$ alkyl or optionally substituted $C_3$-$C_5$ cycloalkyl; each $R^{32c}$ are independently optionally substituted $C_1$-$C_6$ alkyl; or two $R^{32c}$ are taken together with the carbon to which they are attached to form a cycloalkyl.

In some embodiments of a compound of Formula (Va-1) or (Vb-1), M is —$CF_3$; n is 1, 2, 3, or 4; each $R^1$ and $R^2$ are independently hydrogen, fluoro, or $C_1$-$C_6$ alkyl; $R^{30c}$ is —$CH_2$— or —$CH(R^{32c})$; $R^{31c}$ is $C_5$-$C_{12}$ alkyl or $C_3$-$C_5$ cycloalkyl; each optionally substituted with halogen, —CN, $C_1$-$C_6$ alkyl, —$CF_3$, cycloalkyl, heterocycloalkyl, —$OR^4$, —$N(R^4R^5)$, —$SR^4$, —$(S═O)_2R^4$, —C(═O)$OR^4$, or —C(═O)$N(R^4R^5)$; and $R^{32c}$ is $C_1$-$C_6$ alkyl.

In some embodiments of a compound of Formula (Va-1) or (Vb-1), M is hydrogen; n is 1, 2, 3, or 4; each $R^1$ and $R^2$ are independently hydrogen, fluoro, or $C_1$-$C_6$ alkyl; $R^{30c}$ is —$CH_2$—, —$CH(R^{32c})$—, or —$C(R^{32c})_2$—; $R^{31c}$ is optionally substituted $C_5$-$C_{12}$ alkyl or optionally substituted $C_3$-$C_5$ cycloalkyl; each $R^{32c}$ are independently optionally substituted $C_1$-$C_6$ alkyl; or two $R^{32c}$ are taken together with the carbon to which they are attached to form a cycloalkyl.

In some embodiments of a compound of Formula (Va-1) or (Vb-1), M is hydrogen; n is 1, 2, 3, or 4; each $R^1$ and $R^2$ are independently hydrogen, fluoro, or $C_1$-$C_6$ alkyl; $R^{30c}$ is —$CH_2$— or —$CH(R^{32c})$; $R^{31c}$ is $C_5$-$C_{12}$ alkyl or $C_3$-$C_5$ cycloalkyl; each optionally substituted with halogen, —CN, $C_1$-$C_6$ alkyl, —$CF_3$, cycloalkyl, heterocycloalkyl, —$OR^4$, —N(R$^4$R$^5$), —SR$^4$, —(S=O)$_2$R$^4$, —C(=O)OR$^4$, or —C(=O)N(R$^4$R$^5$); and R$^{32'}$ is C$_1$-C$_6$ alkyl.

In some embodiments of a compound of Formula (Va-1) or (Vb-1), M is —CN, —OR$^4$, —SR$^4$, —C(=O)R$^4$, or alkynyl; n is 1, 2, 3, or 4; each R$^1$ and R$^2$ are independently hydrogen, fluoro, or C$_1$-C$_6$ alkyl; R$^{30c}$ is —CH$_2$—, —CH(R$^{32c}$)—, or —C(R$^{32c}$)$_2$—; R$^{31c}$ is optionally substituted C$_5$-C$_{12}$ alkyl or optionally substituted C$_3$-C$_5$ cycloalkyl; each R$^{32c}$ are independently optionally substituted C$_1$-C$_6$ alkyl; or two R$^{32c}$ are taken together with the carbon to which they are attached to form a cycloalkyl; provided that the compound is not (((((tetrahydro-2H-pyran-4-yl)oxy)carbonyl)oxy)methyl 2-hydroxy-3-(4-oxopentanamido)-3,4-dihydro-2H-benzo[e][1,2]oxaborinine-8-carboxylate.

In some embodiments of a compound of Formula (Va-1) or (Vb-1), M is —CN, —OR$^4$, —SR$^4$, —C(=O)R$^4$, or alkynyl; n is 1, 2, 3, or 4; each R$^1$ and R$^2$ are independently hydrogen, fluoro, or C$_1$-C$_6$ alkyl; R$^{30c}$ is —CH$_2$— or —CH(R$^{32c}$); R$^{31c}$ is C$_5$-C$_{12}$ alkyl or C$_3$-C$_5$ cycloalkyl; each optionally substituted with halogen, —CN, C$_1$-C$_6$ alkyl, —CF$_3$, cycloalkyl, heterocycloalkyl, —OR$^4$, —N(R$^4$R$^5$), —SR$^4$, —(S=O)$_2$R$^4$, —C(=O)OR$^4$, or —C(=O)N(R$^4$R$^5$); and R$^{32c}$ is C$_1$-C$_6$ alkyl; provided that the compound is not (((((tetrahydro-2H-pyran-4-yl)oxy)carbonyl)oxy)methyl 2-hydroxy-3-(4-oxopentanamido)-3,4-dihydro-2H-benzo[e][1,2]oxaborinine-8-carboxylate.

Preparation of Compounds

Described herein are compounds described herein that inhibit the activity of beta-lactamases, and processes for their preparation. Also described herein are pharmaceutically acceptable salts. Pharmaceutical compositions comprising at least one such compound or a pharmaceutically acceptable salt, and a pharmaceutically acceptable excipient are also provided.

Compounds described herein may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, Advanced Organic Chemistry 4th Ed., (Wiley 1992); Carey and Sundberg, Advanced Organic Chemistry 4th Ed., Vols. A and B (Plenum 2000, 2001); Green and Wuts, Protective Groups in Organic Synthesis 3rd Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989), (all of which are incorporated by reference in their entirety). General methods for the preparation of compounds as disclosed herein may be derived from known reactions in the field, and the reactions may be modified by the use of appropriate reagents and conditions, as would be recognized by the skilled person, for the introduction of the various moieties found in the formulas as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers/Stereoisomers

In some embodiments, due to the oxophilic nature of the boron atom, the compounds described herein may convert to or exist in equilibrium with alternate forms, particularly in milieu that contain water (aqueous solution, plasma, etc.). Accordingly, the compounds described herein may associate into intramolecular dimers, trimers, and related combinations.

The compounds are present in a closed, cyclic form of Formula (Ia), (IIa), (IIIa), (IVa), (Va), or an open, acyclic form of Formula (Ib), (IIb), (IIIb), (IVb), (Vb), or mixtures thereof. Accordingly, the compounds described herein may exist in an equilibrium between the "closed" cyclic form shown in Formula (Ia), (IIa), (IIIa), (IVa), or (Va) and the "open" acyclic form shown in Formula (Ib), (IIb), (IIIb), (IVb), or (Vb). In addition the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Tautomers

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

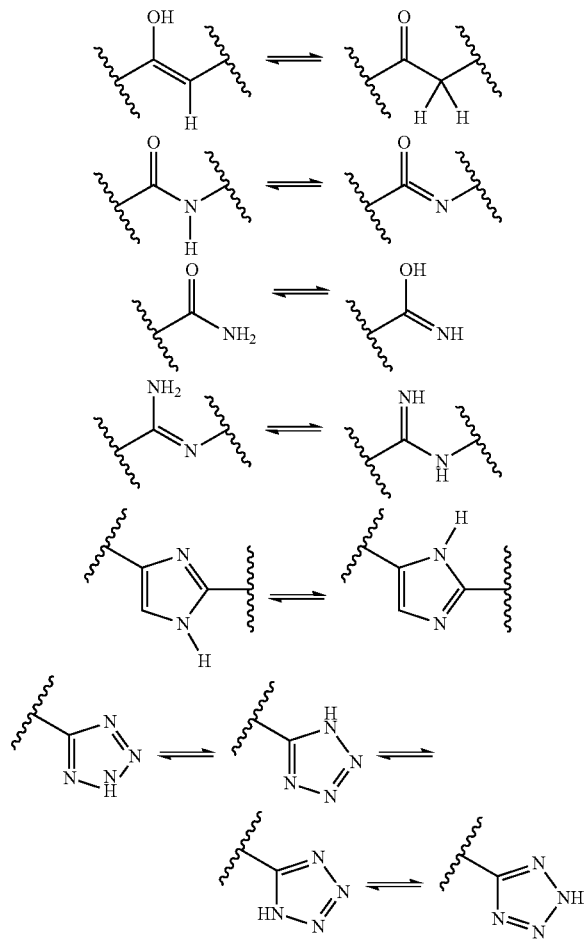

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, N+($C_1$-$C_4$ alkyl)$_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Pharmaceutical Compositions/Formulations

In another aspect, provided herein are pharmaceutical compositions comprising a compound described herein, or a pharmaceutically acceptable salt, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

Provided herein are pharmaceutical compositions that include a compound described herein and at least one pharmaceutically acceptable inactive ingredient. In some embodiments, the compounds described herein are administered as pharmaceutical compositions in which a compound described herein is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound described herein with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combinations thereof The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound described herein are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein as an active ingredient in free-acid or free-base form, or in a pharmaceutically acceptable salt form. In addition, the methods and pharmaceutical compositions described herein include the use of N-oxides (if appropriate), crystalline forms, amorphous phases.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Combination Treatment

The compounds described herein may be used in combination with one or more antibiotics in the treatment of bacterial infections. Such antibiotics may be administered, by a route and in an amount commonly used therefore, contemporaneously or sequentially with a compound described herein. When a compound described herein is used contemporaneously with one or more antibiotic, a pharmaceutical composition in unit dosage form containing such other drugs and the compound of the present invention is preferred. However, the combination therapy may also include therapies in which the compound described herein and one or more antibiotics are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound described herein. In some embodiments, a pharmaceutical composition comprising a compound described herein further comprises a beta-lactam antibiotic. In certain embodiments, the beta-lactam antibiotic is a penicillin, cephalosporin, carbapenem, monobactam, bridged monobactam, or a combination thereof The above combinations include combinations of a compound described herein not only with one antibiotic, but also with two or more antibiotics. Likewise, compounds described herein, either in combination with an antibiotic or by themselves, may be used in combination with other drugs that are used in the prevention, treatment, control, amelioration, or reduction of risk of bacterial infections or conditions associated with bacterial infections. Such other drugs may be administered, by a route and in an amount commonly used therefore, contemporaneously or sequentially with a compound described herein. When a compound described herein is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound described herein. The weight ratio of the compound described herein to the second active ingredient may be varied and will depend upon the effective dose of each ingredient. Generally, an effective dose of each will be used.

In some embodiments, the compounds described herein are used in combination with one or more antibiotics in the treatment of bacterial infections. In certain embodiments, the bacterial infection is an upper or lower respiratory tract infection, a urinary tract infection, an intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof Penicillins include, but are not limited to, amoxicillin, ampicillin, azidocillin, azlocillin, bacampicillin, benzathine benzylpenicillin, benzathine phenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, ticarcillin. Penems include, but are not limited to, faropenem. Carbapenems include, but are not limited to, biapenem, ertapenem, doripenem, imipenem, meropenem, panipenem. Cephalosporins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftaroline fosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, loracarbef. Monobactams include, but are not limited to, aztreonam, carumonam, nocardicin A, tigemonam.

Provided herein are methods of treating a bacterial infection in a subject, comprising administering to the subject a compound of Formula (Ia), (Ib), (IIa), (IIb), (IIIa), (IIIb), (IVa), (IVb), (Va), or (Vb), or pharmaceutically acceptable salts, isomers, stereoisomers, dimers, trimers, tautomers, or N-oxides thereof, in combination with a therapeutically effective amount of a beta-lactam antibiotic. In some embodiments, the method comprises administering a compound of Formula (Ia) or (Ib), or pharmaceutically acceptable salts, isomers, stereoisomers, dimers, trimers, tautomers, or N-oxides thereof, in combination with a therapeutically effective amount of ertapenem. In some embodiments, the method comprises administering a compound of Formula (IIa) or (IIb), or pharmaceutically acceptable salts, isomers, stereoisomers, dimers, trimers, tautomers, or N-oxides thereof, in combination with a therapeutically effective amount of ertapenem. In some embodiments, the method comprises administering a compound of Formula (IIIa) or (IIIb), or pharmaceutically acceptable salts, isomers, stereoisomers, dimers, trimers, tautomers, or N-oxides thereof, in combination with a therapeutically effective amount of ertapenem. In some embodiments, the method comprises administering a compound of Formula (IVa) or (IVb), or pharmaceutically acceptable salts, isomers, stereoisomers, dimers, trimers, tautomers, or N-oxides thereof, in combination with a therapeutically effective amount of ertapenem. In some embodiments, the method comprises administering a compound of Formula (Va) or (Vb), or pharmaceutically acceptable salts, isomers, stereoisomers, dimers, trimers, tautomers, or N-oxides thereof, in combination with a therapeutically effective amount of ertapenem. In some embodiments, the method comprises administering a compound of Formula (Ia) or (Ib), or pharmaceutically acceptable salts, isomers, stereoisomers, dimers, trimers, tautomers, or N-oxides thereof, in combination with a therapeutically effective amount of ceftriaxone. In some embodiments, the method comprises administering a compound of Formula (IIa) or (IIb), or pharmaceutically acceptable salts, isomers, stereoisomers, dimers, trimers, tautomers, or N-oxides thereof, in combination with a therapeutically effective amount of ceftriaxone. In some embodiments, the method comprises administering a compound of Formula (IIIa) or (IIIb), or pharmaceutically acceptable salts, isomers, stereoisomers, dimers, trimers, tautomers, or N-oxides thereof, in combination with a therapeutically effective amount of ceftriaxone. In some embodiments, the method comprises administering a compound of Formula (IVa) or (IVb), or pharmaceutically acceptable salts, isomers, stereoisomers, dimers, trimers, tautomers, or N-oxides thereof, in combination with a therapeutically effective amount of ceftriaxone. In some embodiments, the method comprises administering a compound of Formula (Va) or (Vb), or pharmaceutically acceptable salts, isomers, stereoisomers, dimers, trimers, tautomers, or N-oxides thereof, in combination with a therapeutically effective amount of ceftriaxone.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds described herein and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Assays for Antibacterial Activity

Assays for the inhibition of beta-lactamase activity are well known in the art. For instance, the ability of a compound to inhibit beta-lactamase activity in a standard enzyme inhibition assay may be used (see, e g, Page, *Biochem J*, 295:295-304 (1993)). Beta-lactamases for use in such assays may be purified from bacterial sources or preferably, are produced by recombinant DNA techniques, since genes and cDNA clones coding for many beta-lactamases are known (see, e g, Cartwright & Waley, *Biochem J* 221 :505-12 (1984)).

Alternatively, the sensitivity of bacteria known, or engineered, to produce a beta-lactamase to an inhibitor may be determined. Other bacterial inhibition assays include agar disk diffusion and agar dilution (see, e.g, Traub & Leonhard, *Chemotherapy* 43 159-67 (1997)). Thus, a beta-lactamase may be inhibited by contacting the beta-lactamase enzyme with an effective amount of an inventive compound or by contacting bacteria that produce the beta-lactamase enzymes with an effective amount of such a compound so that the beta-lactamase in the bacteria is contacted with the inhibitor. The contacting may take place in vitro or in vivo. "Contacting" means that the beta-lactamase and the inhibitor are brought together so that the inhibitor can bind to the beta-lactamase. Amounts of a compound effective to inhibit a beta-lactamase may be determined empirically, and making such determinations is within the skill in the art. Inhibition includes both reduction and elimination of beta-lactamase activity.

Methods

The present disclosure also provides methods for inhibiting bacterial growth, by, e.g., reducing bacterial resistance to a β-lactam antibiotic, such methods comprising contacting a bacterial cell culture, or a bacterially infected cell culture, tissue, or organism, with a beta-lactamase inhibitor described herein. Preferably, the bacteria to be inhibited by administration of a beta-lactamase inhibitor described herein are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, a compound described herein is administered to an experimental cell culture in vitro to prevent the growth of beta-lactam resistant bacteria. In certain other embodiments, a compound described herein is administered to a mammal, including a human to prevent the growth of beta-lactam resistant bacteria in vivo. The method according to this embodiment comprises administering a therapeutically effective amount of a beta-lactamase inhibitor for a therapeutically effective period of time to a mammal, including a human. Preferably, the beta-lactamase inhibitor is administered in the form of a pharmaceutical composition as described above. In some embodiments, a beta-lactam antibiotic is co-administered with the beta-lactamase inhibitor as described above.

In another aspect provided herein are methods of treating a bacterial infection, which method comprises administering to a subject a pharmaceutical composition comprising a compound described herein, or a pharmaceutically acceptable salt thereof, and a pharmaceutically acceptable excipient. In some embodiments, the methods of treating a bacterial infection in a subject comprises administering to the subject a pharmaceutical composition as described herein, optionally in combination with a beta-lactam antibiotic. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae,*

Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, or Staphylococcus saccharolyticus In some embodiments, the infection that is treated or prevented comprises a bacteria that includes *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter cob, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* or *Bacteroides splanchnicus.*

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
BOP benzotriazol-1-yl-oxytris (dimethylamino) phosphonium
t-Bu tert-butyl
Cbz benzyl carbamate
Cy Cyclohexyl
DBU 1,8-Diazabicyclo[5.4.0] undec-7-ene
DCC dicyclohexylcarbodiimide
DCM dichloromethane ($CH_2Cl_2$)
DIC 1,3-diisopropylcarbodiimide
DEAD diethyl azodicarboxylate
DIAD diisopropyl azodicarboxylate
DIEA diisopropylethylamine
DMAP 4-(N,N-dimethylamino)pyridine
DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI 1-ethyl-3-(3-dimethylaminopropyl) carbodiimide HCl
eq equivalent(s)
Et ethyl
$Et_2O$ diethyl ether
EtOH ethanol
EtOAc ethyl acetate
HATU (1-[Bis(dimethylamino)methylene]-1H- 1,2,3-triazolo [4,5-b]pyridinium 3-oxid hexafluorophosphate)
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
LC iquid chromatography
Me methyl
MeI methyliodide
MeOH methanol
MOMCl methoxymethylchloride
MOM methoxymethyl
MS mass spectroscopy
NMP N-methyl-pyrrolidin-2-one
NMR nuclear magnetic resonance
PyBOP benzotriazole-1-yl-oxytris-pyrrolidino-phosphonium hexafluorophosphate
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
$Tf_2O$ triflate anhydride
TMG 1,1,3,3-Tetramethylguanidine
THF tetrahydrofuran
THP tetrahydropyran
TLC thin layer chromatography
XPHOS 2-Dicyclohexylphosphino-2',4',6'-triisopropylbiphenyl General Examples for the Preparation of Compounds The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as SciFinder or Reaxys.

Certain compounds of the invention, compounds of Formula (IV) (SCHEME 1) are prepared from the corresponding functional-group-protected boronic acid esters (Intermediate A) by treatment with a Lewis acid such as $BCl_3$, $AlCl_3$, or $BBr_3$ in a solvent such as dichloromethane, at a temperature between −78° C. and room temperature followed by an aqueous quench. The conversion can also be made by treatment with an aqueous acid such as HBr or HCl in a solvent mixture of acetonitrile and hexane in the presence of phenylboronic acid at room temperature.

SCHEME 1

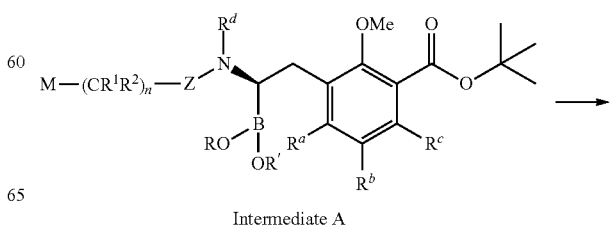

Intermediate A

-continued

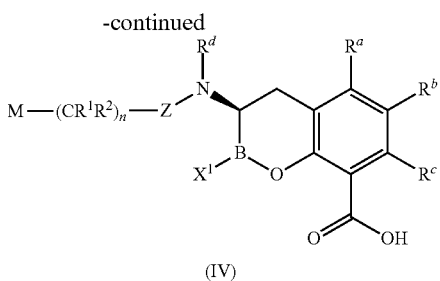

(IV)

Alternatively, compounds of Formula (IV) are obtained from Intermediate A by treatment of Intermediate A with aqueous hydrochloric acid (around 3-5 Molar) in dioxane at a temperature between room temperature and 110° C.

SCHEME 2

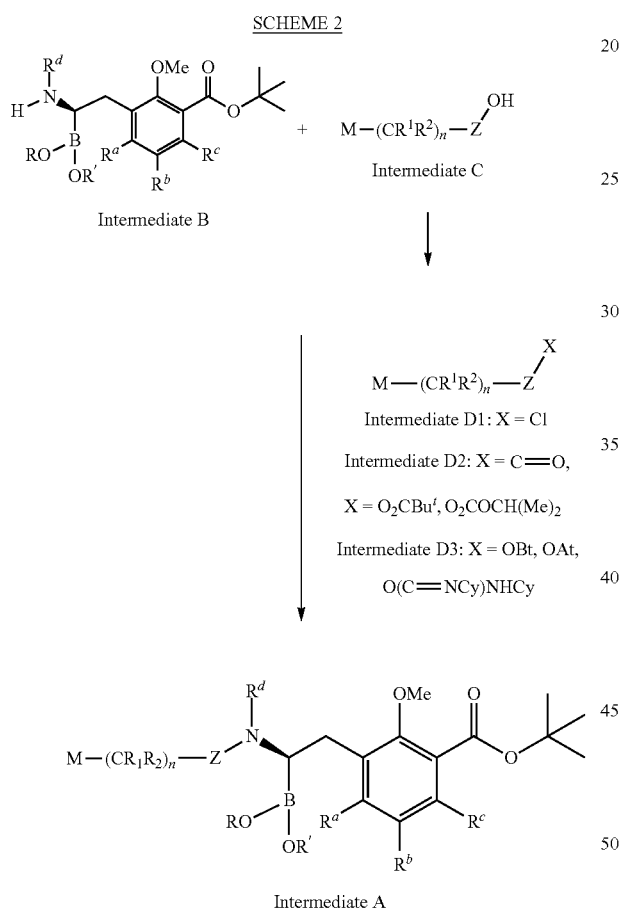

Intermediate B

Intermediate C

Intermediate D1: X = Cl

Intermediate D2: X = C=O,

X = O$_2$CBu$^t$, O$_2$COCH(Me)$_2$

Intermediate D3: X = OBt, OAt,

O(C=NCy)NHCy

Intermediate A

The requisite boronic acid esters (Intermediate A) are obtained (SCHEME 2) by coupling of amine (Intermediate B) with carboxylic acid (Intermediate C). This transformation is effected by first activating the acid functionality as an acid chloride, anhydride or reactive ester (Intermediates D1, D2, and D3), followed by treatment of the activated substrate with (Intermediate B) in a solvent such as DMF, DMA, NMP, THF or dichloromethane (or a mixture thereof) at about room temperature, usually in the presence of a non-nucleophilic base such as 4-methyl-morpholine, triethylamine, pyridine, or diisopropylethylamine.

Formation of the acid chloride (Intermediate D1) involves treatment of (Intermediate C) with a chlorinating agent such as thionyl chloride, phosphorous pentachloride or oxalyl chloride, in a solvent such as dichloromethane, in the presence of a catalyst such as DMF, at around room temperature. In certain cases, DMF is also used as a co-solvent. Formation of the anhydride (Intermediate D2) (Z is C=O) involves treatment of (Intermediate C) with a sterically hindered acid chloride or chloroformate, such as trimethylacetyl chloride or isopropylchloroformate, in an inert solvent such as dichloromethane, in the presence of a non-nucleophilic base, such as triethylamine or diisopropylamine at room temperature or below. Formation of the activated ester (Intermediate D3) involves treatment of (Intermediate C) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119).

The requisite acids (Intermediate C) are commercially available or may be synthesized in a few steps from commercially available starting materials following methods described in the literature.

Certain compounds of the invention, such as compounds of Formula (I), (II), (III), or (V) (SCHEME 3) are prepared from the corresponding functional-group-protected boronic acid esters (Intermediate E) by treatment with a Lewis acid such as AlCl$_3$, in a solvent such as dichloromethane, at room temperature followed by an aqueous or water/methanol quench. The reaction can also be accomplished by treatment with an aqueous acid such as HBr or HCl in a solvent mixture of acetonitrile and hexane in the presence of phenylboronic acid at room temperature.

SCHEME 3

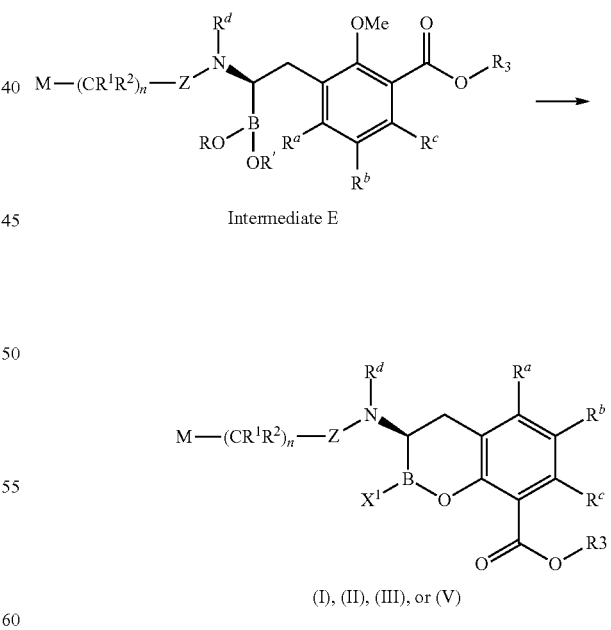

Intermediate E (I), (II), (III), or (V)

Alternatively, compounds of Formula (II) can be obtained by treatment of compounds of Formula (IV) with hydrochloric acid (around 3-5 Molar in dioxane) in an alcohol solvent such as pentanol, ethanol -hexanol, or 3-methylbutanol at a temperature between room temperature and 120° C. (SCHEME 4).

SCHEME 4

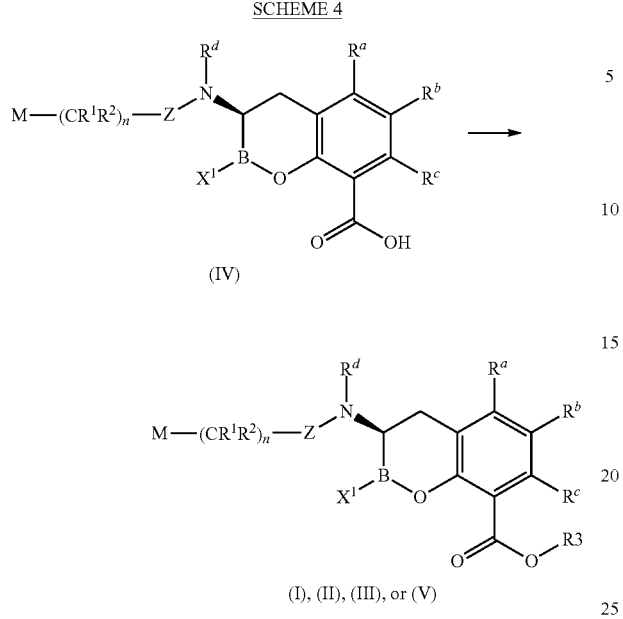

(IV)

(I), (II), (III), or (V)

Compounds of the invention, such as compounds of Formula (I) and Formula (III) can be prepared by treatment of the acid (IV) with a base such as lithium tert-butoxide or lithium hydroxide and a corresponding alkyl chloride, bromide or iodide or an alkyl triflate, mesylate, or tosylate in a solvent such as DMA or DMF. In addition, certain compounds of the invention, such as compounds of Formula (I) and Formula (III) can be prepared by treatment of acid (IV) with NaOH in water to isolate the sodium salt which is followed by treatment with a base such as sodium bicarbonate or sodium carbonate and an alkyl chloride, bromide or iodide or an alkyl triflate, mesylate, or tosylate (in some cases sodium iodide can be included) in a solvent such as DMA or DMF (SCHEME 4).

The desired protected carboxylic acid esters (Intermediate E) are prepared by treatment of the t-butyl ester (Intermediate A) with anhydrous acid such as hydrochloric acid (4 Molar) in dioxane or trifluoroacetic acid at room temperature. The resulting acid (Intermediate F) can be alkylated by addition of an inorganic base such as sodium carbonate, potassium carbonate, or cesium fluoride or an organic base such as triethylamine along with an alkyl halide such as iodoethane, 1-iodobutane, chloromethyl pivalate, or bromomethyl acetate in a solvent such as DMF at room temperature or above. In some cases, sodium iodide can also be added (SCHEME 5).

SCHEME 5

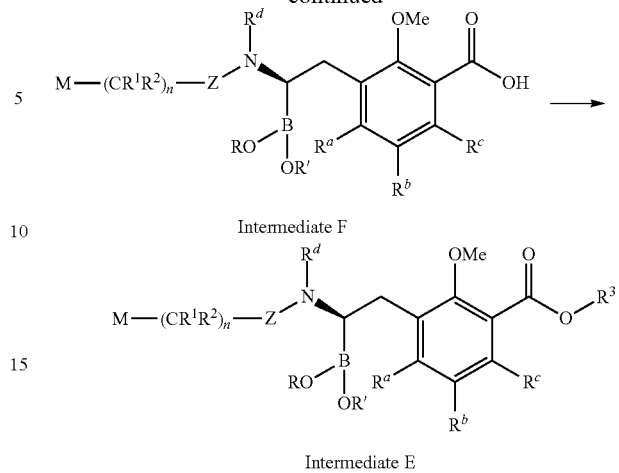

Intermediate A

Intermediate F

Intermediate E

SYNTHETIC EXAMPLES

The following preparations of compounds of Formula (I), (II), (III), (IV), or (V) and intermediates thereof are given to enable those of skill in the art to more clearly understand and to practice the present invention. They should not be considered as limiting the scope of the invention, but merely as illustrative and representative thereof.

Example 1: (R)-3-(2,2-difluorobutanamido)-2-hydroxy-3,4-dihydro-2H-benzo [e] [1,2] oxaborinine -8-carboxylic acid

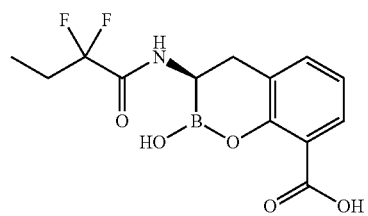 [SMILES: CCC(F)(F)C(=O)N[C@H]1Cc2cccc(C(=O)O)c2OB1O]

Step 1. Synthesis of 3-[2-(2,2-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester.

To a cooled (−25° C.) solution of [(1S)-2-(3-tert-butoxycarbonyl-2-methoxy-phenyl)-1-chloro -ethyl]boronic acid (+) pinanediol ester (1.51 g, 3.36 mmol) in THF (8.5 mL) was added lithium bis -trimethylsilylamide (3.5 mL, 1M in THF) dropwise. On complete addition, the cold bath was removed and stirring continued for 1 h to give a solution of [(1R)-1-[bis(trimethylsilyl)amino]-2-(3-tert-butoxycarbonyl -2-methoxy-phenyl)ethyl]boronic acid (+) pinanediol ester, approximately 0.26 M in THF. This solution was used directly in the next operation.

In a separate flask: To a mixture of 2,2-difluorobutyric acid (0.165 g, 1.33 mmol) and HATU (0.556 g, 1.46 mmol) was added DMA (4.2 mL) followed by N-methylmorpholine (0.17 mL, 1.55 mmol). The resulting solution was stirred for 1.5 h then a solution of [(1R)-1-[bis(trimethylsilyl)amino]-2-(3-tert -butoxycarbonyl-2-methoxy-phenyl)ethyl]boronic acid (+) pinanediol ester in THF (prepared above) was added. This mixture was stirred for 18 h, quenched with water, and extracted two times with diethyl ether. The combined organic layers were washed with brine, dried over MgSO$_4$, and concentrated. The residue was purified by silica chromatography (5-100% ethyl acetate/hexane) to give the title compound. ESI-MS m/z 536 (MH)$^+$.

Step 2. (R)-3-(2,2-difluorobutanamido)-2-hydroxy-3,4-dihydro-2H-benzo[e] [1,2]oxaborinine-8-carboxylic acid.

Boron tribromide (1.5 mL, 1.0 M in CH$_2$Cl$_2$, 1.50 mmol) was added to a solution of 3-[2-(2,2-Difluoro-butyrylamino)-2-(2,9,9-trimethyl-3,5-dioxa-4-bora-tricyclo [6.1.1.02,6]dec-4-yl) -ethyl]-2-methoxy -benzoic acid tert-butyl ester (0.271 g, 0.506 mmol) in dichloromethane (5 mL) at −78 ° C. and the reaction stirred at −78 ° C. for 40 min then warmed to 0° C. for 45 min. The reaction mixture was quenched with water and stirred for 1 h. The reaction mixture was concentrated and then extracted two times with hexane. The product remained in the aqueous layer and was purified by reverse phase HPLC. Pure fractions were concentrated by lyophilization to give the title compound as a white solid. ESI-MS m/z 314 (MH)$^+$.

Example 2: (R)-2-hydroxy-3-(5,5,5-trifluoropentanamido)-3,4-dihydro-2H-benzo[e][1,2]oxaborinine-8-carboxylic acid

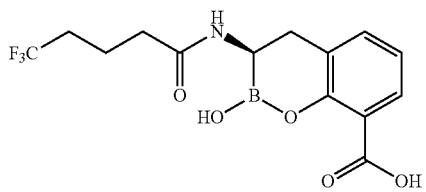 [SMILES: O=C(CCCC(F)(F)F)N[C@H]1Cc2cccc(C(=O)O)c2OB1O]

Step 1. Synthesis of 2-Methoxy-3-[2-(5,5,5-trifluoro-pentanoylamino)-2-(2,9,9-trimethyl-3,5-dioxa-4-bora-tricyclo [6.1.1.02,6]dec-4-yl)-ethyl]-benzoic acid tert-butyl ester.

Prepared from [(1R)-1-[bis(trimethylsilyl)amino]-2-(3-tert-butoxycarbonyl-2-methoxy -phenyl)ethyl]boronic acid (+) pinanediol ester and 5,5,5-trifluoropentanoic acid following the procedure in Step 1 of Example 1. The crude product was purified by silica chromatography (5-100% ethyl acetate/hexane) to give the title compound. ESI-MS m/z 568 (MH)$^+$.

Step 2. Synthesis of (R)-2-hydroxy-3-(5,5,5-trifluoropentanamido)-3,4-dihydro-2H-benzo[e][1,2]oxaborinine-8-carboxylic acid.

Prepared from 2-Methoxy-3-[2-(5,5,5-trifluoro-pentanoylamino)-2-(2,9,9-trimethyl-3,5-dioxa-4-bora-tricyclo [6.1.1.02,6]dec-4-yl)-ethyl]-benzoic acid tert-butyl ester following the procedure in Step 2 of Example 1. The crude product was purified by reverse phase preparative HPLC and dried using lyophilization. ESI-MS m/z 346 (MH)$^+$.

Example 3: (R)-3-(3,3-difluorobutanamido)-2-hydroxy-3,4-dihydro-2H-benzo [e][1,2]oxaborinine -8-carboxylic acid

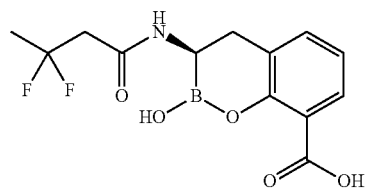 [SMILES: CC(F)(F)CC(=O)N[C@H]1Cc2cccc(C(=O)O)c2OB1O]

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester.

To a mixture of 3,3-difluorobutanoic acid (0.810 g, 6.53 mmol) in DMA (17 mL) was added HATU (2.73 g, 7.18 mmol) followed by pyridine (0.53 mL, 6.55 mmol). The resulting solution was stirred for 1.5 h then a solution of [(1R)-1-[bis(trimethylsilyl)amino]-2-(3-tert-butoxycarbonyl-2-methoxy -phenyl)ethyl]boronic acid (+) pinanediol ester in THF (prepared in Step 1 of Example 1) was added. This mixture was stirred for 18 h, quenched with water, and extracted two times with diethyl ether. The combined organic layers were washed with brine, dried over MgSO$_4$, and concentrated. The residue was purified by silica chromatography (10-100% ethyl acetate/hexane) to give the title compound. ESI-MS m/z 536 (MH)$^+$.

Step 2. Synthesis of (R)-3-(3,3-difluorobutanamido)-2-hydroxy-3,4-dihydro-2H-benzo[e][1,2]oxaborinine-8-carboxylic acid.

Prepared from 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester following the procedure in Step 2 of Example 1. The crude product was purified by reverse phase preparative HPLC and dried using lyophilization. ESI-MS m/z 314 (MH)$^+$.

Example 4: (R)-2-Hydroxy-3-propionylamino-3,4-dihydro-2H-benzo [e][1,2]oxaborinine-8-carboxylic acid pentyl ester

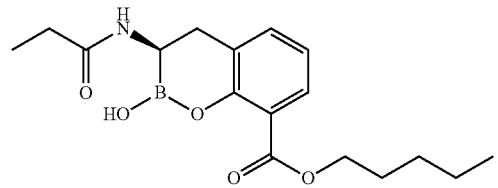 [SMILES: CCCCCOC(=O)c1cccc2c1OB(O)[C@@H](NC(=O)CC)C2]

Step 1. Synthesis of 3-[2-Propionylamino-2-(2,9,9-trimethyl-3,5-dioxa-4-bora-tricyclo[6.1.1.02,6]dec -4-yl)-ethyl]-2-methoxy-benzoic acid tert-butyl ester.

Prepared from [(1R)-1-[bis(trimethylsilyl)amino]-2-(3-tert-butoxycarbonyl-2-methoxy -phenyl)ethyl]boronic acid (+) pinanediol ester and propionic acid following the procedure in Step 1 of Example 1. The residue was purified by silica chromatography (70% ethyl acetate/hexane) to give the title compound. ESI-MS m/z 486 (MH)$^+$.

Step 2. Synthesis of 2-Hydroxy-3-propionylamino-3,4-dihydro-2H-benzo[e][1,2]oxaborinine-8-carboxylic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester following the procedure in Step 2 of Example 1. The crude product was purified by reverse phase preparative HPLC and dried using lyophilization to give the title compound. ESI-MS m/z 264 (MH)$^+$.

Step 3. Synthesis of (R)-2-Hydroxy-3-propionylamino-3,4-dihydro-2H-benzo[e][1,2]oxaborinine-8-carboxylic acid pentyl ester.

To 2-hydroxy-3-propionylamino-3,4-dihydro-2H-benzo [e][1,2]oxaborinine-8-carboxylic acid (0.1 g, 0.38 mmol) in 1-pentanol (7.8 mL) was added 4N HCl/dioxane (2.42 mL, 9.7 mmol) and was stirred at room temperature overnight. The reaction was concentrated in vacuo and the crude Example 5: (Isobutyryloxy)methyl (R)-2-hydroxy-3-propionamido-3,4-dihydro-2H -benzo [e][1,2]oxaborinine-8-carboxylate

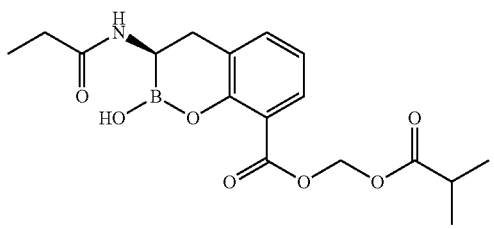 [SMILES: CCC(=O)N[C@H]1Cc2cccc(C(=O)OCOC(=O)C(C)C)c2OB1O]

A 1 M solution of lithium tert-butoxide in hexanes (0.46 mL, 0.46 mmol) was added dropwise to a stirred solution of (R)-2-hydroxy-3-propionamido-3,4-dihydro-2H-benzo [e][1,2]oxaborinine-8-carboxylic acid (100 mg, 0.38 mmol) in anhydrous DMA (3 mL) at room temperature, under Argon. Iodomethyl isobutyrate (434 mg, 1.90 mmol) was added next via syringe, and the reaction was monitored by LCMS and stopped after an additional 20 minutes, when complete conversion of the substrate was observed. The reaction mixture was diluted with ethyl acetate (15-20 mL) and quenched by addition of a saturated aqueous solution of ammonium chloride (2 mL). The resulting mixture was transferred to a separatory funnel and the layers were separated. The organic phase was washed with water (5 mL), then with brine (5 mL), and the volatiles were evaporated under reduced pressure to give a residue, which was washed with hexanes (3 mL) to remove most of the unreacted iodomethyl isobutyrate. Reverse phase flash chromatography (acetonitrile/water 0-80% gradient, modified with 0.1% TFA), followed by evaporation of solvent under high vacuum afforded the title compound as an off-white amorphous solid. ESI-MS m/z 386 (M+Na)$^+$.

Example 6: (R)-3-Propionylamino-2-hydroxy-3,4-dihydro-2H-benzo [e][1,2]oxaborinine-8-carboxylic acid hexyl ester

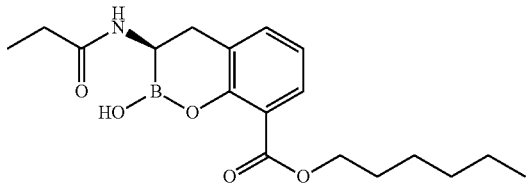 [SMILES: CCCCCCOC(=O)c1cccc2c1OB(O)[C@@H](NC(=O)CC)C2]

Step 1. Synthesis of 3-Propionylamino-2-hydroxy-3,4-dihydro-2H-benzo[e][1,2]oxaborinine-8-carboxylic acid.
Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 1M boron tribromide in dichloromethane following the procedure described in Step 2 of Example 1. The crude product was purified by reverse phase preparative HPLC and dried using lyophilization to give the title compound. ESI-MS m/z 264 (MH)$^+$.

Step 2. Synthesis of 3-Propionylamino-2-hydroxy-3,4-dihydro-2H-benzo[e][1,2]oxaborinine-8-carboxylic acid hexyl ester.
Prepared from 3-propionylamino-2-hydroxy-3,4-dihydro-2H-benzo[e][1,2]oxaborinine-8-carboxylic acid and 1-hexanol following the procedure described in Step 3 of Example 4. The crude product was purified by reverse phase preparative HPLC and dried using lyophilization to give the title compound. ESI-MS m/z 348 (MH)$^+$.

Example 7: (R)-3-Propionylamino-2-hydroxy-3,4-dihydro-2H-benzo [e][1,2]oxaborinine-8-carboxylic acid 3-methyl-butyl ester

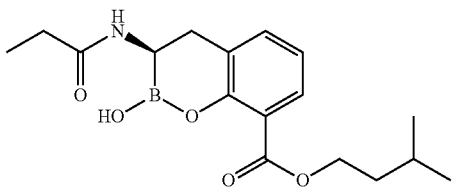 [SMILES: CCC(=O)N[C@H]1Cc2cccc(C(=O)OCCC(C)C)c2OB1O]

Step 1. Synthesis of 3-Propionylamino-2-hydroxy-3,4-dihydro-2H-benzo[e][1,2]oxaborinine-8-carboxylic acid.
Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 1M boron tribromide in dichloromethane following the procedure described in Step 2 of Example 1. The crude product was purified by reverse phase preparative HPLC and dried using lyophilization to give the title compound. ESI-MS m/z 264 (MH)$^+$.
Step 2. Synthesis of (R)-3-Propionylamino-2-hydroxy-3,4-dihydro-2H-benzo[e][1,2]oxaborinine-8-carboxylic acid 3-methyl-butyl ester.
Prepared from 3-propionylamino-2-hydroxy-3,4-dihydro-2H-benzo[e][1,2]oxaborinine-8-carboxylic acid and 3-methyl-1-butanol following the procedure described in Step 3 of Example 4. The crude product was purified by reverse phase preparative HPLC and dried using lyophilization to give the title compound. ESI-MS m/z 334 (MH)$^+$.

Example 8: (R)-2-Hydroxy-3-propionylamino-3,4-dihydro-2H-benzo [e][1,2]oxaborinine-8-carboxylic acid 4-methyl-pentyl ester

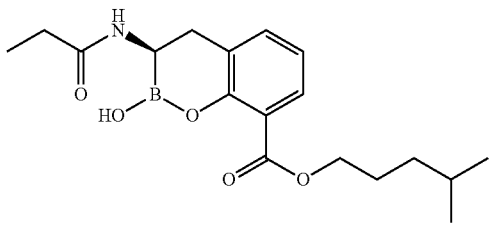 [SMILES: CCC(=O)N[C@H]1Cc2cccc(C(=O)OCCCC(C)C)c2OB1O]

Step 1. Synthesis of 3-Propionylamino-2-hydroxy-3,4-dihydro-2H-benzo[e][1,2]oxaborinine-8-carboxylic acid.
Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 1M boron tribromide in dichloromethane following the procedure described in Step 2 of Example 1. The crude product was purified by reverse phase preparative HPLC and dried using lyophilization to give the title compound. ESI-MS m/z 264 (MH)⁺.

Step 2. Synthesis of (R)-2-Hydroxy-3-propionylamino-3,4-dihydro-2H-benzo[e][1,2]oxaborinine-8-carboxylic acid 4-methyl-pentyl ester.

Prepared from 3-propionylamino-2-hydroxy-3,4-dihydro-2H-benzo[e][1,2]oxaborinine-8-carboxylic acid and 4-methyl-pentanol following the procedure described in Step 3 of Example 4. The crude product was purified by reverse phase preparative HPLC and dried using lyophilization to give the title compound. ESI-MS m/z 348 (MH)⁺.

Example 9: (R)-2-Hydroxy-3-propionylamino-3,4-dihydro-2H-benzo [e][1,2]oxaborinine-8-carboxylic acid 3,3-dimethyl-butyl ester

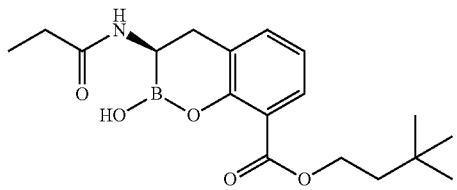 [SMILES: CCC(=O)N[C@H]1Cc2cccc(C(=O)OCCC(C)(C)C)c2OB1O]

Step 1. Synthesis of 3-Propionylamino-2-hydroxy-3,4-dihydro-2H-benzo[e][1,2]oxaborinine-8-carboxylic acid.

Prepared from 3-[2-propionylamino-2-(2,9,9-trimethyl-3,5-dioxa-4-bora-tricyclo[6.1.1.0²,⁶]dec -4-yl)-ethyl]-2-methoxy-benzoic acid tert-butyl ester and 1M boron tribromide in dichloromethane following the procedure described in Step 2 of Example 1. The crude product was purified by reverse phase preparative HPLC and dried using lyophilization to give the title compound. ESI-MS m/z 264 (MH)⁺.

Step 2. Synthesis of (R)-2-Hydroxy-3-propionylamino-3,4-dihydro-2H-benzo[e][1,2]oxaborinine-8-carboxylic acid 3,3-dimethyl-butyl ester.

Prepared from 3-propionylamino-2-hydroxy-3,4-dihydro-2H-benzo[e][1,2]oxaborinine-8-carboxylic acid and 3,3-dimethyl-1-butanol following the procedure described in Step 3 of Example 4. The crude product was purified by reverse phase preparative HPLC and dried using lyophilization to give the title compound. ESI-MS m/z 348 (MH)⁺.

Example 10: (R)-2-Hydroxy-3-propionylamino-3,4-dihydro-2H-benzo[e][1,2]oxaborinine-8-carboxylic acid 2-ethyl-butyl ester

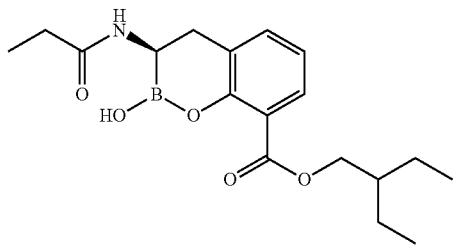 [SMILES: CCC(=O)N[C@H]1Cc2cccc(C(=O)OCC(CC)CC)c2OB1O]

Step 1. Synthesis of 3-Propionylamino-2-hydroxy-3,4-dihydro-2H-benzo[e][1,2]oxaborinine-8-carboxylic acid.

Prepared from 3-[2-propionylamino-2-(2,9,9-trimethyl-3,5-dioxa-4-bora-tricyclo[6.1.1.0²,⁶]dec -4-yl)-ethyl]-2-methoxy-benzoic acid tert-butyl ester and 1M boron tribromide in dichloromethane following the procedure described in Step 2 of Example 1. The crude product was purified by reverse phase preparative HPLC and dried using lyophilization to give the title compound. ESI-MS m/z 264 (MH)⁺.

Step 2. Synthesis of (R)-2-Hydroxy-3-propionylamino-3,4-dihydro-2H-benzo[e][1,2]oxaborinine-8-carboxylic acid 2-ethyl-butyl ester.

Prepared from 3-propionylamino-2-hydroxy-3,4-dihydro-2H-benzo[e][1,2]oxaborinine-8-carboxylic acid and 2-ethyl-1-butanol following the procedure described in Step 3 of Example 4. The crude product was purified by reverse phase preparative HPLC and dried using lyophilization to give the title compound. ESI-MS m/z 348 (MH)⁺.

Example 11: 2-(Diethylamino)-2-oxoethyl (R)-2-hydroxy-3-propionamido-3,4-dihydro-2H-benzo[e][1,2]oxaborinine-8-carboxylate

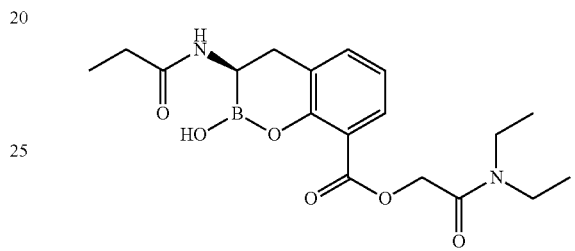

2-(Diethylamino)-2-oxoethyl (R)-2-hydroxy-3-propionamido-3,4-dihydro-2H -benzo[e][1,2]oxaborinine-8-carboxylate was prepared from (R)-2-hydroxy-3-propionamido-3,4-dihydro-2H -benzo[e][1,2]oxaborinine-8-carboxylic acid and 2-bromo—N,N-diethylacetamide by a procedure similar to Example 5. ESI-MS m/z 377 (MH)⁺.

Example 12: (R)-2-Hydroxy-3-propionylamino-3,4-dihydro-2H-benzo[e][1,2]oxaborinine-8-carboxylic acid 2-cyclohexylethyl ester

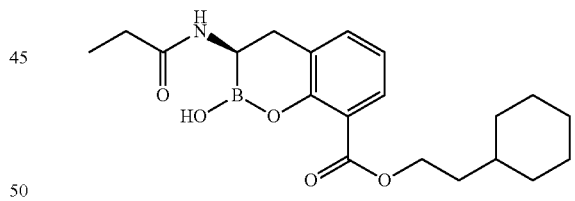

Step 1. Synthesis of 3-Propionylamino-2-hydroxy-3,4-dihydro-2H-benzo[e][1,2]oxaborinine-8-carboxylic acid.

Prepared from 3-[2-propionylamino-2-(2,9,9-trimethyl-3,5-dioxa-4-bora-tricyclo[6.1.1.0²,⁶]dec -4-yl)-ethyl]-2-methoxy-benzoic acid tert-butyl ester and 1M boron tribromide in dichloromethane following the procedure described in Step 2 of Example 1. The crude product was purified by reverse phase preparative HPLC and dried using lyophilization to give the title compound. ESI-MS m/z 264 (MH)⁺.

Step 2. Synthesis of (R)-2-Hydroxy-3-propionylamino-3,4-dihydro-2H-benzo[e][1,2]oxaborinine-8-carboxylic acid 2-cyclohexyl-ethyl ester.

Prepared from 3-propionylamino-2-hydroxy-3,4-dihydro-2H-benzo[e][1,2]oxaborinine-8-carboxylic acid and 2-cyclohexyl-ethanol following the procedure described in Step 3 of Example 4. The crude product was purified by reverse phase preparative HPLC and dried using lyophilization to give the title compound. ESI-MS m/z 374 (MH)+.

Example 13: (R)-2-Hydroxy-3-propionylamino-3,4-dihydro-2H-benzo [e][1,2]oxaborinine-8-carboxylic acid pentanoyloxymethyl ester

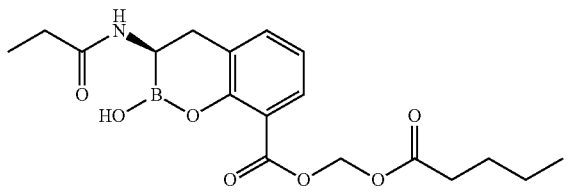 [SMILES: CCCCC(=O)OCOC(=O)c1cccc2c1OB(O)[C@@H](NC(=O)CC)C2]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

To 3-[2-propionylamino-2-(2,9,9-trimethyl-3,5-dioxa-4-bora-tricyclo[6.1.1.02,6]dec-4-yl)-ethyl]-2-methoxy-benzoic acid tert-butyl ester (7.72 g, 15.9 mmol) was added 4N HCl/dioxane (65 mL) and was stirred at room temperature overnight. The product was azeotroped with toluene and dried under high vacuum to give a solid. ESI-MS m/z 430 (MH)+.

Step 3. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester.

To 3-[2-propionylamino-2-(2,9,9-trimethyl-3,5-dioxa-4-bora-tricyclo[6.1.1.02,6]dec-4-yl)-ethyl]-2-methoxy-benzoic acid (1.9 g, 4.43 mmol) in anhydrous N,N-dimethylformamide (26 mL) under an atmosphere of argon was added potassium carbonate (3 g, 22.1 mmol), followed by chloroiodomethane (3.23 mL, 44.3 mmol) and stirred at room temperature for 3.5 h. The reaction was diluted with ethyl acetate, washed with water/brine, dried over sodium sulfate, and concentrated. The crude product was purified by flash chromatography on silica gel (2% methanol/dichloromethane). ESI-MS m/z 478 (MH)+.

Step 4. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid pentanoyloxymethyl ester.

To 2-methoxy-3-[2-propionylamino-2-(2,9,9-trimethyl-3,5-dioxa-4-bora-tricyclo [6.1.1.02,6]dec -4-yl)-ethyl]-benzoic acid chloromethyl ester (0.4 g, 0.84 mmol) in anhydrous N,N-dimethylformamide (3.2 mL) under an atmosphere of argon was added valeric acid (0.09 mL, 0.84 mmol) and triethylamine (0.35 mL, 2.52 mmol), followed by sodium iodide (0.14 g, 0.92 mmol) and was stirred at 60° C. overnight. The reaction was diluted with ethyl acetate, washed with water/brine, dried over sodium sulfate, and concentrated. The crude product was purified by flash chromatography on silica gel with preparative TLC plates (70-80% ethyl acetate/hexane). ESI-MS m/z 544 (MH)+.

Step 5. Synthesis of (R)-2-Hydroxy-3-propionylamino-3,4-dihydro-2H-benzo[e][1,2]oxaborinine-8-carboxylic acid pentanoyloxymethyl ester.

To 2-methoxy-3-[2-prop ionylamino-2-(2,9,9-trimethyl-3,5-dioxa-4-bora-tricyclo [6.1.1.02,6]dec -4-yl)-ethyl]-benzoic acid pentanoyloxymethyl ester (0.09 g, 0.16 mmol) in dichloromethane under an atmosphere of argon was added aluminum chloride (0.09 g, 0.65 mmol) and was stirred at room temperature for 45 min. The reaction was quenched with water/methanol and the dichloromethane was concentrated off. The crude product was purified by reverse phase preparative HPLC and dried using lyophilization to give the title compound. ESI-MS m/z 400 (M+Na)+.

Example 14: (R)-2-Hydroxy-3-propionylamino-3,4-dihydro-2H-benzo[e][1,2]oxaborinine-8-carboxylic acid benzyl ester

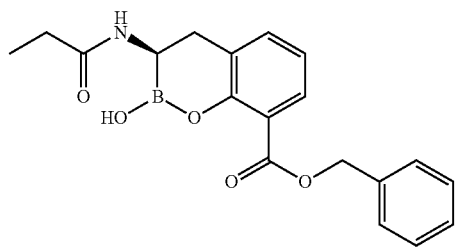 [SMILES: CCC(=O)N[C@H]1Cc2cccc(C(=O)OCc3ccccc3)c2OB1O]

Step 1. Synthesis of 3-Propionylamino-2-hydroxy-3,4-dihydro-2H-benzo[e][1,2]oxaborinine-8-carboxylic acid.

Prepared from 3-[2-propionylamino-2-(2,9,9-trimethyl-3, 5-dioxa-4-bora-tricyclo[6.1.1.02,6]dec -4-yl)-ethyl]-2-methoxy-benzoic acid tert-butyl ester and 1M boron tribromide in dichloromethane following the procedure described in Step 2 of Example 1. The crude product was purified by reverse phase preparative HPLC and dried using lyophilization to give the title compound. ESI-MS m/z 264 (MH)+.

Step 2. Synthesis of (R)-2-Hydroxy-3-propionylamino-3,4-dihydro-2H-benzo[e][1,2]oxaborinine-8-carboxylic acid benzyl ester.

Prepared from 3-propionylamino-2-hydroxy-3,4-dihydro-2H-benzo[e][1,2]oxaborinine-8-carboxylic acid and benzyl alcohol following the procedure described in Step 3 of Example 4. The crude product was purified by reverse phase preparative HPLC and dried using lyophilization to give the title compound. ESI-MS m/z 354 (MH)+.

Example 15: (R)-2-Hydroxy-3-propionylamino-3,4-dihydro-2H-benzo[e][1,2]oxaborinine-8-carboxylic acid 2-tetrahydro-pyran-4-yl-acetoxymethyl ester

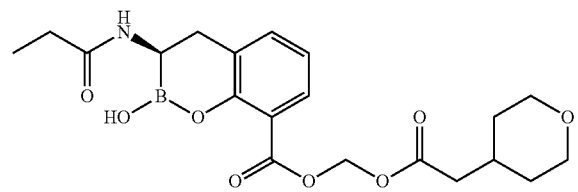 [SMILES: CCC(=O)N[C@H]1Cc2cccc(C(=O)OCOC(=O)CC3CCOCC3)c2OB1O]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1 S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 478 (MH)+.

Step 4. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid 2-tetrahydro-pyran-4-yl-acetoxymethyl ester.

Prepared from 2-methoxy-3-[2-propionylamino -2-(2,9,9-trimethyl-3,5-dioxa-4-bora -tricyclo[6.1.1.02,6]dec-4-yl)-ethyl]-benzoic acid chloromethyl ester and tetrahydropyranyl-4-acetic acid following the procedure in Step 4 of Example 13. The crude product was purified by flash chromatography on silica gel with preparative TLC plates (7% methanol/dichloromethane). ESI-MS m/z 586 (MH)+.

Step 5. Synthesis of (R)-2-Hydroxy-3-propionylamino-3,4-dihydro-2H-benzo[e][1,2]oxaborinine-8-carboxylic acid 2-tetrahydro-pyran-4-yl-acetoxymethyl ester.

Prepared from 2-methoxy-3-[2-propionylamino -2-(2,9,9-trimethyl-3,5-dioxa-4-bora -tricyclo[6.1.1.02,6]dec-4-yl)-ethyl]-benzoic acid 2-tetrahydro-pyran-4-yl-acetoxymethyl ester and aluminum chloride following the procedure in Step 5 of Example 13. The crude product was purified by reverse phase preparative HPLC and dried using lyophilization to give the title compound. ESI-MS m/z 442 (M+Na)+.

Example 16: (R)-Hexanedioic acid 2-hydroxy-3-propionylamino-3,4-dihydro-2H -benzo[e][1,2]oxaborinine-8-carbonyloxymethyl ester methyl ester

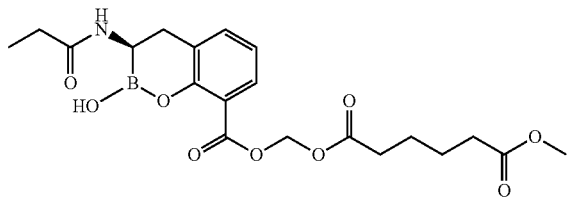 [SMILES: CCC(=O)N[C@H]1Cc2cccc(C(=O)OCOC(=O)CCCCC(=O)OC)c2OB1O]

Step 1. Synthesis of 3-12-Propionylamino-2-(2,9,9-trimethyl-3,5-dioxa-4-bora-tricyclo[6.1.1.02,61dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)+.

Step 2. Synthesis of 3-12-Propionylamino-2-(2,9,9-trimethyl-3,5-dioxa-4-bora-tricyclo[6.1.1.02,61dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 2-Methoxy-3-[2-propionylamino-2-(2, 9,9-trimethyl-3,5-dioxa-4-bora -tricyclo[6.1.1.02,6]dec-4-yl)-ethyl]-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 478 (MH)+.

Step 4. Synthesis of Hexanedioic acid 2-methoxy-3-[2-propionylamino-2-(2,9,9-trimethyl-3,5-dioxa-4-bora-tricyclo[6.1.1.02,6]dec-4-yl)-ethyl]-benzoyloxymethyl ester methyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester and mono-methyl adipate following the procedure in Step 4 of Example 13. The crude product was purified by flash chromatography on silica gel with preparative TLC plates (7% methanol/dichloromethane). ESI-MS m/z 602 (MH)+.

Step 5. Synthesis of (R)-Hexanedioic acid 2-hydroxy-3-propionylamino-3,4-dihydro-2H -benzo[e][1,2]oxaborinine-8-carbonyloxymethyl ester methyl ester.

Prepared from hexanedioic acid 2-methoxy-3-[2-propionylamino-2-(2,9,9-trimethyl-3,5-dioxa-4-bora-tricyclo [6.1.1.02,6]dec-4-yl)-ethyl]-benzoyloxymethyl ester methyl ester and aluminum chloride following the procedure in Step 5 of Example 13. The crude product was purified by reverse phase preparative HPLC and dried using lyophilization to give the title compound. ESI-MS m/z 458 (M+Na)+.

Example 17: (R)-2-Hydroxy-3-propionylamino-3,4-dihydro-2H-benzo[e][1,2]oxaborinine-8-carboxylic acid 2-pyridin-3-yl-acetoxymethyl ester

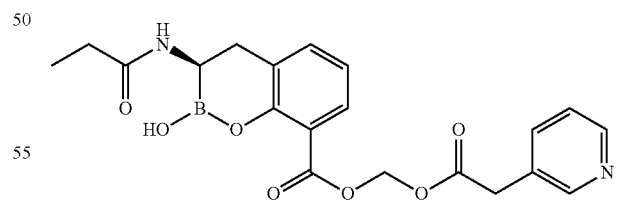

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 478 (MH)+.

Step 4. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid 2-pyridin-3-yl-acetoxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester and 3-pyridineacetic acid hydrochloride following the procedure in Step 4 of Example 13. The crude product was purified by flash chromatography on silica gel with preparative TLC plates (9% methanol/dichloromethane). ESI-MS m/z 579 (MH)+.

Step 5. Synthesis of (R)-2-Hydroxy-3-propionylamino-3,4-dihydro-2H-benzo[e][1,2]oxaborinine-8-carboxylic acid 2-pyridin-3-yl-acetoxymethyl ester trifluoroacetate.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid 2-pyridin-3-yl-acetoxymethyl ester and aluminum chloride following the procedure in Step 5 of Example 13. The crude product was purified by reverse phase preparative HPLC and dried using lyophilization to give the title compound. ESI-MS m/z 435 (M+Na)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 478 (MH)+.

Step 4. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid 4,4,4-trifluoro-butyryloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester and 4,4,4-trifluorobutyric acid following the procedure in Step 4 of Example 13. The crude product was purified by flash chromatography on silica gel with preparative TLC plates (7% methanol/dichloromethane). ESI-MS m/z 584 (MH)+.

Step 5. Synthesis of (R)-2-Hydroxy-3-propionylamino-3,4-dihydro-2H-benzo[e][1,2]oxaborinine-8-carboxylic acid 4,4,4-trifluoro-butyryloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid 4,4,4-trifluoro-butyryloxymethyl ester and aluminum chloride following the procedure in Step 5 of Example 13. The crude product was purified by reverse phase preparative HPLC and dried using lyophilization to give the title compound. ESI-MS m/z 440 (M+Na)+.

Example 18: (R)-2-Hydroxy-3-propionylamino-3,4-dihydro-2H-benzo[e][1,2]oxaborinine-8-carboxylic acid 4,4,4-trifluoro-butyryloxymethyl ester

Example 19: (5-Methyl-2-oxo-1,3-dioxol-4-yl)methyl (R)-2-hydroxy-3-propionamido-3,4-dihydro -2H-benzo[e][1,2]oxaborinine-8-carboxylate

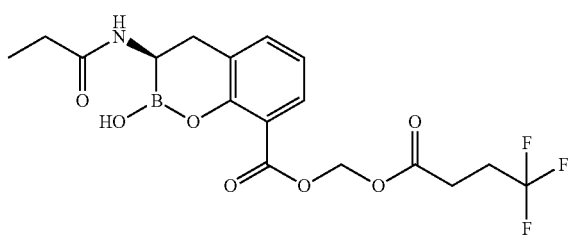 [SMILES: CCC(=O)N[C@H]1Cc2cccc(C(=O)OCOC(=O)CCC(F)(F)F)c2OB1O]

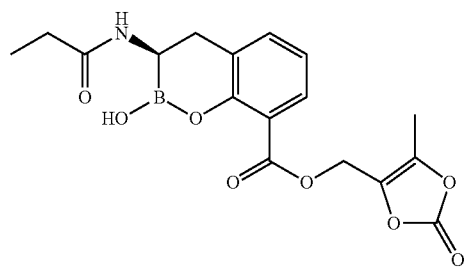 [SMILES: CCC(=O)N[C@H]1Cc2cccc(C(=O)OCc3oc(=O)oc3C)c2OB1O]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)+.

(5-Methyl-2-oxo-1,3-dioxol-4-yl)methyl (R)-2-hydroxy-3-propionamido-3,4-dihydro-2H -benzo[e][1,2]oxaborinine-8-carboxylate was prepared from (R)-2-hydroxy-3-propionamido-3,4-dihydro -2H-benzo [e][1,2]oxaborinine-8-carboxylic acid and 4-(bromomethyl)-5-methyl-1,3-dioxol-2-one by a procedure similar to Example 5. ESI-MS m/z 398 (M+Na)+.

Example 20: (R)-Succinic acid 2-hydroxy-3-propionylamino-3,4-dihydro-2H-benzo[e][1,2]oxaborinine-8-carbonyloxymethyl ester methyl ester

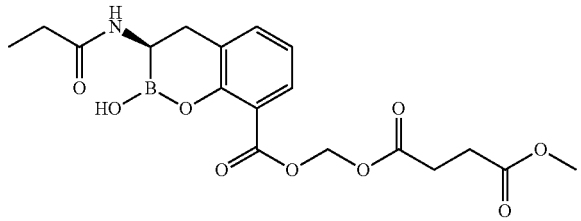 [SMILES: CCC(=O)N[C@H]1Cc2cccc(C(=O)OCOC(=O)CCC(=O)OC)c2OB1O]

Step 1. Synthesis of 3-[2-Propionylamino-2-(2,9,9-trimethyl-3,5-dioxa-4-bora-tricyclo[6.1.1.0 2,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)$^+$.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)$^+$.

Step 3. Synthesis of 2-Methoxy-3-[2-propionylamino-2-(2,9,9-trimethyl-3,5-dioxa-4-bora-tricyclo[6.1.1.02,6]dec-4-yl)-ethyl]-benzoic acid chloromethyl ester.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 478 (MH)$^+$.

Step 4. Synthesis of Succinic acid 2-methoxy-3-[2-propionylamino-2-(2,9,9-trimethyl-3,5-dioxa-4-bora -tricyclo [6.1.1.02,6]dec-4-yl)-ethyl]-benzoyloxymethyl ester methyl ester.

Prepared from 2-methoxy-3-[2-propionylamino -2-(2,9,9-trimethyl-3,5-dioxa-4-bora -tricyclo[6.1.1.02,6]dec-4-yl)-ethyl]-benzoic acid chloromethyl ester and 4-methoxy-4-oxobutanoic acid following the procedure in Step 4 of Example 13. The crude product was purified by flash chromatography on silica gel with preparative TLC plates (7% methanol/dichloromethane). ESI-MS m/z 574 (MH)$^+$.

Step 5. Synthesis of (R)-Succinic acid 2-hydroxy-3-propionylamino-3,4-dihydro-2H -benzo[e][1,2]oxaborinine-8-carbonyloxymethyl ester methyl ester.

Prepared from succinic acid 2-methoxy-3-[2-propionylamino-2-(2,9,9-trimethyl-3,5-dioxa-4-bora -tricyclo [6.1.1.02,6]dec-4-yl)-ethyl]-benzoyloxymethyl ester methyl ester and aluminum chloride following the procedure in Step 5 of Example 13. The crude product was purified by reverse phase preparative HPLC and dried using lyophilization to give the title compound. ESI-MS m/z 430 (M+Na)$^+$.

Example 21: (R)-2-Hydroxy-3-propionylamino-3,4-dihydro-2H-benzo[e][1,2]oxaborinine-8-carboxylic acid 3-dimethylcarbamoyl-propionyloxymethyl ester

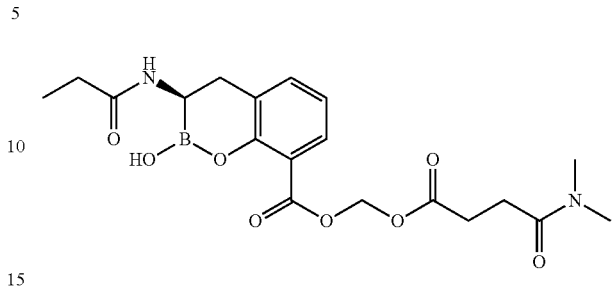

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)$^+$.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)$^+$.

Step 3. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 478 (MH)$^+$.

Step 4. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid 3-dimethylcarbamoyl-propionyloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester and N,N-dimethylsuccinamic acid following the procedure in Step 4 of Example 13. The crude product was purified by flash chromatography on silica gel with preparative TLC plates (9% methanol/dichloromethane). ESI-MS m/z 587 (MH)$^+$.

Step 5. Synthesis of (R)-2-Hydroxy-3-propionylamino-3,4-dihydro-2H-benzo[e][1,2]oxaborinine-8-carboxylic acid 3-dimethylcarbamoyl-propionyloxymethyl ester.

Prepared from 2-methoxy-3-[2-propionylamino-2-(2,9,9-trimethyl-3,5-dioxa-4-bora -tricyclo [6.1.1.02,6]dec-4-yl)-ethyl]-benzoic acid 3-dimethylcarbamoyl-propionyloxymethyl ester and aluminum chloride following the procedure in Step 5 of Example 13. The crude product was purified by reverse phase preparative HPLC and dried using lyophilization to give the title compound. ESI-MS m/z 443 (M+Na)$^+$.

Example 22: 3-Oxo-1,3-dihydroisobenzofuran-1-yl (3R)-2-hydroxy-3-propionamido-3,4-dihydro -2H-benzo [e][1,2]oxaborinine-8-carboxylate

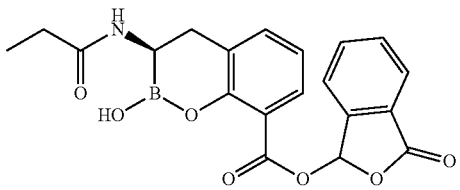 [SMILES: CCC(=O)N[C@H]1Cc2cccc(C(=O)OC3OC(=O)c4ccccc43)c2OB1O]

3-Oxo-1,3-dihydroisobenzofuran-1-yl (3R)-2-hydroxy-3-propionamido-3,4-dihydro-2H -benzo[e][1,2]oxaborinine-8-carboxylate (a 1:1 mixture of diastereoisomers) was prepared from (R)-2-hydroxy-3-propionamido-3,4-dihydro-2H-benzo[e][1,2]oxaborinine-8-carboxylic acid and rac-3-bromoisobenzofuran-1(3H)-one by a procedure similar to Example 5. ESI-MS m/z 396 (MH)+.

Example 23: ((Ethoxycarbonyl)oxy)methyl (R)-2-hydroxy-3-propionamido-3,4-dihydro-2H -benzo[e][1,2]oxaborinine-8-carboxylate

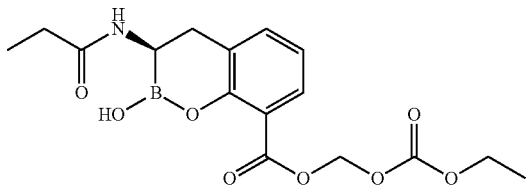 [SMILES: CCOC(=O)OCOC(=O)c1cccc2c1OB(O)[C@@H](NC(=O)CC)C2]

((Ethoxycarbonyl)oxy)methyl (R)-2-hydroxy-3-propionamido-3,4-dihydro-2H -benzo[e][1,2]oxaborinine-8-carboxylate was prepared from (R)-2-hydroxy-3-propionamido-3,4-dihydro-2H -benzo[e][1,2]oxaborinine-8-carboxylic acid and chloromethyl ethyl carbonate by a procedure similar to Example 5, with the exception that the reaction was conducted at 45° C., instead of room temperature. ESI -MS m/z 388 (M+Na)+.

Example 24: ((Isopropoxycarbonyl)oxy)methyl (R)-2-hydroxy-3-propionamido-3,4-dihydro-2H -benzo [e][1,2]oxaborinine-8-carboxylate

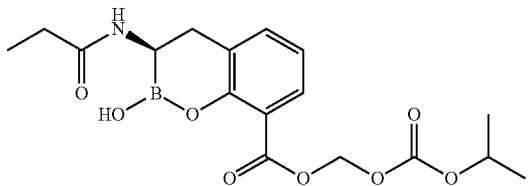 [SMILES: CCC(=O)N[C@H]1Cc2cccc(C(=O)OCOC(=O)OC(C)C)c2OB1O]

((Isopropoxycarbonyl)oxy)methyl (R)-2-hydroxy-3-propionamido-3,4-dihydro-2H -benzo[e][1,2]oxaborinine-8-carboxylate was prepared from (R)-2-hydroxy-3-propionamido-3,4-dihydro-2H -benzo[e][1,2]oxaborinine-8-carboxylic acid and chloromethyl isopropyl carbonate by a procedure similar to Example 5, with the exception that the reaction was conducted at 45° C., instead of room temperature. ESI -MS m/z 402 (M+Na)+.

Example 25: (R)-2-Hydroxy-3-(4,4,4-trifluoro-butyrylamino)-3,4-dihydro-2H -benzo[e][1,2]oxaborinine-8-carboxylic acid 2,2-dimethyl-propionyloxymethyl ester

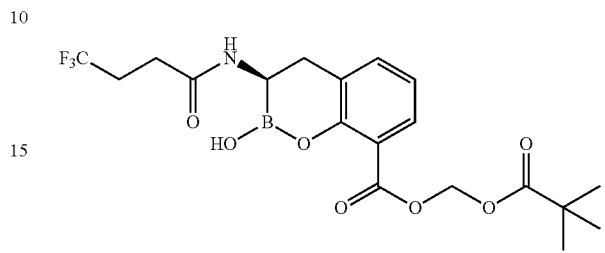

Step 1. Synthesis of 2-Methoxy-3-[2-(4,4,4-trifluoro-butyrylamino)-2-(2,9,9-trimethyl-3,5-dioxa-4-bora-tricyclo [6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 4,4,4-trifluorobutyric acid following the procedure in Step 1 of Example 1. The crude product was purified by flash chromatography on silica gel (10-100% ethyl acetate/hexane). ESI-MS m/z 554 (MH)+.

Step 2. Synthesis of 2-Methoxy-3-[2-(4,4,4-trifluoro-butyrylamino)-2-(2,9,9-trimethyl-3,5-dioxa-4-bora-tricyclo [6.1.1.02,6]dec-4-yl)-ethyl]-benzoic acid.

Prepared from 2-Methoxy-3-[2-(4,4,4-trifluoro-butyrylamino)-2-(2,9,9-trimethyl-3,5-dioxa-4-bora-tricyclo [6.1.1.02,6]dec-4-yl)-ethyl]-benzoic acid tert-butyl ester and 4N HCl/dioxane following the procedure in Step 2 of Example 13. ESI-MS m/z 498 (MH)+.

Step 3. Synthesis of 2-Methoxy-3-[2-(4,4,4-trifluoro-butyrylamino)-2-(2,9,9-trimethyl-3,5-dioxa-4-bora-tricyclo [6.1.1.02,6]dec-4-yl)-ethyl]-benzoic acid 2,2-dimethyl-propionyloxymethyl ester.

To a solution of 2-Methoxy-3-[2-(4,4,4-trifluoro-butyrylamino)-2-(2,9,9-trimethyl-3,5-dioxa-4-bora-tricyclo [6.1.1.02,6]dec-4-yl)-ethyl]-benzoic acid (0.598 g, 1.20 mmol), sodium iodide (0.199 g, 1.33 mmol), and DMF (6.0 mL) was added chloromethyl pivalate (0.44 mL, 3.05 mmol) and triethylamine (0.50 mL, 3.59 mmol) under argon. The reaction was heated at 60° C. for 16 h. The reaction was quenched with water and extracted three times with ethyl acetate. The combined organic layers were washed with brine, dried over MgSO4, filtered, and concentrated. The crude product was purified by flash chromatography on silica gel (10-100% ethyl acetate/hexane). ESI-MS m/z 612 (MH)+.

Step 4. Synthesis of (R)-2-Hydroxy-3-(4,4,4-trifluoro-butyrylamino)-3,4-dihydro-2H -benzo[e][1,2]oxaborinine-8-carboxylic acid 2,2-dimethyl-propionyloxymethyl ester.

To a solution of 2-Methoxy-3-[2-(4,4,4-trifluoro-butyrylamino)-2-(2,9,9-trimethyl-3,5-dioxa-4-bora-tricyclo [6.1.1.02,6]dec-4-yl)-ethyl]-benzoic acid 2,2-dimethyl-propionyloxymethyl ester (0.380 g, 0.621 mmol) and acetonitrile (6.0 mL) under argon was added phenylboronic acid (0.092 g, 0.755 mmol), hexane (6.0 mL), and hydrobromic acid (0.310 g, 48% in H2O, 1.84 mmol). The reaction was stirred for 5 h with the hexane layer being removed and replaced at 1.5 h and 3 h. The reaction was quenched with water, layers separated, and the aqueous layer concentrated to remove acetonitrile. The crude product was purified by reverse phase preparative HPLC and dried using lyophilization to give the title compound. ESI-MS m/z 468 (M+Na)⁺.

Example 26: (R)-2-Hydroxy-3-(4,4,4-trifluoro-butyrylamino)-3,4-dihydro-2H-benzo[e][1,2]oxaborinine-8-carboxylic acid 2-ethyl-butyryloxymethyl ester

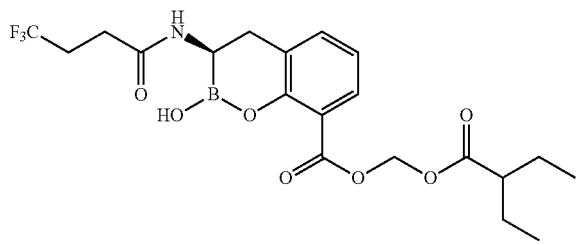 [SMILES: CCC(CC)C(=O)OCOC(=O)c1cccc2c1OB(O)[C@@H](NC(=O)CCC(F)(F)F)C2]

Step 1. Synthesis of 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid 2-ethyl-butyryloxymethyl ester.

Prepared from 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid (Steps 1 and 2 of Example 25) and chloromethyl 2-ethylbutyrate following the procedure in Step 3 of Example 25. The crude product was purified by flash chromatography on silica gel (10-100% ethyl acetate/hexane). ESI-MS m/z 626 (MH)⁺.

Step 2. Synthesis of (R)-2-Hydroxy-3-(4,4,4-trifluoro-butyrylamino)-3,4-dihydro-2H-benzo[e][1,2]oxaborinine-8-carboxylic acid 2-ethyl-butyryloxymethyl ester.

Prepared from 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid 2-ethyl-butyryloxymethyl ester following the procedure in Step 4 of Example 25. The crude product was purified by reverse phase preparative HPLC and dried using lyophilization to give the title compound. ESI-MS m/z 482 (M+Na)⁺.

Example 27: (R)-2-Hydroxy-3-(4,4,4-trifluoro-butyrylamino)-3,4-dihydro-2H-benzo[e][1,2]oxaborinine-8-carboxylic acid benzoyloxymethyl ester

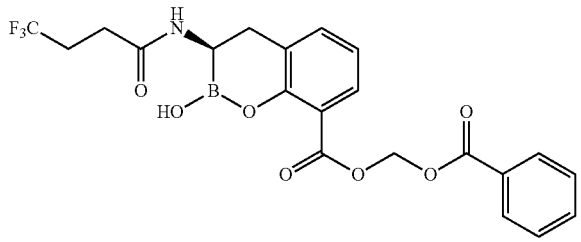 [SMILES: O=C(CCC(F)(F)F)N[C@H]1Cc2cccc(C(=O)OCOC(=O)c3ccccc3)c2OB1O]

Step 1. Synthesis of 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid benzoyloxymethyl ester.

Prepared from 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid (Steps 1 and 2 of Example 25) and benzoic acid chloromethyl ester following the procedure in Step 3 of Example 25. The crude product was purified by flash chromatography on silica gel (10-100% ethyl acetate/hexane). ESI-MS m/z 632 (MH)⁺.

Step 2. Synthesis of (R)-2-Hydroxy-3-(4,4,4-trifluoro-butyrylamino)-3,4-dihydro-2H-benzo[e][1,2]oxaborinine-8-carboxylic acid benzoyloxymethyl ester.

Prepared from 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid benzoyloxymethyl ester following the procedure in Step 4 of Example 25. The crude product was purified by reverse phase preparative HPLC and dried using lyophilization to give the title compound. ESI-MS m/z 488 (M+Na)⁺.

Example 28: (R)-2-Hydroxy-3-(4,4,4-trifluoro-butyrylamino)-3,4-dihydro-2H-benzo[e][1,2]oxaborinine-8-carboxylic acid isobutyryloxymethyl ester

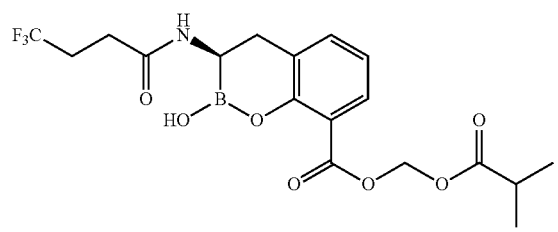 [SMILES: CC(C)C(=O)OCOC(=O)c1cccc2c1OB(O)[C@@H](NC(=O)CCC(F)(F)F)C2]

Step 1. Synthesis of 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid isobutyryloxymethyl ester.

Prepared from 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid (Steps 1 and 2 of Example 25) and isobutyric acid chloromethyl ester following the procedure in Step 3 of Example 25. The crude product was purified by flash chromatography on silica gel (10-100% ethyl acetate/hexane). ESI-MS m/z 598 (MH)⁺.

Step 2. Synthesis of (R)-2-Hydroxy-3-(4,4,4-trifluoro-butyrylamino)-3,4-dihydro-2H-benzo[e][1,2]oxaborinine-8-carboxylic acid isobutyryloxymethyl ester.

Prepared from 2-Methoxy-3-[2-(4,4,4-trifluoro-butyrylamino)-2-(2,9,9-trimethyl-3,5-dioxa-4-bora-tricyclo[6.1.1.0²,⁶]dec-4-yl)-ethyl]-benzoic acid isobutyryloxymethyl ester following the procedure in Step 4 of Example 25. The crude product was purified by reverse phase preparative HPLC and dried using lyophilization to give the title compound. ESI-MS m/z 454 (M+Na)⁺.

Example 29: 2-Hydroxy-3-(4,4,4-trifluoro-butyrylamino)-3,4-dihydro-2H-benzo[e][1,2]oxaborinine-8-carboxylic acid 1-ethoxycarbonyloxy-ethyl ester

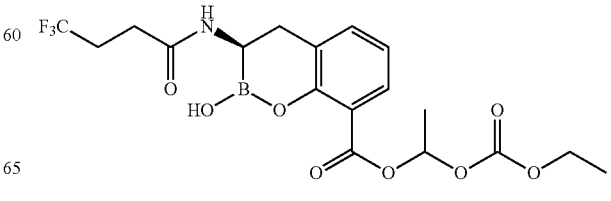

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid 1-ethoxycarbonyloxy-ethyl ester.

Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid (Steps 1 and 2 of Example 25) and 1-chloroethyl ethyl carbonate following the procedure in Step 3 of Example 25. The crude product was purified by flash chromatography on silica gel (10-100% ethyl acetate/hexane). ESI-MS m/z 614 (MH)+.

Step 2. Synthesis of 2-Hydroxy-3-(4,4,4-trifluoro-butyrylamino)-3,4-dihydro-2H -benzo[e][1,2]oxaborinine-8-carboxylic acid 1-ethoxycarbonyloxy-ethyl ester.

Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid 1-ethoxycarbonyloxy-ethyl ester following the procedure in Step 4 of Example 25. The crude product was purified by reverse phase preparative HPLC and dried using lyophilization to give the title compound. ESI-MS m/z 470 (M+Na)+.

Example 30: 2-Hydroxy-3-(4,4,4-trifluoro-butyrylamino)-3,4-dihydro-2H -benzo[e][1,2]oxaborinine-8-carboxylic acid 1-isopropoxycarbonyloxy-ethyl ester

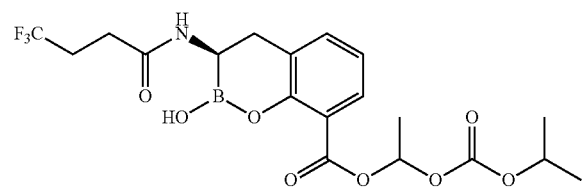 [SMILES: CC(C)OC(=O)OC(C)OC(=O)c1cccc2c1OB(O)[C@@H](NC(=O)CCC(F)(F)F)C2]

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid 1-isopropoxycarbonyloxy-ethyl ester.

Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid (Steps 1 and 2 of Example 25) and 1-chloroethyl isopropyl carbonate following the procedure in Step 3 of Example 25. The crude product was purified by flash chromatography on silica gel (10-100% ethyl acetate/hexane). ESI-MS m/z 628 (MH)+.

Step 2. Synthesis of 2-Hydroxy-3-(4,4,4-trifluoro-butyrylamino)-3,4-dihydro-2H -benzo[e][1,2]oxaborinine-8-carboxylic acid 1-isopropoxycarbonyloxy-ethyl ester.

Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid 1-isopropoxycarbonyloxy-ethyl ester following the procedure in Step 4 of Example 25. The crude product was purified by reverse phase preparative HPLC and dried using lyophilization to give the title compound. ESI-MS m/z 484 (M+Na)+.

Example 31: (R)-2-Hydroxy-3-propionylamino-3,4-dihydro-2H-benzo [e][1,2]oxaborinine-8-carboxylic acid 2-methoxy-2-methyl-propionyloxymethyl ester

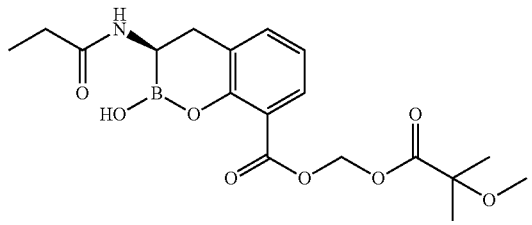 [SMILES: CCC(=O)N[C@H]1Cc2cccc(C(=O)OCOC(=O)C(C)(C)OC)c2OB1O]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 478 (MH)+.

Step 4. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid 2-methoxy-2-methyl-propionyloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester and 2-methoxy-2-methylpropanoic acid following the procedure in Step 4 of Example 13. The crude product was purified by flash chromatography on silica gel with preparative TLC plates (5% methanol/dichloromethane). ESI-MS m/z 560 (MH)+.

Step 5. Synthesis of (R)-2-Hydroxy-3-propionylamino-3,4-dihydro-2H-benzo[e][1,2]oxaborinine-8-carboxylic acid 2-methoxy-2-methyl-propionyloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid 2-methoxy-2-methyl-propionyloxymethyl ester and aluminum chloride following the procedure in Step 5 of Example 13. The crude product was purified by reverse phase preparative HPLC and dried using lyophilization to give the title compound. ESI-MS m/z 416 (M+Na)+.

Example 32: (R)-2-Hydroxy-3-propionylamino-3,4-dihydro-2H-benzo[e][1,2]oxaborinine-8-carboxylic acid 2-ethoxy-2-methyl-propionyloxymethyl ester

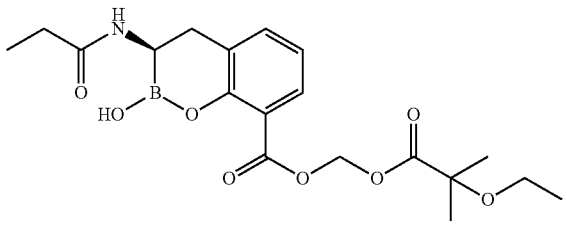 [SMILES: CCOC(C)(C)C(=O)OCOC(=O)c1cccc2c1OB(O)[C@@H](NC(=O)CC)C2]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (70% ethyl acetate/hexane). ESI-MS m/z 486 (MH)$^+$.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)$^+$.

Step 3. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 478 (MH)$^+$.

Step 4. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid 2-ethoxy-2-methyl-propionyloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid chloromethyl ester and 2-ethoxy-2-methylpropanoic acid following the procedure in Step 4 of Example 13. The crude product was purified by flash chromatography on silica gel with preparative TLC plates (7% methanol/dichloromethane). ESI-MS m/z 574 (MH)$^+$.

Step 5. Synthesis of (R)-2-Hydroxy-3-propionylamino-3,4-dihydro-2H-benzo[e][1,2]oxaborinine-8-carboxylic acid 2-ethoxy-2-methyl-propionyloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid 2-ethoxy-2-methyl-propionyloxymethyl ester and aluminum chloride following the procedure in Step 5 of Example 13. The crude product was purified by reverse phase preparative HPLC and dried using lyophilization to give the title compound. ESI-MS m/z 430 (M+Na)$^+$.

Example 33: (R)-2-Hydroxy-3-(4,4,4-trifluoro-butyrylamino)-3,4-dihydro-2H -benzo[e][1,2]oxaborinine-8-carboxylic acid ethyl ester

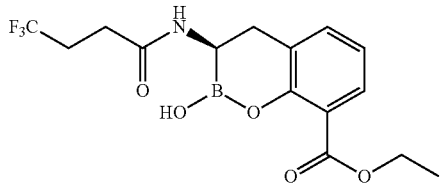 [SMILES: CCOC(=O)c1cccc2c1OB(O)[C@@H](NC(=O)CCC(F)(F)F)C2]

A solution of 2-hydroxy-3-(4,4,4-trifluoro-butyrylamino)-3,4-dihydro-2H -benzo[e][1,2]oxaborinine-8-carboxylic acid (29.5 mg, 0.089 mmol), ethyl alcohol (4 mL) and 4N HCl in dioxane (1 mL, 4 mmol) was stirred at ambient temperature for 30 min. An additional aliquot of 4N HCl/dioxane (1 mL) was added and the reaction warmed to 45° C. and held for 2.75 h. The solution was cooled and allowed to stir an additional 18 h then concentrated in vacuo. The crude product was purified by flash chromatography on $C_{18}$ reverse phase silica gel using a gradient of 10% to 40% IPA/H$_2$O and dried via lyophilization. ESI-MS m/z 360 (MH)$^+$.

Example 34: (R)-2-Hydroxy-3-(4,4,4-trifluoro-butyrylamino)-3,4-dihydro-2H -benzo[e][1,2]oxaborinine-8-carboxylic acid benzyl ester

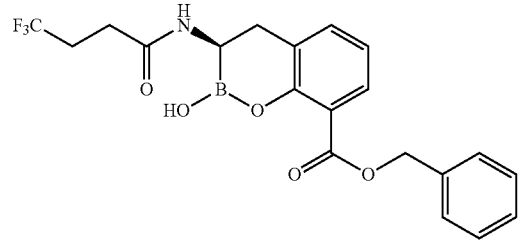 [SMILES: O=C(CCC(F)(F)F)N[C@H]1Cc2cccc(C(=O)OCc3ccccc3)c2OB1O]

A solution of 2-hydroxy-3-(4,4,4-trifluoro-butyrylamino)-3,4-dihydro-2H -benzo[e][1,2]oxaborinine-8-carboxylic acid (34.8 mg, 0.11 mmol), benzyl alcohol (5 mL) and 4N HCl in dioxane (1 mL, 4 mmol) was stirred at ambient temperature for 2 days. The majority of the benzyl alcohol was removed in vacuo, and the residue purified by flash chromatography on $C_{18}$ reverse phase silica gel using a gradient of 10% to 70% IPA/H$_2$O and dried via lyophilization. ESI-MS m/z 422 (MH)$^+$.

Example 35: (R)-2-Hydroxy-3-(4,4,4-trifluoro-butyrylamino)-3,4-dihydro-2H -benzo[e][1,2]oxaborinine-8-carboxylic acid acetoxymethyl ester

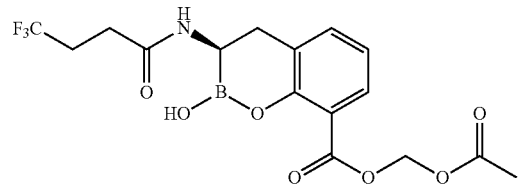 [SMILES: CC(=O)OCOC(=O)c1cccc2c1OB(O)[C@@H](NC(=O)CCC(F)(F)F)C2]

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid acetoxymethyl ester.

Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid (Steps 1 and 2 of Example 25) and chloromethyl acetate following the procedure in Step 3 of Example 25. The crude product was purified by flash chromatography on silica gel (10-100% ethyl acetate/hexane). ESI-MS m/z 570 (MH)+.

Step 2. Synthesis of (R)-2-Hydroxy-3-(4,4,4-trifluoro-butyrylamino)-3,4-dihydro-2H -benzo[e][1,2]oxaborinine-8-carboxylic acid acetoxymethyl ester.

Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid acetoxymethyl ester following the procedure in Step 4 of Example 25. The crude product was purified by reverse phase preparative HPLC and dried using lyophilization to give the title compound. ESI-MS m/z 426 (M+Na)+.

Example 36: 2-Hydroxy-3-(4,4,4-trifluoro-butyrylamino)-3,4-dihydro-2H -benzo[e][1,2]oxaborinine-8-carboxylic acid 1-acetoxy-ethyl ester

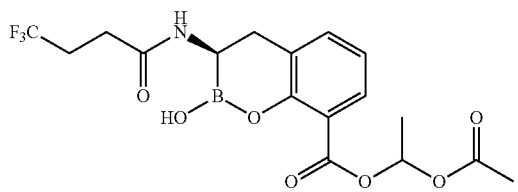 [SMILES: CC(=O)OC(C)OC(=O)c1cccc2c1OB(O)[C@@H](NC(=O)CCC(F)(F)F)C2]

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid 1-acetoxy-ethyl ester.

Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid (Steps 1 and 2 of Example 25) and 1-bromoethyl acetate following the procedure in Step 3 of Example 25. The crude product was purified by flash chromatography on silica gel (10-100% ethyl acetate/hexane). ESI-MS m/z 584 (MH)+.

Step 2. Synthesis of 2-Hydroxy-3-(4,4,4-trifluoro-butyrylamino)-3,4-dihydro-2H -benzo[e][1,2]oxaborinine-8-carboxylic acid 1-acetoxy-ethyl ester.

Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid 1-acetoxy-ethyl ester following the procedure in Step 4 of Example 25. The crude product was purified by reverse phase preparative HPLC and dried using lyophilization to give the title compound. ESI-MS m/z 440 (M+Na)+.

Example 37: (R)-2-Hydroxy-3-(4,4,4-trifluoro-butyrylamino)-3,4-dihydro-2H -benzo[e][1,2]oxaborinine-8-carboxylic acid 2-methoxy-2-methyl-propionyloxymethyl ester

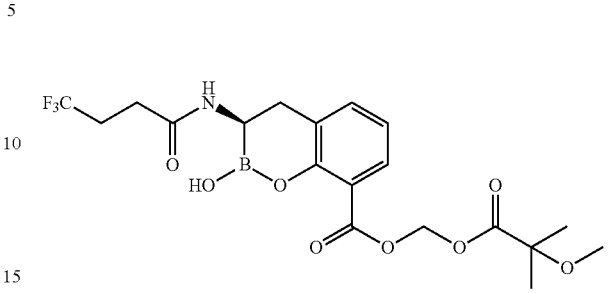

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 4,4,4-trifluorobutyric acid following the procedure in Step 1 of Example 1. The crude product was purified by flash chromatography on silica gel (50% ethyl acetate/hexane). ESI-MS m/z 554 (MH)+.

Step 2. Synthesis of 3-[2-(4,4,4-Trifluoro-butyrylamino)-2-(2,9,9-trimethyl-3,5-dioxa-4-bora -tricyclo[6.1.1.02,6]dec-4-yl)-ethyl]-2-methoxy-benzoic acid.

Prepared from 2-methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid tert-butyl ester and 4N HCl/dioxane following the procedure in Step 2 of Example 13. ESI-MS m/z 498 (MH)+.

Step 3. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid chloromethyl ester.

Prepared from 3-[2-(4,4,4-trifluoro-butyrylamino)-2-(2,9,9-trimethyl-3,5-dioxa-4-bora -tricyclo[6.1.1.02,6]dec-4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 546 (MH)+.

Step 4. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid 2-methoxy-2-methyl-propionyloxymethyl ester.

Prepared from 2-methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid chloromethyl ester and 2-methoxy-2-methylpropanoic acid following the procedure in Step 4 of Example 13. The crude product was purified by flash chromatography on silica gel with preparative TLC plates (5% methanol/dichloromethane). ESI-MS m/z 628 (MH)+.

Step 5. Synthesis of (R)-2-Hydroxy-3-(4,4,4-trifluoro-butyrylamino)-3,4-dihydro-2H -benzo[e][1,2]oxaborinine-8-carboxylic acid 2-methoxy-2-methyl-propionyloxymethyl ester.

To 2-methoxy-3-[2-(4,4,4-trifluoro-butyrylamino)-2-(2,9,9-trimethyl-3,5-dioxa-4-bora -tricyclo[6.1.1.02,6]dec-4-yl)-ethyl]-benzoic acid 2-methoxy-2-methyl-propionyloxymethyl ester (0.110 g, 0.2 mmol) in acetonitrile (2 mL) was added phenylboronic acid (0.03 g, 0.22 mmol), hexanes (2 mL), followed by 48% hydrobromic acid in water (0.07 mL, 0.59 mmol) and was stirred at room temperature for 3 h. The reaction was quenched with water, the two layers were separated, and the acetonitrile was concentrated off. The crude product was purified by reverse phase preparative HPLC and dried using lyophilization to give the title compound. ESI-MS m/z 484 (M+Na)+.

Example 38: (R)-2-Hydroxy-3-(4,4,4-trifluoro-butyrylamino)-3,4-dihydro-2H-benzo[e][1,2]oxaborinine-8-carboxylic acid 2-ethoxy-2-methyl-propionyloxymethyl ester

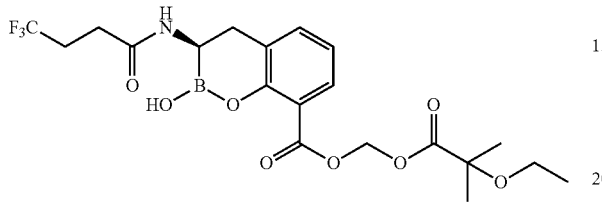

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid tert-butyl ester.
Prepared from [(1 S)-2-(3-tert-butoxycarbonyl-2-methoxy-phenyl)-1-chloro-ethyl]b oronic acid (+) pinanediol ester and 4,4,4-trifluorobutyric acid following the procedure in Step 1 of Example 1. The crude product was purified by flash chromatography on silica gel (50% ethyl acetate/hexane). ESI-MS m/z 554 (MH)+.
Step 2. Synthesis of 3-[2-(4,4,4-Trifluoro-butyrylamino)-2-(2,9,9-trimethyl-3,5-dioxa-4-bora-tricyclo[6.1.1.02,6]dec-4-yl)-ethyl]-2-methoxy-benzoic acid.
Prepared from 2-methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid tert-butyl ester and 4N HCl/dioxane following the procedure in Step 2 of Example 13. ESI-MS m/z 498 (MH)+.
Step 3. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid chloromethyl ester.
Prepared from 3-[2-(4,4,4-trifluoro-butyrylamino)-2-(2,9,9-trimethyl-3,5-dioxa-4-bora-tricyclo[6.1.1.02,6]dec-4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 546 (MH)+.
Step 4. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid 2-ethoxy-2-methyl-propionyloxymethyl ester.
Prepared from 2-methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid chloromethyl ester and 2-ethoxy-2-methylpropanoic acid following the procedure in Step 4 of Example 13. The crude product was purified by flash chromatography on silica gel with preparative TLC plates (5% methanol/dichloromethane). ESI-MS m/z 642 (MH)+.
Step 5. Synthesis of (R)-2-Hydroxy-3-(4,4,4-trifluoro-butyrylamino)-3,4-dihydro-2H-benzo[e][1,2]oxaborinine-8-carboxylic acid 2-ethoxy-2-methyl-propionyloxymethyl ester.
Prepared from 2-ethoxy-3-[2-(4,4,4-trifluoro-butyrylamino)-2-(2,9,9-trimethyl-3,5-dioxa-4-bora -tricyclo[6.1.1.02,6]dec-4-yl)-ethyl]-benzoic acid 2-ethoxy-2-methyl-propionyloxymethyl ester and 48% hydrobromic acid in water following the procedure in Step 5 of Example 37. The crude product was purified by reverse phase preparative HPLC and dried using lyophilization to give the title compound. ESI-MS m/z 498 (M+Na)+.

Example 39: (R)-2-Hydroxy-3-(4,4,4-trifluoro-butyrylamino)-3,4-dihydro-2H-benzo[e][1,2]oxaborinine-8-carboxylic acid ethoxycarbonyloxymethyl ester

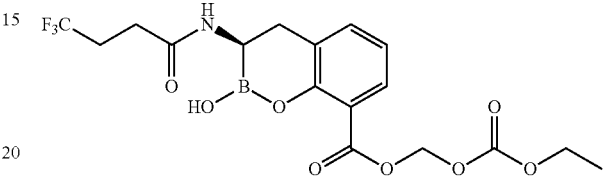

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid ethoxycarbonyloxymethyl ester.
Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid (Steps 1 and 2 of Example 25) and chloromethyl ethyl carbonate following the procedure in Step 3 of Example 25. The crude product was purified by flash chromatography on silica gel (10-100% ethyl acetate/hexane). ESI-MS m/z 600 (MH)+.
Step 2. Synthesis of (R)-2-Hydroxy-3-(4,4,4-trifluoro-butyrylamino)-3,4-dihydro-2H-benzo[e][1,2]oxaborinine-8-carboxylic acid ethoxycarbonyloxymethyl ester.
Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid ethoxycarbonyloxymethyl ester following the procedure in Step 4 of Example 25. The crude product was purified by reverse phase preparative HPLC and dried using lyophilization to give the title compound. ESI-MS m/z 456 (M+Na)+.

Example 40: (R)-2-Hydroxy-3-(4,4,4-trifluoro-butyrylamino)-3,4-dihydro-2H-benzo[e][1,2]oxaborinine-8-carboxylic acid isopropoxycarbonyloxymethyl ester

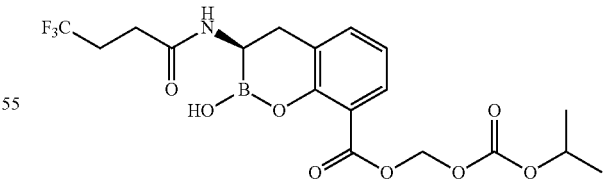

Step 1. Synthesis of 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid isopropoxycarbonyloxymethyl ester.
Prepared from 2-Methoxy-3-[2-(4,4,4-trifluoro-butyrylamino)-2-(2,9,9-trimethyl-3,5-dioxa-4-bora-tricyclo[6.1.1.02,6]dec-4-yl)-ethyl]-benzoic acid (Steps 1 and 2 of Example 25) and chloromethyl isopropyl carbonate following the procedure in Step 3 of Example 25. The crude product was purified by flash chromatography on silica gel (10-100% ethyl acetate/hexane). ESI-MS m/z 614 (MH)⁺.
Step 2. Synthesis of (R)-2-Hydroxy-3-(4,4,4-trifluoro-butyrylamino)-3,4-dihydro-2H -benzo[e][1,2]oxaborinine-8-carboxylic acid isopropoxycarbonyloxymethyl ester.

Prepared from 2-Methoxy-3-[2-(4,4,4-trifluoro-butyrylamino)-2-(2,9,9-trimethyl-3,5-dioxa-4-bora-tricyclo [6.1.1.0²,⁶]dec-4-yl)-ethyl]-benzoic acid isopropoxycarbonyloxymethyl ester following the procedure in Step 4 of Example 25. The crude product was purified by reverse phase preparative HPLC and dried using lyophilization to give the title compound. ESI-MS m/z 470 (M+Na)⁺.

Example 41: (R)-2-Hydroxy-3-(4,4,4-trifluoro-butyrylamino)-3,4-dihydro-2H -benzo[e][1,2]oxaborinine-8-carboxylic acid butoxycarbonyloxymethyl ester

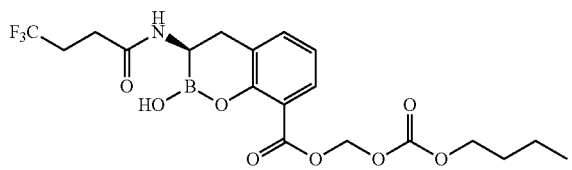 [SMILES: CCCCOC(=O)OCOC(=O)c1cccc2c1OB(O)[C@@H](NC(=O)CCC(F)(F)F)C2]

Step 1. Synthesis of 2-hydroxy-3-(4,4,4-trifluoro-butyrylamino)-3,4-dihydro-2H -benzo[e][1,2]oxaborinine-8-carboxylic acid sodium salt.

To a slurry of 2-hydroxy-3-(4,4,4-trifluoro-butyrylamino)-3,4-dihydro-2H -benzo[e][1,2]oxaborinine-8-carboxylic acid (119 mg, 0.36 mmol) in H₂O (2 mL) was added 1N NaOH (820 μL, 0.82 mmol). The mixture was stirred for 5 mins, resulting in a clear solution. The pH was adjusted to pH 9-10 using 1N HCl and then lyophilized to give a pale yellow solid which was used without purification.

Step 2. Synthesis of (R)-2-Hydroxy-3-(4,4,4-trifluoro-butyrylamino)-3,4-dihydro-2H -benzo[e][1,2]oxaborinine-8-carboxylic acid butoxycarbonyloxymethyl ester.

To a solution of 2-hydroxy-3-(4,4,4-trifluoro-butyrylamino)-3,4-dihydro-2H -benzo[e][1,2]oxaborinine-8-carboxylic acid sodium salt (0.14 mmol) in N, N-dimethylacetamide (DMA, 400 μL) was added NaHCO₃ (12 mg, 0.14 mmol) followed by a solution of chloromethyl butyl carbonate (69 mg, 0.41 mmol) in 280 μL DMA. Sodium iodide (12 mg, 0.07 mmol) was added and the reaction warmed to 50° C. After 4h, the mixture was cooled, diluted with 0.1N HCl and then concentrated to a thick slurry. The crude product was purified by flash chromatography on C₁₈ reverse phase silica gel using a gradient of 10% to 70% IPA/H₂O and dried via lyophilization. ESI-MS m/z 462 (MH)⁺.

Example 42: (R)-2-Hydroxy-3-(4,4,4-trifluoro-butyrylamino)-3,4-dihydro-2H -benzo[e][1,2]oxaborinine-8-carboxylic acid cyclohexyloxycarbonyloxymethyl ester

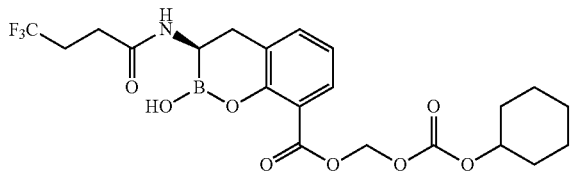 [SMILES: O=C(CCC(F)(F)F)N[C@H]1Cc2cccc(C(=O)OCOC(=O)OC3CCCCC3)c2OB1O]

To a solution of 2-hydroxy-3-(4,4,4-trifluoro-butyrylamino)-3,4-dihydro-2H -benzo[e][1,2]oxaborinine-8-carboxylic acid sodium salt (0.13 mmol) in DMF (300 μL) was added NaHCO₃ (11 mg, 0.13 mmol) followed by a solution of chloromethyl cyclohexyl carbonate (26 mg, 0.13 mmol). Sodium iodide (9 mg, 0.06 mmol) was added and the reaction stirred at ambient temperature for 17 h. An additional aliquot of chloromethyl cyclohexyl carbonate (12 mg) was added. The mixture was warmed to 40° C. and stirred for 4 h. An additional aliquot of chloromethyl cyclohexyl carbonate (12 mg) was added and the reaction stirred at ambient temperature for 3 h. The reaction was quenched with water, 1N HCl was added and the mixture extracted with hexanes (3x). The organic layers were combined and washed with H₂O. The aqueous layers were combined and the title compound isolated by flash chromatography on C₁₈ reverse phase silica gel using a gradient of 10% to 50% IPA/H₂O and dried via lyophilization. ESI-MS m/z 510 (M+Na)⁺.

Example 43: 2-Hydroxy-3-(4,4,4-trifluoro-butyrylamino)-3,4-dihydro-2H -benzo[e][1,2]oxaborinine-8-carboxylic acid 1-cyclohexyloxycarbonyloxyethyl ester

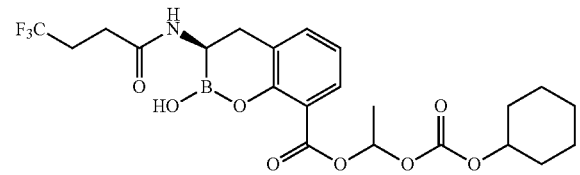 [SMILES: CC(OC(=O)OC1CCCCC1)OC(=O)c1cccc2c1OB(O)[C@@H](NC(=O)CCC(F)(F)F)C2]

A solution of 2-hydroxy-3-(4,4,4-trifluoro-butyrylamino)-3,4-dihydro-2H -benzo[e][1,2]oxaborinine-8-carboxylic acid sodium salt (0.18 mmol), 1-chloroethyl cyclohexyl carbonate (75 mg, 0.36 mmol), NaHCO₃ (23 mg, 0.27 mmol) and NaI (27 mg, 0.18 mmol) in DMF (0.72 mL) was stirred at ambient temperature for 3 days. The mixture was diluted with 0.1N HCl and extracted with hexanes (3x). The organic layers were combined and washed with H₂O. The aqueous layers were combined and the title compound isolated by flash chromatography on C₁₈ reverse phase silica gel using a gradient of 25% to 50% acetonitrile/H₂O and dried via lyophilization. ESI-MS m/z 524 (M+Na)⁺.

Example 44: (R)-2-Hydroxy-3-(4,4,4-trifluoro-butyrylamino)-3,4-dihydro-2H -benzo[e][1,2]oxaborinine-8-carboxylic acid 3-oxo-1,3-dihydro-isobenzofuran-1-yl ester

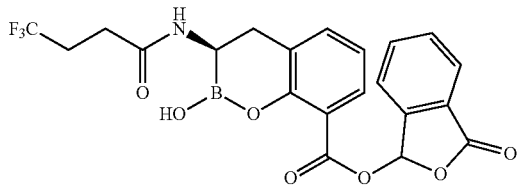 [SMILES: O=C(CCC(F)(F)F)N[C@H]1Cc2cccc(C(=O)OC3OC(=O)c4ccccc43)c2OB1O]

Step 1. Synthesis of 2-Methoxy-3-[2-(4,4,4-trifluoro-butyrylamino)-2-(2,9,9-trimethyl-3,5-dioxa-4-bora-tricyclo [6.1.1.0²,⁶]dec-4-yl)-ethyl]-benzoic acid 3-oxo-1,3-dihydro-isobenzofuran-1-yl ester.

Prepared from 2-Methoxy-3-[2-(4,4,4-trifluoro-butyrylamino)-2-(2,9,9-trimethyl-3,5-dioxa-4-bora-tricyclo [6.1.1.0²,⁶]dec-4-yl)-ethyl]-benzoic acid (Steps 1 and 2 of Example 25) and 3-bromophthalide following the procedure in Step 3 of Example 25. The crude product was purified by flash chromatography on silica gel (10-100% ethyl acetate/hexane). ESI-MS m/z 630 (MH)+.

Step 2. Synthesis of (R)-2-Hydroxy-3-(4,4,4-trifluoro-butyrylamino)-3,4-dihydro-2H -benzo[e][1,2]oxaborinine-8-carboxylic acid 3-oxo-1,3-dihydro-isobenzofuran-1-yl ester.

Prepared from 2-Methoxy-3-[2-(4,4,4-trifluoro-butyrylamino)-2-(2,9,9-trimethyl-3,5-dioxa-4-bora-tricyclo [6.1.1.02,6]dec-4-yl)-ethyl]-benzoic acid 3-oxo-1,3-dihydro-isobenzofuran-1-yl ester following the procedure in Step 4 of Example 25. The crude product was purified by reverse phase preparative HPLC and dried using lyophilization to give the title compound. ESI-MS m/z 486 (M+Na)+.

Example 45: (R)-2-Hydroxy-3-(4,4,4-trifluoro-butyrylamino)-3,4-dihydro-2H -benzo[e][1,2]oxaborinine-8-carboxylic acid 5-methyl-2-oxo-11,31dioxo1-4-ylmethyl ester

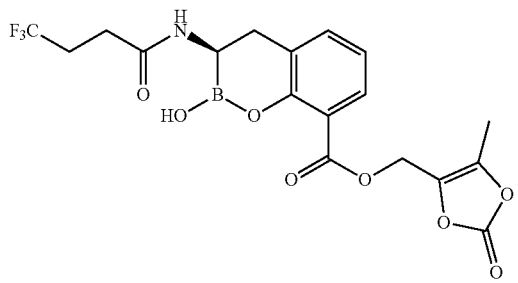 [SMILES: Cc1oc(=O)oc1COC(=O)c1cccc2c1OB(O)[C@@H](NC(=O)CCC(F)(F)F)C2]

A mixture of 2-hydroxy-3-(4,4,4-trifluoro-butyrylamino)-3,4-dihydro-2H -benzo[e][1,2]oxaborinine-8-carboxylic acid sodium salt (0.125 mmol), 4-chloromethyl-5-methyl-[1,3]dioxol-2-one (29 mg, 0.195 mmol), NaHCO$_3$ (15 mg, 0.18 mmol), NaI (0.07 mmol) in DMF (600 µL) was stirred for 3 h. The reaction was quenched with water, diluted with 1 N HCl and extracted twice with 4/1 hexanes/Et$_2$O. The combined organic layers were washed once with water, the aqueous layers were combined and the title compound isolated by flash chromatography on C$_{18}$ reverse phase silica gel using a gradient of 10% to 35% acetonitrile/H$_2$O and dried via lyophilization. ESI-MS m/z 444 (MH)+.

Example 46: Ethyl (R)-2-hydroxy-3-(5,5,5-trifluoropentanamido)-3,4-dihydro-2H -benzo [e][1,2]oxaborinine-8-carboxylate

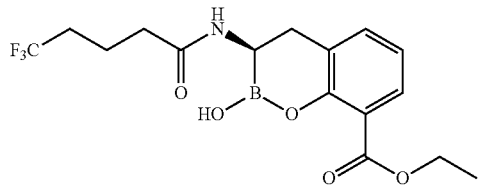 [SMILES: CCOC(=O)c1cccc2c1OB(O)[C@@H](NC(=O)CCCC(F)(F)F)C2]

Ethyl (R)-2-hydroxy-3-(5,5,5-trifluoropentanamido)-3,4-dihydro-2H-benzo [e][1,2]oxaborinine-8-carboxylate was prepared from (R)-2-hydroxy-3-(5,5,5-trifluoropentanamido)-3,4-dihydro-2H -benzo[e][1,2]oxaborinine-8-carboxylic acid (Example 2) and iodoethane by a procedure similar to Example 5, with the exception that the reaction was conducted at 45° C., instead of room temperature. ESI-MS m/z 374 (MH)+.

Example 47: Benzyl (R)-2-hydroxy-3-(5,5,5-trifluoropentanamido)-3,4-dihydro-2H -benzo [e][1,2]oxaborinine-8-carboxylate

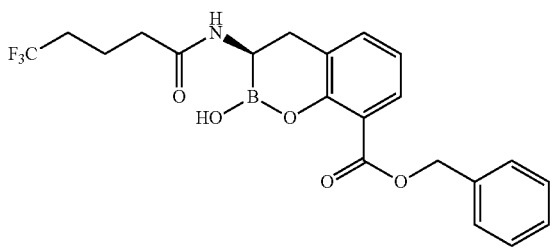 [SMILES: O=C(CCCC(F)(F)F)N[C@H]1Cc2cccc(C(=O)OCc3ccccc3)c2OB1O]

Benzyl (R)-2-hydroxy-3-(5,5,5-trifluoropentanamido)-3,4-dihydro-2H-benzo [e][1,2]oxaborinine- 8-carboxylate was prepared from (R)-2-hydroxy-3-(5,5,5-trifluoropentanamido)-3,4-dihydro-2H -benzo[e][1,2]oxaborinine-8-carboxylic acid (Example 2) and benzyl bromide by a procedure similar to Example 5. ESI-MS m/z 436 (MH)+.

Example 48: Acetoxymethyl (R)-2-hydroxy-3-(5,5,5-trifluoropentanamido)-3,4-dihydro-2H -benzo [e][1,2]oxaborinine-8-carboxvlate

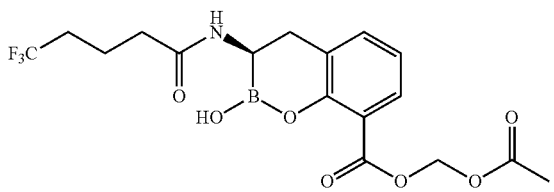 [SMILES: CC(=O)OCOC(=O)c1cccc2c1OB(O)[C@@H](NC(=O)CCCC(F)(F)F)C2]

Acetoxymethyl (R)-2-hydroxy-3-(5,5,5-trifluoropentanamido)-3,4-dihydro-2H -benzo[e][1,2]oxaborinine-8-carboxylate was prepared from (R)-2-hydroxy-3-(5,5,5-trifluoropentanamido) -3,4-dihydro-2H-benzo[e][1,2]oxaborinine-8-carboxylic acid (Example 2) and bromomethyl acetate by a procedure similar to Example 5. ESI-MS m/z 418 (MH)+, 440 (M+Na)+.

Example 49: 2-Hydroxy-3-(5,5,5-trifluoro-pentanoylamino)-3,4-dihydro-2H -benzo[e][1,2]oxaborinine-8-carboxylic acid 1-acetoxy-ethyl ester

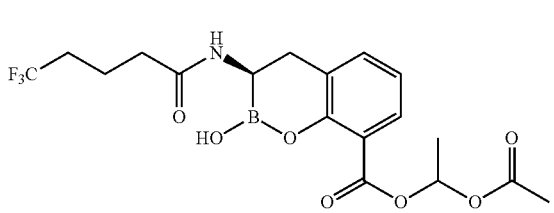 [SMILES: CC(=O)OC(C)OC(=O)c1cccc2c1OB(O)[C@@H](NC(=O)CCCC(F)(F)F)C2]

The title compound was prepared from 2-hydroxy-3-(5,5,5-trifluoro-pentanoylamino)-3,4-dihydro-2H-benzo[e][1,2]oxaborinine-8-carboxylic acid and 1-bromoethyl acetate using the general procedure described in Steps 1 and 2 of Example 41 with the exception that DMF was used as solvent in Step 2. The crude product was purified with flash chromatography on $C_{18}$ reverse phase silica gel using a gradient of 10% to 50% acetonitrile/$H_2O$ and dried via lyophilization. ESI-MS m/z 454 (M+Na)+.

Example 50: (R)-2-Hydroxy-3-(5,5,5-trifluoro-pentanoylamino)-3,4-dihydro-2H-benzo[e][1,2]oxaborinine-8-carboxylic acid isobutyryloxymethyl ester

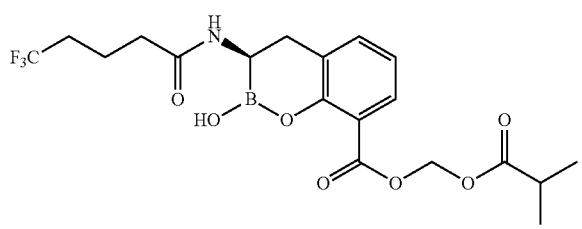 [SMILES: CC(C)C(=O)OCOC(=O)c1cccc2c1OB(O)[C@@H](NC(=O)CCCC(F)(F)F)C2]

Step 1. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid isobutyryloxymethyl ester.

Prepared from 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid (Steps 1 and 2 of Example 25) and isobutyric acid chloromethyl ester following the procedure in Step 3 of Example 25. The crude product was purified by flash chromatography on silica gel (10-100% ethyl acetate/hexane). ESI-MS m/z 612 (MH)+.

Step 2. Synthesis of (R)-2-Hydroxy-3-(5,5,5-trifluoro-pentanoylamino)-3,4-dihydro-2H-benzo[e][1,2]oxaborinine-8-carboxylic acid isobutyryloxymethyl ester.

Prepared from 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid isobutyryloxymethyl ester following the procedure in Step 4 of Example 25. The crude product was purified by reverse phase preparative HPLC and dried using lyophilization to give the title compound. ESI-MS m/z 468 (M+Na)+.

Example 51: (R)-2-Hydroxy-3-(5,5,5-trifluoro-pentanoylamino)-3,4-dihydro-2H-benzo[e][1,2]oxaborinine-8-carboxylic acid 2-ethyl-butyryloxymethyl ester

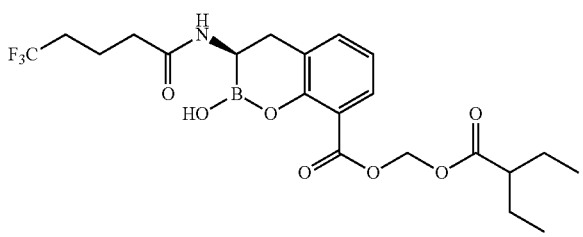 [SMILES: CCC(CC)C(=O)OCOC(=O)c1cccc2c1OB(O)[C@@H](NC(=O)CCCC(F)(F)F)C2]

Step 1. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 2-ethyl-butyryloxymethyl ester.

Prepared from 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid (Steps 1 and 2 of Example 25) and chloromethyl 2-ethylbutyrate following the procedure in Step 3 of Example 25. The crude product was purified by flash chromatography on silica gel (10-100% ethyl acetate/hexane). ESI-MS m/z 640 (MH)+.

Step 2. Synthesis of (R)-2-Hydroxy-3-(5,5,5-trifluoro-pentanoylamino)-3,4-dihydro-2H-benzo[e][1,2]oxaborinine-8-carboxylic acid 2-ethyl-butyryloxymethyl ester.

Prepared from 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 2-ethyl-butyryloxymethyl ester following the procedure in Step 4 of Example 25. The crude product was purified by reverse phase preparative HPLC and dried using lyophilization to give the title compound. ESI-MS m/z 496 (M+Na)+.

Example 52: (R)-2-Hydroxy-3-(5,5,5-trifluoro-pentanoylamino)-3,4-dihydro-2H-benzo[e][1,2]oxaborinine-8-carboxylic acid 2,2-dimethyl-propionyloxymethyl ester

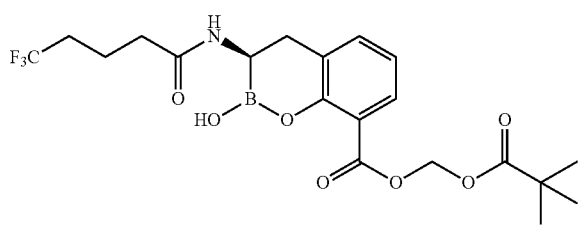 [SMILES: CC(C)(C)C(=O)OCOC(=O)c1cccc2c1OB(O)[C@@H](NC(=O)CCCC(F)(F)F)C2]

Step 1. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 2,2-dimethyl-propionyloxymethyl ester.

Prepared from 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid (Steps 1 and 2 of Example 25) and chloromethyl pivalate following the procedure in Step 3 of Example 25. The crude product was purified by flash chromatography on silica gel (10-100% ethyl acetate/hexane). ESI-MS m/z 626 (MH)+.

Step 2. Synthesis of (R)-2-Hydroxy-3-(5,5,5-trifluoro-pentanoylamino)-3,4-dihydro-2H-benzo[e][1,2]oxaborinine-8-carboxylic acid 2,2-dimethyl-propionyloxymethyl ester.

Prepared from 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 2,2-dimethyl-propionyloxymethyl ester following the procedure in Step 4 of Example 25. The crude product was purified by reverse phase preparative HPLC and dried using lyophilization to give the title compound. ESI-MS m/z 482 (M+Na)+.

Example 53: (R)-2-Hydroxy-3-(5,5,5-trifluoro-pentanoylamino)-3,4-dihydro-2H -benzo[e][1,2]oxaborinine-8-carboxylic acid 2-methoxy-2-methyl-propionyloxymethyl ester

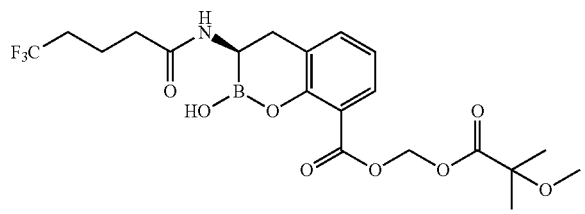 [SMILES: COC(C)(C)C(=O)OCOC(=O)c1cccc2c1OB(O)[C@@H](NC(=O)CCCC(F)(F)F)C2]

Step 1. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 5,5,5-trifluoro-pentanoic acid following the procedure in Step 1 of Example 1. The crude product was purified by flash chromatography on silica gel (50% ethyl acetate/hexane). ESI-MS m/z 568 (MH)+.

Step 2. Synthesis of 3-[2-(5,5,5-Trifluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid tert-butyl ester and 4N HCl/dioxane following the procedure in Step 2 of Example 13. ESI-MS m/z 512 (MH)+.

Step 3. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid chloromethyl ester.

Prepared from 3-[2-(5,5,5-trifluoro-pentanoylamino)-2-(2,9,9-trimethyl-3,5-dioxa-4-bora -tricyclo[6.1.1.02,6]dec-4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 560 (MH)+.

Step 4. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 2-methoxy-2-methyl-propionyloxymethyl ester.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid chloromethyl ester and 2-methoxy-2-methylpropanoic acid following the procedure in Step 4 of Example 13. The crude product was purified by flash chromatography on silica gel with preparative TLC plates (5% methanol/dichloromethane). ESI-MS m/z 642 (MH)+.

Step 5. Synthesis of (R)-2-Hydroxy-3-(5,5,5-trifluoro-pentanoylamino)-3,4-dihydro-2H -benzo[e][1,2]oxaborinine-8-carboxylic acid 2-methoxy-2-methyl-propionyloxymethyl ester.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 2-methoxy-2-methyl-propionyloxymethyl ester and 48% hydrobromic acid in water following the procedure in Step 5 of Example 37. The crude product was purified by reverse phase preparative HPLC and dried using lyophilization to give the title compound. ESI -MS m/z 498 (M+Na)+.

Example 54: (R)-2-Hydroxy-3-(5,5,5-trifluoro-pentanoylamino)-3,4-dihydro-2H -benzo[e][1,2]oxaborinine-8-carboxylic acid 2-eethoxy-2-methyl-propionyloxymethyl ester

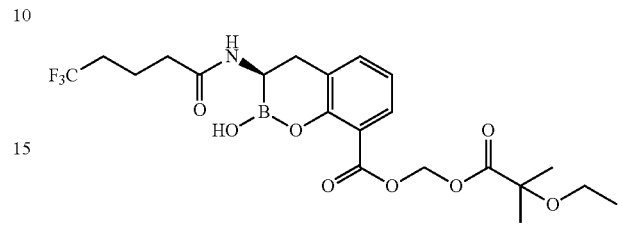

Step 1. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 5,5,5-trifluoro-pentanoic acid following the procedure in Step 1 of Example 1. The crude product was purified by flash chromatography on silica gel (50% ethyl acetate/hexane). ESI-MS m/z 568 (MH)+.

Step 2. Synthesis of 3-[2-(5,5,5-Trifluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid tert-butyl ester and 4N HCl/dioxane following the procedure in Step 2 of Example 13. ESI-MS m/z 512 (MH)+.

Step 3. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid chloromethyl ester.

Prepared from 3-[2-(5,5,5-trifluoro-pentanoylamino)-2-(2,9,9-trimethyl-3,5-dioxa-4-bora -tricyclo[6.1.1.02,6]dec-4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 560 (MH)+.

Step 4. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 2-ethoxy-2-methyl-propionyloxymethyl ester.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid chloromethyl ester and 2-ethoxy-2-methylpropanoic acid following the procedure in Step 4 of Example 13. The crude product was purified by flash chromatography on silica gel with preparative TLC plates (5% methanol/dichloromethane). ESI-MS m/z 656 (MH)+.

Step 5. Synthesis of (R)-2-Hydroxy-3-(5,5,5-trifluoro-pentanoylamino)-3,4-dihydro-2H -benzo[e][1,2]oxaborinine-8-carboxylic acid 2-methoxy-2-methyl-propionyloxymethyl ester.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 2-methoxy-2-methyl-propionyloxymethyl ester and 48% hydrobromic acid in water following the procedure in Step 5 of Example 37. The crude product was purified by reverse phase preparative HPLC and dried using lyophilization to give the title compound. ESI -MS m/z 512 (M+Na)+.

Example 55: (R)-2-Hydroxy-3-(5,5,5-trifluoro-pentanoylamino)-3,4-dihydro-2H -benzo[e][1,2]oxaborinine-8-carboxylic acid benzoyloxymethyl ester

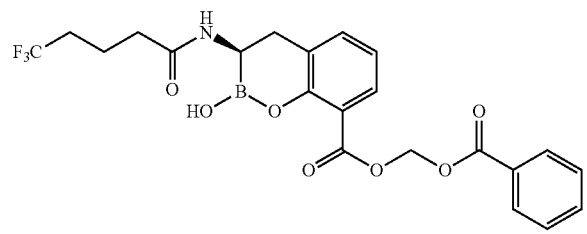 [SMILES: O=C(CCCC(F)(F)F)N[C@H]1Cc2cccc(C(=O)OCOC(=O)c3ccccc3)c2OB1O]

Step 1. Synthesis of 2-Methoxy-3-[2-(5,5,5-trifluoro-pentanoylamino)-2-(2,9,9-trimethyl-3,5-dioxa-4-bora-tricyclo [6.1.1.02,6]dec-4-yl)-ethyl]-benzoic acid tert-butyl ester.

Prepared from [(1 S)-2-(3-tert-butoxycarbonyl-2-methoxy-phenyl)-1-chloro-ethyl]b oronic acid (+) pinanediol ester and 5,5,5-trifluoro-pentanoic acid following the procedure in Step 1 of Example 1. The crude product was purified by flash chromatography on silica gel (50% ethyl acetate/hexane). ESI-MS m/z 568 (MH)+.

Step 2. Synthesis of 3-[2-(5,5,5-Trifluoro-pentanoylamino)-2-(2,9,9-trimethyl-3,5-dioxa-4-bora -tricyclo[6.1.1.02,6] dec-4-yl)-ethyl]-2-methoxy-benzoic acid.

Prepared from 2-methoxy-3-[2-(5,5,5-trifluoro-pentanoylamino)-2-(2,9,9-trimethyl-3,5-dioxa-4-bora-tricyclo [6.1.1.02,6]dec-4-yl)-ethyl]-benzoic acid tert-butyl ester and 4N HCl/dioxane following the procedure in Step 2 of Example 13. ESI-MS m/z 512 (MH)+.

Step 3. Synthesis of 2-Methoxy-3-[2-(5,5,5-trifluoro-pentanoylamino)-2-(2,9,9-trimethyl-3,5-dioxa-4-bora-tricyclo [6.1.1.02,6]dec-4-yl)-ethyl]-benzoic acid benzoyloxymethyl ester.

To 3-[2-(5,5,5-trifluoro-pentanoylamino)-2-(2,9,9-trimethyl-3,5-dioxa-4-bora -tricyclo[6.1.1.02,6]dec-4-yl)-ethyl]-2-methoxy-benzoic acid (0.33 g, 0.65 mmol) in anhydrous DMF under an atmosphere of argon was added triethylamine (0.27 mL, 1.95 mmol) and benzoic acid chloromethyl ester (0.23 mL, 1.63 mmol), followed by sodium iodide (0.11 g, 0.72 mmol) and stirred at 60° C. overnight. The reaction was diluted with ethyl acetate, washed with water/brine, dried over sodium sulfate, and concentrated. The crude product was purified by flash chromatography on silica gel with preparative TLC plates (70% ethyl acetate/hexane). ESI-MS m/z 646 (MH)+.

Step 4. Synthesis of (R)-2-Hydroxy-3-(5,5,5-trifluoro-pentanoylamino)-3,4-dihydro-2H -benzo[e][1,2]oxaborinine-8-carboxylic acid benzoyloxymethyl ester.

Prepared from 2-methoxy-3-[2-(5,5,5-trifluoro-pentanoylamino)-2-(2,9,9-trimethyl-3,5-dioxa-4-bora-tricyclo [6.1.1.02,6]dec-4-yl)-ethyl]-benzoic acid benzoyloxymethyl ester and 48% hydrobromic acid in water following the procedure in Step 5 of Example 37. The crude product was purified by reverse phase preparative HPLC and dried using lyophilization to give the title compound. ESI-MS m/z 502 (M+Na)+.

Example 56: ((Ethoxycarbonyl)oxy)methyl (R)-2-hydroxy-3-(5,5,5-trifluoropentanamido)-3,4-dihydro-2H-benzo [e][1,2]oxaborinine-8-carboxylate

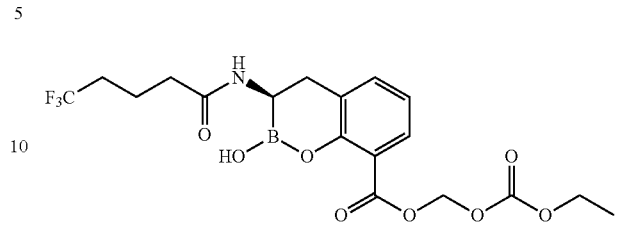

((Ethoxycarbonyl)oxy)methyl (R)-2-hydroxy-3-(5,5,5-trifluorop entanamido)-3 ,4-dihydro-2H -benzo[e][1,2]oxaborinine-8-carboxylate was prepared from (R)-2-hydroxy-3-(5,5,5-trifluoropentanamido) -3,4-dihydro-2H-benzo[e][1, 2]oxaborinine-8-carboxylic acid (Example 2) and ethyl (iodomethyl) carbonate by a procedure similar to Example 5. ESI-MS m/z 470 (M+Na)+.

Example 57: ((Isopropoxycarbonyl)oxy)methyl (R)-2-hydroxy-3-(5,5,5-trifluoropentanamido)-3,4-dihydro-2H-benzo [e][1,2]oxaborinine-8-carboxylate

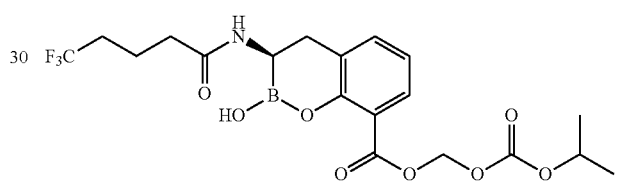

((Isopropoxycarbonyl)oxy)methyl (R)-2-hydroxy -3-(5,5, 5-trifluorop entanamido)-3 ,4-dihydro-2H -benzo[e][1,2] oxaborinine-8-carboxylate was prepared from (R)-2-hydroxy-3-(5,5,5-trifluoropentanamido) -3,4-dihydro-2H-benzo [e][1,2]oxaborinine-8-carboxylic acid (Example 2) and chloromethyl isopropyl carbonate by a procedure similar to Example 5, with the exception that the reaction was conducted at 45° C., instead of room temperature. ESI-MS m/z 484 (M+Na)+.

Example 58: (R)-2-Hydroxy-3-(5,5,5-trifluoro-pentanoylamino)-3,4-dihydro-2H -benzo[e][1,2]oxaborinine-8-carboxylic acid butoxycarbonyloxymethyl ester

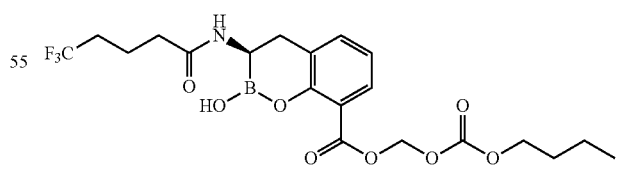

The title compound was prepared from 2-hydroxy-3-(5, 5,5-trifluoro-pentanoylamino)-3,4-dihydro-2H-benzo[e][1, 2]oxaborinine-8-carboxylic acid and chloromethyl n-butyl carbonate using the general procedure described in Steps 1 and 2 of Example 41 with the exception that DMF was used as solvent in Step 2. The crude product was purified with flash chromatography on $C_{18}$ reverse phase silica gel using a gradient of 20% to 50% acetonitrile/H₂O and dried via lyophilization. ESI-MS m/z 476 (MH)⁺.

Example 59: (R)-2-Hydroxy-3-(5,5,5-trifluoro-pentanoylamino)-3,4-dihydro-2H -benzo[e][1,2]oxaborinine-8-carboxylic acid cyclohexyloxycarbonyloxymethyl ester

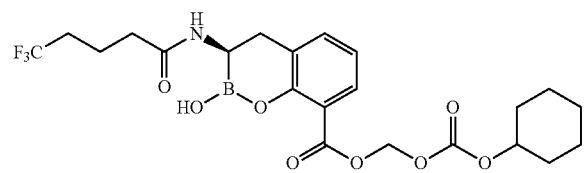 [SMILES: O=C(CCCC(F)(F)F)N[C@H]1Cc2cccc(C(=O)OCOC(=O)OC3CCCCC3)c2OB1O]

The title compound was prepared from 2-hydroxy-3-(5,5,5-trifluoro-pentanoylamino)-3,4-dihydro-2H-benzo[e][1,2]oxaborinine-8-carboxylic acid and chloromethyl cyclohexyl carbonate using the general procedure described in Steps 1 and 2 of Example 41 with the exception that DMF was used as solvent in Step 2. The crude product was purified with flash chromatography on C₁₈ reverse phase silica gel using a gradient of 20% to 60% acetonitrile/H₂O and dried via lyophilization. ESI-MS m/z 524 (M+Na)⁺.

Example 60: 2-Hydroxy-3-(5,5,5-trifluoro-pentanoylamino)-3,4-dihydro-2H -benzo[e][1,2]oxaborinine-8-carboxylic acid 1-ethoxycarbonyloxyethyl ester

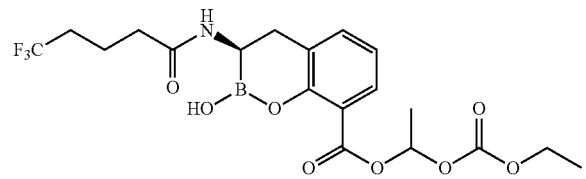 [SMILES: CCOC(=O)OC(C)OC(=O)c1cccc2c1OB(O)[C@@H](NC(=O)CCCC(F)(F)F)C2]

Step 1. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]b oronic acid (+) pinanediol ester and 5,5,5-trifluoro-pentanoic acid following the procedure in Step 1 of Example 1. The crude product was purified by flash chromatography on silica gel (50% ethyl acetate/hexane). ESI-MS m/z 568 (MH)⁺.

Step 2. Synthesis of 3-[2-(5,5,5-Trifluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid tert-butyl ester and 4N HCl/dioxane following the procedure in Step 2 of Example 13. ESI-MS m/z 512 (MH)⁺.

Step 3. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 1-propionyloxyethyl ester.

Prepared from 3-[2-(5,5,5-trifluoro-pentanoylamino)-2-(2,9,9-trimethyl-3,5-dioxa-4-bora -tricyclo[6.1.1.02,6]dec-4-yl)-ethyl]-2-methoxy-benzoic acid and chloroethyl ethyl carbonate following the procedure in Step 3 of Example 55. The crude product was purified by flash chromatography on silica gel with preparative TLC plates (70% ethyl acetate/hexane). ESI-MS m/z 628 (MH)⁺.

Step 4. Synthesis of 2-Hydroxy-3-(5,5,5-trifluoro-pentanoylamino)-3,4-dihydro-2H -benzo[e][1,2]oxaborinine-8-carboxylic acid 1-ethoxycarbonyloxy-ethyl ester.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 1-propionyloxyethyl ester and 48% hydrobromic acid in water following the procedure in Step 5 of Example 37. The crude product was purified by reverse phase preparative HPLC and dried using lyophilization to give the title compound. ESI-MS m/z 484 (M+Na)⁺.

Example 61: 2-Hydroxy-3-(5,5,5-trifluoro-pentanoylamino)-3,4-dihydro-2H -benzo[e][1,2]oxaborinine-8-carboxylic acid 1-isopropoxycarbonyloxy-ethyl ester

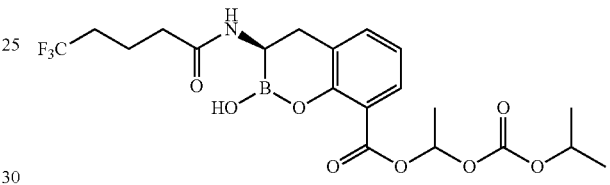

Step 1. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 5,5,5-trifluoro-pentanoic acid following the procedure in Step 1 of Example 1. The crude product was purified by flash chromatography on silica gel (50% ethyl acetate/hexane). ESI-MS m/z 568 (MH)⁺.

Step 2. Synthesis of 3-[2-(5,5,5-Trifluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid tert-butyl ester and 4N HCl/dioxane following the procedure in Step 2 of Example 13. ESI-MS m/z 512 (MH)⁺.

Step 3. Synthesis of 2-Methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 1-isobutyryloxyethyl ester.

Prepared from 3-[2-(5,5,5-trifluoro-pentanoylamino)-2-(2,9,9-trimethyl-3,5-dioxa-4-bora -tricyclo[6.1.1.02,6]dec-4-yl)-ethyl]-2-methoxy-benzoic acid and chloroethyl isopropyl carbonate following the procedure in Step 3 of Example 55. The crude product was purified by flash chromatography on silica gel with preparative TLC plates (70% ethyl acetate/hexane). ESI-MS m/z 642 (MH)⁺.

Step 4. Synthesis of 2-Hydroxy-3-(5,5,5-trifluoro-pentanoylamino)-3,4-dihydro-2H -benzo[e][1,2]oxaborinine-8-carboxylic acid 1-isopropoxycarbonyloxy-ethyl ester.

Prepared from 2-methoxy-3-[2-(5,5,5-trifluoro-pentanoylamino)-2-(2,9,9-trimethyl-3,5-dioxa-4-bora-tricyclo[6.1.1.02,6]dec-4-yl)-ethyl]-benzoic acid 1-isobutyryloxyethyl ester and 48% hydrobromic acid in water following the procedure in Step 5 of Example 37. The crude product was purified by reverse phase preparative HPLC and dried using lyophilization to give the title compound. ESI-MS m/z 498 (M+Na)⁺.

Example 62: 2-Hydroxy-3-(5,5,5-trifluoro-pentanoylamino)-3,4-dihydro-2H -benzo[e][1,2]oxaborinine-8-carboxylic acid 1-cyclohexyloxycarbonyloxy-ethyl ester

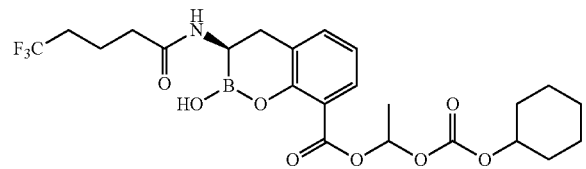 [SMILES: CC(OC(=O)OC1CCCCC1)OC(=O)c1cccc2c1OB(O)[C@@H](NC(=O)CCCC(F)(F)F)C2]

The title compound was prepared from 2-hydroxy-3-(5,5,5-trifluoro-pentanoylamino)-3,4-dihydro-2H-benzo[e][1,2]oxaborinine-8-carboxylic acid and 1-chloroethyl cyclohexyl carbonate using the general procedure described in Steps 1 and 2 of Example 41 with the exception that DMF was used as solvent in Step 2. The crude product was purified with flash chromatography on C$_{18}$ reverse phase silica gel using a gradient of 20% to 50% acetonitrile/H$_2$O and dried via lyophilization. ESI-MS m/z 538 (M+Na)⁺.

Example 63: 3-Oxo-1,3-dihydroisobenzofuran-1-yl (3R)-2-hydroxy-3-(5,5,5-trifluoropentanamido) -3,4-dihydro-2H-benzo [e][1,2]oxaborinine-8-carboxylate

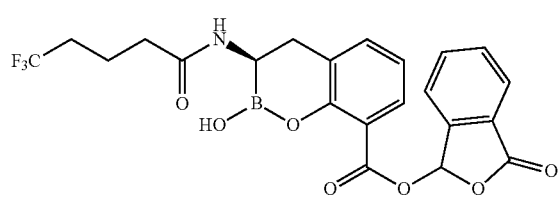 [SMILES: O=C(CCCC(F)(F)F)N[C@H]1Cc2cccc(C(=O)OC3OC(=O)c4ccccc43)c2OB1O]

3-Oxo-1,3-dihydroisobenzofuran-1-yl (3R)-2-hydroxy-3-(5,5,5-trifluoropentanamido)-3,4-dihydro-2H-benzo[e][1,2]oxaborinine-8-carboxylate (mixture of diastereoisomers) was prepared from (R)-2-hydroxy-3-(5,5,5-trifluoropentanamido)-3,4-dihydro-2H-benzo [e][1,2]oxaborinine-8-carboxylic acid (Example 2) and rac-3-bromoisobenzofuran-1(3H)-one by a procedure similar to Example 5. ESI-MS m/z 478 (MH)⁺.

Example 64: (5-Methyl-2-oxo-1,3-dioxol-4-yl) methyl (R)-2-hydroxy-3-(5,5,5-trifluoropentanamido) -3,4-dihydro-2H-benzo [e][1,2]oxaborinine-8-carboxylate

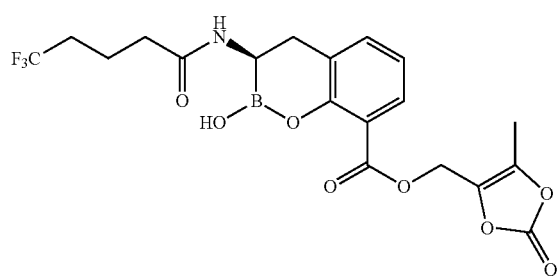 [SMILES: Cc1oc(=O)oc1COC(=O)c1cccc2c1OB(O)[C@@H](NC(=O)CCCC(F)(F)F)C2]

(5-Methyl-2-oxo-1,3-dioxol-4-yl)methyl (R)-2-hydroxy-3-(5,5,5-trifluoropentanamido)-3,4-dihydro-2H-benzo [e][1,2]oxaborinine-8-carboxylate was prepared from (R)-2-hydroxy-3-(5,5,5-trifluoropentanamido)-3,4-dihydro-2H-benzo [e][1,2]oxaborinine-8-carboxylic acid (Example 2) and 4-(bromomethyl)-5-methyl-1,3-dioxol-2-one by a procedure similar to Example 5. ESI-MS m/z 480 (M+Na)⁺.

Example 65: (R)-3-(3,3-Difluoro-butyrylamino)-2-hydroxy-3,4-dihydro-2H -benzo[e][1,2]oxaborinine-8-carboxylic acid ethyl ester

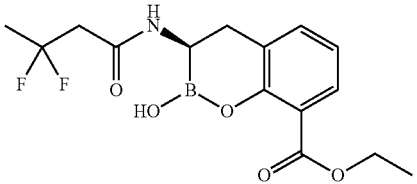 [SMILES: CCOC(=O)c1cccc2c1OB(O)[C@@H](NC(=O)CC(C)(F)F)C2]

The title compound was prepared from 2-hydroxy-3-(5,5,5-trifluoro-pentanoylamino)-3,4-dihydro-2H-benzo[e][1,2]oxaborinine-8-carboxylic acid using the general procedure described in Example 33 with the exception that the reaction was performed at room temperature and stirred for 24 h. The crude product was purified with flash chromatography on C$_{18}$ reverse phase silica gel using a gradient of 15% to 35% acetonitrile/H$_2$O and dried via lyophilization. ESI-MS m/z 342 (MH)⁺.

Example 66: (R)-3-(3,3-Difluoro-butyrylamino)-2-hydroxy-3,4-dihydro-2H -benzo[e][1,2]oxaborinine-8-carboxylic acid benzyl ester

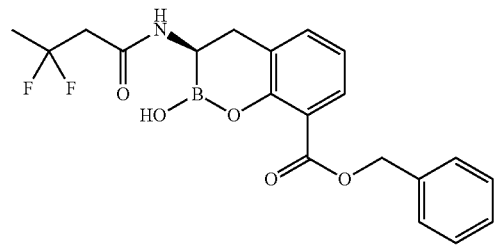 [SMILES: CC(F)(F)CC(=O)N[C@H]1Cc2cccc(C(=O)OCc3ccccc3)c2OB1O]

The title compound was prepared from 2-hydroxy-3-(5,5,5-trifluoro-pentanoylamino)-3,4-dihydro-2H-benzo[e][1,2]oxaborinine-8-carboxylic acid using the general procedure described in Example 34. The crude product was purified with flash chromatography on C$_{18}$ reverse phase silica gel using a gradient of 20% to 40% acetonitrile/H$_2$O and dried via lyophilization. ESI-MS m/z 404 (MH)⁺.

Example 67: Acetoxymethyl (R)-3-(3,3-difluorobutanamido)-2-hydroxy-3,4-dihydro-2H -benzo [e][1,2]oxaborinine-8-carboxylate

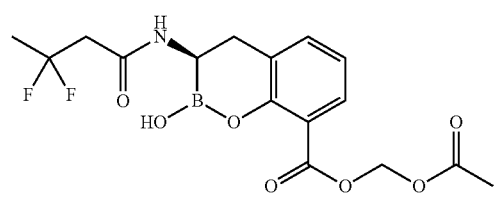 [SMILES: CC(=O)OCOC(=O)c1cccc2c1OB(O)[C@@H](NC(=O)CC(C)(F)F)C2]

Acetoxymethyl (R)-3-(3,3-difluorobutanamido)-2-hydroxy-3,4-dihydro-2H -benzo[e][1,2]oxaborinine-8-carboxylate was prepared from (R)-3-(3,3-difluorobutanamido)-2-hydroxy-3,4-dihydro-2H-benzo[e][1,2]oxaborinine-8-carboxylic acid (Example 3) and bromomethyl acetate by a procedure similar to Example 5. ESI-MS m/z 386 (MH)$^+$, 408 (M+Na)$^+$.

Example 68: 3-(3,3-Difluoro-butyrylamino)-2-hydroxy-3,4-dihydro-2H-benzo[e][1,2]oxaborinine-8-carboxylic acid 1-acetoxy-ethyl ester

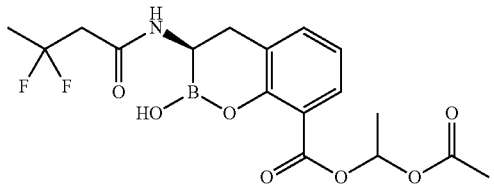

Step 1. Synthesis of 3-[2-(3,3-difluoro-butyrylamino)-2-(2,9,9-trimethyl-3,5-dioxa-4-bora -tricyclo[6.1.1.0$^{2,6}$]dec-4-yl)-ethyl]-2-methoxy-benzoic acid 1-acetoxy-ethyl ester.

A solution of 3-[2-(3,3-difluoro-butyrylamino)-2-(2,9,9-trimethyl-3,5-dioxa-4-bora -tricyclo[6.1.1.0$^{2,6}$]dec-4-yl)-ethyl]-2-methoxy-benzoic acid (145 mg, 0.3 mmol), 1-bromoethyl acetate (153 mg, 0.9 mmol) and CsF (135 mg, 0.9 mmol) in DMF (1.5 mL) was stirred at ambient temperature for 19 h. The reaction was quenched with water and extracted twice with ethyl acetate. The organic layers were combined, washed with water and brine, dried (Na$_2$SO$_4$), and concentrated in vacuo. The crude product was purified with flash chromatography on silica gel using a gradient of 20% to 100% ethyl acetate/hexane. ESI -MS m/z 588 (M+Na)$^+$.

Step 2. Synthesis of (R)- 3-(3,3-difluoro-butyrylamino)-2-hydroxy-3,4-dihydro-2H -benzo[e][1,2]oxaborinine-8-carboxylic acid 1-acetoxy-ethyl ester.

3-[2-(3,3-Difluoro-butyrylamino)-2-(2,9,9-trimethyl-3,5-dioxa-4-bora-tricyclo [6.1.1.0$^{2,6}$]dec-4-yl)-ethyl]-2-methoxy-benzoic acid 1-acetoxy-ethyl ester (16 mg, 0.028 mmol) was partitioned between hexane (1 mL) and acetonitrile (1 mL). Phenylboronic acid (5 mg, 0.04 mmol) was added followed by 2 drops of 48% HBr. After 1 h an additional portion of HBr (2 drops) was added and the reaction stirred for an additional 90 min. The mixture was diluted with water and the hexane layer pipetted off. The volatile organics were removed in vacuo, and the crude product was purified with flash chromatography on C$_{18}$ reverse phase silica gel using a gradient of 10% to 20% acetonitrile/H$_2$O and dried via lyophilization. ESI -MS m/z 422 (M+Na)$^+$.

Example 69: Isobutyryloxy)methyl (R)-3-(3,3-difluorobutanamido)-2-hydroxy-3,4-dihydro-2H -benzo[e][1,2]oxaborinine-8-carboxylate

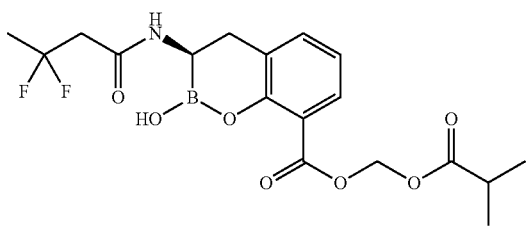 [SMILES: CC(C)C(=O)OCOC(=O)c1cccc2c1OB(O)[C@@H](NC(=O)CC(C)(F)F)C2]

Isobutyryloxy)methyl (R)-3-(3,3-difluorobutanamido)-2-hydroxy-3,4-dihydro-2H -benzo[e][1,2]oxaborinine-8-carboxylate was prepared from (R)-3-(3,3-difluorobutanamido)-2-hydroxy-3,4-dihydro-2H-benzo[e][1,2]oxaborinine-8-carboxylic acid (Example 3) and iodomethyl isobutyrate by a procedure similar to Example 5. ESI-MS m/z 436 (M+Na)$^+$. EXAMPLE 70: (R)-3-(3,3-Difluorobutyrylamino)-2-hydroxy-3,4-dihydro-2H -benzo[e][1,2]oxaborinine-8-carboxylic acid 2-ethyl-butyryloxymethyl ester

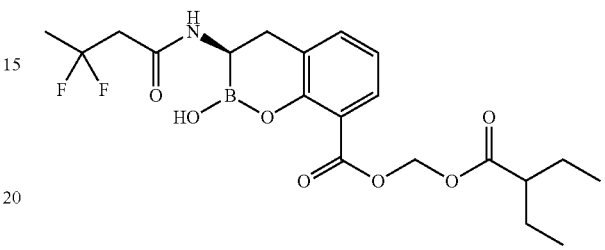

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester.

To a mixture of 3,3-difluorobutanoic acid (0.65 g, 5.24 mmol) and DMA (14 mL) was added HATU (2.18 g, 5.73 mmol) followed by pyridine (0.42 mL, 5.19 mmol). The resulting solution was stirred for 1.25 h then a solution of [(1R)-1-[bis(trimethylsilyl)amino]-2-(3-tert-butoxycarbonyl-2-methoxy -phenyl)ethyl]boronic acid (+) pinanediol ester (4.59 mmol) in THF (15 mL) (prepared as in Step 1 Example 1) was added. This mixture was stirred for 20 h, quenched with water, and extracted two times with diethyl ether. The combined organic layers were washed with brine, dried over MgSO$_4$, and concentrated. The residue was purified by silica chromatography (10-100% ethyl acetate/hexane) to give the title compound. ESI-MS m/z 536 (MH)$^+$.

Step 2. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid.

Prepared from 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester and 4N HCl/dioxane following the procedure in Step 2 of Example 13. ESI-MS m/z 480 (MH)$^+$.

Step 3. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid 2-ethyl-butyryloxymethyl ester.

To a solution of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid (0.180 g, 0.38 mmol), sodium iodide (0.061 g, 0.41 mmol), cesium fluoride (0.172 g, 1.13 mmol) and DMF (3.8 mL) was added chloromethyl 2-ethylbutyrate (0.15 mL, 0.94 mmol) under argon. The reaction was stirred at room temperature for 17 h. The reaction was quenched with water and extracted three times with ethyl acetate. The combined organic layers were washed with brine, dried over MgSO$_4$, filtered, and concentrated. The crude product was purified by flash chromatography on silica gel (5-100% ethyl acetate/hexane). ESI-MS m/z 608 (MH)$^+$.

Step 4. Synthesis of (R)-3-(3,3-Difluoro-butyrylamino)-2-hydroxy-3,4-dihydro-2H -benzo[e][1,2]oxaborinine-8-carboxylic acid 2-ethyl-butyryloxymethyl ester.

Prepared from 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid 2-ethyl-butyryloxymethyl ester following the procedure in Step 4 of Example 25. The crude product was purified by reverse phase preparative HPLC and dried using lyophilization to give the title compound. ESI-MS m/z 464 (M+Na)$^+$.

Example 71: (R)-3-(3,3-Difluoro-butyrylamino)-2-hydroxy-3,4-dihydro-2H -benzo[e][1,2]oxaborinine-8-carboxylic acid 2,2-dimethyl-propionyloxymethyl ester

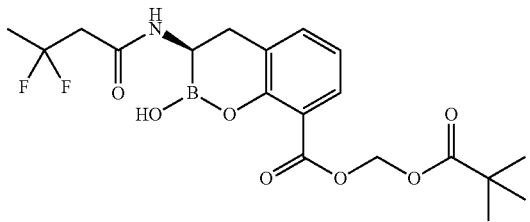 [SMILES: CC(F)(F)CC(=O)N[C@H]1Cc2cccc(C(=O)OCOC(=O)C(C)(C)C)c2OB1O]

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid 2,2-dimethyl-propionyloxymethyl ester.

Prepared from 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid (Steps 1 and 2 of Example 70) and chloromethyl pivalate following the procedure in Step 3 of Example 70. The crude product was purified by flash chromatography on silica gel (5-100% ethyl acetate/hexane). ESI-MS m/z 594 (MH)$^+$.

Step 2. Synthesis of (R)-3-(3,3-Difluoro-butyrylamino)-2-hydroxy-3,4-dihydro-2H -benzo[e][1,2]oxaborinine-8-carboxylic acid 2,2-dimethyl-propionyloxymethyl ester.

Prepared from 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid 2,2-dimethyl-propionyloxymethyl ester following the procedure in Step 4 of Example 25. The crude product was purified by reverse phase preparative HPLC and dried using lyophilization to give the title compound. ESI-MS m/z 450 (M+Na)$^+$.

Example 72: (R)-3-(3,3-Difluoro-butyrylamino)-2-hydroxy-3,4-dihydro-2H -benzo[e][1,2]oxaborinine-8-carboxylic acid 2-methoxy-2-methyl-propionyloxymethyl ester

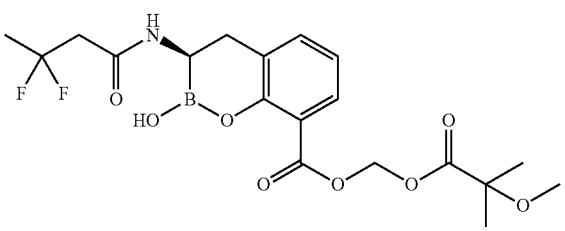 [SMILES: COC(C)(C)C(=O)OCOC(=O)c1cccc2c1OB(O)[C@@H](NC(=O)CC(C)(F)F)C2]

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3,3-difluoro-butyric acid following the procedure in Step 1 of Example 70. The crude product was purified by flash chromatography on silica gel. ESI-MS m/z 536 (MH)$^+$.

Step 2. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester and 4N HCl/dioxane following the procedure in Step 2 of Example 13. ESI-MS m/z 480 (MH)$^+$.

Step 3. Synthesis of 2-Methoxy-3-[2-(3,3-difluoro-butyrylamino)-2-(2,9,9-trimethyl-3,5-dioxa-4-bora -tricyclo[6.1.1.02,6]dec-4-yl)-ethyl]-benzoic acid chloromethyl ester.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid and chloroiodomethane following the procedure in Step 3 of Example 13. The crude product was purified by flash chromatography on silica gel with preparative TLC plates (5% methanol/dichloromethane). ESI-MS m/z 528 (MH)$^+$.

Step 4. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid 2-methoxy-2-methyl-propionyloxymethyl ester.

To 2-methoxy-3-[2-(3,3-difluoro-butyrylamino)-2-(2,9,9-trimethyl-3,5-dioxa-4-bora -tricyclo[6.1.1.02,6]dec-4-yl)-ethyl]-benzoic acid chloromethyl ester (0.05 g, 0.1 mmol) in DMF (1 mL) under an atmosphere of argon was added 2-methoxy-2-methylpropanoic acid (0.02 mL, 0.14 mmol) and cesium fluoride (0.04 g, 0.3 mmol), followed by sodium iodide (0.02 g, 0.1 mmol) and was stirred at room temperature overnight. The reaction was diluted with ethyl acetate, washed with water/brine, dried over sodium sulfate, filtered, and concentrated. The crude product was taken directly on to the next step without further purification. ESI-MS m/z 610 (MH)$^+$.

Step 5. Synthesis of (R)-3-(3,3-Difluoro-butyrylamino)-2-hydroxy-3,4-dihydro-2H -benzo[e][1,2]oxaborinine-8-carboxylic acid 2-methoxy-2-methyl-propionyloxymethyl ester.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid 2-methoxy-2-methyl-propionyloxymethyl ester and 48% hydrobromic acid in water following the procedure in Step 5 of Example 37. The crude product was purified by reverse phase preparative HPLC and dried using lyophilization to give the title compound. ESI-MS m/z 466 (M+Na)$^+$.

Example 73: (R)-3-(3,3-Difluoro-butyrylamino)-2-hydroxy-3,4-dihydro-2H -benzo[e][1,2]oxaborinine-8-carboxylic acid 2-ethoxy-2-methyl-propionyloxymethyl ester

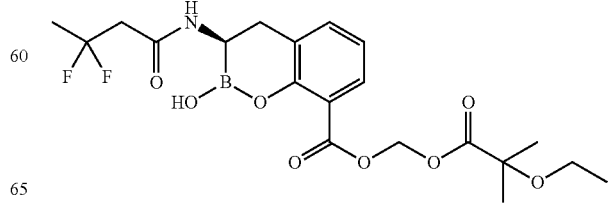

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3,3-difluoro-butyric acid following the procedure in Step 1 of Example 70. The crude product was purified by flash chromatography on silica gel. ESI-MS m/z 536 (MH)+.

Step 2. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester and 4N HCl/dioxane following the procedure in Step 2 of Example 13. ESI-MS m/z 480 (MH)+.

Step 3. Synthesis of 2-Methoxy-3-[2-(3,3-difluoro-butyrylamino)-2-(2,9,9-trimethyl-3,5-dioxa-4-bora -tricyclo[6.1.1.02,6]dec-4-yl)-ethyl]-benzoic acid chloromethyl ester.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid and chloroiodomethane following the procedure in Step 3 of Example 13. The crude product was purified by flash chromatography on silica gel with preparative TLC plates (5% methanol/dichloromethane). ESI-MS m/z 528 (MH)+.

Step 4. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid 2-ethoxy-2-methyl-propionyloxymethyl ester.

Prepared from 2-methoxy-3-[2-(3,3-difluoro-butyrylamino)-2-(2,9,9-trimethyl-3,5-dioxa-4-bora -tricyclo[6.1.1.02,6]dec-4-yl)-ethyl]-benzoic acid chloromethyl ester and 2-ethoxy-2-methylpropanoic acid following the procedure in Step 4 of Example 72. ESI-MS m/z 624 (MH)+.

Step 5. Synthesis of (R)-3-(3,3-Difluoro-butyrylamino)-2-hydroxy-3,4-dihydro-2H -benzo[e][1,2]oxaborinine-8-carboxylic acid 2-ethoxy-2-methyl-propionyloxymethyl ester.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid 2-ethoxy-2-methyl-propionyloxymethyl ester and 48% hydrobromic acid in water following the procedure in Step 5 of Example 37. The crude product was purified by reverse phase preparative HPLC and dried using lyophilization to give the title compound. ESI-MS m/z 480 (M+Na)+.

Example 74: (R)-3-(3,3-Difluoro-butyrylamino)-2-hydroxy-3,4-dihydro-2H -benzo[e][1,2]oxaborinine-8-carboxylic acid benzoyloxymethyl ester

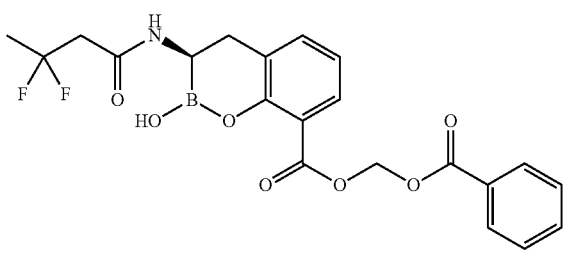 [SMILES: CC(F)(F)CC(=O)N[C@H]1Cc2cccc(C(=O)OCOC(=O)c3ccccc3)c2OB1O]

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3,3-difluoro-butyric acid following the procedure in Step 1 of Example 70. The crude product was purified by flash chromatography on silica gel. ESI-MS m/z 536 (MH)+.

Step 2. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester and 4N HCl/dioxane following the procedure in Step 2 of Example 13. ESI-MS m/z 480 (MH)+.

Step 3. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid benzoyloxymethyl ester.

To 3-[2-(3,3-difluoro-butyrylamino)-2-(2,9,9-trimethyl-3,5-dioxa-4-bora-tricyclo[6.1.1.02,6]dec -4-yl)-ethyl]-2-methoxy-benzoic acid (0.13 g, 0.26 mmol) in anhydrous DMF (2 mL) under an atmosphere of argon was added sodium carbonate (0.09 g, 0.78 mmol) and benzoic acid chloromethyl ester (0.09 mL, 0.65 mmol), followed by sodium iodide (0.04 g, 0.29 mmol) and stirred at 60 ° C. for 1 h. The reaction was diluted with ethyl acetate, washed with water/brine, dried over sodium sulfate, and concentrated. The crude product was purified by flash chromatography on silica gel with preparative TLC plates (50% ethyl acetate/hexane). ESI-MS m/z 614 (MH)+.

Step 4. Synthesis of (R)-3-(3,3-Difluoro-butyrylamino)-2-hydroxy-3,4-dihydro-2H -benzo[e][1,2]oxaborinine-8-carboxylic acid benzoyloxymethyl ester.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid benzoyloxymethyl ester and 48% hydrobromic acid in water following the procedure in Step 5 of Example 37. The crude product was purified by reverse phase preparative HPLC and dried using lyophilization to give the title compound. ESI-MS m/z 470 (M+Na)+.

Example 75: ((Ethoxycarbonyl)oxy)methyl (R)-3-(3,3-difluorobutanamido)-2-hydroxy-3,4-dihydro -2H-benzo [e][1,2]oxaborinine-8-carboxylate

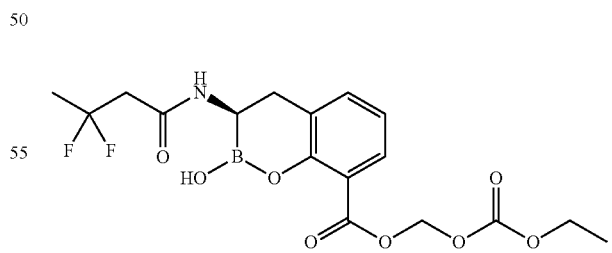

((Ethoxycarbonyl)oxy)methyl (R)-3-(3,3-difluorobutanamido)-2-hydroxy-3,4-dihydro-2H -benzo[e][1,2]oxaborinine-8-carboxylate was prepared from (R)-3-(3,3-difluorobutanamido)-2-hydroxy-3,4-dihydro-2H-benzo[e][1,2] oxaborinine-8-carboxylic acid (Example 3) and ethyl (iodomethyl) carbonate by a procedure similar to Example 5. ESI-MS m/z 438 (M+Na)+.

Example 76: (R)-3-(3,3-Difluoro-butyrylamino)-2-hydroxy-3,4-dihydro-2H-benzo[e][1,2]oxaborinine-8-carboxylic acid isopropoxycarbonyloxymethyl ester

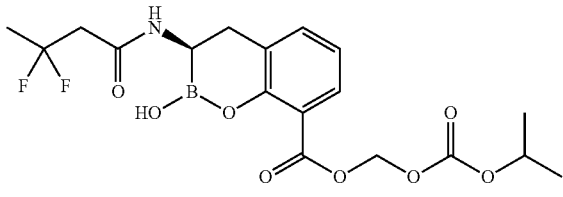 [SMILES: CC(C)OC(=O)OCOC(=O)c1cccc2c1OB(O)[C@@H](NC(=O)CC(C)(F)F)C2]

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid isopropoxycarbonyloxymethyl ester.

Prepared from 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid (Steps 1 and 2 of Example 70) and chloromethyl isopropyl carbonate following the procedure in Step 3 of Example 70. The crude product was purified by flash chromatography on silica gel (5-100% ethyl acetate/hexane). ESI-MS m/z 596 (MH)$^+$. Step 2. Synthesis of (R)-3-(3,3-Difluoro-butyrylamino)-2-hydroxy-3,4-dihydro-2H -benzo[e][1,2]oxaborinine-8-carboxylic acid isopropoxycarbonyloxymethyl ester.

Prepared from 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid isopropoxycarbonyloxymethyl ester following the procedure in Step 4 of Example 25. The crude product was purified by reverse phase preparative HPLC and dried using lyophilization to give the title compound. ESI-MS m/z 452 (M+Na)$^+$.

Example 77: (R)-3-(3,3-Difluoro-butyrylamino)-2-hydroxy-3,4-dihydro-2H-benzo[e][1,2]oxaborinine-8-carboxylic acid butoxycarbonyloxymethyl ester

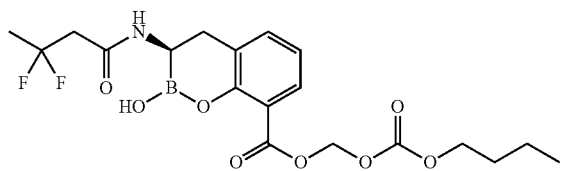 [SMILES: CCCCOC(=O)OCOC(=O)c1cccc2c1OB(O)[C@@H](NC(=O)CC(C)(F)F)C2]

To a solution of 3-(3,3-difluoro-butyrylamino)-2-hydroxy-3,4-dihydro-2H -benzo[e][1,2]oxaborinine-8-carboxylic acid (25.8 mg, 0.082 mmol) in DMF (500 4) was added lithium tert-butoxide solution (1M in THF, 90 µL, 0.09 mmol) followed immediately by a solution of iodomethyl n-butyl carbonate (62 mg, 0.24 mmol) in DMF (200 4). The solution was stirred for 90 min, quenched with water and extracted twice with hexane. The organic layers were combined and washed with water. The aqueous layers were combined, and the crude product purified with flash chromatography on C$_{18}$ reverse phase silica gel using a gradient of 10% to 40% acetonitrile/H$_2$O and dried via lyophilization. ESI-MS m/z 466 (M+Na)$^+$.

Example 78: (R)-3-(3,3-Difluoro-butyrylamino)-2-hydroxy-3,4-dihydro-2H-benzo[e][1,2]oxaborinine-8-carboxylic acid cyclohexyloxycarbonyloxymethyl ester

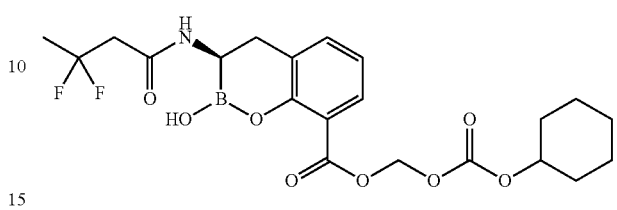

To a solution of 3-(3,3-difluoro-butyrylamino)-2-hydroxy-3,4-dihydro-2H -benzo[e][1,2]oxaborinine-8-carboxylic acid (24.5 mg, 0.078 mmol) in DMF (500 µL) was added lithium tert-butoxide solution (1M in THF, 90 µL, 0.09 mmol) followed immediately by a solution of iodomethyl cyclohexyl carbonate (47 mg, 0.165 mmol) in DMF (200 µL). After stirring for 1 h, the reaction was quenched with 0.1N HCl and extracted twice with hexane. The organic layers were combined and washed with water. The aqueous layers were combined, the volatile organics removed in vacuo, and the crude product was purified with flash chromatography on C$_{18}$ reverse phase silica gel using a gradient of 20% to 40% acetonitrile/H$_2$O and dried via lyophilization. ESI-MS m/z 492 (M+Na)$^+$.

Example 79: 3-(3,3-Difluoro-butyrylamino)-2-hydroxy-3,4-dihydro-2H-benzo[e][1,2]oxaborinine-8-carboxylic acid 1-ethoxycarbonyloxy-ethyl ester

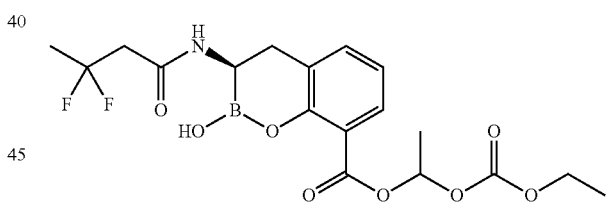

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3,3-difluoro-butyric acid following the procedure in Step 1 of Example 70. The crude product was purified by flash chromatography on silica gel. ESI-MS m/z 536 (MH)$^+$.

Step 2. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester and 4N HCl/dioxane following the procedure in Step 2 of Example 13. ESI-MS m/z 480 (MH)$^+$.

Step 3. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid 1-ethoxycarbonyloxyethyl ester.

To 3-[2-(3,3-difluoro-butyrylamino)-2-(2,9,9-trimethyl-3,5-dioxa-4-bora-tricyclo[6.1.1.02,6]dec- 4-yl)-ethyl]-2-methoxy-benzoic acid (0.32 g, 0.66 mmol) in anhydrous DMF (2.6 mL) under an atmosphere of argon was added cesium fluoride (0.3 g, 1.98 mmol) and chloroethyl ethyl carbonate (0.22 mL, 1.65 mmol), followed by sodium iodide (0.11 g, 0.72 mmol) and stirred at room temperature overnight. The reaction was diluted with ethyl acetate, washed with water/brine, dried over sodium sulfate, and concentrated. The crude product was purified by flash chromatography on silica gel with preparative TLC plates (50% ethyl acetate/hexane). ESI-MS m/z 596 (MH)+.

Step 4. Synthesis of 3-(3,3-Difluoro-butyrylamino)-2-hydroxy-3,4-dihydro-2H -benzo[e][1,2]oxaborinine-8-carboxylic acid 1-ethoxycarbonyloxy-ethyl ester.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid 1-ethoxycarbonyloxy-ethyl ester and 48% hydrobromic acid in water following the procedure in Step 5 of Example 37. The crude product was purified by reverse phase preparative HPLC and dried using lyophilization to give the title compound. ESI-MS m/z 452 (M+Na)+.

Example 80: 3-(3,3-Difluoro-butyrylamino)-2-hydroxy-3,4-dihydro-2H-benzo [e][1,2]oxaborinine-8-carboxylic acid 1-isopropoxycarbonyloxy-ethyl ester

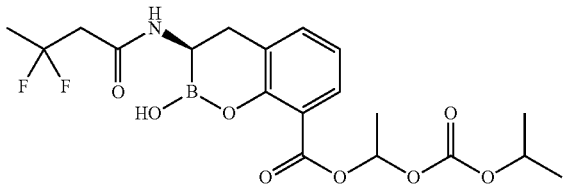 [SMILES: CC(C)OC(=O)OC(C)OC(=O)c1cccc2c1OB(O)[C@@H](NC(=O)CC(C)(F)F)C2]

Step 1. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 3,3-difluoro-butyric acid following the procedure in Step 1 of Example 70. The crude product was purified by flash chromatography on silica gel. ESI-MS m/z 536 (MH)+.

Step 2. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid tert-butyl ester and 4N HCl/dioxane following the procedure in Step 2 of Example 13. ESI-MS m/z 480 (MH)+.

Step 3. Synthesis of 3-[2-(3,3-Difluoro-butyrylamino)-2-(2,9,9-trimethyl-3,5-dioxa-4-bora -tricyclo[6.1.1.02,6]dec-4-yl)-ethyl]-2-methoxy-benzoic acid isopropoxycarbonyloxymethyl ester.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid and chloroethyl isopropyl carbonate following the procedure in Step 3 of Example 79. ESI-MS m/z 610 (MH)+.

Step 4. Synthesis of 3-(3,3-Difluoro-butyrylamino)-2-hydroxy-3,4-dihydro-2H -benzo[e][1,2]oxaborinine-8-carboxylic acid 1-isopropoxycarbonyloxy-ethyl ester.

Prepared from 3-[2-(3,3-difluoro-butyrylamino)-2-(2,9,9-trimethyl-3,5-dioxa-4-bora -tricyclo[6.1.1.02,6]dec-4-yl)-ethyl]-2-methoxy-benzoic acid isopropoxycarbonyloxymethyl ester and 48% hydrobromic acid in water following the procedure in Step 5 of Example 37. The crude product was purified by reverse phase preparative HPLC and dried using lyophilization to give the title compound. ESI-MS m/z 466 (M+Na)+.

Example 81: 3-(3,3-Difluoro-butyrylamino)-2-hydroxy-3,4-dihydro-2H-benzo [e][1,2]oxaborinine-8-carboxylic acid 1-cyclohexyloxycarbonyloxy-ethyl ester

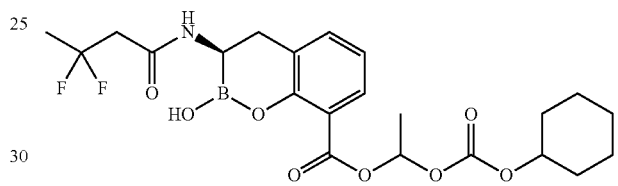

The title compound was prepared from 1-chloroethyl cyclohexyl carbonate using the general procedure described in Steps 1 and 2 of Example 68 with the exception that Step 1 was stirred for 3 days. The crude product was purified with flash chromatography on $C_{18}$ reverse phase silica gel using a gradient of 20% to 50% acetonitrile/H$_2$O and dried via lyophilization. ESI-MS m/z 506 (M+Na)+.

Example 82: 3-Oxo-1,3-dihydroisobenzofuran-1-yl (3R)-3-(3,3-difluorobutanamido)-2-hydroxy-3,4-dihydro-2H-benzo [e][1,2]oxaborinine-8-carboxylate

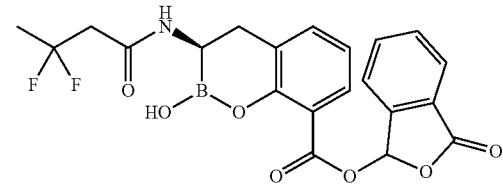 [SMILES: CC(F)(F)CC(=O)N[C@H]1Cc2cccc(C(=O)OC3OC(=O)c4ccccc43)c2OB1O]

3-Oxo-1,3-dihydroisobenzofuran-l-yl (3R)-3-(3,3-difluorobutanamido)-2-hydroxy-3,4-dihydro -2H-benzo [e][1,2] oxaborinine-8-carboxylate (a 1:1 mixture of diastereoisomers) was prepared from (R)-3-(3,3-difluorobutanamido)-2-hydroxy-3,4-dihydro-2H-benzo [e][1,2]oxaborinine-8-carboxylic acid (Example 3) and rac-3-bromoisobenzofuran-1(3H)-one by a procedure similar to Example 5. ESI-MS m/z 446 (MH)+.

Example 83: (5-Methyl-2-oxo-1,3-dioxol-4-yl) methyl (R)-3-(3,3-difluorobutanamido)-2-hydroxy-3,4-dihydro-2H-benzo [e][1,2]oxaborinine-8-carboxylate

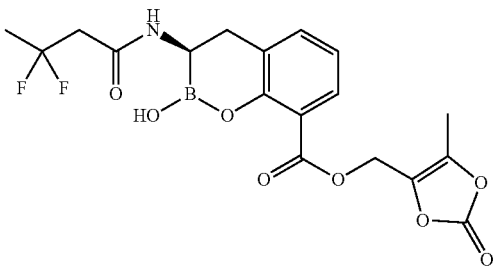 [SMILES: Cc1oc(=O)oc1COC(=O)c1cccc2c1OB(O)[C@@H](NC(=O)CC(C)(F)F)C2]

(5-Methyl-2-oxo-1,3-dioxol-4-yl)methyl (R)-3-(3,3-difluorobutanamido)-2-hydroxy-3,4-dihydro -2H-benzo [e][1,2]oxaborinine-8-carboxylate was prepared from (R)-3-(3,3-difluorobutanamido)-2-hydroxy -3,4-dihydro-2H-benzo [e][1,2]oxaborinine-8-carboxylic acid (Example 3) and 4-(bromomethyl)-5-methyl -1,3-dioxol-2-one by a procedure similar to Example 5. ESI-MS m/z 448 (M+Na)$^+$.

Example 84: Heptyl (R)-2-hydroxy-3-propionamido-3,4-dihydro-2H-benzo[e][1,2]oxaborinine-8-carboxylate

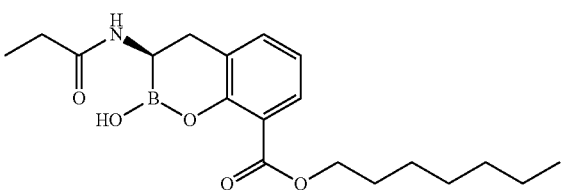 [SMILES: CCCCCCCOC(=O)c1cccc2c1OB(O)[C@@H](NC(=O)CC)C2]

Heptyl (R)-2-hydroxy-3-prop ionamido -3,4-dihydro-2H-b enzo [e][1,2]oxaborinine-8-carboxylate was prepared from (R)-2-hydroxy-3-prop ionamido-3,4-dihydro-2H-benzo [e][1,2]oxaborinine-8-carboxylic acid and 1-iodoheptane by a procedure similar to Example 5, with the exception that the reaction was conducted at 45° C., instead of room temperature. ESI-MS m/z 362 (MH)$^+$.

Example 85: (R)-3-(4,4-Difluoro-pentanoylamino)-2-hydroxy-3,4-dihydro-2H -benzo[e][1,2]oxaborinine-8-carboxylic acid

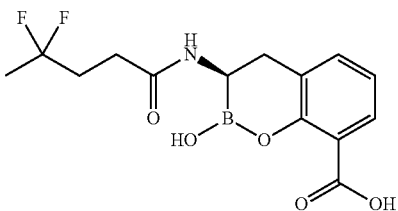 [SMILES: CC(F)(F)CCC(=O)N[C@H]1Cc2cccc(C(=O)O)c2OB1O]

Step 1. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from [(1R)-1-[bis(trimethylsilyl)amino]-2-(3-tert-butoxycarbonyl-2-methoxy -phenyl)ethyl]boronic acid (+) pinanediol ester and 4,4-difluoropentanoic acid following the procedure in Step 1 and Step 2 of Example 25. ESI-MS m/z 494 (MH)$^+$.

Step 2. Synthesis of (R)-3-(4,4-Difluoro-pentanoylamino)-2-hydroxy-3,4-dihydro-2H -benzo[e][1,2]oxaborinine-8-carboxylic acid.

To a solution of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid (0.310 g, 0.63 mmol) and acetonitrile (6.0 mL) was added phenylboronic acid (0.085 g, 0.70 mmol), hexane (6.0 mL), and hydrobromic acid (48% in H$_2$O, 0.995 g, 5.90 mmol) and the reaction stirred at room temperature for 4.5 h. Hexane was removed and replaced at 1.5 and 3 h. The reaction was quenched with water, layers separated, and the aqueous layer concentrated to remove acetonitrile. The crude product was purified by reverse phase preparative HPLC and dried using lyophilization. ESI-MS m/z 328 (MH)$^+$.

Example 86: (R)-3-(4,4-Difluoro-pentanoylamino)-2-hydroxy-3,4-dihydro-2H -benzo[e][1,2]oxaborinine-8-carboxylic acid 2,2-dimethyl-propionyloxymethyl ester

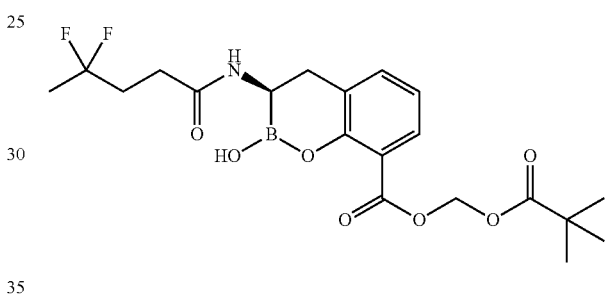

Step 1. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from [(1R)-1-[bis(trimethylsilyl)amino]-2-(3-tert-butoxycarbonyl-2-methoxy -phenyl)ethyl]boronic acid (+) pinanediol ester and 4,4-difluoropentanoic acid following the procedure in Step 1 and Step 2 of Example 25. ESI-MS m/z 494 (MH)$^+$.

Step 2. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid 2,2-dimethyl-propionyloxymethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid and chloromethyl pivalate following the procedure in Step 3 of Example 55. The crude product was purified by flash chromatography on silica gel with preparative TLC plates (50% ethyl acetate/hexane). ESI-MS m/z 608 (MH)$^+$.

Step 3. Synthesis of (R)-3-(4,4-Difluoro-pentanoylamino)-2-hydroxy-3,4-dihydro-2H -benzo[e][1,2]oxaborinine-8-carboxylic acid 2,2-dimethyl-propionyloxymethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid 2,2-dimethyl-propionyloxymethyl ester and 48% hydrobromic acid in water following the procedure in Step 5 of Example 37. The crude product was purified by reverse phase preparative HPLC and dried using lyophilization to give the title compound. ESI -MS m/z 464 (M+Na)$^+$.

Example 87: (R)-3-(4,4-Difluoro-pentanoylamino)-2-hydroxy-3,4-dihydro-2H-benzo[e][1,2]oxaborinine-8-carboxylic acid 2-ethyl-butyryloxymethyl ester

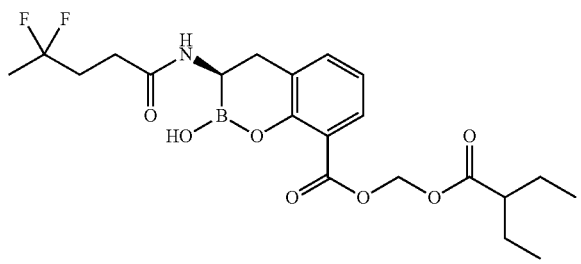 [SMILES: CCC(CC)C(=O)OCOC(=O)c1cccc2c1OB(O)[C@@H](NC(=O)CCC(C)(F)F)C2]

Step 1. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from [(1R)-1-[bis(trimethylsilyl)amino]-2-(3-tert-butoxycarbonyl-2-methoxy-phenyl)ethyl]boronic acid (+) pinanediol ester and 4,4-difluoropentanoic acid following the procedure in Step 1 and Step 2 of Example 25. ESI-MS m/z 494 (MH)+.

Step 2. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid 2-ethyl-butyryloxymethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid and chloromethyl 2-ethylbutyrate following the procedure in Step 3 of Example 55. The crude product was purified by flash chromatography on silica gel with preparative TLC plates (50% ethyl acetate/hexane). ESI-MS m/z 622 (MH)+.

Step 3. Synthesis of (R)-3-(4,4-Difluoro-pentanoylamino)-2-hydroxy-3,4-dihydro-2H -benzo[e][1,2]oxaborinine-8-carboxylic acid 2-ethyl-butyryloxymethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid 2-ethyl-butyryloxymethyl ester and 48% hydrobromic acid in water following the procedure in Step 5 of Example 37. The crude product was purified by reverse phase preparative HPLC and dried using lyophilization to give the title compound. ESI-MS m/z 478 (M+Na)+.

Example 88: (R)-3-(4,4-Difluoro-pentanoylamino)-2-hydroxy-3,4-dihydro-2H-benzo[e][1,2]oxaborinine-8-carboxylic acid isobutyryloxymethyl ester

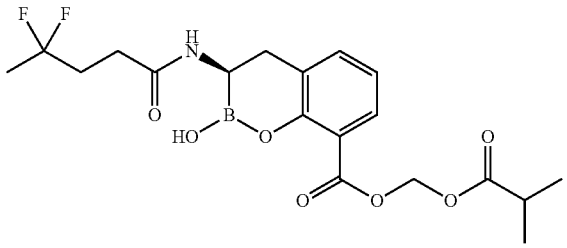 [SMILES: CC(C)C(=O)OCOC(=O)c1cccc2c1OB(O)[C@@H](NC(=O)CCC(C)(F)F)C2]

Step 1. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from [(1R)-1-[bis(trimethylsilyl)amino]-2-(3-tert-butoxycarbonyl-2-methoxy-phenyl)ethyl]boronic acid (+) pinanediol ester and 4,4-difluoropentanoic acid following the procedure in Step 1 and Step 2 of Example 25. ESI-MS m/z 494 (MH)+.

Step 3. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid isobutyryloxymethyl ester.

Prepared from 3-[2-(4,4-difluoro-pentanoylamino)-2-(2, 9,9-trimethyl-3,5-dioxa-4-bora -tricyclo[6.1.1.02,6]dec-4-yl)-ethyl]-2-methoxy-benzoic acid and chloromethyl isobutyrate following the procedure in Step 3 of Example 55. The crude product was purified by flash chromatography on silica gel with preparative TLC plates (50% ethyl acetate/hexane). ESI-MS m/z 594 (MH)+. Step 4. Synthesis of (R)-3-(4,4-Difluoro-pentanoylamino)-2-hydroxy-3,4-dihydro-2H -benzo[e][1,2]oxaborinine-8-carboxylic acid isobutyryloxymethyl ester.

Prepared from 3-[2-(4,4-difluoro-pentanoylamino)-2-(2, 9,9-trimethyl-3,5-dioxa-4-bora -tricyclo[6.1.1.02,6]dec-4-yl)-ethyl]-2-methoxy-benzoic acid isobutyryloxymethyl ester and 48% hydrobromic acid in water following the procedure in Step 5 of Example 37. The crude product was purified by reverse phase preparative HPLC and dried using lyophilization to give the title compound. ESI-MS m/z 450 (M+Na)+.

Example 89: (R)-3-(4,4-Difluoro-pentanoylamino)-2-hydroxy-3,4-dihydro-2H-benzo[e][1,2]oxaborinine-8-carboxylic acid ethoxycarbonyloxymethyl ester

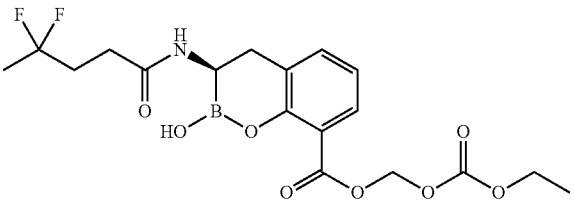 [SMILES: CCOC(=O)OCOC(=O)c1cccc2c1OB(O)[C@@H](NC(=O)CCC(C)(F)F)C2]

Step 1. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid ethoxycarbonyloxymethyl ester.

Prepared from 2-Methoxy-3-[2-(4,4-Difluoro-pentanoylamino)-2-(2,9,9-trimethyl-3,5-dioxa-4-bora-tricyclo [6.1.1.02,6]dec-4-yl)-ethyl]-benzoic acid (Steps 1 and 2 of Example 25) and chloromethyl ethyl carbonate following the procedure in Step 3 of Example 25. The crude product was purified by flash chromatography on silica gel (10-100% ethyl acetate/hexane). ESI-MS m/z 596 (MH)+.

Step 2. Synthesis of (R)-3-(4,4-Difluoro-pentanoylamino)-2-hydroxy-3,4-dihydro-2H -benzo[e][1,2]oxaborinine-8-carboxylic acid ethoxycarbonyloxymethyl ester.

Prepared from 3-[2-(4,4-difluoro-pentanoylamino)-2-(2, 9,9-trimethyl-3,5-dioxa-4-bora -tricyclo[6.1.1.02,6]dec-4-yl)-ethyl]-2-methoxy-benzoic acid ethoxycarbonyloxymethyl ester following the procedure in Step 4 of Example 25. The crude product was purified by reverse phase preparative

Example 90: (R)-3-(4,4-Difluoro-pentanoylamino)-2-hydroxy-3,4-dihydro-2H-benzo[e][1,2]oxaborinine-8-carboxylic acid isopropoxycarbonyloxymethyl ester HPLC and dried using lyophilization to give the title compound. ESI-MS m/z 452 (M+Na)+.

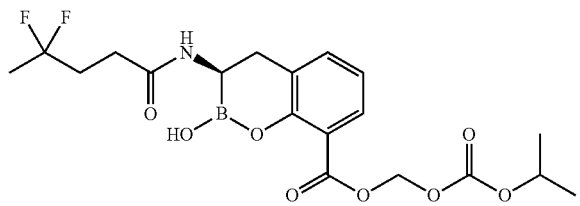 [SMILES: CC(C)OC(=O)OCOC(=O)c1cccc2c1OB(O)[C@@H](NC(=O)CCC(C)(F)F)C2]

Step 1. Synthesis of 3-[2-(4,4-Difluoro-pentanoylamino)-2-(2,9,9-trimethyl-3,5-dioxa-4-bora-tricyclo[6.1.1.0 2,6]dec-4-yl)-ethyl]-2-methoxy-benzoic acid isopropoxycarbonyloxymethyl ester.

Prepared from 2-Methoxy-3-[2-(4,4-Difluoro-pentanoylamino)-2-(2,9,9-trimethyl-3,5-dioxa-4-bora-tricyclo[6.1.1.0 2,6]dec-4-yl)-ethyl]-benzoic acid (Steps 1 and 2 of Example 25) and chloromethyl ethyl carbonate following the procedure in Step 3 of Example 25. The crude product was purified by flash chromatography on silica gel (10-100% ethyl acetate/hexane). ESI-MS m/z 610 (MH)+. Step 2. Synthesis of (R)-3-(4,4-Difluoro-pentanoylamino)-2-hydroxy-3,4-dihydro-2H-benzo[e][1,2]oxaborinine-8-carboxylic acid isopropoxycarbonyloxymethyl ester.

Prepared from 3-[2-(4,4-Difluoro-pentanoylamino)-2-(2,9,9-trimethyl-3,5-dioxa-4-bora-tricyclo[6.1.1.0 2,6]dec-4-yl)-ethyl]-2-methoxy-benzoic acid isopropoxycarbonyloxymethyl ester following the procedure in Step 4 of Example 25. The crude product was purified by reverse phase preparative HPLC and dried using lyophilization to give the title compound. ESI-MS m/z 466 (M+Na)+.

Example 91: 2-Morpholinoethyl (R)-2-hydroxy-3-(4,4,4-trifluorobutanamido)-3,4-dihydro-2H-benzo[e][1,2]oxaborinine-8-carboxylate

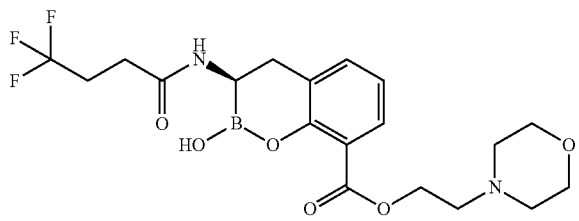 [SMILES: O=C(CCC(F)(F)F)N[C@H]1Cc2cccc(C(=O)OCCN3CCOCC3)c2OB1O]

2-Morpholinoethyl—(R)-2-hydroxy-3-(4,4,4-trifluorobutanamido)-3,4-dihydro-2H-benzo[e][1,2]oxaborinine-8-carboxylate was prepared from (R)-2-hydroxy-3-(4,4,4-trifluorobutanamido)-3,4-dihydro-2H-benzo[e][1,2]oxaborinine-8-carboxylic acid and 4-(2-bromoethyl)morpholine by a procedure similar to Example 5. ESI-MS m/z 445 (MH)+.

Example 92: (5-Isobutyl-2-oxo-1,3-dioxol-4-yl)methyl (R)-2-hydroxy-3-(4,4,4-trifluorobutanamido)-3,4-dihydro-2H-benzo[e][1,2]oxaborinine-8-carboxylate

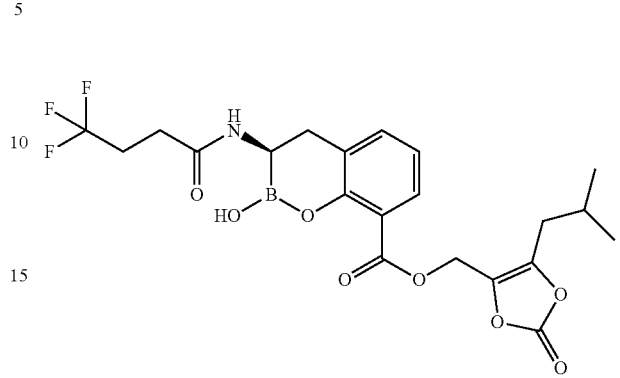

(5-Isobutyl-2-oxo-1,3-dioxol-4-yl)methyl (R)-2-hydroxy-3-(4,4,4-trifluorobutanamido)-3,4-dihydro-2H-benzo[e][1,2]oxaborinine-8-carboxylate was prepared from (R)-2-hydroxy-3-(4,4,4-trifluorobutanamido)-3,4-dihydro-2H-benzo[e][1,2]oxaborinine-8-carboxylic acid and 4-(bromomethyl)-5-isobutyl-1,3-dioxol-2-one (prepared by a procedure similar to Park, J. -H., et al. *Bioorg. Med. Chem. Lett.* 2010, 20, 5895-5899) by a procedure similar to Example 5. ESI-MS m/z 508 (M+Na)+.

Example 93: (R)-Nicotinic acid 2-hydroxy-3-(4,4,4-trifluoro-butyrylamino-3,4-dihydro-2H-benzo[e][1,2]oxaborinine-8-carbonyloxymethyl ester

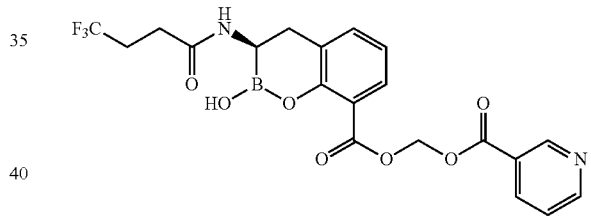

Step 1. Synthesis of 2-Methoxy-3-[2-(4,4,4-trifluoro-butyrylamino)-2-(2,9,9-trimethyl-3,5-dioxa-4-bora-tricyclo[6.1.1.0 2,6]dec-4-yl)-ethyl]-benzoic acid tert-butyl ester.

Prepared from [(1S)-2-(3-tert-butoxycarbonyl-2-methoxy-phenyl)-1-chloro-ethyl]boronic acid (+) pinanediol ester and 4,4,4-trifluorobutyric acid following the procedure in Step 1 of Example 1. The crude product was purified by flash chromatography on silica gel (50% ethyl acetate/hexane). ESI-MS m/z 554 (MH)+.

Step 2. Synthesis of 3-[2-(4,4,4-Trifluoro-butyrylamino)-2-(2,9,9-trimethyl-3,5-dioxa-4-bora-tricyclo[6.1.1.0 2,6]dec-4-yl)-ethyl]-2-methoxy-benzoic acid.

Prepared from 2-methoxy-3-[2-(4,4,4-trifluoro-butyrylamino)-2-(2,9,9-trimethyl-3,5-dioxa-4-bora-tricyclo[6.1.1.0 2,6]dec-4-yl)-ethyl]-benzoic acid tert-butyl ester and 4N HCl/dioxane following the procedure in Step 2 of Example 13. ESI-MS m/z 498 (MH)+.

Step 3. Synthesis of 2-Methoxy-3-[2-(4,4,4-trifluoro-butyrylamino)-2-(2,9,9-trimethyl-3,5-dioxa-4-bora-tricyclo[6.1.1.0 2,6]dec-4-yl)-ethyl]-benzoic acid chloromethyl ester.

Prepared from 3-[2-(4,4,4-trifluoro-butyrylamino)-2-(2,9,9-trimethyl-3,5-dioxa-4-bora-tricyclo[6.1.1.0 2,6]dec-4-yl)-ethyl]-2-methoxy-benzoic acid and chloroiodomethane following the procedure in Step 3 of Example 13. The crude product was purified by flash chromatography on silica gel (2% methanol/dichloromethane). ESI-MS m/z 546 (MH)+.

Step 4. Synthesis of Nicotinic acid 2-methoxy-3-[2-(4,4,4-trifluoro-butyrylamino)-2-(2,9,9-trimethyl -3,5-dioxa-4-bora-tricyclo[6.1.1.02,6]dec-4-yl)-ethyl]-benzoyloxymethyl ester.

Prepared from 2-methoxy-3-[2-(4,4,4-trifluoro-butyrylamino)-2-(2,9,9-trimethyl-3,5-dioxa-4-bora-tricyclo [6.1.1.02,6]dec-4-yl)-ethyl]-benzoic acid chloromethyl ester and nicotinic acid following the procedure in Step 4 of Example 13. The crude product was purified by flash chromatography on silica gel with preparative TLC plates (5% methanol/dichloromethane). ESI-MS m/z 633 (MH)+.

Step 5. Synthesis of (R)-Nicotinic acid 2-hydroxy-3-(4,4,4-trifluoro-butyrylamino-3,4-dihydro-2H -benzo[e][1,2]oxa-borinine-8-carbonyloxymethyl ester.

Prepared from nicotinic acid 2-methoxy-3-[2-(4,4,4-trifluoro-butyrylamino)-2-(2,9,9-trimethyl -3,5-dioxa-4-bora-tricyclo[6.1.1.02,6]dec-4-yl)-ethyl]-benzoyloxymethyl ester and 48% hydrobromic acid in water following the procedure in Step 5 of Example 37. The crude product was purified by reverse phase preparative HPLC and dried using lyophilization to give the title compound. ESI-MS m/z 467 (MH)+.

Example 94: (5-Isobutyl-2-oxo-1,3-dioxo1-4-Amethyl (R)-3-(3,3-difluorobutanamido)-2-hydroxy -3,4-dihydro-2H-benzo[e][1,2]oxaborinine-8-carboxylate

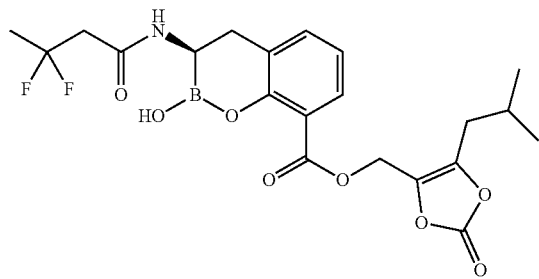 [SMILES: CC(C)Cc1oc(=O)oc1COC(=O)c1cccc2c1OB(O)[C@@H](NC(=O)CC(C)(F)F)C2]

(5-Isobutyl-2-oxo-1,3-dioxo1-4-yl)methyl (R)-3-(3,3-difluorobutanamido)-2-hydroxy-3,4-dihydro -2H -benzo[e][1,2]oxaborinine-8-carboxylate was prepared from (R)-3-(3,3-difluorobutanamido)-2-hydroxy-3,4-dihydro-2H-benzo[e][1,2]oxaborinine-8-carboxylic acid (Example 3) and 4-(bromomethyl)-5-isobutyl-1,3-dioxol-2-one by a procedure similar to Example 5. ESI-MS m/z 490 (M+Na)+.

Example 95: (R)-3-(4,4-Difluoro-pentanoylamino)-2-hydroxy-3,4-dihydro-2H -benzo[e][1,2]oxaborinine-8-carboxylic acid acetoxymethyl ester

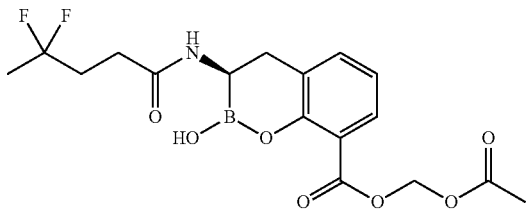 [SMILES: CC(=O)OCOC(=O)c1cccc2c1OB(O)[C@@H](NC(=O)CCC(C)(F)F)C2]

Step 1. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid acetoxymethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid (Steps 1 and 2 of Example 25) and bromomethylacetate following the procedure in Step 3 of Example 25. The crude product was purified by flash chromatography on silica gel (70% ethyl acetate/hexane). ESI-MS m/z 566 (MH)+.

Step 2. Synthesis of (R)-3-(4,4-Difluoro-pentanoylamino)-2-hydroxy-3,4-dihydro-2H -benzo[e][1,2]oxaborinine-8-carboxylic acid acetoxymethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid acetoxymethyl ester and 48% hydrobromic acid in water following the procedure in Step 5 of Example 37. The crude product was purified by reverse phase preparative HPLC and dried using lyophilization to give the title compound. ESI-MS m/z 422 (M+Na)+.

Example 96: (R)-3-(4,4-Difluoro-pentanoylamino)-2-hydroxy-3,4-dihydro-2H -benzo[e][1,2]oxaborinine-8-carboxylic acid 2-ethoxy-2-methyl-propionyloxymethyl ester

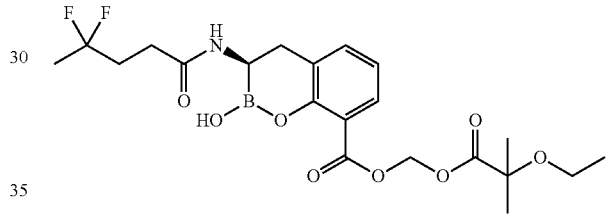

Step 1. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 4,4-difluoropentanoic acid following the procedure in Step 1 of Example 1. The crude product was purified by flash chromatography on silica gel (50% ethyl acetate/hexane). ESI-MS m/z 550 (MH)+.

Step 2. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid tert-butyl ester and 4N HCl/dioxane following the procedure in Step 2 of Example 13. ESI-MS m/z 494 (MH)+.

Step 3. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy benzoic acid chloromethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 542 (MH)+.

Step 4. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-benzoic acid 2-ethoxy-2-methyl-propionyloxymethyl ester.

Prepared from 3-[2-(4,4-difluoro-pentanoylamino)-2-(2,9,9-trimethyl-3,5-dioxa-4-bora-tricyclo[6.1.1.02,6]dec-4-yl)-ethyl]-2-methoxy benzoic acid chloromethyl ester and 2-ethoxy-2methylpropanoic acid following the procedure in Step 4 of Example 13. The crude product was purified by flash chromatography on silica gel with preparative TLC plates (5% methanol/dichloromethane). ESI-MS m/z 638 (MH)+.

Step 5. Synthesis of (R)-3-(4,4-Difluoro-pentanoylamino)-2-hydroxy-3,4-dihydro-2H-benzo[e][1,2]oxaborinine-8-carboxylic acid 2-ethoxy-2-methyl-propionyloxymethyl ester.

Prepared from 3-[2-(4,4-difluoro-pentanoylamino)-2-(2,9,9-trimethyl-3,5-dioxa-4-bora-tricyclo[6.1.1.02,6]dec-4-yl)-ethyl]-benzoic acid 2-ethoxy-2-methyl-propionyloxymethyl ester and 48% hydrobromic acid in water following the procedure in Step 5 of Example 37. The crude product was purified by reverse phase preparative HPLC and dried using lyophilization to give the title compound. ESI-MS m/z 494 (M+Na)+.

Example 97: (R)-3-(4,4-Difluoro-pentanoylamino)-2-hydroxy-3,4-dihydro-2H-benzo[e][1,2]oxaborinine-8-carboxylic acid benzoyloxymethyl ester

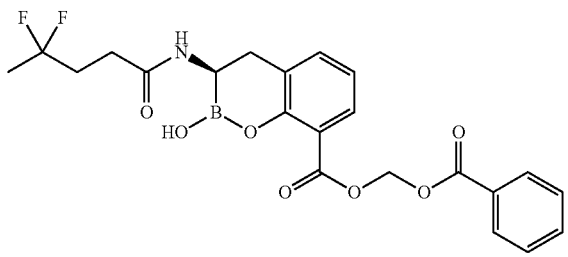 [SMILES: CC(F)(F)CCC(=O)N[C@H]1Cc2cccc(C(=O)OCOC(=O)c3ccccc3)c2OB1O]

Step 1. Synthesis of 3-[2-(4,4-Difluoro-pentanoylamino)-2-(2,9,9-trimethyl-3,5-dioxa-4-bora-tricyclo[6.1.1.02,6]dec-4-yl)-ethyl]-2-methoxy-benzoic acid benzoyloxymethyl ester.

Prepared from 3-[2-(4,4-difluoro-pentanoylamino)-2-(2,9,9-trimethyl-3,5-dioxa-4-bora-tricyclo[6.1.1.02,6]dec-4-yl)-ethyl]-2-methoxy-benzoic acid (Steps 1 and 2 of Example 25) and chloromethylbenzoic acid following the procedure in Step 3 of Example 25. The crude product was purified by flash chromatography on silica gel with preparative TLC plates (30% ethyl acetate/hexanes). ESI-MS m/z 628 (MH)+.

Step 2. Synthesis of (R)-3-(4,4-Difluoro-pentanoylamino)-2-hydroxy-3,4-dihydro-2H-benzo[e][1,2]oxaborinine-8-carboxylic acid benzoyloxymethyl ester.

Prepared from 3-[2-(4,4-difluoro-pentanoylamino)-2-(2,9,9-trimethyl-3,5-dioxa-4-bora-tricyclo[6.1.1.02,6]dec-4-yl)-ethyl]-2-methoxy-benzoic acid benzoyloxymethyl ester and 48% hydrobromic acid in water following the procedure in Step 5 of Example 37. The crude product was purified by reverse phase preparative HPLC and dried using lyophilization to give the title compound. ESI-MS m/z 484 (M+Na)+.

Example 98: (R)-3-(4,4-Difluoro-pentanoylamino)-2-hydroxy-3,4-dihydro-2H-benzo[e][1,2]oxaborinine-8-carboxylic acid butoxycarbonyloxymethyl ester

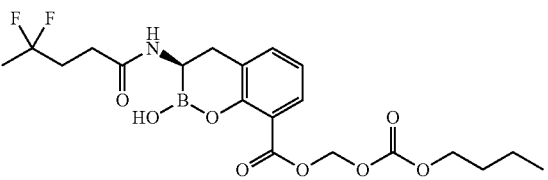 [SMILES: CCCCOC(=O)OCOC(=O)c1cccc2c1OB(O)[C@@H](NC(=O)CCC(C)(F)F)C2]

Step 1. Synthesis of 3-[2-(4,4-Difluoro-pentanoylamino)-2-(2,9,9-trimethyl-3,5-dioxa-4-bora-tricyclo[6.1.1.02,6]dec-4-yl)-ethyl]-2-methoxy-benzoic acid butoxycarbonyloxymethyl ester.

Prepared from 3-[2-(4,4-difluoro-pentanoylamino)-2-(2,9,9-trimethyl-3,5-dioxa-4-bora-tricyclo[6.1.1.02,6]dec-4-yl)-ethyl]-2-methoxy-benzoic acid (Steps 1 and 2 of Example 25) and butylchloromethyl carbonate following the procedure in Step 3 of Example 25. The crude product was purified by flash chromatography on silica gel with preparative TLC plates (30% ethyl acetate/hexanes). ESI-MS m/z 624 (MH)+.

Step 2. Synthesis of (R)-3-(4,4-Difluoro-pentanoylamino)-2-hydroxy-3,4-dihydro-2H-benzo[e][1,2]oxaborinine-8-carboxylic acid butoxycarbonyloxymethyl ester.

Prepared from 3-[2-(4,4-difluoro-pentanoylamino)-2-(2,9,9-trimethyl-3,5-dioxa-4-bora-tricyclo[6.1.1.02,6]dec-4-yl)-ethyl]-2-methoxy-benzoic acid butoxycarbonyloxymethyl ester and 48% hydrobromic acid in water following the procedure in Step 5 of Example 37. The crude product was purified by reverse phase preparative HPLC and dried using lyophilization to give the title compound. ESI-MS m/z 480 (M+Na)+.

Example 99: (R)-3-(4,4-Difluoro-pentanoylamino)-2-hydroxy-3,4-dihydro-2H-benzo[e][1,2]oxaborinine-8-carboxylic acid cyclohexyloxycarbonyloxymethyl ester

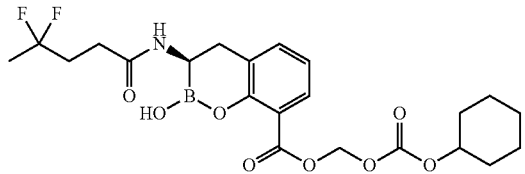 [SMILES: CC(F)(F)CCC(=O)N[C@H]1Cc2cccc(C(=O)OCOC(=O)OC3CCCCC3)c2OB1O]

Step 1. Synthesis of 3-[2-(4,4-Difluoro-pentanoylamino)-2-(2,9,9-trimethyl-3,5-dioxa-4-bora-tricyclo[6.1.1.02,6]dec-4-yl)-ethyl]-2-methoxy-benzoic acid cyclohexyloxycarbonyloxymethyl ester.

Prepared from 3-[2-(4,4-difluoro-pentanoylamino)-2-(2,9,9-trimethyl-3,5-dioxa-4-bora-tricyclo[6.1.1.02,6]dec-4-yl)-ethyl]-2-methoxy-benzoic acid (Steps 1 and 2 of Example 25) and chloromethylcyclohexyl carbonate following the procedure in Step 3 of Example 25. The crude product was purified by flash chromatography on silica gel with preparative TLC plates (30% ethyl acetate/hexanes). ESI-MS m/z 650 (MH)+.

Step 2. Synthesis of (R)-3-(4,4-Difluoro-pentanoylamino)-2-hydroxy-3,4-dihydro-2H -benzo[e][1,2]oxaborinine-8-carboxylic acid cyclohexyloxycarbonyloxymethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid cyclohexyloxycarbonyloxymethyl ester and 48% hydrobromic acid in water following the procedure in Step 5 of Example 37. The crude product was purified by reverse phase preparative HPLC and dried using lyophilization to give the title compound. ESI -MS m/z 506 (M+Na)$^+$.

Example 100: (5-Isobutyl-2-oxo-1,3-dioxol-4-yl) methyl (R)-3-(4,4-difluoropentanamido)-2-hydroxy-3,4-dihydro-2H-benzo[e][1,2]oxaborinine-8-carboxylate

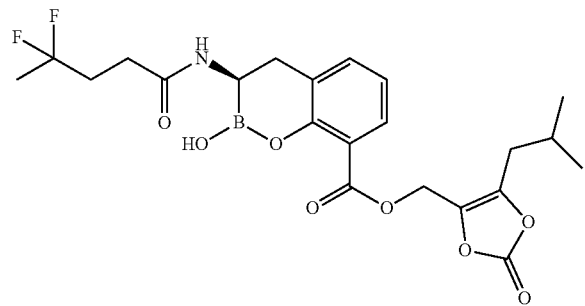 [SMILES: CC(C)Cc1oc(=O)oc1COC(=O)c1cccc2c1OB(O)[C@@H](NC(=O)CCC(C)(F)F)C2]

(5-Isobutyl-2-oxo-1,3-dioxol-4-yl)methyl (R)-3-(4,4-difluoropentanamido)-2-hydroxy-3,4-dihydro-2H-benzo[e][1,2]oxaborinine-8-carboxylate was prepared from 3-((R)-2-(4,4-difluoropentanamido) -2-((3aS,4S,6S,7aR)-3a,5,5-trimethylhexahydro-4,6-methanobenzo[d][1,3,2] dioxaborol-2-yl)ethyl)-2-ethoxybenzoic acid and 4-(bromomethyl)-5-isobutyl-1,3-dioxol-2-one by a procedure similar to Example 86. ESI-MS m/z 504 (M+Na)$^+$.

Example 101: (R)-Nicotinic acid 3-(4,4-difluoropentanoylamino)-2-hydroxy-3,4-dihydro-2H -benzo[e][1,2]oxaborinine-8-carbonyloxymethyl ester

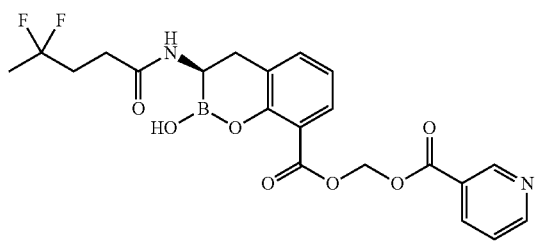 [SMILES: CC(F)(F)CCC(=O)N[C@H]1Cc2cccc(C(=O)OCOC(=O)c3cccnc3)c2OB1O]

Step 1. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and 4,4-difluoropentanoic acid following the procedure in Step 1 of Example 1. The crude product was purified by flash chromatography on silica gel (50% ethyl acetate/hexane). ESI-MS m/z 550 (MH)$^+$.

Step 2. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy-benzoic acid.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid tert-butyl ester and 4N HCl/dioxane following the procedure in Step 2 of Example 13. ESI-MS m/z 494 (MH)$^+$.

Step 3. Synthesis of 3-[2-(4,4-Difluoro-pentanoylamino)-2-(2,9,9-trimethyl-3,5-dioxa-4-bora -tricyclo[6.1.1.02,6]dec-4-yl)-ethyl]-2-methoxy benzoic acid chloromethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 542 (MH)$^+$.

Step 4. Synthesis of Nicotinic acid 3-[2-(4,4-difluoro-pentanoylamino)-2-(2,9,9-trimethyl-3,5-dioxa-4-bora-tricyclo [6.1.1.02,6]dec-4-yl)-ethyl]-benzoic acid 2-methoxy-benzoyloxymethyl ester.

Prepared from 3-[2-(4,4-difluoro-pentanoylamino)-2-(2,9,9-trimethyl-3,5-dioxa-4-bora -tricyclo[6.1.1.02,6]dec-4-yl)-ethyl]-2-methoxy benzoic acid chloromethyl ester and nicotinic acid following the procedure in Step 4 of Example 13. The crude product was purified by flash chromatography on silica gel with preparative TLC plates (6% methanol/dichloromethane). ESI-MS m/z 629 (MH)$^+$.

Step 5. Synthesis of (R)-Nicotinic acid 3-(4,4-difluoropentanoylamino)-2-hydroxy-3,4-dihydro-2H -benzo[e][1,2] oxaborinine-8-carbonyloxymethyl ester.

Prepared from nicotinic acid 3-[2-(4,4-difluoro-pentanoylamino)-2-(2,9,9-trimethyl-3,5-dioxa-4-bora-tricyclo [6.1.1.02,6]dec-4-yl)-ethyl]-benzoic acid 2-methoxy-benzoyloxymethyl ester and 48% hydrobromic acid in water following the procedure in Step 5 of Example 37. The crude product was purified by reverse phase preparative HPLC and dried using lyophilization to give the title compound. ESI-MS m/z 463 (MH)$^+$.

Example 102: (3R)-3-(2-fluoropropanamido)-2-hydroxy-3,4-dihydro-2H -benzo[e][1,2]oxaborinine-8-carboxylic acid

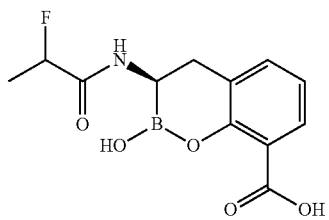 [SMILES: CC(F)C(=O)N[C@H]1Cc2cccc(C(=O)O)c2OB1O]

(3R)-3-(2-Fluoropropanamido)-2-hydroxy-3,4-dihydro-2H-benzo[e][1,2]oxaborinine-8-carboxylic acid was prepared as a mixture of diastereoisomers in a ~1:1 ratio from [(1,9-2-(3-tert-butoxycarbonyl-2-methoxy-phenyl)-1-chloro-ethyl]boronic acid (+) pinanediol ester and 2-fluoropropanoic acid by a procedure similar to Example 1. ESI-MS m/z 282 (MH)$^+$.

Example 103: 2-Morpholinoethyl (R)-2-hydroxy-3-propionamido-3,4-dihydro-2H-benzo[e][1,2]oxaborinine-8-carboxylate

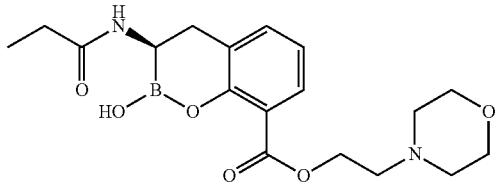 [SMILES: CCC(=O)N[C@H]1Cc2cccc(C(=O)OCCN3CCOCC3)c2OB1O]

2-morpholinoethyl (R)-2-hydroxy-3-propionamido-3,4-dihydro-2H-benzo[e][1,2]oxaborinine-8-carboxylate was prepared from (R)-2-hydroxy-3-propionamido-3,4-dihydro-2H-benzo[e][1,2]oxaborinine-8-carboxylic acid and 4-(2-bromoethyl)morpholine by a procedure similar to Example 5. ESI-MS m/z 377 (MH)+.

Example 104: 2-(Methylsulfonyl)ethyl (R)-2-hydroxy-3-propionamido-3,4-dihydro-2H-benzo[e][1,2]oxaborinine-8-carboxylate

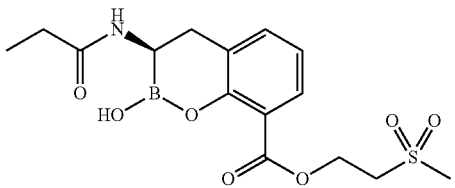 [SMILES: CCC(=O)N[C@H]1Cc2cccc(C(=O)OCCS(C)(=O)=O)c2OB1O]

2-(Methylsulfonyl)ethyl (R)-2-hydroxy-3-propionamido-3,4-dihydro-2H-benzo[e][1,2]oxaborinine-8-carboxylate was prepared from 2-methoxy-3-((R)-2-propionamido-2-((3aS,4S,6S,7aR)-3a,5,5-trimethylhexahydro-4,6-methanobenzo[d][1,3,2]dioxaborol-2-yl)ethyl)benzoic acid and (methylsulfonyl) ethene by a procedure similar to Example 25, except for using $Cs_2CO_3$ instead of triethylamine in Step 3. ESI-MS m/z 392 (M+Na)+.

Example 105: (5-Isobutyl-2-oxo-1,3-dioxol-4-yl)methyl (R)-2-hydroxy-3-propionamido-3,4-dihydro-2H-benzo[e][1,2]oxaborinine-8-carboxylate

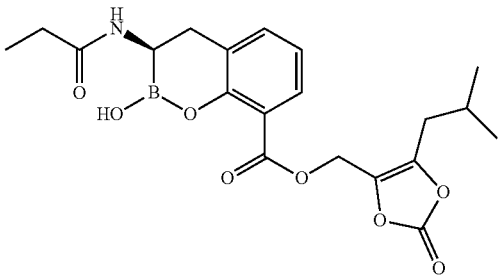 [SMILES: CCC(=O)N[C@H]1Cc2cccc(C(=O)OCc3oc(=O)oc3CC(C)C)c2OB1O]

(5-Isobutyl-2-oxo-1,3-dioxol-4-yl)methyl (R)-2-hydroxy-3-propionamido-3,4-dihydro-2H-benzo[e][1,2]oxaborinine-8-carboxylate was prepared from (R)-2-hydroxy-3-propionamido-3,4-dihydro-2H-benzo[e][1,2]oxaborinine-8-carboxylic acid and 4-(bromomethyl)-5-isobutyl-1,3-dioxol-2-one by a procedure similar to Example 5. ESI-MS m/z 440 (M+Na)+.

Example 106: (R)-2-Hydroxy-3-propionylamino-3,4-dihydro-2H-benzo[e][1,2]oxaborinine-8-carboxylic acid 4,4-difluoro-butyryloxymethyl ester

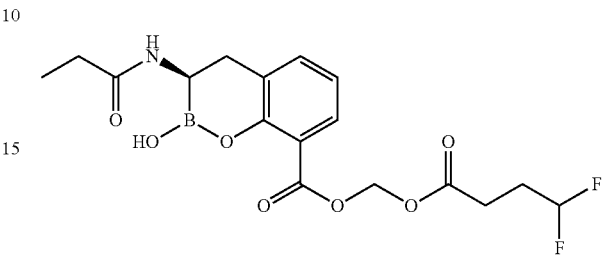

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1 S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (50% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 478 (MH)+.

Step 4. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid 4,4-difluoro-butyryloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid chloromethyl ester and 4,4-difluorobutanoic acid following the procedure in Step 4 of Example 13. The crude product was purified by flash chromatography on silica gel with preparative TLC plates (5% methanol/dichloromethane). ESI-MS m/z 566 (MH)+.

Step 5. Synthesis of (R)-2-Hydroxy-3-propionylamino-3,4-dihydro-2H-1-oxa-2-bora-naphthalene-8-carboxylic acid 4,4-difluoro-butyryloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid 4,4-difluoro-butyryloxymethyl ester and 48% hydrobromic acid in water following the procedure in Step 5 of Example 37. The crude product was purified by reverse phase preparative HPLC and dried using lyophilization to give the title compound. ESI-MS m/z 422 (M+Na)+.

Example 107: (R)-2-Hydroxy-3-propionylamino-3,4-dihydro-2H-benzo[e][1,2]oxaborinine-8-carboxylic acid 3-fluoro-propionyloxymethyl ester

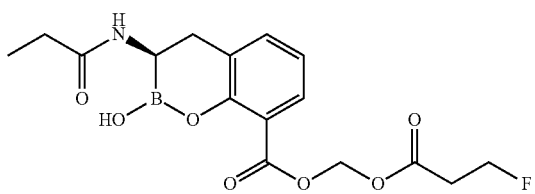 [SMILES: CCC(=O)N[C@H]1Cc2cccc(C(=O)OCOC(=O)CCF)c2OB1O]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (50% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 478 (MH)+.

Step 4. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid 3-fluoro-propionyloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid chloromethyl ester and 3-fluoropropanoic acid following the procedure in Step 4 of Example 13. The crude product was purified by flash chromatography on silica gel with preparative TLC plates (50%ethyl acetate/hexane). ESI-MS m/z 534 (MH)+.

Step 5. Synthesis of (R)-2-Hydroxy-3-propionylamino-3,4-dihydro-2H-benzo[e][1,2]oxaborinine-8-carboxylic acid 3-fluoro-propionyloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid 3-fluoro-propionyloxymethyl ester and 48% hydrobromic acid in water following the procedure in Step 5 of Example 37. The crude product was purified by reverse phase preparative HPLC and dried using lyophilization to give the title compound. ESI-MS m/z 390 (M+Na)+.

Example 108: (R)-2-Hydroxy-3-propionylamino-3,4-dihydro-2H-benzo[e][1,2]oxaborinine-8-carboxylic acid 1-ethyl-propoxy-carbonyloxymethyl ester

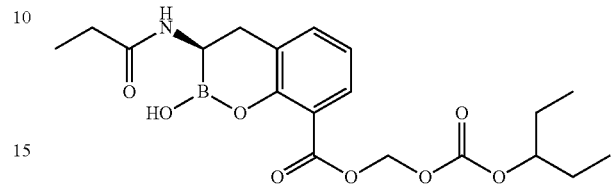

Step 1. Synthesis of chloromethyl pentan-3-yl carbonate.

To chloromethyl chloroformate (1 g, 7.8 mmol) in dichloromethane (2.3 mL) under an atmosphere of argon at 0 °C. was added 3-pentanol (0.86 mL, 7.8 mmol) dropwise, followed by pyridine (0.62 mL, 7.8 mmol) dropwise and slowly warmed to room temperature overnight. The white suspension was diluted with dichloromethane, washed with aq. citric acid, followed by aq. sodium bicarbonate, and brine then dried over sodium sulfate, and concentrated to give a pale yellow oil. Step 2. Synthesis of 2-Methoxy-3-[2-propionylamino-2-(2,9,9-trimethyl-3,5-dioxa-4-bora -tricyclo [6.1.1.02,6]dec-4-yl)-ethyl]-benzoic acid 1-ethyl-propoxy-carbonyloxymethyl ester.

Prepared from 2-methoxy-3-[2-prop ionylamino-2-(2,9,9-trimethyl-3,5-dioxa-4-bora -tricyclo[6.1.1.02,6]dec-4-yl)-ethyl]-benzoic acid (Steps 1 and 2 of Example 25) and chloromethyl pentan-3-yl carbonate (Step 1 of Example 108) following the procedure in Step 3 of Example 25. The crude product was purified by flash chromatography on silica gel with preparative TLC plates (30% ethyl acetate/hexane). ESI-MS m/z 574 (MH)+.

Step 3. Synthesis of (R)-2-Hydroxy-3-propionylamino-3,4-dihydro-2H-benzo[e][1,2]oxaborinine-8-carboxylic acid 1-ethyl-propoxy-carbonyloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid 1-ethyl-propoxy-carbonyloxymethyl ester and 48% hydrobromic acid in water following the procedure in Step 5 of Example 37. The crude product was purified by reverse phase preparative HPLC and dried using lyophilization to give the title compound. ESI-MS m/z 430 (M+Na)+.

Example 109: (R)-2-Hydroxy-3-propionylamino-3,4-dihydro-2H-benzo[e][1,2]oxaborinine-8-carboxylic acid cyclopentanecarbonyloxymethyl ester

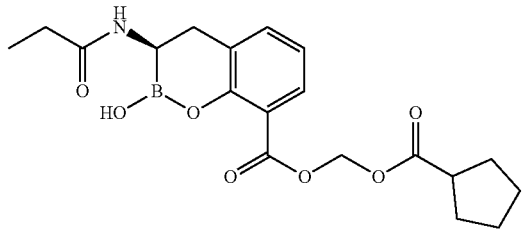 [SMILES: CCC(=O)N[C@H]1Cc2cccc(C(=O)OCOC(=O)C3CCCC3)c2OB1O]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (50% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid chloromethyl ester.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 478 (MH)+.

Step 4. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid cyclopentanecarbonyloxymethyl ester.

Prepared from 3-[2-propionylamino-2-(2,9,9-trimethyl-3,5-dioxa-4-b ora-tricyclo [6.1.1.02,6]dec -4-yl)-ethyl]-2-methoxy-benzoic acid chloromethyl ester and cyclopentanecarboxylic acid following the procedure in Step 4 of Example 13. The crude product was purified by flash chromatography on silica gel with preparative TLC plates (50%ethyl acetate/hexane). ESI-MS m/z 556 (MH)+.

Step 5. Synthesis of (R)-2-Hydroxy-3-propionylamino-3,4-dihydro-2H-benzo[e][1,2]oxaborinine-8-carboxylic acid cyclopentanecarbonyloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid cyclopentanecarbonyloxymethyl ester and 48% hydrobromic acid in water following the procedure in Step 5 of Example 37. The crude product was purified by reverse phase preparative HPLC and dried using lyophilization to give the title compound. ESI-MS m/z 412 (M+Na)+.

Example 110: (R)-2-Hydroxy-3-propionylamino-3,4-dihydro-2H-benzo[e][1,2]oxaborinine-8-carboxylic acid cyclopentyloxycarbonyloxymethyl ester

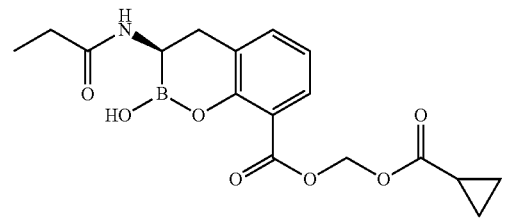

Step 1. Synthesis of 2-Methoxy-3-[2-propionylamino-2-(2,9,9-trimethyl-3,5-dioxa-4-bora -tricyclo[6.1.1.02,6]dec-4-yl)-ethyl]-benzoic acid cyclopentyloxycarbonyloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid (Steps 1 and 2 of Example 25) and chloromethyl cyclopentyl carbonate (Step 1 of Example 108) following the procedure in Step 3 of Example 25. The crude product was purified by flash chromatography on silica gel with preparative TLC plates (30% ethyl acetate/hexane). ESI-MS m/z 572 (MH)+.

Step 2. Synthesis of (R)-2-Hydroxy-3-propionylamino-3,4-dihydro-2H-benzo[e][1,2]oxaborinine-8-carboxylic acid cyclopentyloxycarbonyloxymethyl ester.

Prepared from 2-methoxy-3-[2-propionylamino-2-(2,9,9-trimethyl-3,5-dioxa-4-bora -tricyclo[6.1.1.02,6]dec-4-yl)-ethyl]-benzoic acid cyclopentyloxycarbonyloxymethyl ester and 48% hydrobromic acid in water following the procedure in Step 5 of Example 37. The crude product was purified by reverse phase preparative HPLC and dried using lyophilization to give the title compound. ESI-MS m/z 428 (M+Na)+.

Example 111: (R)-2-Hydroxy-3-propionylamino-3,4-dihydro-2H-benzo[e][1,2]oxaborinine-8-carboxylic acid cyclopropanecarbonyloxymethyl ester

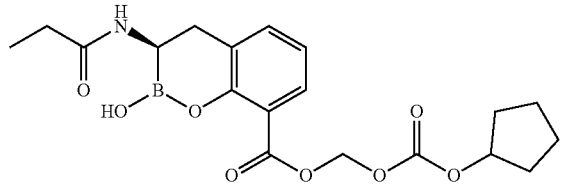 [SMILES: CCC(=O)N[C@H]1Cc2cccc(C(=O)OCOC(=O)OC3CCCC3)c2OB1O]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (50% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 478 (MH)+.

Step 4. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid cyclopropanecarbonyloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid chloromethyl ester and cyclopropanecarboxylic acid following the procedure in Step 4 of Example 13. The crude product was purified by flash chromatography on silica gel with preparative TLC plates (70%ethyl acetate/hexane). ESI-MS m/z 528 (MH)+.

Step 5. Synthesis of (R)-2-Hydroxy-3-propionylamino-3,4-dihydro-2H-benzo[e][1,2]oxaborinine-8-carboxylic acid cyclopropanecarbonyloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid cyclopropanecarbonyloxymethyl ester and 48% hydrobromic acid in water following the procedure in Step 5 of Example 37. The crude product was purified by reverse phase preparative HPLC and dried using lyophilization to give the title compound. ESI-MS m/z 384 (M+Na)+.

Example 112: (R)-2-Hydroxy-3-propionylamino-3,4-dihydro-2H-benzo[e][1,2]oxaborinine-8-carboxylic acid cyclobutanecarbonyloxymethyl ester

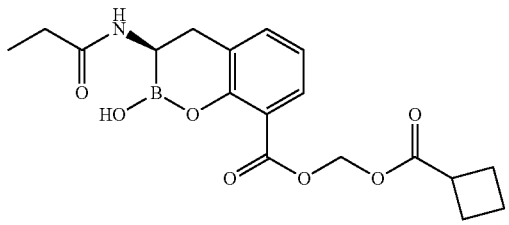 [SMILES: CCC(=O)N[C@H]1Cc2cccc(C(=O)OCOC(=O)C3CCC3)c2OB1O]

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (50% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 478 (MH)+.

Step 4. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid cyclobutanecarbonyloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid chloromethyl ester and cyclobutanecarboxylic acid following the procedure in Step 4 of Example 13. The crude product was purified by flash chromatography on silica gel with preparative TLC plates (60%ethyl acetate/hexane). ESI-MS m/z 542 (MH)+.

Step 5. Synthesis of (R)-2-Hydroxy-3-propionylamino-3,4-dihydro-2H-benzo[e][1,2]oxaborinine-8-carboxylic acid cyclobutanecarbonyloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid cyclobutanecarbonyloxymethyl ester and 48% hydrobromic acid in water following the procedure in Step 5 of Example 37. The crude product was purified by reverse phase preparative HPLC and dried using lyophilization to give the title compound. ESI-MS m/z 398 (M+Na)+.

Example 113: (R)-Nicotinic acid 2-Hydroxy-3-propionylamino-3,4-dihydro-2H -benzo[e][1,2]oxaborinine-8-carbonyloxymethyl ester

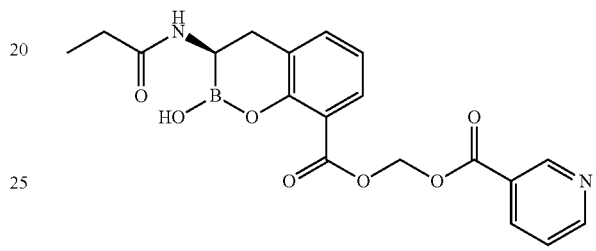

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (50% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid chloromethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 478 (MH)+.

Step 4. Synthesis of Nicotinic acid 2-methoxy-3-[2-propionylamino-2-(2,9,9-trimethyl-3,5-dioxa-4-bora-tricyclo [6.1.1.02,6]dec-4-yl)-ethyl]-benzoyloxymethyl ester.

Prepared from 3-[2-propionylamino-2-(2,9,9-trimethyl-3,5-dioxa-4-bora-tricyclo[6.1.1.02,6]dec -4-yl)-ethyl]-2-methoxy-benzoic acid chloromethyl ester and nicotinic acid following the procedure in Step 4 of Example 13. The crude product was purified by flash chromatography on silica gel with preparative TLC plates (6% methanol/dichloromethane). ESI-MS m/z 565 (MH)+.

Step 5. Synthesis of (R)-Nicotinic acid 2-Hydroxy-3-propionylamino-3,4-dihydro-2H-benzo[e][1,2]oxaborinine-8-carbonyloxymethyl ester.

Prepared from nicotinic acid 2-methoxy-3-[2-propionylamino-2-(2,9,9-trimethyl-3,5-dioxa-4-bora-tricyclo[6.1.1.02,6]dec-4-yl)-ethyl]-benzoyloxymethyl ester and 48% hydrobromic acid in water following the procedure in Step 5 of Example 37. The crude product was purified by reverse phase preparative HPLC and dried using lyophilization to give the title compound. ESI-MS m/z 399 (MH)+.

Example 114: (R)-2-Hydroxy-3-propionylamino-3,4-dihydro-2H-benzo[e][1,2]oxaborinine-8-carboxylic acid cyclopropoxycarbonyloxymethyl ester

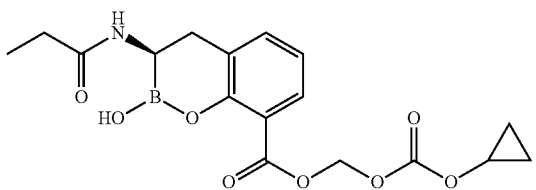 [SMILES: CCC(=O)N[C@H]1Cc2cccc(C(=O)OCOC(=O)OC3CC3)c2OB1O]

Step 1. Synthesis of 2-Methoxy-3-[2-propionylamino-2-(2,9,9-trimethyl-3,5-dioxa-4-bora-tricyclo[6.1.1.02,6]dec-4-yl)-ethyl]-benzoic acid cyclopropoxycarbonyloxymethyl ester.

Prepared from 2-methoxy-3-[2-propionylamino-2-(2,9,9-trimethyl-3,5-dioxa-4-bora-tricyclo[6.1.1.02,6]dec-4-yl)-ethyl]-benzoic acid (Steps 1 and 2 of Example 25) and chloromethyl cyclopropyl carbonate (Step 1 of Example 108) following the procedure in Step 3 of Example 25. The crude product was purified by flash chromatography on silica gel with preparative TLC plates (70% ethyl acetate/hexane). ESI-MS m/z 544 (MH)+.

Step 2. Synthesis of (R)-2-Hydroxy-3-propionylamino-3,4-dihydro-2H-benzo[e][1,2]oxaborinine-8-carboxylic acid cyclopropoxycarbonyloxymethyl ester.

Prepared from 2-methoxy-3-[2-propionylamino-2-(2,9,9-trimethyl-3,5-dioxa-4-bora-tricyclo[6.1.1.02,6]dec-4-yl)-ethyl]-benzoic acid cyclopropoxycarbonyloxymethyl ester and 48% hydrobromic acid in water following the procedure in Step 5 of Example 37. The crude product was purified by reverse phase preparative HPLC and dried using lyophilization to give the title compound. ESI-MS m/z 400 (M+Na)+.

Example 115: (R)-2-Hydroxy-3-propionylamino-3,4-dihydro-2H-benzo[e][1,2]oxaborinine-8-carboxylic acid cyclobutoxycarbonyloxymethyl ester

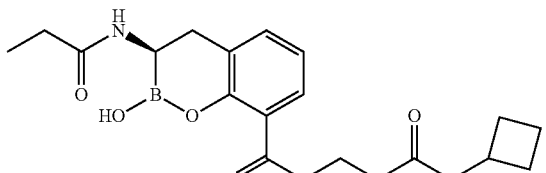

Step 1. Synthesis of 2-Methoxy-3-[2-propionylamino-2-(2,9,9-trimethyl-3,5-dioxa-4-bora-tricyclo[6.1.1.02,6]dec-4-yl)-ethyl]-benzoic acid cyclobutoxycarbonyloxymethyl ester.

Prepared from 2-methoxy-3-[2-propionylamino-2-(2,9,9-trimethyl-3,5-dioxa-4-bora-tricyclo[6.1.1.02,6]dec-4-yl)-ethyl]-benzoic acid (Steps 1 and 2 of Example 25) and chloromethyl cyclobutyl carbonate (Step 1 of Example 108) following the procedure in Step 3 of Example 25. The crude product was purified by flash chromatography on silica gel with preparative TLC plates (60% ethyl acetate/hexane). ESI-MS m/z 558 (MH)+.

Step 2. Synthesis of (R)-2-Hydroxy-3-propionylamino-3,4-dihydro-2H-benzo[e][1,2]oxaborinine-8-carboxylic acid cyclobutoxycarbonyloxymethyl ester.

Prepared from 2-methoxy-3-[2-propionylamino-2-(2,9,9-trimethyl-3,5-dioxa-4-bora-tricyclo[6.1.1.02,6]dec-4-yl)-ethyl]-benzoic acid cyclobutoxycarbonyloxymethyl ester and 48% hydrobromic acid in water following the procedure in Step 5 of Example 37. The crude product was purified by reverse phase preparative HPLC and dried using lyophilization to give the title compound. ESI-MS m/z 414 (M+Na)+.

Example 116: (R)-2-Hydroxy-3-propionylamino-3,4-dihydro-2H-benzo[e][1,2]oxaborinine-8-carboxylic acid 2-ethylsulfanyl-2-methyl-propionyloxymethyl ester

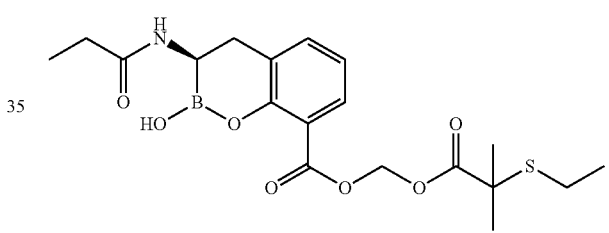

Step 1. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid tert-butyl ester.

Prepared from [(1S)-2-(3-tert-butoxycarbonyl-2-methoxy-phenyl)-1-chloro-ethyl]boronic acid (+) pinanediol ester and propionic acid following the procedure in Step 1 of Example 1. The crude product was purified by flash chromatography on silica gel (50% ethyl acetate/hexane). ESI-MS m/z 486 (MH)+.

Step 2. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid.

Prepared from 3-[2-propionylamino-2-(2,9,9-trimethyl-3,5-dioxa-4-b ora-tricyclo [6.1.1.02,6]dec-4-yl)-ethyl]-2-methoxy-benzoic acid tert-butyl ester and 4N HCl/dioxane following the procedure in Step 2 of Example 13. ESI-MS m/z 430 (MH)+.

Step 3. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid chloromethyl ester.

Prepared from 3-[2-propionylamino-2-(2,9,9-trimethyl-3,5-dioxa-4-bora-tricyclo [6.1.1.02,6]dec-4-yl)-ethyl]-2-methoxy-benzoic acid and chloroiodomethane following the procedure in Step 3 of Example 13. The crude product was purified by flash chromatography on silica gel (3% methanol/dichloromethane). ESI-MS m/z 478 (MH)+.

Step 4. Synthesis of 3-[2-Propionylamino-2-(2,9,9-trimethyl-3,5-dioxa-4-bora-tricyclo[6.1.1.02,6]dec-4-yl)-ethyl]-2-methoxy-benzoic acid 2-ethylsulfanyl-2-methyl-propionyloxymethyl ester.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid chloromethyl ester and 2-(ethylsulfanyl)-2-methyl-propanoic acid following the procedure in Step 4 of Example 13. The crude product was purified by flash chromatography on silica gel with preparative TLC plates (50%ethyl acetate/hexane). ESI-MS m/z 590 (MH)⁺.

Step 5. Synthesis of (R)-2-Hydroxy-3-propionylamino-3,4-dihydro-2H-benzo[e][1,2]oxaborinine-8-carboxylic acid 2-ethylsulfanyl-2-methyl-propionyloxymethyl ester.

Prepared from 3-[2-propionylamino-2-(2,9,9-trimethyl-3,5-dioxa-4-bora-tricyclo [6.1.1.02,6]dec -4-yl)-ethyl]-2-methoxy-benzoic acid 2-ethylsulfanyl-2-methyl-propionyloxymethyl ester and 48% hydrobromic acid in water following the procedure in Step 5 of Example 37. The crude product was purified by reverse phase preparative HPLC and dried using lyophilization to give the title compound. ESI-MS m/z 446 (M+Na)⁺.

Example 117: 2-Methyl-1-(propionyloxy)propyl (3R)-2-hydroxy-3-(5,5,5-trifluoropentanamido) -3,4-dihydro-2H-benzo [e][1,2]oxaborinine-8-carboxylate

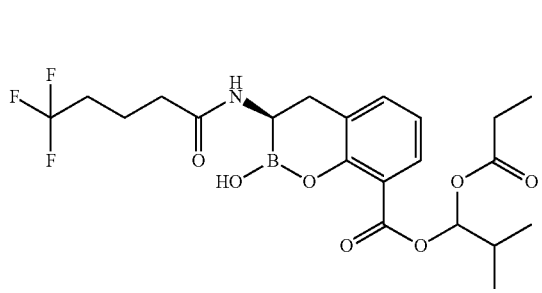 [SMILES: CCC(=O)OC(OC(=O)c1cccc2c1OB(O)[C@@H](NC(=O)CCCC(F)(F)F)C2)C(C)C]

2-Methyl-1-(propionyloxy)propyl (3R)-2-hydroxy-3-(5,5,5-trifluorop entanamido)-3 ,4-dihydro -2H-b enzo [e][1,2] oxaborinine-8-carboxylate was prepared as mixture of diastereoisomers in a ~1:1 ratio from 2-methoxy-3-((R)-2-(5,5,5-trifluoropentanamido)-2-((3aS,4S,6S,7aR)-3a,5,5-trimethylhexahydro-4,6-methanobenzo[d][1,3,2]dioxaborol-2-yl)ethyl)benzoic acid and 1-chloro-2-methylpropyl propionate by a procedure similar to Example 25. ESI-MS m/z 496.2 (M+Na)⁺.

TABLE 1

Examples of compounds of Formula (Ia), (IIa), (IIIa), (IVa), or (Va).

| Ex. | Structure | MW | ESI-MS (m/z) for [MH]+ |
|---|---|---|---|
| 1 | 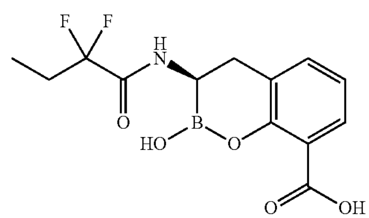 [SMILES: CCC(F)(F)C(=O)N[C@H]1Cc2cccc(C(=O)O)c2OB1O] | 313 | 314 |
| 2 | 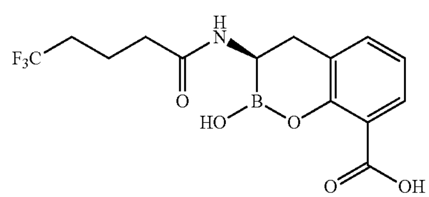 [SMILES: O=C(CCCC(F)(F)F)N[C@H]1Cc2cccc(C(=O)O)c2OB1O] | 345 | 346 |
| 3 | 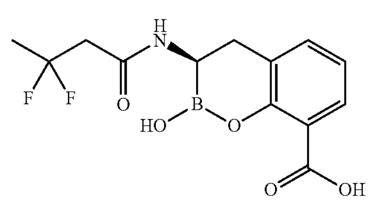 [SMILES: CC(F)(F)CC(=O)N[C@H]1Cc2cccc(C(=O)O)c2OB1O] | 313 | 314 |
| 4 | 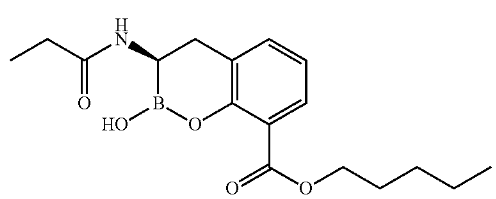 [SMILES: CCCCCOC(=O)c1cccc2c1OB(O)[C@@H](NC(=O)CC)C2] | 333 | 334 |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 5 | 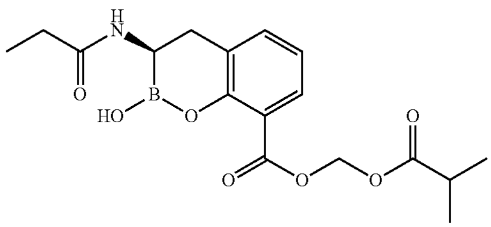 [SMILES: CCC(=O)N[C@H]1Cc2cccc(C(=O)OCOC(=O)C(C)C)c2OB1O] | 363 | 386 (+Na) |
| 6 | 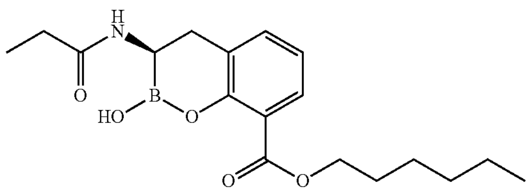 [SMILES: CCCCCCOC(=O)c1cccc2c1OB(O)[C@@H](NC(=O)CC)C2] | 347 | 348 |
| 7 | 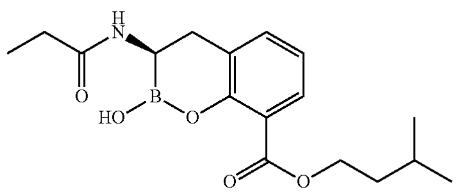 [SMILES: CCC(=O)N[C@H]1Cc2cccc(C(=O)OCCC(C)C)c2OB1O] | 333 | 334 |
| 8 | 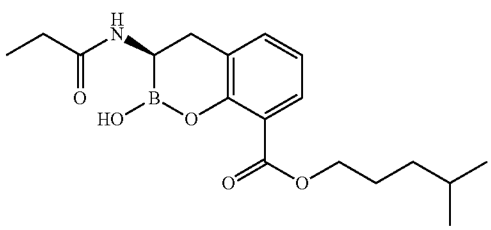 [SMILES: CCC(=O)N[C@H]1Cc2cccc(C(=O)OCCCC(C)C)c2OB1O] | 347 | 348 |
| 9 | 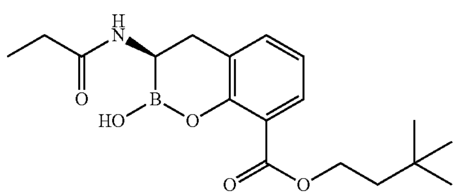 [SMILES: CCC(=O)N[C@H]1Cc2cccc(C(=O)OCCC(C)(C)C)c2OB1O] | 347 | 348 |
| 10 | 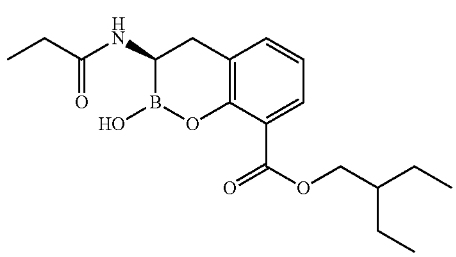 [SMILES: CCC(=O)N[C@H]1Cc2cccc(C(=O)OCC(CC)CC)c2OB1O] | 347 | 348 |
| 11 | 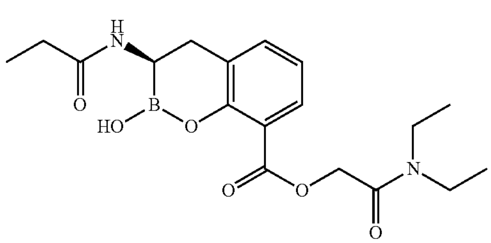 [SMILES: CCC(=O)N[C@H]1Cc2cccc(C(=O)OCC(=O)N(CC)CC)c2OB1O] | 376 | 377 |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 12 | 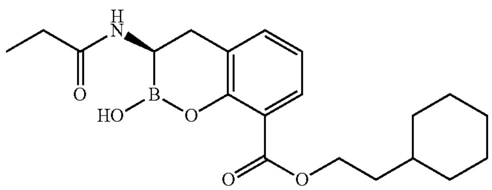 [SMILES: CCC(=O)N[C@H]1Cc2cccc(C(=O)OCCC3CCCCC3)c2OB1O] | 373 | 374 |
| 13 | 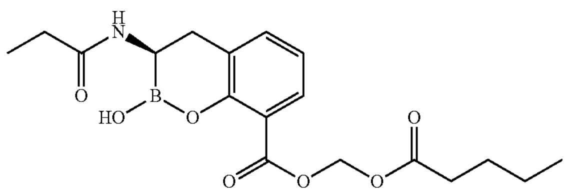 [SMILES: CCCCC(=O)OCOC(=O)c1cccc2c1OB(O)[C@@H](NC(=O)CC)C2] | 377 | 400 (+Na) |
| 14 | 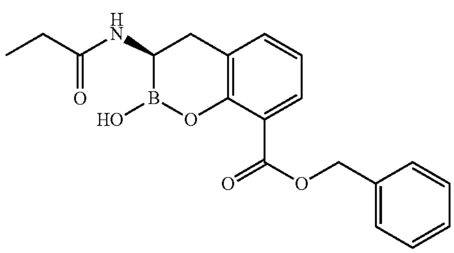 [SMILES: CCC(=O)N[C@H]1Cc2cccc(C(=O)OCc3ccccc3)c2OB1O] | 353 | 354 |
| 15 | 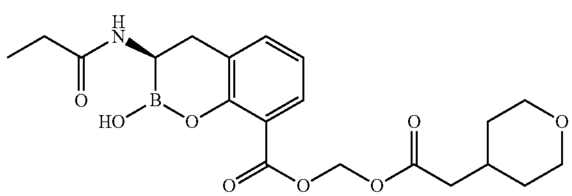 [SMILES: CCC(=O)N[C@H]1Cc2cccc(C(=O)OCOC(=O)CC3CCOCC3)c2OB1O] | 419 | 442 (+Na) |
| 16 | 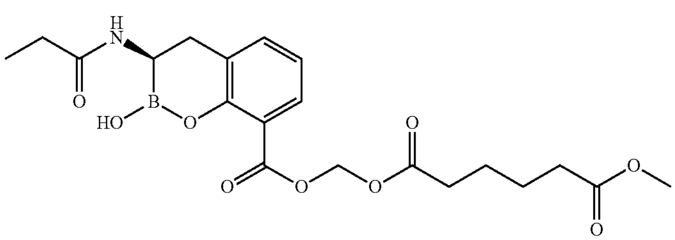 [SMILES: CCC(=O)N[C@H]1Cc2cccc(C(=O)OCOC(=O)CCCCC(=O)OC)c2OB1O] | 435 | 458 (+Na) |
| 17 | 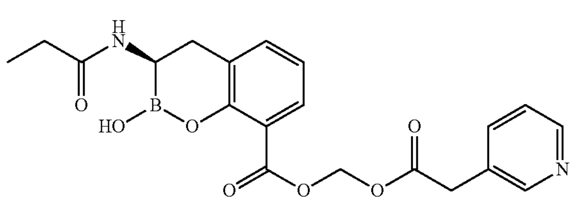 [SMILES: CCC(=O)N[C@H]1Cc2cccc(C(=O)OCOC(=O)Cc3cccnc3)c2OB1O] | 412 | 435 (+Na) |
| 18 | 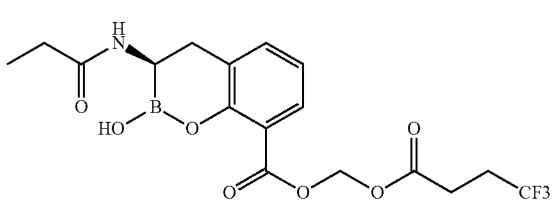 [SMILES: CCC(=O)N[C@H]1Cc2cccc(C(=O)OCOC(=O)CCC(F)(F)F)c2OB1O] | 417 | 440 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 19 | 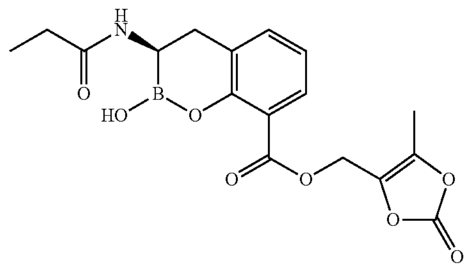 [SMILES: CCC(=O)N[C@H]1Cc2cccc(C(=O)OCc3oc(=O)oc3C)c2OB1O] | 375 | 398 (+Na) |
| 20 | 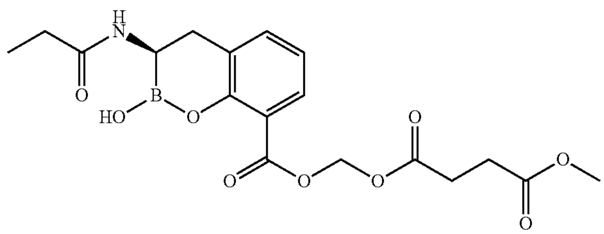 [SMILES: CCC(=O)N[C@H]1Cc2cccc(C(=O)OCOC(=O)CCC(=O)OC)c2OB1O] | 407 | 430 (+Na) |
| 21 | 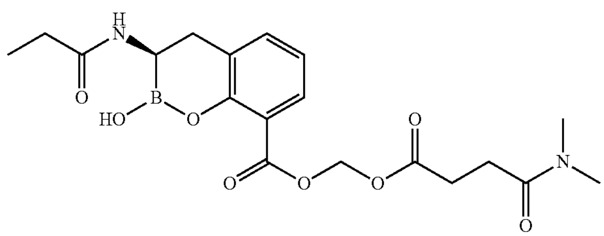 [SMILES: CCC(=O)N[C@H]1Cc2cccc(C(=O)OCOC(=O)CCC(=O)N(C)C)c2OB1O] | 420 | 443 (+Na) |
| 22 | 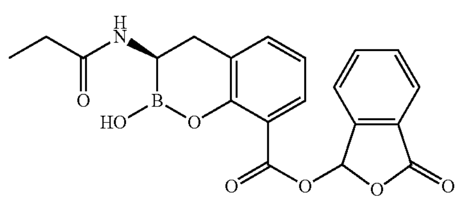 [SMILES: CCC(=O)N[C@H]1Cc2cccc(C(=O)OC3OC(=O)c4ccccc43)c2OB1O] | 395 | 396 |
| 23 | 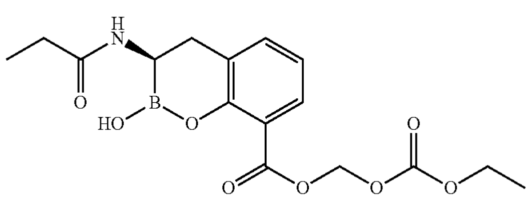 [SMILES: CCOC(=O)OCOC(=O)c1cccc2c1OB(O)[C@@H](NC(=O)CC)C2] | 365 | 388 (+Na) |
| 24 | 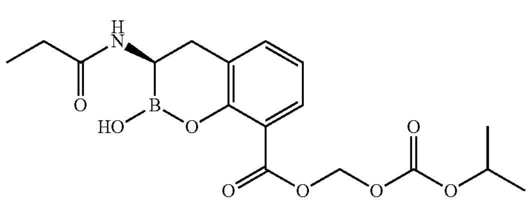 [SMILES: CCC(=O)N[C@H]1Cc2cccc(C(=O)OCOC(=O)OC(C)C)c2OB1O] | 379 | 402 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 25 | 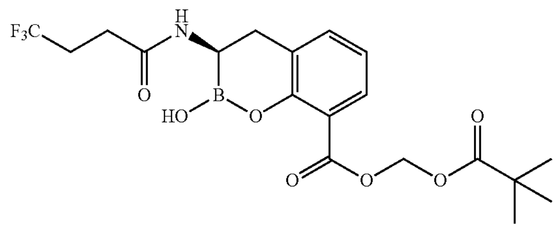 [SMILES: CC(C)(C)C(=O)OCOC(=O)c1cccc2c1OB(O)[C@@H](NC(=O)CCC(F)(F)F)C2] | 445 | 468 (+Na) |
| 26 | 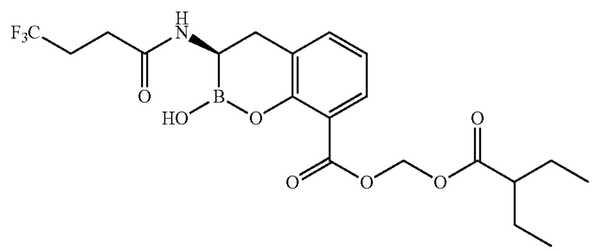 [SMILES: CCC(CC)C(=O)OCOC(=O)c1cccc2c1OB(O)[C@@H](NC(=O)CCC(F)(F)F)C2] | 459 | 482 (+Na) |
| 27 | 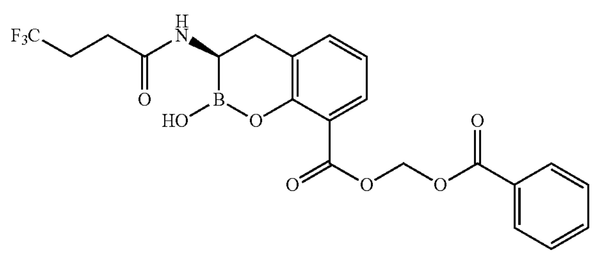 [SMILES: O=C(CCC(F)(F)F)N[C@H]1Cc2cccc(C(=O)OCOC(=O)c3ccccc3)c2OB1O] | 465 | 488 (+Na) |
| 28 | 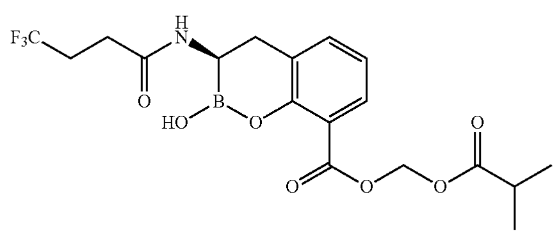 [SMILES: CC(C)C(=O)OCOC(=O)c1cccc2c1OB(O)[C@@H](NC(=O)CCC(F)(F)F)C2] | 431 | 454 (+Na) |
| 29 | 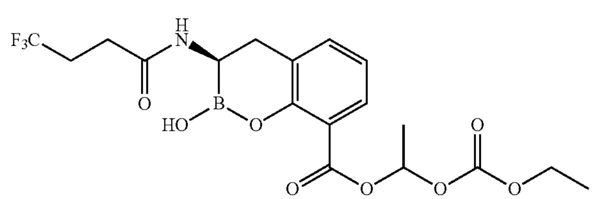 [SMILES: CCOC(=O)OC(C)OC(=O)c1cccc2c1OB(O)[C@@H](NC(=O)CCC(F)(F)F)C2] | 447 | 470 (+Na) |
| 30 | 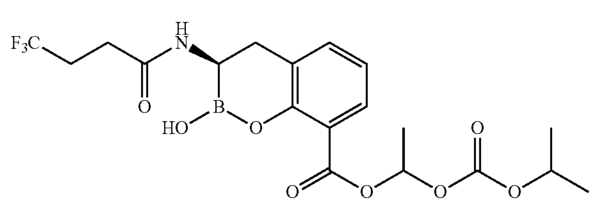 [SMILES: CC(C)OC(=O)OC(C)OC(=O)c1cccc2c1OB(O)[C@@H](NC(=O)CCC(F)(F)F)C2] | 461 | 484 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 31 | 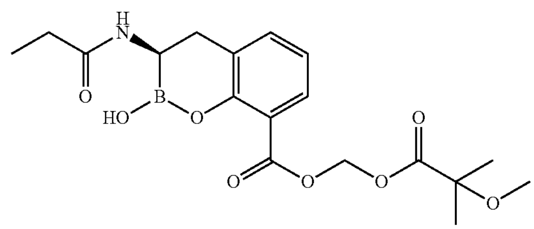 [SMILES: CCC(=O)N[C@H]1Cc2cccc(C(=O)OCOC(=O)C(C)(C)OC)c2OB1O] | 393 | 416 (+Na) |
| 32 | 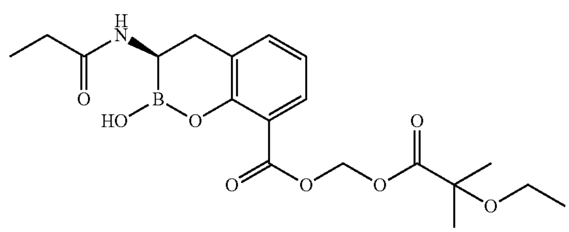 [SMILES: CCOC(C)(C)C(=O)OCOC(=O)c1cccc2c1OB(O)[C@@H](NC(=O)CC)C2] | 407 | 430 (+Na) |
| 33 | 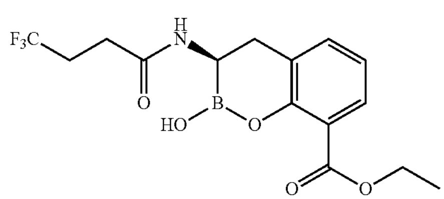 [SMILES: CCOC(=O)c1cccc2c1OB(O)[C@@H](NC(=O)CCC(F)(F)F)C2] | 359 | 360 |
| 34 | 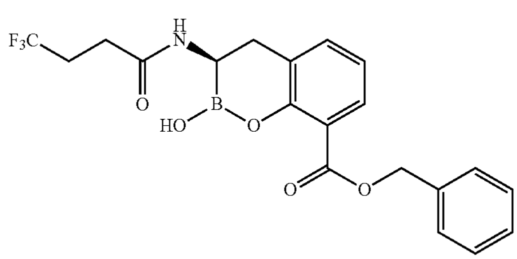 [SMILES: O=C(CCC(F)(F)F)N[C@H]1Cc2cccc(C(=O)OCc3ccccc3)c2OB1O] | 421 | 422 |
| 35 | 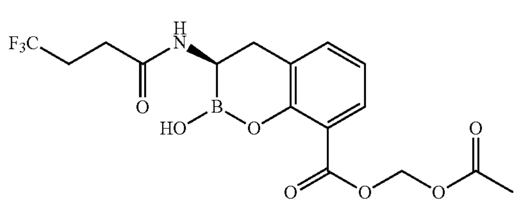 [SMILES: CC(=O)OCOC(=O)c1cccc2c1OB(O)[C@@H](NC(=O)CCC(F)(F)F)C2] | 403 | 426 (+Na) |
| 36 | 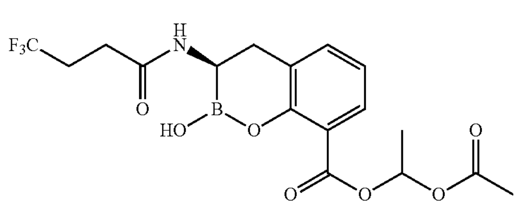 [SMILES: CC(=O)OC(C)OC(=O)c1cccc2c1OB(O)[C@@H](NC(=O)CCC(F)(F)F)C2] | 417 | 440 (+Na) |
| 37 | 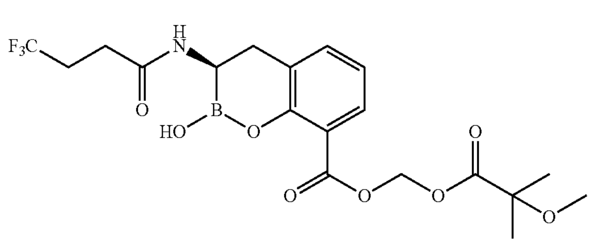 [SMILES: COC(C)(C)C(=O)OCOC(=O)c1cccc2c1OB(O)[C@@H](NC(=O)CCC(F)(F)F)C2] | 461 | 484 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 38 | 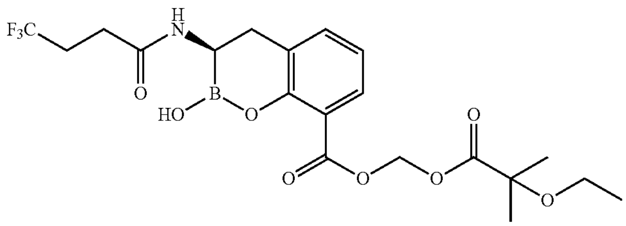 [SMILES: CCOC(C)(C)C(=O)OCOC(=O)c1cccc2c1OB(O)[C@@H](NC(=O)CCC(F)(F)F)C2] | 475 | 498 (+Na) |
| 39 | 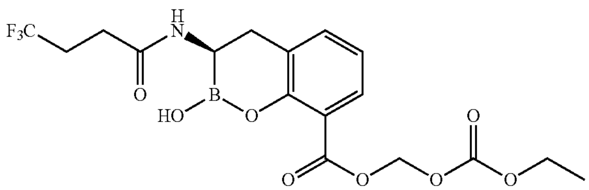 [SMILES: CCOC(=O)OCOC(=O)c1cccc2c1OB(O)[C@@H](NC(=O)CCC(F)(F)F)C2] | 433 | 456 (+Na) |
| 40 | 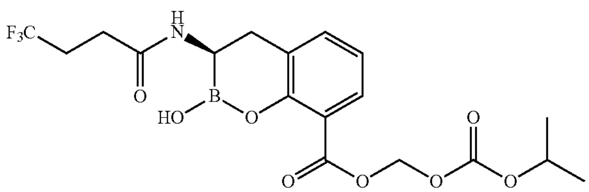 [SMILES: CC(C)OC(=O)OCOC(=O)c1cccc2c1OB(O)[C@@H](NC(=O)CCC(F)(F)F)C2] | 447 | 470 (+Na) |
| 41 | 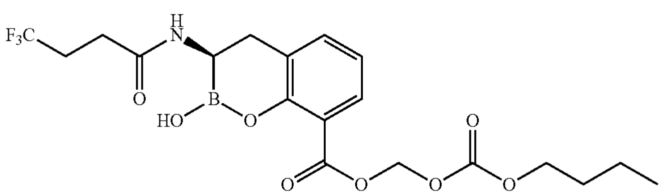 [SMILES: CCCCOC(=O)OCOC(=O)c1cccc2c1OB(O)[C@@H](NC(=O)CCC(F)(F)F)C2] | 461 | 462 |
| 42 | 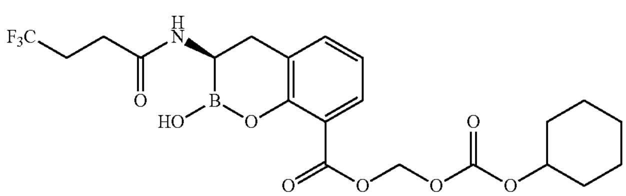 [SMILES: O=C(CCC(F)(F)F)N[C@H]1Cc2cccc(C(=O)OCOC(=O)OC3CCCCC3)c2OB1O] | 487 | 510 (+Na) |
| 43 | 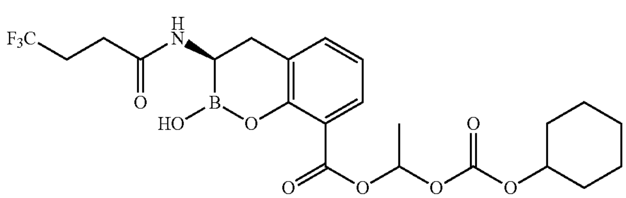 [SMILES: CC(OC(=O)OC1CCCCC1)OC(=O)c1cccc2c1OB(O)[C@@H](NC(=O)CCC(F)(F)F)C2] | 501 | 524 (+Na) |
| 44 | 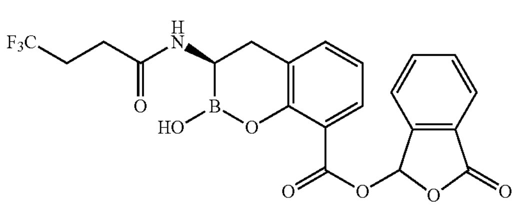 [SMILES: O=C(CCC(F)(F)F)N[C@H]1Cc2cccc(C(=O)OC3OC(=O)c4ccccc43)c2OB1O] | 463 | 486 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 45 | 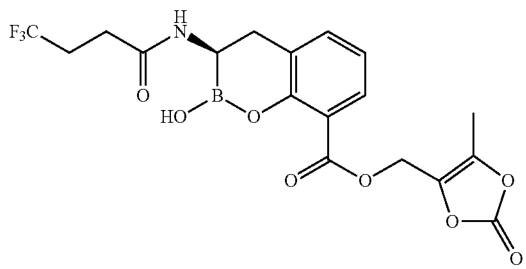 [SMILES: Cc1oc(=O)oc1COC(=O)c1cccc2c1OB(O)[C@@H](NC(=O)CCC(F)(F)F)C2] | 443 | 444 |
| 46 | 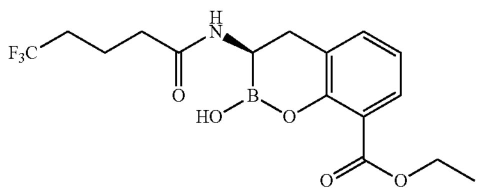 [SMILES: CCOC(=O)c1cccc2c1OB(O)[C@@H](NC(=O)CCCC(F)(F)F)C2] | 373 | 374 |
| 47 | 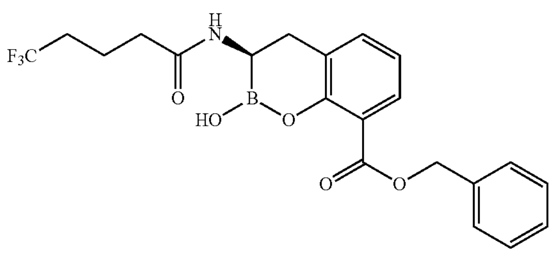 [SMILES: O=C(CCCC(F)(F)F)N[C@H]1Cc2cccc(C(=O)OCc3ccccc3)c2OB1O] | 435 | 436 |
| 48 | 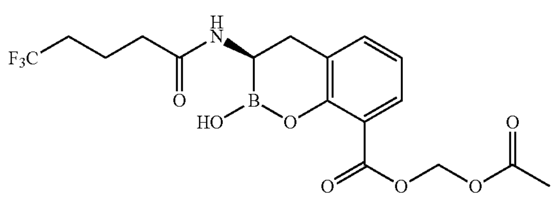 [SMILES: CC(=O)OCOC(=O)c1cccc2c1OB(O)[C@@H](NC(=O)CCCC(F)(F)F)C2] | 417 | 440 (+Na) |
| 49 | 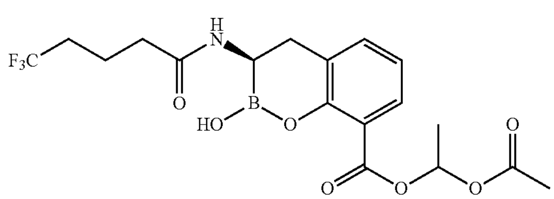 [SMILES: CC(=O)OC(C)OC(=O)c1cccc2c1OB(O)[C@@H](NC(=O)CCCC(F)(F)F)C2] | 431 | 454 (+Na) |
| 50 | 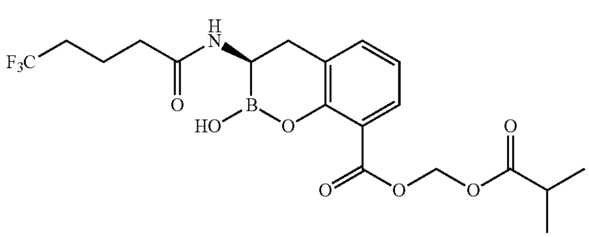 [SMILES: CC(C)C(=O)OCOC(=O)c1cccc2c1OB(O)[C@@H](NC(=O)CCCC(F)(F)F)C2] | 445 | 468 (+Na) |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 51 | 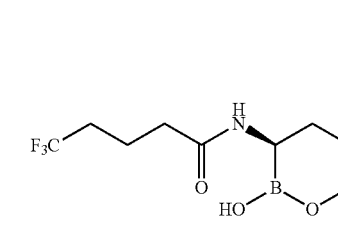 | 473 | 496 (+Na) |
| 52 | 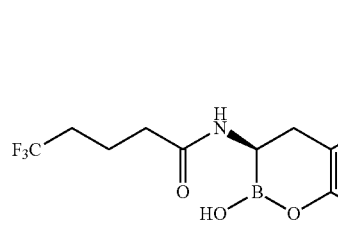 | 459 | 482 (+Na) |
| 53 | 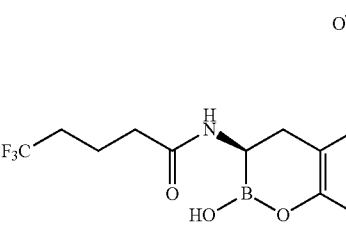 | 475 | 498 (+Na) |
| 54 | 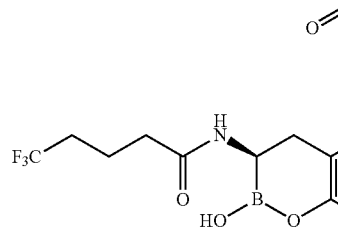 | 489 | 512 (+Na) |
| 55 | 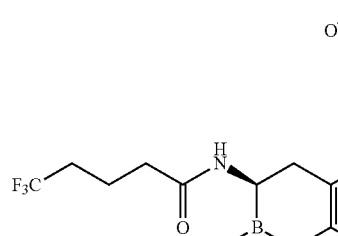 | 479 | 502 (+Na) |
| 56 | 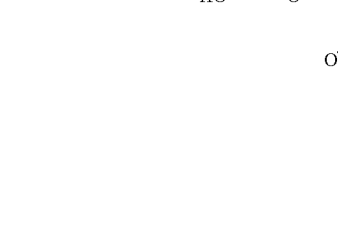 | 447 | 470 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 57 | 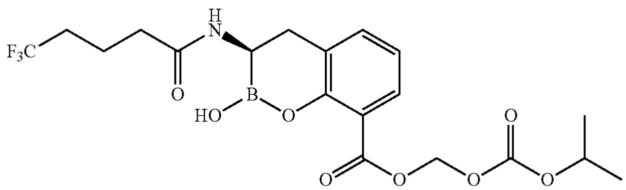 [SMILES: CC(C)OC(=O)OCOC(=O)c1cccc2c1OB(O)[C@@H](NC(=O)CCCC(F)(F)F)C2] | 461 | 484 (+Na) |
| 58 | 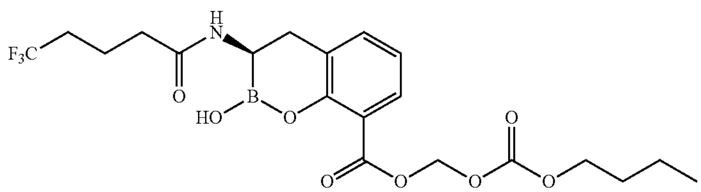 [SMILES: CCCCOC(=O)OCOC(=O)c1cccc2c1OB(O)[C@@H](NC(=O)CCCC(F)(F)F)C2] | 475 | 476 |
| 59 | 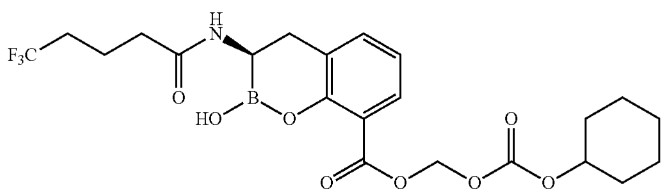 [SMILES: O=C(CCCC(F)(F)F)N[C@H]1Cc2cccc(C(=O)OCOC(=O)OC3CCCCC3)c2OB1O] | 501 | 524 (+Na) |
| 60 | 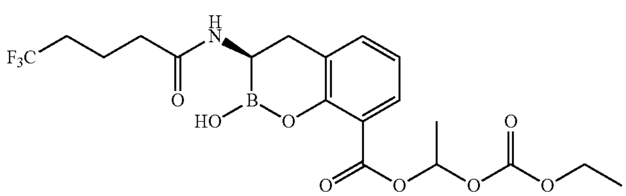 [SMILES: CCOC(=O)OC(C)OC(=O)c1cccc2c1OB(O)[C@@H](NC(=O)CCCC(F)(F)F)C2] | 461 | 484 (+Na) |
| 61 | 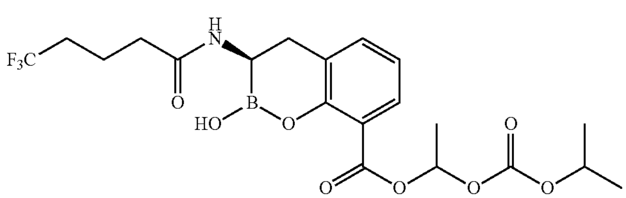 [SMILES: CC(C)OC(=O)OC(C)OC(=O)c1cccc2c1OB(O)[C@@H](NC(=O)CCCC(F)(F)F)C2] | 475 | 498 (+Na) |
| 62 | 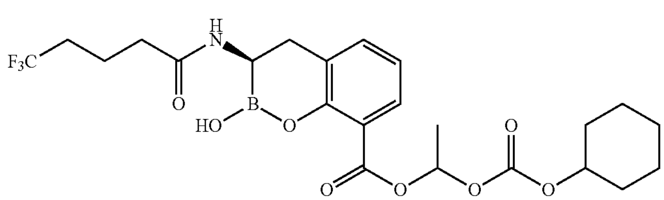 [SMILES: CC(OC(=O)OC1CCCCC1)OC(=O)c1cccc2c1OB(O)[C@@H](NC(=O)CCCC(F)(F)F)C2] | 515 | 538 (+Na) |
| 63 | 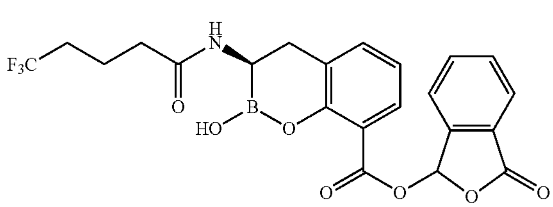 [SMILES: O=C(CCCC(F)(F)F)N[C@H]1Cc2cccc(C(=O)OC3OC(=O)c4ccccc43)c2OB1O] | 477 | 478 |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 64 | 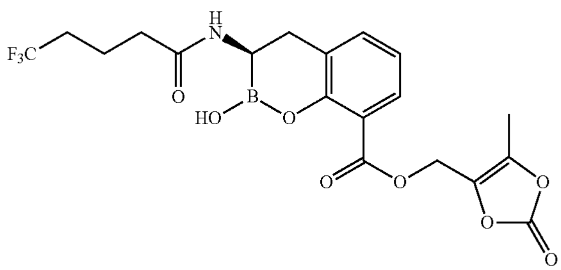 [SMILES: Cc1oc(=O)oc1COC(=O)c1cccc2c1OB(O)[C@@H](NC(=O)CCCC(F)(F)F)C2] | 457 | 480 (+Na) |
| 65 | 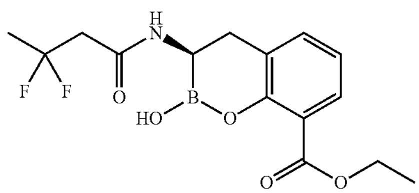 [SMILES: CCOC(=O)c1cccc2c1OB(O)[C@@H](NC(=O)CC(C)(F)F)C2] | 341 | 342 |
| 66 | 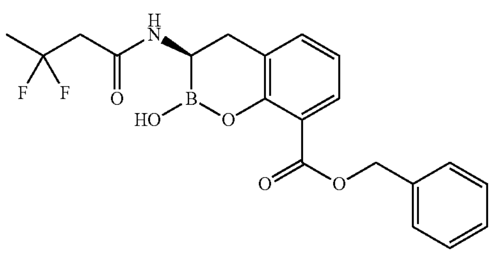 [SMILES: CC(F)(F)CC(=O)N[C@H]1Cc2cccc(C(=O)OCc3ccccc3)c2OB1O] | 403 | 404 |
| 67 | 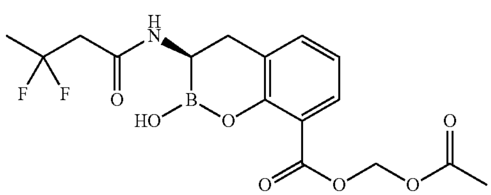 [SMILES: CC(=O)OCOC(=O)c1cccc2c1OB(O)[C@@H](NC(=O)CC(C)(F)F)C2] | 385 | 408 (+Na) |
| 68 | 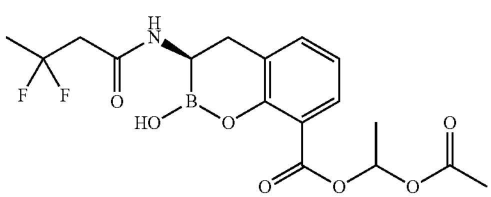 [SMILES: CC(=O)OC(C)OC(=O)c1cccc2c1OB(O)[C@@H](NC(=O)CC(C)(F)F)C2] | 399 | 422 (+Na) |
| 69 | 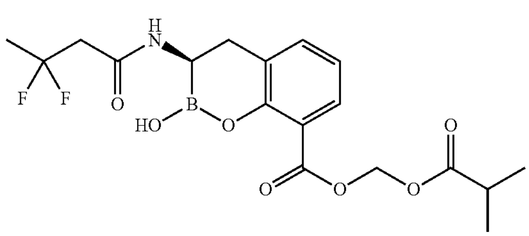 [SMILES: CC(C)C(=O)OCOC(=O)c1cccc2c1OB(O)[C@@H](NC(=O)CC(C)(F)F)C2] | 413 | 436 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 70 | 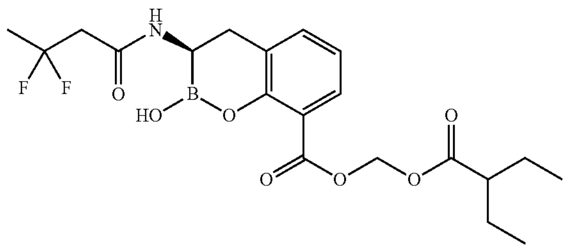 [SMILES: CCC(CC)C(=O)OCOC(=O)c1cccc2c1OB(O)[C@@H](NC(=O)CC(C)(F)F)C2] | 441 | 464 (+Na) |
| 71 | 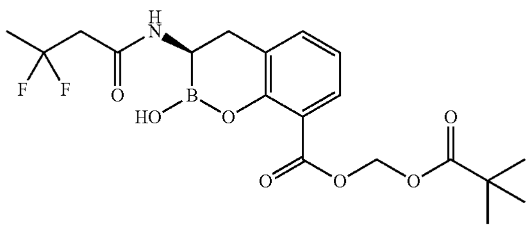 [SMILES: CC(F)(F)CC(=O)N[C@H]1Cc2cccc(C(=O)OCOC(=O)C(C)(C)C)c2OB1O] | 427 | 450 (+Na) |
| 72 | 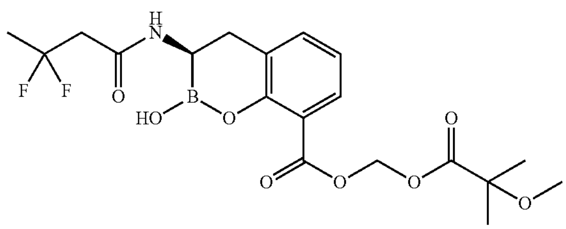 [SMILES: COC(C)(C)C(=O)OCOC(=O)c1cccc2c1OB(O)[C@@H](NC(=O)CC(C)(F)F)C2] | 443 | 466 (+Na) |
| 73 | 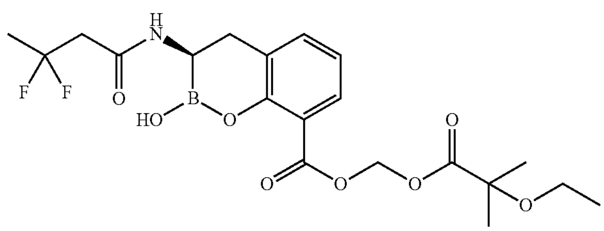 [SMILES: CCOC(C)(C)C(=O)OCOC(=O)c1cccc2c1OB(O)[C@@H](NC(=O)CC(C)(F)F)C2] | 457 | 480 (+Na) |
| 74 | 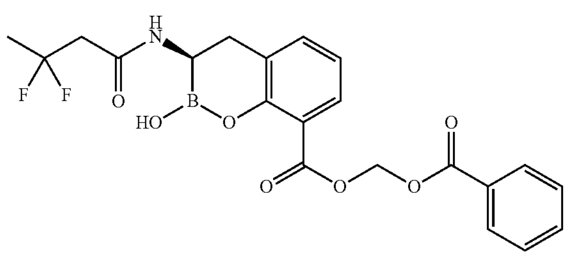 [SMILES: CC(F)(F)CC(=O)N[C@H]1Cc2cccc(C(=O)OCOC(=O)c3ccccc3)c2OB1O] | 447 | 470 (+Na) |
| 75 | 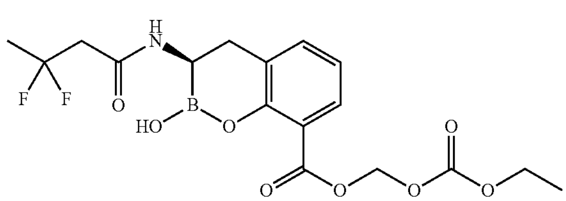 [SMILES: CCOC(=O)OCOC(=O)c1cccc2c1OB(O)[C@@H](NC(=O)CC(C)(F)F)C2] | 415 | 438 (+Na) |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 76 | 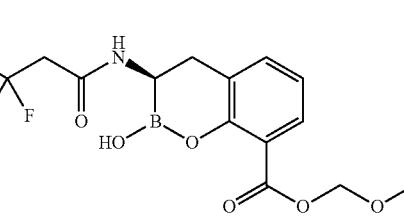 | 429 | 452 (+Na) |
| 77 | 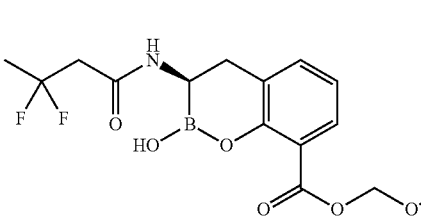 | 443 | 466 (+Na) |
| 78 | 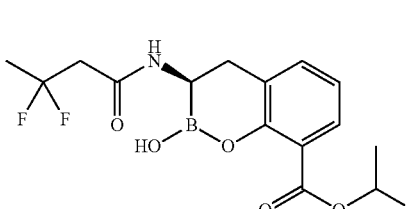 | 469 | 492 (+Na) |
| 79 | 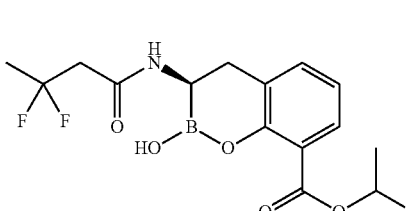 | 429 | 452 (+Na) |
| 80 | 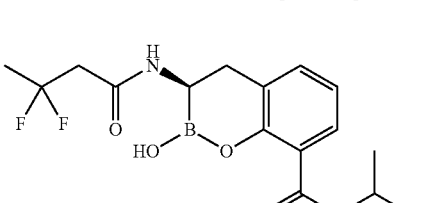 | 443 | 466 (+Na) |
| 81 | 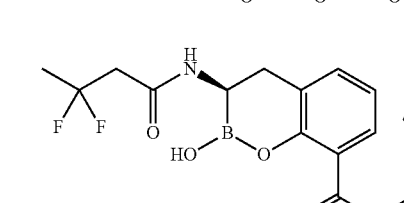 | 483 | 506 (+Na) |
| 82 | 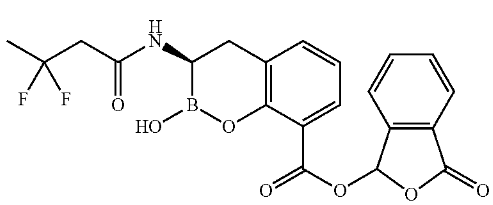 [SMILES: CC(F)(F)CC(=O)N[C@H]1Cc2cccc(C(=O)OC3OC(=O)c4ccccc43)c2OB1O] | 445 | 446 |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 83 | 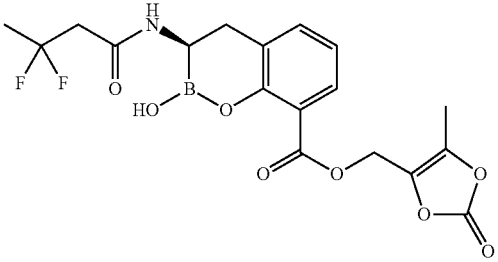 [SMILES: Cc1oc(=O)oc1COC(=O)c1cccc2c1OB(O)[C@@H](NC(=O)CC(C)(F)F)C2] | 425 | 448 (+Na) |
| 84 | 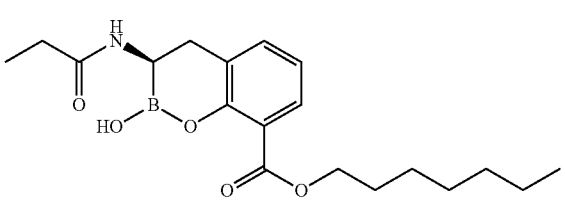 [SMILES: CCCCCCCOC(=O)c1cccc2c1OB(O)[C@@H](NC(=O)CC)C2] | 361 | 362 |
| 85 | 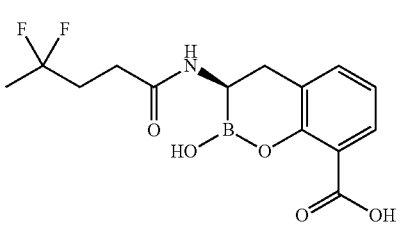 [SMILES: CC(F)(F)CCC(=O)N[C@H]1Cc2cccc(C(=O)O)c2OB1O] | 327 | 328 |
| 86 | 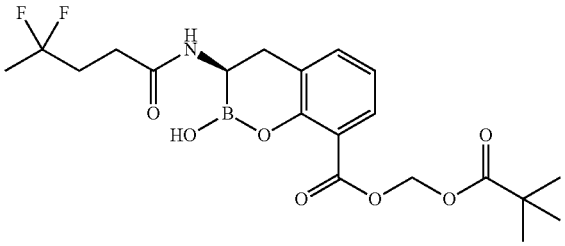 [SMILES: CC(F)(F)CCC(=O)N[C@H]1Cc2cccc(C(=O)OCOC(=O)C(C)(C)C)c2OB1O] | 441 | 464 (+Na) |
| 87 | 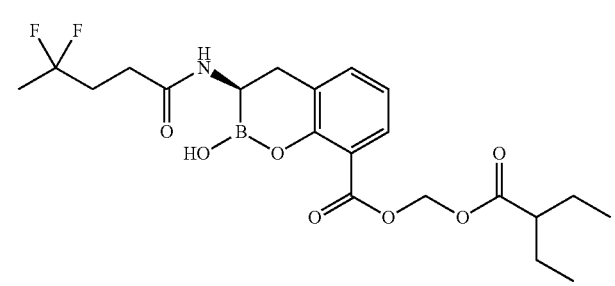 [SMILES: CCC(CC)C(=O)OCOC(=O)c1cccc2c1OB(O)[C@@H](NC(=O)CCC(C)(F)F)C2] | 455 | 478 (+Na) |
| 88 | 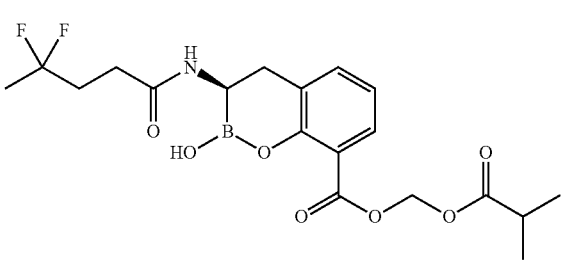 [SMILES: CC(C)C(=O)OCOC(=O)c1cccc2c1OB(O)[C@@H](NC(=O)CCC(C)(F)F)C2] | 427 | 450 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 89 | 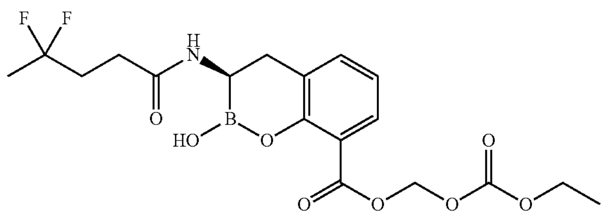 | 429 | 452 (+Na) |
| 90 | 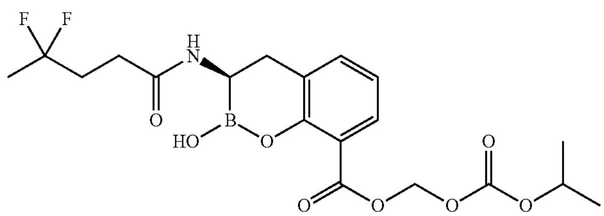 | 443 | 466 (+Na) |
| 91 | 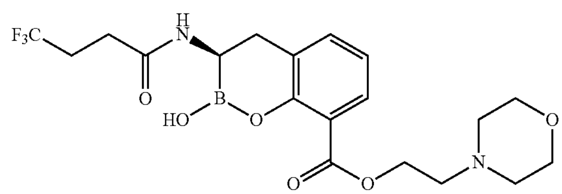 [SMILES: O=C(CCC(F)(F)F)N[C@H]1Cc2cccc(C(=O)OCCN3CCOCC3)c2OB1O] | 444 | 445 |
| 92 | 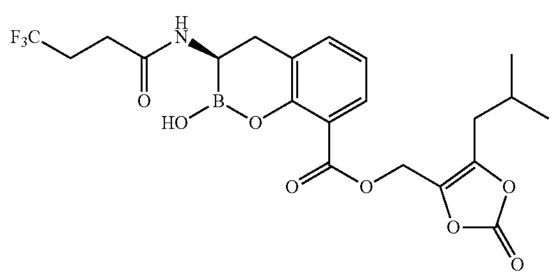 [SMILES: CC(C)Cc1oc(=O)oc1COC(=O)c1cccc2c1OB(O)[C@@H](NC(=O)CCC(F)(F)F)C2] | 485 | 508 (+Na) |
| 93 | 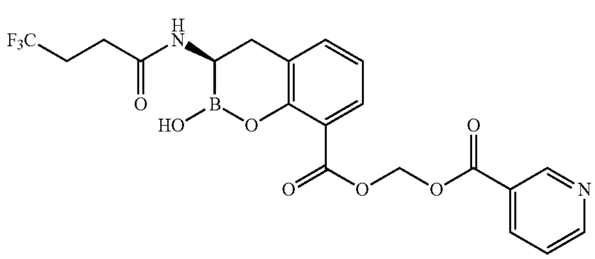 [SMILES: O=C(CCC(F)(F)F)N[C@H]1Cc2cccc(C(=O)OCOC(=O)c3cccnc3)c2OB1O] | 466 | 467 |
| 94 | 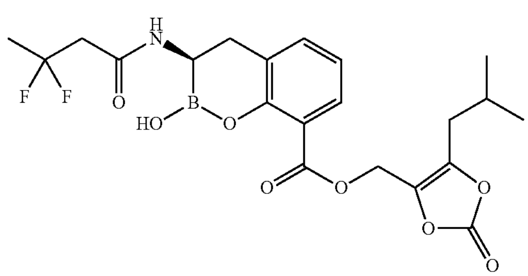 [SMILES: CC(C)Cc1oc(=O)oc1COC(=O)c1cccc2c1OB(O)[C@@H](NC(=O)CC(C)(F)F)C2] | 467 | 490 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 95 | 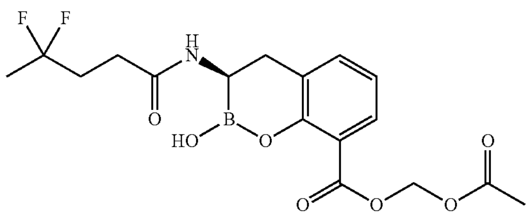 [SMILES: CC(=O)OCOC(=O)c1cccc2c1OB(O)[C@@H](NC(=O)CCC(C)(F)F)C2] | 399 | 422 (+Na) |
| 96 | 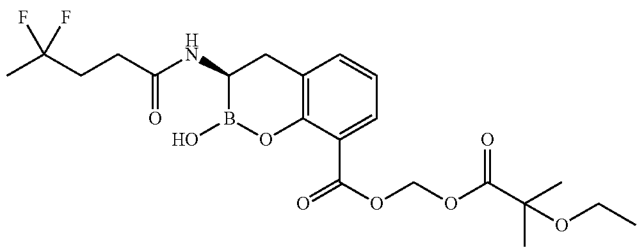 [SMILES: CCOC(C)(C)C(=O)OCOC(=O)c1cccc2c1OB(O)[C@@H](NC(=O)CCC(C)(F)F)C2] | 471 | 494 (+Na) |
| 97 | 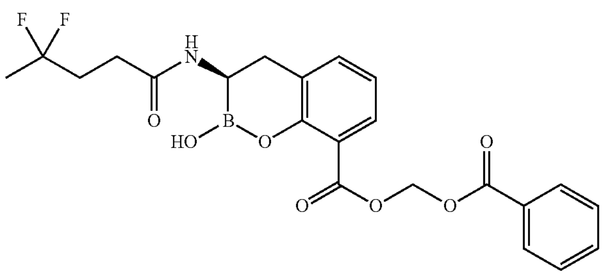 [SMILES: CC(F)(F)CCC(=O)N[C@H]1Cc2cccc(C(=O)OCOC(=O)c3ccccc3)c2OB1O] | 461 | 484 (+Na) |
| 98 | 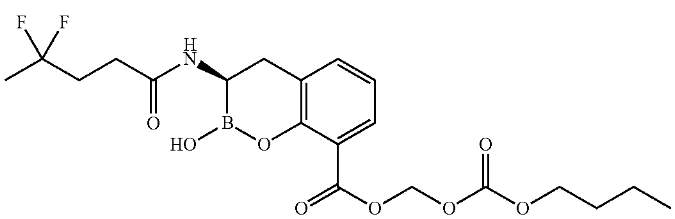 [SMILES: CCCCOC(=O)OCOC(=O)c1cccc2c1OB(O)[C@@H](NC(=O)CCC(C)(F)F)C2] | 457 | 480 (+Na) |
| 99 | 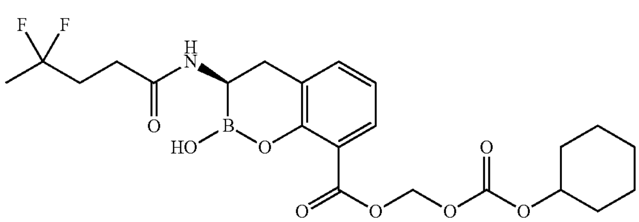 [SMILES: CC(F)(F)CCC(=O)N[C@H]1Cc2cccc(C(=O)OCOC(=O)OC3CCCCC3)c2OB1O] | 483 | 506 (+Na) |
| 100 | 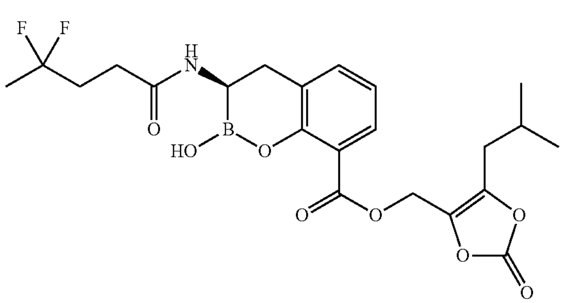 [SMILES: CC(C)Cc1oc(=O)oc1COC(=O)c1cccc2c1OB(O)[C@@H](NC(=O)CCC(C)(F)F)C2] | 481 | 504 (+Na) |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 101 | 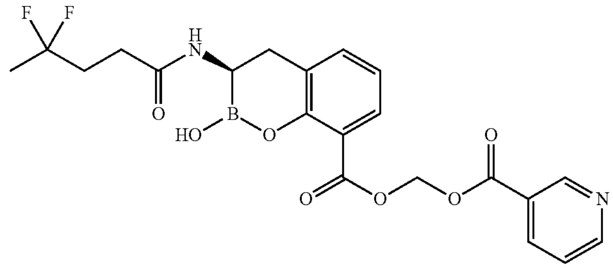 [SMILES: CC(F)(F)CCC(=O)N[C@H]1Cc2cccc(C(=O)OCOC(=O)c3cccnc3)c2OB1O] | 462 | 463 |
| 102 | 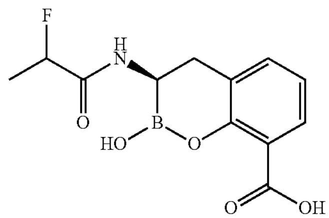 [SMILES: CC(F)C(=O)N[C@H]1Cc2cccc(C(=O)O)c2OB1O] | 281 | 282 |
| 103 | 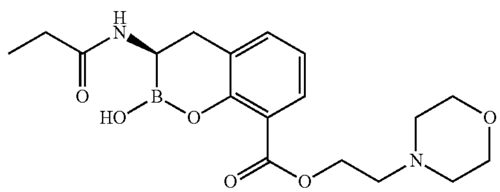 [SMILES: CCC(=O)N[C@H]1Cc2cccc(C(=O)OCCN3CCOCC3)c2OB1O] | 376 | 377 |
| 104 | 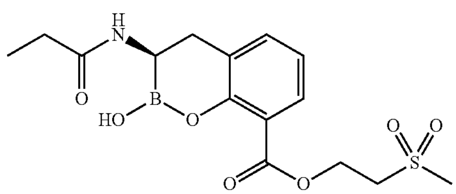 [SMILES: CCC(=O)N[C@H]1Cc2cccc(C(=O)OCCS(C)(=O)=O)c2OB1O] | 369 | 392 (+Na) |
| 105 | 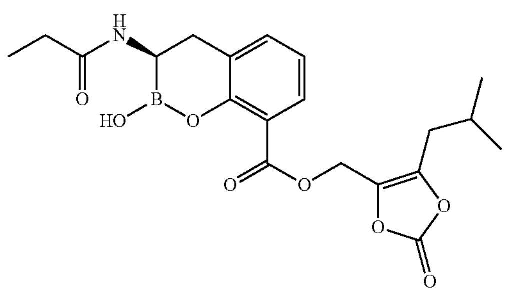 [SMILES: CCC(=O)N[C@H]1Cc2cccc(C(=O)OCc3oc(=O)oc3CC(C)C)c2OB1O] | 417 | 440 (+Na) |
| 106 | 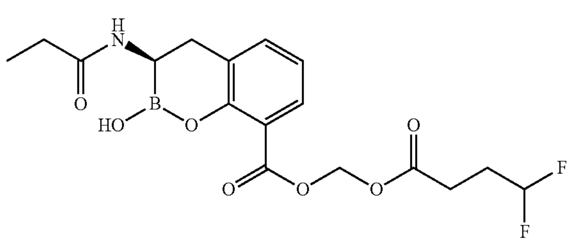 [SMILES: CCC(=O)N[C@H]1Cc2cccc(C(=O)OCOC(=O)CCC(F)F)c2OB1O] | 399 | 422 (+Na) |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 107 | 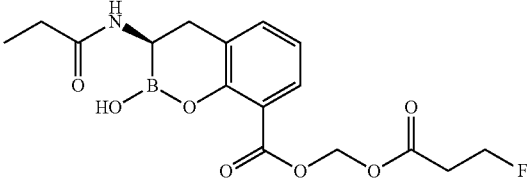 [SMILES: CCC(=O)N[C@H]1Cc2cccc(C(=O)OCOC(=O)CCF)c2OB1O] | 367 | 390 (+Na) |
| 108 | 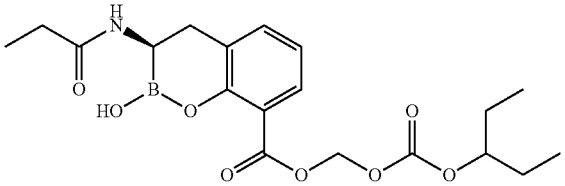 [SMILES: CCC(=O)N[C@H]1Cc2cccc(C(=O)OCOC(=O)OC(CC)CC)c2OB1O] | 407 | 430 (+Na) |
| 109 | 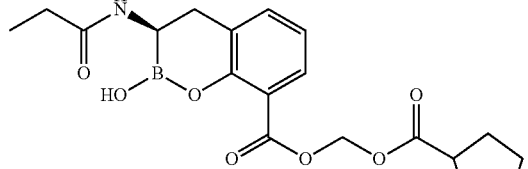 | 389 | 412 (+Na) |
| 110 | 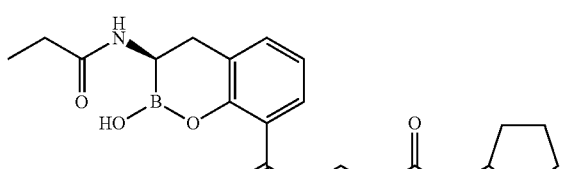 | 405 | 428 (+Na) |
| 111 | 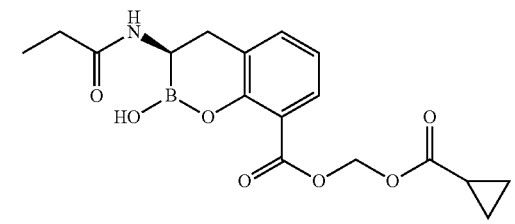 [SMILES: CCC(=O)N[C@H]1Cc2cccc(C(=O)OCOC(=O)C3CC3)c2OB1O] | 361 | 384 (+Na) |
| 112 | 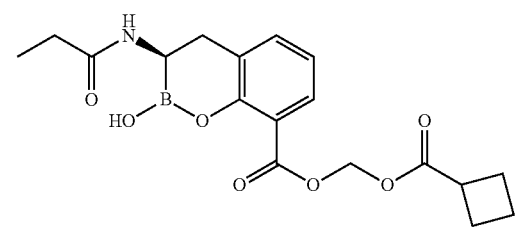 [SMILES: CCC(=O)N[C@H]1Cc2cccc(C(=O)OCOC(=O)C3CCC3)c2OB1O] | 375 | 398 (+Na) |
| 113 | 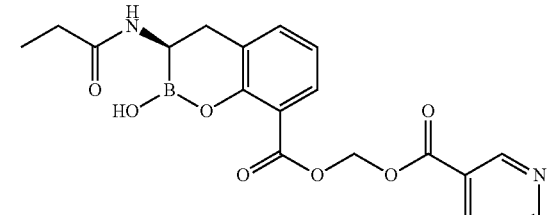 | 398 | 399 |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 114 | 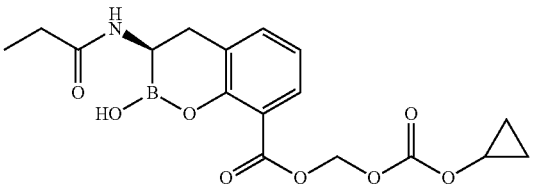 [SMILES: CCC(=O)N[C@H]1Cc2cccc(C(=O)OCOC(=O)OC3CC3)c2OB1O] | 377 | 400 (+Na) |
| 115 | 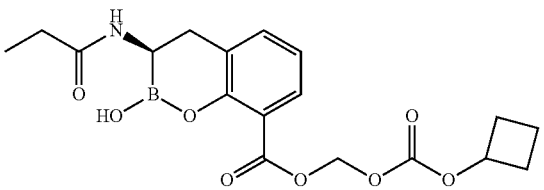 [SMILES: CCC(=O)N[C@H]1Cc2cccc(C(=O)OCOC(=O)OC3CCC3)c2OB1O] | 391 | 414 (+Na) |
| 116 | 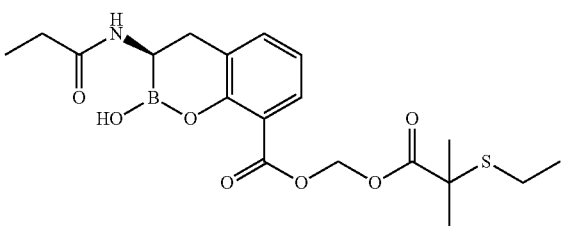 [SMILES: CCSC(C)(C)C(=O)OCOC(=O)c1cccc2c1OB(O)[C@@H](NC(=O)CC)C2] | 423 | 446 (+Na) |
| 117 | 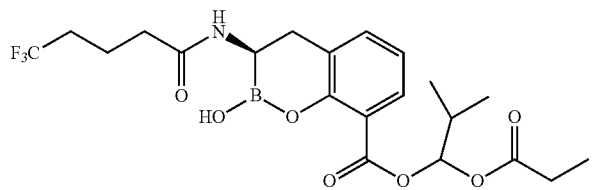 [SMILES: CCC(=O)OC(OC(=O)c1cccc2c1OB(O)[C@@H](NC(=O)CCCC(F)(F)F)C2)C(C)C] | 473 | 496 (+Na) |
| 118 | 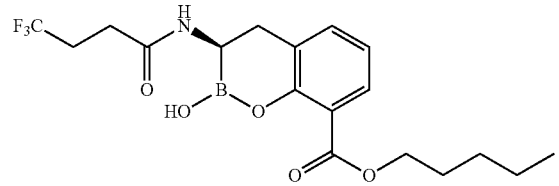 [SMILES: CCCCCOC(=O)c1cccc2c1OB(O)[C@@H](NC(=O)CCC(F)(F)F)C2] | 401 | |
| 119 | 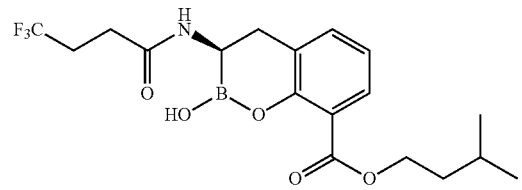 [SMILES: CC(C)CCOC(=O)c1cccc2c1OB(O)[C@@H](NC(=O)CCC(F)(F)F)C2] | 401 | |
| 120 | 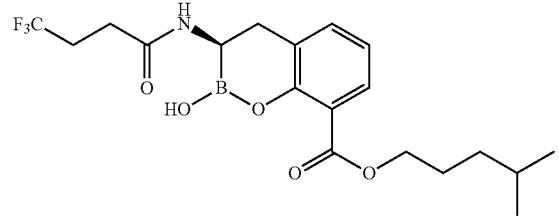 [SMILES: CC(C)CCCOC(=O)c1cccc2c1OB(O)[C@@H](NC(=O)CCC(F)(F)F)C2] | 415 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 121 | 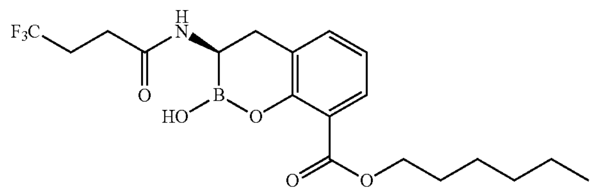 [SMILES: CCCCCCOC(=O)c1cccc2c1OB(O)[C@@H](NC(=O)CCC(F)(F)F)C2] | 415 | |
| 122 | 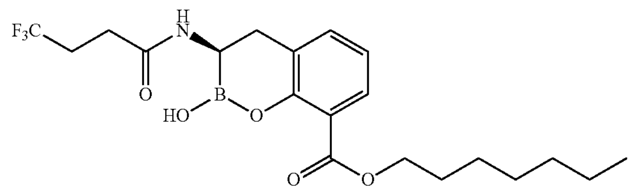 [SMILES: CCCCCCCOC(=O)c1cccc2c1OB(O)[C@@H](NC(=O)CCC(F)(F)F)C2] | 429 | |
| 123 | 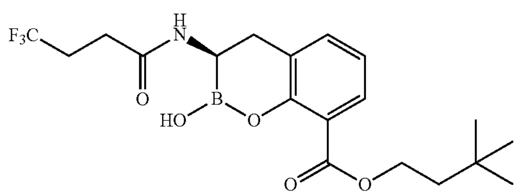 [SMILES: CC(C)(C)CCOC(=O)c1cccc2c1OB(O)[C@@H](NC(=O)CCC(F)(F)F)C2] | 415 | |
| 124 | 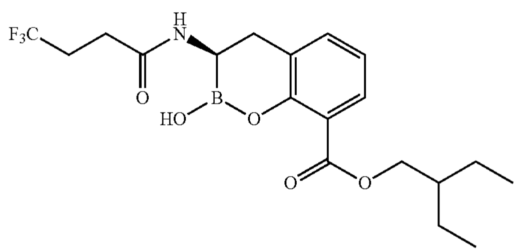 [SMILES: CCC(CC)COC(=O)c1cccc2c1OB(O)[C@@H](NC(=O)CCC(F)(F)F)C2] | 415 | |
| 125 | 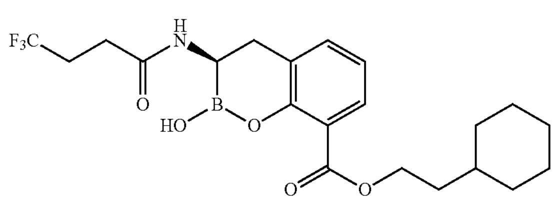 [SMILES: O=C(CCC(F)(F)F)N[C@H]1Cc2cccc(C(=O)OCCC3CCCCC3)c2OB1O] | 441 | |
| 126 | 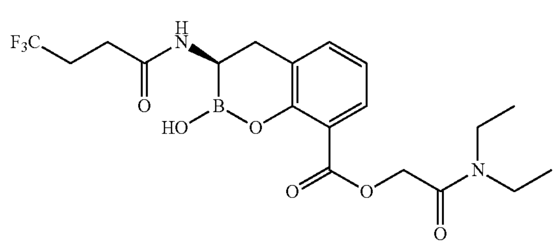 [SMILES: CCN(CC)C(=O)COC(=O)c1cccc2c1OB(O)[C@@H](NC(=O)CCC(F)(F)F)C2] | 444 | |
| 127 | 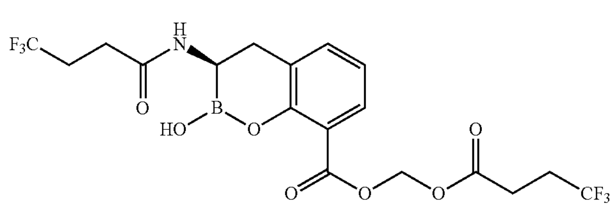 [SMILES: O=C(CCC(F)(F)F)N[C@H]1Cc2cccc(C(=O)OCOC(=O)CCC(F)(F)F)c2OB1O] | 485 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 128 | 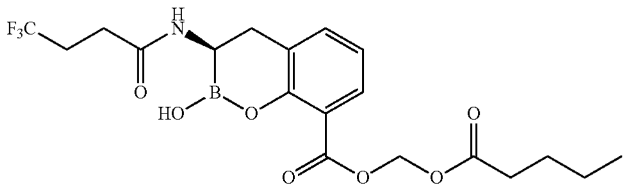 [SMILES: CCCCC(=O)OCOC(=O)c1cccc2c1OB(O)[C@@H](NC(=O)CCC(F)(F)F)C2] | 445 | |
| 129 | 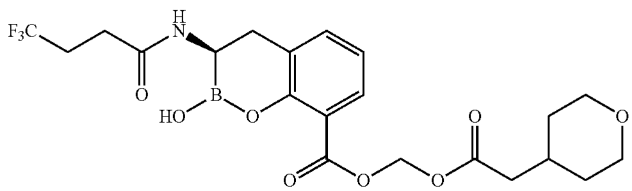 [SMILES: O=C(CCC(F)(F)F)N[C@H]1Cc2cccc(C(=O)OCOC(=O)CC3CCOCC3)c2OB1O] | 487 | |
| 130 | 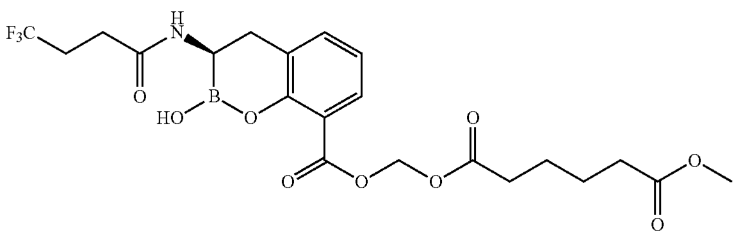 [SMILES: COC(=O)CCCCC(=O)OCOC(=O)c1cccc2c1OB(O)[C@@H](NC(=O)CCC(F)(F)F)C2] | 503 | |
| 131 | 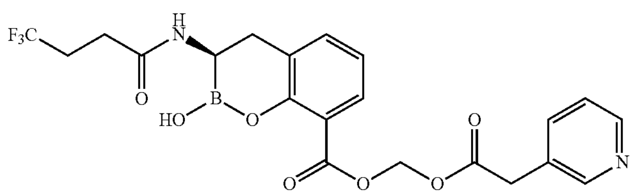 [SMILES: O=C(CCC(F)(F)F)N[C@H]1Cc2cccc(C(=O)OCOC(=O)Cc3cccnc3)c2OB1O] | 480 | |
| 132 | 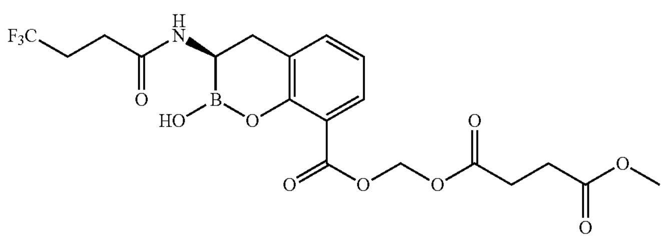 [SMILES: COC(=O)CCC(=O)OCOC(=O)c1cccc2c1OB(O)[C@@H](NC(=O)CCC(F)(F)F)C2] | 475 | |
| 133 | 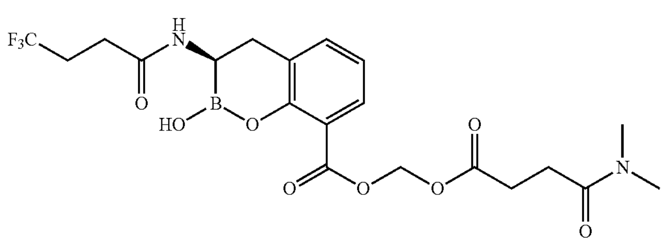 [SMILES: CN(C)C(=O)CCC(=O)OCOC(=O)c1cccc2c1OB(O)[C@@H](NC(=O)CCC(F)(F)F)C2] | 488 | |
| 134 | 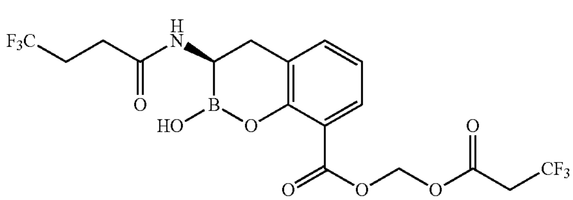 [SMILES: O=C(CCC(F)(F)F)N[C@H]1Cc2cccc(C(=O)OCOC(=O)CC(F)(F)F)c2OB1O] | 471 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 135 | 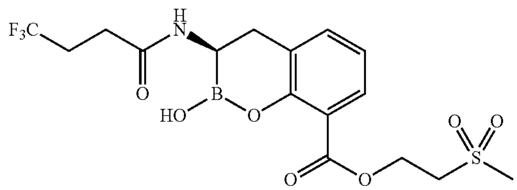 [SMILES: CS(=O)(=O)CCOC(=O)c1cccc2c1OB(O)[C@@H](NC(=O)CCC(F)(F)F)C2] | | 437 |
| 136 | 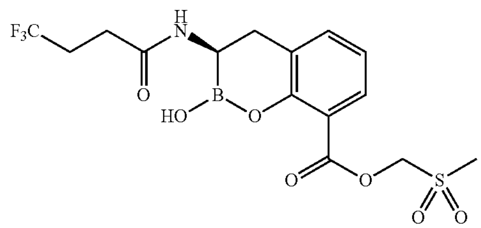 [SMILES: CS(=O)(=O)COC(=O)c1cccc2c1OB(O)[C@@H](NC(=O)CCC(F)(F)F)C2] | | 423 |
| 137 | 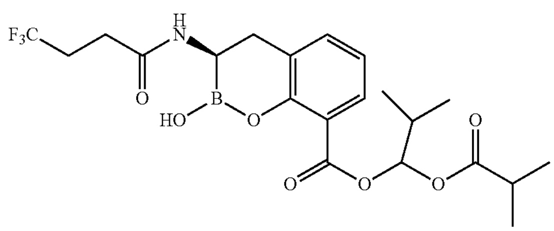 [SMILES: CC(C)C(=O)OC(OC(=O)c1cccc2c1OB(O)[C@@H](NC(=O)CCC(F)(F)F)C2)C(C)C] | | 473 |
| 138 | 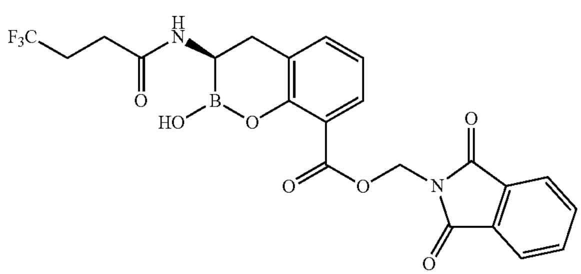 [SMILES: O=C(CCC(F)(F)F)N[C@H]1Cc2cccc(C(=O)OCN3C(=O)c4ccccc4C3=O)c2OB1O] | | 490 |
| 139 | 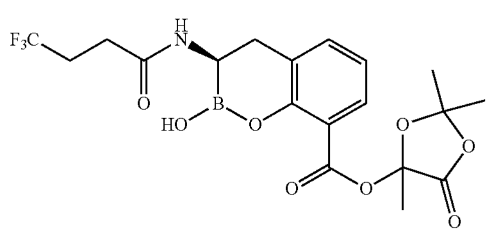 [SMILES: CC1(C)OC(=O)C(C)(OC(=O)c2cccc3c2OB(O)[C@@H](NC(=O)CCC(F)(F)F)C3)O1] | | 459 |
| 140 | 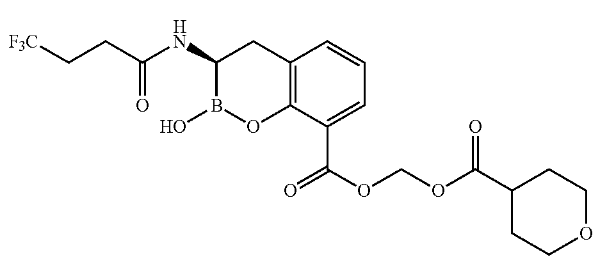 [SMILES: O=C(CCC(F)(F)F)N[C@H]1Cc2cccc(C(=O)OCOC(=O)C3CCOCC3)c2OB1O] | | 473 |

… TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 141 | 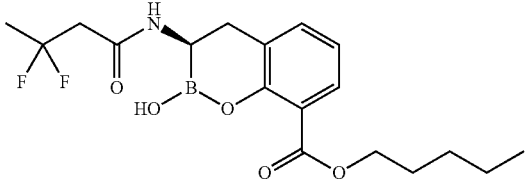 [SMILES: CCCCCOC(=O)c1cccc2c1OB(O)[C@@H](NC(=O)CC(C)(F)F)C2] | 383 | |
| 142 | 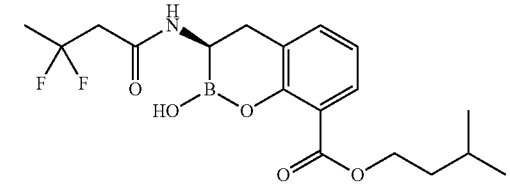 [SMILES: CC(C)CCOC(=O)c1cccc2c1OB(O)[C@@H](NC(=O)CC(C)(F)F)C2] | 383 | |
| 143 | 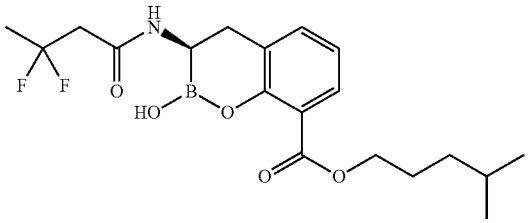 [SMILES: CC(C)CCCOC(=O)c1cccc2c1OB(O)[C@@H](NC(=O)CC(C)(F)F)C2] | 397 | |
| 144 | 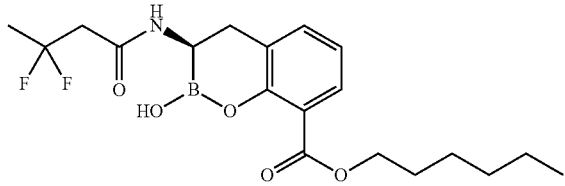 [SMILES: CCCCCCOC(=O)c1cccc2c1OB(O)[C@@H](NC(=O)CC(C)(F)F)C2] | 397 | |
| 145 | 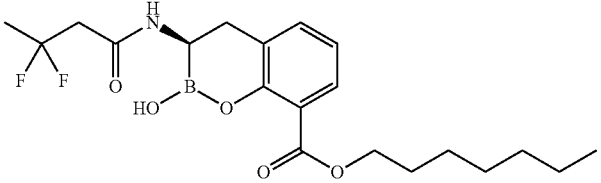 [SMILES: CCCCCCCOC(=O)c1cccc2c1OB(O)[C@@H](NC(=O)CC(C)(F)F)C2] | 411 | |
| 146 | 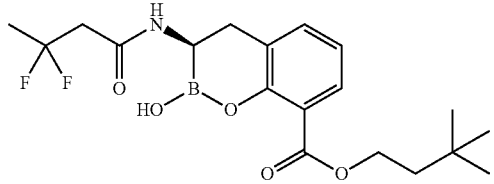 [SMILES: CC(C)(C)CCOC(=O)c1cccc2c1OB(O)[C@@H](NC(=O)CC(C)(F)F)C2] | 397 | |
| 147 | 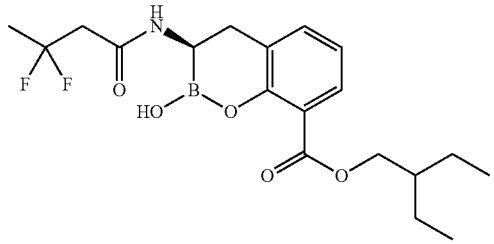 [SMILES: CCC(CC)COC(=O)c1cccc2c1OB(O)[C@@H](NC(=O)CC(C)(F)F)C2] | 397 | |

US 10,464,952 B2
TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 148 | 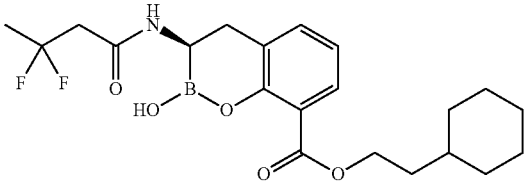 [SMILES: CC(F)(F)CC(=O)N[C@H]1Cc2cccc(C(=O)OCCC3CCCCC3)c2OB1O] | 423 | |
| 149 | 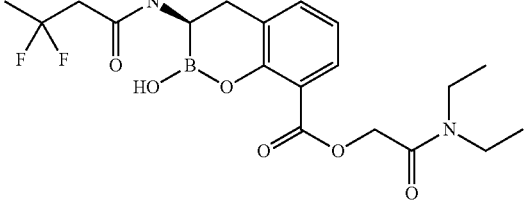 | 426 | |
| 150 | 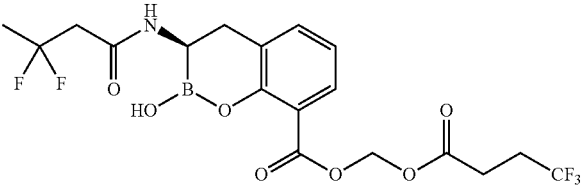 [SMILES: CC(F)(F)CC(=O)N[C@H]1Cc2cccc(C(=O)OCOC(=O)CCC(F)(F)F)c2OB1O] | 467 | |
| 151 | 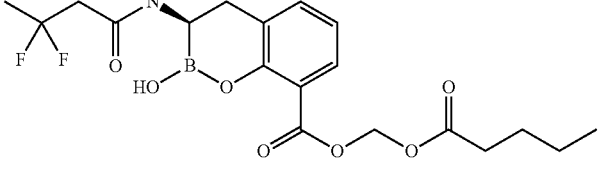 | 427 | |
| 152 | 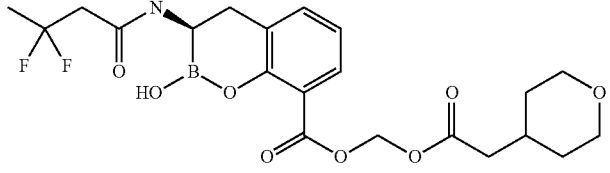 | 469 | |
| 153 | 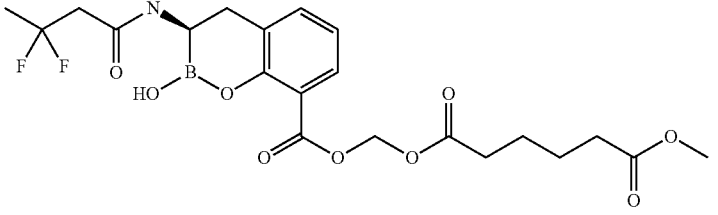 | 485 | |
| 154 | 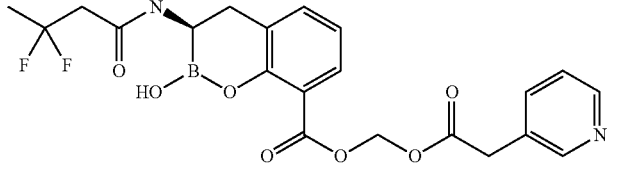 | 462 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 155 | 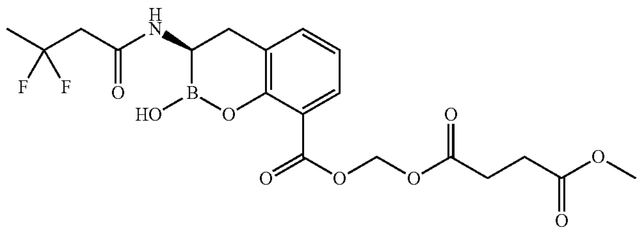 [SMILES: COC(=O)CCC(=O)OCOC(=O)c1cccc2c1OB(O)[C@@H](NC(=O)CC(C)(F)F)C2] | 457 | |
| 156 | 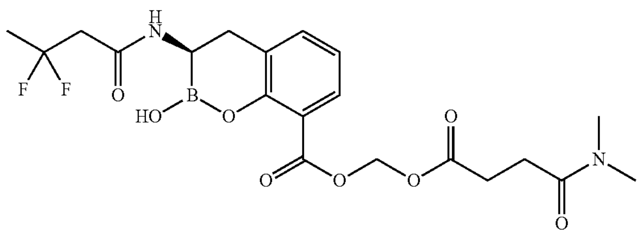 [SMILES: CN(C)C(=O)CCC(=O)OCOC(=O)c1cccc2c1OB(O)[C@@H](NC(=O)CC(C)(F)F)C2] | 470 | |
| 157 | 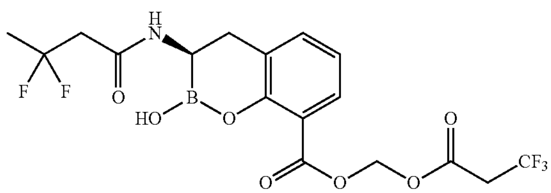 [SMILES: CC(F)(F)CC(=O)N[C@H]1Cc2cccc(C(=O)OCOC(=O)CC(F)(F)F)c2OB1O] | 453 | |
| 158 | 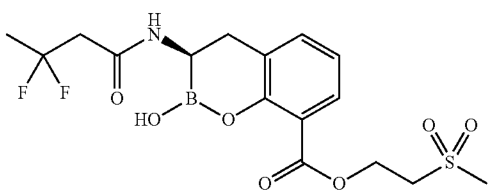 [SMILES: CC(F)(F)CC(=O)N[C@H]1Cc2cccc(C(=O)OCCS(C)(=O)=O)c2OB1O] | 419 | |
| 159 | 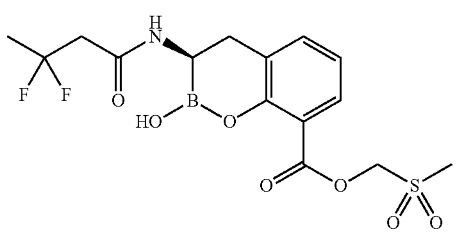 [SMILES: CC(F)(F)CC(=O)N[C@H]1Cc2cccc(C(=O)OCS(C)(=O)=O)c2OB1O] | 405 | |
| 160 | 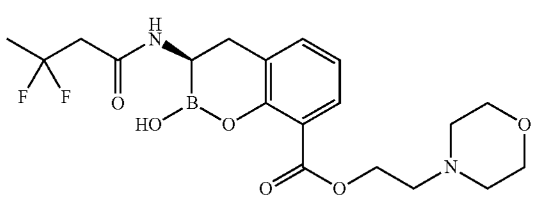 [SMILES: CC(F)(F)CC(=O)N[C@H]1Cc2cccc(C(=O)OCCN3CCOCC3)c2OB1O] | 426 | |
| 161 | 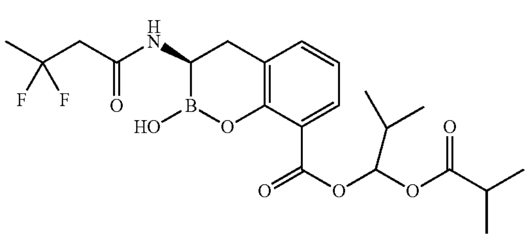 [SMILES: CC(C)C(=O)OC(OC(=O)c1cccc2c1OB(O)[C@@H](NC(=O)CC(C)(F)F)C2)C(C)C] | 455 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 162 | 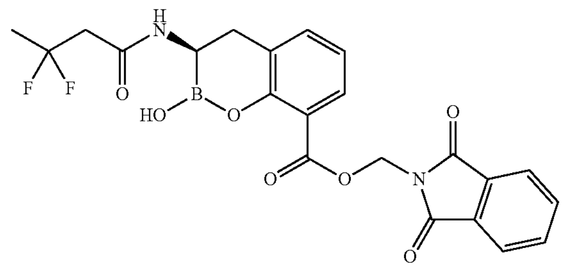 [SMILES: CC(F)(F)CC(=O)N[C@H]1Cc2cccc(C(=O)OCN3C(=O)c4ccccc4C3=O)c2OB1O] | 472 | |
| 163 | 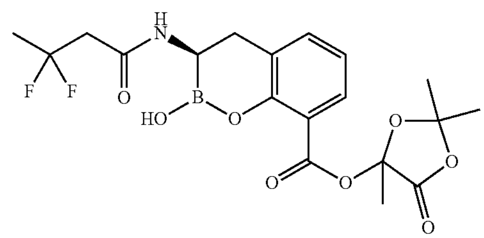 [SMILES: CC(F)(F)CC(=O)N[C@H]1Cc2cccc(C(=O)OC3(C)OC(C)(C)OC3=O)c2OB1O] | 441 | |
| 164 | 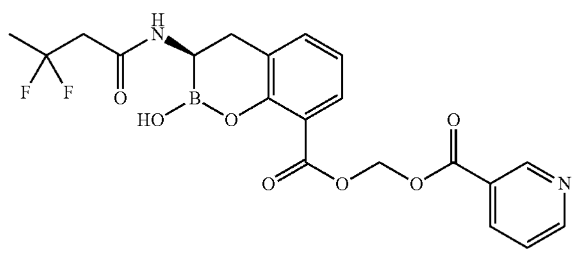 [SMILES: CC(F)(F)CC(=O)N[C@H]1Cc2cccc(C(=O)OCOC(=O)c3cccnc3)c2OB1O] | 448 | |
| 165 | 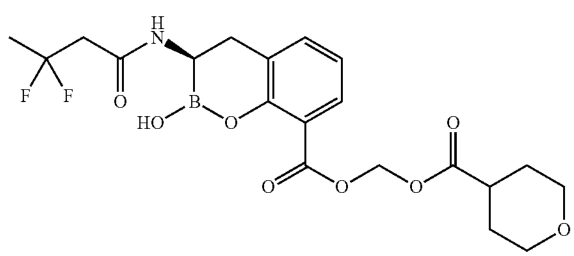 [SMILES: CC(F)(F)CC(=O)N[C@H]1Cc2cccc(C(=O)OCOC(=O)C3CCOCC3)c2OB1O] | 455 | |
| 166 | 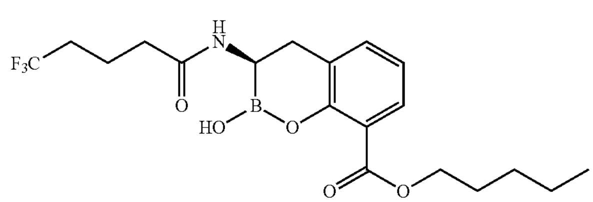 [SMILES: CCCCCOC(=O)c1cccc2c1OB(O)[C@@H](NC(=O)CCCC(F)(F)F)C2] | 415 | |
| 167 | 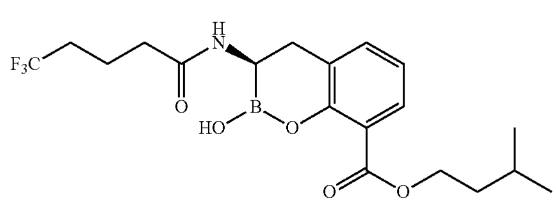 [SMILES: CC(C)CCOC(=O)c1cccc2c1OB(O)[C@@H](NC(=O)CCCC(F)(F)F)C2] | 415 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 168 | 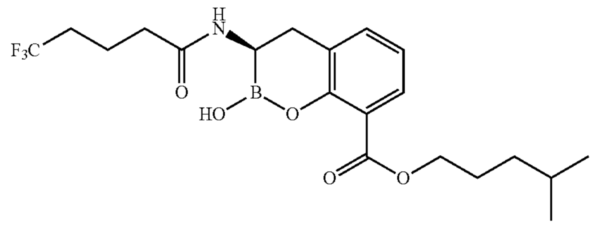 [SMILES: CC(C)CCCOC(=O)c1cccc2c1OB(O)[C@@H](NC(=O)CCCC(F)(F)F)C2] | 429 | |
| 169 | 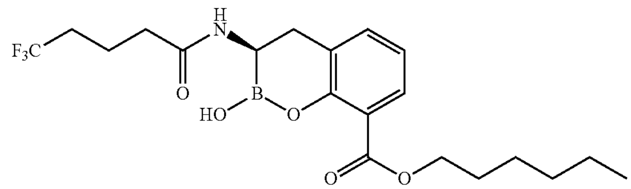 [SMILES: CCCCCCOC(=O)c1cccc2c1OB(O)[C@@H](NC(=O)CCCC(F)(F)F)C2] | 429 | |
| 170 | 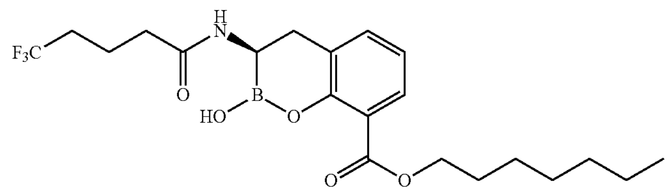 [SMILES: CCCCCCCOC(=O)c1cccc2c1OB(O)[C@@H](NC(=O)CCCC(F)(F)F)C2] | 443 | |
| 171 | 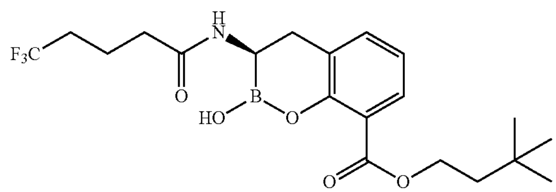 [SMILES: CC(C)(C)CCOC(=O)c1cccc2c1OB(O)[C@@H](NC(=O)CCCC(F)(F)F)C2] | 429 | |
| 172 | 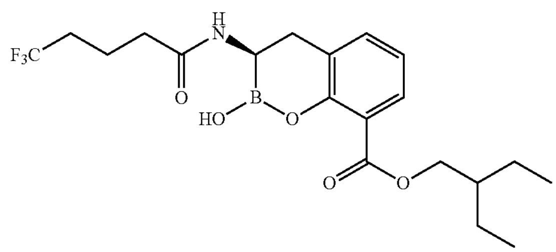 [SMILES: CCC(CC)COC(=O)c1cccc2c1OB(O)[C@@H](NC(=O)CCCC(F)(F)F)C2] | 429 | |
| 173 | 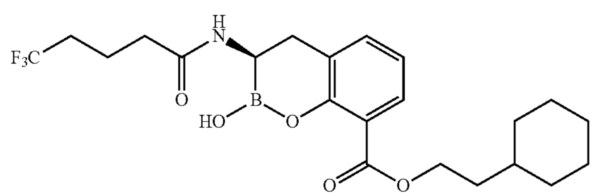 [SMILES: O=C(CCCC(F)(F)F)N[C@H]1Cc2cccc(C(=O)OCCC3CCCCC3)c2OB1O] | 455 | |
| 174 | 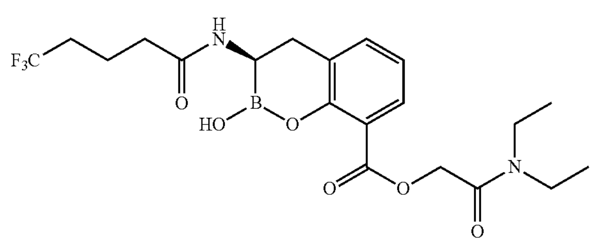 [SMILES: CCN(CC)C(=O)COC(=O)c1cccc2c1OB(O)[C@@H](NC(=O)CCCC(F)(F)F)C2] | 458 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 175 | 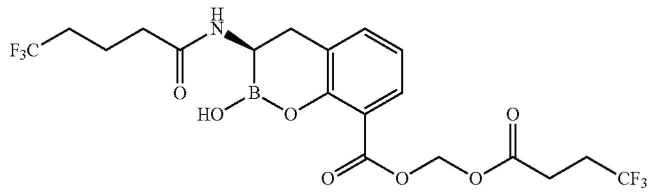 [SMILES: O=C(CCCC(F)(F)F)N[C@H]1Cc2cccc(C(=O)OCOC(=O)CCC(F)(F)F)c2OB1O] | 499 | |
| 176 | 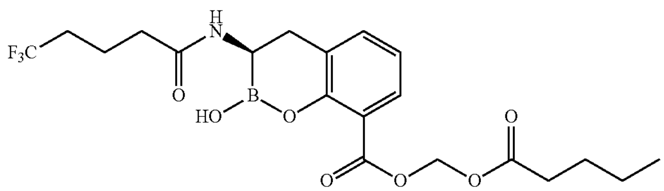 [SMILES: CCCCC(=O)OCOC(=O)c1cccc2c1OB(O)[C@@H](NC(=O)CCCC(F)(F)F)C2] | 459 | |
| 177 | 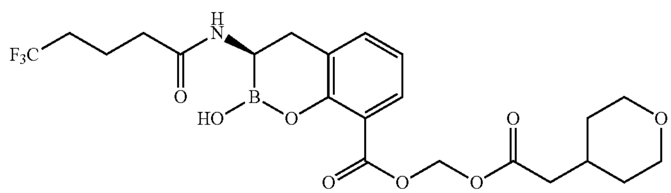 [SMILES: O=C(CCCC(F)(F)F)N[C@H]1Cc2cccc(C(=O)OCOC(=O)CC3CCOCC3)c2OB1O] | 501 | |
| 178 | 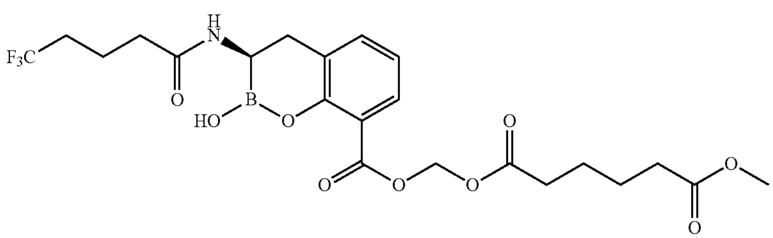 [SMILES: COC(=O)CCCCC(=O)OCOC(=O)c1cccc2c1OB(O)[C@@H](NC(=O)CCCC(F)(F)F)C2] | 517 | |
| 179 | 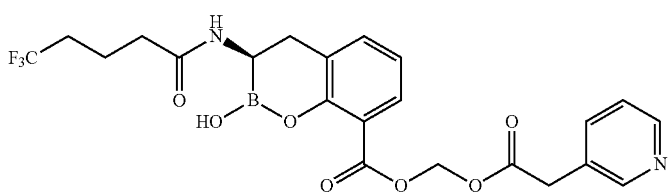 [SMILES: O=C(CCCC(F)(F)F)N[C@H]1Cc2cccc(C(=O)OCOC(=O)Cc3cccnc3)c2OB1O] | 494 | |
| 180 | 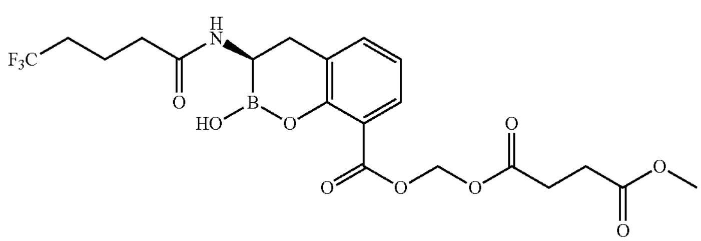 [SMILES: COC(=O)CCC(=O)OCOC(=O)c1cccc2c1OB(O)[C@@H](NC(=O)CCCC(F)(F)F)C2] | 489 | |
| 181 | 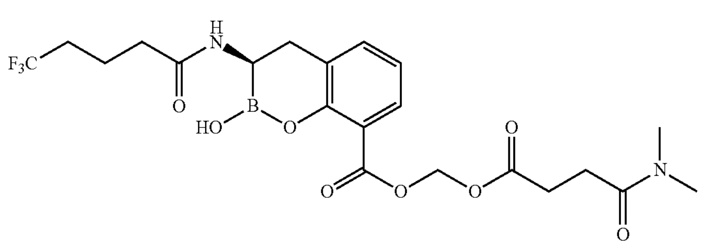 [SMILES: CN(C)C(=O)CCC(=O)OCOC(=O)c1cccc2c1OB(O)[C@@H](NC(=O)CCCC(F)(F)F)C2] | 502 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 182 | 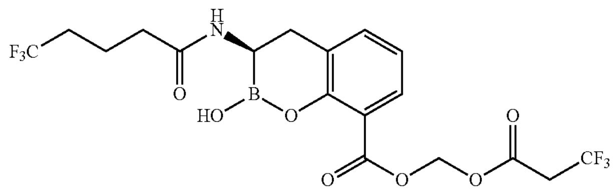 [SMILES: O=C(CCCC(F)(F)F)N[C@H]1Cc2cccc(C(=O)OCOC(=O)CC(F)(F)F)c2OB1O] | 485 | |
| 183 | 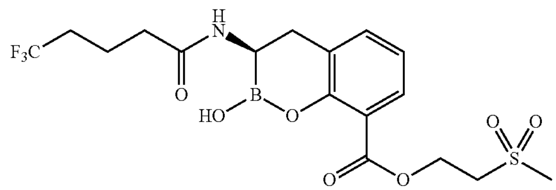 [SMILES: CS(=O)(=O)CCOC(=O)c1cccc2c1OB(O)[C@@H](NC(=O)CCCC(F)(F)F)C2] | 451 | |
| 184 | 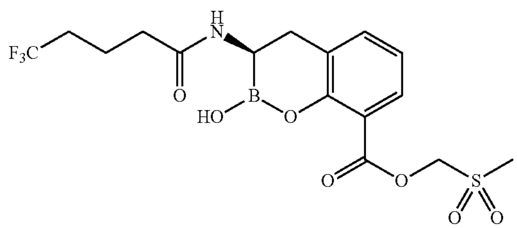 [SMILES: CS(=O)(=O)COC(=O)c1cccc2c1OB(O)[C@@H](NC(=O)CCCC(F)(F)F)C2] | 437 | |
| 185 | 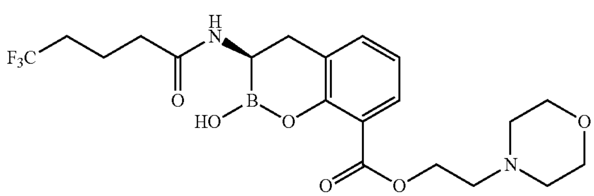 [SMILES: O=C(CCCC(F)(F)F)N[C@H]1Cc2cccc(C(=O)OCCN3CCOCC3)c2OB1O] | 458 | |
| 186 | 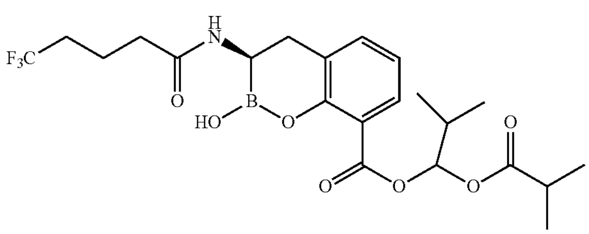 [SMILES: CC(C)C(=O)OC(OC(=O)c1cccc2c1OB(O)[C@@H](NC(=O)CCCC(F)(F)F)C2)C(C)C] | 487 | |
| 187 | 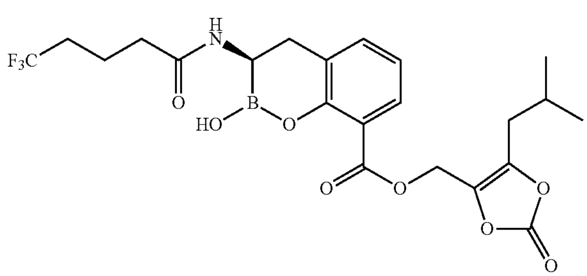 [SMILES: CC(C)Cc1oc(=O)oc1COC(=O)c1cccc2c1OB(O)[C@@H](NC(=O)CCCC(F)(F)F)C2] | 499 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 188 | 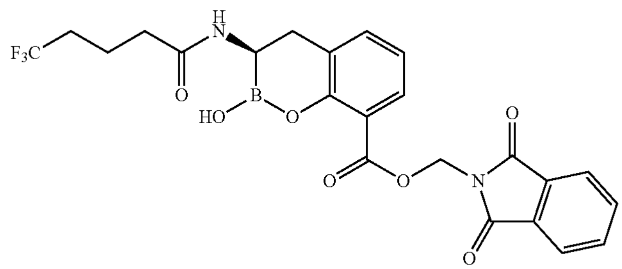 [SMILES: O=C(CCCC(F)(F)F)N[C@H]1Cc2cccc(C(=O)OCN3C(=O)c4ccccc4C3=O)c2OB1O] | 504 | |
| 189 | 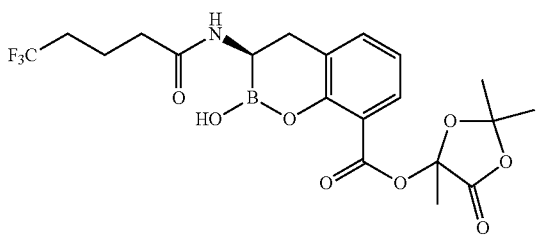 [SMILES: CC1(C)OC(=O)C(C)(OC(=O)c2cccc3c2OB(O)[C@@H](NC(=O)CCCC(F)(F)F)C3)O1] | 473 | |
| 190 | 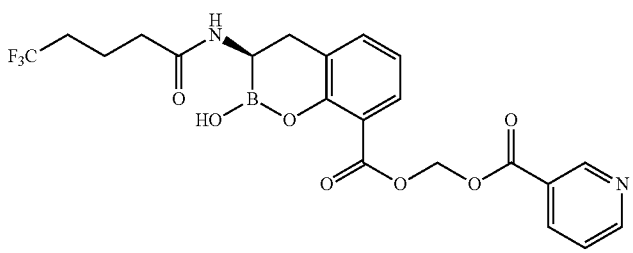 [SMILES: O=C(CCCC(F)(F)F)N[C@H]1Cc2cccc(C(=O)OCOC(=O)c3cccnc3)c2OB1O] | 480 | |
| 191 | 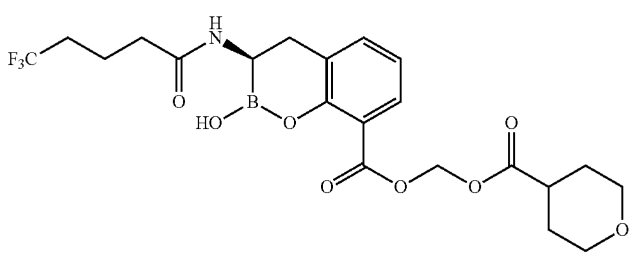 [SMILES: O=C(CCCC(F)(F)F)N[C@H]1Cc2cccc(C(=O)OCOC(=O)C3CCOCC3)c2OB1O] | 487 | |
| 192 | 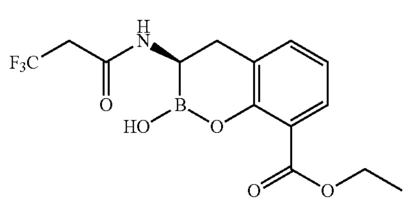 [SMILES: CCOC(=O)c1cccc2c1OB(O)[C@@H](NC(=O)CC(F)(F)F)C2] | 345 | |
| 193 | 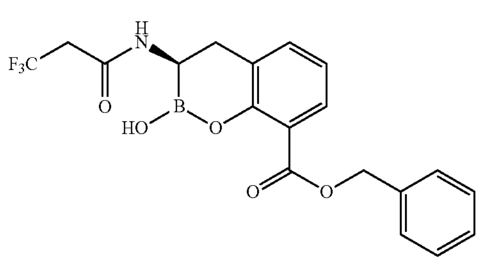 [SMILES: O=C(CC(F)(F)F)N[C@H]1Cc2cccc(C(=O)OCc3ccccc3)c2OB1O] | 407 | |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 194 | 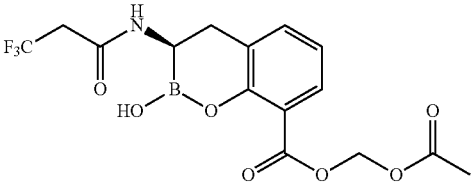 [SMILES: CC(=O)OCOC(=O)c1cccc2c1OB(O)[C@@H](NC(=O)CC(F)(F)F)C2] | 389 | |
| 195 | 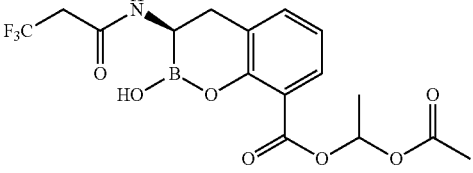 | 403 | |
| 196 | 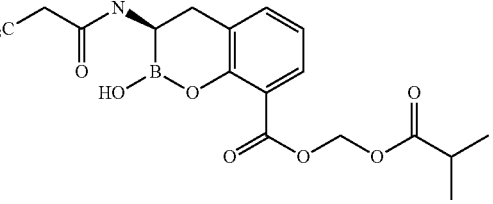 | 417 | |
| 197 | 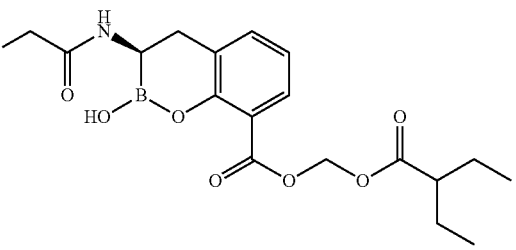 | 445 | |
| 198 | 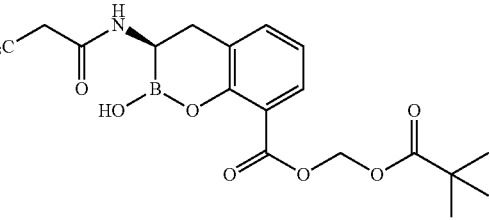 | 431 | |
| 199 | 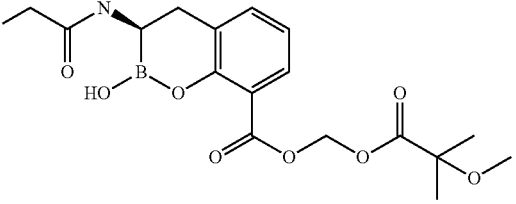 | 447 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 200 | 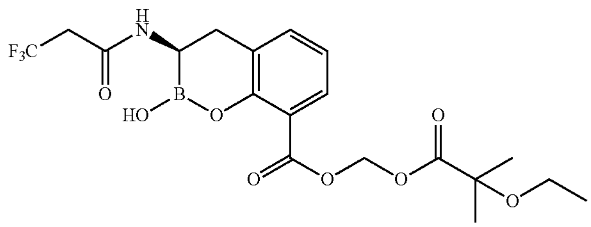 [SMILES: CCOC(C)(C)C(=O)OCOC(=O)c1cccc2c1OB(O)[C@@H](NC(=O)CC(F)(F)F)C2] | 461 | |
| 201 | 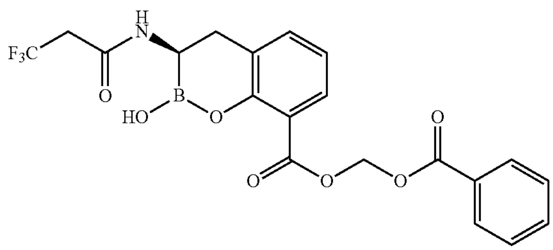 [SMILES: O=C(CC(F)(F)F)N[C@H]1Cc2cccc(C(=O)OCOC(=O)c3ccccc3)c2OB1O] | 451 | |
| 202 | 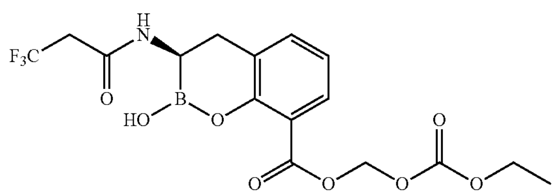 [SMILES: CCOC(=O)OCOC(=O)c1cccc2c1OB(O)[C@@H](NC(=O)CC(F)(F)F)C2] | 419 | |
| 203 | 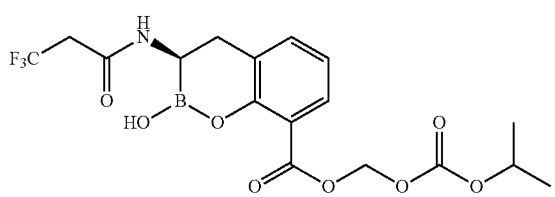 [SMILES: CC(C)OC(=O)OCOC(=O)c1cccc2c1OB(O)[C@@H](NC(=O)CC(F)(F)F)C2] | 433 | |
| 204 | 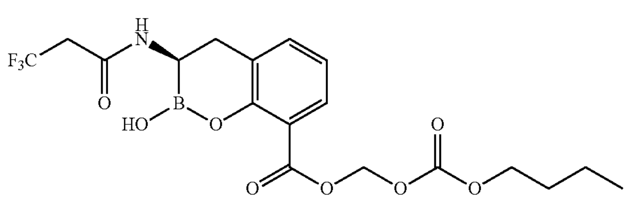 [SMILES: CCCCOC(=O)OCOC(=O)c1cccc2c1OB(O)[C@@H](NC(=O)CC(F)(F)F)C2] | 447 | |
| 205 | 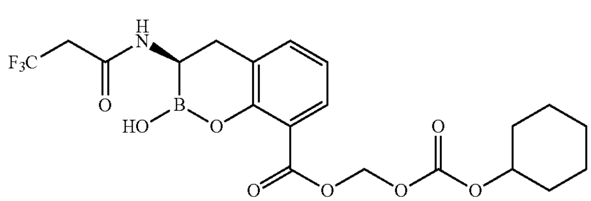 [SMILES: O=C(CC(F)(F)F)N[C@H]1Cc2cccc(C(=O)OCOC(=O)OC3CCCCC3)c2OB1O] | 473 | |
| 206 | 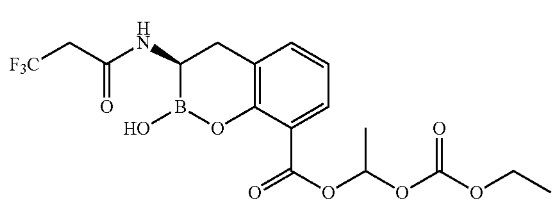 [SMILES: CCOC(=O)OC(C)OC(=O)c1cccc2c1OB(O)[C@@H](NC(=O)CC(F)(F)F)C2] | 433 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 207 | 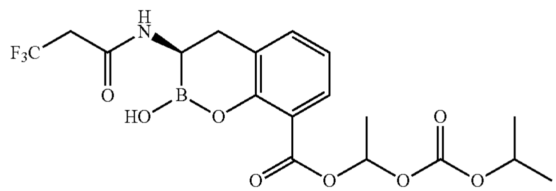 [SMILES: CC(C)OC(=O)OC(C)OC(=O)c1cccc2c1OB(O)[C@@H](NC(=O)CC(F)(F)F)C2] | | 447 |
| 208 | 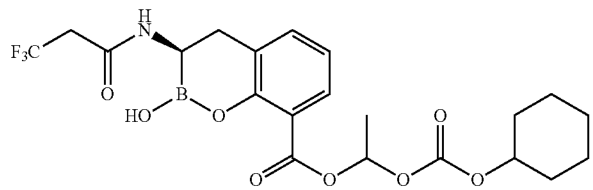 [SMILES: CC(OC(=O)OC1CCCCC1)OC(=O)c1cccc2c1OB(O)[C@@H](NC(=O)CC(F)(F)F)C2] | | 487 |
| 209 | 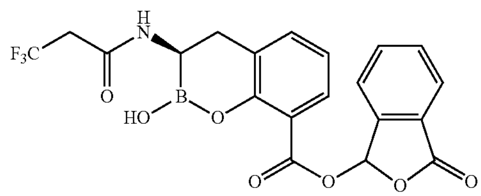 [SMILES: O=C(CC(F)(F)F)N[C@H]1Cc2cccc(C(=O)OC3OC(=O)c4ccccc43)c2OB1O] | | 449 |
| 210 | 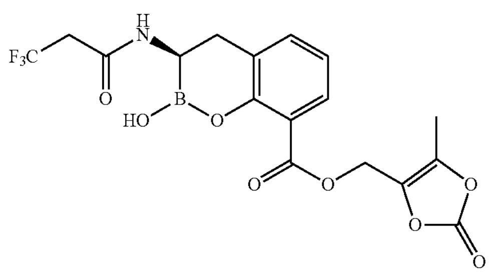 [SMILES: Cc1oc(=O)oc1COC(=O)c1cccc2c1OB(O)[C@@H](NC(=O)CC(F)(F)F)C2] | | 429 |
| 211 | 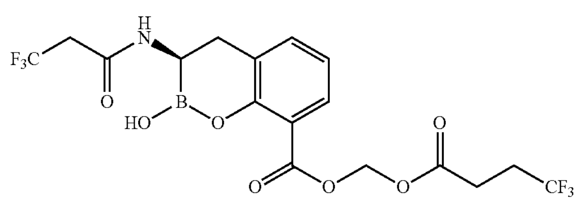 [SMILES: O=C(CC(F)(F)F)N[C@H]1Cc2cccc(C(=O)OCOC(=O)CCC(F)(F)F)c2OB1O] | | 471 |
| 212 | 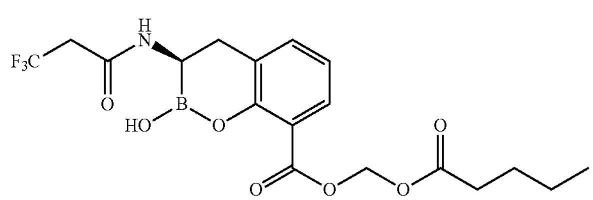 [SMILES: CCCCC(=O)OCOC(=O)c1cccc2c1OB(O)[C@@H](NC(=O)CC(F)(F)F)C2] | | 431 |
| 213 | 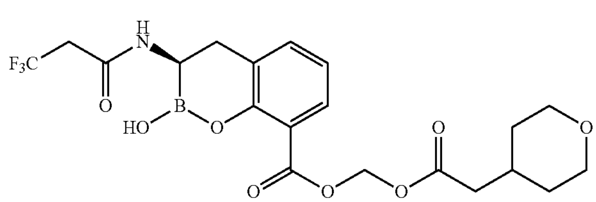 [SMILES: O=C(CC(F)(F)F)N[C@H]1Cc2cccc(C(=O)OCOC(=O)CC3CCOCC3)c2OB1O] | | 473 |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 214 | 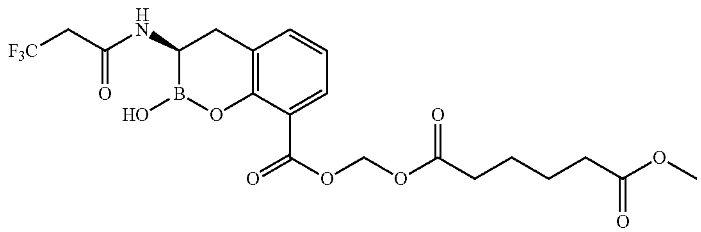 [SMILES: COC(=O)CCCCC(=O)OCOC(=O)c1cccc2c1OB(O)[C@@H](NC(=O)CC(F)(F)F)C2] | 489 | |
| 215 | 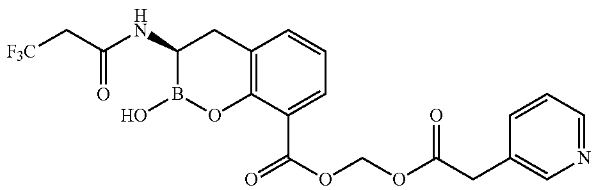 [SMILES: O=C(CC(F)(F)F)N[C@H]1Cc2cccc(C(=O)OCOC(=O)Cc3cccnc3)c2OB1O] | 466 | |
| 216 | 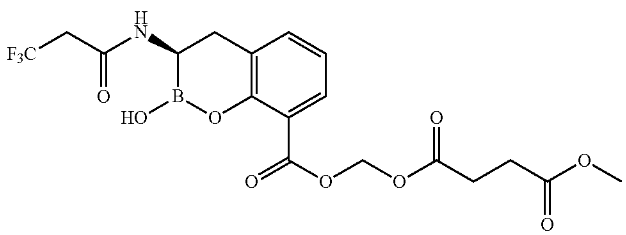 [SMILES: COC(=O)CCC(=O)OCOC(=O)c1cccc2c1OB(O)[C@@H](NC(=O)CC(F)(F)F)C2] | 461 | |
| 217 | 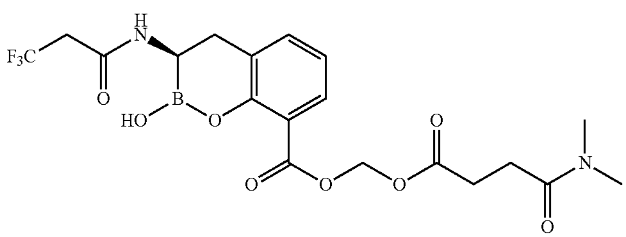 [SMILES: CN(C)C(=O)CCC(=O)OCOC(=O)c1cccc2c1OB(O)[C@@H](NC(=O)CC(F)(F)F)C2] | 474 | |
| 218 | 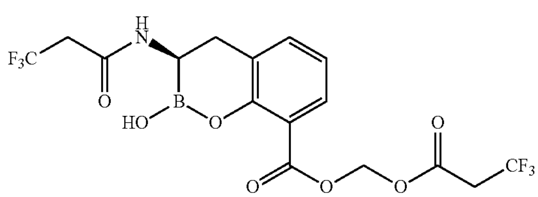 [SMILES: O=C(CC(F)(F)F)N[C@H]1Cc2cccc(C(=O)OCOC(=O)CC(F)(F)F)c2OB1O] | 457 | |
| 219 | 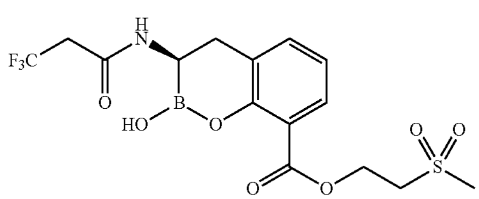 [SMILES: CS(=O)(=O)CCOC(=O)c1cccc2c1OB(O)[C@@H](NC(=O)CC(F)(F)F)C2] | 423 | |
| 220 | 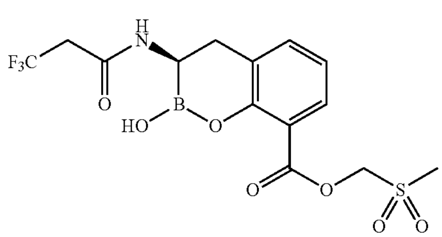 [SMILES: CS(=O)(=O)COC(=O)c1cccc2c1OB(O)[C@@H](NC(=O)CC(F)(F)F)C2] | 409 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 221 | 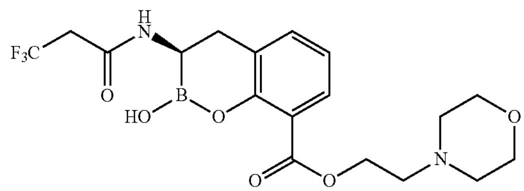 [SMILES: O=C(CC(F)(F)F)N[C@H]1Cc2cccc(C(=O)OCCN3CCOCC3)c2OB1O] | | 430 |
| 222 | 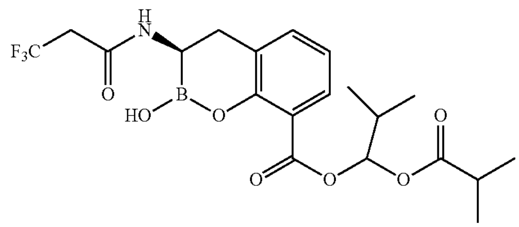 [SMILES: CC(C)C(=O)OC(OC(=O)c1cccc2c1OB(O)[C@@H](NC(=O)CC(F)(F)F)C2)C(C)C] | | 459 |
| 223 | 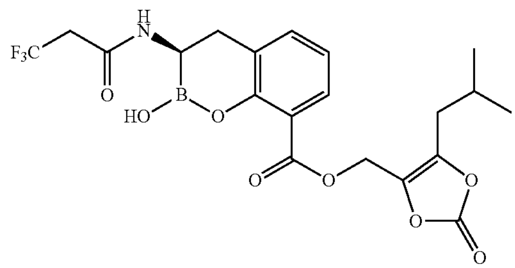 [SMILES: CC(C)Cc1oc(=O)oc1COC(=O)c1cccc2c1OB(O)[C@@H](NC(=O)CC(F)(F)F)C2] | | 471 |
| 224 | 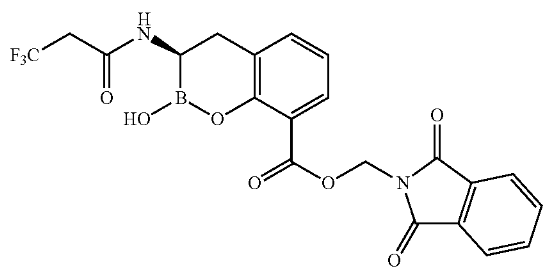 [SMILES: O=C(CC(F)(F)F)N[C@H]1Cc2cccc(C(=O)OCN3C(=O)c4ccccc4C3=O)c2OB1O] | | 476 |
| 225 | 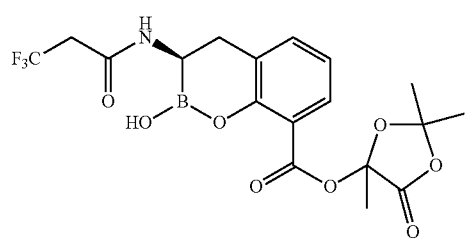 [SMILES: CC1(C)OC(=O)C(C)(OC(=O)c2cccc3c2OB(O)[C@@H](NC(=O)CC(F)(F)F)C3)O1] | | 445 |
| 226 | 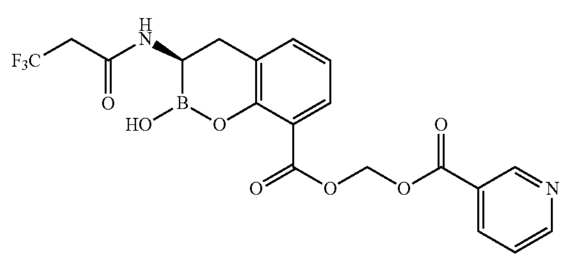 [SMILES: O=C(CC(F)(F)F)N[C@H]1Cc2cccc(C(=O)OCOC(=O)c3cccnc3)c2OB1O] | | 452 |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 227 | 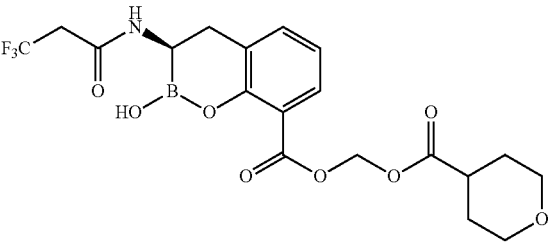 | 459 | |
| 228 | 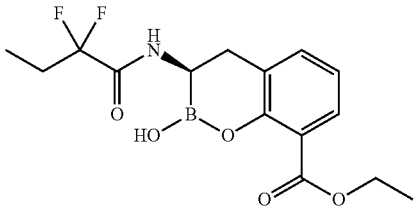 [SMILES: CCOC(=O)c1cccc2c1OB(O)[C@@H](NC(=O)C(F)(F)CC)C2] | 341 | |
| 229 | 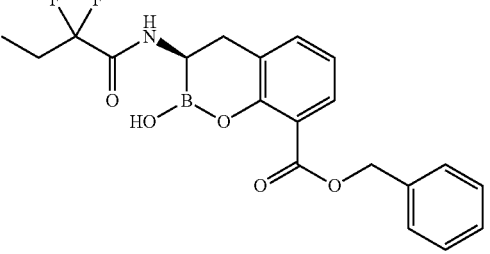 | 403 | |
| 230 | 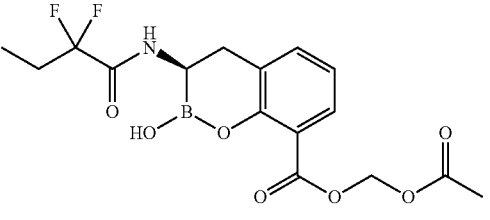 [SMILES: CCC(F)(F)C(=O)N[C@H]1Cc2cccc(C(=O)OCOC(C)=O)c2OB1O] | 385 | |
| 231 | 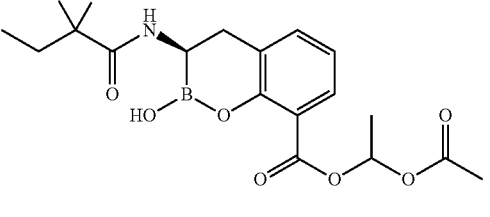 | 399 | |
| 232 | 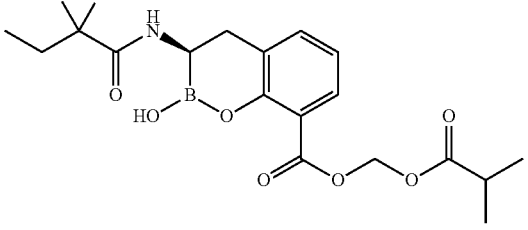 | 413 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 233 | 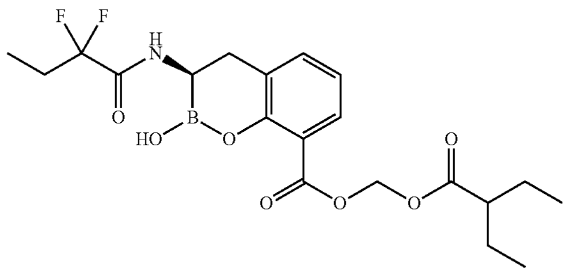 [SMILES: CCC(CC)C(=O)OCOC(=O)c1cccc2c1OB(O)[C@@H](NC(=O)C(F)(F)CC)C2] | 441 | |
| 234 | 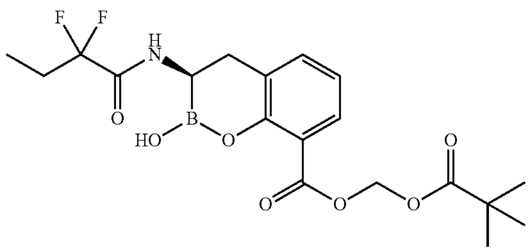 [SMILES: CCC(F)(F)C(=O)N[C@H]1Cc2cccc(C(=O)OCOC(=O)C(C)(C)C)c2OB1O] | 427 | |
| 235 | 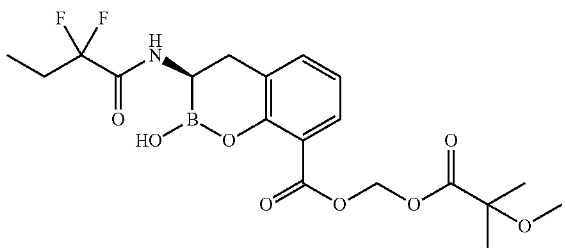 [SMILES: CCC(F)(F)C(=O)N[C@H]1Cc2cccc(C(=O)OCOC(=O)C(C)(C)OC)c2OB1O] | 443 | |
| 236 | 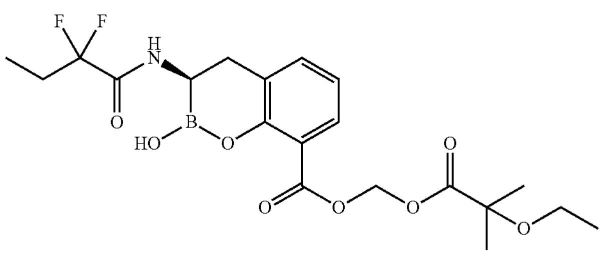 [SMILES: CCOC(C)(C)C(=O)OCOC(=O)c1cccc2c1OB(O)[C@@H](NC(=O)C(F)(F)CC)C2] | 457 | |
| 237 | 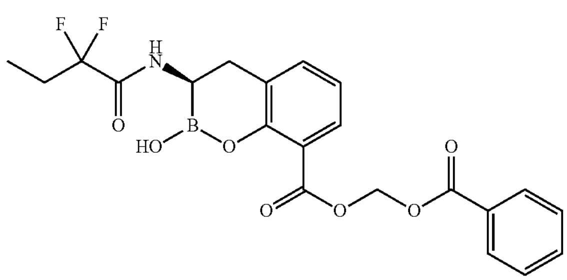 [SMILES: CCC(F)(F)C(=O)N[C@H]1Cc2cccc(C(=O)OCOC(=O)c3ccccc3)c2OB1O] | 447 | |
| 238 | 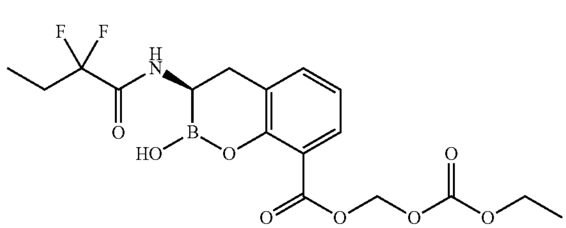 [SMILES: CCOC(=O)OCOC(=O)c1cccc2c1OB(O)[C@@H](NC(=O)C(F)(F)CC)C2] | 415 | |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 239 | 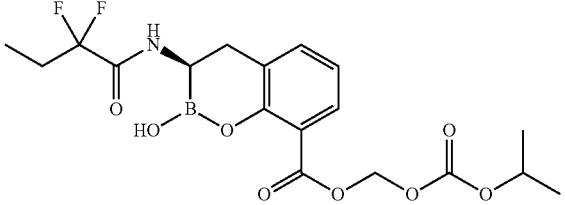 [SMILES: CCC(F)(F)C(=O)N[C@H]1Cc2cccc(C(=O)OCOC(=O)OC(C)C)c2OB1O] | 429 | |
| 240 | 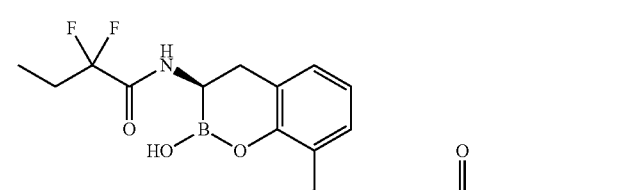 | 443 | |
| 241 | 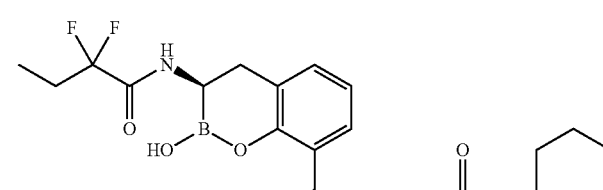 | 469 | |
| 242 | 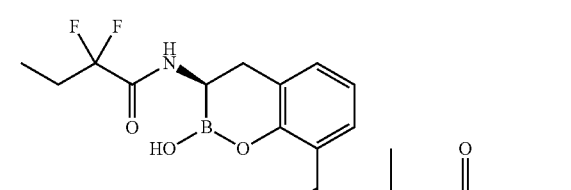 | 429 | |
| 243 | 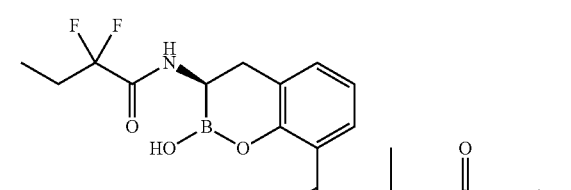 | 443 | |
| 244 | 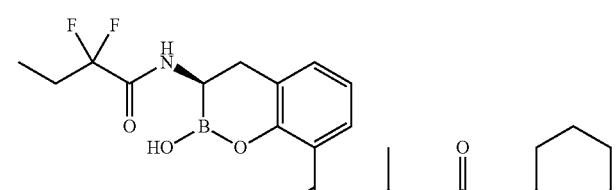 | 483 | |
| 245 | 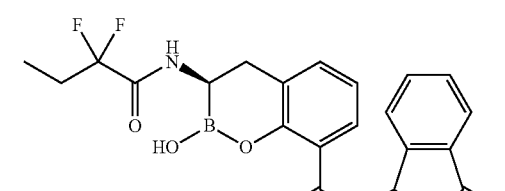 | 445 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 246 | 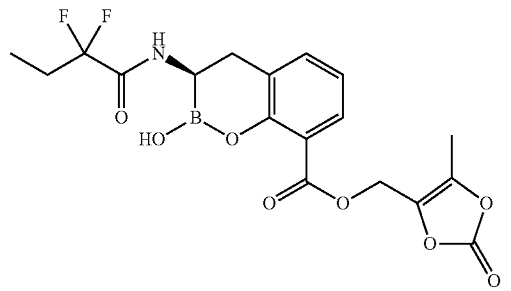 [SMILES: CCC(F)(F)C(=O)N[C@H]1Cc2cccc(C(=O)OCc3oc(=O)oc3C)c2OB1O] | | 425 |
| 247 | 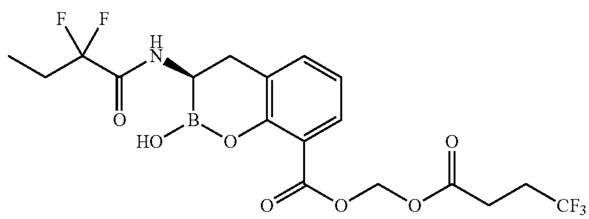 [SMILES: CCC(F)(F)C(=O)N[C@H]1Cc2cccc(C(=O)OCOC(=O)CCC(F)(F)F)c2OB1O] | | 467 |
| 248 | 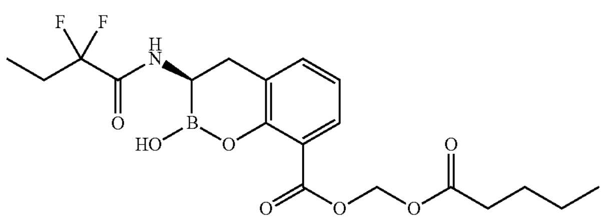 [SMILES: CCCCC(=O)OCOC(=O)c1cccc2c1OB(O)[C@@H](NC(=O)C(F)(F)CC)C2] | | 427 |
| 249 | 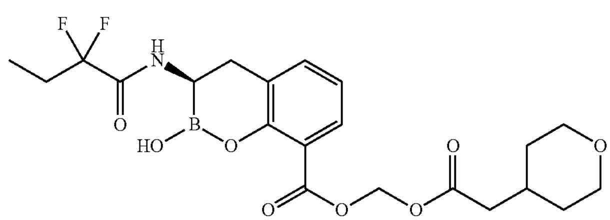 [SMILES: CCC(F)(F)C(=O)N[C@H]1Cc2cccc(C(=O)OCOC(=O)CC3CCOCC3)c2OB1O] | | 469 |
| 250 | 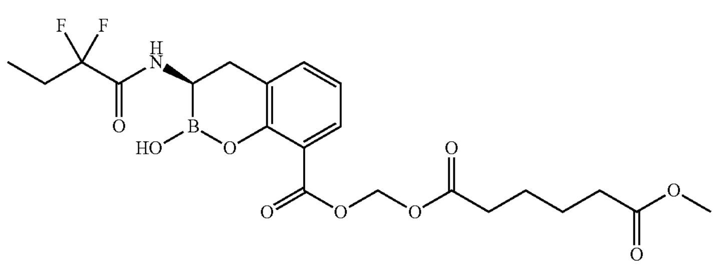 [SMILES: CCC(F)(F)C(=O)N[C@H]1Cc2cccc(C(=O)OCOC(=O)CCCCC(=O)OC)c2OB1O] | | 485 |
| 251 | 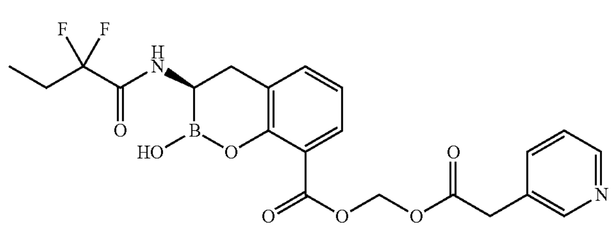 [SMILES: CCC(F)(F)C(=O)N[C@H]1Cc2cccc(C(=O)OCOC(=O)Cc3cccnc3)c2OB1O] | | 462 |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 252 | 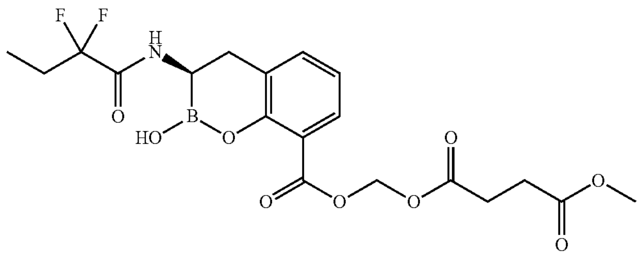 [SMILES: CCC(F)(F)C(=O)N[C@H]1Cc2cccc(C(=O)OCOC(=O)CCC(=O)OC)c2OB1O] | 457 | |
| 253 | 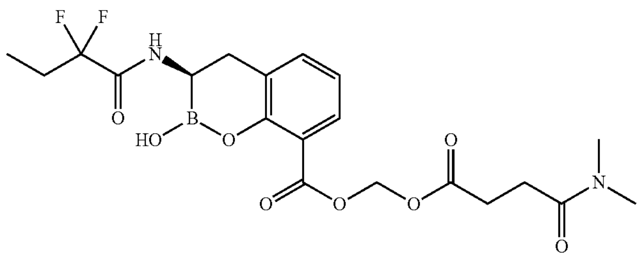 [SMILES: CCC(F)(F)C(=O)N[C@H]1Cc2cccc(C(=O)OCOC(=O)CCC(=O)N(C)C)c2OB1O] | 470 | |
| 254 | 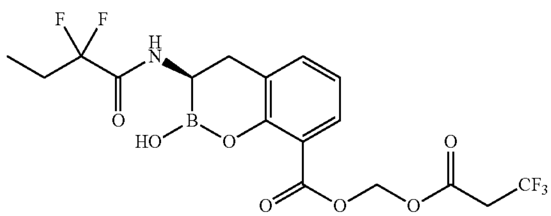 [SMILES: CCC(F)(F)C(=O)N[C@H]1Cc2cccc(C(=O)OCOC(=O)CC(F)(F)F)c2OB1O] | 453 | |
| 255 | 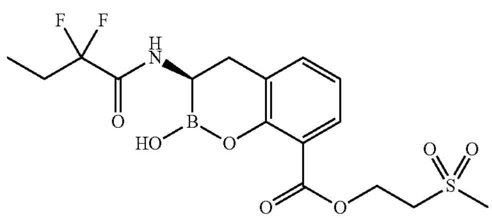 [SMILES: CCC(F)(F)C(=O)N[C@H]1Cc2cccc(C(=O)OCCS(C)(=O)=O)c2OB1O] | 419 | |
| 256 | 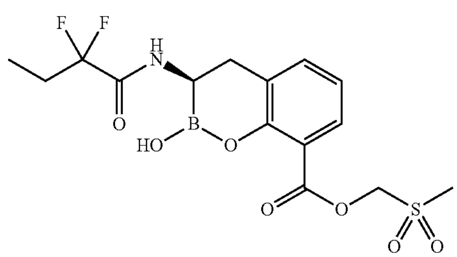 [SMILES: CCC(F)(F)C(=O)N[C@H]1Cc2cccc(C(=O)OCS(C)(=O)=O)c2OB1O] | 405 | |
| 257 | 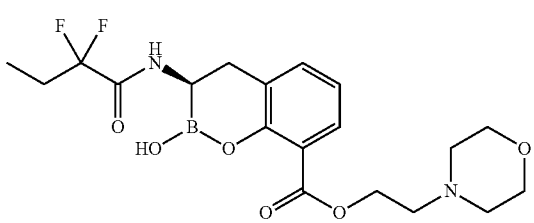 [SMILES: CCC(F)(F)C(=O)N[C@H]1Cc2cccc(C(=O)OCCN3CCOCC3)c2OB1O] | 426 | |

US 10,464,952 B2
263                                                                                                  264
TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 258 | 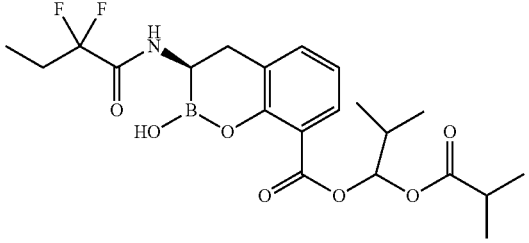 [SMILES: CCC(F)(F)C(=O)N[C@H]1Cc2cccc(C(=O)OC(OC(=O)C(C)C)C(C)C)c2OB1O] | 455 | |
| 259 | 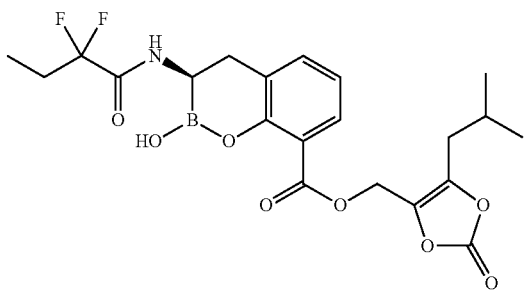 [SMILES: CCC(F)(F)C(=O)N[C@H]1Cc2cccc(C(=O)OCc3oc(=O)oc3CC(C)C)c2OB1O] | 467 | |
| 260 | 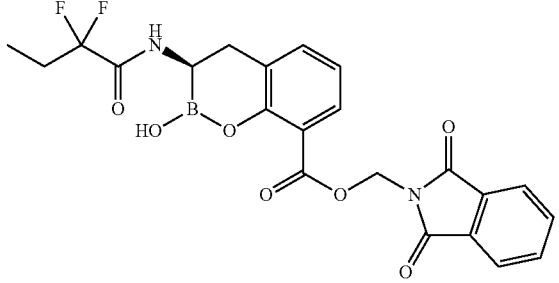 [SMILES: CCC(F)(F)C(=O)N[C@H]1Cc2cccc(C(=O)OCN3C(=O)c4ccccc4C3=O)c2OB1O] | 472 | |
| 261 | 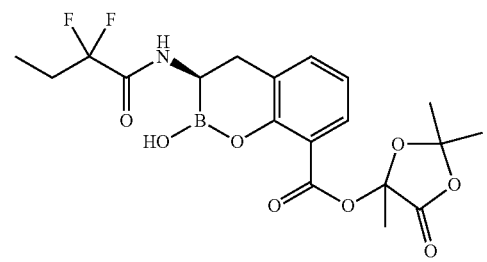 [SMILES: CCC(F)(F)C(=O)N[C@H]1Cc2cccc(C(=O)OC3(C)OC(C)(C)OC3=O)c2OB1O] | 441 | |
| 262 | 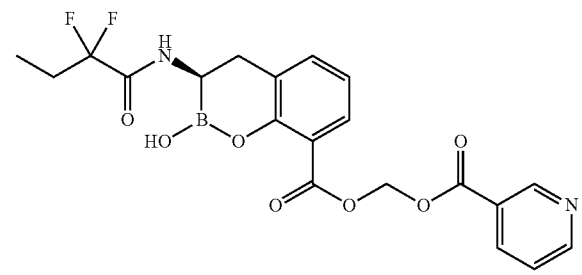 [SMILES: CCC(F)(F)C(=O)N[C@H]1Cc2cccc(C(=O)OCOC(=O)c3cccnc3)c2OB1O] | 448 | |

TABLE 1-continued
Examples of compounds of Formula (Ia), (IIa), (IIIa), (IVa), or (Va).
| Ex. | Structure | MW | ESI-MS (m/z) for [MH]+ |
|---|---|---|---|
| 263 | 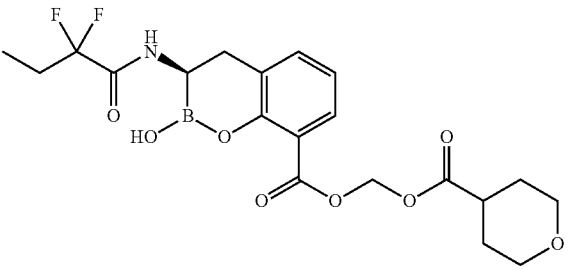 [SMILES: CCC(F)(F)C(=O)N[C@H]1Cc2cccc(C(=O)OCOC(=O)C3CCOCC3)c2OB1O] | 455 | |
| 264 | 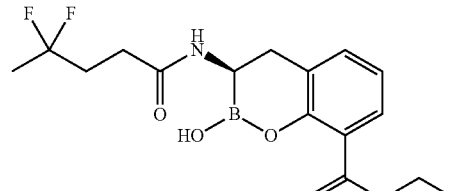 | 355 | |
| 265 | 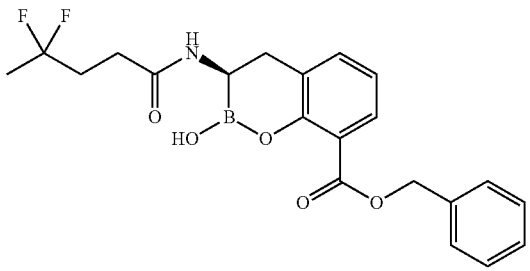 [SMILES: CC(F)(F)CCC(=O)N[C@H]1Cc2cccc(C(=O)OCc3ccccc3)c2OB1O] | 417 | |
| 266 | 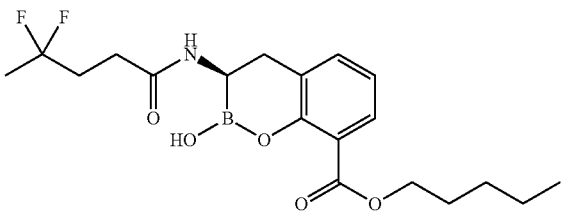 [SMILES: CCCCCOC(=O)c1cccc2c1OB(O)[C@@H](NC(=O)CCC(C)(F)F)C2] | 397 | |
| 267 | 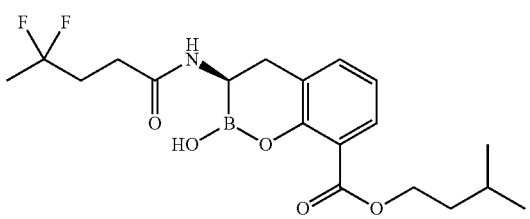 [SMILES: CC(C)CCOC(=O)c1cccc2c1OB(O)[C@@H](NC(=O)CCC(C)(F)F)C2] | 397 | |
| 268 | 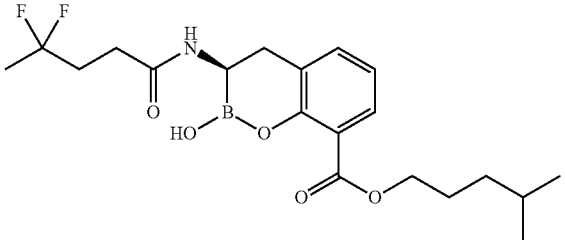 [SMILES: CC(C)CCCOC(=O)c1cccc2c1OB(O)[C@@H](NC(=O)CCC(C)(F)F)C2] | 411 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 269 | 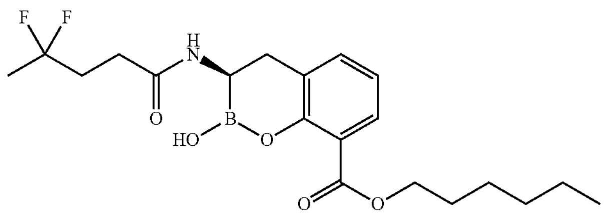 [SMILES: CCCCCCOC(=O)c1cccc2c1OB(O)[C@@H](NC(=O)CCC(C)(F)F)C2] | | 411 |
| 270 | 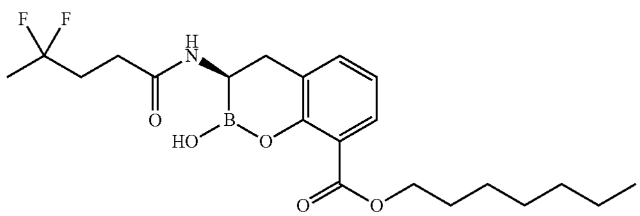 [SMILES: CCCCCCCOC(=O)c1cccc2c1OB(O)[C@@H](NC(=O)CCC(C)(F)F)C2] | | 425 |
| 271 | 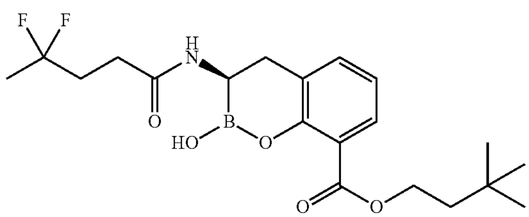 [SMILES: CC(C)(C)CCOC(=O)c1cccc2c1OB(O)[C@@H](NC(=O)CCC(C)(F)F)C2] | | 411 |
| 272 | 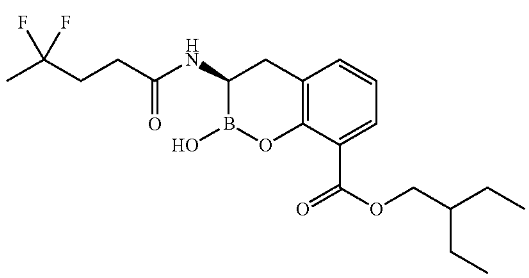 [SMILES: CCC(CC)COC(=O)c1cccc2c1OB(O)[C@@H](NC(=O)CCC(C)(F)F)C2] | | 411 |
| 273 | 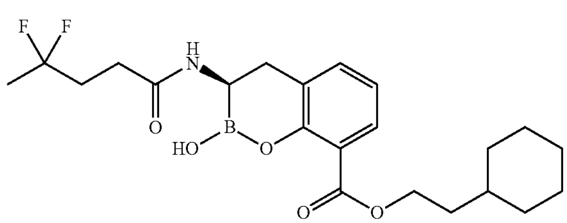 [SMILES: CC(F)(F)CCC(=O)N[C@H]1Cc2cccc(C(=O)OCCC3CCCCC3)c2OB1O] | | 437 |
| 274 | 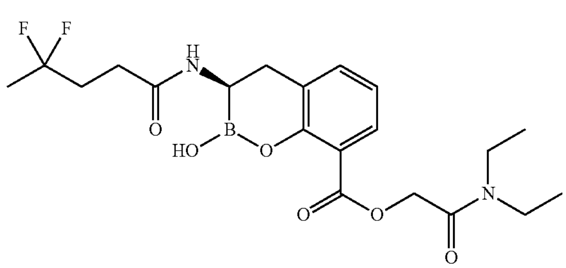 [SMILES: CCN(CC)C(=O)COC(=O)c1cccc2c1OB(O)[C@@H](NC(=O)CCC(C)(F)F)C2] | | 440 |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 275 | 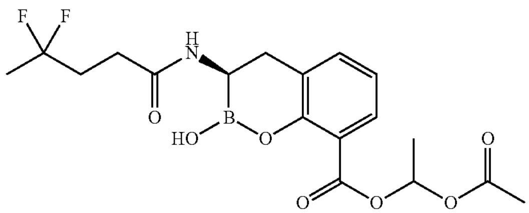 [SMILES: CC(=O)OC(C)OC(=O)c1cccc2c1OB(O)[C@@H](NC(=O)CCC(C)(F)F)C2] | 413 | |
| 276 | 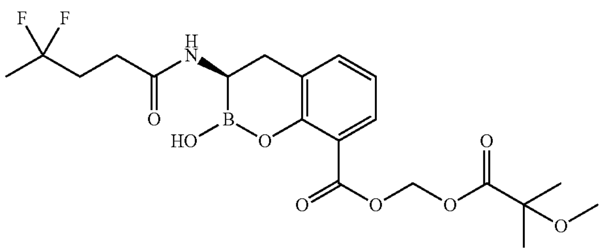 [SMILES: COC(C)(C)C(=O)OCOC(=O)c1cccc2c1OB(O)[C@@H](NC(=O)CCC(C)(F)F)C2] | 457 | |
| 277 | 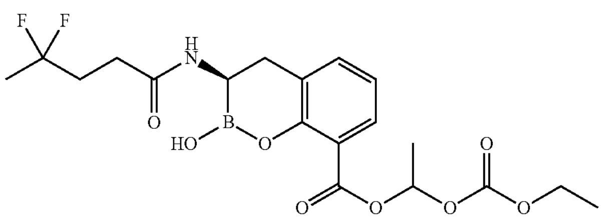 [SMILES: CCOC(=O)OC(C)OC(=O)c1cccc2c1OB(O)[C@@H](NC(=O)CCC(C)(F)F)C2] | 443 | |
| 278 | 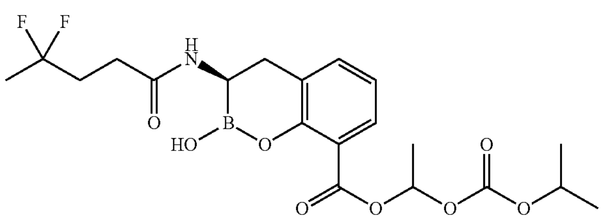 [SMILES: CC(C)OC(=O)OC(C)OC(=O)c1cccc2c1OB(O)[C@@H](NC(=O)CCC(C)(F)F)C2] | 457 | |
| 279 | 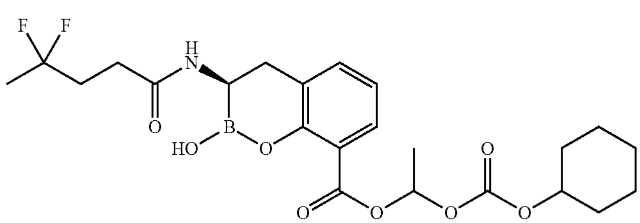 [SMILES: CC(OC(=O)OC1CCCCC1)OC(=O)c1cccc2c1OB(O)[C@@H](NC(=O)CCC(C)(F)F)C2] | 497 | |
| 280 | 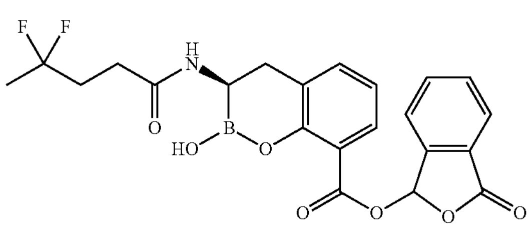 [SMILES: CC(F)(F)CCC(=O)N[C@H]1Cc2cccc(C(=O)OC3OC(=O)c4ccccc43)c2OB1O] | 459 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 281 | 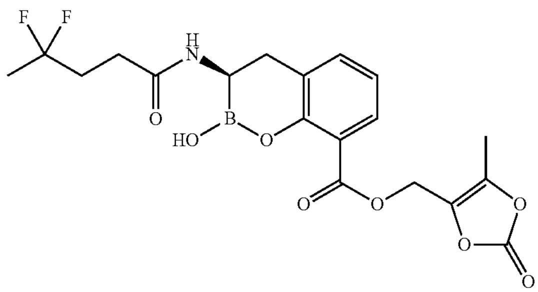 [SMILES: Cc1oc(=O)oc1COC(=O)c1cccc2c1OB(O)[C@@H](NC(=O)CCC(C)(F)F)C2] | 439 | |
| 282 | 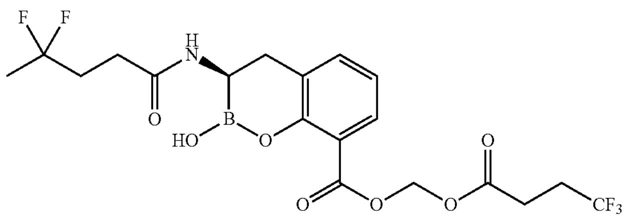 [SMILES: CC(F)(F)CCC(=O)N[C@H]1Cc2cccc(C(=O)OCOC(=O)CCC(F)(F)F)c2OB1O] | 481 | |
| 283 | 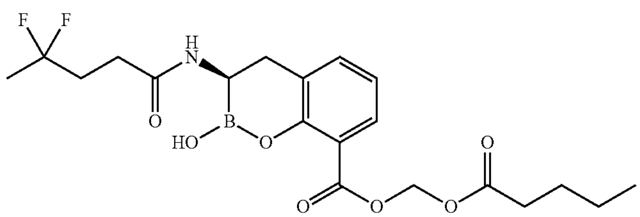 [SMILES: CCCCC(=O)OCOC(=O)c1cccc2c1OB(O)[C@@H](NC(=O)CCC(C)(F)F)C2] | 441 | |
| 284 | 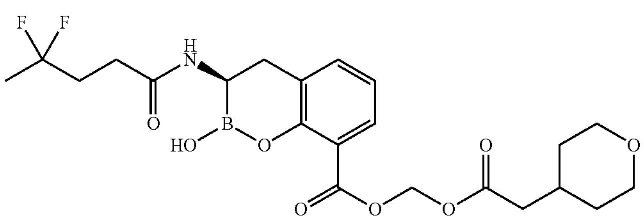 [SMILES: CC(F)(F)CCC(=O)N[C@H]1Cc2cccc(C(=O)OCOC(=O)CC3CCOCC3)c2OB1O] | 483 | |
| 285 | 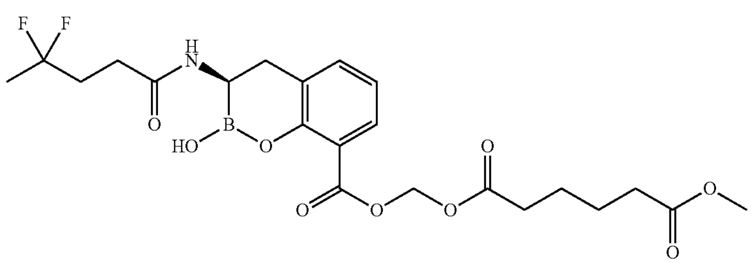 [SMILES: COC(=O)CCCCC(=O)OCOC(=O)c1cccc2c1OB(O)[C@@H](NC(=O)CCC(C)(F)F)C2] | 499 | |
| 286 | 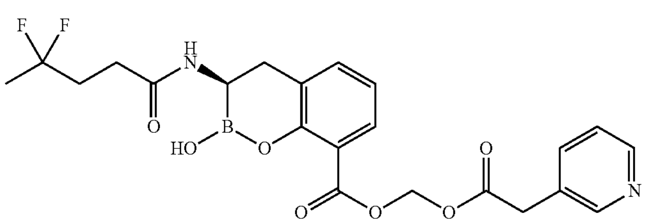 [SMILES: CC(F)(F)CCC(=O)N[C@H]1Cc2cccc(C(=O)OCOC(=O)Cc3cccnc3)c2OB1O] | 476 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 287 | 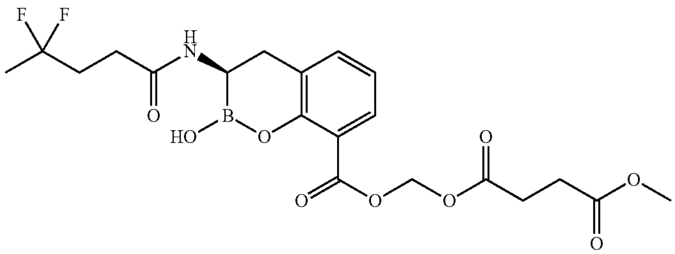 [SMILES: COC(=O)CCC(=O)OCOC(=O)c1cccc2c1OB(O)[C@@H](NC(=O)CCC(C)(F)F)C2] | 471 | |
| 288 | 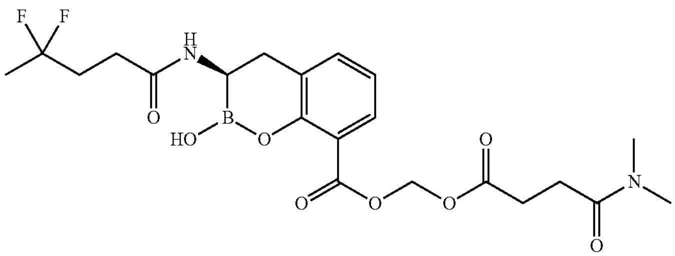 [SMILES: CN(C)C(=O)CCC(=O)OCOC(=O)c1cccc2c1OB(O)[C@@H](NC(=O)CCC(C)(F)F)C2] | 484 | |
| 289 | 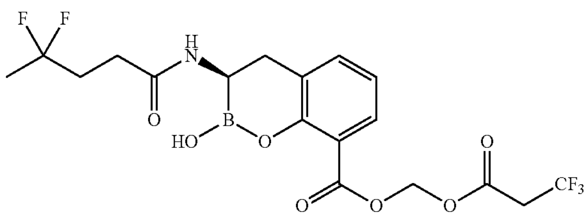 [SMILES: CC(F)(F)CCC(=O)N[C@H]1Cc2cccc(C(=O)OCOC(=O)CC(F)(F)F)c2OB1O] | 467 | |
| 290 | 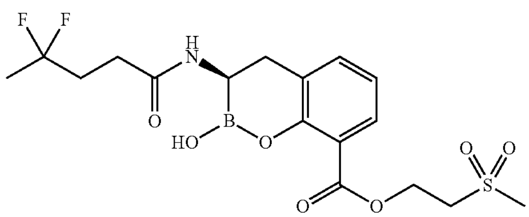 [SMILES: CC(F)(F)CCC(=O)N[C@H]1Cc2cccc(C(=O)OCCS(C)(=O)=O)c2OB1O] | 433 | |
| 291 | 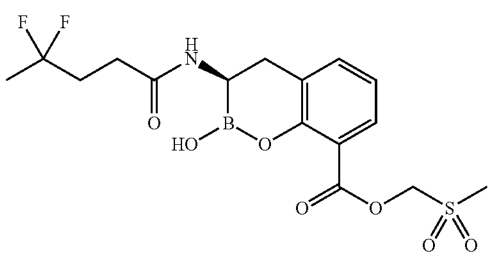 [SMILES: CC(F)(F)CCC(=O)N[C@H]1Cc2cccc(C(=O)OCS(C)(=O)=O)c2OB1O] | 419 | |
| 292 | 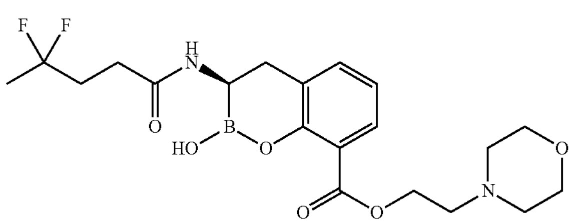 [SMILES: CC(F)(F)CCC(=O)N[C@H]1Cc2cccc(C(=O)OCCN3CCOCC3)c2OB1O] | 440 | |

TABLE 1-continued

Examples of compounds of Formula (Ia), (IIa), (IIIa), (IVa), or (Va).

| Ex. | Structure | MW | ESI-MS (m/z) for [MH]+ |
|---|---|---|---|
| 293 | | | 469 |
| 294 | | | 486 |
| 295 | | | 455 |
| 296 | | | 469 |

Example 297: Parenteral Composition

To prepare a parenteral pharmaceutical composition suitable for administration by injection, 100 mg of a compound described herein, or a water soluble pharmaceutically acceptable salt thereof, is dissolved in DMSO and then mixed with 10 ml of 0.9% sterile saline solution. The mixture is incorporated into a dosage unit suitable for administration by injection.

Example 298: Oral Composition

To prepare a pharmaceutical composition for oral delivery, 100 mg of a compound described herein, or pharmaceutically acceptable salt thereof, is mixed with 750 mg of starch. The mixture is incorporated into an oral dosage unit for, such as a hard gelatin capsule, which is suitable for oral administration.

BIOLOGICAL EXAMPLES

Example I: Experimental Method for β-Lactamase Enzyme Assays

Isolation of β-Lactamases.

For SHV-5, KPC-2, p99AmpC and OXA-4813-lactamases, *E. coli* BL21(DE3) bacterial cells carrying expression plasmids (expressed as native untagged proteins) for the individual β-lactamases were grown in 1L of Superbroth (Teknova Inc. Hollister, Calif.) supplemented with 100 μg/ml kanamycin selection and 1×5052 (0.5% glycerol, 0.05% glucose and 0.2% α-lactose) at 35° C. for 18-20 hours. Cells were harvested by centrifugation (4,000 xg, 4° C., 20 min), re-suspended in 50 ml of 10 mM HEPES pH 7.5 (1/20 of the initial volume). The cells were lysed by sonication (5 pulses of 45 seconds) at 45 Won ice. The lysates were clarified by centrifugation at 10,000 xg for 40 minutes at 4° C. Samples were diluted 5-fold in 50 mM sodium acetate pH 5.0, stored overnight at 4° C., after which they were centrifuged at 10,000 xg for 30 minutes to clarify, and filtered through 0.45 µm filters. The samples were loaded onto a 5 ml Capto S sepharose cation exchange column (GE Healthcare) pre-equilibrated with 50 mM sodium acetate pH 5.0. The column was washed with 5 column volumes of 50 mM sodium acetate pH 5.0 to wash out unbound protein and a linear gradient of NaCl (0 to 500 mM) was used to elute the protein (over 16 CV) from the column. Fractions were assayed for β-lactamase activity using Centa (Calbiochem, Gibbstown, N.J.) or Nitrocefin (EMD Millipore chemicals, Darmstadt, Germany) as a reporter β-lactamase substrate for activity in the isolated fractions. Active fractions were pooled, concentrated and further purified by gel filtration chromatography on a Superdex 75 prep grade gel filtration column (GE Healthcare, Piscataway, N.J.) pre -equilibrated in 50 mM Hepes pH 7.5, 150 mM NaCl. Active fractions were pooled, concentrated, and quantitated by BCA protein determination (ThermoScientific, Rockford, Ill.), dialyzed into PBS and frozen at −8° C. in 20% glycerol until use.

For VIM-2 metallo β-lactamase, the procedure was identical with the following exceptions, first the protein was not pH adjusted to pH 5 with 50 mM sodium acetate. Second, the chromatography step was changed to a 5 ml Q sepharose anion exchange column pre-equilibrated with 50 mM Hepes pH 7.5, and elution of the protein was achieved by a linear gradient of NaCl (0-600 mM). Finally, the VIM-2 purification required a second run (3$^{rd}$ step) on the Q sepharose anion exchange column to achieve acceptable purity (>90%).

β-Lactamase Inhibition.

To determine the level of inhibition of β-lactamase enzymes, compounds were diluted in PBS at pH 7.4 to yield concentrations ranging from 100 to 0.00005 µM in 96-well microtiter plates. An equal volume of diluted enzyme stock was added, and the plates were incubated at 37° C. for 15 min. Nitrocefin was used as substrate for p99 AmpC, VIM-2 and OXA-48 and dispensed into each well at a final concentration of 100 µM. Absorbance at 486 nm was immediately monitored for 10 min using a Biotek Powerwave XS2 microplate spectrophotometer using the GEN5 software package (Biotek Instruments, Winooski Vt.). In an analogous fashion, imipenem was used as substrate for KPC-2 and Cefotaxime was used for SHV-5, while changes in absorbance upon hydrolysis of the β-lactam ring were monitored at 300 nm and 260 nm respectively in UV-transparent 96-well microtiter assay plates. Maximum rates of hydrolysis were compared to those in control wells (without inhibitors), and percentages of enzyme inhibition were calculated for each concentration of inhibitor. The concentration of inhibitor needed to reduce the initial rate of hydrolysis of substrate by 50% ($IC_{50}$) was calculated as the residual activity of β-lactamase at 486 nm using GraFit version 7 kinetics software package (Erithacus Software, Surrey, UK).

Example II: Inhibition of Diverse β-Lactamases by Exemplary Compounds

Using the methodology described above, examples of the current invention were evaluated for their ability to inhibit β-lactamase enzymes from all four Ambler classifications (A through D). The results of these assays are summarized in Table 2 for representative enzymes across different subtyl)es (note SHV-5 represents an Ambler Class A Extended Spectrum β-Lactamase, KPC-2 exemplifies a Class A carbapenemase, p99 AmpC represents chromosomal Class C enzyme, OXA-48 represents a Class D oxacillinase and VIM-2 represents a class B zinc-dependent metallo-β-lactamase also possessing carbapenemase activity), where A represents an $IC_{50}$ of 10-100 µM, B represents an $IC_{50}$ of 1 to 10 µM, C represents an $IC_{50}$ of 0.1 to 1 µM, and D represents an $IC_{50}$ of <0.1 µM. NT=Not tested.

TABLE 2

Inhibition of Diverse β-Lactamases by Exemplary Compounds.

| EXAMPLE | Class A | | Class B | Class C | Class D |
| | SHV-5 | KPC-2 | VIM-2 | AmpC | OXA-48 |
| --- | --- | --- | --- | --- | --- |
| 1 | D | C | B | D | C |
| 2 | D | D | B | D | C |
| 3 | D | C | B | D | C |
| 85 | D | D | B | D | B |
| 102 | D | D | B | D | C |

Example III: In Vitro Antibacterial Assays of β-Lactamase Inhibition

To determine the ability of test compounds to potentiate the inhibition of the growth of bacterial strains that produce beta-lactamase enzymes, classic cell based broth microdilution MIC assays were employed. Six bacteria strains producing beta-lactamase enzymes were used: E. coli expressing the Class A Extended Spectrum Beta-Lactamase (ESBL) CTX-M-15, E. cloacae expressing the Class C P99, K. pneumoniae expressing the Class A carbapenemase KPC-3, P.aeruginosa expressing the Class B carbapenemase VIM-2, K. pneumoniae expressing the class A carbapenemase KPC-2 and the class B carbapenemase VIM-4, and K. pneumoniae producing the Class D carbapenemase OXA-48. The assay was conducted in Cation Adjusted Mueller Hinton Broth (CAMHB, BD #212322, BD Diagnostic Systems, Sparks, Md.). Bacteria strains were grown for 3-5 hours in CAMHB broth. Test compounds were added to a microtiter plate in 2-fold serial dilutions in CAMHB in a final concentration range of 32 µg/mL to 0.015 µg/mL. An overlay of CAMHB containing a Beta-lactam was added to the compounds at a final static concentration of 4 µg/mL. Ceftazidime (CAZ, Sigma #C3809-1G, Sigma-Aldrich, St. Louis, Mo.) was used as the partner antibiotic for E. coli expressing Ambler Class A ESBL CTX-M-15 (MIC alone>128 µg/mL), and E. cloacae expressing Class C P99 (MIC alone=128 µg/mL). Meropenem (Mero, U.S. Pat. No. 1,392,454, U.S. Pharmacopeia, Rockville, Md.) was used as the partner antibiotic for K. pneumoniae expressing Ambler Class A carbapenemase KPC-3 (MIC alone>128 µg/mL), P. aeruginosa expressing Class A carbapenemase VIM-2 (MIC alone=16 µg/mL), K. pneumoniae expressing the Ambler Class A carbapenemase KPC-2 and Ambler Class B carbapenemase VIM-4 (MIC alone =64 µg/mL), and K. pneumoniae expressing the Class D carbapenemase OXA-48 (MIC alone=128 µg/mL). Titration of test compounds with MIC readout indicates the concentration of test article needed to sufficiently inhibit beta-lactamase enzyme activity and protect the intrinsic antibacterial activity of the beta-lactam. In addition to the titration of test compounds the MICs of a panel of control beta-lactams is also tested to ensure the strains are behaving consistently from test to test. Once the test compound and antibiotics are added the plates can be inoculated according to CLSI broth microdilution method. After inoculation, the plates are incubated for 16-20 hours at 37° C., then the Minimal Inhibitory Concentration (MIC) of the test compound is determined visually.

Using the methodology described above, examples of the current invention were evaluated for their ability to inhibit the growth of β-lactamase-producing bacteria in the presence of a β-lactam antibiotic.

Representative results are shown in Table 3 where A represents an MIC of the fixed β-lactam antibiotic in the presence of >32 μg/mL of a β-lactamase inhibitor of exemplary compounds, B represents the MIC in the presence of between 8 and 32 μg/mL of a β-lactamase inhibitor of exemplary compounds, and C represents the MIC in the presence of ≤4 μg/mL of a β-lactamase inhibitor of exemplary compounds. NT=Not Tested.

ing carboxylic acid determined following oral dosing of the ester compound ("AUC(oral)") and the plasma AUC determined after intravenous dosing ("AUC(IV)") of the carboxylic acid, using the formula AUC(oral)/AUC(IV)*100 corrected for molecular weight difference between the ester and corresponding carboxylic acid. The bioanalysis was conducted using triple-quadrupole mass spectrometer-based LC-MS/MS methods with internal standard. LC-MS/MS methods were developed for all test compounds. Duplicate standard curves were run at the beginning and end of the sample run. Calibration curves consisted of standards prepared in blank plasma including a double blank, a single blank containing the internal standard only and a minimum of 5 standards with a lower limit of quantification (LLOQ) of approximately 1 ng/mL. Linearity was assessed by a minimum of 5 standards (with at least one standard at both the bottom and top of the range), back calculated to +20% of their nominal concentrations.

TABLE 3

Broad spectrum inhibition of bacterial growth. MIC of example compounds of the invention in the presence of a fixed amount (4 μg/mL) of designated β-lactam antibiotics ceftazidime (CAZ) and meropenem (Mero).

| | MIC (μg/mL) of exemplary compounds in presence of fixed β-lactams | | | | | |
|---|---|---|---|---|---|---|
| | Fixed CAZ ESBLs (Class A and C) | | Fixed Mero Carbapenemases (Classes A, B, and D) | | | |
| EXAMPLE | E. coli ESBL4 CTX-M-15 | E. cl. 144200 p99 AmpC | K. P. 156319 KPC-3 | P. aerug. 2775 VIM-2 | K.P. A-1797 KPC-2 VIM-4 | K. P. 11978 OXA-48 |
| 1 | C | C | B | C | B | C |
| 2 | C | C | C | B | C | C |
| 3 | C | C | C | C | C | C |
| 85 | C | C | C | C | B | C |
| 102 | C | C | C | C | B | C |

Example IV: Absolute Oral Bioavailability Assessments in Sprague-Dawley Rats An in vivo pharmacokinetics model to measure the plasma levels of carboxylic acid ester compounds after oral dosing was performed. Male Sprague Dawley rats weighing approximately 250 g at treatment were double cannulated in the jugular and femoral veins for blood sample collection and IV dose administration, respectively. Three rats were utilized per dose group. Test compounds were solubilized in a 5% DMSO:sodium acetate/acetic acid buffer (with a final pH of approximately 5.0) for IV administration. Dosing formulations for oral gavage dosing were prepared in a 5% DMSO:0.5% Tween 80 (polysorbate 80) in sodium acetate/acetic acid buffer (with a final pH of approximately 5.0). All dosing was conducted at a 5 mg/kg dose level for IV and 10 mg/kg dose level for PO. For IV dosing, 0.5 mL blood samples were drawn at pre-dose, and 0.083, 0.25, 0.5, 1, 2, 4, and 8 h post-dose. For oral dosing, 0.5 mL blood samples were drawn at pre-dose, and 0.25, 0.5, 1, 2, 4, and 8 h post-dose. Blood was collected into tubes containing PMSF (phenylmethylsulfonyl fluoride), centrifuged, and plasma stored frozen prior to bioanalysis.

The absolute bioavailabilities (F) of exemplified compounds are shown in Table 4, wherein A represents F(%) less than 10%, B represents F(%) between 10% and 30%, and C represents F(%)>30%. The bioavailabilities shown in Table 4 were calculated using the plasma AUC of the correspond-

TABLE 4

Bioavailabilities of Test Compounds in rat plasma after oral gavage dosing.

| Example # | F(%) |
|---|---|
| 25 | C |
| 26 | C |
| 27 | B |
| 28 | B |
| 30 | C |
| 35 | B |
| 37 | A |
| 38 | C |
| 39 | B |
| 40 | C |
| 42 | C |
| 44 | B |
| 45 | B |
| 48 | B |
| 51 | C |
| 67 | B |
| 69 | B |
| 70 | B |
| 76 | B |
| 87 | C |
| 89 | C |
| 90 | C |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (Ia) or (Ib) or pharmaceutically acceptable salts, isomers, stereoisomers, dimers, trimers, tautomers, or N-oxides thereof:

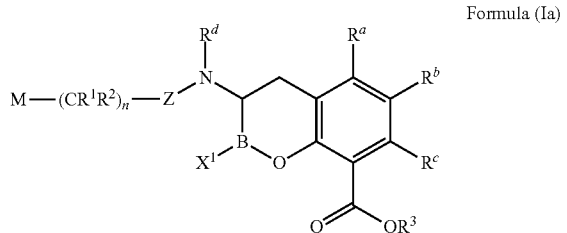

Formula (Ia)

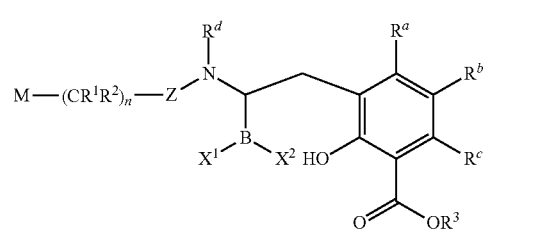

Formula (Ib)

wherein:

$M-(CR^1R^2)_n-\{$ is

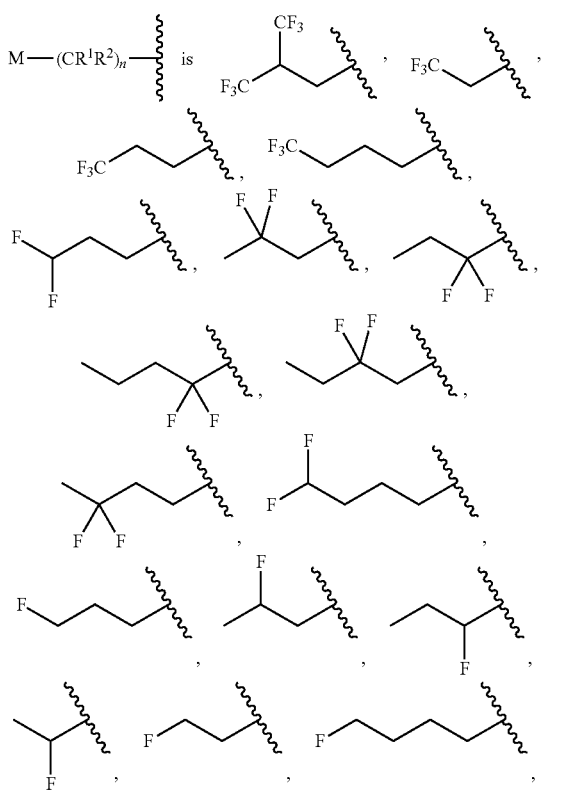

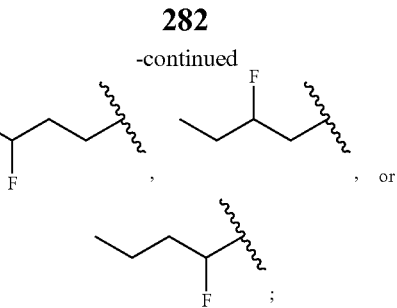

$X^1$ and $X^2$ are independently —$OR^4$ or F; when present;
$Z$ is >$C(=O)$, >$C(=S)$, or >$S(=O)_2$;
$R^3$ is $R^{31}$, —$(R^{30})_q OR^{31}$, —$(R^{30})_q O(R^{30})_q OR^{31}$, —$R^{30}OC(=O)R^{31}$, —$R^{30}OC(=O)OR^{31}$, —$R^{30}OC(=O)NHR^{31}$, —$R^{30}OC(=O)N(R^{31})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;
each q are independently 1, 2, 3, 4, 5, or 6;
each $R^{30}$ are independently —$CH_2$—, —$CH(R^{32})$—, or —$C(R^{32})_2$—;
each $R^{31}$ are independently optionally substituted $C_1$-$C_{12}$ alkyl, optionally substituted alkoxyalkyl, optionally substituted $C_1$-$C_{12}$ alkenyl, optionally substituted $C_1$-$C_{12}$ alkynyl, optionally substituted cycloalkyl, optionally substituted heterocycloalkyl, optionally substituted aryl, optionally substituted heteroaryl, optionally substituted alkylcycloalkyl, optionally substituted alkylheterocycloalkyl, optionally substituted alkylaryl, or optionally substituted alkylheteroaryl; or
two $R^{31}$ are taken together with the nitrogen to which they are attached to form a heterocycloalkyl;
each $R^{32}$ is independently optionally substituted $C_1$-$C_6$ alkyl;
or two $R^{32}$ are taken together with the carbon to which they are attached to form a cycloalkyl;
$R^a$, $R^b$, $R^c$ are independently hydrogen, fluoro, chloro, bromo, optionally substituted $C_1$-$C_6$ alkyl, optionally substituted cycloalkyl, optionally substituted heterocloalkyl, optionally substituted aryl, optionally substituted heteroaryl, —$OR^4$, —$N(R^4R^5)$, or —$SR^4$; and
$R^d$, $R^4$, and $R^5$ are independently hydrogen, —OH, —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;
or $R^4$ and $R^5$ are taken together with the nitrogen to which they are attached to form a heterocycloalkyl.

2. The compound of claim 1, or pharmaceutically acceptable salts, isomers, stereoisomers, dimers, trimers, tautomers, or N-oxides thereof, wherein $R^3$ is $R^{31}$, —$R^{30}OC(=O)R^{31}$, or —$R^{30}OC(=O)OR^{31}$.

3. The compound of claim 1, or pharmaceutically acceptable salts, isomers, stereoisomers, dimers, trimers, tautomers, or N-oxides thereof, wherein $R^a$, $R^b$, and $R^c$ are hydrogen; and $R^d$ is hydrogen or $C_1$-$C_4$ alkyl.

4. The compound of claim 1, or pharmaceutically acceptable salts, isomers, stereoisomers, dimers, trimers, tautomers, or N-oxides thereof, wherein $X^1$ and $X^2$ are —OH; when present and Z is >$C(=O)$.

5. The compound of claim 1, wherein the compound is:
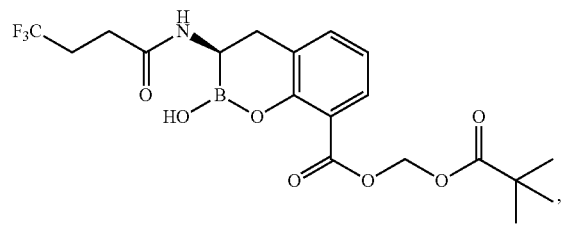 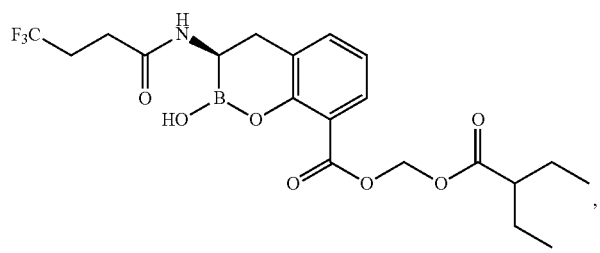
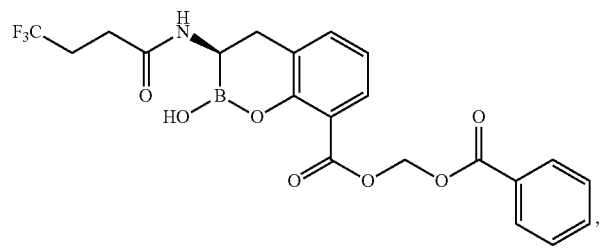 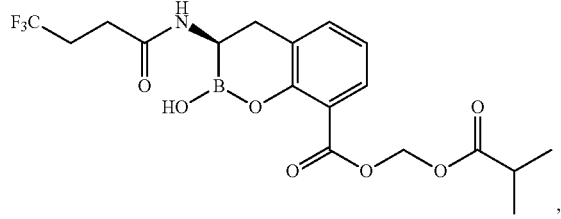
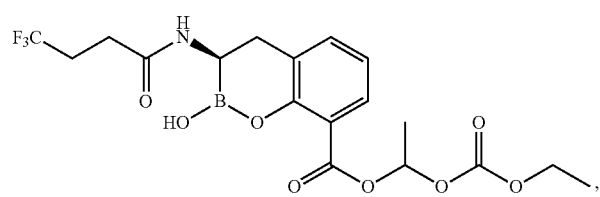 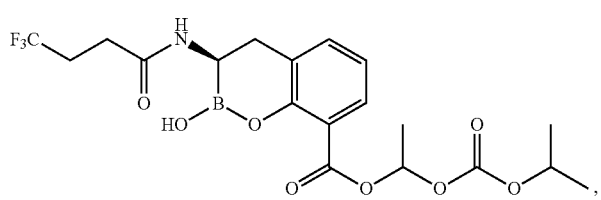
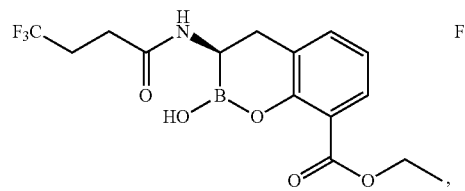 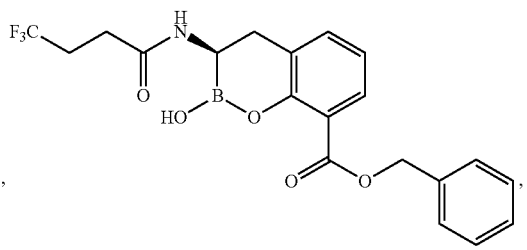
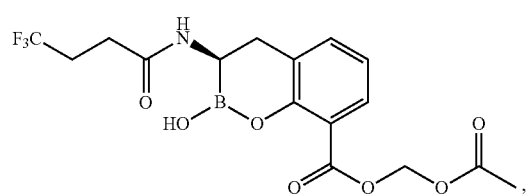 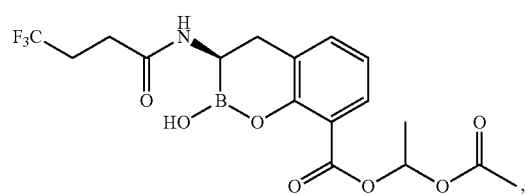
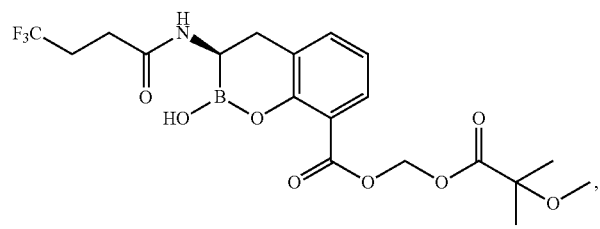
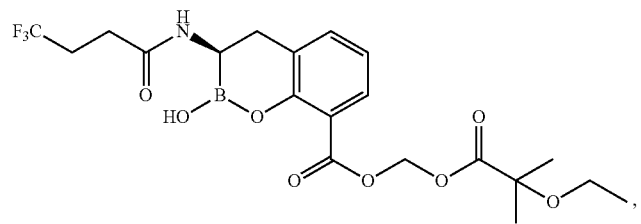

285
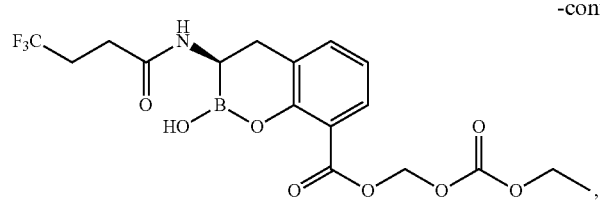
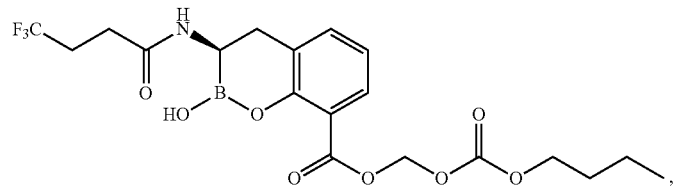
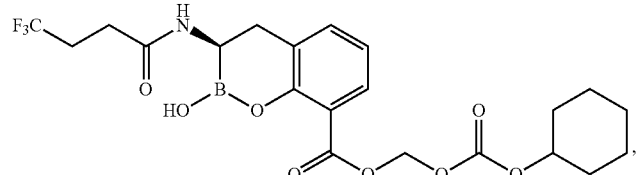
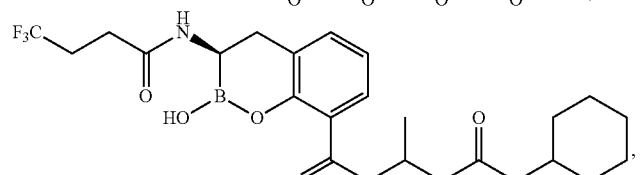
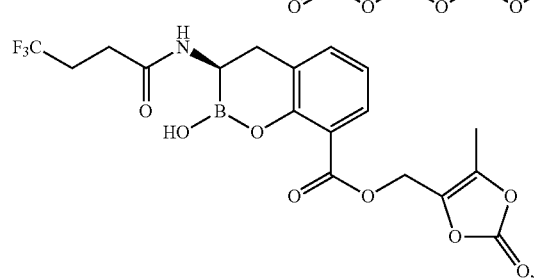
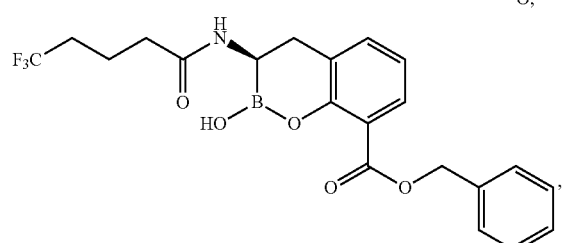
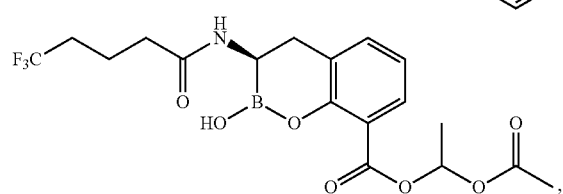
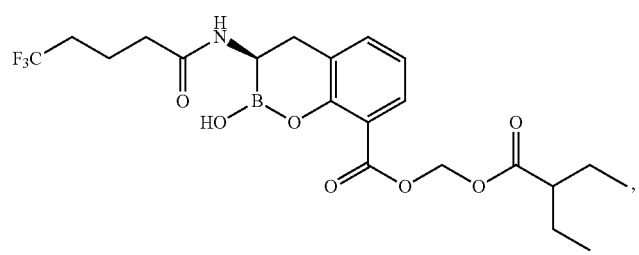
286
-continued
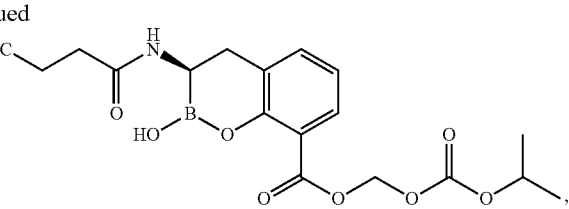
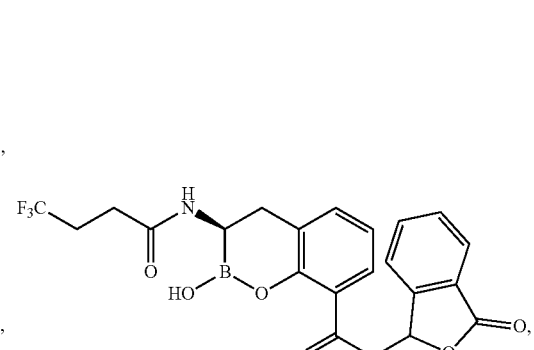
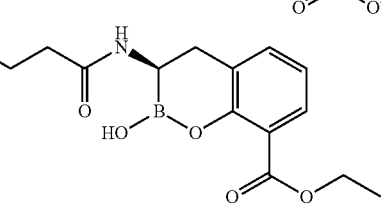
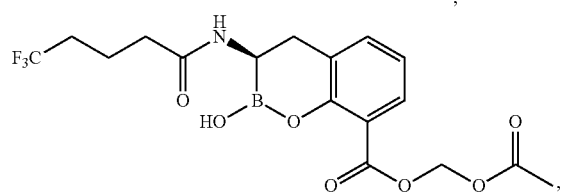
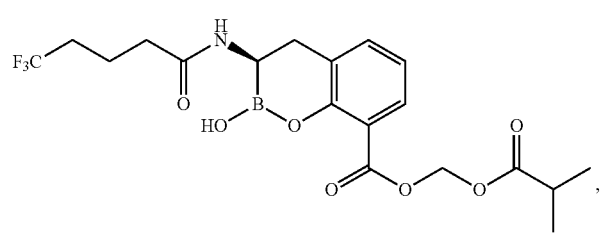

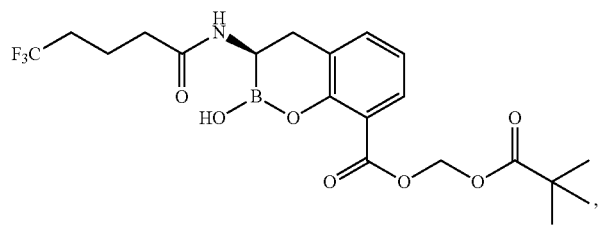
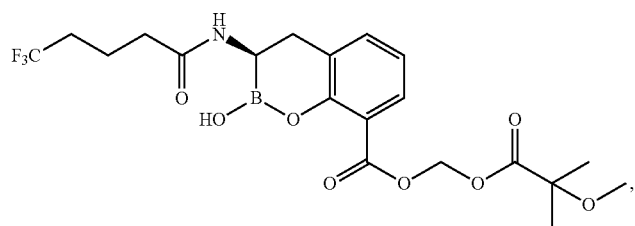
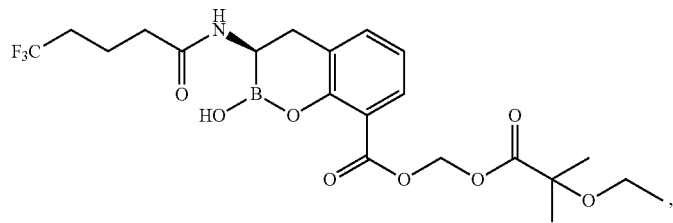
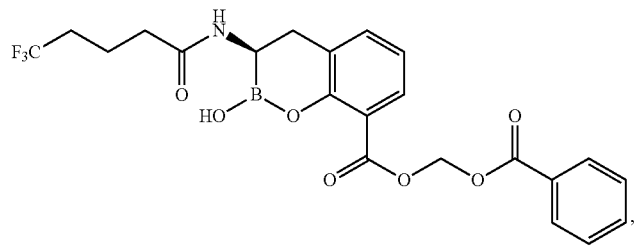
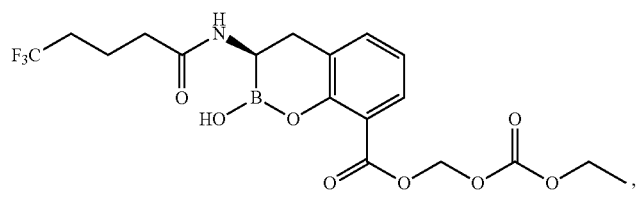
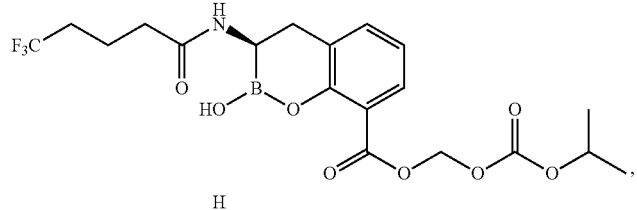
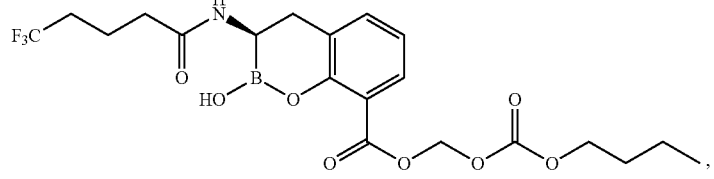
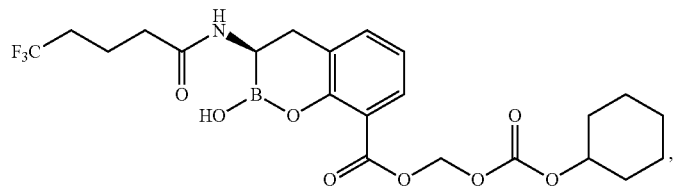

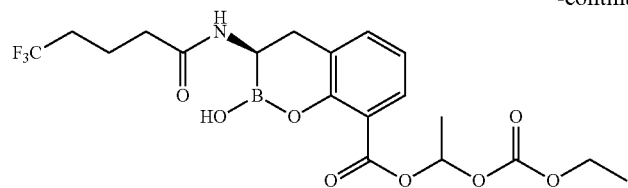
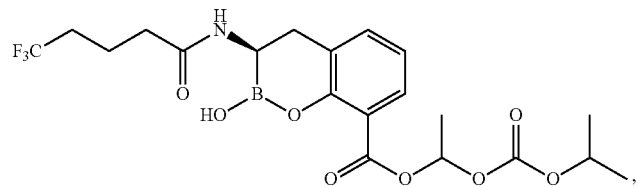
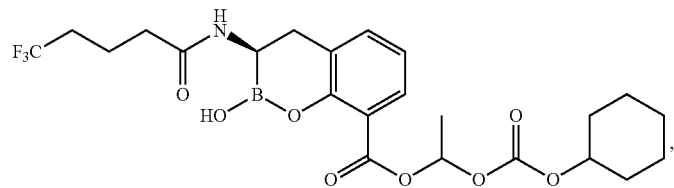
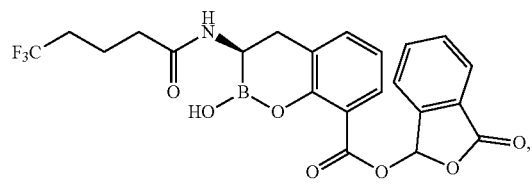
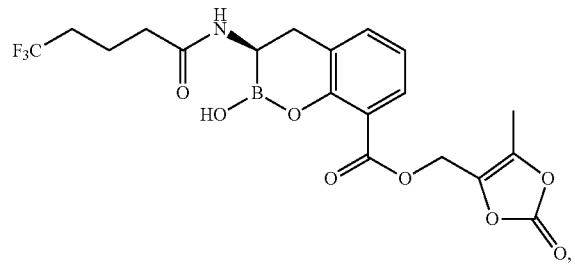
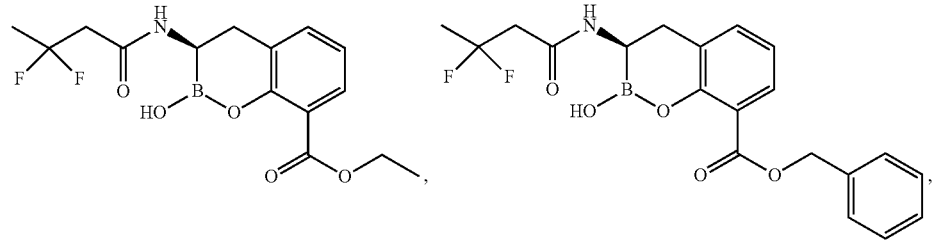
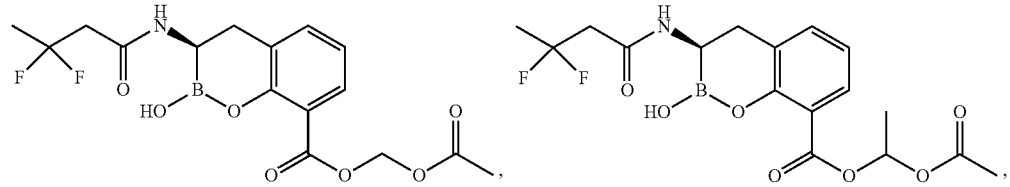
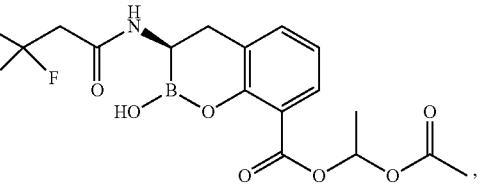
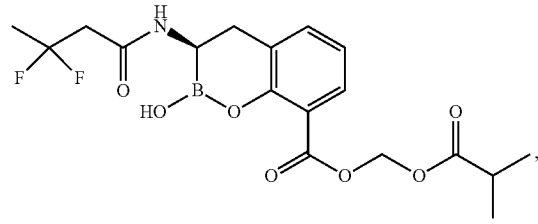
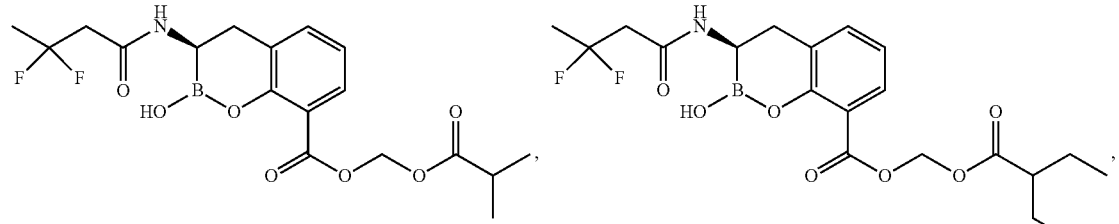
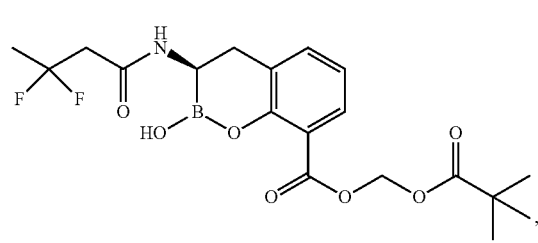
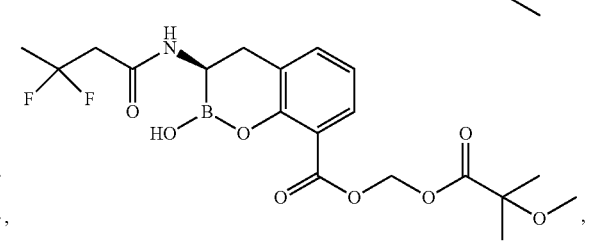

291
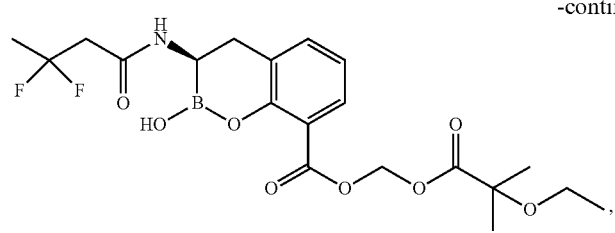
292
-continued
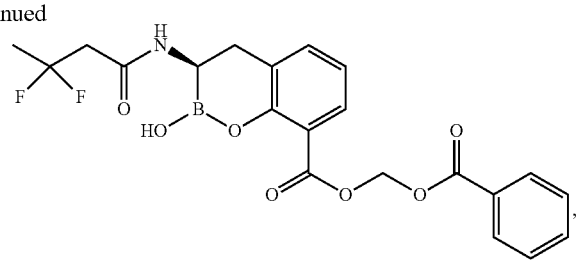
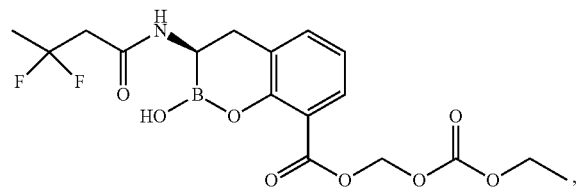
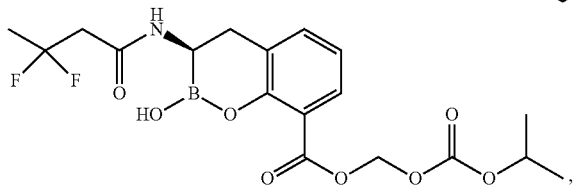
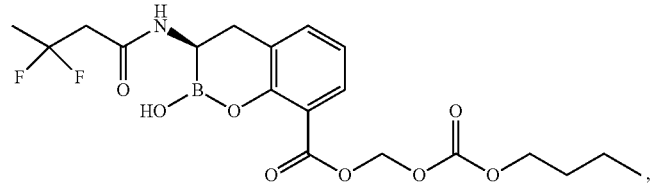
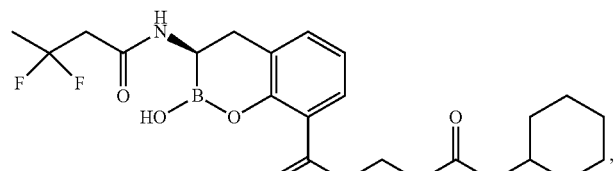
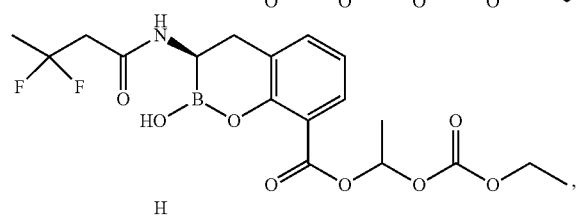
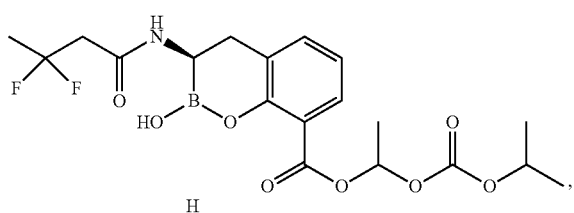
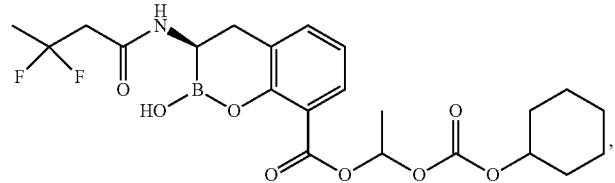
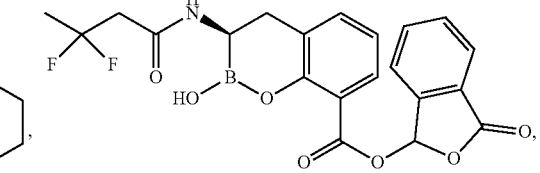
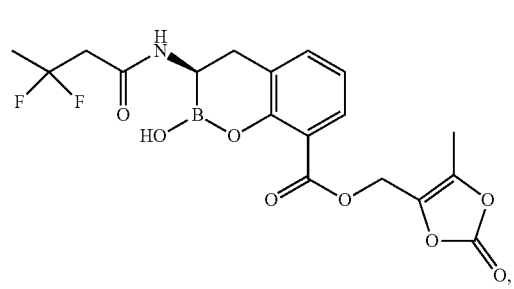
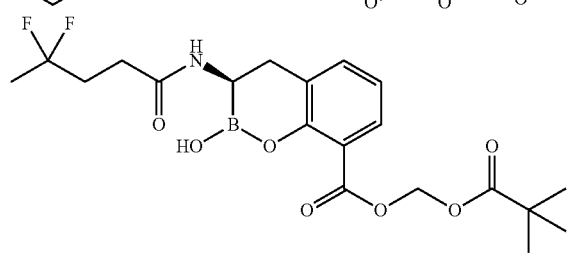
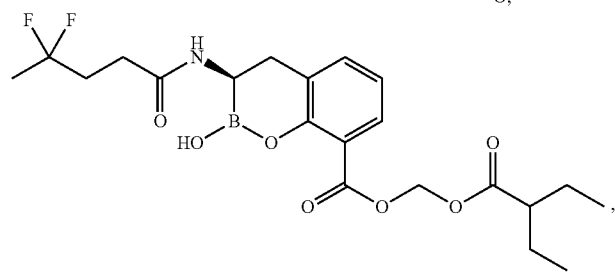
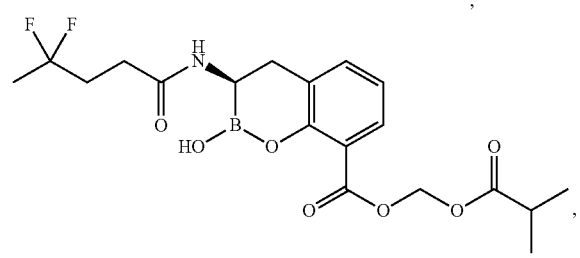

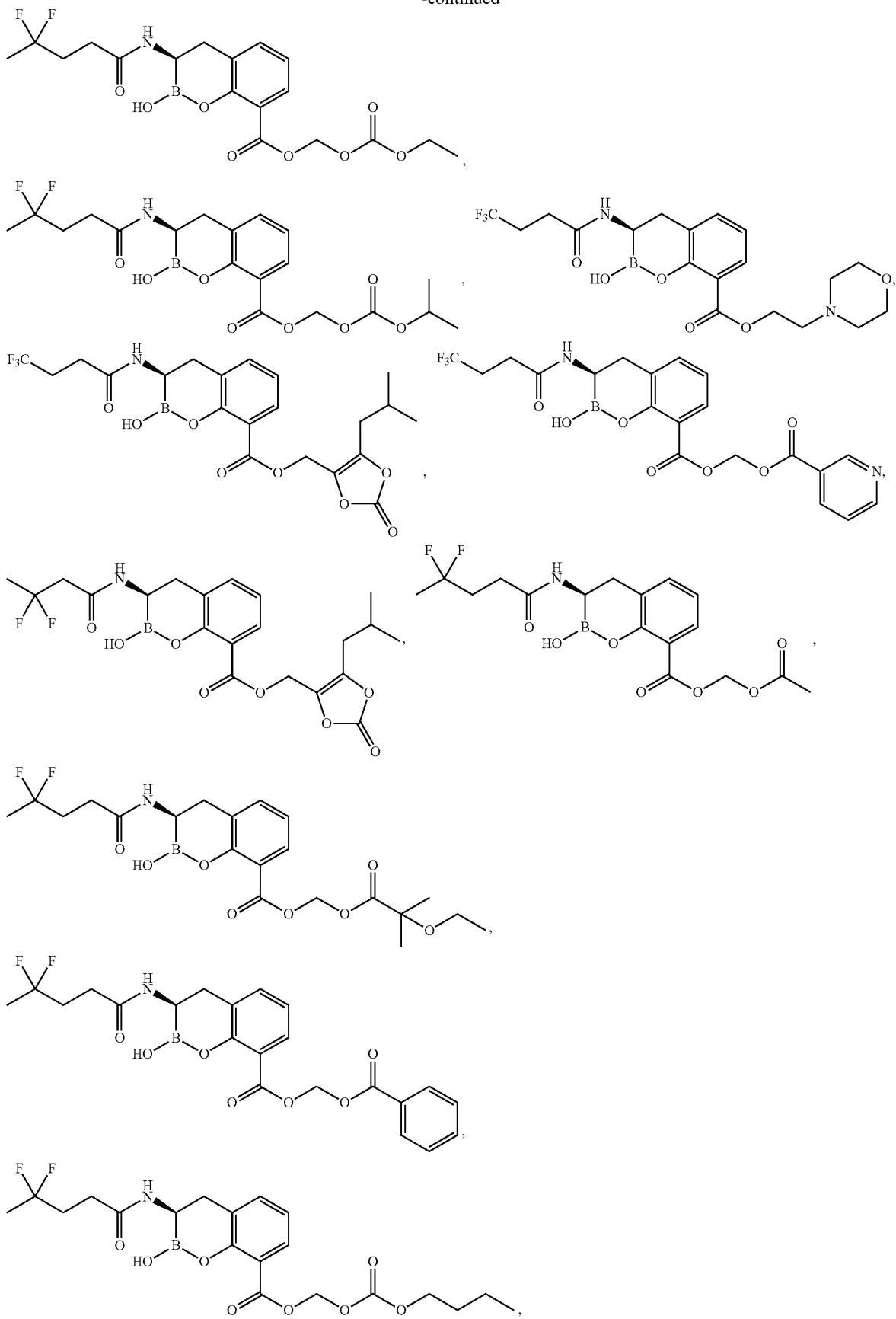

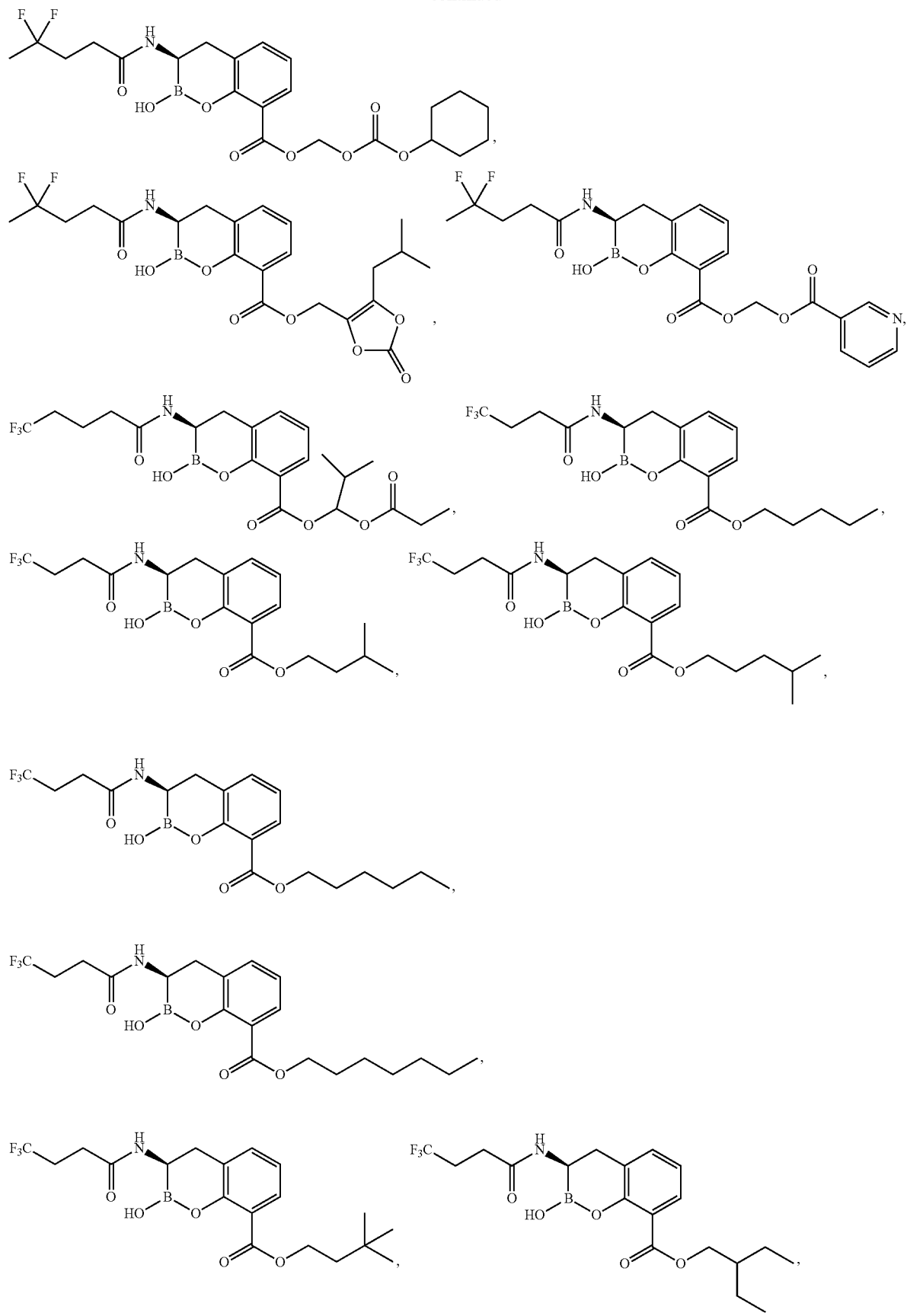

297
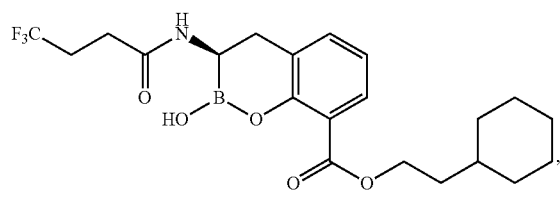
298
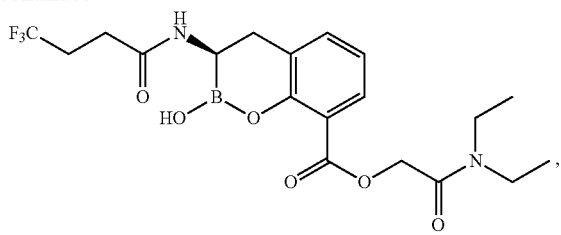
-continued
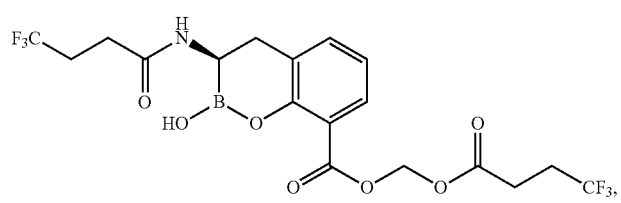
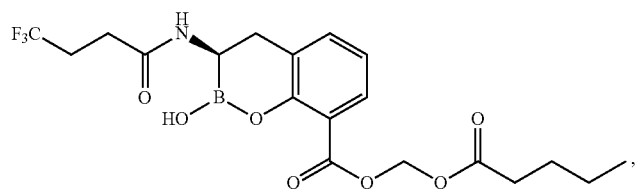
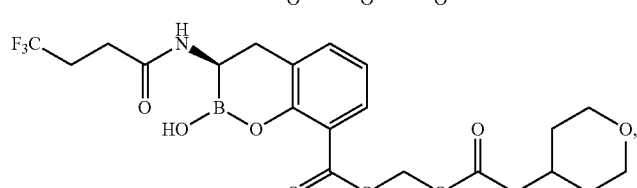
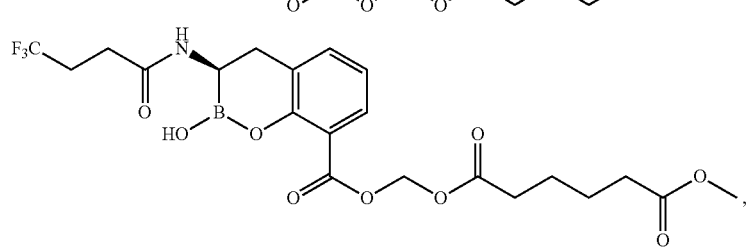
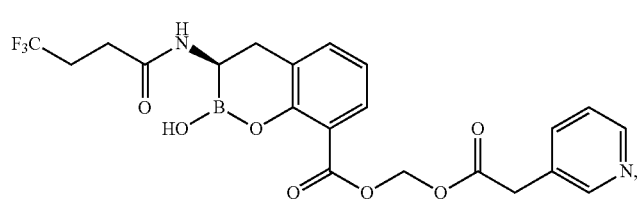
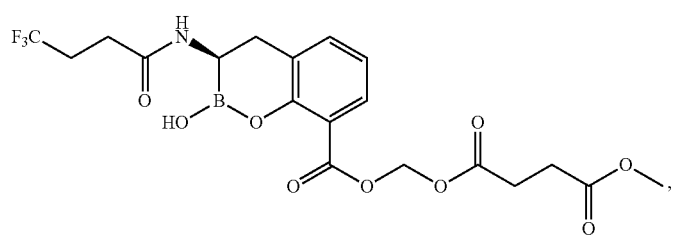
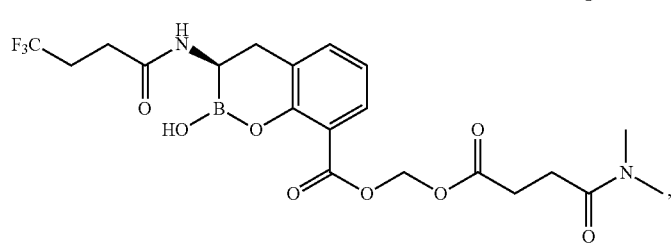

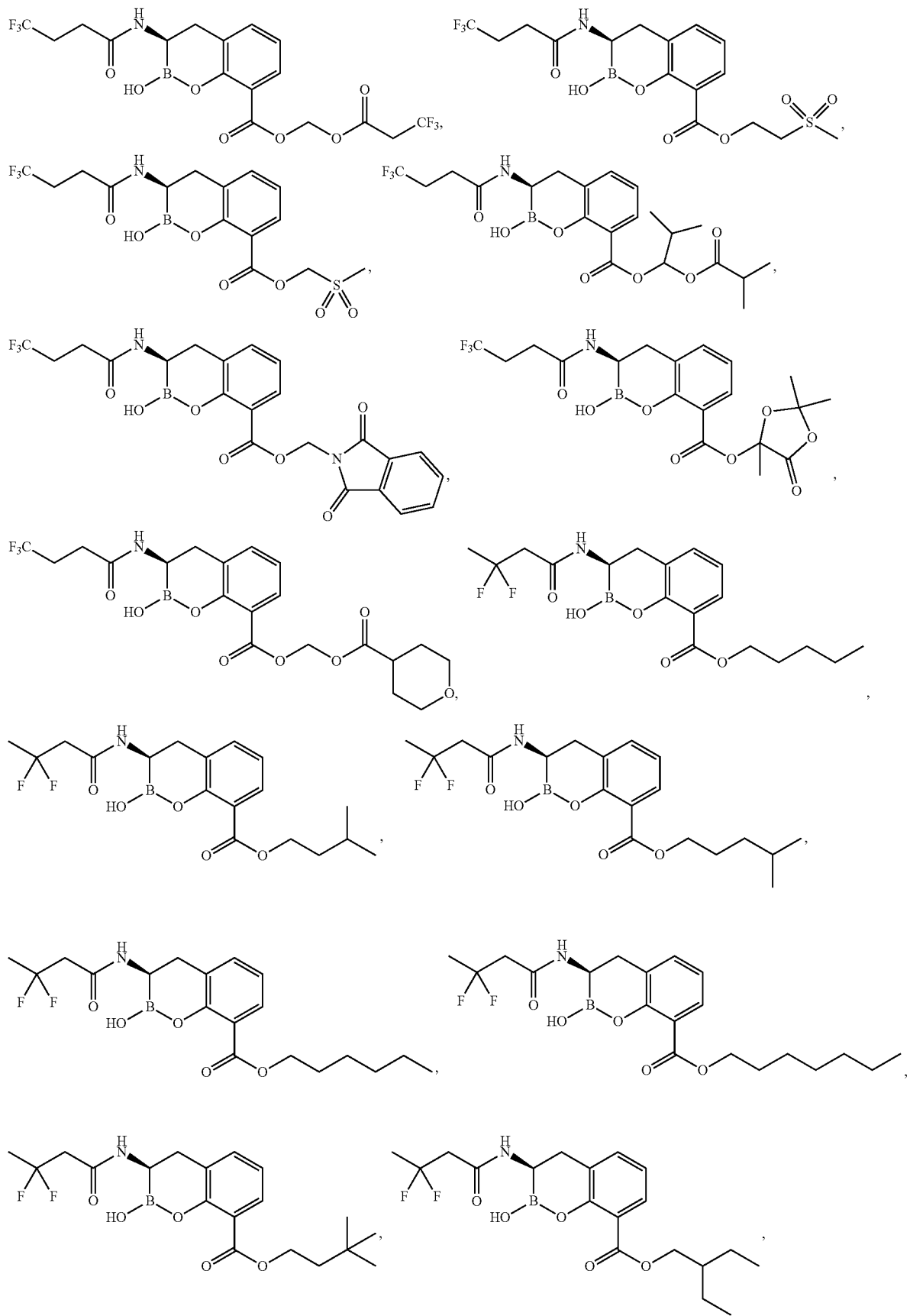

301
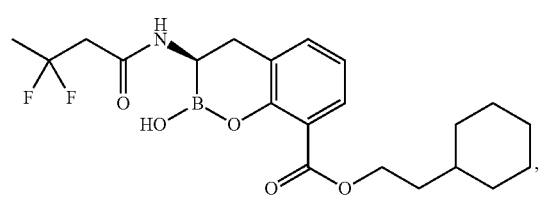
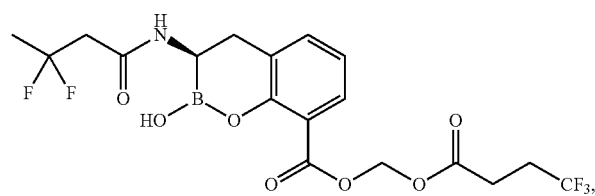
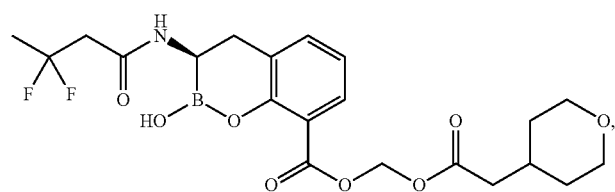
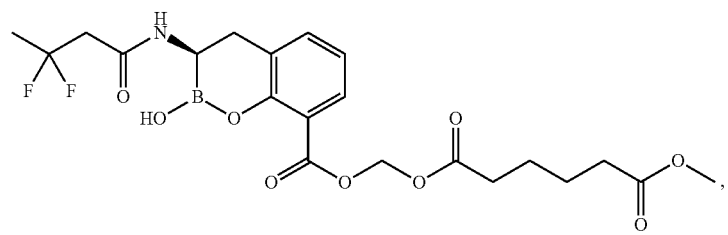
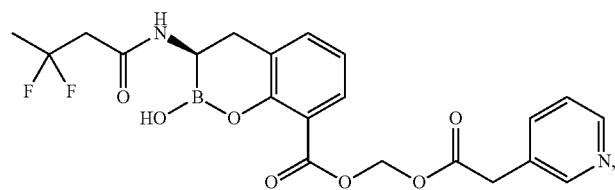
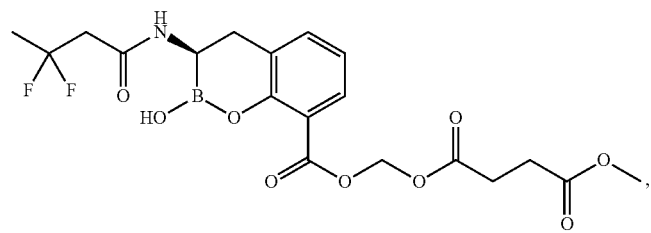
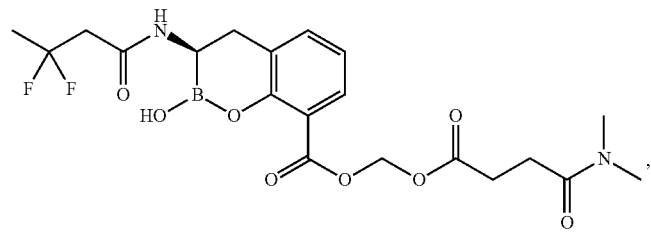
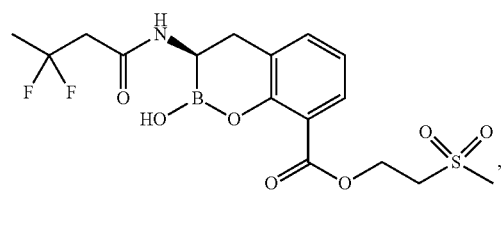
302
-continued
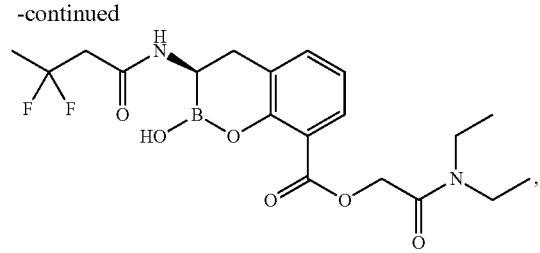
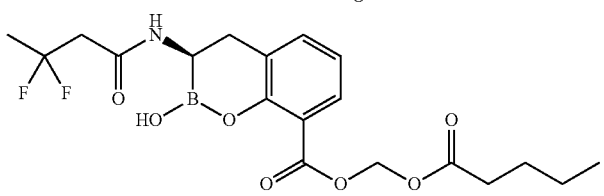
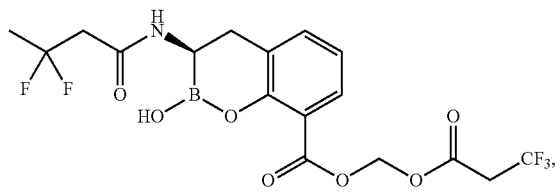
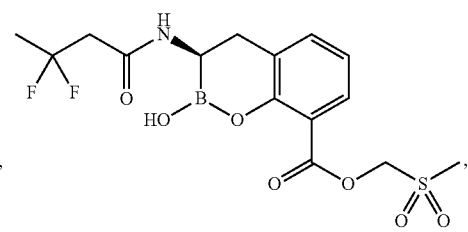

303
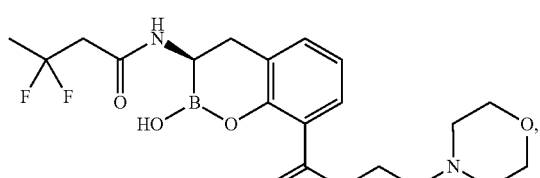
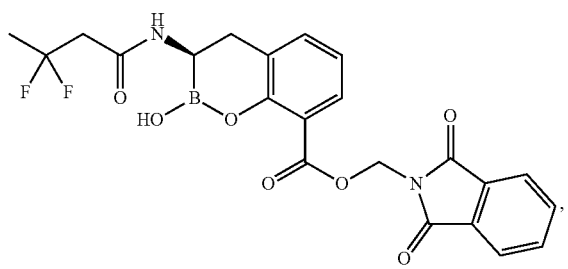
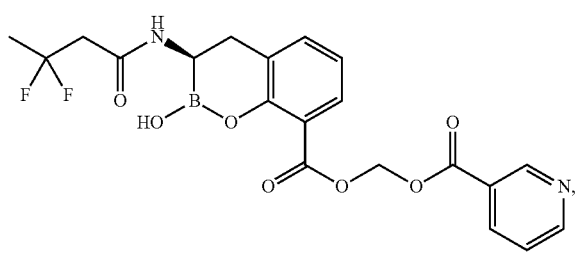
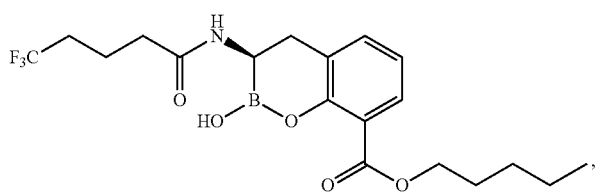
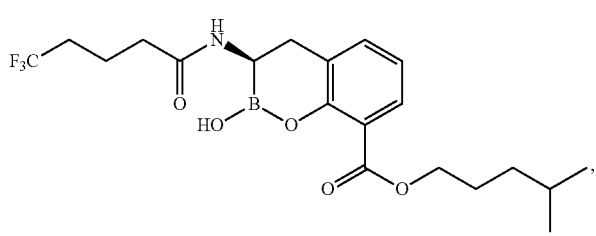
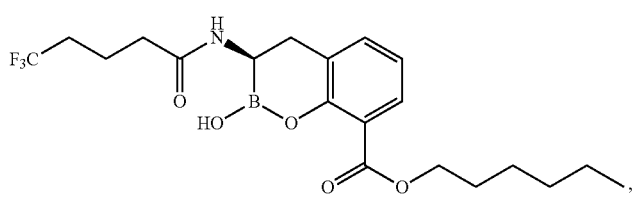
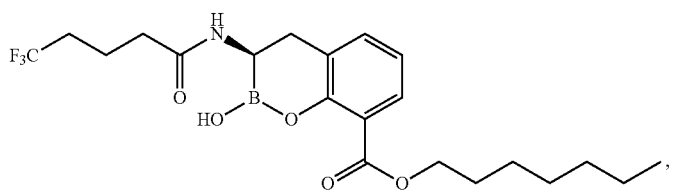
-continued
304
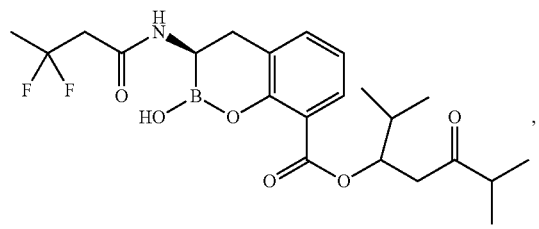
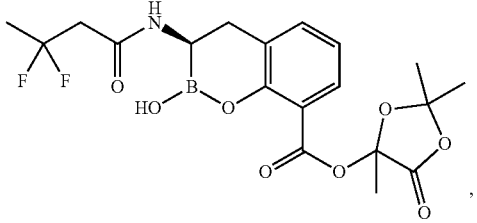
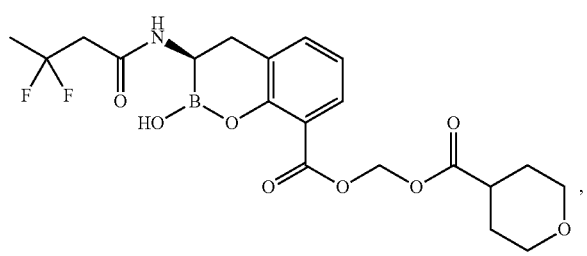
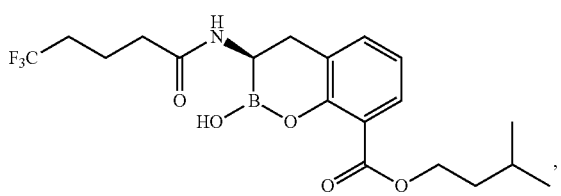

305
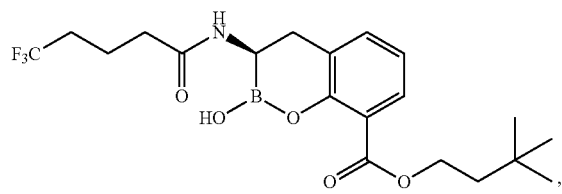
306
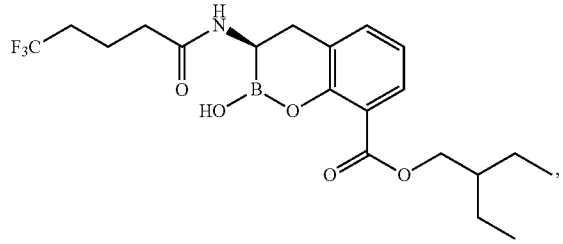
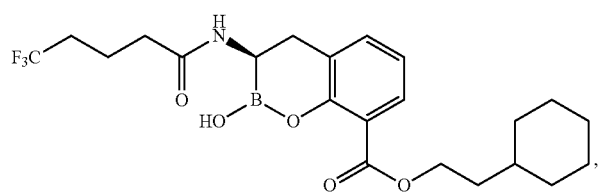
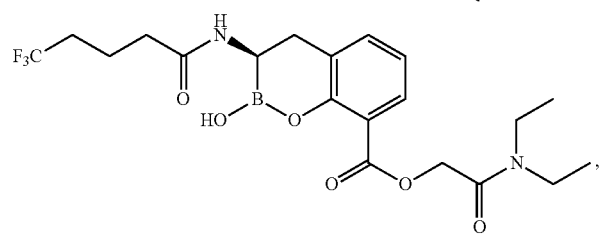
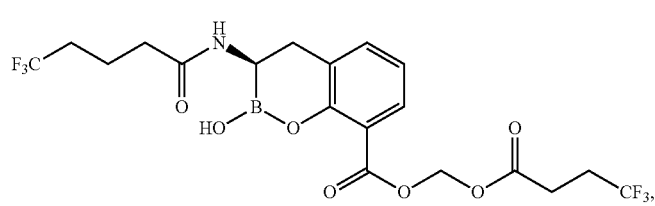
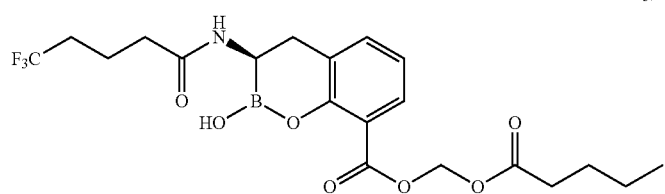
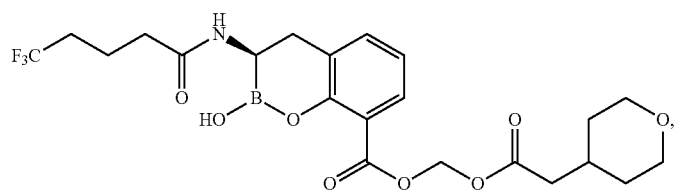
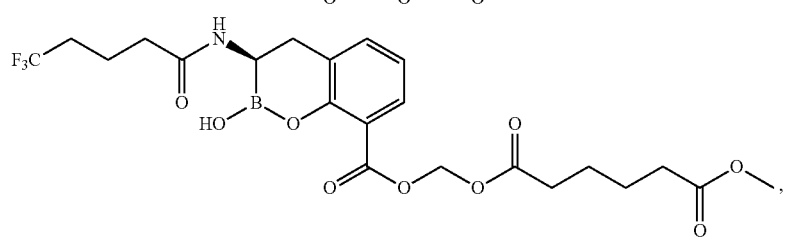
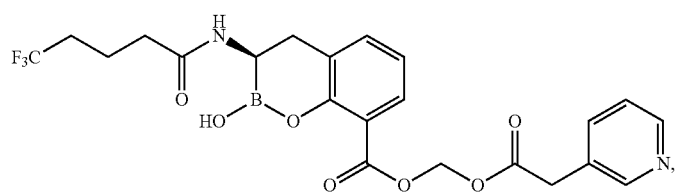
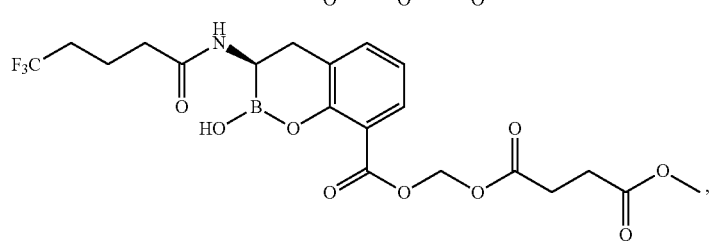

-continued
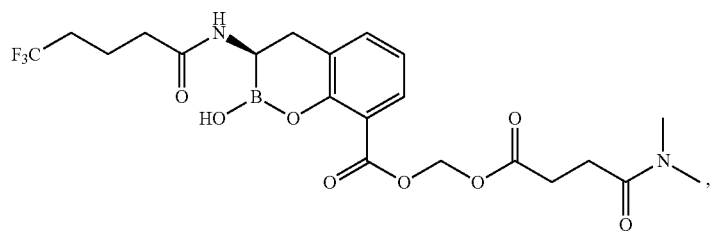
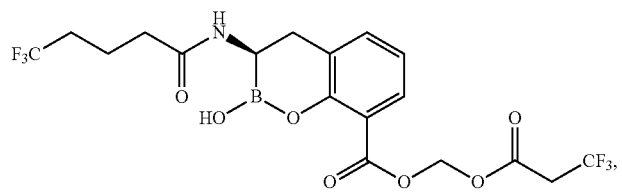
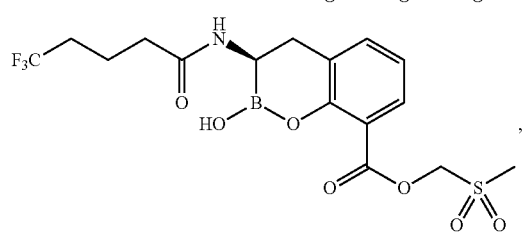
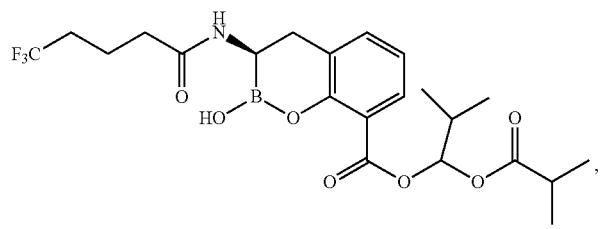
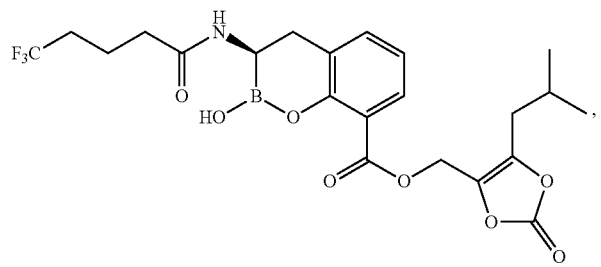
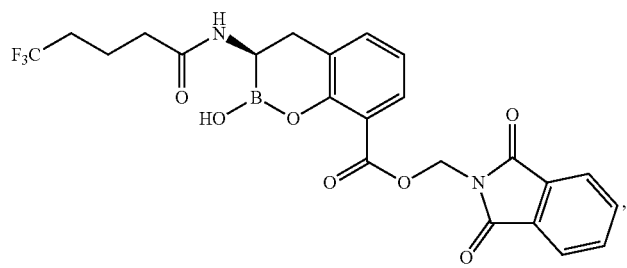
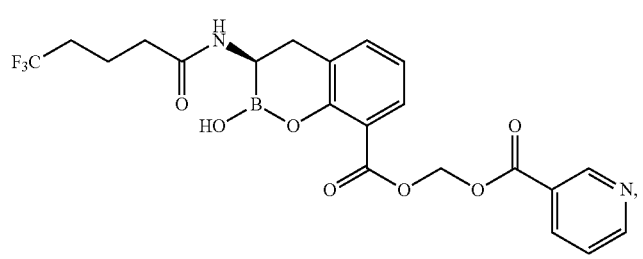

-continued
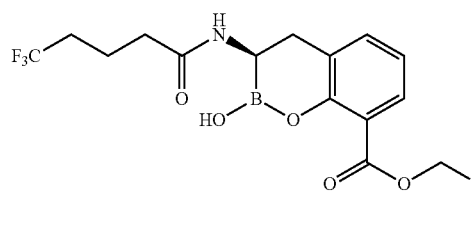 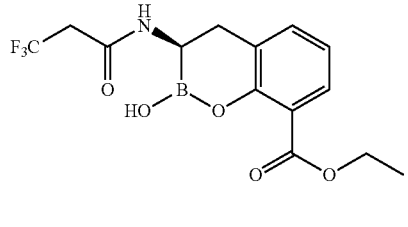
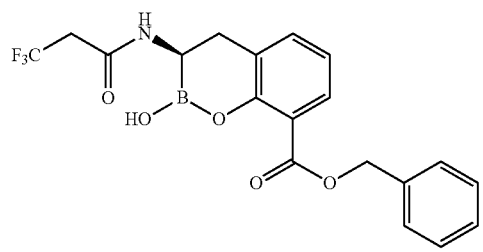 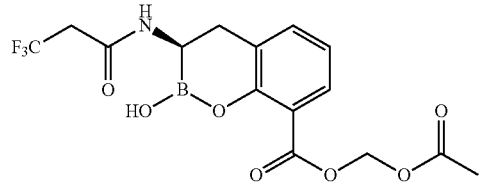
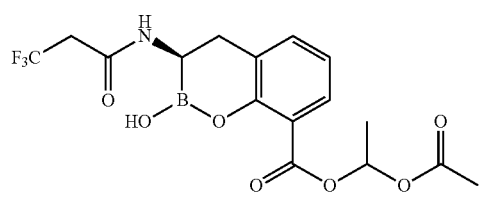 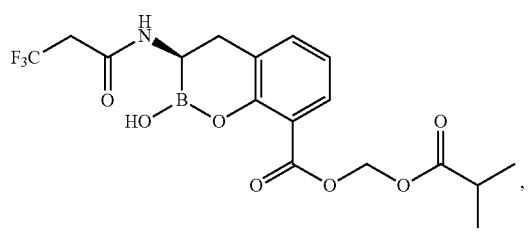
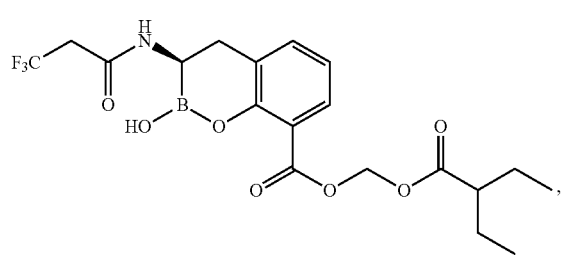 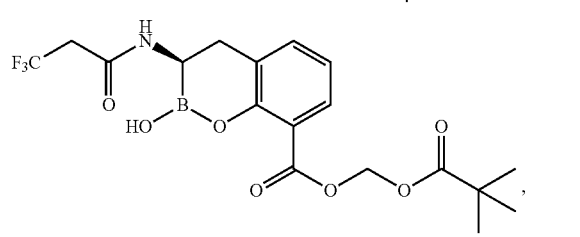
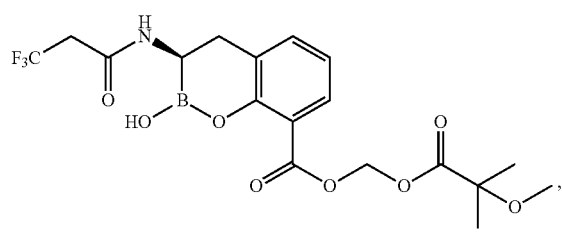 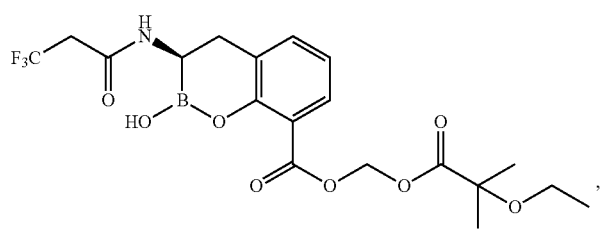
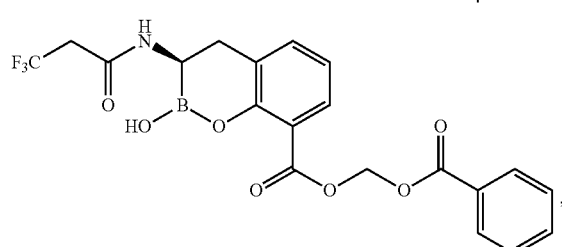 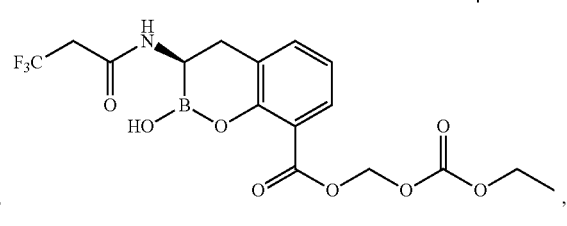
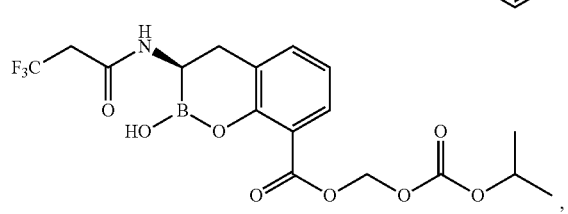 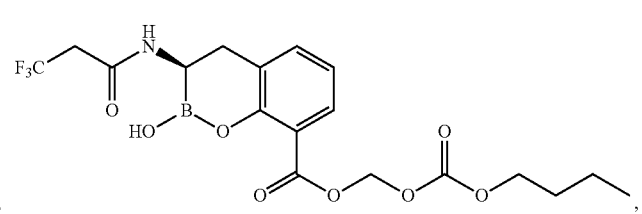

311 312
-continued
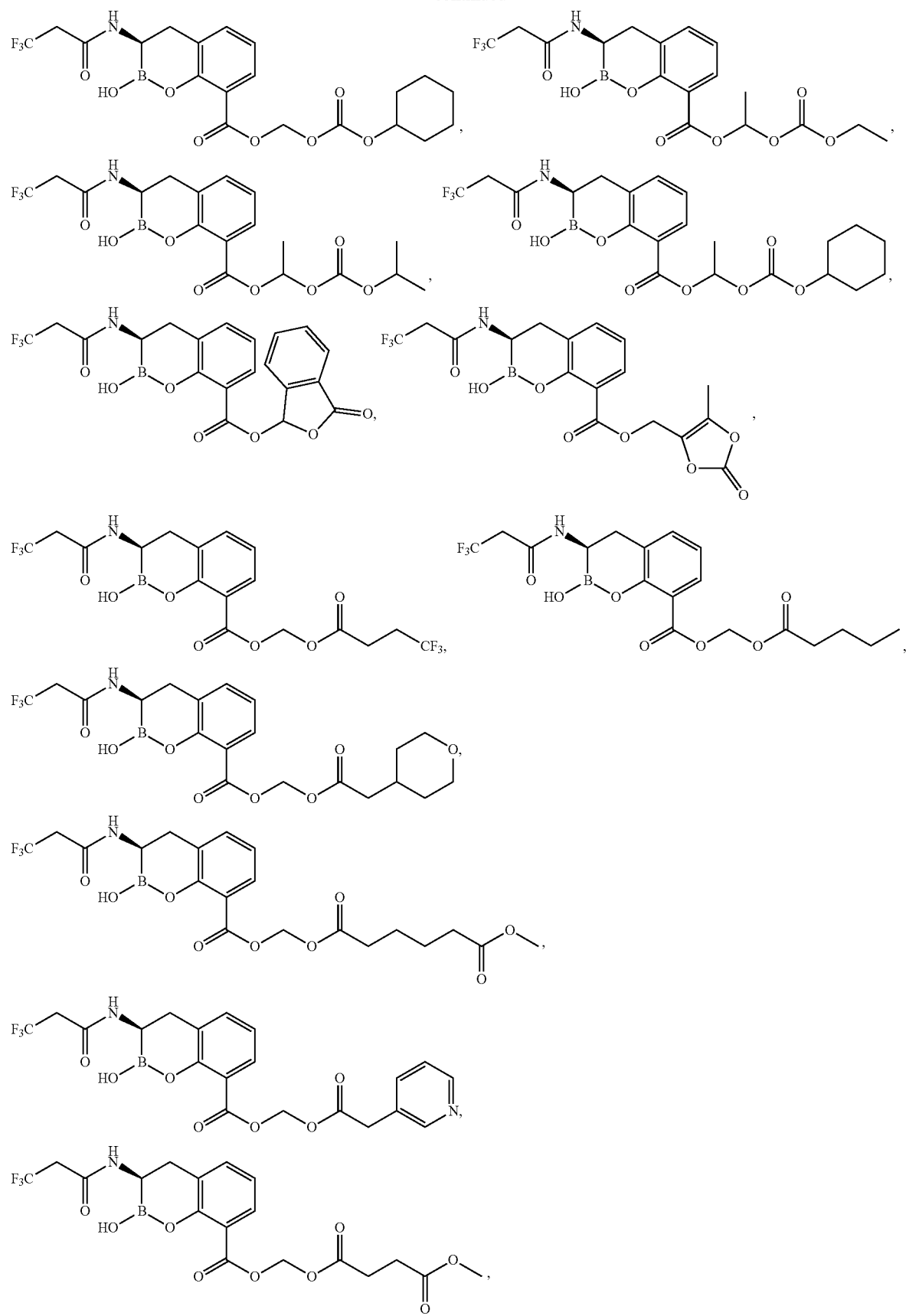

-continued
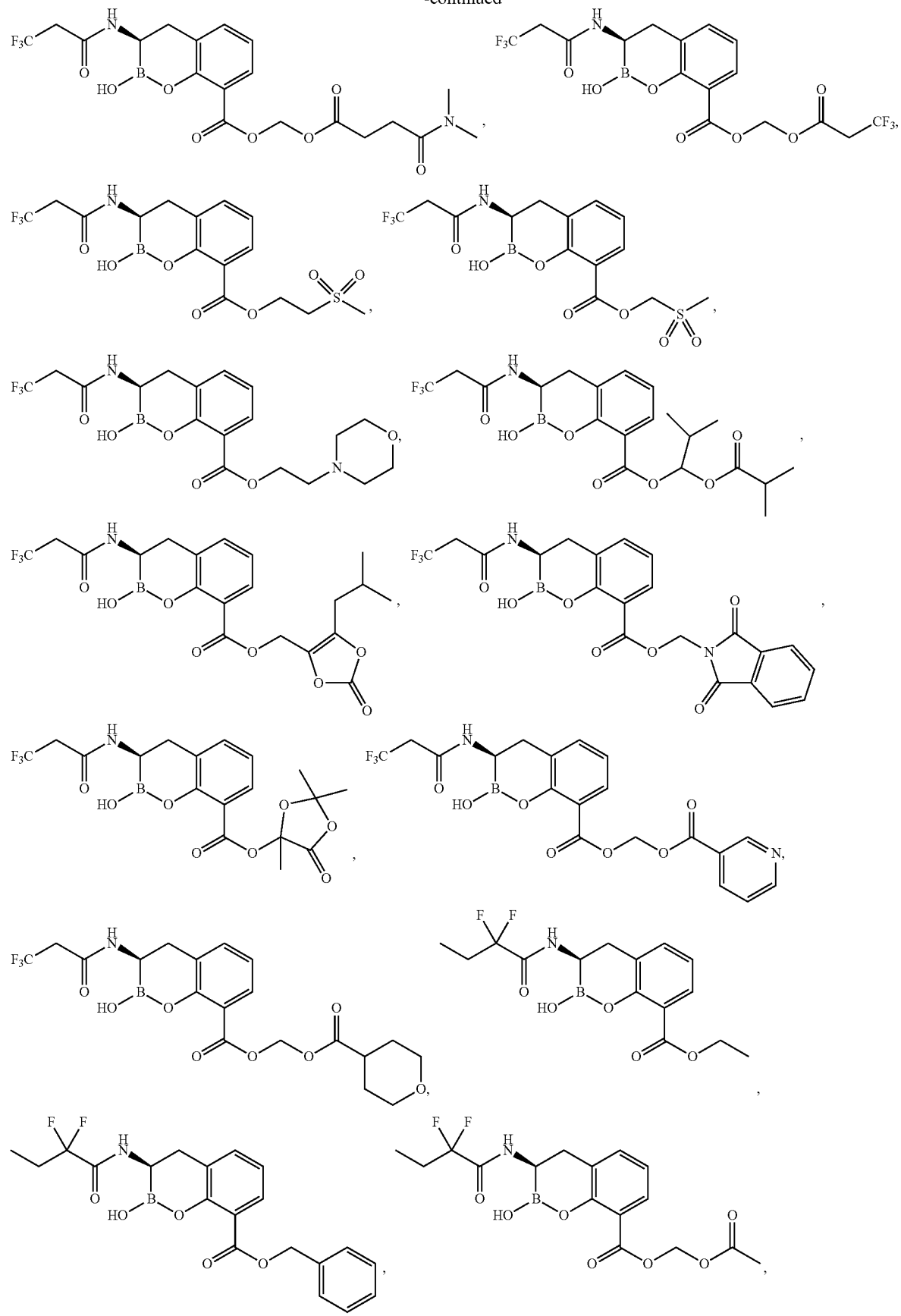

315
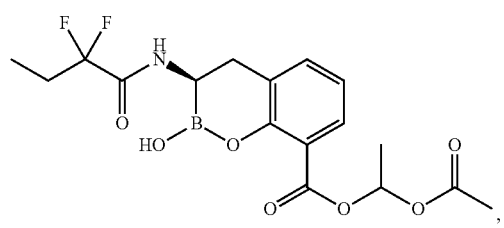
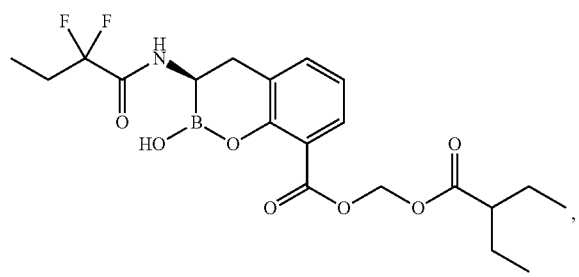
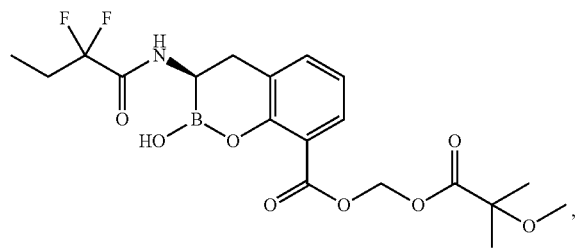
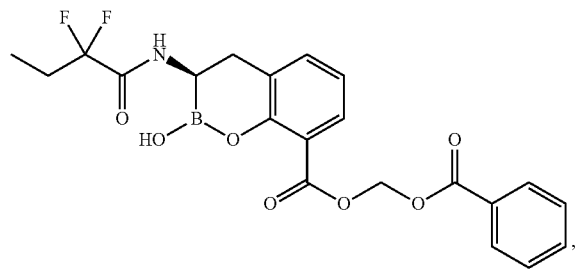
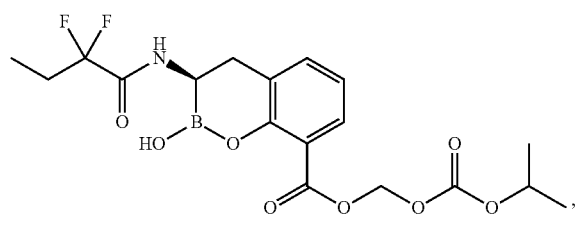
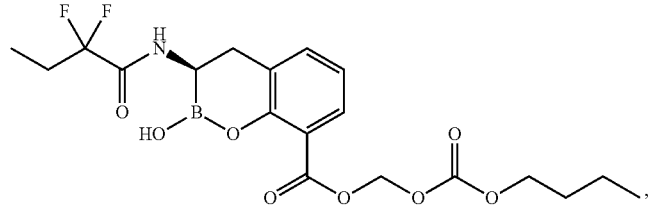
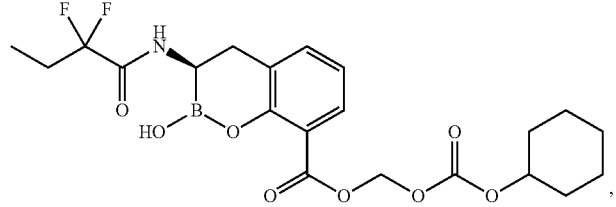
316
-continued
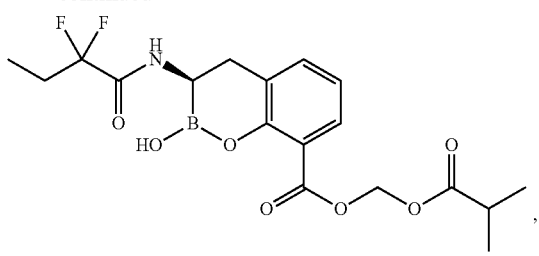
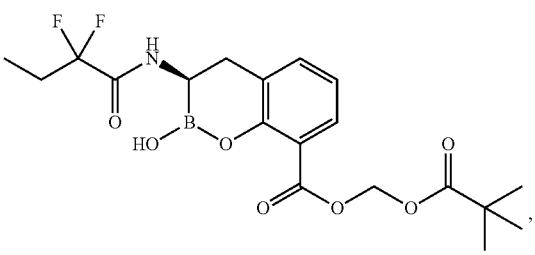
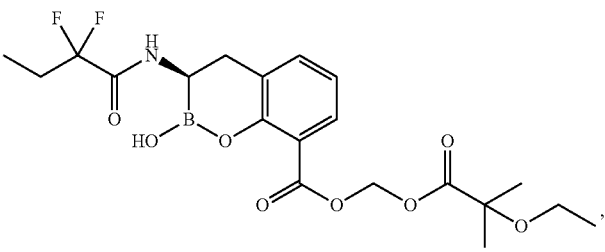
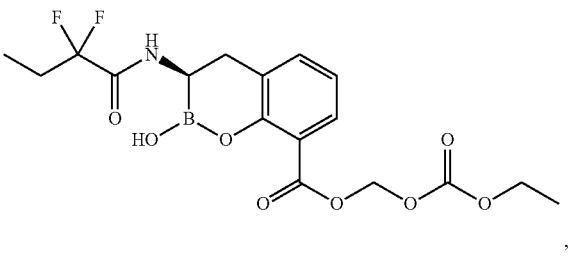

317
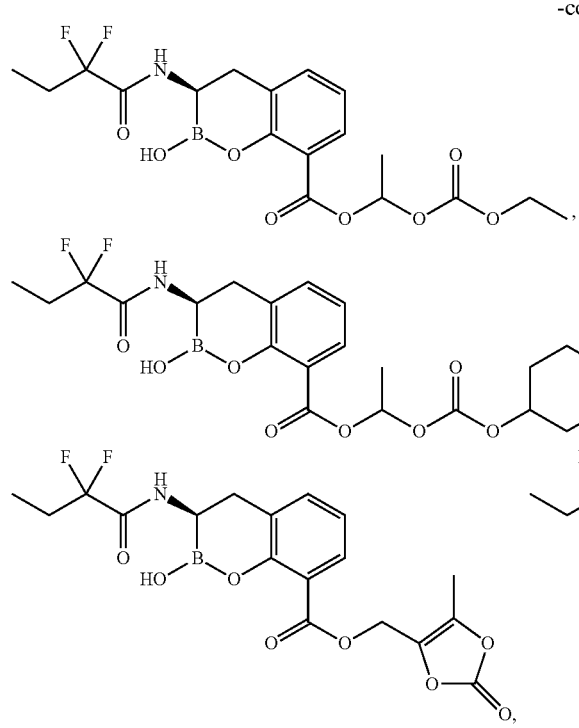
318
-continued
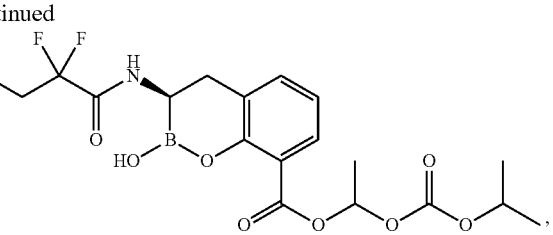
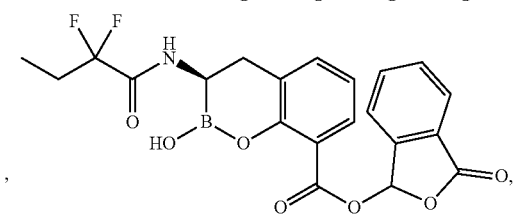
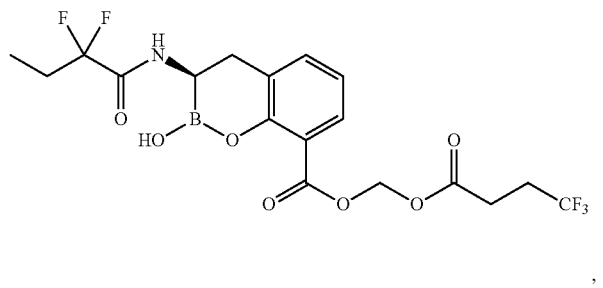
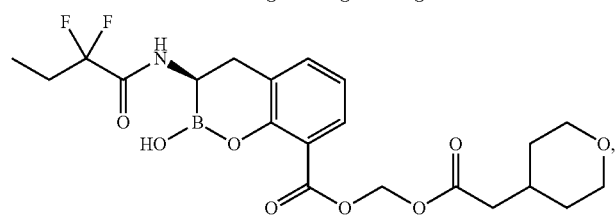
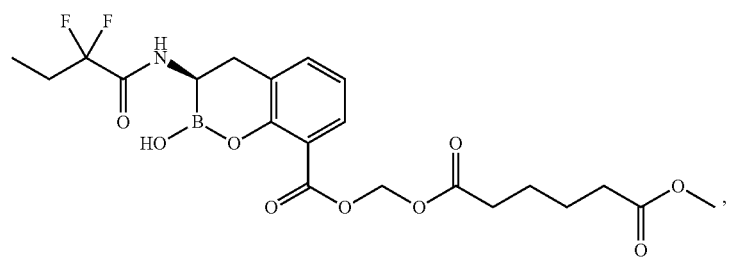
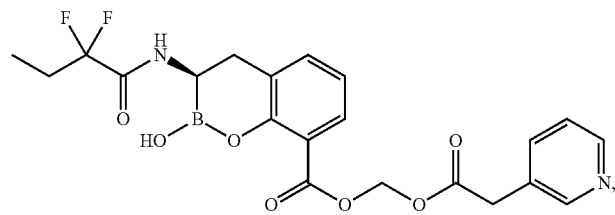

-continued
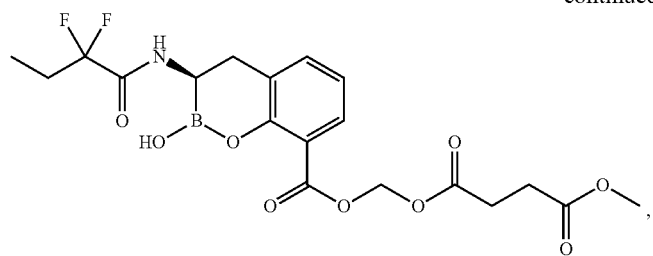
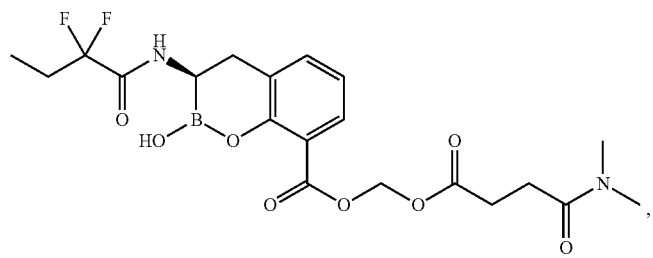
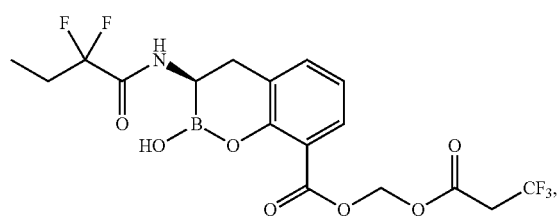
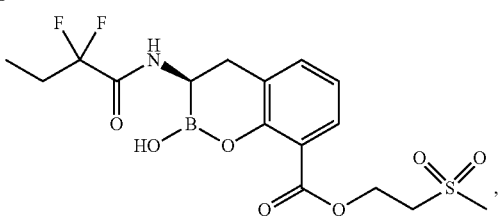
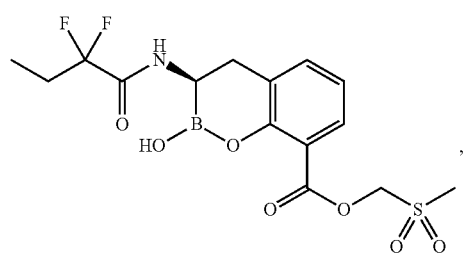
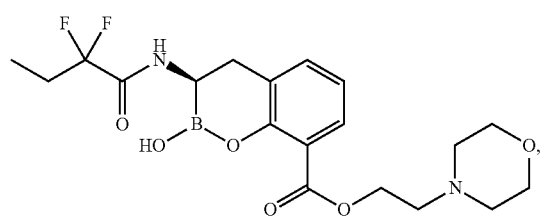
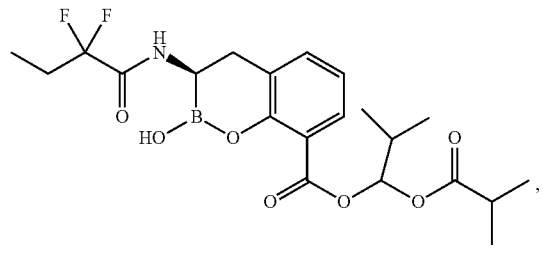
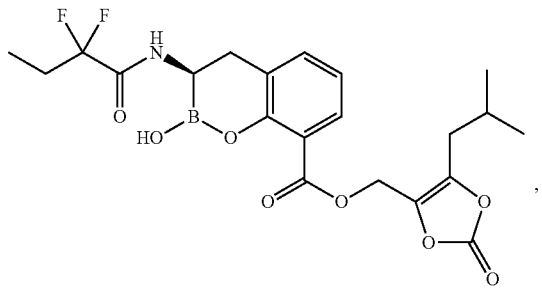
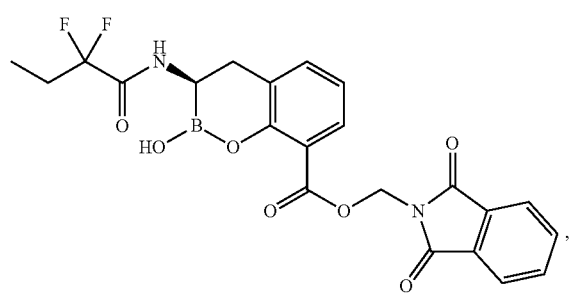
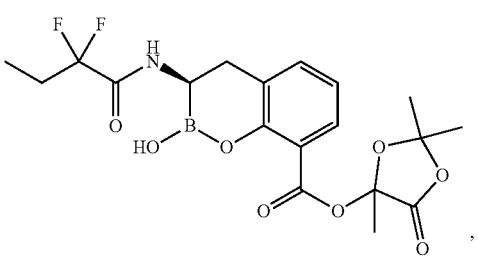

321
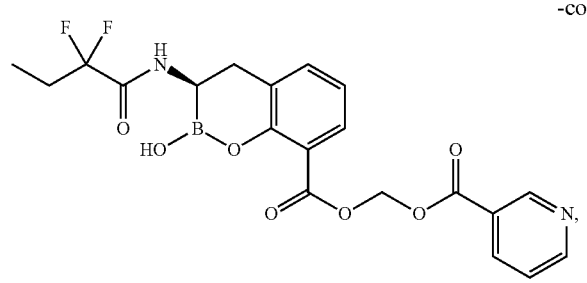
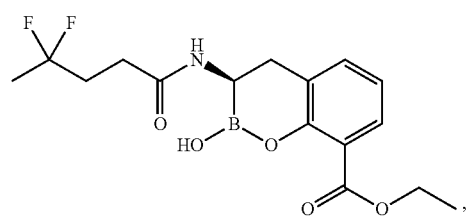
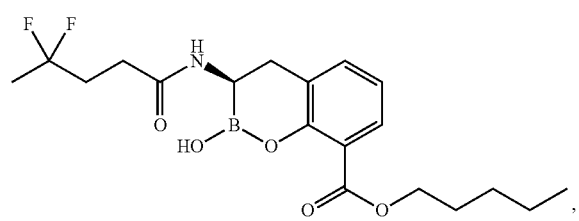
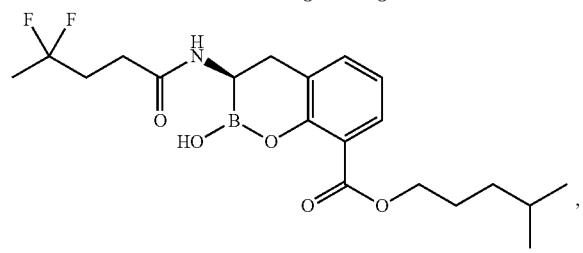
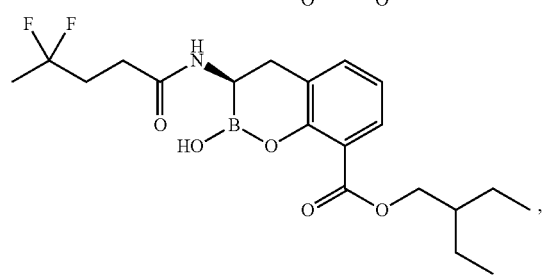
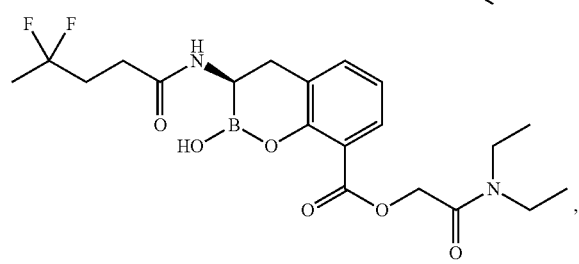
322
-continued
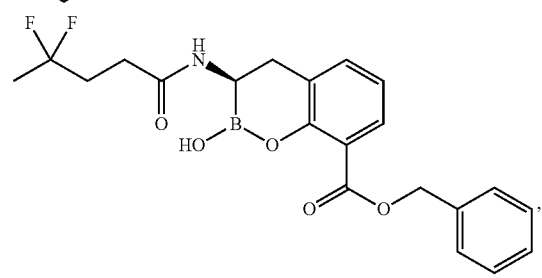
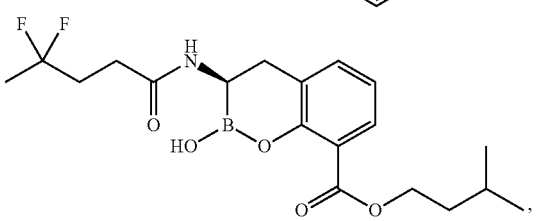
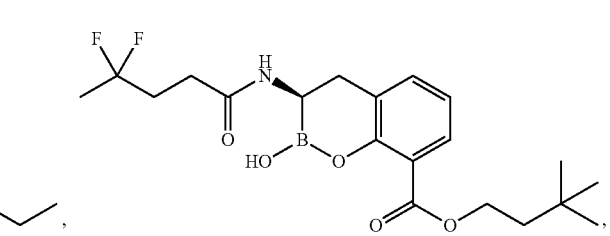
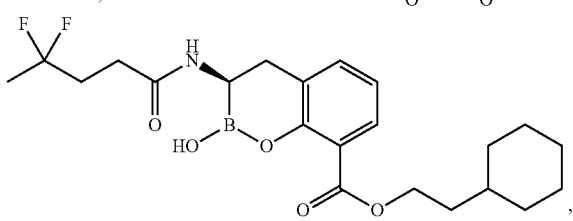
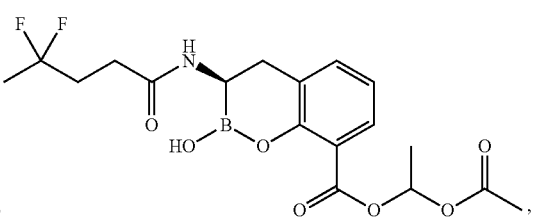

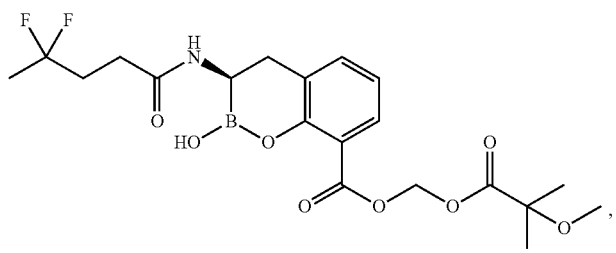
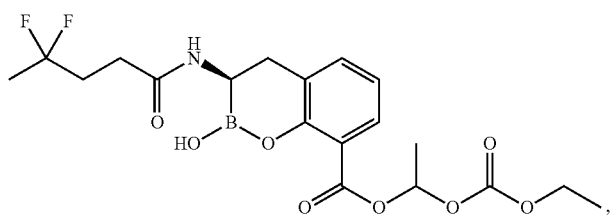
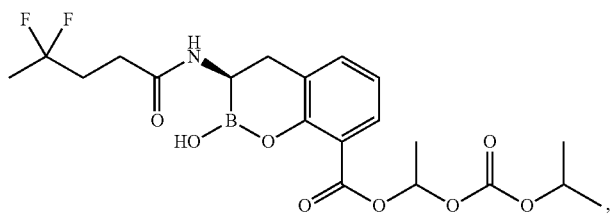
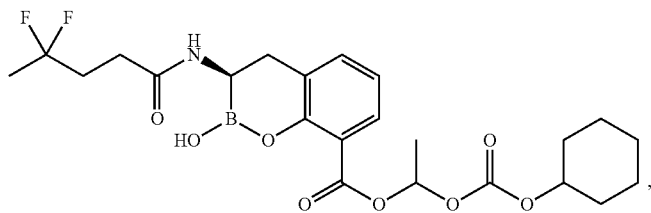
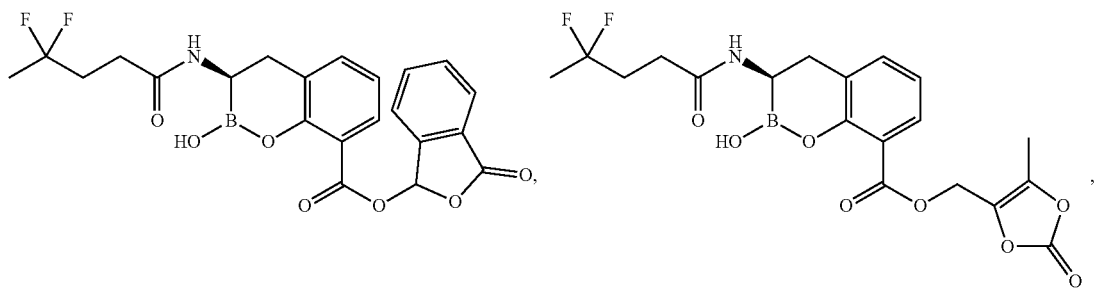
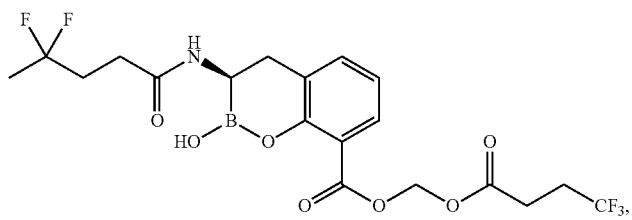
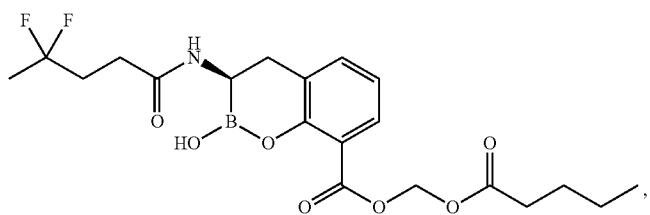

-continued
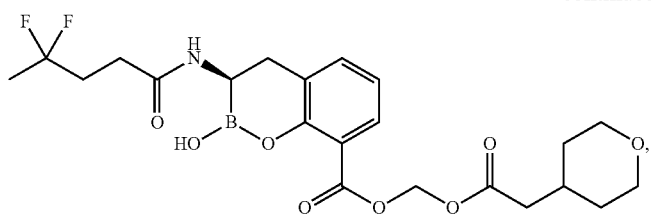
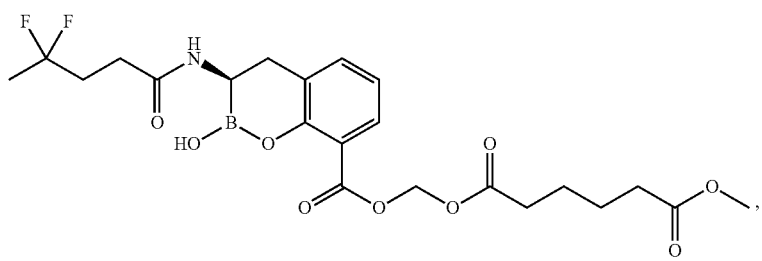
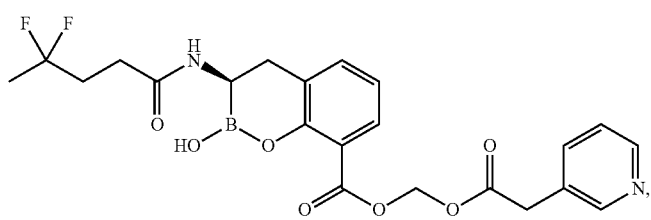
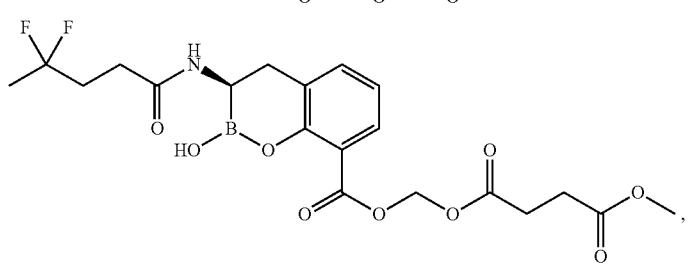
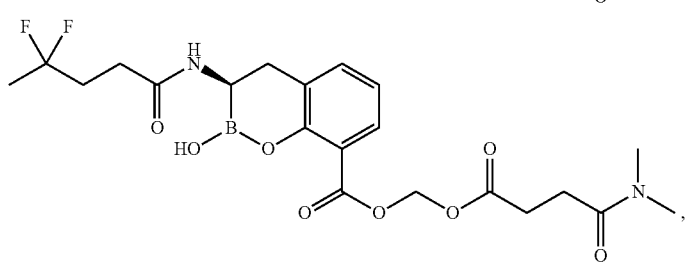
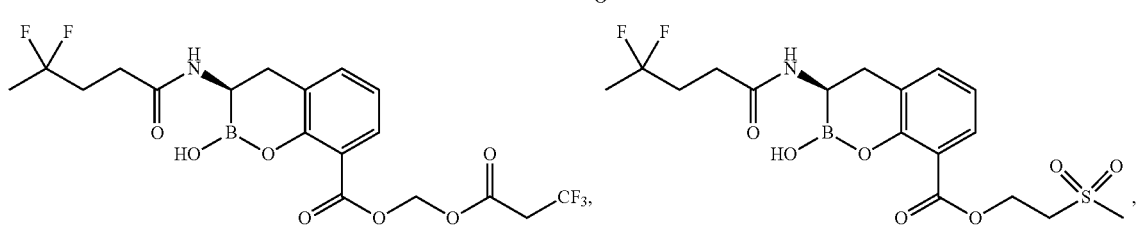
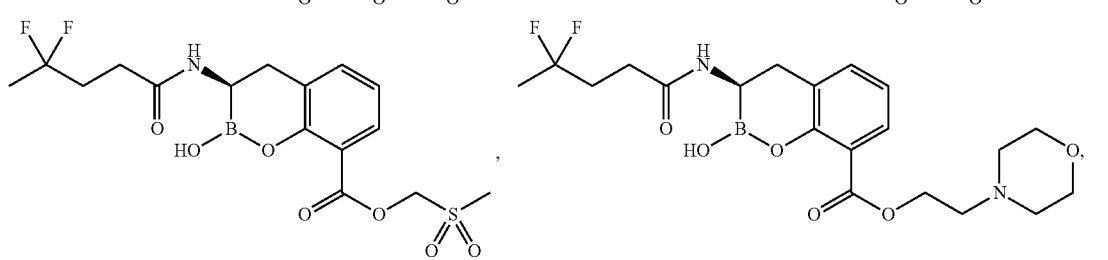

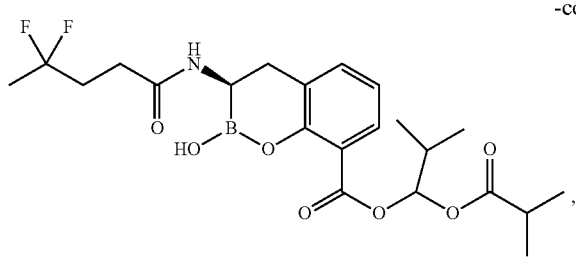

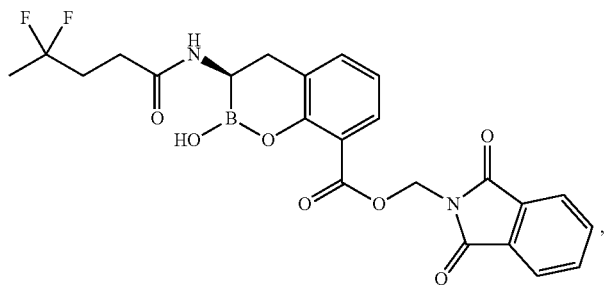

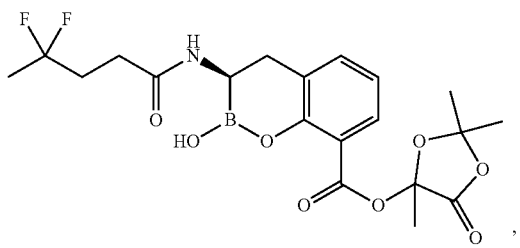

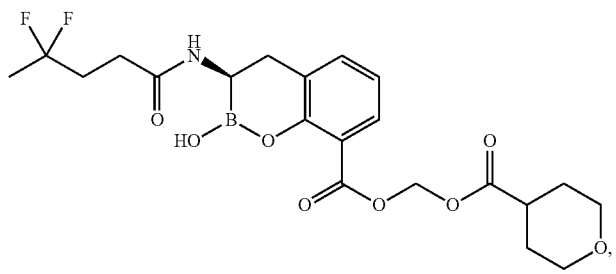

or pharmaceutically acceptable salts, isomers, stereoisomers, dimers, trimers, tautomers, or N-oxides thereof, wherein the compound is present in a closed form, an open form, or mixtures thereof.

6. A pharmaceutical composition comprising at least one compound of claim 1, or pharmaceutically acceptable salts, isomers, stereoisomers, dimers, trimers, tautomers, or N-oxides thereof, and a pharmaceutically acceptable excipient.

7. A method of treating a bacterial infection in a subject, comprising administering to the subject a compound of claim 1, or pharmaceutically acceptable salts, isomers, stereoisomers, dimers, trimers, tautomers, or N-oxides thereof.

8. A compound of Formula (IVa) or (IVb) or pharmaceutically acceptable salts, isomers, stereoisomers, dimers, trimers, tautomers, or N-oxides thereof:

Formula (IVa)

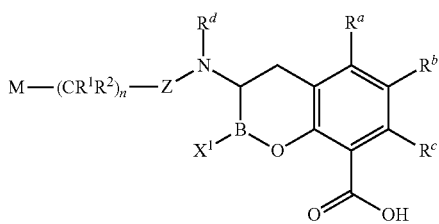

Formula (IVb)

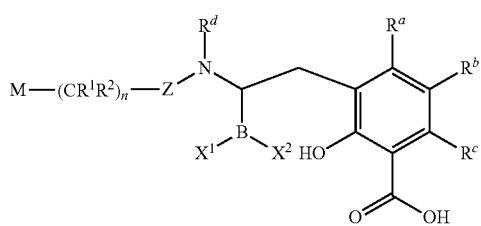

wherein:

$M-(CR^1R^2)_n-\{$ is

-continued

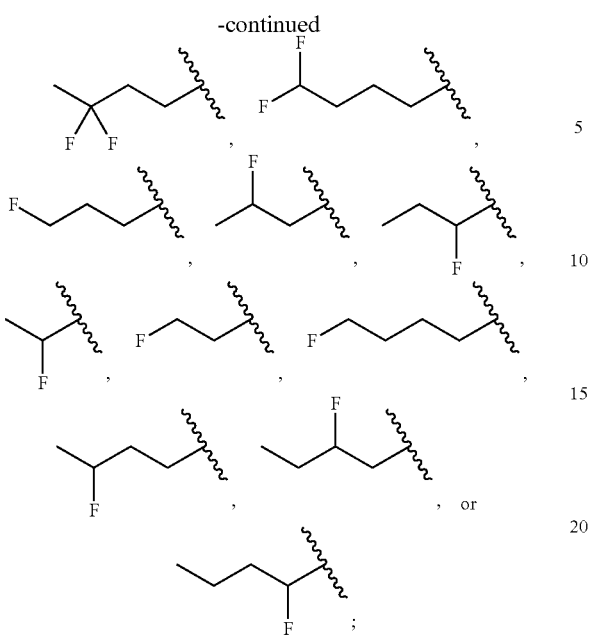

$X^1$ and $X^2$ are independently —$OR^4$ or F; when present;
Z is >C(=O), >C(=S), or >S(=O)$_2$;

$R^a$, $R^b$, $R^c$ are independently hydrogen, fluoro, chloro, bromo, optionally substituted $C_1$-$C_6$ alkyl, optionally substituted cycloalkyl, optionally substituted heterocycloalkyl, optionally substituted aryl, optionally substituted heteroaryl, —$OR^4$, —$N(R^4R^5)$, or —$SR^4$; and $R^d$, $R^4$, and $R^5$ are independently hydrogen, —OH, —CN, —$CF_3$, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, (poly-ethylene-glycol)-ethyl, or an optionally substituted saccharide;

or $R^4$ and $R^5$ are taken together with the nitrogen to which they are attached to form a heterocycloalkyl.

9. The compound of claim 8, or pharmaceutically acceptable salts, isomers, stereoisomers, dimers, trimers, tautomers, or N-oxides thereof, wherein $R^a$, $R^b$, and $R^c$ are hydrogen; and $R^d$ is hydrogen or $C_1$-$C_4$ alkyl.

10. The compound of claim 8, or pharmaceutically acceptable salts, isomers, stereoisomers, dimers, trimers, tautomers, or N-oxides thereof, wherein $X^1$ and $X^2$ are —OH; when present; and Z is >C(=O).

11. The compound of claim 8, wherein the compound is:

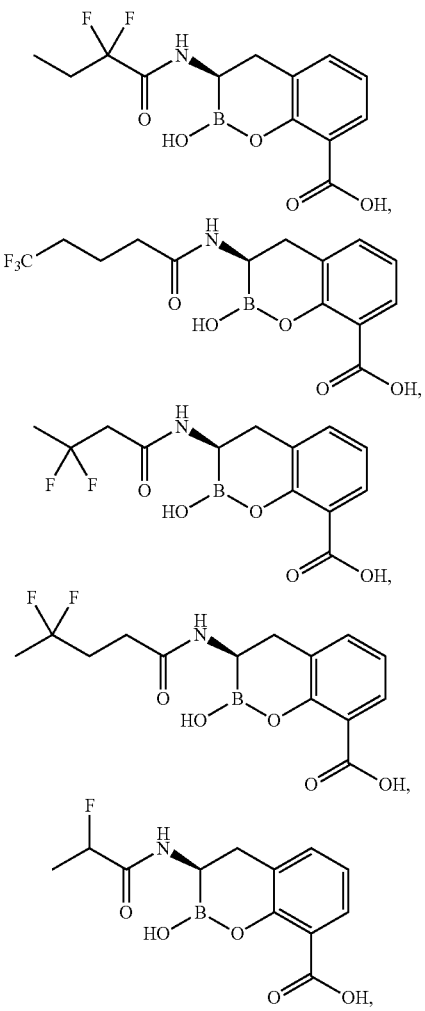

or pharmaceutically acceptable salts, isomers, stereoisomers, dimers, trimers, tautomers, or N-oxides thereof, wherein the compound is present in a closed form, an open form, or mixtures thereof.

12. A pharmaceutical composition comprising at least one compound of claim 8, or pharmaceutically acceptable salts, isomers, stereoisomers, dimers, trimers, tautomers, or N-oxides thereof, and a pharmaceutically acceptable excipient.

13. A method of treating a bacterial infection in a subject, comprising administering to the subject a compound of claim 8, or pharmaceutically acceptable salts, isomers, stereoisomers, dimers, trimers, tautomers, or N-oxides thereof.

* * * * *